(12) United States Patent
Klein et al.

(10) Patent No.: US 11,613,587 B2
(45) Date of Patent: Mar. 28, 2023

(54) COMBINATION THERAPY OF T CELL ACTIVATING BISPECIFIC ANTIGEN BINDING MOLECULES AND PD-1 AXIS BINDING ANTAGONISTS

(71) Applicant: Hoffmann-La Roche Inc., Little Falls, NJ (US)

(72) Inventors: Christian Klein, Bonstetten (CH); Vaios Karanikas, Adliswil (CH); Pablo Umana, Wollerau (CH); Alfred Zippelius, Basel (CH); Daniela Stefanie Thommen, Basel (CH); Jens Schreiner, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 376 days.

(21) Appl. No.: 16/988,540

(22) Filed: Aug. 7, 2020

(65) Prior Publication Data

US 2021/0087291 A1 Mar. 25, 2021

Related U.S. Application Data

(60) Division of application No. 15/600,011, filed on May 19, 2017, now Pat. No. 10,781,262, which is a continuation of application No. PCT/EP2015/076682, filed on Nov. 16, 2015.

(30) Foreign Application Priority Data

| Nov. 20, 2014 | (EP) | 14194136 |
| Jan. 22, 2015 | (EP) | 15152141 |
| May 11, 2015 | (EP) | 15167173 |

(51) Int. Cl.
| C07K 16/00 | (2006.01) |
| C07K 16/30 | (2006.01) |
| C07K 16/28 | (2006.01) |
| A61K 47/68 | (2017.01) |
| C07K 16/46 | (2006.01) |
| A61K 39/00 | (2006.01) |

(52) U.S. Cl.
CPC .......... *C07K 16/30* (2013.01); *A61K 47/6829* (2017.08); *A61K 47/6849* (2017.08); *C07K 16/28* (2013.01); *C07K 16/2803* (2013.01); *C07K 16/2809* (2013.01); *C07K 16/2818* (2013.01); *C07K 16/3023* (2013.01); *C07K 16/3046* (2013.01); *C07K 16/3069* (2013.01); *C07K 16/468* (2013.01); *A61K 2039/505* (2013.01); *A61K 2039/507* (2013.01); *C07K 2317/21* (2013.01); *C07K 2317/24* (2013.01); *C07K 2317/31* (2013.01); *C07K 2317/34* (2013.01); *C07K 2317/35* (2013.01); *C07K 2317/55* (2013.01); *C07K 2317/56* (2013.01); *C07K 2317/565* (2013.01); *C07K 2317/73* (2013.01); *C07K 2317/76* (2013.01); *C07K 2317/77* (2013.01); *C07K 2317/92* (2013.01); *C07K 2319/55* (2013.01)

(58) Field of Classification Search
None
See application file for complete search history.

(56) References Cited

U.S. PATENT DOCUMENTS

| 5,547,668 | A | 8/1996 | Kranz et al. |
| 5,571,894 | A | 11/1996 | Wels et al. |
| 5,587,458 | A | 12/1996 | King et al. |
| 5,591,828 | A | 1/1997 | Bosslet et al. |
| 5,731,168 | A | 3/1998 | Carter et al. |
| 5,821,337 | A | 10/1998 | Carter et al. |
| 5,869,046 | A | 2/1999 | Presta et al. |
| 6,248,516 | B1 | 6/2001 | Winter et al. |
| 6,737,056 | B1 | 5/2004 | Presta |
| 6,809,185 | B1 | 10/2004 | Schoonjans et al. |
| 7,332,581 | B2 | 2/2008 | Presta |
| 7,608,413 | B1 | 10/2009 | Joseloff et al. |
| 7,695,936 | B2 | 4/2010 | Carter et al. |
| 8,227,577 | B2 | 7/2012 | Klein et al. |
| 8,242,247 | B2 | 8/2012 | Klein et al. |
| 8,703,132 | B2 | 4/2014 | Imhof-Jung et al. |
| 8,709,421 | B2 | 4/2014 | Heiss et al. |
| 8,796,424 | B2 | 8/2014 | Croasdale et al. |
| 8,834,877 | B2 | 9/2014 | O'Shannessy |
| 8,969,526 | B2 | 3/2015 | Baehner et al. |
| 9,068,008 | B2 | 6/2015 | Mossner et al. |
| 9,266,938 | B2 | 2/2016 | Ast et al. |
| 9,266,967 | B2 | 2/2016 | Klein et al. |

(Continued)

FOREIGN PATENT DOCUMENTS

| CN | 103037900 A | 4/2013 |
| CN | 103842030 A | 6/2014 |

(Continued)

OTHER PUBLICATIONS

Atwell et al., "Stable heterodimers from remodeling the domain interface of a homodimer using a phage display library," J Mol Biol. 270(1):26-35 (1997).

(Continued)

*Primary Examiner* — Mark Halvorson
(74) *Attorney, Agent, or Firm* — Clark & Elbing LLP; Karen L. Elbing

(57) ABSTRACT

The present invention generally relates to T cell activating bispecific antigen binding molecules, PD-1 axis binding antagonists, and in particular to combination therapies employing such T cell activating bispecific antigen binding molecules and PD-1 axis binding antagonists, and their use of these combination therapies for the treatment of cancer.

29 Claims, 76 Drawing Sheets

Specification includes a Sequence Listing.

(56) References Cited

U.S. PATENT DOCUMENTS

| | | | |
|---|---|---|---|
| 9,382,323 | B2 | 7/2016 | Brinkmann et al. |
| 9,447,159 | B2 | 9/2016 | Ast et al. |
| 9,526,797 | B2 | 12/2016 | Gerdes et al. |
| 2007/0111281 | A1 | 5/2007 | Sondermann et al. |
| 2008/0241152 | A1 | 10/2008 | Alitalo et al. |
| 2009/0252683 | A1 | 10/2009 | Kischel et al. |
| 2010/0015133 | A1 | 1/2010 | Igawa et al. |
| 2010/0150918 | A1 | 6/2010 | Kufer et al. |
| 2010/0316645 | A1 | 12/2010 | Imhof-Jung et al. |
| 2011/0293613 | A1 | 12/2011 | Brinkmann et al. |
| 2012/0164137 | A1 | 6/2012 | Sass et al. |
| 2012/0189620 | A1 | 7/2012 | Oyesiku |
| 2012/0225071 | A1 | 9/2012 | Klein et al. |
| 2012/0276125 | A1 | 11/2012 | Ast et al. |
| 2013/0022601 | A1 | 1/2013 | Brinkmann et al. |
| 2013/0045492 | A1 | 2/2013 | Babb et al. |
| 2013/0058936 | A1 | 3/2013 | Bruenker et al. |
| 2013/0058937 | A1 | 3/2013 | Auer et al. |
| 2013/0060011 | A1 | 3/2013 | Bruenker et al. |
| 2013/0078249 | A1 | 3/2013 | Ast et al. |
| 2013/0171095 | A1 | 7/2013 | Bernett et al. |
| 2013/0273054 | A1 | 10/2013 | Bossenmaier et al. |
| 2014/0088295 | A1 | 3/2014 | Smith et al. |
| 2014/0099254 | A1 | 4/2014 | Chang et al. |
| 2014/0112914 | A1 | 4/2014 | Nezu et al. |
| 2014/0120096 | A1 | 5/2014 | Bakker et al. |
| 2014/0154254 | A1 | 6/2014 | Kannan et al. |
| 2014/0205610 | A1 | 7/2014 | Ando et al. |
| 2014/0242079 | A1 | 8/2014 | Bacac et al. |
| 2014/0242080 | A1 | 8/2014 | Jaeger et al. |
| 2014/0288275 | A1 | 9/2014 | Moore et al. |
| 2014/0294823 | A1 | 10/2014 | Moore et al. |
| 2014/0294833 | A1 | 10/2014 | Desjarlais et al. |
| 2014/0302064 | A1 | 10/2014 | Moore |
| 2014/0308285 | A1 | 10/2014 | Yan et al. |
| 2014/0322217 | A1 | 10/2014 | Moore et al. |
| 2014/0363426 | A1 | 12/2014 | Moore et al. |
| 2014/0370013 | A1 | 12/2014 | Desjarlais et al. |
| 2014/0377270 | A1 | 12/2014 | Moore et al. |
| 2015/0094451 | A1 | 4/2015 | Fischer et al. |
| 2015/0166661 | A1 | 6/2015 | Chen et al. |
| 2015/0218274 | A1 | 8/2015 | Sabatos-Peyton et al. |
| 2015/0274845 | A1 | 10/2015 | Bruenker et al. |
| 2015/0315296 | A1 | 11/2015 | Schaefer et al. |
| 2015/0343088 | A1 | 12/2015 | Matsuyama et al. |
| 2015/0368351 | A1 | 12/2015 | Vu et al. |
| 2015/0376287 | A1 | 12/2015 | Vu et al. |
| 2016/0075785 | A1 | 3/2016 | Ast et al. |
| 2016/0130347 | A1 | 5/2016 | Bruenker et al. |
| 2016/0145354 | A1 | 5/2016 | Bacac et al. |
| 2016/0175397 | A1 | 6/2016 | Umana et al. |
| 2016/0208017 | A1 | 7/2016 | Ast et al. |
| 2016/0208019 | A1 | 7/2016 | Bacac et al. |
| 2016/0263240 | A1 | 9/2016 | Ast et al. |
| 2016/0297881 | A1 | 10/2016 | Vu et al. |
| 2016/0368985 | A1 | 12/2016 | Hotzel et al. |
| 2017/0008971 | A1 | 1/2017 | Dennis et al. |
| 2017/0096485 | A1 | 4/2017 | Bacac et al. |
| 2017/0096495 | A1 | 4/2017 | Bacac et al. |
| 2017/0114146 | A1 | 4/2017 | Klein et al. |
| 2017/0174786 | A1 | 6/2017 | Bacac et al. |
| 2017/0190783 | A1 | 7/2017 | Bacac et al. |
| 2017/0209573 | A1 | 7/2017 | Bacac et al. |
| 2017/0253670 | A1 | 9/2017 | Klein et al. |
| 2017/0267783 | A1 | 9/2017 | Nezu et al. |
| 2017/0306018 | A1 | 10/2017 | Vu et al. |
| 2017/0306036 | A1 | 10/2017 | Vu et al. |
| 2017/0306044 | A1 | 10/2017 | Vu et al. |
| 2017/0327579 | A1 | 11/2017 | Vu et al. |
| 2017/0327580 | A1 | 11/2017 | Vu et al. |

FOREIGN PATENT DOCUMENTS

| | | | |
|---|---|---|---|
| EA | 201791121 | A1 | 4/2018 |
| EP | 0404097 | B1 | 9/1996 |
| EP | 1870459 | A1 | 12/2007 |
| EP | 1870459 | A4 | 9/2010 |
| EP | 2578230 | A1 | 4/2013 |
| EP | 2647707 | A1 | 10/2013 |
| EP | 2647707 | A4 | 4/2014 |
| EP | 1870459 | B1 | 6/2016 |
| JP | 2012-522523 | A | 9/2012 |
| WO | WO-91/03493 | A1 | 3/1991 |
| WO | WO-93/16185 | A2 | 8/1993 |
| WO | WO-96/01126 | A1 | 1/1996 |
| WO | WO-96/27011 | A1 | 9/1996 |
| WO | WO-96/40210 | A1 | 12/1996 |
| WO | WO-98/50431 | A2 | 11/1998 |
| WO | WO-98/50431 | A3 | 1/1999 |
| WO | WO-02/09573 | A2 | 2/2002 |
| WO | WO-2004/113388 | A2 | 12/2004 |
| WO | WO-2005/044859 | A2 | 5/2005 |
| WO | WO-2005/080431 | A2 | 9/2005 |
| WO | WO-2006/082515 | A2 | 8/2006 |
| WO | WO-2006/116592 | A2 | 11/2006 |
| WO | WO-2006/121168 | A1 | 11/2006 |
| WO | WO-2007/024715 | A2 | 3/2007 |
| WO | WO-2007/042261 | A2 | 4/2007 |
| WO | WO-2007/075270 | A2 | 7/2007 |
| WO | WO-2007/110205 | A2 | 10/2007 |
| WO | WO-2007/146968 | A2 | 12/2007 |
| WO | WO-2007/147901 | A1 | 12/2007 |
| WO | WO-2008/031577 | A1 | 3/2008 |
| WO | WO-2007/024715 | A3 | 10/2008 |
| WO | WO-2008/119566 | A2 | 10/2008 |
| WO | WO-2008/119567 | A2 | 10/2008 |
| WO | WO-2007/024715 | A9 | 4/2009 |
| WO | WO-2009/070642 | A1 | 6/2009 |
| WO | WO-2009/080251 | A1 | 7/2009 |
| WO | WO-2009/080252 | A1 | 7/2009 |
| WO | WO-2009/080253 | A1 | 7/2009 |
| WO | WO-2009/080254 | A1 | 7/2009 |
| WO | WO-2009/089004 | A1 | 7/2009 |
| WO | WO-2010/115589 | A1 | 10/2010 |
| WO | WO-2010/129304 | A2 | 11/2010 |
| WO | WO-2010/136172 | A1 | 12/2010 |
| WO | WO-2010/145792 | A1 | 12/2010 |
| WO | WO-2010/145793 | A1 | 12/2010 |
| WO | WO-2010/129304 | A3 | 2/2011 |
| WO | WO-2011/028952 | A1 | 3/2011 |
| WO | WO-2011/090754 | A1 | 7/2011 |
| WO | WO-2011/090762 | A1 | 7/2011 |
| WO | WO-2011/106528 | A1 | 9/2011 |
| WO | WO-2011/143545 | A1 | 11/2011 |
| WO | WO-2011/159877 | A2 | 12/2011 |
| WO | WO-2012/054654 | A2 | 4/2012 |
| WO | WO-2012/058768 | A1 | 5/2012 |
| WO | WO-2012/061759 | A2 | 5/2012 |
| WO | WO-2012/058768 | A8 | 6/2012 |
| WO | WO-2012/073985 | A1 | 6/2012 |
| WO | WO-2012/130831 | A1 | 10/2012 |
| WO | WO-2012/135675 | A2 | 10/2012 |
| WO | WO-2012/158818 | A2 | 11/2012 |
| WO | WO-2012/162067 | A2 | 11/2012 |
| WO | WO-2013/006490 | A2 | 1/2013 |
| WO | WO-2013/012722 | A1 | 1/2013 |
| WO | WO-2013/019906 | A1 | 2/2013 |
| WO | WO-2013/026831 | A1 | 2/2013 |
| WO | WO-2013/026833 | A1 | 2/2013 |
| WO | WO-2013/026837 | A1 | 2/2013 |
| WO | WO-2013/096291 | A2 | 6/2013 |
| WO | WO-2013/157953 | A1 | 10/2013 |
| WO | WO-2013/157954 | A1 | 10/2013 |
| WO | WO-2013/172951 | A1 | 11/2013 |
| WO | WO-2014/022540 | A1 | 2/2014 |
| WO | WO-2014/028560 | A2 | 2/2014 |
| WO | WO-2014/047231 | A1 | 3/2014 |
| WO | WO-2014/051433 | A1 | 4/2014 |
| WO | WO-2014/056783 | A1 | 4/2014 |
| WO | WO-2014/028560 | A3 | 5/2014 |
| WO | WO-2014/081955 | A1 | 5/2014 |
| WO | WO-2014/087863 | A1 | 6/2014 |
| WO | WO-2014/104270 | A1 | 7/2014 |
| WO | WO-2014/110601 | A1 | 7/2014 |

(56) References Cited

FOREIGN PATENT DOCUMENTS

| WO | WO-2014/122143 A1 | 8/2014 |
|---|---|---|
| WO | WO-2014/122144 A1 | 8/2014 |
| WO | WO-2014/122251 A2 | 8/2014 |
| WO | WO-2014/131694 A1 | 9/2014 |
| WO | WO-2014/131712 A1 | 9/2014 |
| WO | WO-2014/141152 A2 | 9/2014 |
| WO | WO-2014/144357 A1 | 9/2014 |
| WO | WO-2014/144722 A2 | 9/2014 |
| WO | WO-2014/151910 A1 | 9/2014 |
| WO | WO-2014/153002 A1 | 9/2014 |
| WO | WO-2014/122251 A3 | 10/2014 |
| WO | WO-2014/161845 A1 | 10/2014 |
| WO | WO-2014/163684 A1 | 10/2014 |
| WO | WO-2014/167022 A1 | 10/2014 |
| WO | WO-2014/141152 A3 | 12/2014 |
| WO | WO-2014/191113 A1 | 12/2014 |
| WO | WO-2014/191113 A8 | 12/2014 |
| WO | WO-2015/048272 A1 | 4/2015 |
| WO | WO-2015/150447 A1 | 10/2015 |
| WO | WO-2016/020065 A1 | 2/2016 |
| WO | WO-2016/020332 A1 | 2/2016 |
| WO | WO-2016/036678 A1 | 3/2016 |
| WO | WO-2016/055592 A1 | 4/2016 |
| WO | WO-2016/055593 A1 | 4/2016 |
| WO | WO-2016/079050 A1 | 5/2016 |
| WO | WO-2016/079081 A1 | 5/2016 |
| WO | WO-2016/079177 A1 | 5/2016 |
| WO | WO-2016/087531 A1 | 6/2016 |
| WO | WO-2016/179003 A1 | 11/2016 |
| WO | WO-2017/021450 A1 | 2/2017 |

OTHER PUBLICATIONS

Booy et al., "Monoclonal and bispecific antibodies as novel therapeutics," Arch Immunol Ther Exp (Warsz). 54(2):85-101 (2006).
Bosch et al., "MCSP/CD3-bispecific single-chain antibody construct engages CD4+ and CD8+ T cells for lysis of MCSP-expressing human uveal melanoma cells," AACR 101st Annual Meeting. Apr. 17-21, Washington, DC. 70(8 Suppl) Abstract 5621 (2010).
Carter, "Bispecific human IgG by design," J Immunol Methods. 248(1-2):7-15 (2001).
Casset et al., "A peptide mimetic of an anti-CD4 monoclonal antibody by rational design," Biochem Biophys Res Commun. 307(1):198-205 (2003).
Chan et al., "Variable region domain exchange in human IgGs promotes antibody complex formation with accompanying structural changes and altered effector functions," Mol Immunol. 41(5):527-38 (2004).
Chen et al., "Selection and analysis of an optimized anti-VEGF antibody: crystal structure of an affinity-matured Fab in complex with antigen," J Mol Biol. 293(4):865-81 (1999).
Cui et al., "Chemically programmed bispecific antibodies that recruit and activate T cells," J Biol Chem. 287(34):28206-14 (2012) (10 pages).
Curran et al., "PD-1 and CTLA-4 combination blockade expands infiltrating T cells and reduces regulatory T and myeloid cells within B16 melanoma tumors," Proc Natl Acad Sci U S A. 107(9):4275-80 (2010).
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," J Immunol. 169(6):3076-84 (2002).
Deyev et al., "Modern Technologies for Creating Synthetic Antibodies for Clinical application," Acta Naturae. 1(1):32-50 (2009) (19 pages).
Diamond et al., "Somatic mutation of the T15 heavy chain gives rise to an antibody with autoantibody specificity," Proc Natl Acad Sci U S A. 81(18):5841-5844 (1984).

Dilek et al., "Targeting CD28, CTLA-4 and PD-L1 costimulation differentially controls immune synapses and function of human regulatory and conventional T-cells," PLoS One. 8(12):e83139 (2013) (14 pages).
Duraiswamy et al., "Dual blockade of PD-1 and CTLA-4 combined with tumor vaccine effectively restores T-cell rejection function in tumors," Cancer Res. 73(12):3591-603 (2013) (14 pages).
Edelman et al., "The covalent structure of an entire gammaG immunoglobulin molecule," Proc Natl Acad Sci U S A. 63(1):78-85 (1969).
Garcia-Bennett et al., "In search of the Holy Grail: Folate-targeted nanoparticles for cancer therapy," Biochem Pharmacol. 81(8):976-84 (2011) (9 pages).
Hasemann et al., "Mutational analysis of arsonate binding by a CRIA+ antibody. VH and VL junctional diversity are essential for binding activity," J Biol Chem. 266(12):7626-32 (1991) (7 pages).
Holliger et al., "'Diabodies': small bivalent and bispecific antibody fragments," Proc Natl Acad Sci U S A. 90(14):6444-8 (1993).
Holliger et al., "Specific killing of lymphoma cells by cytotoxic T-cells mediated by a bispecific diabody," Protein Eng. 9(3):299-305 (1996).
Honeychurch et al., "Bispecific Ab therapy of B-cell lymphoma: target cell specificity of antibody derivatives appears critical in determining therapeutic outcome," Cancer Immunol Immunother. 45(3-4):171-3(1997).
Hudson et al., "Engineered antibodies," Nat Med. 9(1):129-34 (2003).
Jackman et al., "Development of a two-part strategy to identify a therapeutic human bispecific antibody that inhibits IgE receptor signaling," J Biol Chem. 285(27):20850-9 (2010) (11 pages).
Kang et al., "Antibody redesign by chain shuffling from random combinatorial immunoglobulin libraries," Proc Natl Acad Sci U.S.A. 88(24):11120-3 (1991).
Kimura et al., "Molecular cloning of a human MafF homologue, which specifically binds to the oxytocin receptor gene in term myometrium," Biochem Biophys Res Commun. 264(1):86-92 (1999).
Kipriyanov et al., "Bispecific tandem diabody for tumor therapy with improved antigen binding and pharmacokinetics," J Mol Biol. 293(1):41-56 (1999).
Klein et al., "Progress in overcoming the chain association issue in bispecific heterodimeric IgG antibodies," MAbs. 4(6):653-63 (2012).
Kontermann, "Dual targeting strategies with bispecific antibodies," MAbs. 4(2):182-97 (2012).
Kopantzev et al., "Differences in gene expression levels between early and later stages of human lung development are opposite to those between normal lung tissue and non-small lung cell carcinoma," Lung Cancer. 62(1):23-34 (2008) (12 pages).
Lamminmäki et al., "Crystal Structure of a Recombinant Anti-Estradiol Fab Fragment in Complex With 17beta-Estradiol," J Biol Chem. 276(39):36687-94 (2001).
Luiten et al., "Chimeric bispecific OC/TR monoclonal antibody mediates lysis of tumor cells expressing the folate-binding protein (MOv18) and displays decreased immunogenicity in patients," J Immunother. 20(6):496-504 (1997).
MacCallum et al., "Antibody-antigen interactions: contact analysis and binding site topography," J Mol Biol. 262(5):732-45 (1996).
Merchant et al., "An efficient route to human bispecific IgG," Nat Biotechnol. 16(7):677-81 (1998).
Mezzanzanica et al., "Human ovarian carcinoma lysis by cytotoxic T cells targeted by bispecific monoclonal antibodies: analysis of the antibody components," Int J Cancer. 41(4):609-15 (1988).
Miller et al., "Design, construction, and in vitro analyses of multivalent antibodies," J Immunol. 170(9):4854-61 (2003).
Moore et al., "A novel bispecific antibody format enables simultaneous bivalent and monovalent co-engagement of distinct target antigens," MAbs. 3(6):546-57 (2011).
Moore et al., "Application of dual affinity retargeting molecules to achieve optimal redirected T-cell killing of B-cell lymphoma," Blood. 117(17):4542-51 (2011) (11 pages).
Nagorsen et al., "Immunomodulatory therapy of cancer with T cell-engaging BiTE antibody blinatumomab," Exp Cell Res. 317(9):1255-60 (2011).

(56) References Cited

OTHER PUBLICATIONS

Ohno et al., "Antigen-binding specificities of antibodies are primarily determined by seven residues of VH," Proc Natl Acad Sci U S A. 82(9):2945-9 (1985).

Osada et al., "CEA/CD3-bispecific T Cell-Engaging (BiTE) Antibody-Mediated T Lymphocyte Cytotoxicity Maximized by Inhibition of Both PD1 and PD-L1," Cancer Immunol Immunother. 64(6):677-88 (2015).

Oshimi et al., "Increased lysis of patient CD10-positive leukemic cells by T cells coated with anti-CD3 Fab' antibody cross-linked to anti-CD10 Fab' antibody," Blood. 77(5):1044-9 (1991).

Padlan et al., "Structure of an antibody-antigen complex: crystal structure of the HyHEL-10 Fab-lysozyme complex," Proc Natl Acad Sci USA. 86(15):5938-5942 (1989).

Pessano et al., "The T3/T cell receptor complex: antigenic distinction between the two 20-kd T3 (T3-delta and T3-epsilon) subunits," EMBO J. 4(2):337-44 (1985).

Ridgway et al., "'Knobs-into-holes' engineering of antibody CH3 domains for heavy chain heterodimerization," Protein Eng. 9(7):617-21 (1996).

Riedle et al., "In vivo activation and expansion of T cells by a bi-specific antibody abolishes metastasis formation of human melanoma cells in SCID mice," Int J Cancer. 75(6):908-18 (1998).

Rudikoff et al., "Single amino acid substitution altering antigen-binding specificity," Proc Natl Acad Sci U S A. 79(6):1979-83 (1982).

Sakuishi et al., "Targeting Tim-3 and PD-1 pathways to reverse T cell exhaustion and restore anti-tumor immunity," J Exp Med. 207(10):2187-94 (2010).

Schaefer et al., "Immunoglobulin domain crossover as a generic approach for the production of bispecific IgG antibodies," Proc Natl Acad Sci U S A. 108(27):11187-92 (2011).

Seimetz et al., "Development and approval of the trifunctional antibody catumaxomab (anti-EpCAM x anti-CD3) as a targeted cancer immunotherapy," Cancer Treat Rev. 36(6):458-67 (2010).

Stubenrauch et al., "Impact of molecular processing in the hinge region of therapeutic IgG4 antibodies on disposition profiles in cynomolgus monkeys," Drug Metab Dispos. 38(1):84-91 (2010).

Sun et al. "Anti-CD20/CD3 T cell-dependent bispecific antibody for the treatment of B cell malignancies," Sci Transl Med. 7(287):287ra70 (2015) (11 pages).

Topalian et al., "Safety, activity, and immune correlates of anti-PD-1 antibody in cancer," N Engl J Med. 366(26):2443-54 (2012).

Torisu-Itakura et al., "Redirected lysis of human melanoma cells by a MCSP/CD3-bispecific BiTE antibody that engages patient-derived T cells," J Immunother. 34(8):597-605 (2011).

Tutt et al., "Trispecific F(ab')3 derivatives that use cooperative signaling via the TCR/CD3 complex and CD2 to activate and redirect resting cytotoxic T cells," J Immunol. 147(1):60-9 (1991).

Vajdos et al., "Comprehensive functional maps of the antigen-binding site of an anti-ErbB2 antibody obtained with shotgun scanning mutagenesis," J Mol Biol. 320(2):415-28 (2002).

Weidle et al., "The intriguing options of multispecific antibody formats for treatment of cancer," Cancer Genomics Proteomics. 10(1):1-18 (2013).

Wolf et al., "BiTEs: bispecific antibody constructs with unique anti-tumor activity," Drug Discov Today. 10(18):1237-44 (2005).

Wu et al., "Humanization of a murine monoclonal antibody by simultaneous optimization of framework and CDR residues," J Mol Biol. 294(1):151-62 (1999).

Yokosuka et al., "Programmed cell death 1 forms negative costimulatory microclusters that directly inhibit T cell receptor signaling by recruiting phosphatase SHP2," J Exp Med. 209(6):1201-17 (2012).

Zhu et al., "Identification of heavy chain residues in a humanized anti-CD3 antibody important for efficient antigen binding and T cell activation," J Immunol. 155(4):1903-10 (1995).

International Preliminary Report on Patentability for International Patent Application No. PCT/EP2015/076682, dated May 23, 2017 (11 pages).

International Search Report and Written Opinion for International Patent Application No. PCT/EP2015/076682, dated Feb. 24, 2016 (19 pages).

Office Action for U.S. Appl. No. 15/600,011, dated Sep. 17, 2019 (15 pages).

Search Report and Written Opinion for Singaporean Patent Application No. 11201704056X, dated Jul. 6, 2018 (11 pages).

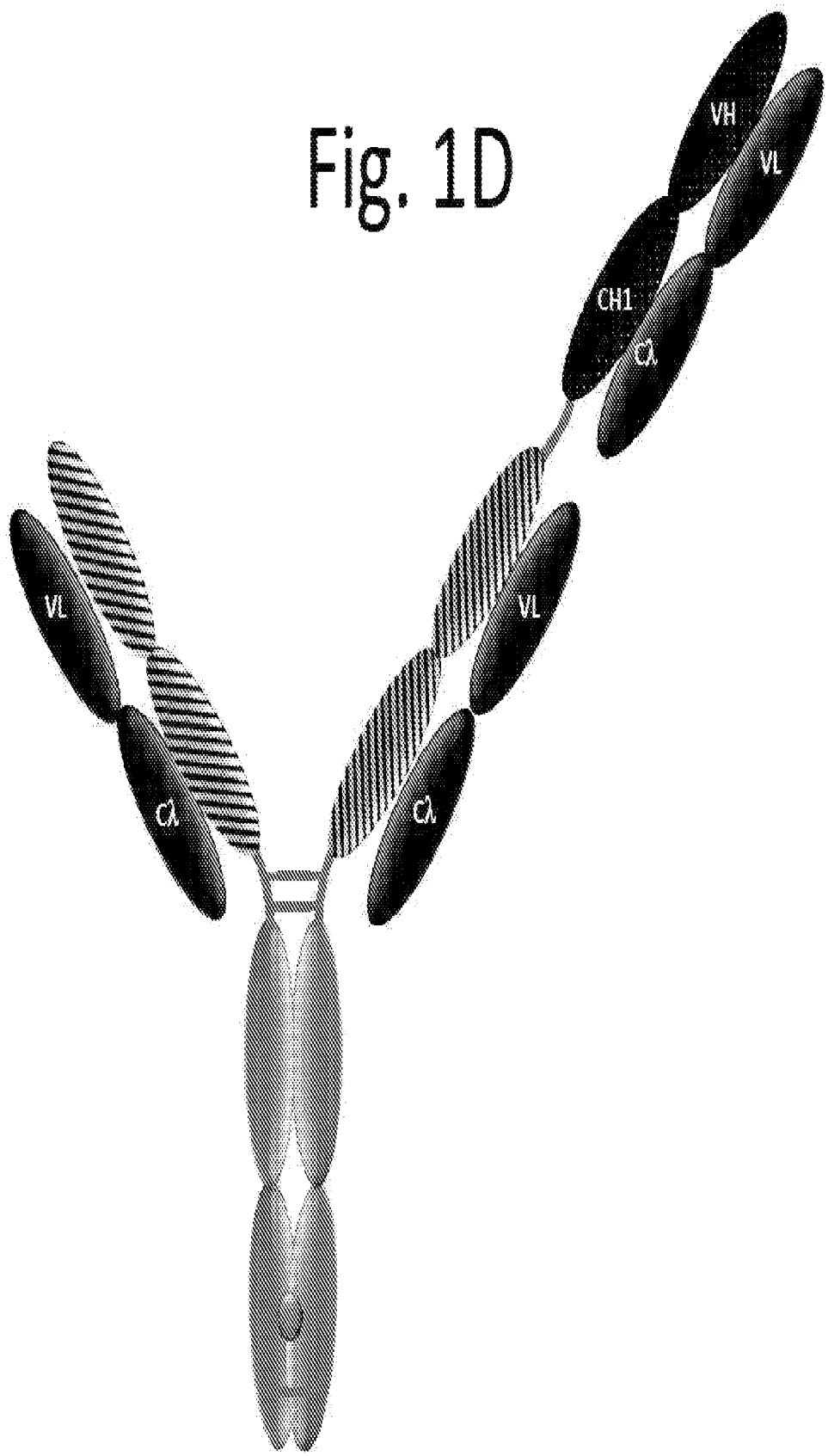

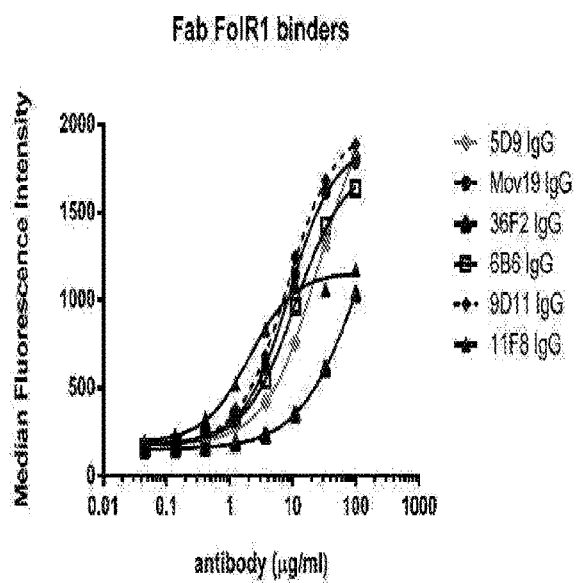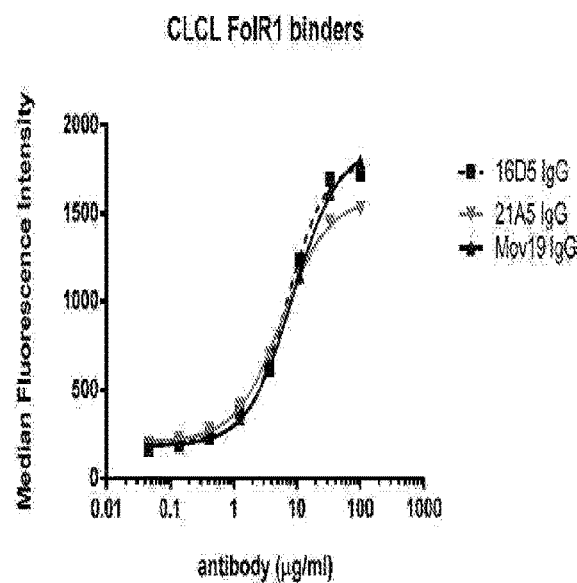
Fig. 4A
Fig. 4B

◆ 16D5 FolR1 TCB  ● 9D11 FolR1 TCB  ▲ DP47 TCB

◆ 16D5 FolR1 TCB   ■ 9D11 FolR1 TCB   ▲ DP47 TCB

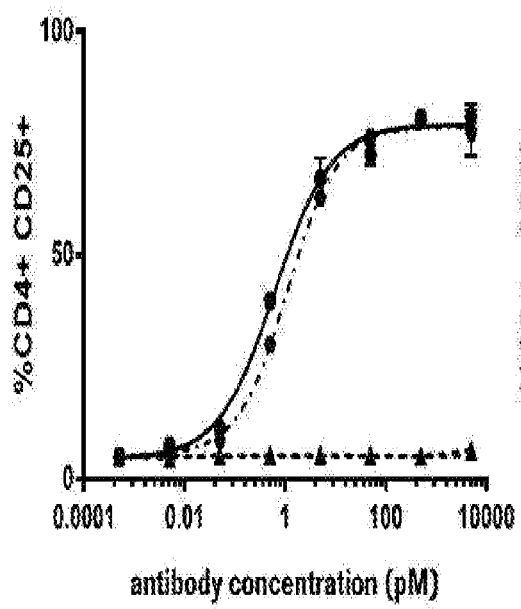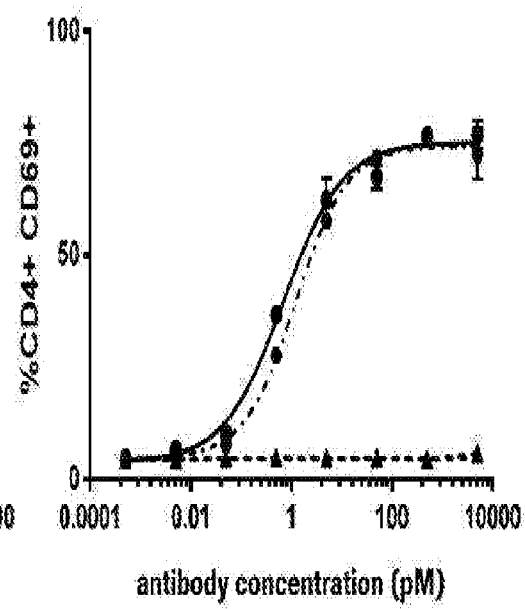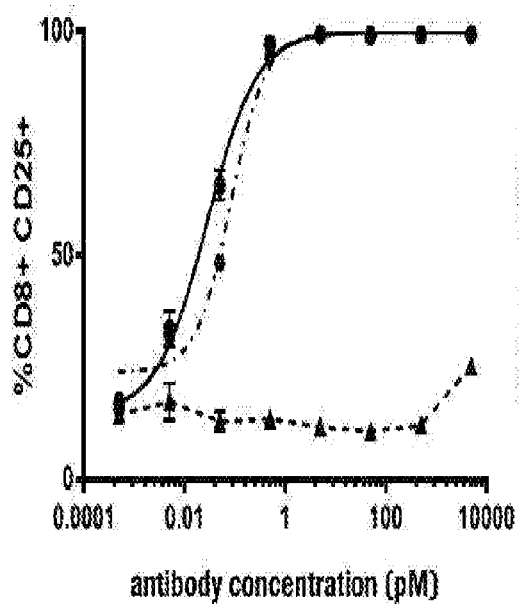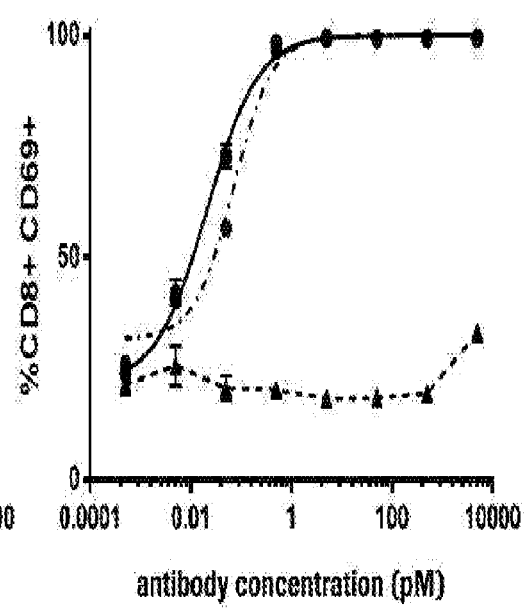

- ■ 36F2 TCB
- ○ 16D5 TCB
- ✢ 16D5 TCB classical
- ◆ 16D5 HT
- ▽ 16D5 1+1
- ✕ DP47 TCB

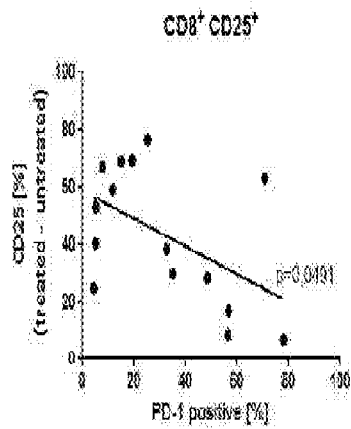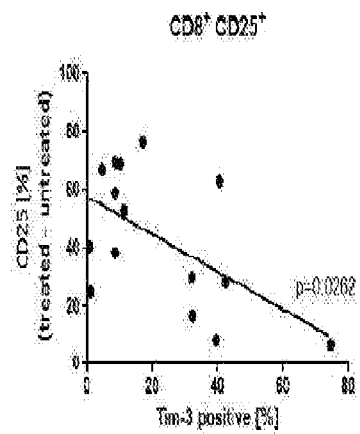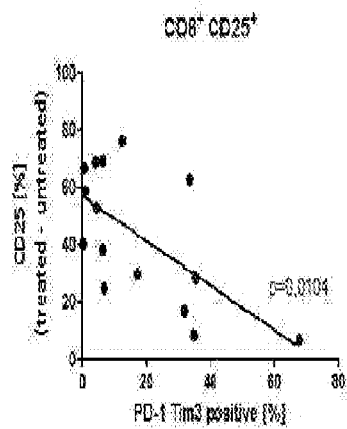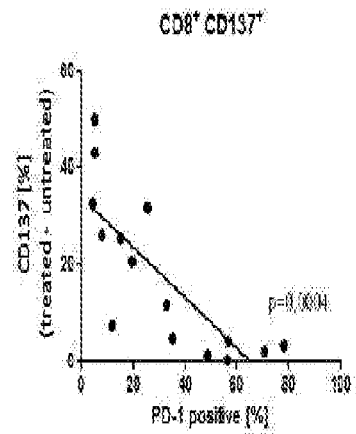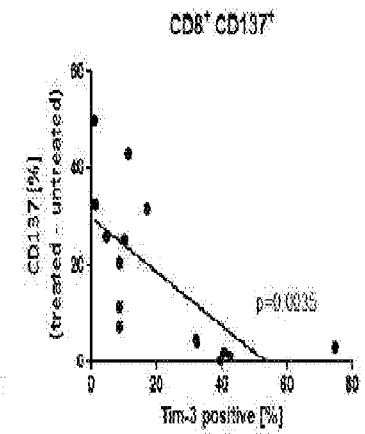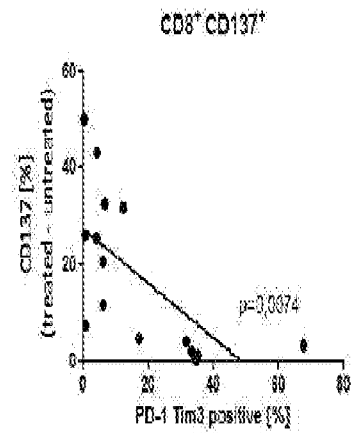

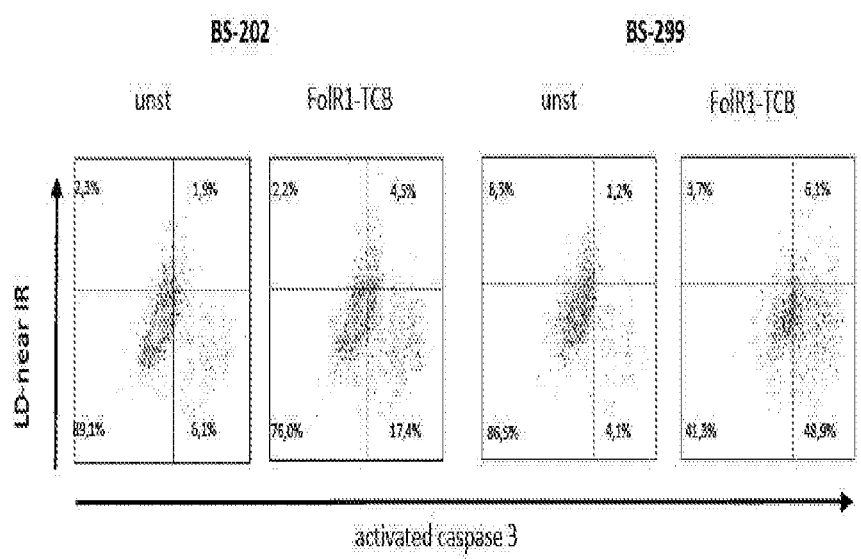

Fig. 18G  Fig. 18H  Fig. 18I
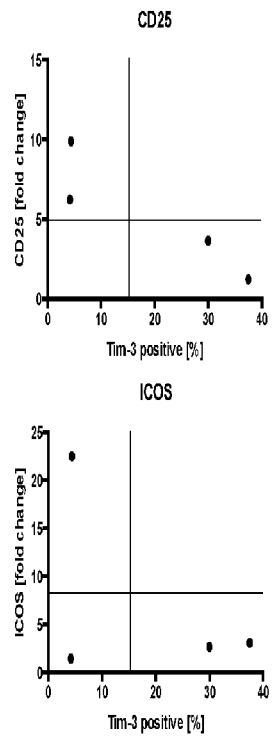
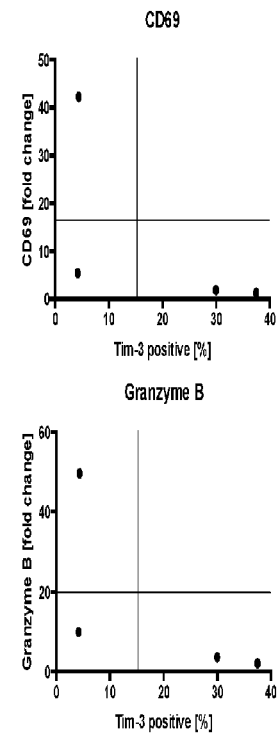
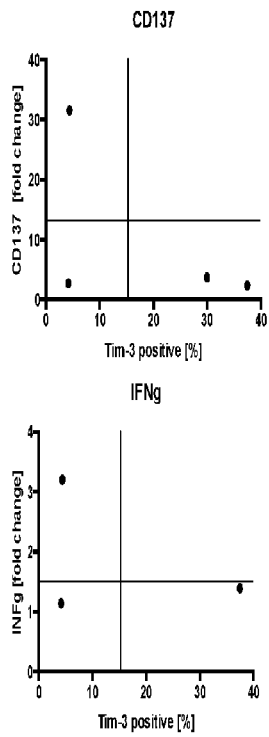
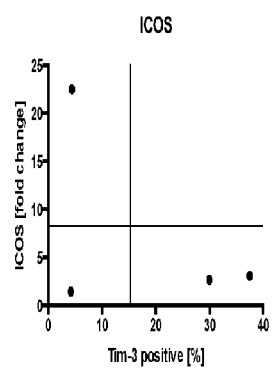
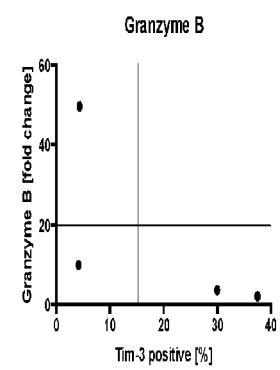
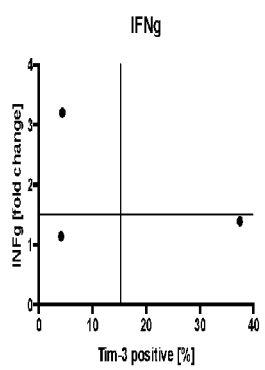
Fig. 18J  Fig. 18K  Fig. 18L Fig. 18M
Fig. 18N
Fig. 18O
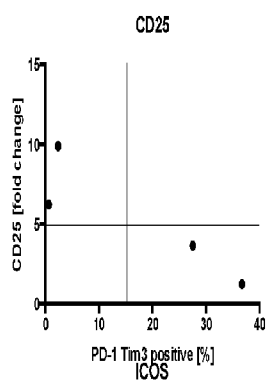
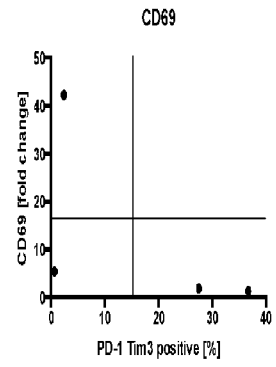
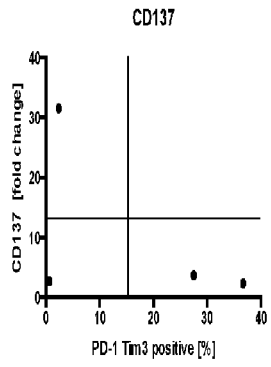
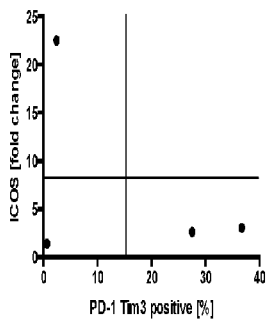
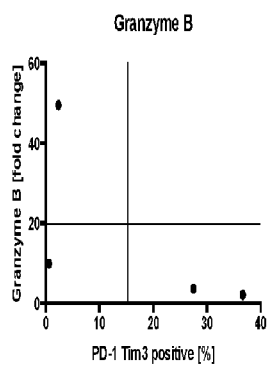
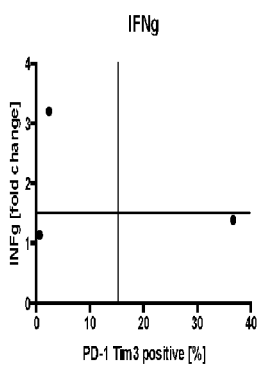
Fig. 18P
Fig. 18Q
Fig. 18R

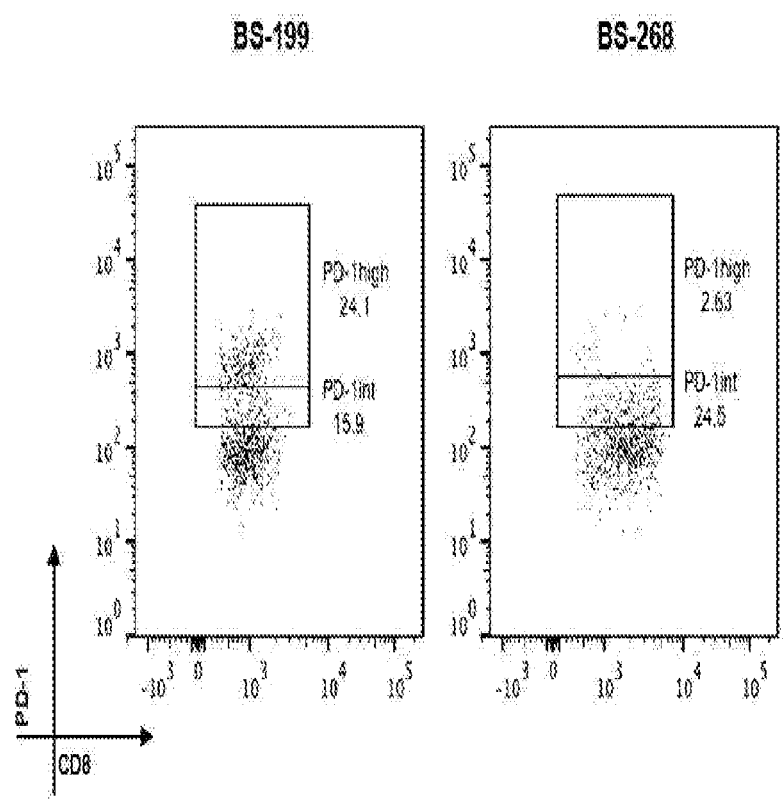

Fig. 25A 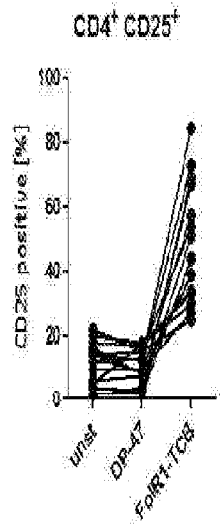 Fig. 25B 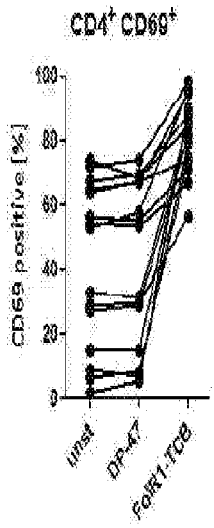 Fig. 25C 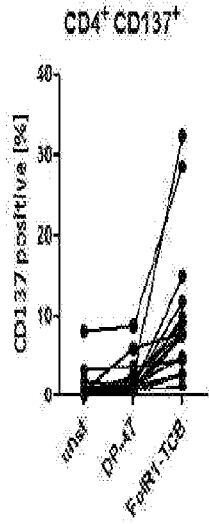 Fig. 25D 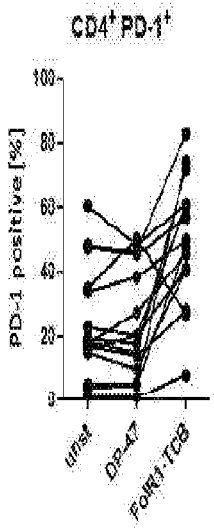 Fig. 25E 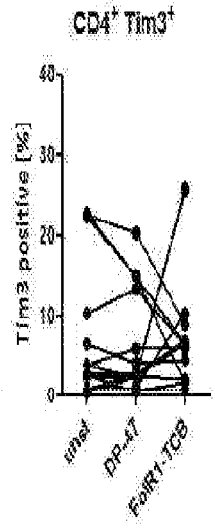
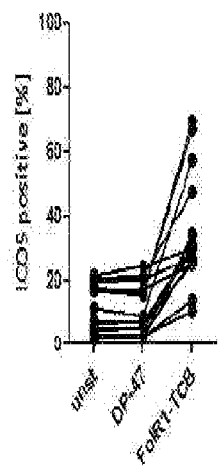 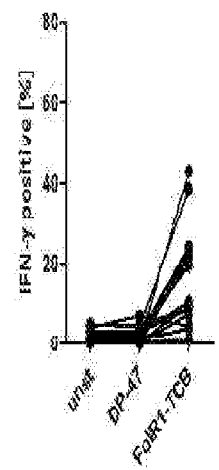 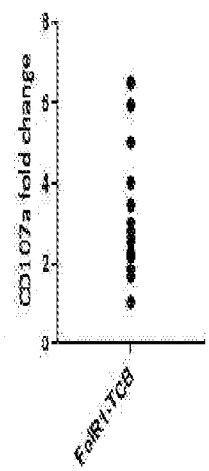 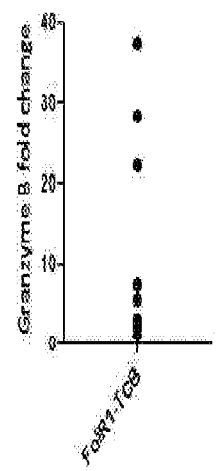
Fig. 25F  Fig. 25G  Fig. 25H  Fig. 25I

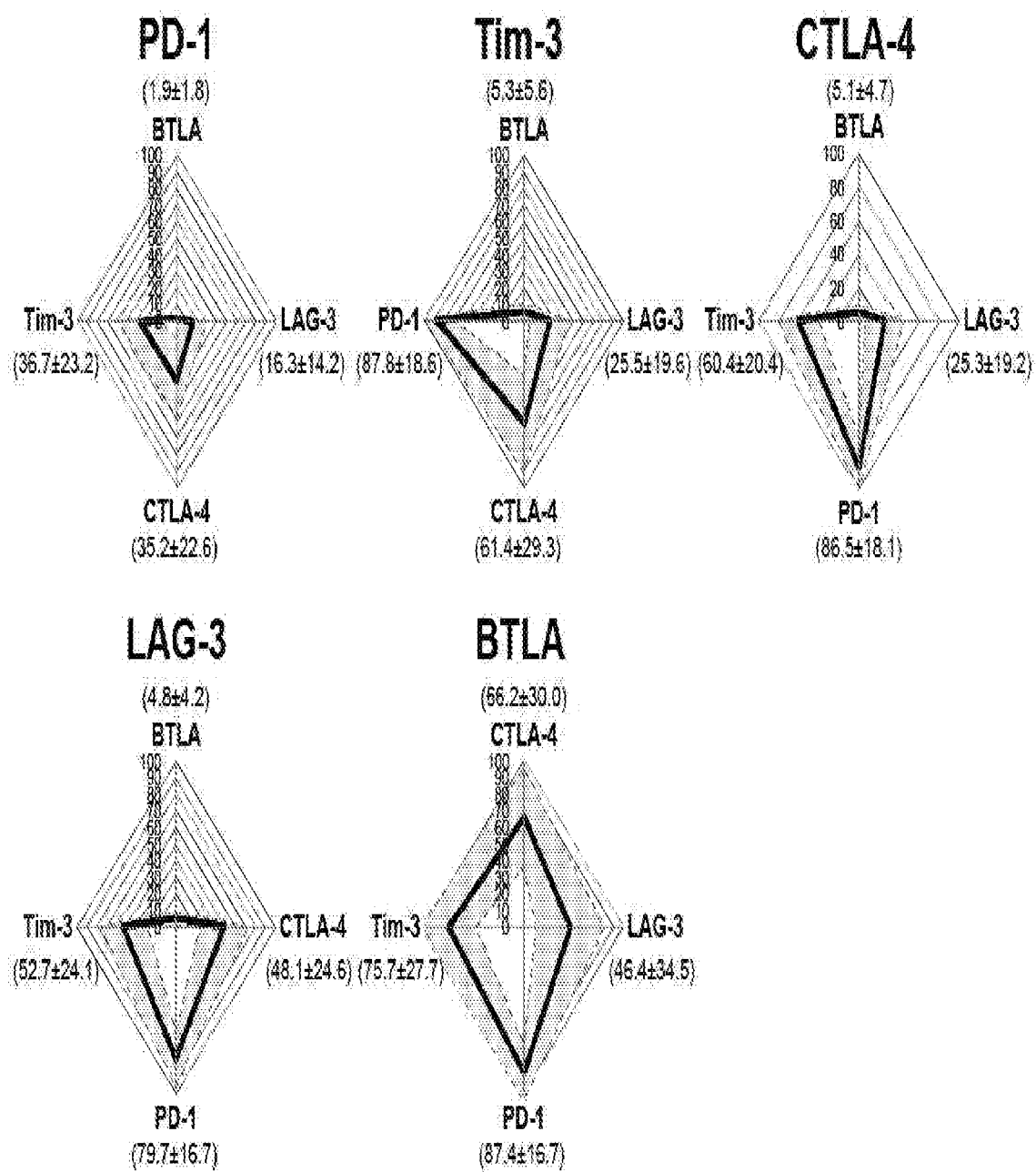

Fig. 34A 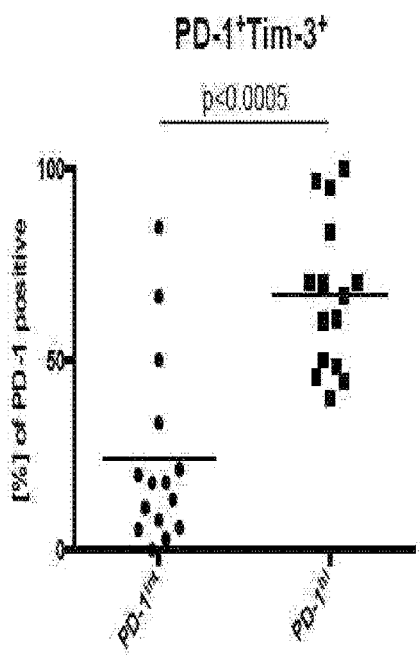 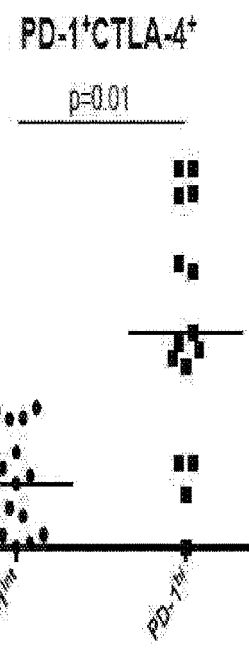 Fig. 34B
Fig. 34C 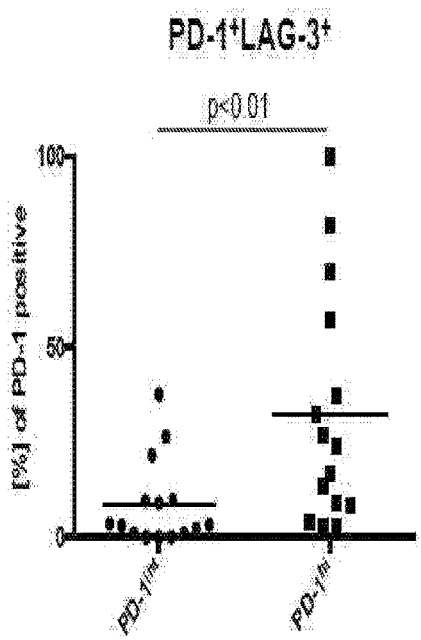 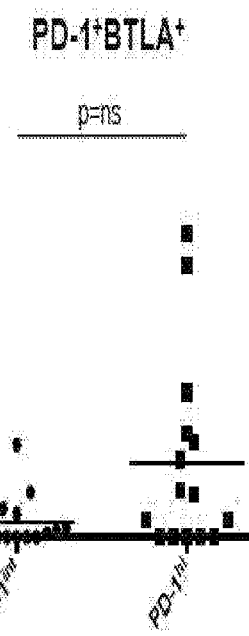 Fig. 34D Fig. 35A
Fig. 35B
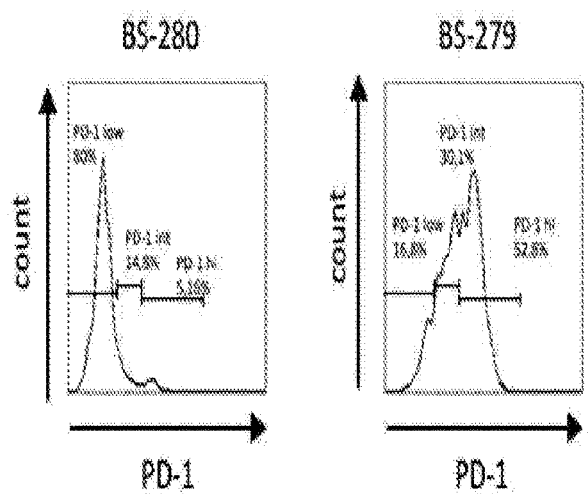
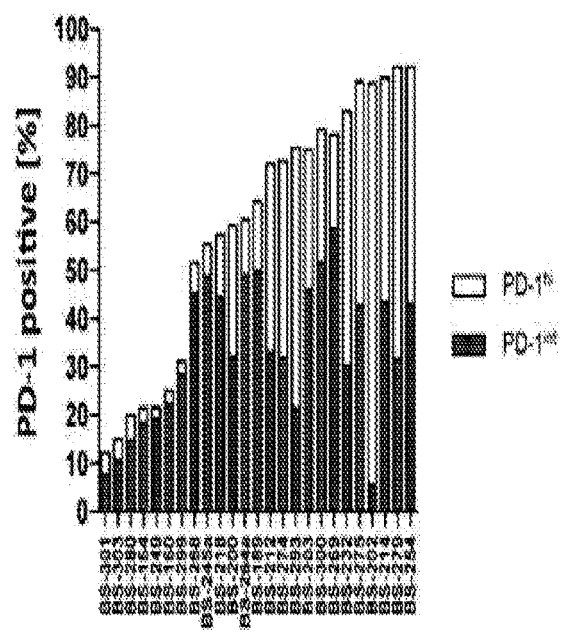

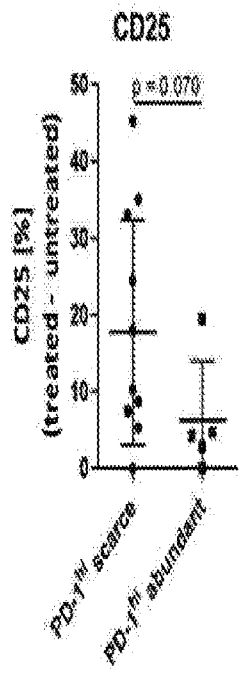
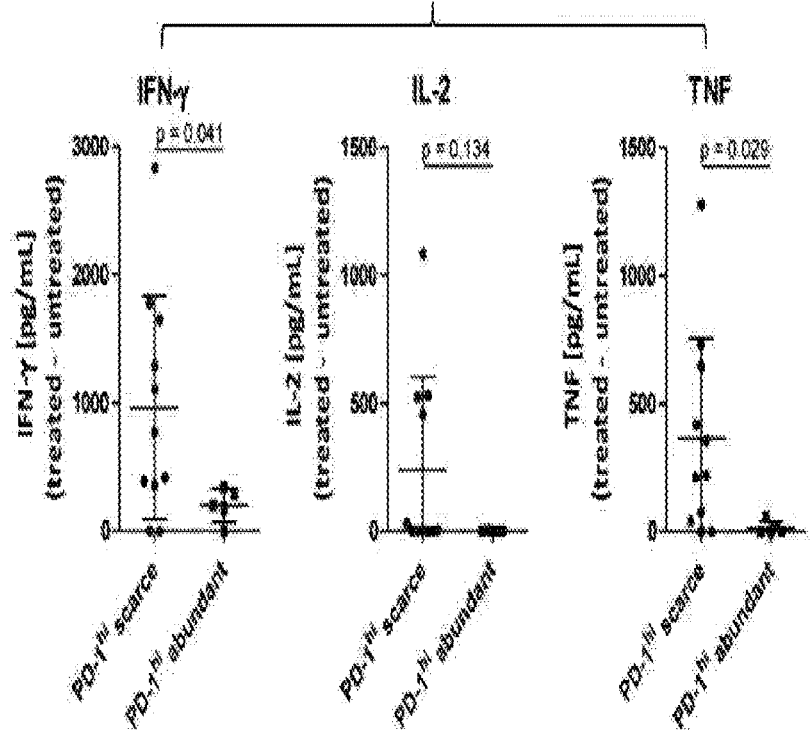
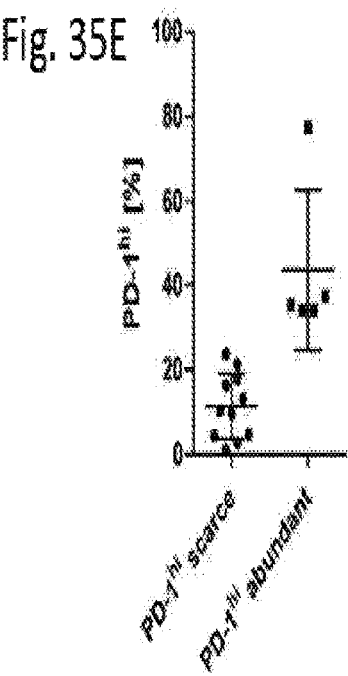
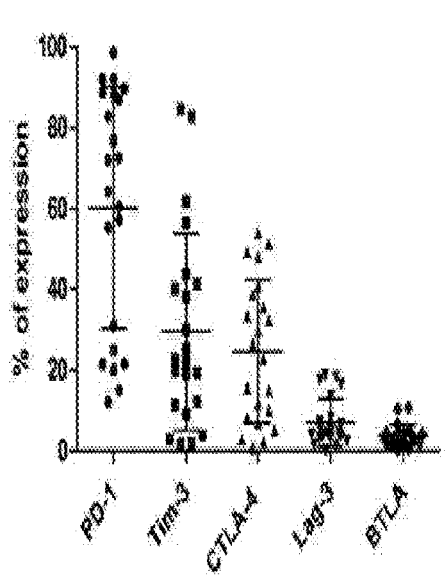

Fig. 36A
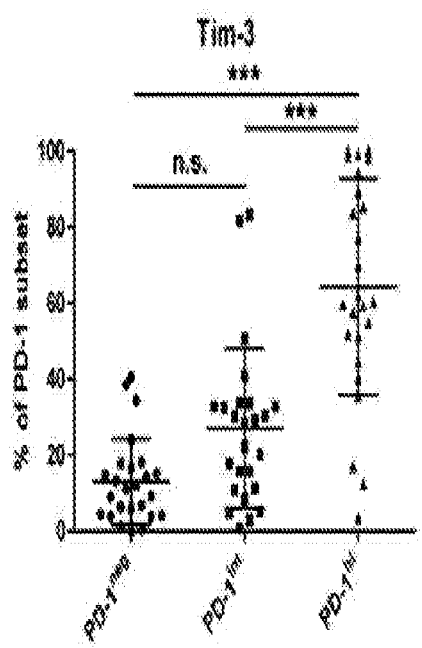
Fig. 36C
Fig. 36B
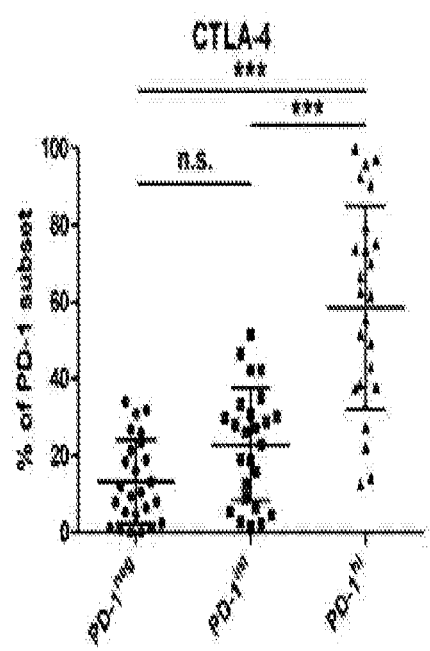
Fig. 36D
Fig. 36E
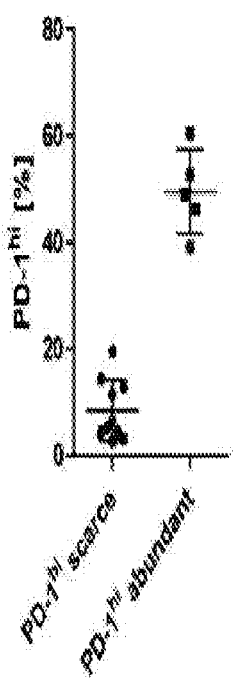
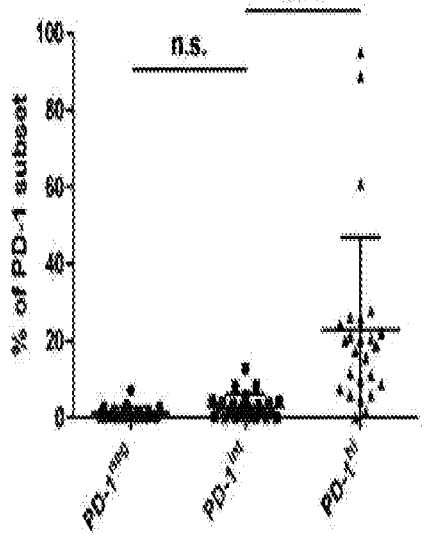
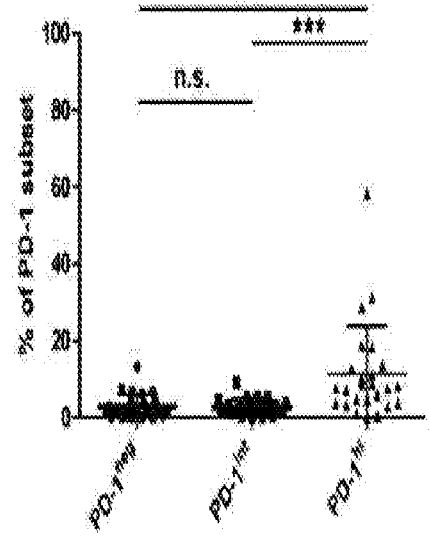

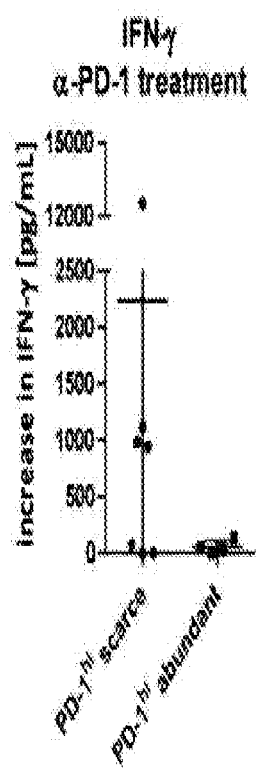 Fig. 38A IFN-γ α-PD-1 treatment
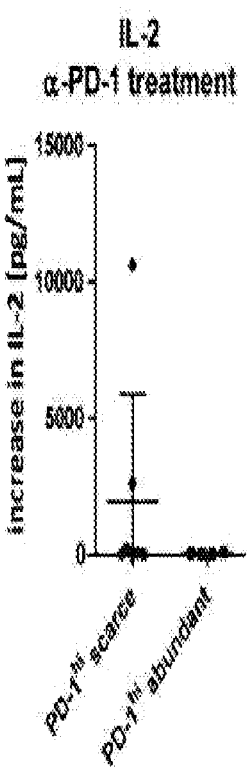 Fig. 38B IL-2 α-PD-1 treatment
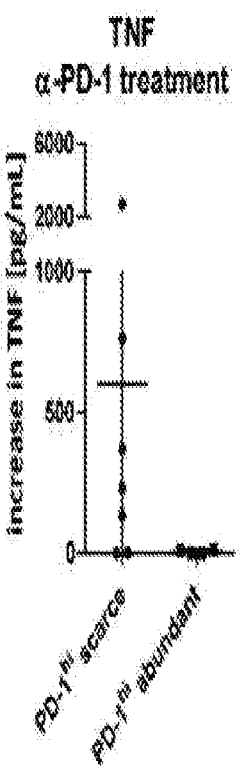 Fig. 38C TNF α-PD-1 treatment
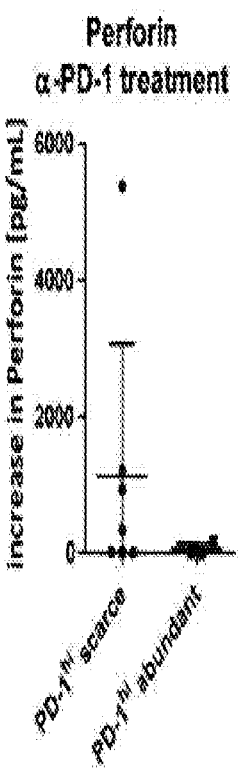 Fig. 38D Perforin α-PD-1 treatment
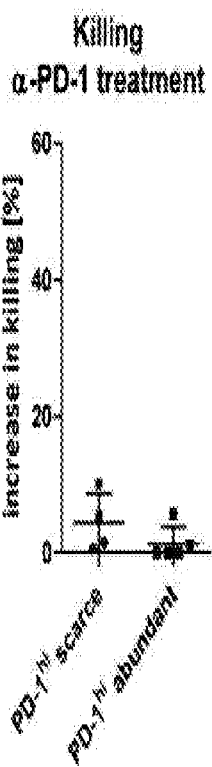 Fig. 38E Killing α-PD-1 treatment

Fig. 39

| Patient-ID | Cancer type | Histopathology | Material | Gender | Age [y] | CD3+ [%] | CD8+ [% of CD3+] | CD4+ [% of CD3+] | FolR1+ [%] | FolR1 [MFI] |
|---|---|---|---|---|---|---|---|---|---|---|
| BS-160 | ovarian cancer | endometrioid adenocarcinoma | pleural effusion | female | 30 | 20.9 | 12.2 | 81.8 | 12.1 | 14300 |
| BS-164 | lung cancer | squamous cell carcinoma | pericardial effusion | male | 71 | 35.2 | 33.2 | 62.3 | 33.8 | 1348 |
| BS-189 | lung cancer | adenocarcinoma | resected tumor | male | 78 | 14.7 | 34.1 | 54.2 | 4.7 | 1981 |
| BS-190 | lung cancer | squamous cell carcinoma | resected tumor | female | 76 | 49.2 | 31.5 | 57.6 | 0.0 | |
| BS-201 | lung cancer | undifferentiated carcinoma | pleural effusion | male | 81 | 16.2 | 56.8 | 32 | 0.0 | |
| BS-203 | lung cancer | adenocarcinoma | pleural effusion | male | 68 | 16.4 | 38.3 | 50.9 | 0.0 | |
| BS-212 | ovarian cancer | serous adenocarcinoma | ascites | female | 66 | 7.95 | 57.7 | 33.2 | 48.7 | 6121 |
| BS-214 | renal cancer | clear cell carcinoma | resected tumor | male | 63 | 35.8 | 63.6 | 15.9 | 18.9 | 4408 |
| BS-218 | ovarian cancer | serous adenocarcinoma | resected tumor | female | 55 | 36.3 | 55.2 | 39.3 | 21.3 | 3927 |
| BS-232 | lung cancer | squamous cell carcinoma | resected tumor | male | 71 | 52.7 | 54.4 | 38.1 | 0.8 | 335 |
| BS-245n | ovarian cancer | serous adenocarcinoma | resected tumor | female | 67 | 16.7 | 26.8 | 66.3 | 20.4 | 7880 |
| BS-249 | renal cancer | clear cell carcinoma | pleural effusion | female | 58 | 9.4 | 28.1 | 50.1 | 0.0 | - |
| BS-254 | lung cancer | adenocarcinoma | resected tumor | male | 68 | 62.7 | 41.3 | 48.9 | 0.6 | 8786 |
| BS-264n | ovarian cancer | serous adenocarcinoma | resected tumor | female | 53 | 34.3 | 43.7 | 44.2 | 5.9 | 2041 |
| BS-268 | lung cancer | adenocarcinoma | resected tumor | male | 63 | 30.3 | 51.1 | 43.0 | 0.5 | 10463 |
| BS-269 | lung cancer | adenocarcinoma | resected tumor | male | 61 | 41.6 | 45.1 | 46.5 | 3.2 | 1836 |
| BS-274 | lung cancer | NOS | resected tumor | male | 81 | 49 | 42.5 | 47.5 | 0.0 | |
| BS-275 | lung cancer | squamous cell carcinoma | resected tumor | female | 84 | 36.4 | 48.9 | 41.7 | 0.0 | |
| BS-279 | lung cancer | large cell carcinoma | resected tumor | male | 87 | 51.3 | 40.4 | 59.5 | 0.3 | 33.8 |
| BS-280 | lung cancer | adenocarcinoma | pleural effusion | female | 60 | 49.2 | 20.8 | 70.3 | 2.9 | 41.8 |
| BS-293 | lung cancer | squamous cell carcinoma | resected tumor | male | 49 | 87.5 | 68.6 | 28.5 | 0.3 | 119 |
| BS-299 | lung cancer | adenocarcinoma | pleural effusion | male | 86 | 38.8 | 13.8 | 84 | 0.0 | |
| BS-300 | lung cancer | adenocarcinoma | resected tumor | male | 74 | 15.5 | 25.7 | 69.8 | 0.4 | 2943 |
| BS-301 | ovarian cancer | serous adenocarcinoma | pleural effusion | female | 73 | 17.8 | 14.4 | 80.7 | 25.9 | 1045 |
| BS-303 | ovarian cancer | serous adenocarcinoma | pleural effusion | female | 55 | 22 | 32.7 | 61.7 | 6.6 | 5405 |

COMBINATION THERAPY OF T CELL ACTIVATING BISPECIFIC ANTIGEN BINDING MOLECULES AND PD-1 AXIS BINDING ANTAGONISTS

CROSS REFERENCE TO RELATED APPLICATIONS

This application is a divisional of U.S. patent application Ser. No. 15/600,011, filed May 19, 2017, which is a continuation of International Application No. PCT/EP2015/076682, filed Nov. 16, 2015, which claims priority to European Patent Application No. 15167173.2, filed May 5, 2015, European Patent Application No. 15152141.6, filed Jan. 22, 2015, and European Patent Application No. 14194136.9, filed Nov. 20, 2014.

SEQUENCE LISTING

The instant application contains a Sequence Listing which has been submitted electronically in ASCII format and is hereby incorporated by reference in its entirety. Said ASCII copy, created on May 18, 2017, is named 51177-012002_Sequence_Listing_8.6.20_ST25.txt and is 527, 213 bytes in size.

FIELD OF THE INVENTION

The present invention relates to combination therapies employing T cell activating bispecific antigen binding molecule and a PD-1 axis binding antagonist, and, optionally, a TIM3 antagonist, and the use of these combination therapies for the treatment of cancer.

BACKGROUND

Monoclonal antibodies are powerful therapeutic agents for the treatment of cancer that selectively target antigens which are differentially expressed on cancer cells.

Bispecific antibodies designed to bind with one antigen binding moiety to a surface antigen on target cells, and with the second antigen binding moiety to an activating, invariant component of the T cell receptor (TCR) complex, have become of interest in recent years. The simultaneous binding of such an antibody to both of its targets will force a temporary interaction between target cell and T cell, causing activation of any cytotoxic T cell and subsequent lysis of the target cell. Hence, the immune response is re-directed to the target cells and is independent of peptide antigen presentation by the target cell or the specificity of the T cell as would be relevant for normal MHC-restricted activation of CTLs. In this context it is crucial that CTLs are only activated when a target cell is presenting the bispecific antibody to them, i.e., the immunological synapse is mimicked. Particularly desirable are bispecific antibodies that do not require lymphocyte preconditioning or co-stimulation in order to elicit efficient lysis of target cells. It is not well understood how TCBs affect the T cell itself beyond activation of certain effector function.

Activation of resting T lymphocytes, or T cells, by antigen-presenting cells (APCs) appears to require two signal inputs. Lafferty et al, Aust. J. Exp. Biol. Med. ScL 53: 27-42 (1975). The primary, or antigen specific, signal is transduced through the T-cell receptor (TCR) following recognition of foreign antigen peptide presented in the context of the major histocompatibility-complex (MHC). The second, or co-stimulatory, signal is delivered to T-cells by co-stimulatory molecules expressed on antigen-presenting cells (APCs), and promotes T-cell clonal expansion, cytokine secretion and effector function. Lenschow et al., Ann. Rev. Immunol. 14:233 (1996). In the absence of co-stimulation, T cells can become refractory to antigen stimulation, do not mount an effective immune response, and may result in exhaustion or tolerance to foreign antigens.

T cells can receive both positive and negative secondary co-stimulatory signals. The balance of positive and negative signals is important to elicit effective immune responses, while maintaining immune tolerance and preventing autoimmunity. Negative secondary signals appear necessary for induction of T-cell tolerance, while positive signals promote T cell activation.

Recently, it has been discovered that T cell dysfunction or anergy occurs concurrently with an induced and sustained expression of the inhibitory receptor, programmed death 1 polypeptide (PD-1). One of its ligands, PD-L1 is overexpressed in many cancers and is often associated with poor prognosis (Okazaki T et al., Intern. Immun. 2007 19(7):813) (Thompson R H et al., Cancer Res 2006, 66(7):3381). Interestingly, the majority of tumor infiltrating T lymphocytes predominantly express PD-1, in contrast to T lymphocytes in normal tissues and peripheral blood T lymphocytes indicating that up-regulation of PD-1 on tumor-reactive T cells can contribute to impaired antitumor immune responses (Blood 2009 1 14(8): 1537).

T cell Immunoglobulin- and Mucin domain-containing molecule 3 (TIM3), is important in immune regulation. This cell surface protein is expressed, preferentially, by type 1 T helper cells and has been implicated in the regulation of macrophage activation, inflammatory conditions and cancer (Majeti R et al., PNAS, 106 (2009) 3396-3401 and WO2009/091547). Binding of TIM-3 to one of its ligands (e.g., galectin-9) can suppress the Th1 response by inducing programmed cell death, thereby supporting peripheral tolerance. Treatment with TIM-3 siRNA or with an anti-TIM-3 antagonist antibody increases secretion of interferon alpha from CD4 positive T-cells, supporting the inhibitory role of TIM-3 in human T cells. Examples of the anti-TIM-3 monoclonal antibodies include are disclosed in WO2013/06490 and US2012/189617 (Ngiow et al., Cancer Res 7:6567 (2011)).

FOLR1 is expressed on tumor cells of various origins, e.g., ovarian and lung cancer. Several approaches to target FOLR1 with therapeutic antibodies, such as farletuzumab, antibody drug conjugates, or adoptive T cell therapy for imaging of tumors have been described (Kandalaft et al., J Transl Med. 2012 Aug. 3; 10:157. doi: 10.1186/1479-5876-10-157; van Dam et al., Nat Med. 2011 Sep. 18; 17(10): 1315-9. doi: 10.1038/nm.2472; Clifton et al., Hum Vaccin. 2011 February; 7(2):183-90. Epub 2011 Feb. 1; Kelemen et al., Int J Cancer. 2006 Jul. 15; 119(2):243-50; Vaitilingam et al., J Nucl Med. 2012 July; 53(7); Teng et al., 2012 August; 9(8):901-8. doi: 10.1517/17425247.2012.694863. Epub 2012 Jun. 5. Some attempts have been made to target folate receptor-positive tumors with constructs that target the folate receptor and CD3 (Kranz et al., Proc Natl Acad Sci USA. Sep. 26, 1995; 92(20): 9057-9061; Roy et al., Adv Drug Deliv Rev. 2004 Apr. 29; 56(8):1219-31; Huiting Cui et al Biol Chem. Aug. 17, 2012; 287(34): 28206-28214; Lamers et al., Int. J. Cancer. 60(4):450 (1995); Thompson et al., MAbs. 2009 July-August; 1(4):348-56. Epub 2009 Jul. 19; Mezzanzanca et al., Int. J. Cancer, 41, 609-615 (1988).

There remains a need for such an optimal therapy for treating, stabilizing, preventing, and/or delaying development of various cancers.

SUMMARY

Broadly, the present invention relates to bispecific antibodies combining a Folate Receptor 1 (FolR1) targeting antigen binding site with a second antigen binding site that targets CD3 and their use in combination with a PD-1 axis binding antagonist, e.g., for the treatment of cancer. In one embodiment, the combination further comprises a TIM3 antagonist. The methods and combinations of the present invention enable enhanced immunotherapy. The advantage over conventional treatment is the specificity of inducing T cell activation only at the site where FolR1 is expressed as well as the reduction and/or reversal of low T cell mediated activity also termed T cell exhaustion due to the combination with a PD-1 axis binding antagonist, and, optionally, a TIM3 antagonist.

Accordingly, in one aspect, the present invention provides a method for treating or delaying progression of a cancer in an individual comprising administering to the individual an effective amount of a T cell activating bispecific antigen binding molecule and a PD-1 axis binding antagonist. In one embodiment, the T cell activating bispecific antigen binding molecule comprises a first antigen binding moiety capable of specific binding to CD3 and a second antigen binding moiety capable of specific binding to Folate Receptor 1 (FolR1). In one embodiment, the first antigen binding moiety comprises at least one heavy chain complementarity determining region (CDR) amino acid sequence selected from the group consisting of SEQ ID NO: 37, SEQ ID NO: 38 and SEQ ID NO: 39 and at least one light chain CDR selected from the group of SEQ ID NO: 32, SEQ ID NO: 33, SEQ ID NO: 34. In one embodiment, the first antigen binding moiety comprises a variable heavy chain comprising an amino acid sequence of SEQ ID NO: 36 and a variable light chain comprising an amino acid sequence of SEQ ID NO: 31. In one embodiment, the T cell activating bispecific antigen binding molecule further comprises a third antigen binding moiety capable of specific binding to FolR1. In one embodiment, the second and third antigen binding moiety capable of specific binding to FolR1 comprise identical heavy chain complementarity determining region (CDR) and light chain CDR sequences. In one embodiment, the third antigen binding moiety is identical to the second antigen binding moiety. In one embodiment, at least one of the first, second and third antigen binding moiety is a Fab molecule.

In one embodiment, the antigen binding moiety capable of specific binding to Folate Receptor 1 (FolR1) comprises at least one heavy chain complementarity determining region (CDR) amino acid sequence selected from the group consisting of SEQ ID NO: 16, SEQ ID NO: 17 and SEQ ID NO: 18 and at least one light chain CDR selected from the group of SEQ ID NO: 32, SEQ ID NO: 33, SEQ ID NO: 34. In one embodiment, the antigen binding moiety capable of specific binding to Folate Receptor 1 (FolR1) comprises a variable heavy chain comprising an amino acid sequence of SEQ ID NO: 15 and a variable light chain comprising an amino acid sequence of SEQ ID NO: 31. In one embodiment, the antigen binding moiety capable of specific binding to Folate Receptor 1 (FolR1) comprises at least one heavy chain complementarity determining region (CDR) amino acid sequence selected from the group consisting of SEQ ID NO: 8, SEQ ID NO: 56 and SEQ ID NO: 57 and at least one light chain CDR selected from the group of SEQ ID NO: 59, SEQ ID NO: 60, SEQ ID NO: 65. In one embodiment, the antigen binding moiety capable of specific binding to Folate Receptor 1 (FolR1) comprises a variable heavy chain comprising an amino acid sequence of SEQ ID NO: 55 and a variable light chain comprising an amino acid sequence of SEQ ID NO: 64. In one embodiment, the antigen binding moiety capable of specific binding to Folate Receptor 1 (FolR1) comprises at least one heavy chain complementarity determining region (CDR) amino acid sequence selected from the group consisting of SEQ ID NO: 8, SEQ ID NO: 9 and SEQ ID NO: 50 and at least one light chain CDR selected from the group of SEQ ID NO: 52, SEQ ID NO: 53, SEQ ID NO: 54. In one embodiment, the antigen binding moiety capable of specific binding to FolR1 comprises:

a) a complementarity determining region heavy chain 1 (CDR-H1) amino acid sequences of SEQ ID NO: 8;
    (b) a CDR-H2 amino acid sequence of SEQ ID NO: 9;
    (c) a CDR-H3 amino acid sequence of SEQ ID NO: 50;
    (d) a complementarity determining region light chain 1 (CDR-L1) amino acid sequence of SEQ ID NO: 52;
    (e) a CDR-L2 amino acid sequence of SEQ ID NO: 53, and
    (f) a CDR-L3 amino acid sequence of SEQ ID NO: 54.

In one such embodiment, the antigen binding moiety capable of specific binding to FolR1 comprises a variable heavy chain comprising an amino acid sequence of SEQ ID NO: 49 and a variable light chain comprising an amino acid sequence of SEQ ID NO: 51.

In one embodiment, the T cell activating bispecific antigen binding molecule binds to a human FolR1, a cynomolgus monkey FolR1 and a murine FolR1.

In one embodiment, the T cell activating bispecific antigen binding molecule induces proliferation of a human CD3 positive T cell in vitro.

In one embodiment, the T cell activating bispecific antigen binding molecule induces human peripheral blood mononuclear cell mediated killing of a FolR1-expressing human tumor cell in vitro.

In one embodiment, the T cell activating bispecific antigen binding molecule induces T cell mediated killing of a FolR1-expressing human tumor cell in vitro. In one embodiment, the T cell activating bispecific antigen binding molecule induces T cell mediated killing of the FolR1-expressing human tumor cell in vitro with an EC50 of between about 36 pM and about 39573 pM after 24 hours. In one embodiment, the T cell activating bispecific antigen binding molecule induces upregulation of cell surface expression of at least one of CD25 and CD69 on the T cell as measured by flow cytometry. In one embodiment, the T cell activating bispecific antigen binding molecule binds human FolR1 with an apparent $K_D$ of about 5.36 pM to about 4 nM. In one embodiment, the T cell activating bispecific antigen binding molecule binds human and cynomolgus FolR1 with an apparent $K_D$ of about 4 nM. In one embodiment, the T cell activating bispecific antigen binding molecule binds murine FolR1 with an apparent $K_D$ of about 1.5 nM. In one embodiment, the T cell activating bispecific antigen binding molecule binds human FolR1 with a monovalent binding $K_D$ of at least about 1000 nM. In one embodiment, the T cell activating bispecific antigen binding molecule binds to FolR1 expressed on a human tumor cell. In one embodiment, the T cell activating bispecific antigen binding molecule binds to a conformational epitope on human FolR1. In one embodiment, the T cell activating bispecific antigen binding molecule does not bind to human Folate Receptor 2 (FolR2) or to human Folate Receptor 3 (FolR3). In one embodiment, the antigen binding moiety binds to a FolR1 polypeptide comprising the amino acids 25 to 234 of human FolR1 (SEQ ID NO:227). In one embodiment, the FolR1 antigen binding moiety binds to a FolR1 polypeptide comprising the amino acid sequence of SEQ ID NOs:227, 230 and 231, and wherein the FolR1 antigen binding moiety does not bind to a FolR polypeptide comprising the amino acid sequence of SEQ ID NOs:228 and 229. In one embodiment, the T cell activating bispecific antigen binding molecule comprises a) a first antigen-binding site that competes for binding to human FolR1 with a reference antibody comprising a variable heavy chain domain (VH) of SEQ ID NO: 49 and a variable light chain domain of SEQ ID NO: 51; and b) a second antigen-binding site that competes for binding to human CD3 with a reference antibody comprising a variable heavy chain domain (VH) of SEQ ID NO: 36 and a variable light chain domain of SEQ ID NO: 31, wherein binding competition is measured using a surface plasmon resonance assay.

In one embodiment, the T cell activating bispecific antigen binding molecule comprises a first, a second, a third, a fourth and a fifth polypeptide chain that form a first, a second and a third antigen binding moiety, wherein the first antigen binding moiety is capable of binding CD3 and the second and the third antigen binding moiety each are capable of binding Folate Receptor 1 (FolR1), wherein a) the first and the second polypeptide chain comprise, in amino (N)-terminal to carboxyl (C)-terminal direction, VLD1 and CLD1; b) the third polypeptide chain comprises, in N-terminal to C-terminal direction, VLD2 and CH1D2; c) the fourth polypeptide chain comprises, in N-terminal to C-terminal direction, VHD1, CH1D1, CH2D1 and CH3D1; d) the fifth polypeptide chain comprises VHD1, CH1D1, VHD2, CLD2, CH2D2 and CH3D2; wherein VLD1 is a first light chain variable domain
VLD2 is a second light chain variable domain
CLD1 is a first light chain constant domain
CLD2 is a second light chain constant domain
VHD1 is a first heavy chain variable domain
VHD2 is a second heavy chain variable domain
CH1D1 is a first heavy chain constant domain 1
CH1D2 is a second heavy chain constant domain 1
CH2D1 is a first heavy chain constant domain 2
CH2D2 is a second heavy chain constant domain 2
CH3D1 is a first heavy chain constant domain 3
CH3D2 is a second heavy chain constant domain 3.

In one such embodiment,
a. the third polypeptide chain and VHD2 and CLD2 of the fifth polypeptide chain form the first antigen binding moiety capable of binding CD3;
b. the first polypeptide chain and VHD1 and CH1D1 of the fourth polypeptide chain form the second binding moiety capable of binding to FolR1; and
c. the second polypeptide chain and VHD1 and CH1D1 of the fifth polypeptide chain form the third binding moiety capable of binding to FolR1.

In one such embodiment, the first and second polypeptide chain comprise the amino acid sequence of SEQ ID NO:399. In one such embodiment, the third polypeptide chain comprises the amino acid sequence of SEQ ID NO:86. In one such embodiment, the fourth polypeptide chain comprises the amino acid sequence of SEQ ID NO:394. In one such embodiment, the fifth polypeptide chain comprises the amino acid sequence of SEQ ID NO:397. In one embodiment,
a. the first and second polypeptide chain comprise the amino acid sequence of SEQ ID NO:399;
b. the third polypeptide chain comprises the amino acid sequence of SEQ ID NO:86;
c. the fourth polypeptide chain comprises the amino acid sequence of SEQ ID NO:394; and
d. the fifth polypeptide chain comprise the amino acid sequence of SEQ ID NO:397.

In some embodiments, the bispecific antibody is bivalent both for FolR1 and CD3.

In some embodiments, the bispecific antibody comprises one or more Fab fragment(s) comprising an antigen binding site specific for CD3, wherein the variable regions or the constant regions of the heavy and light chain are exchanged.

In some embodiments, the bispecific antibody comprises an Fc domain, at least one Fab fragment comprising the antigen binding site specific for FolR1, and at least one Fab fragment comprising the antigen binding site specific for CD3 wherein either the variable regions or the constant regions of the heavy and light chain of at least one Fab fragment are exchanged.

In some embodiments, the bispecific antibody comprises:
a) an Fc domain,
b) a first and second Fab fragment each comprising an antigen binding site specific for FolR1,
c) a third Fab fragment comprising an antigen binding site specific for CD3, wherein the third Fab fragment is connected at the C-terminus of the variable heavy chain (VH) to the second subunit of the Fc domain and wherein the third Fab fragment is connected at the N-terminus of the variable heavy chain to the C-terminus of the second Fab fragment.

In one embodiment at least one of said Fab fragments is connected to the Fc domain via a peptide linker.

In one embodiment said bispecific antibody comprises an Fc domain, which comprises one or more amino acid substitution that reduces binding to Fc receptors and/or effector function. In one embodiment said one or more amino acid substitution is at one or more positions selected from the group of L234, L235, and P329. In one embodiment each subunit of the Fc domain comprises three amino acid substitutions that abolish binding to an activating or inhibitory Fc receptor and/or effector function wherein said amino acid substitutions are L234A, L235A and P329G.

In some embodiments, the PD-1 axis binding antagonist is selected from the group consisting of a PD-1 binding antagonist, a PDL1 binding antagonist and a PDL2 binding antagonist.

In some embodiments, the PD-1 axis binding antagonist is a PD-binding antagonist. In some embodiments, the PD-1 binding antagonist inhibits the binding of PD-1 to its ligand binding partners. In some embodiments, the PD-1 binding antagonist inhibits the binding of PD-1 to PDL1. In some embodiments, the PD-binding antagonist inhibits the binding of PD-1 to PDL2. In some embodiments, the PD-1 binding antagonist inhibits the binding of PD-1 to both PDL1 and PDL2. In some embodiments, PD-1 binding antagonist is an antibody. In some embodiments, the anti-PD-1 antibody is a monoclonal antibody. In some embodiments, the anti-PD-1 antibody is an antibody fragment selected from the group consisting of Fab, Fab'-SH, Fv, scFv, and (Fab')2 fragments. In some embodiments, PD-1 binding antagonist is nivolumab, pembrolizumab, CT-011, or AMP-224.

In some embodiments, the PD-1 axis binding antagonist is a PDL1 binding antagonist. In some embodiments, the PDL1 binding antagonist inhibits the binding of PDL1 to PD-1. In some embodiments, the PDL1 binding antagonist inhibits the binding of PDL1 to B7-1. In some embodiments, the PDL1 binding antagonist inhibits the binding of PDL1 to both PD-1 and B7-1. In some embodiments, the PDL1 binding antagonist is an anti-PDL1 antibody. In some embodiments, the anti-PDL1 antibody is a monoclonal antibody. In some embodiments, the anti-PDL1 antibody is an antibody fragment selected from the group consisting of Fab, Fab'-SH, Fv, scFv, and (Fab')2 fragments. In some embodiments, the anti-PDL1 antibody is a humanized antibody or a human antibody. In some embodiments, the PDL1 binding antagonist is selected from the group consisting of: YW243.55.S70, MPDL3280A, MDX-1105, and MEDI4736.

In some embodiments, the anti-PDL1 antibody comprises a heavy chain comprising HVR-H1 sequence of SEQ ID NO:289, HVR-H2 sequence of SEQ ID NO:290, and HVR-H3 sequence of SEQ ID NO:291; and a light chain comprising HVR-L1 sequence of SEQ ID NO:292, HVR-L2 sequence of SEQ ID NO:293, and HVR-L3 sequence of SEQ ID NO:294. In some embodiments, anti-PDL1 antibody comprises a heavy chain variable region comprising the amino acid sequence of SEQ ID NO:280 or SEQ ID NO:281 and a light chain variable region comprising the amino acid sequence of SEQ ID NO:383. In some embodiments, the anti-PDL1 antibody comprises a heavy chain comprising the amino acid sequence of SEQ ID NO:278 and/or a light chain comprising the amino acid sequence of SEQ ID NO:279.

In some embodiments, the PD-1 axis binding antagonist is a PDL2 binding antagonist. In some embodiments, PDL2 binding antagonist is an antibody. In some embodiments, the anti-PDL2 antibody is a monoclonal antibody. In some embodiments, the anti-PDL2 antibody is an antibody fragment selected from the group consisting of Fab, Fab'-SH, Fv, scFv, and (Fab')2 fragments. In some embodiments, PDL2 binding antagonist is an immunoadhesin.

In one embodiment, the method of any of the above embodiments further comprises administering to the individual a T cell immunoglobulin mucin 3 (TIM3) antagonist. In one embodiment, the TIM3 antagonist is an anti-TIM3 antibody. In one embodiment, the anti-TIM3 antibody induces internalization of TIM3 on a TIM3 expressing cell of at least 45% after 120 Minutes at 37° C. wherein internalization is measured by FACS analysis. In one embodiment, the anti-TIM3 antibody has one or more of the following properties:
    a) competes for binding to TIM3 with an anti-Tim3 antibody comprising the VH of SEQ ID NO:7 and VL of SEQ ID NO: 8
    b) binds to a human and cynomolgoues TIM3
    c) shows as immunoconjugate a cytotoxic activity on TIM3 expressing cells
    d) induces interferon-gamma release.

In one embodiment, the anti-TIM3 antibody has one or more of the following properties:
    a. competes for binding to TIM3 with an anti-Tim3 antibody comprising the VH of SEQ ID NO:7 and VL of SEQ ID NO: 8
    b. binds to a human and cynomolgoues TIM3
    c. shows as immunoconjugate a cytotoxic activity on TIM3 expressing cells
    d. induces interferon-gamma release.

In one embodiment, the anti-TIM3 antibody is a monoclonal antibody. In one embodiment, the anti-TIM3 antibody is a human, humanized, or chimeric antibody. In one embodiment, the anti-TIM3 antibody is an antibody fragment that binds to TIM3. In one embodiment, the anti-TIM3 antibody is Fab fragment. In one embodiment, the anti-TIM3 antibody comprises:
    A) (a) a VH domain comprising (i) HVR-H1 comprising the amino acid sequence of SEQ ID NO:304, (ii) HVR-H2 comprising the amino acid sequence of SEQ ID NO:305, and (iii) HVR-H3 comprising an amino acid sequence selected from SEQ ID NO:306; and (b) a VL domain comprising (i) HVR-L1 comprising the amino acid sequence of SEQ ID NO:307; (ii) HVR-L2 comprising the amino acid sequence of SEQ ID NO:308 and (iii) HVR-L3 comprising the amino acid sequence of SEQ ID NO:309; or
    B) (a) a VH domain comprising (i) HVR-H1 comprising the amino acid sequence of SEQ ID NO:304, (ii) HVR-H2 comprising the amino acid sequence of SEQ ID NO:305, and (iii) HVR-H3 comprising an amino acid sequence selected from SEQ ID NO:306; and (b) a VL domain comprising (i) HVR-L1 comprising the amino acid sequence of SEQ ID NO:314; (ii) HVR-L2 comprising the amino acid sequence of SEQ ID NO:308 and (iii) HVR-L3 comprising the amino acid sequence of SEQ ID NO:309; or
    C) (a) a VH domain comprising (i) HVR-H1 comprising the amino acid sequence of SEQ ID NO:304, (ii) HVR-H2 comprising the amino acid sequence of SEQ ID NO:305, and (iii) HVR-H3 comprising an amino acid sequence selected from SEQ ID NO:306; and (b) a VL domain comprising (i) HVR-L1 comprising the amino acid sequence of SEQ ID NO:315; (ii) HVR-L2 comprising the amino acid sequence of SEQ ID NO:308 and (iii) HVR-L3 comprising the amino acid sequence of SEQ ID NO:309; or
    D) (a) a VH domain comprising (i) HVR-H1 comprising the amino acid sequence of SEQ ID NO:316, (ii) HVR-H2 comprising the amino acid sequence of SEQ ID NO:317, and (iii) HVR-H3 comprising an amino acid sequence selected from SEQ ID NO:318; and (b) a VL domain comprising (i) HVR-L1 comprising the amino acid sequence of SEQ ID NO:319; (ii) HVR-L2 comprising the amino acid sequence of SEQ ID NO:320 and (iii) HVR-L3 comprising the amino acid sequence of SEQ ID NO:321; or
    E) (a) a VH domain comprising (i) HVR-H1 comprising the amino acid sequence of SEQ ID NO:324, (ii) HVR-H2 comprising the amino acid sequence of SEQ ID NO:325, and (iii) HVR-H3 comprising an amino acid sequence selected from SEQ ID NO:326; and (b) a VL domain comprising (i) HVR-L1 comprising the amino acid sequence of SEQ ID NO:327; (ii) HVR-L2 comprising the amino acid sequence of SEQ ID NO:328 and (iii) HVR-L3 comprising the amino acid sequence of SEQ ID NO:329; or.
    F) (a) a VH domain comprising (i) HVR-H1 comprising the amino acid sequence of SEQ ID NO:332, (ii) HVR-H2 comprising the amino acid sequence of SEQ ID NO:333, and (iii) HVR-H3 comprising an amino acid sequence selected from SEQ ID NO:334; and (b) a VL domain comprising (i) HVR-L1 comprising the amino acid sequence of SEQ ID NO:335; (ii) HVR-L2 comprising the amino acid sequence of SEQ ID NO:336 and (iii) HVR-L3 comprising the amino acid sequence of SEQ ID NO:337; or
    G) (a) a VH domain comprising (i) HVR-H1 comprising the amino acid sequence of SEQ ID NO:340, (ii) HVR-H2 comprising the amino acid sequence of SEQ ID NO:341, and (iii) HVR-H3 comprising an amino acid sequence selected from SEQ ID NO:342; and (b) a VL domain comprising (i) HVR-L1 comprising the amino acid sequence of SEQ ID NO:343; (ii) HVR-L2 comprising the amino acid sequence of SEQ ID NO:344 and (iii) HVR-L3 comprising the amino acid sequence of SEQ ID NO:345; or H) (a) a VH domain comprising (i) HVR-H1 comprising the amino acid sequence of SEQ ID NO:348, (ii) HVR-H2 comprising the amino acid sequence of SEQ ID NO:349, and (iii) HVR-H3 comprising an amino acid sequence selected from SEQ ID NO:350; and (b) a VL domain comprising (i) HVR-L1 comprising the amino acid sequence of SEQ ID NO:351; (ii) HVR-L2 comprising the amino acid sequence of SEQ ID NO:352 and (iii) HVR-L3 comprising the amino acid sequence of SEQ ID NO:353; or I) (a) a VH domain comprising (i) HVR-H1 comprising the amino acid sequence of SEQ ID NO:356, (ii) HVR-H2 comprising the amino acid sequence of SEQ ID NO:357, and (iii) HVR-H3 comprising an amino acid sequence selected from SEQ ID NO:358; and (b) a VL domain comprising (i) HVR-L1 comprising the amino acid sequence of SEQ ID NO:359; (ii) HVR-L2 comprising the amino acid sequence of SEQ ID NO:360 and (iii) HVR-L3 comprising the amino acid sequence of SEQ ID NO:361; or J) (a) a VH domain comprising (i) HVR-H1 comprising the amino acid sequence of SEQ ID NO:364, (ii) HVR-H2 comprising the amino acid sequence of SEQ ID NO:365, and (iii) HVR-H3 comprising an amino acid sequence selected from SEQ ID NO:366; and (b) a VL domain comprising (i) HVR-L1 comprising the amino acid sequence of SEQ ID NO:367; (ii) HVR-L2 comprising the amino acid sequence of SEQ ID NO:368 and (iii) HVR-L3 comprising the amino acid sequence of SEQ ID NO:369.

In one embodiment, the anti-TIM3 antibody is a full length IgG1 antibody with mutations S228P, L235E and P329G according to the EU index of Kabat numbering. In one embodiment, the anti-TIM3 antibody is any one of the antibodies described in WO 2011/155607, WO 2013/006490, WO 03/063792, WO 2009/097394, and WO 2011/159877. In one embodiment, the anti-TIM3 antibody is F38-2E2.

In one embodiment, the cancer contains a KRAS wild-type. In one embodiment, the cancer contains an activating KRAS mutation.

In one embodiment, the treatment results in a sustained response in the individual after cessation of the treatment. In one embodiment, at least one of the T cell activating bispecific antigen binding molecule and the PD-1 axis binding antagonist is administered continuously. In one embodiment, at least one of the T cell activating bispecific antigen binding molecule and the PD-1 axis binding antagonist is administered intermittently. In one embodiment, the PD-1 axis binding antagonist is administered before the FolR1 TCB. In one embodiment, the PD-1 axis binding antagonist is administered simultaneous with the FolR1 TCB. In one embodiment, the PD-1 axis binding antagonist is administered after the FolR1 TCB. In one embodiment, the cancer is selected from the group consisting of ovarian cancer, lung cancer, breast cancer, renal cancer, colorectal cancer, endometrial cancer. In one embodiment, at least one of the T cell activating bispecific antigen binding molecule and the PD-1 axis binding antagonist is administered intravenously, intramuscularly, subcutaneously, topically, orally, transdermally, intraperitoneally, intraorbitally, by implantation, by inhalation, intrathecally, intraventricularly, or intranasally.

In one embodiment, T cells in the individual have enhanced activation, proliferation and/or effector function relative to prior to the administration of the combination. In one embodiment, T cells in the individual have enhanced activation, proliferation and/or effector function relative to administration of the T cell activating bispecific antigen binding molecule alone. In one embodiment, T cell effector function is secretion of at least one of IL-2, IFN-γ and TNF-α. In one embodiment, the individual comprises less than about 15% PD-1$^{hi}$ expressing tumor-infiltrating T cells.

In one aspect, the invention provides for a method of enhancing immune function in an individual having a FolR1 positive cancer comprising administering to the individual an effective amount of a combination of a T cell activating bispecific antigen binding molecule specific for Folate Receptor 1 (FolR1) and CD3, and a PD-1 axis binding antagonist. In one embodiment, T cells in the individual have enhanced activation, proliferation and/or effector function relative to prior to the administration of the combination. In one embodiment, T cells in the individual have enhanced activation, proliferation and/or effector function relative to administration of the T cell activating bispecific antigen binding molecule alone. In one embodiment, T cell effector function is secretion of at least one of IL-2, IFN-γ and TNF-α.

In one embodiment, the individual comprises less than about 15% PD-1$^{hi}$ expressing tumor-infiltrating T cells.

In another aspect, the invention provides for a method of selecting a patient for treatment with a combination of a T cell activating bispecific antigen binding molecule specific for Folate Receptor 1 (FolR1) and CD3, and a PD-1 axis binding antagonist comprising measuring the level of PD-1 expression, wherein a patient having less than about 15% PD-1$^{hi}$ expressing T cells is selected for treatment with the combination.

In another aspect, the invention provides for a kit comprising a T cell activating bispecific antigen binding molecule specific for Folate Receptor 1 (FolR1) and CD3, and a package insert comprising instructions for using the T cell activating bispecific antigen binding molecule with a PD-1 axis binding antagonist to treat or delay progression of cancer in an individual. In one embodiment, the kit further comprises instructions for using the T cell activating bispecific antigen binding molecule with a TIM3 antagonist.

In another aspect, the invention provides for a kit comprising a T cell activating bispecific antigen binding molecule specific for Folate Receptor 1 (FolR1) and CD3 and a PD-1 axis binding antagonist, and a package insert comprising instructions for using the T cell activating bispecific antigen binding molecule and the PD-1 axis binding antagonist to treat or delay progression of cancer in an individual. In one embodiment, the kit further comprises a TIM3 antagonist. In one embodiment, the PD-1 axis binding antagonist is an anti-PD-1 antibody or an anti-PDL-1 antibody. In one embodiment, the PD-1 axis binding antagonist is an anti-PD-1 immunoadhesin.

In another aspect, the invention provides for a pharmaceutical composition comprising a T cell activating bispecific antigen binding molecule specific for Folate Receptor 1 (FolR1) and CD3, a PD-1 axis binding antagonist and a pharmaceutically acceptable carrier. In one embodiment, the pharmaceutical composition further comprises a TIM3 antagonist.

In another aspect, the invention provides for a use of a combination of a T cell activating bispecific antigen binding molecule specific for Folate Receptor 1 (FolR1) and CD3 and a PD-1 axis binding antagonist in the manufacture of a medicament for the treatment of cancer. In one embodiment, the medicament is for treatment of ovarian cancer, lung cancer, breast cancer, renal cancer, colorectal cancer, endometrial cancer.

In certain embodiments of all aspects of the present invention, advantageously said T cell activating bispecific antigen binding molecule and/or PD-1 axis binding antagonist is human or humanized.

In some embodiments, the bispecific antibody comprises an Fc domain, at least one Fab fragment comprising the antigen binding site specific for FolR1, and at least one Fab fragment comprising the antigen binding site specific for CD3.

In one aspect, the invention provides for a method for treating or delaying progression of a cancer in an individual comprising administering to the individual an effective amount of a T cell activating bispecific antigen binding molecule and a TIM3 antagonist. In some embodiments, the T cell activating bispecific antigen binding molecule comprises an Fc domain, two Fab fragments comprising each an antigen binding site specific for FolR1, and one Fab fragment comprising an antigen binding site specific for CD3.

In a further aspect, the present invention provides the use of a combination of a T cell activating bispecific antigen binding molecule that binds to FolR1 and CD3, and a PD-1 axis binding antagonist in the manufacture of a medicament for the treatment of cancer.

In a further aspect, the present invention provides the use of a combination of a T cell activating bispecific antigen binding molecule that binds to FolR1 and CD3, a PD-1 axis binding antagonist and a TIM3 antagonist in the manufacture of a medicament for the treatment of cancer.

Embodiments of the present invention will now be described by way of example and not limitation with reference to the accompanying figures. However various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

BRIEF DESCRIPTION OF THE FIGURES

FIGS. 1A-I illustrate exemplary configurations of the T cell activating bispecific antigen binding molecules (TCBs) of the invention. All constructs except the kappa-lambda format in (FIG. 1I) have P329G LALA mutations and comprise knob-into-hole Fc fragments with knob-into-hole modifications. (FIG. 1A) Illustration of the "FolR1 TCB 2+1 inverted (common light chain)". The FolR1 binder is fused at the C-terminus of the Fab heavy chain to the N-terminus of the first subunit of the Fc domain comprising the knob modification. These constructs are not crossed and have three times the same VLCL light chain. (FIG. 1B) Illustration of the "FolR1 TCB 1+1 head-to-tail (common light chain)". These constructs are not crossed and have two times the same VLCL light chain. (FIG. 1C) Illustration of the "FolR1 TCB 1+1 classical (common light chain)". These constructs are not crossed and have two times the same VLCL light chain. (FIG. 1D) Illustration of the "FolR1 TCB 2+1 classical (common light chain)". The CD3 binder is fused at the C-terminus of the Fab heavy chain to the N-terminus of the first subunit of the Fc domain comprising the knob modification. These constructs are not crossed and have three times the same VLCL light chain. (FIG. 1E) Illustration of the "FolR1 TCB 2+1 crossfab classical". These constructs comprise a Ck-VH chain for the CD3 binder instead of the conventional CH1-VH chain. The CD3 binder is fused at the C-terminus of the Fab heavy chain to the N-terminus of the first subunit of the Fc domain comprising the knob modification. (FIG. 1F) Illustration of the "FolR1 TCB 2+1 crossfab inverted". These constructs comprise a Ck-VH chain for the CD3 binder instead of the conventional CH1-VH chain. The FolR1 binder is fused at the C-terminus of the Fab heavy chain to the N-terminus of the first subunit of the Fc domain comprising the knob modification. (FIG. 1G) Illustration of the "FolR1 TCB 1+1 crossfab head-to-tail". These constructs comprise a Ck-VH chain for the CD3 binder instead of the conventional CH1-VH chain. (FIG. 1H) Illustration of the "FolR1 TCB 1+1 crossfab classical". These constructs comprise a Ck-VH chain for the CD3 binder instead of the conventional CH1-VH chain. FIG. 1I illustrates the CD3/FolR1 kappa-lambda antibody format. These constructs comprise a crossed common light chain VLCH1 and one crossed VHCL chain specific for CD3 and one crossed VHCL chain specific for FolR1.

FIGS. 4A-B depict graphs summarizing cross-reactivity of FolR1 binders to cyFoLR1. Cross-reactivity of the FolR1 antibodies to cyno FolR1 was addressed on HEK cells transiently transfected with cyFolR1 by flow cytometry. The antibodies were detected with a fluorescently labeled anti-human secondary antibody.

FIGS. 7A-L depict graphs summarizing T cell mediated killing of HT-29 and SKOV3 cells. FolR1 TCBs were used to test T cell mediated killing of HT-29 and SKOV3 tumor cells and upregulation of activation marker on T cells upon killing. (FIGS. 7A-D) T cell mediated killing of HT-29 and SKOV3 cells in the presence of 9D11 FolR1 TCB and 16D5 FolR1 TCB was measured by LDH release after 24 h and 48 h. DP47 TCB was included as negative control. After 48 h incubation upregulation of the activation marker CD25 and CD69 on CD8 T cells and CD4 T cells upon killing of SKOV3 (FIGS. 7E-H) or HT-29 (FIG. 7I-L) tumor cells was assessed by flow cytometry.

FIG. 12O shows that FolR1-TCB-induced tumor cell killing varies largely in tumor digests and malignant effusions. FolR1 positive and negative tumor digests, malignant effusions or PBMCs from healthy donors were co-cultured with exogenously added fluorescently labeled $FolR1^+$ Skov3 cells at an E:T ratio of 1:1 for 24 h in the presence or absence of FolR1-TCB. The FolR1-TCB-induced specific killing of the Skov3 cells was determined by flow cytometry by measuring activated caspase 3 and the live/dead marker LIVE/DEAD®-near-IR. FolR1-TCB-mediated killing was calculated as follows: % specific killing=100−[(% of Skov3 live cells in FolR1-TCB treated sample/% of Skov3 live cells in untreated sample)×100]. FACS plots show FolR1-TCB-induced killing in a representative patient. The p-values were calculated using the unpaired Mann-Whitney test.

FIGS. 14A-L show FolR1-TCB induced T cell activation inversely correlates with expression of PD-1 and Tim-3. Tumor digests or malignant effusions were cultured for 24 h in the presence or absence of FolR1-TCB. The expression of activation markers or markers of T cell function on $CD8^+$ T cells was determined by flow cytometry. The FolR1-TCB induced expression of CD25 (FIG. 4A-C), CD137 (FIG. 14D-F), ICOS (FIG. 14G-I) and granzyme B (FIG. 14J-L) was correlated to baseline single- or co-expression of the inhibitory receptors PD-1 and Tim-3.

FIGS. 16A-F show FolR1-TCB induced tumor cell killing inversely correlates with co-expression of PD-1 and Tim-3. Tumor digests or malignant effusions were co-cultured with exogenously added fluorescence labelled Skov3 cells at a T cell to target cell ratio of 1:1 for 24 h in the presence or absence of FolR1 TCB. The FolR1-TCB specific killing of the Skov3 cells was determined by flow cytometry by measuring activated caspase 3 and the live/dead marker Live/Dead-near-IR. The specific killing was correlated to baseline single or co-expression of the inhibitory receptors PD-1, Tim-3 and CTLA-4.

(FIG. 17A-D) The expression of activation markers or markers of T cell function on $CD8^+$ T cells was determined by flow cytometry. (FIG. 17E-H) Graphs showing the baseline expression of inhibitory receptors.

FIG. 19G shows the gating strategy for one representative donor. FIG. 19H shows results of analysis and heat mapping of indicated cell subsets based on the percentage of expression, with the use of an Excel conditional formatting program.

FIG. 21L-N show increased cumulative expression of inhibitory receptors with tumor progression. The cumulative expression of the inhibitory receptors PD-1, Tim-3, CTLA-4, LAG-3 and BTLA, as represented by the iR score, was correlated to the nodal status and the TNM stage.

FIGS. 23A-E show that the effect of PD-1 or combined PD-1/Tim-3 blockade varies between patients. Digests were stimulated by agonistic anti-CD3/anti-CD28 antibodies with the addition of blocking antibodies to PD-1 alone or in combination with Tim-3. Secretion of IFN-γ, TNF-α and IL-2 was determined by ELISA and normalized to $1 \times 10^6$ T cells. FIG. 23A-C show T cells from a patient where T cell function can be rescued by addition of blocking Abs (BS-268) and T cells from a patient with no response to PD-1 or PD-1/Tim-3 blockade. The difference in expression ([% expression Ab treated]-[% expression untreated]) is shown. FIG. 23D shows respective flow cytometry plots with PD-1$^{hi}$ and PD-1$^{int}$ subsets. FIG. 23E shows a summary of IL-2, TNF-α and IFN-γ secretion by T cells from six patients, as determined by ELISA and normalized to $1 \times 10^6$ CD3$^+$ T cells.

FIGS. 25A-I show activation of CD4$^+$ T cells in tumor digests and malignant effusions upon exposure to FolR1-TCB. Tumor digests or malignant effusions were cultured for 24 h in the presence or absence of FolR1-TCB or the control TCB DP-47. The expression of activation markers or markers of T cell function on CD8$^+$ T cells was determined by flow cytometry.

FIG. 30B shows binding of anti-TIM3 antibodies to Pfeiffer cells (antibody designation clone 0016 refers to antibody Tim3_0016, clone 0016 refers to antibody Tim3_0016 variant (antibody Tim3_0018), clone 0022 refers to antibody Tim3_00122, etc.).

FIG. 33 shows a radar plot of expression of inhibitory receptors on NSCLC associated TILs. Co-expression of inhibitory receptors on tumor-infiltrating CD8$^+$ T-cells positive for the indicated immune checkpoint is shown as a radar plot indicating the mean expression and standard deviation of the four other receptors.

FIGS. 34A-D show the percentage of PD-1$^{hi}$ or PD-1$^{int}$ CD8$^+$ T cells expressing additional immune checkpoints. Each dot represents one patient samples. The p values were calculated using the Wilcoxon rank sum test.

FIGS. 35A-F show intratumoral T cell inhibitory receptor expression and T cell function. FIG. 35A shows the gating strategy for identification of PD-1$^{hi}$, PD-1$^{int}$, and PD-1$^{neg}$ CD8$^+$ subsets of T-cells from two representative patients. FIG. 35B shows distribution of inidicated T cell subsets in the tumor samples analyzed. FIG. 35C shows that T-cell functions induced by anti-CD3/-CD28 stimulation depend on the PD-1 expression level of CD8$^+$ T-cells. Tumor digests and malignant effusions were cultured for 24 h in the presence or absence of agonistic anti-CD3/-CD28 antibodies. The increase in the expression of CD25 on CD8$^+$ T-cells (FIG. 35C) and the increase in the effector cytokines IFN-γ, IL-2, and TNF (FIG. 35D) were determined in PD-1$^{hi}$ scarce and abundant tumors. p-values were calculated using the unpaired Mann-Whitney test. Tumor samples were divided according to the percentage of PD-1$^{hi}$ expressing CD8$^+$ cells in two groups with PD-1$^{hi}$ scarce and abundant expression, respectively (FIG. 35E). The expression level of the inhibitory receptors PD-1, Tim-3, CTLA-4, Lag-3, and BTLA was determined by flow cytometry on CD8$^+$ T-cells from tumor digests or malignant effusions (FIG. 35F).

FIGS. 36A-E show patterns of inhibitory receptor expression and percentage of scarce and abundant CD8$^+$ T-cells. FIG. 36A-D show co-expression of Tim-3, CTLA-4, Lag-3, and BTLA on PD-1$^{hi}$, PD-1$^{int}$, and PD-1$^{neg}$ CD8$^+$ T-cells. The p-values were calculated using one-way ANOVA with Bonferroni post-hoc-test. FIG. 36E: FolR1$^+$ tumor samples were divided according to the percentage of PD-1$^{hi}$ expressing CD8$^+$ cells in two groups with PD-1$^{hi}$ scarce and abundant expression, respectively.

FIG. 37H shows target cell killing. Both FolR1 positive and negative tumor samples were adjusted by addition of the FolR1$^+$ Skov3 cell line to an E:T ratio of 1:1 and killing was compared in PD-1$^{hi}$ scarce and abundant tumors. p-values were calculated using the unpaired Mann-Whitney test.

FIGS. 38A-E show that PD-1 blockade increases cytokine production but not their cytolytic function in T-cells from PD-1$^{hi}$ scarce tumors only. FIG. 38A-D: FolR1$^+$ tumor digests or malignant effusions were cultured for 24 h with FolR1-TCB in the presence or absence of a PD-1 blocking antibody. IFN-γ, IL-2, TNF, and perforin in the cell culture supernatants were determined by Cytometric Bead Array or ELISA and normalized to the amount of 1×10$^5$ CD3$^+$ T-cells (IFN-γ, IL-2, TNF, FIG. 38A-C) or CD3$^+$CD8$^+$ T-cells (perforin, FIG. 38D). The increase in cytokine secretion upon combined FolR1-TCB and anti-PD-1 treatment compared with FolR1-TCB alone was determined in PD-1$^{hi}$ scarce and abundant tumors. FIG. 38E: Tumor digests or malignant effusions were co-cultured with exogenously added fluorescently labeled Skov3 cells at an E:T ratio of 1:1 for 24 h in the presence or absence of a PD-1 blocking antibody and FolR1-TCB. The increase in specific killing by the anti-PD-1 antibody was compared in PD-1$^{hi}$ scarce and abundant tumors. p-values were calculated using the unpaired Mann-Whitney test.

FIG. 39 shows detailed patient characteristics.

FIG. 40A shows the expression of FolR1 on Skov3. Shaded histogram: isotype control; open histogram: anti-FolR1-antibody. FIG. 40B: The expression of the activation markers CD25, CD137, and ICOS on CD8$^+$ T-cells was determined by flow cytometry. FIG. 40C: IFN-v. IL-2, and TNF in the cell culture supernatants were determined by ELISA and normalized to the amount of 1×10$^5$ CD3$^+$ T-cells.

DETAILED DESCRIPTION OF EMBODIMENTS OF THE INVENTION

I. Definitions

Figure 1A:
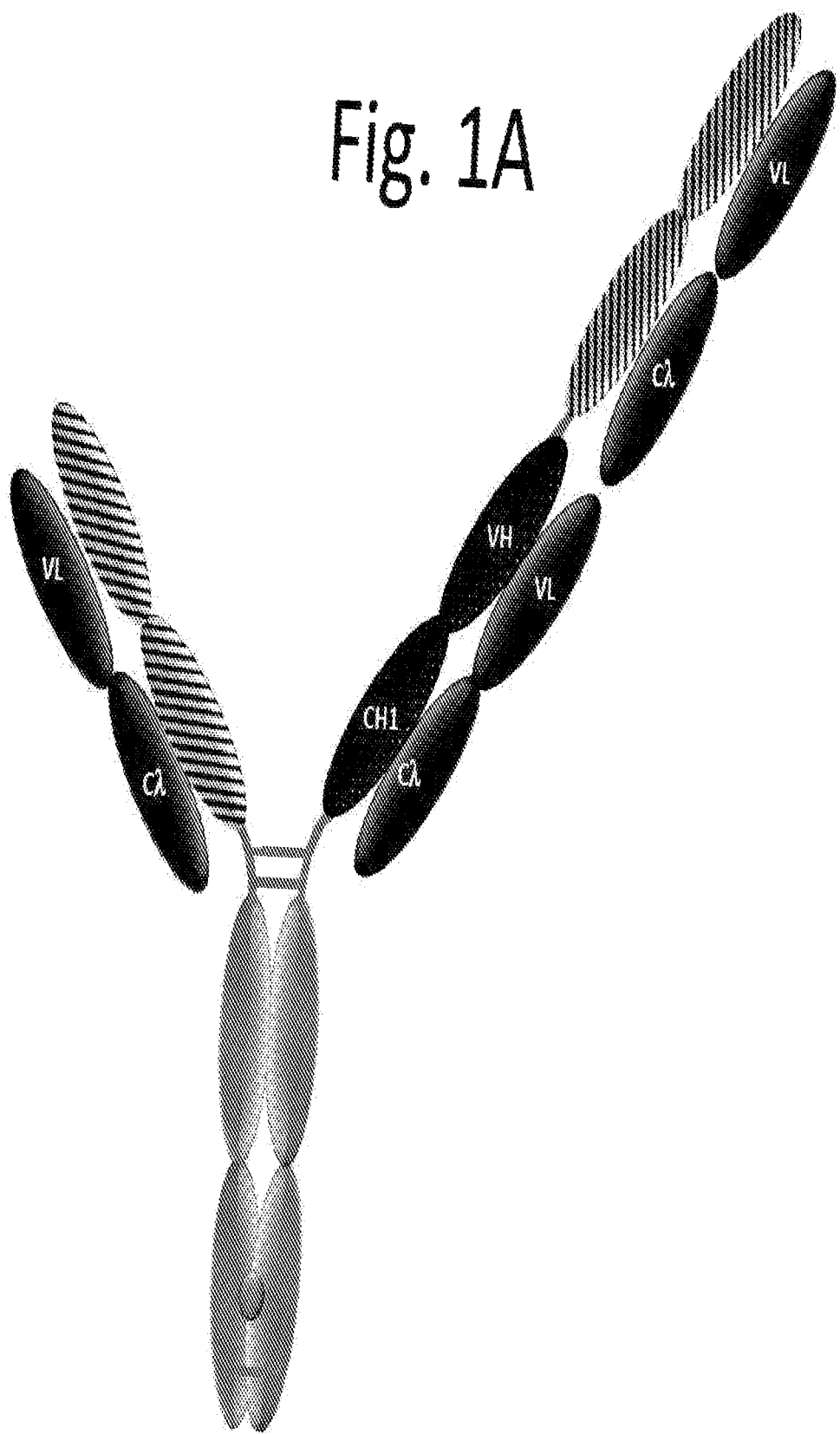
Figure 1B:
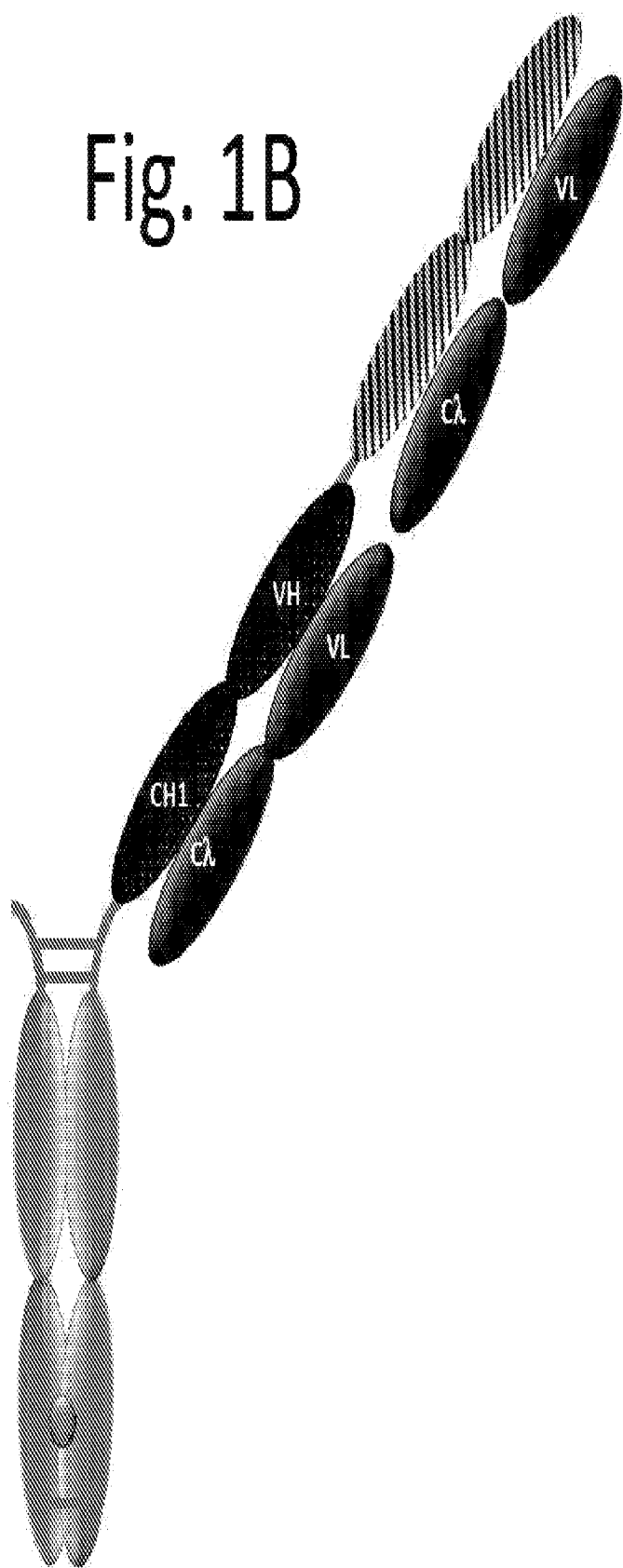
Figure 1C:
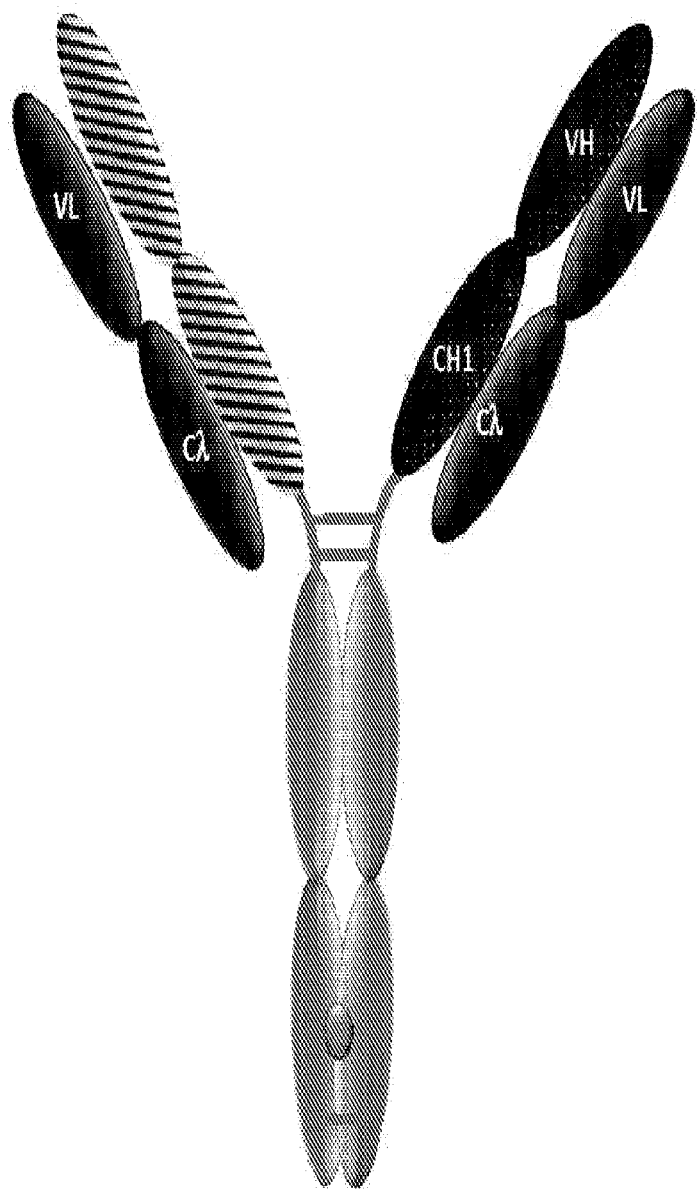
Figure 1E:
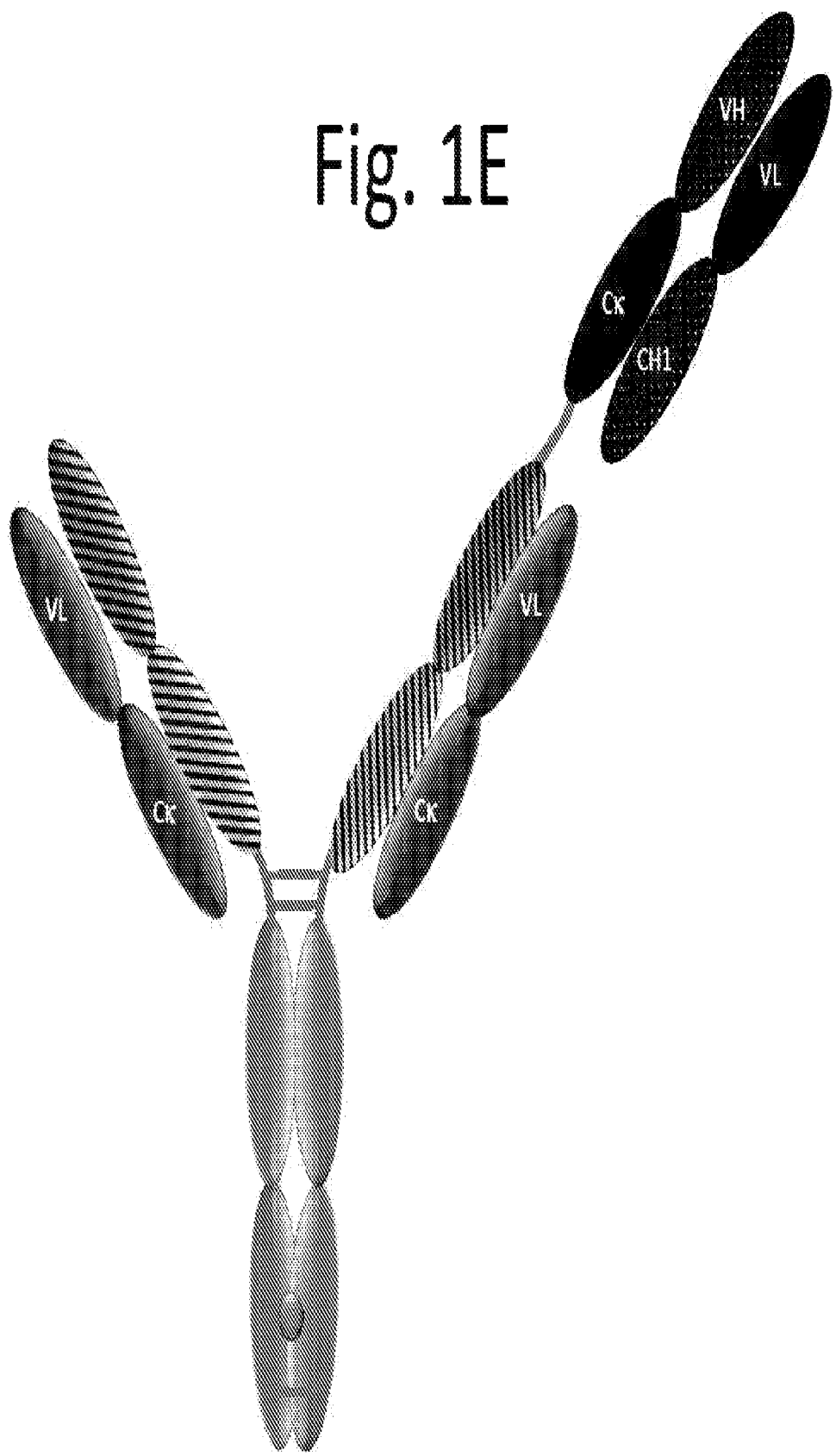
Figure 1F:
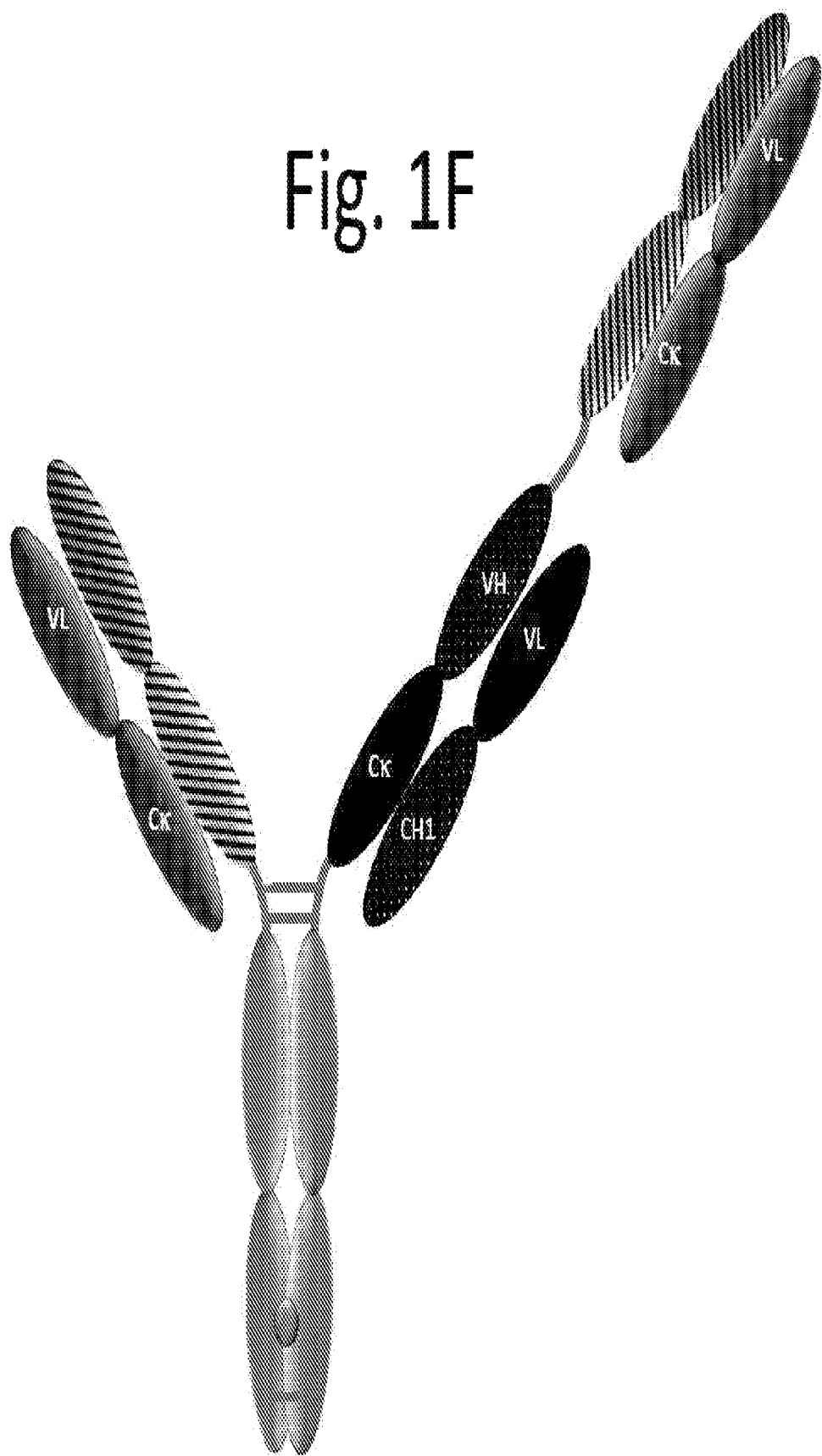
Figure 1G:
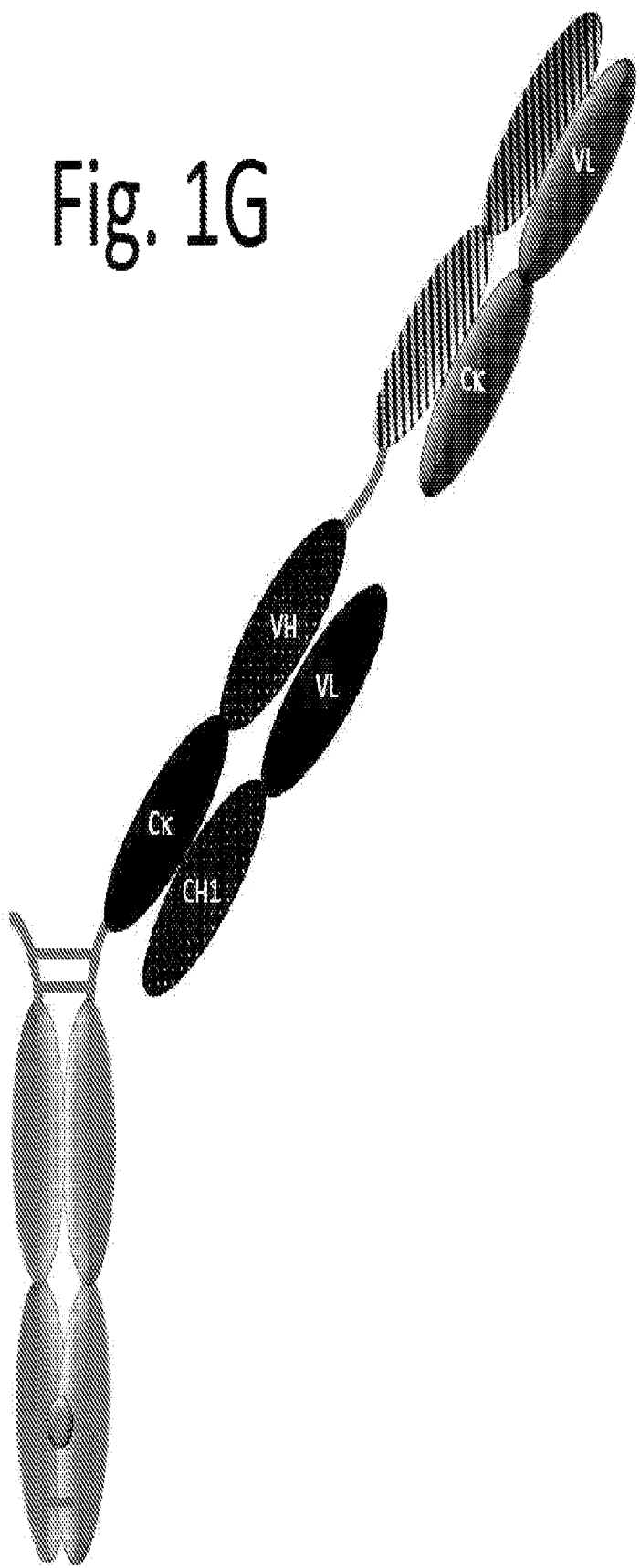
Figure 1H:
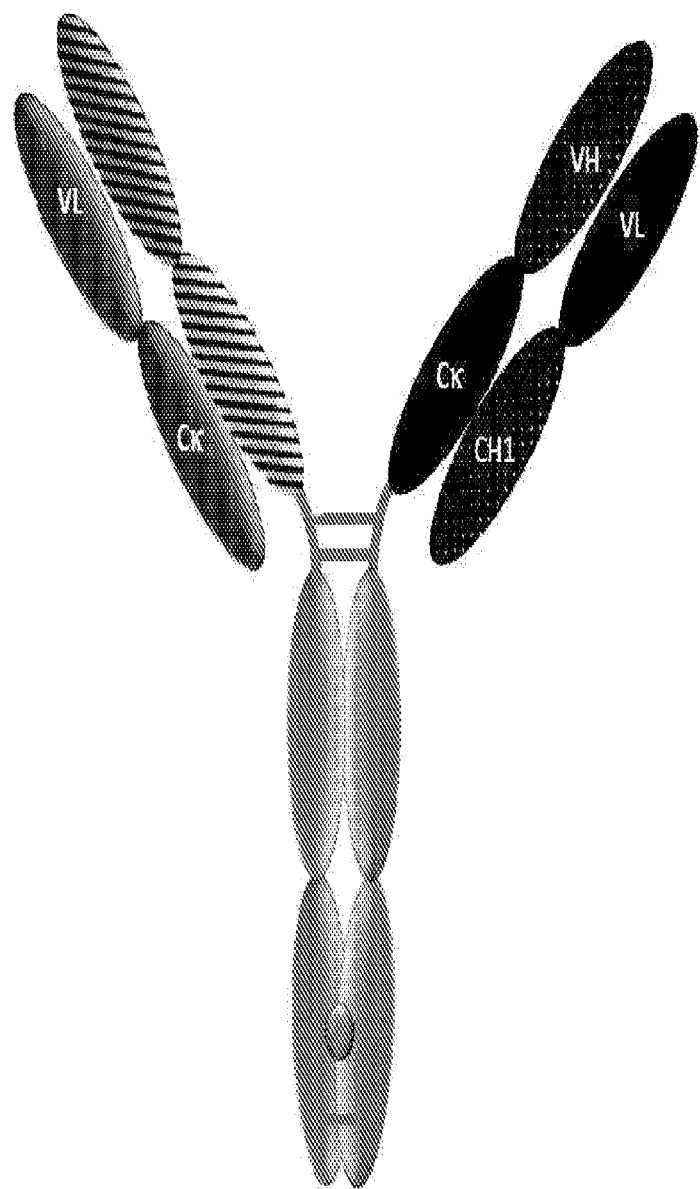
Figure 1I:
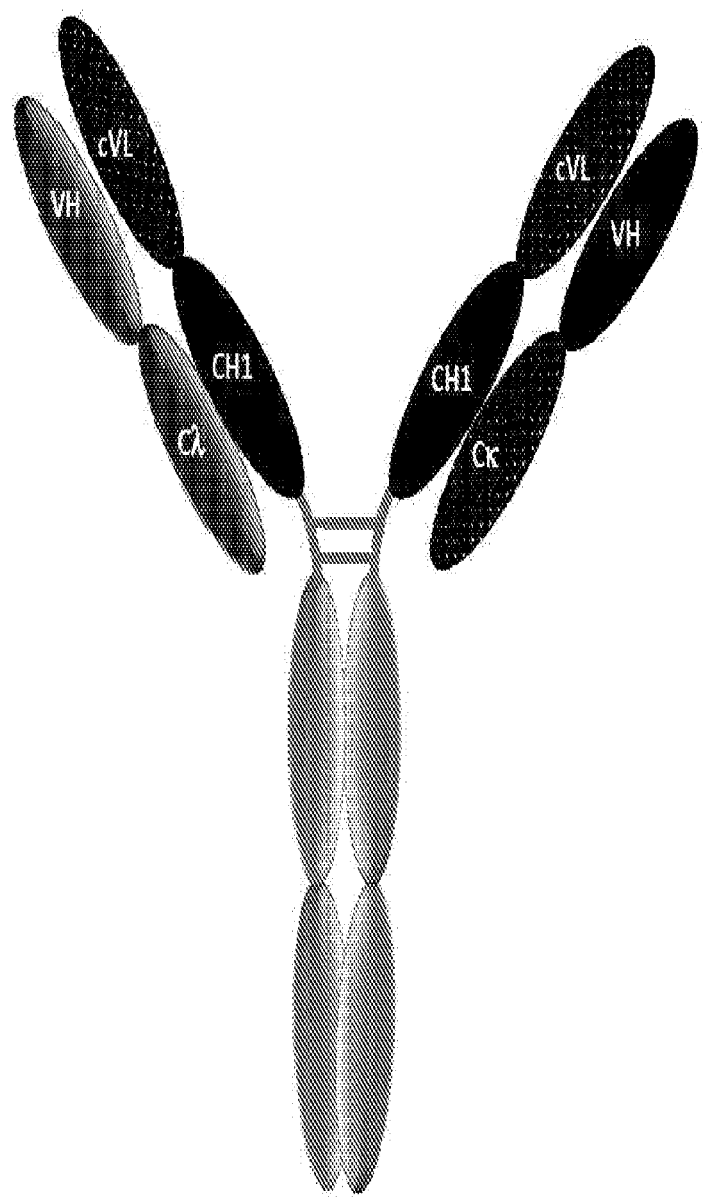

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "A bispecific antibody that specifically binds Folate Receptor 1 (FolR1) and CD3," "T cell activating bispecific antigen binding molecule specific for FolR1 and CD3" and "FolR1 TCB" are used interchangeably herein and refer to a bispecific antibody that is capable of binding FolR1 and CD3 with sufficient affinity such that the antibody is useful as a diagnostic and/or therapeutic agent in targeting CD3$^+$ T cells to FolR2$^+$ target cells.

The terms "anti-TIM3 antibody" and "TIM3 antibody" are used synonymously herein to refer to an antibody that specifically binds to TIM3. An anti-TIM3 antibody described herein refers to an antibody that is capable of binding TIM3, especially a TIM3 polypeptide expressed on a cell surface, with sufficient affinity such that the antibody is useful as a diagnostic and/or therapeutic agent. In one embodiment, the extent of binding of an antibody that specifically binds TIM3 to an unrelated non-TIM3 protein is less than about 10% of the binding of the antibody to TIM3 as measured, e.g., by a radioimmunoassay (RIA) or flow cytometry (FACS). In certain embodiments, an antibody that specifically binds TIM3 has a dissociation constant (Kd) of ≤1 μM, ≤100 nM, ≤10 nM, ≤1 nM, ≤0.1 nM, ≤0.01 nM, or ≤0.001 nM (e.g., 10$^{-8}$ M or less, e.g. from 10$^{-8}$ M to 10$^{-13}$ M, e.g., from 10$^{-9}$ M to 10$^{-13}$ M). In certain embodiments, an antibody that specifically binds TIM3 binds to an epitope of TIM3 that is conserved among DR5 from different species. Preferably said antibody binds to human and cynomolgus monkey TIM3. The term "An antibody that specifically binds TIM3" also encompasses bispecific antibodies that are capable of binding TIM3 and a second antigen.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies, cross-Fab fragments; linear antibodies; single-chain antibody molecules (e.g. scFv); and multispecific antibodies formed from antibody fragments. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

As used herein, "Fab fragment" refers to an antibody fragment comprising a light chain fragment comprising a VL domain and a constant domain of a light chain (CL), and a VH domain and a first constant domain (CH1) of a heavy chain. In one embodiment the bispecific antibodies of the invention comprise at least one Fab fragment, wherein either the variable regions or the constant regions of the heavy and light chain are exchanged. Due to the exchange of either the variable regions or the constant regions, said Fab fragment is also referred to as "cross-Fab fragment" or "xFab fragment" or "crossover Fab fragment". Two different chain compositions of a crossover Fab molecule are possible and comprised in the bispecific antibodies of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab $_{(VLVH)}$. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab $_{(CLCH1)}$. Bispecific antibody formats comprising crossover Fab fragments have been described, for example, in WO 2009/080252, WO 2009/080253, WO 2009/080251, WO 2009/080254, WO 2010/136172, WO 2010/145792 and WO 2013/026831.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction:
a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments a) VH-CH1-linker-VL-CL, b) VL-CL-linker-VH-CH1, c) VH-CL-linker-VL-CH1 and d) VL-CH1-linker-VH-CL, are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering). The term "N-terminus" denotes the last amino acid of the N-terminus. The term "C-terminus" denotes the last amino acid of the C-terminus. By "fused" or "connected" is meant that the components (e.g. a Fab molecule and an Fc domain subunit) are linked by peptide bonds, either directly or via one or more peptide linkers.

The term "linker" as used herein refers to a peptide linker and is preferably a peptide with an amino acid sequence with a length of at least 5 amino acids, preferably with a length of 5 to 100, more preferably of 10 to 50 amino acids. In one embodiment said peptide linker is $(G_xS)_n$ (SEQ ID NOS 384 and 385) or $(G_xS)_nG_m$ (SEQ ID NOS 429 and 430) with G=glycine, S=serine, and (x=3, n=3, 4, 5 or 6, and m=0, 1, 2 or 3) or (x=4, n=2, 3, 4 or 5 and m=0, 1, 2 or 3), preferably x=4 and n=2 or 3, more preferably with x=4, n=2. In one embodiment said peptide linker is $(G_4S)_2$ (SEQ ID NO: 386).

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g. $\gamma_1$ (IgG$_1$), $\gamma_2$ (IgG$_2$), $\gamma_3$ (IgG$_3$), $\gamma_4$ (IgG$_4$), $\alpha_1$ (IgA$_1$) and $\beta_2$ (IgA$_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more antibody variable domains (also called antibody variable regions). Preferably, an antigen binding domain comprises an antibody light chain variable region (VL) and an antibody heavy chain variable region (VH).

The term "chimeric" antibody refers to an antibody in which a portion of the heavy and/or light chain is derived from a particular source or species, while the remainder of the heavy and/or light chain is derived from a different source or species, usually prepared by recombinant DNA techniques. Chimeric antibodies comprising a rabbit variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See e.g. Morrison, S. L., et al., Proc. Natl. Acad. Sci. USA 81 (1984) 6851-6855; U.S. Pat. Nos. 5,202,238 and 5,204,244.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); antibody-dependent cellular phagocytosis (ADCP), cytokine secretion, immune complex-mediated antigen uptake by antigen presenting cells; down regulation of cell surface receptors (e.g. B cell receptor); and B cell activation.

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Particular amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

An "effective amount" of an agent, e.g., a pharmaceutical formulation, refers to an amount effective, at dosages and for periods of time necessary, to achieve the desired therapeutic or prophylactic result.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991. A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. As also mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation.)

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "hypervariable region" or "HVR," as used herein refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (12), 91-96 (13), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., *J. Mol. Biol.* 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table A as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE A

| CDR Definitions[1] | | | |
|---|---|---|---|
| CDR | Kabat | Chothia | AbM[2] |
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding a bispecific antibody that specifically binds DR5 and FAP antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

A "blocking" antibody or an "antagonist" antibody is one that inhibits or reduces a biological activity of the antigen it binds. In some embodiments, blocking antibodies or antagonist antibodies substantially or completely inhibit the biological activity of the antigen. For example, the anti-PD-L1 antibodies of the invention block the signaling through PD-1 so as to restore a functional response by T-cells (e.g., proliferation, cytokine production, target cell killing) from a dysfunctional state to antigen stimulation.

An "agonist" or activating antibody is one that enhances or initiates signaling by the antigen to which it binds. In some embodiments, agonist antibodies cause or activate signaling without the presence of the natural ligand.

The term "package insert" is used to refer to instructions customarily included in commercial packages of therapeutic products, that contain information about the indications, usage, dosage, administration, combination therapy, contraindications and/or warnings concerning the use of such therapeutic products.

"No substantial cross-reactivity" means that a molecule (e.g., an antibody) does not recognize or specifically bind an antigen different from the actual target antigen of the molecule (e.g. an antigen closely related to the target antigen), particularly when compared to that target antigen. For example, an antibody may bind less than about 10% to less than about 5% to an antigen different from the actual target antigen, or may bind said antigen different from the actual target antigen at an amount consisting of less than about 10%, 9%, 8% 7%, 6%, 5%, 4%, 3%, 2%, 1%, 0.5%, 0.2%, or 0.1%, preferably less than about 2%, 1%, or 0.5%, and most preferably less than about 0.2% or 0.1% antigen different from the actual target antigen.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "PD-1 axis binding antagonist" is a molecule that inhibits the interaction of a PD-1 axis binding partner with either one or more of its binding partner, so as to remove T-cell dysfunction resulting from signaling on the PD-1 signaling axis—with a result being to restore or enhance T-cell function {e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonists" is a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 described herein. In another specific aspect, a PD-binding antagonist is Merck 3745 described herein. In another specific aspect, a PD-1 binding antagonist is CT-01 1 described herein.

The term "PD-L1 binding antagonists" is a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L 1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L 1 antibody. In a specific aspect, an anti-PD-L1 antibody is YW243.55.S70 described herein. In another specific aspect, an anti-PD-L1 antibody is MDX-1 105 described herein. In still another specific aspect, an anti-PD-L1 antibody is MPDL3280A described herein.

The term "PD-L2 binding antagonists" is a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

A "PD-1 oligopeptide" "PD-L1 oligopeptide" or "PD-L2 oligopeptide" is an oligopeptide that binds, preferably specifically, to a PD-1, PD-L1 or PD-L2 negative costimulatory polypeptide, respectively, including a receptor, ligand or signaling component, respectively, as described herein. Such oligopeptides may be chemically synthesized using known oligopeptide synthesis methodology or may be prepared and purified using recombinant technology. Such oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more. Such oligopeptides may be identified using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al, Proc. Natl. Acad. Sci. U.S.A., 82: 178-182 (1985); Geysen et al, in Synthetic Peptides as Antigens, 130-149 (1986); Geysen et al., J. Immunol. Metk, 102:259-274 (1987); Schoofs et al., J. Immunol., 140:61 1-616 (1988), Cwirla, S. E. et al. Proc. Natl. Acad. Sci. USA, 87:6378 (1990); Lowman, H. B. et al. Biochemistry, 30: 10832 (1991); Clackson, T. et al. Nature, 352: 624 (1991); Marks, J. D. et al., J. Mol. Biol., 222:581 (1991); Kang, A. S. et al. Proc. Natl. Acad. Sci. USA, 88:8363 (1991), and Smith, G. P., Current Opin. Biotechnol, 2:668 (1991).

The term "anergy" refers to the state of unresponsiveness to antigen stimulation resulting from incomplete or insufficient signals delivered through the T-cell receptor (e.g. increase in intracellular $Ca^{+2}$ in the absence of ras-activation). T cell anergy can also result upon stimulation with antigen in the absence of co-stimulation, resulting in the cell becoming refractory to subsequent activation by the antigen even in the context of costimulation. The unresponsive state can often be overriden by the presence of lnterleukin-2. Anergic T-cells do not undergo clonal expansion and/or acquire effector functions.

The term "exhaustion" refers to T cell exhaustion as a state of T cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

"Enhancing T-cell function" means to induce, cause or stimulate a T-cell to have a sustained or amplified biological function, or renew or reactivate exhausted or inactive T-cells. Examples of enhancing T-cell function include: increased secretion of γ-interferon from $CD8^+$ T-cells, increased proliferation, increased antigen responsiveness (e.g., viral, pathogen, or tumor clearance) relative to such levels before the intervention. In one embodiment, the level of enhancement is as least 50%, alternatively 60%, 70%, 80%, 90%, 100%, 120%, 150%, 200%. The manner of measuring this enhancement is known to one of ordinary skill in the art.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance. [0046] "Immunogenecity" refers to the ability of a particular substance to provoke an immune response. Tumors are immunogenic and enhancing tumor immunogenicity aids in the clearance of the tumor cells by the immune response. Examples of enhancing tumor immunogenicity include treatment with anti-PDL antibodies and a ME inhibitor.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1.5×, 2.0×, 2.5×, or 3.0× length of the treatment duration.

The term "Fibroblast activation protein (FAP)", as used herein, refers to any native FAP from any vertebrate source, including mammals such as primates (e.g. humans) and rodents (e.g., mice and rats), unless otherwise indicated. The term encompasses "full-length," unprocessed FAP as well as any form of FAP that results from processing in the cell. The term also encompasses naturally occurring variants of FAP, e.g., splice variants or allelic variants. Preferably, an anti-FAP antibody of the invention binds to the extracellular domain of FAP. The amino acid sequence of exemplary FAP polypeptide sequences, including the sequence of human FAP, are disclosed in WO 2012/020006.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term cancer as used herein refers to proliferative diseases, such as the cancer is colorectal cancer, sarcoma, head and neck cancer, squamous cell carcinoma, breast cancer, pancreatic cancer, gastric cancer, non-small-cell lung carcinoma, small-cell lung cancer and mesothelioma, including refractory versions of any of the above cancers, or a combination of one or more of the above cancers. In one embodiment, the cancer is colorectal cancer and optionally the chemotherapeutic agent is Irinotecan. In embodiments in which the cancer is sarcoma, optionally the sarcoma is chondrosarcoma, leiomyosarcoma, gastrointestinal stromal tumours, fibrosarcoma, osteosarcoma, liposarcoma or malignant fibrous histiocytoma.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6*th* ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991). As used herein, the term "antigen binding molecule" refers in its broadest sense to a molecule that specifically binds an antigenic determinant. Examples of antigen binding molecules are immunoglobulins and derivatives, e.g. fragments, thereof.

The term "antigen-binding site of an antibody" when used herein refer to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

Antibody specificity refers to selective recognition of the antibody for a particular epitope of an antigen. Natural antibodies, for example, are monospecific. "Bispecific antibodies" according to the invention are antibodies which have two different antigen-binding specificities. Antibodies of the present invention are specific for two different antigens, i.e. DR5 as first antigen and FAP as second antigen.

The term "monospecific" antibody as used herein denotes an antibody that has one or more binding sites each of which bind to the same epitope of the same antigen.

The term "bispecific" means that the antigen binding molecule is able to specifically bind to at least two distinct antigenic determinants. Typically, a bispecific antigen binding molecule comprises at least two antigen binding sites, each of which is specific for a different antigenic determinant. In certain embodiments the bispecific antigen binding molecule is capable of simultaneously binding two antigenic determinants, particularly two antigenic determinants expressed on two distinct cells.

The antibody provided herein is a multispecific antibody, e.g. a bispecific antibody. Multispecific antibodies are monoclonal antibodies that have binding specificities for at least two different sites. Provided herein is a bispecific antibody, with binding specificities for FAP and DR5. In certain embodiments, bispecific antibodies may bind to two different epitopes of DR5. Bispecific antibodies may also be used to localize cytotoxic agents to cells which express DR5. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising at least one antigen binding site that binds to FAP or DR5 as well as another, different antigen (see, US 2008/0069820, for example).

The term "valent" as used within the current application denotes the presence of a specified number of binding sites in an antibody molecule. As such, the terms "bivalent", "tetravalent", and "hexavalent" denote the presence of two binding sites, four binding sites, and six binding sites, respectively, in an antibody molecule. The bispecific antibodies according to the invention are at least "bivalent" and may be "trivalent" or "multivalent" (e.g. "tetravalent" or "hexavalent").

Antibodies of the present invention have two or more binding sites and are bispecific. That is, the antibodies may be bispecific even in cases where there are more than two binding sites (i.e. that the antibody is trivalent or multivalent). Bispecific antibodies of the invention include, for example, multivalent single chain antibodies, diabodies and triabodies, as well as antibodies having the constant domain structure of full length antibodies to which further antigen-binding sites (e.g., single chain Fv, a VH domain and/or a VL domain, Fab, or (Fab)2) are linked via one or more peptide-linkers. The antibodies can be full length from a single species, or be chimerized or humanized.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

As used herein, the expressions "cell", "cell line", and "cell culture" are used interchangeably and all such designations include progeny. Thus, the words "transfectants" and "transfected cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

As used herein, the term "binding" or "specifically binding" refers to the binding of the antibody to an epitope of the antigen in an in-vitro assay, preferably in a surface plasmon resonance assay (SPR, BIAcore, GE-Healthcare Uppsala, Sweden). The affinity of the binding is defined by the terms ka (rate constant for the association of the antibody from the antibody/antigen complex), kD (dissociation constant), and KD (kD/ka). Binding or specifically binding means a binding affinity (KD) of $10^{-8}$ mol/l or less, preferably $10^{-9}$ M to $10^{-13}$ mol/l.

Binding of the antibody to the death receptor can be investigated by a BIAcore assay (GE-Healthcare Uppsala, Sweden). The affinity of the binding is defined by the terms ka (rate constant for the association of the antibody from the antibody/antigen complex), kD (dissociation constant), and KD (kD/ka)

"Reduced binding", for example reduced binding to an Fc receptor, refers to a decrease in affinity for the respective interaction, as measured for example by SPR. For clarity the term includes also reduction of the affinity to zero (or below the detection limit of the analytic method), i.e. complete abolishment of the interaction. Conversely, "increased binding" refers to an increase in binding affinity for the respective interaction.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. The T cell activating bispecific antigen binding molecules of the invention are capable of inducing T cell activation. Suitable assays to measure T cell activation are known in the art described herein.

A "target cell antigen" as used herein refers to an antigenic determinant presented on the surface of a target cell, for example a cell in a tumor such as a cancer cell or a cell of the tumor stroma. In particular "target cell antigen" refers to Folate Receptor 1.

As used herein, the terms "first" and "second" with respect to antigen binding moieties etc., are used for convenience of distinguishing when there is more than one of each type of moiety. Use of these terms is not intended to confer a specific order or orientation of the T cell activating bispecific antigen binding molecule unless explicitly so stated.

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins referred to as antigens herein, e.g., FolR1 and CD3, can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants. Exemplary human proteins useful as antigens include, but are not limited to: FolR1 (Folate receptor alpha (FRA); Folate binding protein (FBP); human FolR1 UniProt no.: P15328; murine FolR1 UniProt no.: P35846; cynomolgus FolR1 UniProt no.: G7PR14) and CD3, particularly the epsilon subunit of CD3 (see UniProt no. P07766 (version 130), NCBI RefSeq no. NP_000724.1, SEQ ID NO:150 for the human sequence; or UniProt no. Q95LI5 (version 49), NCBI GenBank no. BAB71849.1, for the cynomolgus [Macaca fascicularis] sequence). The T cell activating bispecific antigen binding molecule of the invention binds to an epitope of CD3 or a target cell antigen that is conserved among the CD3 or target antigen from different species. In certain embodiments the T cell activating bispecific antigen binding molecule of the invention binds to CD3 and FolR1, but does not bind to FolR2 (Folate receptor beta; FRB; human FolR2 UniProt no.: P14207) or FolR3 (Folate receptor gamma; human FolR3 UniProt no.: P41439).

As used herein, the terms "engineer, engineered, engineering," particularly with the prefix "glyco-," as well as the term "glycosylation engineering" are considered to include any manipulation of the glycosylation pattern of a naturally occurring or recombinant polypeptide or fragment thereof. Glycosylation engineering includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation. In one embodiment, the glycosylation engineering is an alteration in glycosyltransferase activity. In a particular embodiment, the engineering results in altered glucosaminyltransferase activity and/or fucosyltransferase activity.

II. Compositions and Methods

In one aspect, the invention is based on the use of a therapeutic combination of a T cell activating bispecific antigen binding molecule, e.g., a T cell activating bispecific antigen binding molecule comprising a first antigen binding site specific for Folate Receptor 1 (FolR1) and a second antigen binding site specific for CD3, and a PD-1 axis binding antagonist, e.g., for the treatment of cancer. In some embodiments the therapeutic combination further includes a TIM3 antagonist.

A. Combination Therapies of a T Cell Activating Bispecific Antigen Binding Molecule and a PD-1 Axis Binding Antagonist Broadly, the present invention relates to T cell activating bispecific antigen binding molecules and their use in combination with a PD-1 axis binding antagonists. The advantage of the combination over monotherapy is that the T cell activating bispecific antigen binding molecules used in the present invention enable re-direction and activation of T cells to the targeted cell while the PD-1 axis binding antagonist enhances T cell function by reducing T cell exhaustion.

In one aspect, provided herein is a method for treating or delaying progression of cancer in an individual comprising administering to the individual an effective amount of a T cell activating bispecific antigen binding molecules, e.g., a FolR1-TCB, and a PD-1 axis binding antagonist. In some embodiments, the treatment results in sustained response in the individual after cessation of the treatment. The methods of this invention may find use in treating conditions where enhanced immunogenicity is desired such as increasing tumor immunogenicity for the treatment of cancer. A variety of cancers may be treated, or their progression may be delayed, including but are not limited to a cancer that may contain a BRAF V600E mutation, a cancer that may contain a BRAF wildtype, a cancer that may contain a KRAS wildtype, or a cancer that may contain an activating KRAS mutation.

In some embodiments, the individual has endometrial cancer. The endometrial cancer may be at early stage or late state. In some embodiments, the individual has melanoma. The melanoma may be at early stage or at late stage. In some embodiments, the individual has colorectal cancer. The colorectal cancer may be at early stage or at late stage. In some embodiments, the individual has lung cancer, e.g., non-small cell lung cancer. The non-small cell lung cancer may be at early stage or at late stage. In some embodiments, the individual has pancreatic cancer. The pancreatic cancer may be at early stage or late state. In some embodiments, the individual has a hematological malignancy. The hematological malignancy may be early stage or late stage. In some embodiments, the individual has ovarian cancer. The ovarian cancer may be at early stage or at late stage. In some embodiments, the individual has breast cancer. The breast cancer may be at early stage or at late stage. In some embodiments, the individual has renal cell carcinoma. The renal cell carcinoma may be at early stage or at late stage.

In some embodiments, the individual is a mammal, such as domesticated animals (e.g., cows, sheep, cats, dogs, and horses), primates (e.g., humans and non-human primates such as monkeys), rabbits, and rodents (e.g., mice and rats). In some embodiments, the individual treated is a human.

In another aspect, provided herein is a method of enhancing immune function in an individual having cancer comprising administering an effective amount of a T cell activating bispecific antigen binding molecules, specifically, a FolR1-TCB, and a PD-1 axis binding antagonist.

In some embodiments, the T cells in the individual have enhanced priming, activation, proliferation and/or effector function relative to prior to the administration of the T cell activating bispecific antigen binding molecules and the PD-1 pathway antagonist. In some embodiments, the T cell effector function is secretion of at least one of IL-2, IFN-γ and TNF-α. In one embodiment, administering a FolR1-TCB and an anti-PDL-1 antibody results in increased T cell secretion of IL-2, IFN-γ and TNF-α. In some embodiments, the T cell is a CD8+ T cell. In some embodiments, the T cell priming is characterized by elevated CD44 expression and/or enhanced cytolytic activity in CD8 T cells. In some embodiments, the CD8 T cell activation is characterized by an elevated frequency of γ-IFT^T CD8 T cells. In some embodiments, the CD8 T cell is an antigen-specific T-cell. In some embodiments, the immune evasion by signaling through PD-L1 surface expression is inhibited. In some embodiments, the cancer has elevated levels of T-cell infiltration.

In some embodiments, the combination therapy of the invention comprises administration of a FolR1-TCB and a PD-1 axis binding antagonist. The FolR1-TCB and a PD-1 axis binding antagonist may be administered in any suitable manner known in the art. For example, FolR1-TCB and a PD-1 axis binding antagonist may be administered sequentially (at different times) or concurrently (at the same time). In some embodiments, the FolR1-TCB is administered continuously. In some embodiments, the FolR1-TCB is administered intermittently. In some embodiments, the FolR1-TCB is administered before administration of the PD-1 axis binding antagonist. In some embodiments, the FolR1-TCB is administered simultaneously with administration of the PD-1 axis binding antagonist. In some embodiments, the FolR1-TCB is administered after administration of the PD-1 axis binding antagonist.

In some embodiments, provided is a method for treating or delaying progression of cancer in an individual comprising administering to the individual an effective amount of a T cell activating bispecific antigen binding molecules, e.g., a FolR1-TCB, and a PD-1 axis binding antagonist, further comprising administering an additional therapy. Specifically contemplated is an embodiment in which the additional therapy comprises a TIM-3 antagonist. Accordingly, in one aspect, provided herein is a method for treating or delaying progression of cancer in an individual comprising administering to the individual an effective amount of a T cell activating bispecific antigen binding molecules, specifically, a FolR1-TCB, a PD-1 axis binding antagonist, and a TIM-3 antagonist. Any TIM3 antagonist, e.g., those described herein, can be used. The additional therapy may also be radiation therapy, surgery (e.g., lumpectomy and a mastectomy), chemotherapy, gene therapy, DNA therapy, viral therapy, R A therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting P13K/AT/mTOR pathway, HSP90 inhibitor, tubulin inhibitor, apoptosis inhibitor, and/or chemopreventative agent. The additional therapy may be one or more of the chemotherapeutic agents described hereabove.

T cell activating bispecific antigen binding molecules, e.g., a FolR1-TCB, and the PD-1 axis binding antagonist may be administered by the same route of administration or by different routes of administration. In some embodiments, T cell activating bispecific antigen binding molecules, e.g., a FolR1-TCB is administered intravenously, intramuscularly, subcutaneously, topically, orally, transdermally, intraperitoneally, intraorbitally, by implantation, by inhalation, intrathecally, intraventricularly, or intranasally. In some embodiments, the PD-1 axis binding antagonist is administered intravenously, intramuscularly, subcutaneously, topically, orally, transdermally, intraperitoneally, intraorbitally, by implantation, by inhalation, intrathecally, intraventricularly, or intranasally. An effective amount of the T cell activating bispecific antigen binding molecules and the PD-1 axis binding antagonist may be administered for prevention or treatment of disease. The appropriate dosage of the T cell activating bispecific antigen binding molecules and/or the PD-1 axis binding antagonist may be determined based on the type of disease to be treated, the type of the T cell activating bispecific antigen binding molecules and the PD-1 axis binding antagonist, the severity and course of the disease, the clinical condition of the individual, the individual's clinical history and response to the treatment, and the discretion of the attending physician.

Any of the T cell activating bispecific antigen binding molecules, PD-1 axis binding antagonists and the TIM-3 antagonists known in the art or described below may be used in the methods.

In a further aspect, the present invention provides a pharmaceutical composition comprising a T cell activating bispecific antigen binding molecules as described herein, a PD-1 axis binding antagonists as described herein and a pharmaceutically acceptable carrier. In some embodiments, the pharmaceutical composition further comprises a TIM3 antagonist.

In a further aspect, the invention provides for a kit comprising a T cell activating bispecific antigen binding molecule specific for Folate Receptor 1 (FolR1) and CD3, and a package insert comprising instructions for using the T cell activating bispecific antigen binding molecule with a PD-1 axis binding antagonist to treat or delay progression of cancer in an individual. In some embodiments, the kit further comprises instructions for using the T cell activating bispecific antigen binding molecule with a TIM3 antagonist. In a further aspect, the invention provides for a kit comprising a T cell activating bispecific antigen binding molecule specific for Folate Receptor 1 (FolR1) and CD3 and a PD-1 axis binding antagonist, and a package insert comprising instructions for using the T cell activating bispecific antigen binding molecule and the PD-1 axis binding antagonist to treat or delay progression of cancer in an individual. In one embodiment, the kit further comprises a TIM3 antagonist. In one of the embodiments, the PD-1 axis binding antagonist is an anti-PD-1 antibody or an anti-PDL-antibody. In one embodiment, the PD-1 axis binding antagonist is an anti-PD-1 immunoadhesin.

In a further aspect, the invention provides a kit comprising:

(i) a first container comprising a composition which comprises a T cell activating bispecific antigen binding molecule specific for Folate Receptor 1 (FolR1) and CD3 as described herein; and (ii) a second container comprising a composition comprising a PD-1 axis binding antagonist.

In a further aspect, the invention provides a kit comprising:

(i) a first container comprising a composition which comprises a T cell activating bispecific antigen binding molecule specific for Folate Receptor 1 (FolR1) and CD3 as described herein;

(ii) a second container comprising a composition comprising a PD-1 axis binding antagonist; and (iii) a third container comprising a composition comprising a TIM3 antagonist.

B. Exemplary T Cell Activating Bispecific Antigen Binding Molecule for Use in the Invention The T cell activating bispecific antigen binding molecule of the invention is bispecific, i.e. it comprises at least two antigen binding moieties capable of specific binding to two distinct antigenic determinants, i.e. to CD3 and to FolR1. According to the invention, the antigen binding moieties are Fab molecules (i.e. antigen binding domains composed of a heavy and a light chain, each comprising a variable and a constant region). In one embodiment said Fab molecules are human. In another embodiment said Fab molecules are humanized. In yet another embodiment said Fab molecules comprise human heavy and light chain constant regions.

The T cell activating bispecific antigen binding molecule of the invention is capable of simultaneous binding to the target cell antigen FolR1 and CD3. In one embodiment, the T cell activating bispecific antigen binding molecule is capable of crosslinking a T cell and a FolR1 expressing target cell by simultaneous binding to the target cell antigen FolR1 and CD3. In an even more particular embodiment, such simultaneous binding results in lysis of the FolR1 expressing target cell, particularly a FolR1 expressing tumor cell. In one embodiment, such simultaneous binding results in activation of the T cell. In other embodiments, such simultaneous binding results in a cellular response of a T lymphocyte, particularly a cytotoxic T lymphocyte, selected from the group of: proliferation, differentiation, cytokine secretion, cytotoxic effector molecule release, cytotoxic activity, and expression of activation markers. In one embodiment, binding of the T cell activating bispecific antigen binding molecule to CD3 without simultaneous binding to the target cell antigen FolR1 does not result in T cell activation.

In one embodiment, the T cell activating bispecific antigen binding molecule is capable of re-directing cytotoxic activity of a T cell to a FolR1 expressing target cell. In a particular embodiment, said re-direction is independent of MHC-mediated peptide antigen presentation by the target cell and and/or specificity of the T cell.

Particularly, a T cell according to some of the embodiments of the invention is a cytotoxic T cell. In some embodiments the T cell is a $CD4^+$ or a $CD8^+$ T cell, particularly a $CD8^+$ T cell.

The T cell activating bispecific antigen binding molecule of the invention comprises at least one antigen binding moiety capable of binding to CD3 (also referred to herein as an "CD3 antigen binding moiety" or "first antigen binding moiety"). In a particular embodiment, the T cell activating bispecific antigen binding molecule comprises not more than one antigen binding moiety capable of specific binding to CD3. In one embodiment the T cell activating bispecific antigen binding molecule provides monovalent binding to CD3. In a particular embodiment CD3 is human CD3 or cynomolgus CD3, most particularly human CD3. In a particular embodiment the CD3 antigen binding moiety is cross-reactive for (i.e. specifically binds to) human and cynomolgus CD3. In some embodiments, the first antigen binding moiety is capable of specific binding to the epsilon subunit of CD3 (see UniProt no. P07766 (version 130), NCBI RefSeq no. NP_000724.1, SEQ ID NO:150 for the human sequence; UniProt no. Q95LI5 (version 49), NCBI GenBank no. BAB71849.1, for the cynomolgus [*Macaca fascicularis*] sequence).

In some embodiments, the CD3 antigen binding moiety comprises at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33, SEQ ID NO: 34.

In one embodiment the CD3 antigen binding moiety comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34.

In one embodiment the CD3 antigen binding moiety comprises a variable heavy chain comprising an amino acid sequence of: SEQ ID NO: 36 and a variable light chain comprising an amino acid sequence of: SEQ ID NO: 31.

In one embodiment the CD3 antigen binding moiety comprises a heavy chain variable region sequence that is at least about 95%, 96%, 97%, 98%, 99% or 100% identical to SEQ ID NO: 36 and a light chain variable region sequence that is at least about 95%, 96%, 97%, 98%, 99% or 100% identical to SEQ ID NO: 31.

The T cell activating bispecific antigen binding molecule of the invention comprises at least one antigen binding moiety capable of binding to the target cell antigen FolR1 (also referred to herein as an "FolR1 binding moiety" or "second" or "third" antigen binding moiety). In one embodiment, the antigen binding moiety capable of binding to the target cell antigen FolR1 does not bind to FolR2 or FolR3. In a particular embodiment the FolR1 antigen binding moiety is cross-reactive for (i.e. specifically binds to) human and cynomolgus FolR1. In certain embodiments, the T cell activating bispecific antigen binding molecule comprises two antigen binding moieties capable of binding to the target cell antigen FolR1. In a particular such embodiment, each of these antigen binding moieties specifically binds to the same antigenic determinant. In an even more particular embodiment, all of these antigen binding moieties are identical. In one embodiment the T cell activating bispecific antigen binding molecule comprises not more than two antigen binding moieties capable of binding to FolR1.

The FolR1 binding moiety is generally a Fab molecule that specifically binds to FolR1 and is able to direct the T cell activating bispecific antigen binding molecule to which it is connected to a target site, for example to a specific type of tumor cell that expresses FolR1. In one aspect the present invention provides a T cell activating bispecific antigen binding molecule comprising (i) a first antigen binding moiety which is a Fab molecule capable of specific binding to CD3, and which comprises at least one heavy chain complementarity determining region (CDR) selected from the group consisting SEQ ID NO: 37, SEQ ID NO: 38 and SEQ ID NO: 39 and at least one light chain CDR selected from the group of SEQ ID NO: 32, SEQ ID NO: 33, SEQ ID NO: 34; and (ii) a second antigen binding moiety which is a Fab molecule capable of specific binding to Folate Receptor 1 (FolR1).

In one embodiment the first antigen binding moiety which is a Fab molecule capable of specific binding to CD3 comprises a variable heavy chain comprising an amino acid sequence of SEQ ID NO: 36 and a variable light chain comprising an amino acid sequence of SEQ ID NO: 31.

In one embodiment the T cell activating bispecific antigen binding molecule additionally comprises (iii) a third antigen binding moiety which is a Fab molecule capable of specific binding to FolR1.

In one such embodiment the second and third antigen binding moiety capable of specific binding to FolR1 comprise identical heavy chain complementarity determining region (CDR) and light chain CDR sequences. In one such embodiment the third antigen binding moiety is identical to the second antigen binding moiety.

In one embodiment the T cell activating bispecific antigen binding molecule of any of the above embodiments additionally comprises an Fc domain composed of a first and a second subunit capable of stable association.

In one embodiment the first antigen binding moiety and the second antigen binding moiety are each fused at the C-terminus of the Fab heavy chain to the N-terminus of the first or second subunit of the Fc domain.

In one embodiment the third antigen binding moiety is fused at the C-terminus of the Fab heavy chain to the N-terminus of the Fab heavy chain of the first antigen binding moiety, optionally via a peptide linker.

In a further particular embodiment, not more than one antigen binding moiety capable of specific binding to CD3 is present in the T cell activating bispecific antigen binding molecule (i.e. the T cell activating bispecific antigen binding molecule provides monovalent binding to CD3).

T Cell Activating Bispecific Antigen Binding Molecule with a Common Light Chain

The inventors of the present invention generated a bispecific antibody wherein the binding moieties share a common light chain that retains the specificity and efficacy of the parent monospecific antibody for CD3 and can bind a second antigen (e.g., FolR1) using the same light chain. The generation of a bispecific molecule with a common light chain that retains the binding properties of the parent antibody is not straight-forward as the common CDRs of the hybrid light chain have to effectuate the binding specificity for both targets. In one aspect the present invention provides a T cell activating bispecific antigen binding molecule comprising a first and a second antigen binding moiety, one of which is a Fab molecule capable of specific binding to CD3 and the other one of which is a Fab molecule capable of specific binding to FolR1, wherein the first and the second Fab molecule have identical VLCL light chains. In one embodiment said identical light chain (VLCL) comprises the light chain CDRs of SEQ ID NO: 32, SEQ ID NO: 33 and SEQ ID NO: 34. In one embodiment said identical light chain (VLCL) comprises SEQ ID NO. 35.

In one embodiment the present invention provides a T cell activating bispecific antigen binding molecule comprising
(i) a first antigen binding moiety which is a Fab molecule capable of specific binding to CD3, and which comprises at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33, SEQ ID NO: 34;
(ii) a second antigen binding moiety which is a Fab molecule capable of specific binding to Folate Receptor 1 (FolR1) and which comprises at least one heavy chain complementarity determining region (CDR) selected from the group consisting of SEQ ID NO: 16, SEQ ID NO: 17 and SEQ ID NO: 18 and at least one light chain CDR selected from the group of SEQ ID NO: 32, SEQ ID NO: 33, SEQ ID NO: 34.

In one such embodiment the CD3 antigen binding moiety comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and the FolR1 antigen binding moiety comprises the heavy chain CDR1 of SEQ ID NO: 16, the heavy chain CDR2 of SEQ ID NO: 17, the heavy chain CDR3 of SEQ ID NO:18, the light chain CDR1 of SEQ ID NO: 32, the light chain CDR2 of SEQ ID NO: 33, and the light chain CDR3 of SEQ ID NO:34.

In one embodiment the present invention provides a T cell activating bispecific antigen binding molecule comprising
(i) a first antigen binding moiety which is a Fab molecule capable of specific binding to CD3 comprising a variable heavy chain comprising an amino acid sequence of SEQ ID NO: 36 and a variable light chain comprising an amino acid sequence of SEQ ID NO: 31.
(ii) a second antigen binding moiety which is a Fab molecule capable of specific binding to Folate Receptor 1 (FolR1) comprising a variable heavy chain comprising an amino acid sequence of SEQ ID NO: 15 and a variable light chain comprising an amino acid sequence of SEQ ID NO: 31.

In a further embodiment, the antigen binding moiety that is specific for FolR1 comprises a heavy chain variable region sequence that is at least about 95%, 96%, 97%, 98%, 99% or 100% identical to SEQ ID NO:15 and a light chain variable region sequence that is at least about 95%, 96%, 97%, 98%, 99% or 100% identical to SEQ ID NO: 31 or variants thereof that retain functionality.

In one embodiment the T cell activating bispecific antigen binding molecule comprises a polypeptide sequence that is at least about 95%, 96%, 97%, 98%, 99% or 100% identical to SEQ ID NO: 36, a polypeptide sequence that is at least about 95%, 96%, 97%, 98%, 99% or 100% identical to SEQ ID NO:15, and a polypeptide sequence that is at least about 95%, 96%, 97%, 98%, 99% or 100% identical to SEQ ID NO: 31.

In one embodiment the T cell activating bispecific antigen binding molecule additionally comprises
(iii) a third antigen binding moiety (which is a Fab molecule) capable of specific binding to FolR1.

In one such embodiment the second and third antigen binding moiety capable of specific binding to FolR1 comprise identical heavy chain complementarity determining region (CDR) and light chain CDR sequences. In one such embodiment the third antigen binding moiety is identical to the second antigen binding moiety.

Hence in one embodiment the present invention provides a T cell activating bispecific antigen binding molecule comprising
(i) a first antigen binding moiety which is a Fab molecule capable of specific binding to CD3, and which comprises at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33, SEQ ID NO: 34;
(ii) a second antigen binding moiety which is a Fab molecule capable of specific binding to Folate Receptor 1 (FolR1) and which comprises at least one heavy chain complementarity determining region (CDR) selected from the group consisting of SEQ ID NO: 16, SEQ ID NO: 17 and SEQ ID NO: 18 and at least one light chain CDR selected from the group of SEQ ID NO: 32, SEQ ID NO: 33, SEQ ID NO: 34.
(iii) a third antigen binding moiety which is a Fab molecule capable of specific binding to Folate Receptor 1 (FolR1) and which comprises at least one heavy chain complementarity determining region (CDR) selected from the group consisting of SEQ ID NO: 16, SEQ ID NO: 17 and SEQ ID NO: 18 and at least one light chain CDR selected from the group of SEQ ID NO: 32, SEQ ID NO: 33, SEQ ID NO: 34.

In one such embodiment the CD3 antigen binding moiety comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and the FolR1 antigen binding moiety comprises the heavy chain CDR1 of SEQ ID NO: 16, the heavy chain CDR2 of SEQ ID NO: 17, the heavy chain CDR3 of SEQ ID NO:18, the light chain CDR1 of SEQ ID NO: 32, the light chain CDR2 of SEQ ID NO: 33, and the light chain CDR3 of SEQ ID NO:34.

In one embodiment the present invention provides a T cell activating bispecific antigen binding molecule comprising
(i) a first antigen binding moiety which is a Fab molecule capable of specific binding to CD3 comprising a variable heavy chain comprising an amino acid sequence of SEQ ID NO: 36 and a variable light chain comprising an amino acid sequence of SEQ ID NO: 31.
(ii) a second antigen binding moiety which is a Fab molecule capable of specific binding to Folate Receptor 1 (FolR1) comprising a variable heavy chain comprising an amino acid sequence of SEQ ID NO: 15 and a variable light chain comprising an amino acid sequence of SEQ ID NO: 31.
(iii) a third antigen binding moiety which is a Fab molecule capable of specific binding to Folate Receptor 1 (FolR1) comprising a variable heavy chain comprising an amino acid sequence of SEQ ID NO: 15 and a variable light chain comprising an amino acid sequence of SEQ ID NO: 31.

In one embodiment the present invention provides a T cell activating bispecific antigen binding molecule comprising
(i) a first antigen binding moiety which is a Fab molecule capable of specific binding to CD3, and which comprises at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33, SEQ ID NO: 34;
(ii) a second antigen binding moiety which is a Fab molecule capable of specific binding to Folate Receptor 1 (FolR1) and which comprises at least one heavy chain complementarity determining region (CDR) selected from the group consisting of SEQ ID NO:16, SEQ ID NO:402 and SEQ ID NO:400 and at least one light chain CDR selected from the group of SEQ ID NO: 32, SEQ ID NO: 33, SEQ ID NO: 34.

In one such embodiment the CD3 antigen binding moiety comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34, and the FolR1 antigen binding moiety comprises the heavy chain CDR1 of SEQ ID NO:16, the heavy chain CDR2 of SEQ ID NO:402, the heavy chain CDR3 of SEQ ID NO:400, the light chain CDR1 of SEQ ID NO: 32, the light chain CDR2 of SEQ ID NO: 33, and the light chain CDR3 of SEQ ID NO:34.

In one embodiment the present invention provides a T cell activating bispecific antigen binding molecule comprising
(i) a first antigen binding moiety which is a Fab molecule capable of specific binding to CD3 comprising a variable heavy chain comprising an amino acid sequence of SEQ ID NO: 36 and a variable light chain comprising an amino acid sequence of SEQ ID NO: 31.
(ii) a second antigen binding moiety which is a Fab molecule capable of specific binding to Folate Receptor 1 (FolR1) comprising a variable heavy chain comprising an amino acid sequence of SEQ ID NO:401 and a variable light chain comprising an amino acid sequence of SEQ ID NO: 31.

In a further embodiment, the antigen binding moiety that is specific for FolR1 comprises a heavy chain variable region sequence that is at least about 95%, 96%, 97%, 98%, 99% or 100% identical to SEQ ID NO:401 and a light chain variable region sequence that is at least about 95%, 96%, 97%, 98%, 99% or 100% identical to SEQ ID NO: 31 or variants thereof that retain functionality.

In one embodiment the T cell activating bispecific antigen binding molecule comprises a polypeptide sequence that is at least about 95%, 96%, 97%, 98%, 99% or 100% identical to SEQ ID NO: 36, a polypeptide sequence that is at least about 95%, 96%, 97%, 98%, 99% or 100% identical to SEQ ID NO:401, and a polypeptide sequence that is at least about 95%, 96%, 97%, 98%, 99% or 100% identical to SEQ ID NO: 31.

In one embodiment the T cell activating bispecific antigen binding molecule additionally comprises
(iii) a third antigen binding moiety (which is a Fab molecule) capable of specific binding to FolR1.

In one such embodiment the second and third antigen binding moiety capable of specific binding to FolR1 comprise identical heavy chain complementarity determining region (CDR) and light chain CDR sequences. In one such embodiment the third antigen binding moiety is identical to the second antigen binding moiety.

Hence in one embodiment the present invention provides a T cell activating bispecific antigen binding molecule comprising
(i) a first antigen binding moiety which is a Fab molecule capable of specific binding to CD3, and which comprises at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33, SEQ ID NO: 34;
(ii) a second antigen binding moiety which is a Fab molecule capable of specific binding to Folate Receptor 1 (FolR1) and which comprises at least one heavy chain complementarity determining region (CDR) selected from the group consisting of SEQ ID NO:16, SEQ ID NO:402 and SEQ ID NO:400 and at least one light chain CDR selected from the group of SEQ ID NO: 32, SEQ ID NO: 33, SEQ ID NO: 34.

(iii) a third antigen binding moiety which is a Fab molecule capable of specific binding to Folate Receptor 1 (FolR1) and which comprises at least one heavy chain complementarity determining region (CDR) selected from the group consisting of SEQ ID NO:16, SEQ ID NO:402 and SEQ ID NO:400 and at least one light chain CDR selected from the group of SEQ ID NO: 32, SEQ ID NO: 33, SEQ ID NO: 34.

In one such embodiment the CD3 antigen binding moiety comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and the FolR1 antigen binding moiety comprises the heavy chain CDR1 of SEQ ID NO:16, the heavy chain CDR2 of SEQ ID NO:402, the heavy chain CDR3 of SEQ ID NO:400, the light chain CDR1 of SEQ ID NO: 32, the light chain CDR2 of SEQ ID NO: 33, and the light chain CDR3 of SEQ ID NO:34.

In one embodiment the present invention provides a T cell activating bispecific antigen binding molecule comprising
(i) a first antigen binding moiety which is a Fab molecule capable of specific binding to CD3 comprising a variable heavy chain comprising an amino acid sequence of SEQ ID NO: 36 and a variable light chain comprising an amino acid sequence of SEQ ID NO: 31.
(ii) a second antigen binding moiety which is a Fab molecule capable of specific binding to Folate Receptor 1 (FolR1) comprising a variable heavy chain comprising an amino acid sequence of SEQ ID NO:401 and a variable light chain comprising an amino acid sequence of SEQ ID NO: 31.
(iii) a third antigen binding moiety which is a Fab molecule capable of specific binding to Folate Receptor 1 (FolR1) comprising a variable heavy chain comprising an amino acid sequence of SEQ ID NO:401 and a variable light chain comprising an amino acid sequence of SEQ ID NO: 31.

Thus, in one embodiment, the invention relates to bispecific molecules wherein at least two binding moieties have identical light chains and corresponding remodeled heavy chains that confer the specific binding to the T cell activating antigen CD3 and the target cell antigen FolR1, respectively. The use of this so-called 'common light chain' principle, i.e. combining two binders that share one light chain but still have separate specificities, prevents light chain mispairing. Thus, there are less side products during production, facilitating the homogenous preparation of T cell activating bispecific antigen binding molecules.

The components of the T cell activating bispecific antigen binding molecule can be fused to each other in a variety of configurations. Exemplary configurations are depicted in FIGS. 1A-I and are further described below.

In some embodiments, said T cell activating bispecific antigen binding molecule further comprises an Fc domain composed of a first and a second subunit capable of stable association. Below exemplary embodiments of T cell activating bispecific antigen binding molecule comprising an Fc domain are described.

T Cell Activating Bispecific Antigen Binding Molecule with a Crossover Fab Fragment The inventors of the present invention generated a second bispecific antibody format wherein one of the binding moieties is a crossover Fab fragment. In one aspect of the invention a monovalent bispecific antibody is provided, wherein one of the Fab fragments of an IgG molecule is replaced by a crossover Fab fragment. Crossover Fab fragments are Fab fragments wherein either the variable regions or the constant regions of the heavy and light chain are exchanged. Bispecific antibody formats comprising crossover Fab fragments have been described, for example, in WO2009080252, WO2009080253, WO2009080251, WO2009080254, WO2010/136172, WO2010/145792 and WO2013/026831. In a particular embodiment, the first antigen binding moiety is a crossover Fab molecule wherein either the variable or the constant regions of the Fab light chain and the Fab heavy chain are exchanged. Such modification prevent mispairing of heavy and light chains from different Fab molecules, thereby improving the yield and purity of the T cell activating bispecific antigen binding molecule of the invention in recombinant production. In a particular crossover Fab molecule useful for the T cell activating bispecific antigen binding molecule of the invention, the variable regions of the Fab light chain and the Fab heavy chain are exchanged. In another crossover Fab molecule useful for the T cell activating bispecific antigen binding molecule of the invention, the constant regions of the Fab light chain and the Fab heavy chain are exchanged.

In one embodiment the T cell activating bispecific antigen binding molecule comprises
(i) a first antigen binding moiety which is a crossover Fab molecule capable of specific binding to CD3, comprising at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33, SEQ ID NO: 34;
(ii) a second antigen binding moiety capable of specific binding to Folate Receptor 1 (FolR1) comprising at least one heavy chain complementarity determining region (CDR) selected from the group consisting of SEQ ID NO: 8, SEQ ID NO: 56 and SEQ ID NO: 57 and at least one light chain CDR selected from the group of SEQ ID NO: 59, SEQ ID NO: 60, SEQ ID NO: 65.

In one such embodiment the CD3 antigen binding moiety comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and the FolR1 antigen binding moiety comprises the heavy chain CDR1 of SEQ ID NO: 8, the heavy chain CDR2 of SEQ ID NO: 56, the heavy chain CDR3 of SEQ ID NO:57, the light chain CDR1 of SEQ ID NO: 59, the light chain CDR2 of SEQ ID NO: 60, and the light chain CDR3 of SEQ ID NO:65.

In one embodiment, the second antigen binding moiety is a conventional Fab molecule.

In one embodiment the T cell activating bispecific antigen binding molecule comprises
(i) a first antigen binding moiety which is a crossover Fab molecule capable of specific binding to CD3 comprising a variable heavy chain comprising an amino acid sequence of SEQ ID NO: 36 and a variable light chain comprising an amino acid sequence of SEQ ID NO: 31.
(ii) a second antigen binding moiety which is a Fab molecule capable of specific binding to Folate Receptor 1 (FolR1) comprising a variable heavy chain comprising an amino acid sequence of SEQ ID NO: 55 and a variable light chain comprising an amino acid sequence of SEQ ID NO: 64.

In one embodiment, the second antigen binding moiety is a conventional Fab molecule.

In a further embodiment, the antigen binding moiety that is specific for FolR1 comprises a heavy chain variable region sequence that is at least about 95%, 96%, 97%, 98%, 99% or 100% identical to SEQ ID NO:55 and a light chain variable region sequence that is at least about 95%, 96%, 97%, 98%, 99% or 100% identical to SEQ ID NO: 64 or variants thereof that retain functionality.

In one embodiment the T cell activating bispecific antigen binding molecule comprises a polypeptide sequence that is at least about 95%, 96%, 97%, 98%, 99% or 100% identical to SEQ ID NO: 36, a polypeptide sequence that is at least about 95%, 96%, 97%, 98%, 99% or 100% identical to SEQ ID NO: 31, a polypeptide sequence that is at least about 95%, 96%, 97%, 98%, 99% or 100% identical to SEQ ID NO:55, and a polypeptide sequence that is at least about 95%, 96%, 97%, 98%, 99% or 100% identical to SEQ ID NO: 64.

In one embodiment the T cell activating bispecific antigen binding molecule additionally comprises
(iii) a third antigen binding moiety capable of specific binding to FolR1.

In one embodiment, the third antigen binding moiety is a conventional Fab molecule. In one embodiment, the third antigen binding moiety is a crossover Fab molecule.

In one such embodiment the second and third antigen binding moiety capable of specific binding to FolR1 comprise identical heavy chain complementarity determining region (CDR) and light chain CDR sequences. In one such embodiment the third antigen binding moiety is identical to the second antigen binding moiety.

In one embodiment the T cell activating bispecific antigen binding molecule comprises
(i) a first antigen binding moiety which is a crossover Fab molecule capable of specific binding to CD3, comprising at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33, SEQ ID NO: 34;
(ii) a second antigen binding moiety capable of specific binding to Folate Receptor 1 (FolR1) comprising at least one heavy chain complementarity determining region (CDR) selected from the group consisting of SEQ ID NO: 8, SEQ ID NO: 56 and SEQ ID NO: 57 and at least one light chain CDR selected from the group of SEQ ID NO: 59, SEQ ID NO: 60, SEQ ID NO: 65.
(iii) a third antigen binding moiety capable of specific binding to Folate Receptor 1 (FolR1) comprising at least one heavy chain complementarity determining region (CDR) selected from the group consisting of SEQ ID NO: 8, SEQ ID NO: 56 and SEQ ID NO: 57 and at least one light chain CDR selected from the group of SEQ ID NO: 59, SEQ ID NO: 60, SEQ ID NO: 65.

In one such embodiment the CD3 antigen binding moiety comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and the FolR1 antigen binding moiety comprises the heavy chain CDR1 of SEQ ID NO: 8, the heavy chain CDR2 of SEQ ID NO: 56, the heavy chain CDR3 of SEQ ID NO:57, the light chain CDR1 of SEQ ID NO: 59, the light chain CDR2 of SEQ ID NO: 60, and the light chain CDR3 of SEQ ID NO:65.

In one embodiment, the second antigen binding moiety and the third antigen binding moiety are both a conventional Fab molecule.

In one embodiment the T cell activating bispecific antigen binding molecule comprises
(i) a first antigen binding moiety which is a crossover Fab molecule capable of specific binding to CD3 comprising a variable heavy chain comprising an amino acid sequence of SEQ ID NO: 36 and a variable light chain comprising an amino acid sequence of SEQ ID NO: 31.
(ii) a second antigen binding moiety which is a Fab molecule capable of specific binding to Folate Receptor 1 (FolR1) comprising a variable heavy chain comprising an amino acid sequence of SEQ ID NO: 55 and a variable light chain comprising an amino acid sequence of SEQ ID NO: 64.
(iii) a third antigen binding moiety which is a Fab molecule capable of specific binding to Folate Receptor 1 (FolR1) comprising a variable heavy chain comprising an amino acid sequence of SEQ ID NO: 55 and a variable light chain comprising an amino acid sequence of SEQ ID NO: 64.

In one embodiment, the second antigen binding moiety and the third antigen binding moiety are both a conventional Fab molecule.

In one embodiment the T cell activating bispecific antigen binding molecule comprises
(i) a first antigen binding moiety which is a crossover Fab molecule capable of specific binding to CD3, comprising at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33, SEQ ID NO: 34;
(ii) a second antigen binding moiety capable of specific binding to Folate Receptor 1 (FolR1) comprising at least one heavy chain complementarity determining region (CDR) selected from the group consisting of SEQ ID NO: 8, SEQ ID NO: 9 and SEQ ID NO: 50 and at least one light chain CDR selected from the group of SEQ ID NO: 52, SEQ ID NO: 53, SEQ ID NO: 54.

In one such embodiment the CD3 antigen binding moiety comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and the FolR1 antigen binding moiety comprises the heavy chain CDR1 of SEQ ID NO: 8, the heavy chain CDR2 of SEQ ID NO: 9, the heavy chain CDR3 of SEQ ID NO:50, the light chain CDR1 of SEQ ID NO: 52, the light chain CDR2 of SEQ ID NO: 53, and the light chain CDR3 of SEQ ID NO:54.

In one embodiment, the second antigen binding moiety is a conventional Fab molecule. In one embodiment, the second antigen binding moiety is a crossover Fab molecule.

In one embodiment the T cell activating bispecific antigen binding molecule comprises
(i) a first antigen binding moiety which is a crossover Fab molecule capable of specific binding to CD3 comprising a variable heavy chain comprising an amino acid sequence of SEQ ID NO: 36 and a variable light chain comprising an amino acid sequence of SEQ ID NO: 31.
(ii) a second antigen binding moiety which is a Fab molecule capable of specific binding to Folate Receptor 1 (FolR1) comprising a variable heavy chain comprising an amino acid sequence of SEQ ID NO: 49 and a variable light chain comprising an amino acid sequence of SEQ ID NO: 51.

In one embodiment, the second antigen binding moiety is a conventional Fab molecule. In one embodiment, the second antigen binding moiety is a crossover Fab molecule.

In a further embodiment, the antigen binding moiety that is specific for FolR1 comprises a heavy chain variable region sequence that is at least about 95%, 96%, 97%, 98%, 99% or 100% identical to SEQ ID NO:49 and a light chain variable region sequence that is at least about 95%, 96%, 97%, 98%, 99% or 100% identical to SEQ ID NO: 51 or variants thereof that retain functionality.

In one embodiment the T cell activating bispecific antigen binding molecule comprises a polypeptide sequence that is at least about 95%, 96%, 97%, 98%, 99% or 100% identical to SEQ ID NO: 36, a polypeptide sequence that is at least about 95%, 96%, 97%, 98%, 99% or 100% identical to SEQ ID NO: 31, a polypeptide sequence that is at least about 95%, 96%, 97%, 98%, 99% or 100% identical to SEQ ID NO:49, and a polypeptide sequence that is at least about 95%, 96%, 97%, 98%, 99% or 100% identical to SEQ ID NO: 51.

In one embodiment the T cell activating bispecific antigen binding molecule additionally comprises
(iii) a third antigen binding moiety capable of specific binding to FolR1.

In one embodiment, the third antigen binding moiety is a conventional Fab molecule. In one embodiment, the second antigen binding moiety is a crossover Fab molecule.

In one such embodiment the second and third antigen binding moiety capable of specific binding to FolR1 comprise identical heavy chain complementarity determining region (CDR) and light chain CDR sequences. In one such embodiment the third antigen binding moiety is identical to the second antigen binding moiety.

In one embodiment the T cell activating bispecific antigen binding molecule comprises
(i) a first antigen binding moiety which is a crossover Fab molecule capable of specific binding to CD3, comprising at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33, SEQ ID NO: 34;
(ii) a second antigen binding moiety capable of specific binding to Folate Receptor 1 (FolR1) comprising at least one heavy chain complementarity determining region (CDR) selected from the group consisting of SEQ ID NO: 8, SEQ ID NO: 9 and SEQ ID NO: 49 and at least one light chain CDR selected from the group of SEQ ID NO: 52, SEQ ID NO: 53, SEQ ID NO: 54.
(iii) a third antigen binding moiety capable of specific binding to Folate Receptor 1 (FolR1) comprising at least one heavy chain complementarity determining region (CDR) selected from the group consisting of SEQ ID NO: 8, SEQ ID NO: 9 and SEQ ID NO: 50 and at least one light chain CDR selected from the group of SEQ ID NO: 52, SEQ ID NO: 53, SEQ ID NO: 54.

In one such embodiment the CD3 antigen binding moiety comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and the FolR1 antigen binding moiety comprises the heavy chain CDR1 of SEQ ID NO: 8, the heavy chain CDR2 of SEQ ID NO: 9, the heavy chain CDR3 of SEQ ID NO:50, the light chain CDR1 of SEQ ID NO: 52, the light chain CDR2 of SEQ ID NO: 53, and the light chain CDR3 of SEQ ID NO:54.

In one embodiment, the second antigen binding moiety and the third antigen binding moiety are both a conventional Fab molecule.

In one embodiment the T cell activating bispecific antigen binding molecule comprises
(i) a first antigen binding moiety which is a crossover Fab molecule capable of specific binding to CD3 comprising a variable heavy chain comprising an amino acid sequence of SEQ ID NO: 36 and a variable light chain comprising an amino acid sequence of SEQ ID NO: 31.

(ii) a second antigen binding moiety which is a Fab molecule capable of specific binding to Folate Receptor 1 (FolR1) comprising a variable heavy chain comprising an amino acid sequence of SEQ ID NO: 49 and a variable light chain comprising an amino acid sequence of SEQ ID NO: 51.

(iii) a third antigen binding moiety which is a Fab molecule capable of specific binding to Folate Receptor 1 (FolR1) comprising a variable heavy chain comprising an amino acid sequence of SEQ ID NO: 49 and a variable light chain comprising an amino acid sequence of SEQ ID NO: 51.

In one embodiment, the second antigen binding moiety and the third antigen binding moiety are both a conventional Fab molecule.

Thus, in one embodiment, the invention relates to bispecific molecules wherein two binding moieties confer specific binding to FolR1 and one binding moiety confers specificity to the T cell activating antigen CD3. One of the heavy chains is modified to ensure proper pairing of the heavy and light chains, thus eliminating the need for a common light chain approach. The presence of two FolR1 binding sites enables appropriate engagement with the target antigen FolR1 and the activation of T cells.

The components of the T cell activating bispecific antigen binding molecule can be fused to each other in a variety of configurations. Exemplary configurations are depicted in FIGS. 1A-I and are further described below.

In some embodiments, said T cell activating bispecific antigen binding molecule further comprises an Fc domain composed of a first and a second subunit capable of stable association. Below exemplary embodiments of T cell activating bispecific antigen binding molecule comprising an Fc domain are described.

T Cell Activating Bispecific Antigen Binding Molecule Formats

As depicted above and in FIGS. 1A-I, in one embodiment the T cell activating bispecific antigen binding molecules comprise at least two Fab fragments having identical light chains (VLCL) and having different heavy chains (VHCL) which confer the specificities to two different antigens, i.e. one Fab fragment is capable of specific binding to a T cell activating antigen CD3 and the other Fab fragment is capable of specific binding to the target cell antigen FolR1.

In another embodiment the T cell activating bispecific antigen binding molecule comprises at least two antigen binding moieties (Fab molecules), one of which is a crossover Fab molecule and one of which is a conventional Fab molecule. In one such embodiment the first antigen binding moiety capable of specific binding to CD3 is a crossover Fab molecule and the second antigen binding moiety capable of specific binding to FolR is a conventional Fab molecule.

These components of the T cell activating bispecific antigen binding molecule can be fused to each other in a variety of configurations. Exemplary configurations are depicted in FIG. 1A-I.

In some embodiments, the first and second antigen binding moiety are each fused at the C-terminus of the Fab heavy chain to the N-terminus of the first or the second subunit of the Fc domain. In a specific such embodiment, the T cell activating bispecific antigen binding molecule essentially consists of a first and a second antigen binding moiety, an Fc domain composed of a first and a second subunit, and optionally one or more peptide linkers, wherein the first and second antigen binding moiety are each fused at the C-terminus of the Fab heavy chain to the N-terminus of the first or the second subunit of the Fc domain. In one such embodiment the first and second antigen binding moiety both are Fab fragments and have identical light chains (VLCL). In another such embodiment the first antigen binding moiety capable of specific binding to CD3 is a crossover Fab molecule and the second antigen binding moiety capable of specific binding to FolR is a conventional Fab molecule.

In one embodiment, the second antigen binding moiety is fused at the C-terminus of the Fab heavy chain to the N-terminus of the first or the second subunit of the Fc domain and the first antigen binding moiety is fused at the C-terminus of the Fab heavy chain to the N-terminus of the Fab heavy chain of the second antigen binding moiety. In a specific such embodiment, the T cell activating bispecific antigen binding molecule essentially consists of a first and a second antigen binding moiety, an Fc domain composed of a first and a second subunit, and optionally one or more peptide linkers, wherein the first antigen binding moiety is fused at the C-terminus of the Fab heavy chain to the N-terminus of the Fab heavy chain of the second antigen binding moiety, and the second antigen binding moiety is fused at the C-terminus of the Fab heavy chain to the N-terminus of the first or the second subunit of the Fc domain. In one such embodiment the first and second antigen binding moiety both are Fab fragments and have identical light chains (VLCL). In another such embodiment the first antigen binding moiety capable of specific binding to CD3 is a crossover Fab molecule and the second antigen binding moiety capable of specific binding to FolR is a conventional Fab molecule. Optionally, the Fab light chain of the first antigen binding moiety and the Fab light chain of the second antigen binding moiety may additionally be fused to each other.

In other embodiments, the first antigen binding moiety is fused at the C-terminus of the Fab heavy chain to the N-terminus of the first or second subunit of the Fc domain. In a particular such embodiment, the second antigen binding moiety is fused at the C-terminus of the Fab heavy chain to the N-terminus of the Fab heavy chain of the first antigen binding moiety. In a specific such embodiment, the T cell activating bispecific antigen binding molecule essentially consists of a first and a second antigen binding moiety, an Fc domain composed of a first and a second subunit, and optionally one or more peptide linkers, wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first or the second subunit of the Fc domain. In one such embodiment the first and second antigen binding moiety both are Fab fragments and have identical light chains (VLCL). In another such embodiment the first antigen binding moiety capable of specific binding to CD3 is a crossover Fab molecule and the second antigen binding moiety capable of specific binding to FolR is a conventional Fab molecule. Optionally, the Fab light chain of the first antigen binding moiety and the Fab light chain of the second antigen binding moiety may additionally be fused to each other.

The antigen binding moieties may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$ (SEQ ID NO: 387), $(SG_4)_n$ (SEQ ID NO: 388), (G$_4$S)$_n$ (SEQ ID NO: 387) or G$_4$(SG$_4$)$_n$ (SEQ ID NO: 389) peptide linkers. "n" is generally a number between 1 and 10, typically between 2 and 4. A particularly suitable peptide linker for fusing the Fab light chains of the first and the second antigen binding moiety to each other is (G$_4$S)$_2$ (SEQ ID NO: 386). An exemplary peptide linker suitable for connecting the Fab heavy chains of the first and the second antigen binding moiety is EPKSC(D)-(G$_4$S)$_2$ (SEQ ID NOS 390 and 391). Additionally, linkers may comprise (a portion of) an immunoglobulin hinge region. Particularly where an antigen binding moiety is fused to the N-terminus of an Fc domain subunit, it may be fused via an immunoglobulin hinge region or a portion thereof, with or without an additional peptide linker.

It has been found by the inventors of the present invention that T cell activating bispecific antigen binding molecule comprising two binding moieties specific for the target cell antigen FolR have superior characteristics compared to T cell activating bispecific antigen binding molecule comprising only one binding moiety specific for the target cell antigen FolR.

Accordingly, in certain embodiments, the T cell activating bispecific antigen binding molecule of the invention further comprises a third antigen binding moiety which is a Fab molecule capable of specific binding to FolR. In one such embodiment the second and third antigen binding moiety capable of specific binding to FolR1 comprise identical heavy chain complementarity determining region (CDR) and light chain CDR sequences, i.e., the heavy chain CDR sequences of the second antigen binding moiety are the same as the heavy chain CDR sequences of the third antigen binding moiety, and the light chain CDR sequences of the second antigen binding moiety are the same as the light chain CDR sequences of the third antigen binding moiety. In one such embodiment the third antigen binding moiety is identical to the second antigen binding moiety (i.e. they comprise the same amino acid sequences).

In one embodiment, the first and second antigen binding moiety are each fused at the C-terminus of the Fab heavy chain to the N-terminus of the first or second subunit of the Fc domain and the third antigen binding moiety is fused at the C-terminus of the Fab heavy chain to the N-terminus to the N-terminus of the Fab heavy chain of the first antigen binding moiety. In a specific such embodiment, the T cell activating bispecific antigen binding molecule essentially consists of a first, a second and a third antigen binding moiety, an Fc domain composed of a first and a second subunit, and optionally one or more peptide linkers, wherein the first and second antigen binding moiety are each fused at the C-terminus of the Fab heavy chain to the N-terminus of the first subunit of the Fc domain and the third antigen binding moiety is fused at the C-terminus of the Fab heavy chain to the N-terminus of the Fab heavy chain of the first antigen binding moiety. In one such embodiment the first, second and third antigen binding moiety are conventional Fab fragments and have identical light chains (VLCL). In another such embodiment the first antigen binding moiety capable of specific binding to CD3 is a crossover Fab molecule and the second and third antigen binding moiety capable of specific binding to FolR is a conventional Fab molecule. Optionally, the Fab light chain of the first antigen binding moiety and the Fab light chain of the third antigen binding moiety may additionally be fused to each other.

In another aspect, the invention provides for a bispecific antibody comprising a) a first antigen-binding site that competes for binding to human FolR1 with a reference antibody comprising a variable heavy chain domain (VH) of SEQ ID NO: 49 and a variable light chain domain of SEQ ID NO: 51; and b) a second antigen-binding site that competes for binding to human CD3 with a reference antibody comprising a variable heavy chain domain (VH) of SEQ ID NO: 36 and a variable light chain domain of SEQ ID NO: 31, wherein binding competition is measured using a surface plasmon resonance assay.

In another aspect, the invention provides for a T cell activating bispecific antigen binding molecule comprising a first antigen binding moiety capable of specific binding to CD3, and a second antigen binding moiety capable of specific binding to Folate Receptor 1 (FolR1), wherein the T cell activating bispecific antigen binding molecule binds to the same epitope on human FolR1 as a first reference antibody comprising a variable heavy chain domain (VH) of SEQ ID NO: 49 and a variable light chain domain of SEQ ID NO: 51; and wherein the T cell activating bispecific antigen binding molecule binds to the same epitope on human CD3 as a second reference antibody comprising a variable heavy chain domain (VH) of SEQ ID NO: 36 and a variable light chain domain of SEQ ID NO: 31.

In another aspect, the invention provides for a T cell activating bispecific antigen binding molecule that comprises a first, second, third, fourth and fifth polypeptide chain that form a first, a second and a third antigen binding moiety wherein the first antigen binding moiety is capable of binding CD3 and the second and the third antigen binding moiety each are capable of binding Folate Receptor 1 (FolR1). The first and the second polypeptide chain comprise, in amino (N)-terminal to carboxyl (C)-terminal direction, a first light chain variable domain (VLD1) and a first light chain constant domain (CLD1). The third polypeptide chain comprises, in N-terminal to C-terminal direction, second light chain variable domain (VLD2) and a second heavy chain constant domain 1 (CH1D2). The fourth polypeptide chain comprises, in N-terminal to C-terminal direction, a first heavy chain variable domain (VHD1), a first heavy chain constant domain 1 (CH1D1), a first heavy chain constant domain 2 (CH2D1) and a first heavy chain constant domain 3 (CH3D1). The fifth polypeptide chain comprises VHD1, CH1D1, a second heavy chain variable domain (VHD2), a second light chain constant domain (CLD2), a second heavy chain constant domain 2 (CH2D2) and a second heavy chain constant domain 3 (CH3D2). The third polypeptide chain and VHD2 and CLD2 of the fifth polypeptide chain form the first antigen binding moiety capable of binding CD3. The second polypeptide chain and VHD1 and CH1D1 of the fifth polypeptide chain form the third binding moiety capable of binding to FolR1. The first polypeptide chain and VHD1 and CH1D1 of the fourth polypeptide chain form the second binding moiety capable of binding to FolR1.

In another embodiment, the second and the third antigen binding moiety are each fused at the C-terminus of the Fab heavy chain to the N-terminus of the first or second subunit of the Fc domain, and the first antigen binding moiety is fused at the C-terminus of the Fab heavy chain to the N-terminus of the Fab heavy chain of the second antigen binding moiety. In a specific such embodiment, the T cell activating bispecific antigen binding molecule essentially consists of a first, a second and a third antigen binding moiety, an Fc domain composed of a first and a second subunit, and optionally one or more peptide linkers, wherein the second and third antigen binding moiety are each fused at the C-terminus of the Fab heavy chain to the N-terminus of the first subunit of the Fc domain and the first antigen binding moiety is fused at the C-terminus of the Fab heavy chain to the N-terminus of the Fab heavy chain of the third antigen binding moiety. In one such embodiment the first, second and third antigen binding moiety are conventional Fab fragments and have identical light chains (VLCL). In another such embodiment the first antigen binding moiety capable of specific binding to CD3 is a crossover Fab molecule and the second and third antigen binding moiety capable of specific binding to FolR is a conventional Fab molecule. Optionally, the Fab light chain of the first antigen binding moiety and the Fab light chain of the second antigen binding moiety may additionally be fused to each other.

The antigen binding moieties may be fused to the Fc domain directly or through a peptide linker. In a particular embodiment the antigen binding moieties are each fused to the Fc domain through an immunoglobulin hinge region. In a specific embodiment, the immunoglobulin hinge region is a human IgG$_1$ hinge region.

In one embodiment the first and the second antigen binding moiety and the Fc domain are part of an immunoglobulin molecule. In a particular embodiment the immunoglobulin molecule is an IgG class immunoglobulin. In an even more particular embodiment the immunoglobulin is an IgG$_1$ subclass immunoglobulin. In another embodiment the immunoglobulin is an IgG$_4$ subclass immunoglobulin. In a further particular embodiment the immunoglobulin is a human immunoglobulin. In other embodiments the immunoglobulin is a chimeric immunoglobulin or a humanized immunoglobulin.

In a particular embodiment said T cell activating bispecific antigen binding molecule the first and the second antigen binding moiety and the Fc domain are part of an immunoglobulin molecule, and the third antigen binding moiety is fused at the C-terminus of the Fab heavy chain to the N-terminus of the Fab heavy chain of the first antigen binding moiety, wherein the first, second and third antigen binding moiety are conventional Fab fragments and have identical light chains (VLCL), wherein the first antigen binding moiety capable of specific binding to CD3 comprises at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33 and SEQ ID NO: 34; and the second and the third antigen binding moiety capable of specific binding to FolR1 comprise at least one heavy chain complementarity determining region (CDR) selected from the group consisting of SEQ ID NO: 16, SEQ ID NO: 17 and SEQ ID NO: 18 and at least one light chain CDR selected from the group of SEQ ID NO: 32, SEQ ID NO: 33 and SEQ ID NO: 34.

In a particular embodiment said T cell activating bispecific antigen binding molecule the first and the second antigen binding moiety and the Fc domain are part of an immunoglobulin molecule, and the third antigen binding moiety is fused at the C-terminus of the Fab heavy chain to the N-terminus of the Fab heavy chain of the first antigen binding moiety, wherein the first, second and third antigen binding moiety are conventional Fab fragments and have identical light chains (VLCL), wherein the first antigen binding moiety capable of specific binding to CD3 comprises a variable heavy chain comprising a sequence of SEQ ID NO: 36, a variable light chain comprising a sequence of SEQ ID NO: 31; and the second and the third antigen binding moiety capable of specific binding to FolR1 comprise a variable heavy chain comprising a sequence of SEQ ID NO: 15, a variable light chain comprising a sequence of SEQ ID NO: 31.

In a particular embodiment said T cell activating bispecific antigen binding molecule the first and the second antigen binding moiety and the Fc domain are part of an immunoglobulin molecule, and the third antigen binding moiety is fused at the C-terminus of the Fab heavy chain to the N-terminus of the Fab heavy chain of the first antigen binding moiety and the first antigen binding moiety capable of specific binding to CD3 is a crossover Fab molecule wherein either the variable or the constant regions of the Fab light chain and the Fab heavy chain are exchanged, comprising at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33 and SEQ ID NO: 34; and the second and the third antigen binding moiety capable of specific binding to FolR1 comprise at least one heavy chain complementarity determining region (CDR) selected from the group consisting of SEQ ID NO: 8, SEQ ID NO: 56 and SEQ ID NO: 57 and at least one light chain CDR selected from the group of SEQ ID NO: 59, SEQ ID NO: 60 and SEQ ID NO: 65.

In a particular embodiment said T cell activating bispecific antigen binding molecule the first and the second antigen binding moiety and the Fc domain are part of an immunoglobulin molecule, and the third antigen binding moiety is fused at the C-terminus of the Fab heavy chain to the N-terminus of the Fab heavy chain of the first antigen binding moiety and the first antigen binding moiety capable of specific binding to CD3 is a crossover Fab molecule wherein either the variable or the constant regions of the Fab light chain and the Fab heavy chain are exchanged, wherein the first antigen binding moiety capable of specific binding to CD3 comprises a variable heavy chain comprising a sequence of SEQ ID NO: 36, a variable light chain comprising a sequence of SEQ ID NO: 31; and the second and the third antigen binding moiety capable of specific binding to FolR1 comprise a variable heavy chain comprising a sequence of SEQ ID NO: 55, a variable light chain comprising a sequence of SEQ ID NO: 65.

In one embodiment the T cell activating bispecific antigen binding molecule is monovalent for each antigen. In a particular embodiment the T cell activating bispecific antigen binding molecule can bind to human CD3 and human folate receptor alpha (FolR1) and was made without employing a hetero-dimerization approach, such as, e.g., knob-into-hole technology. For example, the molecule can be produced by employing a common light chain library and CrossMab technology. In a particular embodiment, The variable region of the CD3 binder is fused to the CH1 domain of a standard human IgG1 antibody to form the VLVH crossed molecule (fused to Fc) which is common for both specificities. To generate the crossed counterparts (VHCL), a CD3 specific variable heavy chain domain is fused to a constant human λ light chain whereas a variable heavy chain domain specific for human FolR1 (e.g., isolated from a common light chain library) is fused to a constant human a light chain. The resulting desired molecule with correctly paired chains comprises both kappa and lambda light chains or fragments thereof. Consequently, this desired bispecific molecule species can be purified from mispaired or homodimeric species with sequential purification steps selecting for kappa and lambda light chain, in either sequence. In one particular embodiment, purification of the desired bispecific antibody employs subsequent purification steps with KappaSelect and LambdaFabSelect columns (GE Healthcare) to remove undesired homodimeric antibodies.

Fc Domain

The Fc domain of the T cell activating bispecific antigen binding molecule consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one embodiment the T cell activating bispecific antigen binding molecule of the invention comprises not more than one Fc domain.

In one embodiment according the invention the Fc domain of the T cell activating bispecific antigen binding molecule is an IgG Fc domain. In a particular embodiment the Fc domain is an $IgG_1$ Fc domain. In another embodiment the Fc domain is an $IgG_4$ Fc domain. In a more specific embodiment, the Fc domain is an $IgG_4$ Fc domain comprising an amino acid substitution at position S228 (Kabat numbering), particularly the amino acid substitution S228P. This amino acid substitution reduces in vivo Fab arm exchange of $IgG_4$ antibodies (see Stubenrauch et al., Drug Metabolism and Disposition 38, 84-91 (2010)). In a further particular embodiment the Fc domain is human.

Fc Domain Modifications Promoting Heterodimerization

T cell activating bispecific antigen binding molecules according to the invention comprise different antigen binding moieties, fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of T cell activating bispecific antigen binding molecules in recombinant production, it will thus be advantageous to introduce in the Fc domain of the T cell activating bispecific antigen binding molecule a modification promoting the association of the desired polypeptides.

Accordingly, in particular embodiments the Fc domain of the T cell activating bispecific antigen binding molecule according to the invention comprises a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

In a specific embodiment said modification is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a particular embodiment, in the CH3 domain of the first subunit of the Fc domain of the T cell activating bispecific antigen binding molecule an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

The protuberance and cavity can be made by altering the nucleic acid encoding the polypeptides, e.g. by site-specific mutagenesis, or by peptide synthesis.

In a specific embodiment, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A).

In yet a further embodiment, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). Introduction of these two cysteine residues results in formation of a disulfide bridge between the two subunits of the Fc domain, thus further stabilizing the dimer (Carter, J Immunol Methods 248, 7-15 (2001)).

In a particular embodiment the antigen binding moiety capable of binding to CD3 is fused (optionally via the antigen binding moiety capable of binding to a target cell antigen) to the first subunit of the Fc domain (comprising the "knob" modification). Without wishing to be bound by theory, fusion of the antigen binding moiety capable of binding to CD3 to the knob-containing subunit of the Fc domain will (further) minimize the generation of antigen binding molecules comprising two antigen binding moieties capable of binding to CD3 (steric clash of two knob-containing polypeptides).

In an alternative embodiment a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

Fc Domain Modifications Abolishing Fc Receptor Binding and/or Effector Function

The Fc domain confers to the T cell activating bispecific antigen binding molecule favorable pharmacokinetic properties, including a long serum half-life which contributes to good accumulation in the target tissue and a favorable tissue-blood distribution ratio. At the same time it may, however, lead to undesirable targeting of the T cell activating bispecific antigen binding molecule to cells expressing Fc receptors rather than to the preferred antigen-bearing cells. Moreover, the co-activation of Fc receptor signaling pathways may lead to cytokine release which, in combination with the T cell activating properties and the long half-life of the antigen binding molecule, results in excessive activation of cytokine receptors and severe side effects upon systemic administration. Activation of (Fc receptor-bearing) immune cells other than T cells may even reduce efficacy of the T cell activating bispecific antigen binding molecule due to the potential destruction of T cells e.g. by NK cells.

Accordingly, in particular embodiments the Fc domain of the T cell activating bispecific antigen binding molecules according to the invention exhibits reduced binding affinity to an Fc receptor and/or reduced effector function, as compared to a native $IgG_1$ Fc domain. In one such embodiment the Fc domain (or the T cell activating bispecific antigen binding molecule comprising said Fc domain) exhibits less than 50%, preferably less than 20%, more preferably less than 10% and most preferably less than 5% of the binding affinity to an Fc receptor, as compared to a native $IgG_1$ Fc domain (or a T cell activating bispecific antigen binding molecule comprising a native $IgG_1$ Fc domain), and/or less than 50%, preferably less than 20%, more preferably less than 10% and most preferably less than 5% of the effector function, as compared to a native $IgG_1$ Fc domain domain (or a T cell activating bispecific antigen binding molecule comprising a native $IgG_1$ Fc domain). In one embodiment, the Fc domain domain (or the T cell activating bispecific antigen binding molecule comprising said Fc domain) does not substantially bind to an Fc receptor and/or induce effector function. In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of CDC, ADCC, ADCP, and cytokine secretion. In a particular embodiment the effector function is ADCC. In one embodiment the Fc domain domain exhibits substantially similar binding affinity to neonatal Fc receptor (FcRn), as compared to a native $IgG_1$ Fc domain domain. Substantially similar binding to FcRn is achieved when the Fc domain (or the T cell activating bispecific antigen binding molecule comprising said Fc domain) exhibits greater than about 70%, particularly greater than about 80%, more particularly greater than about 90% of the binding affinity of a native $IgG_1$ Fc domain (or the T cell activating bispecific antigen binding molecule comprising a native $IgG_1$ Fc domain) to FcRn.

In certain embodiments the Fc domain is engineered to have reduced binding affinity to an Fc receptor and/or reduced effector function, as compared to a non-engineered Fc domain. In particular embodiments, the Fc domain of the T cell activating bispecific antigen binding molecule comprises one or more amino acid mutation that reduces the binding affinity of the Fc domain to an Fc receptor and/or effector function. Typically, the same one or more amino acid mutation is present in each of the two subunits of the Fc domain. In one embodiment the amino acid mutation reduces the binding affinity of the Fc domain to an Fc receptor. In one embodiment the amino acid mutation reduces the binding affinity of the Fc domain to an Fc receptor by at least 2-fold, at least 5-fold, or at least 10-fold. In embodiments where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one embodiment the T cell activating bispecific antigen binding molecule comprising an engineered Fc domain exhibits less than 20%, particularly less than 10%, more particularly less than 5% of the binding affinity to an Fc receptor as compared to a T cell activating bispecific antigen binding molecule comprising a non-engineered Fc domain. In a particular embodiment the Fc receptor is an Fcγ receptor. In some embodiments the Fc receptor is a human Fc receptor. In some embodiments the Fc receptor is an activating Fc receptor. In a specific embodiment the Fc receptor is an activating human Fcγ receptor, more specifically human FcγRIIIa, FcγRI or FcγRIIa, most specifically human FcγRIIIa. Preferably, binding to each of these receptors is reduced. In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the Fc domain to said receptor, is achieved when the Fc domain (or the T cell activating bispecific antigen binding molecule comprising said Fc domain) exhibits greater than about 70% of the binding affinity of a non-engineered form of the Fc domain (or the T cell activating bispecific antigen binding molecule comprising said non-engineered form of the Fc domain) to FcRn. The Fc domain, or T cell activating bispecific antigen binding molecules of the invention comprising said Fc domain, may exhibit greater than about 80% and even greater than about 90% of such affinity. In certain embodiments the Fc domain of the T cell activating bispecific antigen binding molecule is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced crosslinking of target-bound antibodies, reduced dendritic cell maturation, or reduced T cell priming. In one embodiment the reduced effector function is one or more selected from the group of reduced CDC, reduced ADCC, reduced ADCP, and reduced cytokine secretion. In a particular embodiment the reduced effector function is reduced ADCC. In one embodiment the reduced ADCC is less than 20% of the ADCC induced by a non-engineered Fc domain (or a T cell activating bispecific antigen binding molecule comprising a non-engineered Fc domain).

In one embodiment the amino acid mutation that reduces the binding affinity of the Fc domain to an Fc receptor and/or effector function is an amino acid substitution. In one embodiment the Fc domain comprises an amino acid substitution at a position selected from the group of E233, L234, L235, N297, P331 and P329. In a more specific embodiment the Fc domain comprises an amino acid substitution at a position selected from the group of L234, L235 and P329. In some embodiments the Fc domain comprises the amino acid substitutions L234A and L235A. In one such embodiment, the Fc domain is an $IgG_1$ Fc domain, particularly a human $IgG_1$ Fc domain. In one embodiment the Fc domain comprises an amino acid substitution at position P329. In a more specific embodiment the amino acid substitution is P329A or P329G, particularly P329G. In one embodiment the Fc domain comprises an amino acid substitution at position P329 and a further amino acid substitution at a position selected from E233, L234, L235, N297 and P331. In a more specific embodiment the further amino acid substitution is E233P, L234A, L235A, L235E, N297A, N297D or P331S. In particular embodiments the Fc domain comprises amino acid substitutions at positions P329, L234 and L235. In more particular embodiments the Fc domain comprises the amino acid mutations L234A, L235A and P329G ("P329G LALA"). In one such embodiment, the Fc domain is an IgG$_1$ Fc domain, particularly a human IgG$_1$Fc domain. The "P329G LALA" combination of amino acid substitutions almost completely abolishes Fcγ receptor binding of a human IgG$_1$ Fc domain, as described in PCT publication no. WO 2012/130831, incorporated herein by reference in its entirety. WO 2012/130831 also describes methods of preparing such mutant Fc domains and methods for determining its properties such as Fc receptor binding or effector functions.

IgG$_4$ antibodies exhibit reduced binding affinity to Fc receptors and reduced effector functions as compared to IgG$_1$ antibodies. Hence, in some embodiments the Fc domain of the T cell activating bispecific antigen binding molecules of the invention is an IgG$_4$ Fc domain, particularly a human IgG$_4$ Fc domain. In one embodiment the IgG$_4$ Fc domain comprises amino acid substitutions at position S228, specifically the amino acid substitution S228P. To further reduce its binding affinity to an Fc receptor and/or its effector function, in one embodiment the IgG$_4$ Fc domain comprises an amino acid substitution at position L235, specifically the amino acid substitution L235E. In another embodiment, the IgG$_4$ Fc domain comprises an amino acid substitution at position P329, specifically the amino acid substitution P329G. In a particular embodiment, the IgG$_4$ Fc domain comprises amino acid substitutions at positions S228, L235 and P329, specifically amino acid substitutions S228P, L235E and P329G. Such IgG$_4$ Fc domain mutants and their Fcγ receptor binding properties are described in PCT publication no. WO 2012/130831, incorporated herein by reference in its entirety.

In a particular embodiment the Fc domain exhibiting reduced binding affinity to an Fc receptor and/or reduced effector function, as compared to a native IgG$_1$ Fc domain, is a human IgG$_1$ Fc domain comprising the amino acid substitutions L234A, L235A and optionally P329G, or a human IgG$_4$ Fc domain comprising the amino acid substitutions S228P, L235E and optionally P329G.

In certain embodiments N-glycosylation of the Fc domain has been eliminated. In one such embodiment the Fc domain comprises an amino acid mutation at position N297, particularly an amino acid substitution replacing asparagine by alanine (N297A) or aspartic acid (N297D).

In addition to the Fc domains described hereinabove and in PCT publication no. WO 2012/130831, Fc domains with reduced Fc receptor binding and/or effector function also include those with substitution of one or more of Fc domain residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing. Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. A suitable such binding assay is described herein. Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor.

Effector function of an Fc domain, or a T cell activating bispecific antigen binding molecule comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the T cell activating bispecific antigen binding molecule is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

Fc Domain Modifications Promoting Heterodimerization

The T cell activating bispecific antigen binding molecule of the invention comprise different antigen binding moieties, some of which are fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of the bispecific antibodies of the invention in recombinant production, it will thus be advantageous to introduce in the Fc domain of the bispecific antibodies of the invention a modification promoting the association of the desired polypeptides.

Accordingly, in particular embodiments, the Fc domain of the bispecific antibodies of the invention comprises a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

In a specific embodiment, said modification is a so-called "knob-into-hole" modification, comprising a "knob" modification in one of the two subunits of the Fc domain and a "hole" modification in the other one of the two subunits of the Fc domain. The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001).

Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a particular embodiment, in the CH3 domain of the first subunit of the Fc domain of the bispecific antibodies of the invention an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

The protuberance and cavity can be made by altering the nucleic acid encoding the polypeptides, e.g. by site-specific mutagenesis, or by peptide synthesis.

In a specific embodiment, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A).

In yet a further embodiment, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). Introduction of these two cysteine residues results in formation of a disulfide bridge between the two subunits of the Fc domain, further stabilizing the dimer (Carter, J Immunol Methods 248, 7-15 (2001)). In an alternative embodiment a modification promoting association of the first and the second subunit of the Fc domain comprises a modification mediating electrostatic steering effects, e.g. as described in WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

In one embodiment, a T cell activating bispecific antigen binding molecule that binds to FolR1 and CD3 according to any of the above embodiments comprises an Immunoglobulin G (IgG) molecule with two binding sites specific for FolR1, wherein the Fc part of the first heavy chain comprises a first dimerization module and the Fc part of the second heavy chain comprises a second dimerization module allowing a heterodimerization of the two heavy chains of the IgG molecule.

In a further preferred embodiment, the first dimerization module comprises knobs and the second dimerization module comprises holes according to the knobs into holes strategy (see Carter P.; Ridgway J. B. B.; Presta L. G.: Immunotechnology, Volume 2, Number 1, February 1996, pp. 73-73(1)).

Biological Properties and Functional Characteristics of T Cell Activating Bispecific Antigen Binding Molecules One of skill in the art can appreciate the advantageous efficiency of a molecule that selectively distinguishes between cancerous and non-cancerous, healthy cells. One way to accomplish this goal is by appropriate target selection. Markers expressed exclusively on tumor cells can be employed to selectively target effector molecules or cells to tumor cells while sparing normal cells that do not express such marker. However, in some instances, so called tumor cell markers are also expressed in normal tissue, albeit at lower levels. This expression in normal tissue raises the possibility of toxicity. Thus, there was a need in the art for molecules that can more selectively target tumor cells. The invention described herein provides for T cell activating bispecific antigen binding molecules that selectively target FolR1-positive tumor cells and not normal, non-cancerous cells that express FolR1 at low levels or not at all. In one embodiment, the T cell activating bispecific antigen binding molecule comprises at least two, preferably two, FolR1 binding moieties of relatively low affinity that confer an avidity effect which allows for differentiation between high and low FolR1 expressing cells. Because tumor cells express FolR1 at high or intermediate levels, this embodiment of the invention selectively binds to, and/or induces killing of, tumor cells and not normal, non-cancerous cells that express FolR1 at low levels or not at all. In one embodiment, the T cell activating bispecific antigen binding molecule is in the 2+1 inverted format. In one embodiment, the T cell activating bispecific antigen binding molecule induces T cell mediated killing of FolR1-positive tumor cells and not non-tumor cells and comprises a CD3 antigen binding moiety that comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and two FolR1 antigen binding moieties that each comprise the heavy chain CDR1 of SEQ ID NO: 8, the heavy chain CDR2 of SEQ ID NO: 9, the heavy chain CDR3 of SEQ ID NO:50, the light chain CDR1 of SEQ ID NO: 52, the light chain CDR2 of SEQ ID NO: 53, and the light chain CDR3 of SEQ ID NO:54.

In one specific embodiment, the T cell activating bispecific antigen binding molecule does not induce killing of a normal cells having less than about 1000 copies of FolR1 its surface. In addition to the above advantageous characteristics, one embodiment of the invention does not require chemical cross linking or a hybrid approach to be produced. Accordingly, in one embodiment, the invention provides for T cell activating bispecific antigen binding molecule capable of production in CHO cells. In one embodiment, the T cell activating bispecific antigen binding molecule comprises humanized and human polypeptides. In one embodiment, the T cell activating bispecific antigen binding molecule does not cause FcgR crosslinking. In one such embodiment, the T cell activating bispecific antigen binding molecule is capable of production in CHO cells and comprises a CD3 antigen binding moiety that comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and two FolR1 antigen binding moieties that each comprise the heavy chain CDR1 of SEQ ID NO: 8, the heavy chain CDR2 of SEQ ID NO: 9, the heavy chain CDR3 of SEQ ID NO:50, the light chain CDR1 of SEQ ID NO: 52, the light chain CDR2 of SEQ ID NO: 53, and the light chain CDR3 of SEQ ID NO:54.

As noted above, some embodiments contemplated herein include T cell activating bispecific antigen binding molecules having two binding moieties that confer specific binding to FolR1 and one binding moiety that confers specificity to the T cell activating antigen CD3, wherein each individual FolR1 binding moiety engages the antigen with low affinity. Because the molecule comprises two antigen binding moieties that confer binding to FolR1, the overall avidity of the molecule, nevertheless, provides effective binding to FolR1-expressing target cells and activation of T cells to induce T cell effector function. Considering that while FolR1 is expressed at various level on tumor cells, it is also expressed at very low levels (e.g., less than about 1000 copies on the cell surface) in certain normal cells, one of skill in the art can readily recognize the advantageous efficiency of such a molecule for use as a therapeutic agent. Such molecule selectively targets tumor cells over normal cells. Such molecule, thus, can be administered to an individual in need thereof with significantly less concern about toxicity resulting from FolR1 positive normal cells compared to molecules that bind to FolR1 with high affinity to induce effector function.

In one embodiment, the T cell activating bispecific antigen binding molecule binds human FolR1 with an apparent $K_D$ of about 5.36 pM to about 4 nM. In one embodiment, the T cell activating bispecific antigen binding molecule binds human and cynomolgus FolR1 with an apparent $K_D$ of about 4 nM. In one embodiment, the T cell activating bispecific antigen binding molecule binds murine FolR1 with an apparent $K_D$ of about 1.5 nM. In one embodiment, the T cell activating bispecific antigen binding molecule binds human FolR1 with a monovalent binding $K_D$ of at least about 1000 nM. In a specific embodiment, the T cell activating bispecific antigen binding molecule binds human and cynomolgus FolR1 with an apparent $K_D$ of about 4 nM, binds murine FolR1 with an apparent $K_D$ of about 1.5 nM, and comprises a CD3 antigen binding moiety that comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and two FolR1 antigen binding moieties that each comprise the heavy chain CDR1 of SEQ ID NO: 8, the heavy chain CDR2 of SEQ ID NO: 9, the heavy chain CDR3 of SEQ ID NO:50, the light chain CDR1 of SEQ ID NO: 52, the light chain CDR2 of SEQ ID NO: 53, and the light chain CDR3 of SEQ ID NO:54. In one embodiment, the T cell activating bispecific antigen binding molecule binds human FolR1 with a monovalent binding $K_D$ of at least about 1000 nM and comprises a CD3 antigen binding moiety that comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and two FolR1 antigen binding moieties that each comprise the heavy chain CDR1 of SEQ ID NO: 8, the heavy chain CDR2 of SEQ ID NO: 9, the heavy chain CDR3 of SEQ ID NO:50, the light chain CDR1 of SEQ ID NO: 52, the light chain CDR2 of SEQ ID NO: 53, and the light chain CDR3 of SEQ ID NO:54. As described above, the T cell activating bispecific antigen binding molecules contemplated herein can induce T cell effector function, e.g., cell surface marker expression, cytokine production, T cell mediated killing. In one embodiment, the T cell activating bispecific antigen binding molecule induces T cell mediated killing of the FolR1-expressing target cell, such as a human tumor cell, in vitro. In one embodiment, the T cell is a CD8 positive T cell. Examples of FolR1-expressing human tumor cells include but are not limited to Hela, Skov-3, HT-29, and HRCEpiC cells. Other FolR1 positive human cancer cells that can be used for in vitro testing are readily available to the skilled artisan. In one embodiment, the T cell activating bispecific antigen binding molecule induces T cell mediated killing of the FolR1-expressing human tumor cell in vitro with an EC50 of between about 36 pM and about 39573 pM after 24 hours. Specifically contemplated are T cell activating bispecific antigen binding molecules that induce T cell mediated killing of the FolR1-expressing tumor cell in vitro with an EC50 of about 36 pM after 24 hours. In one embodiment, the T cell activating bispecific antigen binding molecule induces T cell mediated killing of the FolR1-expressing tumor cell in vitro with an EC50 of about 178.4 pM after 24 hours. In one embodiment, the T cell activating bispecific antigen binding molecule induces T cell mediated killing of the FolR1-expressing tumor cell in vitro with an EC50 of about 134.5 pM or greater after 48 hours. The EC50 can be measure by methods known in the art, for example by methods disclosed herein by the examples.

In one embodiment, the T cell activating bispecific antigen binding molecule of any of the above embodiments induces upregulation of cell surface expression of at least one of CD25 and CD69 on the T cell as measured by flow cytometry. In one embodiment, the T cell is a CD4 positive T cell or a CD8 positive T cell.

In one embodiment, the T cell activating bispecific antigen binding molecule of any of the above embodiments binds to FolR1 expressed on a human tumor cell. In one embodiment, the T cell activating bispecific antigen binding molecule of any of the above embodiments binds to a conformational epitope on human FolR1. In one embodiment, the T cell activating bispecific antigen binding molecule of any of the above embodiments does not bind to human Folate Receptor 2 (FolR2) or to human Folate Receptor 3 (FolR3). In one embodiment of the T cell activating bispecific antigen binding molecule of any of the above embodiments, the antigen binding moiety binds to a FolR polypeptide comprising the amino acids 25 to 234 of human FolR1 (SEQ ID NO:227). In one embodiment of the T cell activating bispecific antigen binding molecule of any of the above embodiments, the FolR1 antigen binding moiety binds to a FolR polypeptide comprising the amino acid sequence of SEQ ID NOs:227, 230 and 231, and wherein the FolR antigen binding moiety does not bind to a FolR polypeptide comprising the amino acid sequence of SEQ ID NOs:228 and 229. In one specific embodiment, the T cell activating bispecific antigen binding molecule comprises a FolR1 antigen binding moiety that binds to a FolR1 polypeptide comprising the amino acid sequence of SEQ ID NOs:227, 230 and 231, and wherein the FolR1 antigen binding moiety does not bind to a FolR polypeptide comprising the amino acid sequence of SEQ ID NOs:228 and 229, and comprises a CD3 antigen binding moiety that comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and two FolR1 antigen binding moieties that each comprise the heavy chain CDR1 of SEQ ID NO: 8, the heavy chain CDR2 of SEQ ID NO: 9, the heavy chain CDR3 of SEQ ID NO:50, the light chain CDR1 of SEQ ID NO: 52, the light chain CDR2 of SEQ ID NO: 53, and the light chain CDR3 of SEQ ID NO:54.

With respect to the FolR1, the T cell activating bispecific antigen binding molecules contemplated herein can have agonist, antagonist or neutral effect. Examples of agonist effect include induction or enhancement of signaling through the FolR1 upon engagement by the FolR1 binding moiety with the FolR1 receptor on the target cell. Examples of antagonist activity include abrogation or reduction of signaling through the FolR1 upon engagement by the FolR1 binding moiety with the FolR1 receptor on the target cell. This can, for example, occur by blocking or reducing the interaction between folate with FolR1.

Exemplary PD-1 Axis Binding Antagonists for Use in the Invention

Provided herein are methods for treating or delaying progression of cancer in an individual comprising administering to the individual an effective amount of a T cell activating bispecific antigen binding molecule and a PD-1 axis binding antagonist. For example, a PD-1 axis binding antagonist includes a PD-1 binding antagonist, a PDL1 binding antagonist and a PDL2 binding antagonist. Alternative names for "PD-1" include CD279 and SLEB2. Alternative names for "PDL1" include B7-H1, B7-4, CD274, and B7-H. Alternative names for "PDL2" include B7-DC, Btdc, and CD273. In some embodiments, PD-1, PDL1, and PDL2 are human PD-1, PDL1 and PDL2.

In some embodiments, the PD-1 binding antagonist is a molecule that inhibits the binding of PD-1 to its ligand binding partners. In a specific aspect the PD-ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

In some embodiments, the anti-PD-1 antibody is nivolumab (CAS Registry Number. 946414-94-4). In a still further embodiment, provided is an isolated anti-PD-1 antibody comprising a heavy chain variable region comprising the heavy chain variable region amino acid sequence from SEQ ID NO:274 and/or a light chain variable region comprising the light chain variable region amino acid sequence from SEQ ID NO:275. In a still further embodiment, provided is an isolated anti-PD-1 antibody comprising a heavy chain and/or a light chain sequence, wherein:
(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:

(SEQ ID NO: 274)
QVQLVESGGGVVQPGRSLRLDCKASGITFSNSGMHWVRQAPGKGLEWVA

VIWYDGSKRYYADSVKGRFTISRDNSKNTLFLQMNSLRAEDTAVYYCAT

NDDYWGQGTLVTVSSASTKGPSVFPLAPCSRSTSESTAALGCLVKDYFP

EPVTVSWNSGALTSGVHTFPAVLQSSGLYSLSSVVTVPSSSLGTKTYTC

NVDHKPSNTKVDKRVESKYGPPCPPCPAPEFLGGPSVFLFPPKPKDTLM

ISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK, or (b) the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence:

(SEQ ID NO: 275)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

In some embodiments, the anti-PD-1 antibody is pembrolizumab (CAS Registry Number. 1374853-91-4). In a still further embodiment, provided is an isolated anti-PD-1 antibody comprising a heavy chain variable region comprising the heavy chain variable region amino acid sequence from SEQ ID NO:276 and/or alight chain variable region comprising the light chain variable region amino acid sequence from SEQ ID NO:277. In a still further embodiment, provided is an isolated anti-PD-1 antibody comprising a heavy chain and/or alight chain sequence, wherein:

(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:

```
                                        (SEQ ID NO: 276)
QVQLVQSGVE

VKKPGASVKVSCKASGYTFT NYYMYWVRQA

PGQGLEWMGG INPSNGGTNF

NEKFKNRVTLTTDSSTTTAY MELKSLQFDD

TAVYYCARRDYRFDMGFDYW

GQGTTVTVSSASTKGPSVFP LAPCSRSTSE

STAALGCLVKDYFPEPVTVS

WNSGALTSGVHTFPAVLQSS GLYSLSSVVT

VPSSSLGTKTYTCNVDHKPS

NTKVDKRVESKYGPPCPPCP APEFLGGPSV

FLFPPKPKDTLMISRTPEVT

CVVVDVSQEDPEVQFNWYVD GVEVHNAKTK

PREEQFNSTYRVVSVLTVLH

QDWLNGKEYKCKVSNKGLPS SIEKTISKAK

GQPREPQVYTLPPSQEEMTK

NQVSLTCLVKGFYPSDIAVE WESNGQPENN

YKTTPPVLDSDGSFFLYSRL

TVDKSRWQEGNVFSCSVMHE ALHNHYTQKS

LSLSLGK,
``` or
(b) the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence:

```
                                        (SEQ ID NO: 277)
EIVLTQSPATLSLSPGERATLSCRASKGVSTSGYSYLHWYQQKPGQAPRL

LIYLASYLESGVPARFSGSGSGTDFTLTISSLEPEDFAVYYCQHSRDLPL

TFGGGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.
```

In some embodiments, the PDL1 binding antagonist is anti-PDL1 antibody. In some embodiments, the anti-PDL1 binding antagonist is selected from the group consisting of YW243.55.S70, MPDL3280A, MDX-1105, and MEDI4736. MDX-1105, also known as BMS-936559, is an anti-PDL1 antibody described in WO2007/005874. Antibody YW243.55.S70 (heavy and light chain variable region sequences shown in SEQ ID Nos. 20 and 21, respectively) is an anti-PDL1 described in WO 2010/077634 A1. MEDI4736 is an anti-PDL1 antibody described in WO2011/066389 and US2013/034559, each incorporated herein by reference as if set forth in their entirety.

Examples of anti-PDL1 antibodies useful for the methods of this invention, and methods for making thereof are described in PCT patent application WO 2010/077634 A1 and U.S. Pat. No. 8,217,149, each incorporated herein by reference as if set forth in their entirety.

In some embodiments, the PD-1 axis binding antagonist is an anti-PDL1 antibody. In some embodiments, the anti-PDL1 antibody is capable of inhibiting binding between PDL1 and PD-1 and/or between PDL1 and B7-1. In some embodiments, the anti-PDL1 antibody is a monoclonal antibody. In some embodiments, the anti-PDL1 antibody is an antibody fragment selected from the group consisting of Fab, Fab'-SH, Fv, scFv, and (Fab')2 fragments. In some embodiments, the anti-PDL1 antibody is a humanized antibody. In some embodiments, the anti-PDL1 antibody is a human antibody.

The anti-PDL1 antibodies useful in this invention, including compositions containing such antibodies, such as those described in WO 2010/077634 A, may be used in combination with a T cell activating antigen binding molecule, and, optionally an anti-TIM3 antagonist antibody, to treat cancer. In some embodiments, the anti-PDL1 antibody comprises a heavy chain variable region comprising the amino acid sequence of SEQ ID NO:382 and a light chain variable region comprising the amino acid sequence of SEQ ID NO:383.

In one embodiment, the anti-PDL1 antibody contains a heavy chain variable region polypeptide comprising an HVR-H1, HVR-H2 and HVR-H3 sequence, wherein:

```
(a) the HVR-H1 sequence is
                                        (SEQ ID NO: 283)
    GFTFSX1SWIH;

(b) the HVR-H2 sequence is
                                        (SEQ ID NO: 284)
    AWIX2PYGGSX3YYADSVKG;

(c) the HVR-H3 sequence is
                                        (SEQ ID NO: 285)
    RHWPGGFDY;
``` further wherein: X1 is D or G; X2 is S or L; X3 is T or S.

In one specific aspect, X1 is D; X2 is S and X3 is T. In another aspect, the polypeptide further comprises variable region heavy chain framework sequences juxtaposed between the HVRs according to the formula: (HC-FR1)-(HVR-H1)-(HC-FR2)-(HVR-H2)-(HC-FR3)-(HVRH3)-(HC-FR4). In yet another aspect, the framework sequences are derived from human consensus framework sequences. In a further aspect, the framework sequences are VH subgroup III consensus framework. In a still further aspect, at least one of the framework sequences is the following:

```
HC-FR1 is
                                        (SEQ ID NO: 295)
    EVQLVESGGGLVQPGGSLRLSCAAS

HC-FR2 is
                                        (SEQ ID NO: 296)
    WVRQAPGKGLEWV

HC-FR3 is
                                        (SEQ ID NO: 297)
    RFTISADTSKNTAYLQMNSLRAEDTAVYYCAR
```

-continued

HC-FR4 is
                                    (SEQ ID NO: 298)
WGQGTLVTVSA.

In a still further aspect, the heavy chain polypeptide is further combined with a variable region light chain comprising an HVR-L1, HVR-L2 and HVR-L3, wherein:

(a) the HVR-L1 sequence is
                                    (SEQ ID NO: 286)
RASQX4X5X6TX7X8A;

(b) the HVR-L2 sequence is
                                    (SEQ ID NO: 287)
SASX9LX10S,;

(c) the HVR-L3 sequence is
                                    (SEQ ID NO: 288)
QQX11X12X13X14PX15T;

further wherein: X4 is D or V; X5 is V or I; X6 is S or N; X7 is A or F; X8 is V or L; X9 is F or T; X10 is Y or A; X11 is Y, G, F, or S; X12 is L, Y, F or W; X13 is Y, N, A, T, G, F or I; X14 is H, V, P, T or I; X15 is A, W, R, P or T.

In a still further aspect, X4 is D; X5 is V; X6 is S X7 is A; X8 is V; X9 is F; X10 is Y; X11 is Y; X12 is L; X13 is Y; X14 is H; X15 is A. In a still further aspect, the light chain further comprises variable region light chain framework sequences juxtaposed between the HVRs according to the formula: (LC-FR1)-(HVR-L1)-(LC-FR2)-(HVR-L2)-(LC-FR3)-(HVR-L3)-(LCFR4).

In a still further aspect, the framework sequences are derived from human consensus framework sequences. In a still further aspect, the framework sequences are VL kappa I consensus framework. In a still further aspect, at least one of the framework sequence is the following:

LC-FR1 is
                                    (SEQ ID NO: 300)
DIQMTQSPSSLSASVGDRVTITC

LC-FR2 is
                                    (SEQ ID NO: 301)
WYQQKPGKAPKLLIY

LC-FR3 is
                                    (SEQ ID NO: 302)
GVPSRFSGSGSGTDFTLTISSLQPEDFATYYC

LC-FR4 is
                                    (SEQ ID NO: 303)
FGQGTKVEIKR.

In another embodiment, provided is an isolated anti-PDL1 antibody or antigen binding fragment comprising a heavy chain and a light chain variable region sequence, wherein:
(a) the heavy chain comprises and HVR-H1, HVR-H2 and HVR-H3, wherein further:

(i) the HVR-H1 sequence is
                                    (SEQ ID NO: 283)
GFTFSX1SWIH (ii) the HVR-H2 sequence is
                                    (SEQ ID NO: 284)
AWIX2PYGGSX3YYADSVKG (iii) the HVR-H3 sequence is
                                    (SEQ ID NO: 285)
RHWPGGFDY (b) the light chain comprises and HVR-L1, HVR-L2 and HVR-L3, wherein further:

(i) the HVR-L1 sequence is
                                    (SEQ ID NO: 286)
RASQX4X5X6TX7X8A (ii) the HVR-L2 sequence is
                                    (SEQ ID NO: 287)
SASX9LX10S (iii) the HVR-L3 sequence is
                                    (SEQ ID NO: 288)
QQX11X12X13X14PX15T Further wherein: X1 is D or G; X2 is S or L; X3 is T or S; X4 is D or V; X5 is V or I; X6 is S or N; X7 is A or F; X8 is V or L; X9 is F or T; X10 is Y or A; X11 is Y, G, F, or S; X12 is L, Y, F or W; X13 is Y, N, A, T, G, F or I; X14 is H, V, P, T or I; X15 is A, W, R, P or T.

In a specific aspect, X1 is D; X2 is S and X3 is T. In another aspect, X4 is D; X5 is V; X6 is S; X7 is A; X8 is V; X9 is F; X10 is Y; X11 is Y; X12 is L; X13 is Y; X14 is H; X15 is A. In yet another aspect, X1 is D; X2 is S and X3 is T, X4 is D; X5 is V; X6 is S; X7 is A; X8 is V; X9 is F; X10 is Y; X11 is Y; X12 is L; X13 is Y; X14 is H and X15 is A.

In a further aspect, the heavy chain variable region comprises one or more framework sequences juxtaposed between the HVRs as: (HC-FR1)-(HVR-H1)-(HC-FR2)-(HVR-H2)-(HCFR3)-(HVR-H3)-(HC-FR4), and the light chain variable regions comprises one or more framework sequences juxtaposed between the HVRs as: (LC-FR1)-(HVR-L1)-(LC-FR2)-(HVRL2)-(LC-FR3)-(HVR-L3)-(LC-FR4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

HC-FR1
                                    (SEQ ID NO: 295)
EVQLVESGGGLVQPGGSLRLSCAAS

HC-FR2
                                    (SEQ ID NO: 296)
WVRQAPGKGLEWV

HC-FR3
                                    (SEQ ID NO: 297)
RFTISADTSKNTAYLQMNSLRAEDTAVYYCAR

HC-FR4
                                    (SEQ ID NO: 298)
WGQGTLVTVSA.

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

LC-FR1
                                    (SEQ ID NO: 300)
DIQMTQSPSSLSASVGDRVTITC

```
LC-FR2
                                (SEQ ID NO: 301)
WYQQKPGKAPKLLIY

LC-FR3
                                (SEQ ID NO: 302)
GVPSRFSGSGSGTDFTLTISSLQPEDFATYYC

LC-FR4
                                (SEQ ID NO: 303)
FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effectorless Fc mutation" or aglycosylation. In still a further embodiment, the effector-less Fc mutation is an N297A or D265A/N297A substitution in the constant region.

In yet another embodiment, provided is an anti-PDL1 antibody comprising a heavy chain and a light chain variable region sequence, wherein:

(a) the heavy chain further comprises and HVR-H1, HVR-H2 and an HVRH3 sequence having at least 85% sequence identity to GFTFSDSWIH (SEQ ID NO:289), AWISPYGG-STYYADSVKG (SEQ ID NO:290), and RHWPGGFDY (SEQ ID NO:291), respectively, or (b) the light chain further comprises an HVR-L1, HVR-L2 and an HVR-L3 sequence having at least 85% sequence identity to RASQDVSTAVA (SEQ ID NO:292), SASFLYS (SEQ ID NO:293) and QQYLHPAT (SEQ ID NO:294), respectively.

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HCFR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
                                (SEQ ID NO: 295)
EVQLVESGGGLVQPGGSLRLSCAAS

HC-FR2
                                (SEQ ID NO: 296)
WVRQAPGKGLEWV

HC-FR3
                                (SEQ ID NO: 297)
RFTISADTSKNTAYLQMNSLRAEDTAVYYCAR

HC-FR4
                                (SEQ ID NO: 298)
WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                                (SEQ ID NO: 300)
DIQMTQSPSSLSASVGDRVTITC

LC-FR2
                                (SEQ ID NO: 301)
WYQQKPGKAPKLLIY

LC-FR3
                                (SEQ ID NO: 302)
GVPSRFSGSGSGTDFTLTISSLQPEDFATYYC

LC-FR4
                                (SEQ ID NO: 303)
FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effectorless Fc mutation" or aglycosylation. In still a further embodiment, the effector-less Fc mutation is an N297A or D265A/N297A substitution in the constant region.

In a still further embodiment, provided is an isolated anti-PDL1 antibody comprising a heavy chain and a light chain variable region sequence, wherein:

(a) the heavy chain sequence has at least 85% sequence identity to the heavy chain sequence:

```
                                (SEQ ID NO: 382)
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSA,
``` or
(b) the light chain sequence has at least 85% sequence identity to the light chain sequence:

```
                                (SEQ ID NO: 383)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.
```

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HCFR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework.

In a still further aspect, one or more of the heavy chain framework sequences is the following:

```
HC-FR1
                                    (SEQ ID NO: 295)
EVQLVESGGGLVQPGGSLRLSCAAS

HC-FR2
                                    (SEQ ID NO: 296)
WVRQAPGKGLEWV

HC-FR3
                                    (SEQ ID NO: 297)
RFTISADTSKNTAYLQMNSLRAEDTAVYYCAR

HC-FR4
                                    (SEQ ID NO: 298)
WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                                    (SEQ ID NO: 300)
DIQMTQSPSSLSASVGDRVTITC

LC-FR2
                                    (SEQ ID NO: 301)
WYQQKPGKAPKLLIY

LC-FR3
                                    (SEQ ID NO: 302)
GVPSRFSGSGSGTDFTLTISSLQPEDFATYYC

LC-FR4
                                    (SEQ ID NO: 303)
FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further embodiment, the effector-less Fc mutation is an N297A or D265A/N297A substitution in the constant region.

In another further embodiment, provided is an isolated anti-PDL1 antibody comprising a heavy chain and a light chain variable region sequence, wherein:

(a) the heavy chain sequence has at least 85% sequence identity to the heavy chain sequence:

```
                                    (SEQ ID NO: 280)
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSS,
``` or (b) the light chain sequence has at least 85% sequence identity to the light chain sequence:

```
                                    (SEQ ID NO: 383)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.
```

In a still further embodiment, provided is an isolated anti-PDL1 antibody comprising a heavy chain and a light chain variable region sequence, wherein:

(a) the heavy chain sequence has at least 85% sequence identity to the heavy chain sequence:

```
                                    (SEQ ID NO: 281)
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSSASTK,
``` or (b) the light chain sequences has at least 85% sequence identity to the light chain sequence:

```
                                    (SEQ ID NO: 282)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.
```

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HCFR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework.

In a still further aspect, one or more of the heavy chain framework sequences is the following:

```
HC-FR1
                                    (SEQ ID NO: 295)
EVQLVESGGGLVQPGGSLRLSCAAS
```

```
HC-FR2
                                    (SEQ ID NO: 296)
WVRQAPGKGLEWV

HC-FR3
                                    (SEQ ID NO: 297)
RFTISADTSKNTAYLQMNSLRAEDTAVYYCAR

HC-FR4
                                    (SEQ ID NO: 299)
WGQGTLVTVSS.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                                    (SEQ ID NO: 300)
DIQMTQSPSSLSASVGDRVTITC

LC-FR2
                                    (SEQ ID NO: 301)
WYQQKPGKAPKLLIY

LC-FR3
                                    (SEQ ID NO: 302)
GVPSRFSGSGSGTDFTLTISSLQPEDFATYYC

LC-FR4
                                    (SEQ ID NO: 303)
FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further embodiment, the effector-less Fc mutation is an N297A or D265A/N297A substitution in the constant region.

In yet another embodiment, the anti-PDL1 antibody is MPDL3280A (CAS Registry Number 1422185-06-5). In a still further embodiment, provided is an isolated anti-PDL1 antibody comprising a heavy chain variable region comprising the heavy chain variable region amino acid sequence from SEQ ID NO:24 or SEQ ID NO:28 and/or a light chain variable region comprising the light chain variable region amino acid sequence from SEQ ID NO:21. In a still further embodiment, provided is an isolated anti-PDL1 antibody comprising a heavy chain and/or a light chain sequence, wherein:
(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:

```
                                    (SEQ ID NO: 278)
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPRE

EQYASTYRVVSVLTVLHQDWLNGKEYKCKVSNKALPAPIEKTISKAKGQ

PREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKS

LSLSPG,
``` or
(b) the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence:

```
                                    (SEQ ID NO: 279)
DIQMTQSPSSLSASVGDRVTITCRASQDVSTAVAWYQQKPGKAPKLLIY

SASFLYSGVPSRFSGSGSGTDFTLTISSLQPEDFATYYCQQYLYHPATF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.
```

In a still further embodiment, the invention provides for compositions comprising any of the above described anti-PDL1 antibodies in combination with at least one pharmaceutically acceptable carrier.

In a still further embodiment, provided is an isolated nucleic acid encoding a light chain or a heavy chain variable region sequence of an anti-PDL1 antibody, wherein:
(a) the heavy chain further comprises and HVR-H1, HVR-H2 and an HVRH3 sequence having at least 85% sequence identity to GFTFSDSWIH (SEQ ID NO:289), AWISPYGG-STYYADSVKG (SEQ ID NO:290) and RHWPGGFDY (SEQ ID NO:291), respectively, and
(b) the light chain further comprises an HVR-L1, HVR-L2 and an HVR-L3 sequence having at least 85% sequence identity to RASQDVSTAVA (SEQ ID NO:292), SASFLYS (SEQ ID NO:293) and QQYLYHPAT (SEQ ID NO:294), respectively.

In a specific aspect, the sequence identity is 86%, 87%, 88%, 89%, 90%, 91%, 92%, 93%, 94%, 95%, 96%, 97%, 98%, 99% or 100%. In aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LCFR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework.

In a still further aspect, one or more of the heavy chain framework sequences is the following:

```
HC-FR1
                                          (SEQ ID NO: 295)
EVQLVESGGGLVQPGGSLRLSCAAS

HC-FR2
                                          (SEQ ID NO: 296)
WVRQAPGKGLEWV

HC-FR3
                                          (SEQ ID NO: 297)
RFTISADTSKNTAYLQMNSLRAEDTAVYYCAR

HC-FR4
                                          (SEQ ID NO: 298)
WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                                          (SEQ ID NO: 300)
DIQMTQSPSSLSASVGDRVTITC

LC-FR2
                                          (SEQ ID NO: 301)
WYQQKPGKAPKLLIY

LC-FR3
                                          (SEQ ID NO: 302)
GVPSRFSGSGSGTDFTLTISSLQPEDFATYYC

LC-FR4
                                          (SEQ ID NO: 303)
FGQGTKVEIKR.
```

In a still further specific aspect, the antibody described herein (such as an anti-PD-1 antibody, an anti-PDL1 antibody, or an anti-PDL2 antibody) further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further aspect, the effector-less Fc mutation is an N297A or D265A/N297A substitution in the constant region.

In a still further aspect, provided herein are nucleic acids encoding any of the antibodies described herein. In some embodiments, the nucleic acid further comprises a vector suitable for expression of the nucleic acid encoding any of the previously described anti-PDL1, anti-PD-1, or anti-PDL2 antibodies. In a still further specific aspect, the vector further comprises a host cell suitable for expression of the nucleic acid. In a still further specific aspect, the host cell is a eukaryotic cell or a prokaryotic cell. In a still further specific aspect, the eukaryotic cell is a mammalian cell, such as Chinese Hamster Ovary (CHO).

The antibody or antigen binding fragment thereof, may be made using methods known in the art, for example, by a process comprising culturing a host cell containing nucleic acid encoding any of the previously described anti-PDL1, anti-PD-1, or anti-PDL2 antibodies or antigen-binding fragment in a form suitable for expression, under conditions suitable to produce such antibody or fragment, and recovering the antibody or fragment.

In some embodiments, the isolated anti-PDL1 antibody is aglycosylated.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Removal of glycosylation sites form an antibody is conveniently accomplished by altering the amino acid sequence such that one of the above-described tripeptide sequences (for N-linked glycosylation sites) is removed. The alteration may be made by substitution of an asparagine, serine or threonine residue within the glycosylation site another amino acid residue (e.g., glycine, alanine or a conservative substitution).

In any of the embodiments herein, the isolated anti-PDL1 antibody can bind to a human PDL1, for example a human PDL1 as shown in UniProtKB/Swiss-Prot Accession No. Q9NZQ7.1, or a variant thereof.

In a still further embodiment, the invention provides for a composition comprising an anti-PDL1, an anti-PD-1, or an anti-PDL2 antibody or antigen binding fragment thereof as provided herein and at least one pharmaceutically acceptable carrier. In some embodiments, the anti-PDL1, anti-PD-1, or anti-PDL2 antibody or antigen binding fragment thereof administered to the individual is a composition comprising one or more pharmaceutically acceptable carrier.

Any of the pharmaceutically acceptable carriers described herein or known in the art may be used.

In some embodiments, the anti-PDL1 antibody described herein is in a formulation comprising the antibody at an amount of about 60 mg/mL, histidine acetate in a concentration of about 20 mM, sucrose in a concentration of about 120 mM, and polysorbate (e.g., polysorbate 20) in a concentration of 0.04% (w/v), and the formulation has a pH of about 5.8. In some embodiments, the anti-PDL1 antibody described herein is in a formulation comprising the antibody in an amount of about 125 mg/mL, histidine acetate in a concentration of about 20 mM, sucrose is in a concentration of about 240 mM, and polysorbate (e.g., polysorbate 20) in a concentration of 0.02% (w/v), and the formulation has a pH of about 5.5.

Exemplary TIM3 Antagonists for Use in the Invention

Provided herein are methods for treating or delaying progression of cancer in an individual comprising administering to the individual an effective amount of a T cell activating bispecific antigen binding molecule, a PD-1 axis binding antagonist, and a TIM-3 antagonist. In one embodiment, the TIM-3 antagonist is an anti-TIM-3 antibody. In some embodiments, the anti-TIM3 induces internalization of TIM3 expressed on a cell of at least 45% after 120 Minutes at 37° C. as determined by FACS analysis. The cell is, e.g., a RPMI8226 cells (ATCC® CCL-155™). In one embodiment, the antibody induces internalization of TIM3 on TIM3 expressing RPMI8226 cells (ATCC® CCL-155™) of at least 55% after 120 Minutes at 37° C. as determined by FACS analysis. In one embodiment, the antibody induces internalization of TIM3 on TIM3 expressing RPMI8226 cells (ATCC® CCL-155™) of at least 60% after 240 Minutes at 37° C. as determined by FACS analysis. In one embodiment, the antibody induces internalization of TIM3 on TIM3 expressing RPMI8226 cells (ATCC® CCL-155™) of at least 65% after 240 Minutes at 37° C. as determined by FACS analysis.

In some embodiments, the anti-TIM3 antibody competes for binding to TIM3 with an anti-Tim3 antibody comprising the VH and VL of Tim3_0016. In some embodiments, the anti-TIM3 antibody binds to a human and cynomolgoues TIM3. In some embodiments, the anti-TIM3 antibody shows as a immunoconjugate a cytotoxic activity on TIM3 expressing cells. In one such embodiment, the immunoconjugate has a relative IC50 value of the cytotoxic activity as *Pseudomonas* exotoxin A conjugate on RPMI-8226 cells of 0.1 or lower. In one embodiment, the anti-TIM3 antibody induces interferon-gamma release as determined by MLR assay.

In certain embodiments, the anti-TIM3 antibody binds to a human and cynomolgoues TIM3 and induces interferon-gamma release as determined by a MLR assay.

In one embodiment, the anti-TIM3 antibody comprises at least one, two, three, four, five, or six HVRs selected from (a) HVR-H1 comprising the amino acid sequence of SEQ ID NO:304; (b) HVR-H2 comprising the amino acid sequence of SEQ ID NO:305; (c) HVR-H3 comprising the amino acid sequence of SEQ ID NO:306; (d) HVR-L1 comprising the amino acid sequence of SEQ ID NO:307; or HVR-L1 comprising the amino acid sequence of SEQ ID NO:314; HVR-L1 comprising the amino acid sequence of SEQ ID NO:315; (e) HVR-L2 comprising the amino acid sequence of SEQ ID NO:308; and (f) HVR-L3 comprising the amino acid sequence of SEQ ID NO:309.

In one embodiment, the anti-TIM3 antibody comprises (a) HVR-H1 comprising the amino acid sequence of SEQ ID NO:304; (b) HVR-H2 comprising the amino acid sequence of SEQ ID NO:305; (c) HVR-H3 comprising the amino acid sequence of SEQ ID NO:306; (d) HVR-L1 comprising the amino acid sequence of SEQ ID NO:307; or HVR-L1 comprising the amino acid sequence of SEQ ID NO:314; or HVR-L1 comprising the amino acid sequence of SEQ ID NO:315; (e) HVR-L2 comprising the amino acid sequence of SEQ ID NO:308; and (f) HVR-L3 comprising the amino acid sequence of SEQ ID NO:309.

In one embodiment, the anti-TIM3 antibody comprises (a) HVR-H1 comprising the amino acid sequence of SEQ ID NO:304; (b) HVR-H2 comprising the amino acid sequence of SEQ ID NO:305; (c) HVR-H3 comprising the amino acid sequence of SEQ ID NO:306; (d) HVR-L1 comprising the amino acid sequence of SEQ ID NO:307; (e) HVR-L2 comprising the amino acid sequence of SEQ ID NO:308; and (f) HVR-L3 comprising the amino acid sequence of SEQ ID NO:309.

In one embodiment, the anti-TIM3 antibody comprises (a) HVR-H1 comprising the amino acid sequence of SEQ ID NO:304; (b) HVR-H2 comprising the amino acid sequence of SEQ ID NO:305; (c) HVR-H3 comprising the amino acid sequence of SEQ ID NO:306; (d) HVR-L1 comprising the amino acid sequence of SEQ ID NO:314; (e) HVR-L2 comprising the amino acid sequence of SEQ ID NO:308; and (f) HVR-L3 comprising the amino acid sequence of SEQ ID NO:309.

In one embodiment, the anti-TIM3 antibody comprises (a) HVR-H1 comprising the amino acid sequence of SEQ ID NO:304; (b) HVR-H2 comprising the amino acid sequence of SEQ ID NO:305; (c) HVR-H3 comprising the amino acid sequence of SEQ ID NO:306; (d) HVR-L1 comprising the amino acid sequence of SEQ ID NO:315; (e) HVR-L2 comprising the amino acid sequence of SEQ ID NO:308; and (f) HVR-L3 comprising the amino acid sequence of SEQ ID NO:309.

In one embodiment, the anti-TIM3 antibody comprises (a) a VH domain comprising at least one, at least two, or all three VH HVR sequences selected from (i) HVR-H1 comprising the amino acid sequence of SEQ ID NO:304, (ii) HVR-H2 comprising the amino acid sequence of SEQ ID NO:305, and (iii) HVR-H3 comprising an amino acid sequence selected from SEQ ID NO:306; and (b) a VL domain comprising at least one, at least two, or all three VL HVR sequences selected from (i) HVR-L1 comprising the amino acid sequence of SEQ ID NO:307; or HVR-L1 comprising the amino acid sequence of SEQ ID NO:314; or HVR-L1 comprising the amino acid sequence of SEQ ID NO:315; (ii) HVR-L2 comprising the amino acid sequence of SEQ ID NO:308 and (c) HVR-L3 comprising the amino acid sequence of SEQ ID NO:309.

In one embodiment, the anti-TIM3 antibody comprises (a) a VH domain comprising (i) HVR-H1 comprising the amino acid sequence of SEQ ID NO:304, (ii) HVR-H2 comprising the amino acid sequence of SEQ ID NO:305, and (iii) HVR-H3 comprising an amino acid sequence selected from SEQ ID NO:306; and (b) a VL domain comprising (i) HVR-L1 comprising the amino acid sequence of SEQ ID NO:307; or HVR-L1 comprising the amino acid sequence of SEQ ID NO:314; or HVR-L1 comprising the amino acid sequence of SEQ ID NO:315; (ii) HVR-L2 comprising the amino acid sequence of SEQ ID NO:308 and (iii) HVR-L3 comprising the amino acid sequence of SEQ ID NO:309.

In one embodiment, the anti-TIM3 antibody comprises (a) a VH domain comprising (i) HVR-H1 comprising the amino acid sequence of SEQ ID NO:304, (ii) HVR-H2 comprising the amino acid sequence of SEQ ID NO:305, and (iii) HVR-H3 comprising an amino acid sequence selected from SEQ ID NO:306; and (b) a VL domain comprising (i) HVR-L1 comprising the amino acid sequence of SEQ ID NO:307; (ii) HVR-L2 comprising the amino acid sequence of SEQ ID NO:308 and (iii) HVR-L3 comprising the amino acid sequence of SEQ ID NO:309.

In one embodiment, the anti-TIM3 antibody comprises (a) a VH domain comprising (i) HVR-H1 comprising the amino acid sequence of SEQ ID NO:304, (ii) HVR-H2 comprising the amino acid sequence of SEQ ID NO:305, and (iii) HVR-H3 comprising an amino acid sequence selected from SEQ ID NO:306; and (b) a VL domain comprising (i) HVR-L1 comprising the amino acid sequence of SEQ ID NO:314; (ii) HVR-L2 comprising the amino acid sequence of SEQ ID NO:308 and (iii) HVR-L3 comprising the amino acid sequence of SEQ ID NO:309.

In one embodiment, the anti-TIM3 antibody comprises (a) a VH domain comprising (i) HVR-H1 comprising the amino acid sequence of SEQ ID NO:304, (ii) HVR-H2 comprising the amino acid sequence of SEQ ID NO:305, and (iii) HVR-H3 comprising an amino acid sequence selected from SEQ ID NO:306; and (b) a VL domain comprising (i)

HVR-L1 comprising the amino acid sequence of SEQ ID NO:315; (ii) HVR-L2 comprising the amino acid sequence of SEQ ID NO:308 and (iii) HVR-L3 comprising the amino acid sequence of SEQ ID NO:309.

In one embodiment such anti-TIM3 antibody comprises
i) comprises a VH sequence of SEQ ID NO:310 and a VL sequence of SEQ ID NO:311;
ii) comprises a VH sequence of SEQ ID NO:312 and a VL sequence of SEQ ID NO:313;
iii) or humanized variant of the VH and VL of the antibody under i) or ii).

In one embodiment, the anti-TIM3 antibody comprises at least one, two, three, four, five, or six HVRs selected from (a) HVR-H1 comprising the amino acid sequence of SEQ ID NO:316; (b) HVR-H2 comprising the amino acid sequence of SEQ ID NO:317; (c) HVR-H3 comprising the amino acid sequence of SEQ ID NO:318; (d) HVR-L1 comprising the amino acid sequence of SEQ ID NO:319; (e) HVR-L2 comprising the amino acid sequence of SEQ ID NO:320; and (f) HVR-L3 comprising the amino acid sequence of SEQ ID NO:321.

In one embodiment, the anti-TIM3 antibody comprises (a) HVR-H1 comprising the amino acid sequence of SEQ ID NO:316; (b) HVR-H2 comprising the amino acid sequence of SEQ ID NO:317; (c) HVR-H3 comprising the amino acid sequence of SEQ ID NO:318; (d) HVR-L1 comprising the amino acid sequence of SEQ ID NO:319; (e) HVR-L2 comprising the amino acid sequence of SEQ ID NO:320; and (f) HVR-L3 comprising the amino acid sequence of SEQ ID NO:321.

In one embodiment, the anti-TIM3 antibody comprises (a) a VH domain comprising at least one, at least two, or all three VH HVR sequences selected from (i) HVR-H1 comprising the amino acid sequence of SEQ ID NO:316, (ii) HVR-H2 comprising the amino acid sequence of SEQ ID NO:317, and (iii) HVR-H3 comprising an amino acid sequence selected from SEQ ID NO:318; and (b) a VL domain comprising at least one, at least two, or all three VL HVR sequences selected from (i) HVR-L1 comprising the amino acid sequence of SEQ ID NO:319; (ii) HVR-L2 comprising the amino acid sequence of SEQ ID NO:320 and (c) HVR-L3 comprising the amino acid sequence of SEQ ID NO:321.

In one embodiment, the anti-TIM3 antibody comprises (a) a VH domain comprising (i) HVR-H1 comprising the amino acid sequence of SEQ ID NO:316, (ii) HVR-H2 comprising the amino acid sequence of SEQ ID NO:317, and (iii) HVR-H3 comprising an amino acid sequence selected from SEQ ID NO:318; and (b) a VL domain comprising (i) HVR-L1 comprising the amino acid sequence of SEQ ID NO:319; (ii) HVR-L2 comprising the amino acid sequence of SEQ ID NO:320 and (iii) HVR-L3 comprising the amino acid sequence of SEQ ID NO:321.

In one embodiment such anti-TIM3 antibody comprises
i) comprises a VH sequence of SEQ ID NO:322 and a VL sequence of SEQ ID NO:323;
ii) or humanized variant of the VH and VL of the antibody under i).

In one embodiment, the anti-TIM3 antibody comprises at least one, two, three, four, five, or six HVRs selected from (a) HVR-H1 comprising the amino acid sequence of SEQ ID NO:324; (b) HVR-H2 comprising the amino acid sequence of SEQ ID NO:325; (c) HVR-H3 comprising the amino acid sequence of SEQ ID NO:326; (d) HVR-L1 comprising the amino acid sequence of SEQ ID NO:327; (e) HVR-L2 comprising the amino acid sequence of SEQ ID NO:328; and (f) HVR-L3 comprising the amino acid sequence of SEQ ID NO:329.

In one embodiment, the anti-TIM3 antibody comprises (a) HVR-H1 comprising the amino acid sequence of SEQ ID NO:324; (b) HVR-H2 comprising the amino acid sequence of SEQ ID NO:325; (c) HVR-H3 comprising the amino acid sequence of SEQ ID NO:326; (d) HVR-L1 comprising the amino acid sequence of SEQ ID NO:327; (e) HVR-L2 comprising the amino acid sequence of SEQ ID NO:328; and (f) HVR-L3 comprising the amino acid sequence of SEQ ID NO:329.

In one embodiment, the anti-TIM3 antibody comprises (a) a VH domain comprising at least one, at least two, or all three VH HVR sequences selected from (i) HVR-H1 comprising the amino acid sequence of SEQ ID NO:324, (ii) HVR-H2 comprising the amino acid sequence of SEQ ID NO:325, and (iii) HVR-H3 comprising an amino acid sequence selected from SEQ ID NO:326; and (b) a VL domain comprising at least one, at least two, or all three VL HVR sequences selected from (i) HVR-L1 comprising the amino acid sequence of SEQ ID NO:327; (ii) HVR-L2 comprising the amino acid sequence of SEQ ID NO:328 and (c) HVR-L3 comprising the amino acid sequence of SEQ ID NO:329.

In one embodiment, the anti-TIM3 antibody comprises (a) a VH domain comprising (i) HVR-H1 comprising the amino acid sequence of SEQ ID NO:324, (ii) HVR-H2 comprising the amino acid sequence of SEQ ID NO:325, and (iii) HVR-H3 comprising an amino acid sequence selected from SEQ ID NO:326; and (b) a VL domain comprising (i) HVR-L1 comprising the amino acid sequence of SEQ ID NO:327; (ii) HVR-L2 comprising the amino acid sequence of SEQ ID NO:328 and (iii) HVR-L3 comprising the amino acid sequence of SEQ ID NO:329.

In one embodiment such anti-TIM3 antibody comprises
i) comprises a VH sequence of SEQ ID NO:330 and a VL sequence of SEQ ID NO:331;
ii) or humanized variant of the VH and VL of the antibody under i).

In one embodiment, the anti-TIM3 antibody comprises at least one, two, three, four, five, or six HVRs selected from (a) HVR-H1 comprising the amino acid sequence of SEQ ID NO:332; (b) HVR-H2 comprising the amino acid sequence of SEQ ID NO:333; (c) HVR-H3 comprising the amino acid sequence of SEQ ID NO:334; (d) HVR-L1 comprising the amino acid sequence of SEQ ID NO:335; (e) HVR-L2 comprising the amino acid sequence of SEQ ID NO:336; and (f) HVR-L3 comprising the amino acid sequence of SEQ ID NO:337.

In one embodiment, the anti-TIM3 antibody comprises (a) HVR-H1 comprising the amino acid sequence of SEQ ID NO:332; (b) HVR-H2 comprising the amino acid sequence of SEQ ID NO:333; (c) HVR-H3 comprising the amino acid sequence of SEQ ID NO:334; (d) HVR-L1 comprising the amino acid sequence of SEQ ID NO:335; (e) HVR-L2 comprising the amino acid sequence of SEQ ID NO:336; and (f) HVR-L3 comprising the amino acid sequence of SEQ ID NO:337.

In one embodiment, the anti-TIM3 antibody comprises (a) a VH domain comprising at least one, at least two, or all three VH HVR sequences selected from (i) HVR-H1 comprising the amino acid sequence of SEQ ID NO:332, (ii) HVR-H2 comprising the amino acid sequence of SEQ ID NO:333, and (iii) HVR-H3 comprising an amino acid sequence selected from SEQ ID NO:334; and (b) a VL domain comprising at least one, at least two, or all three VL HVR sequences selected from (i) HVR-L1 comprising the amino acid sequence of SEQ ID NO:335; (ii) HVR-L2 comprising the amino acid sequence of SEQ ID NO:336 and (c) HVR-L3 comprising the amino acid sequence of SEQ ID NO:337.

In one embodiment, the anti-TIM3 antibody comprises (a) a VH domain comprising (i) HVR-H1 comprising the amino acid sequence of SEQ ID NO:332, (ii) HVR-H2 comprising the amino acid sequence of SEQ ID NO:333, and (iii) HVR-H3 comprising an amino acid sequence selected from SEQ ID NO:334; and (b) a VL domain comprising (i) HVR-L1 comprising the amino acid sequence of SEQ ID NO:335; (ii) HVR-L2 comprising the amino acid sequence of SEQ ID NO:336 and (iii) HVR-L3 comprising the amino acid sequence of SEQ ID NO:337.

In one embodiment such anti-TIM3 antibody comprises
i) comprises a VH sequence of SEQ ID NO:338 and a VL sequence of SEQ ID NO:339;
ii) or humanized variant of the VH and VL of the antibody under i).

In one aspect, the invention provides an anti-TIM3 antibody comprising at least one, two, three, four, five, or six HVRs selected from (a) HVR-H1 comprising the amino acid sequence of SEQ ID NO:340; (b) HVR-H2 comprising the amino acid sequence of SEQ ID NO:341; (c) HVR-H3 comprising the amino acid sequence of SEQ ID NO:342; (d) HVR-L1 comprising the amino acid sequence of SEQ ID NO:343; (e) HVR-L2 comprising the amino acid sequence of SEQ ID NO:344; and (f) HVR-L3 comprising the amino acid sequence of SEQ ID NO:345.

In one embodiment, the anti-TIM3 antibody comprises (a) HVR-H1 comprising the amino acid sequence of SEQ ID NO:340; (b) HVR-H2 comprising the amino acid sequence of SEQ ID NO:341; (c) HVR-H3 comprising the amino acid sequence of SEQ ID NO:342; (d) HVR-L1 comprising the amino acid sequence of SEQ ID NO:343; (e) HVR-L2 comprising the amino acid sequence of SEQ ID NO:344; and (f) HVR-L3 comprising the amino acid sequence of SEQ ID NO:345.

In one embodiment, the anti-TIM3 antibody comprises (a) a VH domain comprising at least one, at least two, or all three VH HVR sequences selected from (i) HVR-H1 comprising the amino acid sequence of SEQ ID NO:340, (ii) HVR-H2 comprising the amino acid sequence of SEQ ID NO:341, and (iii) HVR-H3 comprising an amino acid sequence selected from SEQ ID NO:342; and (b) a VL domain comprising at least one, at least two, or all three VL HVR sequences selected from (i) HVR-L1 comprising the amino acid sequence of SEQ ID NO:343; (ii) HVR-L2 comprising the amino acid sequence of SEQ ID NO:344 and (c) HVR-L3 comprising the amino acid sequence of SEQ ID NO:345.

In one embodiment, the anti-TIM3 antibody comprises (a) a VH domain comprising (i) HVR-H1 comprising the amino acid sequence of SEQ ID NO:340, (ii) HVR-H2 comprising the amino acid sequence of SEQ ID NO:341, and (iii) HVR-H3 comprising an amino acid sequence selected from SEQ ID NO:342; and (b) a VL domain comprising (i) HVR-L1 comprising the amino acid sequence of SEQ ID NO:343; (ii) HVR-L2 comprising the amino acid sequence of SEQ ID NO:344 and (iii) HVR-L3 comprising the amino acid sequence of SEQ ID NO:345.

In one embodiment such anti-TIM3 antibody comprises
i) comprises a VH sequence of SEQ ID NO:346 and a VL sequence of SEQ ID NO:347;
ii) or humanized variant of the VH and VL of the antibody under i).

In one embodiment, the anti-TIM3 antibody comprises at least one, two, three, four, five, or six HVRs selected from (a) HVR-H1 comprising the amino acid sequence of SEQ ID NO:348; (b) HVR-H2 comprising the amino acid sequence of SEQ ID NO:349; (c) HVR-H3 comprising the amino acid sequence of SEQ ID NO:350; (d) HVR-L1 comprising the amino acid sequence of SEQ ID NO:351; (e) HVR-L2 comprising the amino acid sequence of SEQ ID NO:352; and (f) HVR-L3 comprising the amino acid sequence of SEQ ID NO:353.

In one aspect, the invention provides an anti-TIM3 antibody comprising (a) HVR-H1 comprising the amino acid sequence of SEQ ID NO:348; (b) HVR-H2 comprising the amino acid sequence of SEQ ID NO:349; (c) HVR-H3 comprising the amino acid sequence of SEQ ID NO:350; (d) HVR-L1 comprising the amino acid sequence of SEQ ID NO:351; (e) HVR-L2 comprising the amino acid sequence of SEQ ID NO:352; and (f) HVR-L3 comprising the amino acid sequence of SEQ ID NO:353.

In one embodiment, the anti-TIM3 antibody comprises (a) a VH domain comprising at least one, at least two, or all three VH HVR sequences selected from (i) HVR-H1 comprising the amino acid sequence of SEQ ID NO:348, (ii) HVR-H2 comprising the amino acid sequence of SEQ ID NO:349, and (iii) HVR-H3 comprising an amino acid sequence selected from SEQ ID NO:350; and (b) a VL domain comprising at least one, at least two, or all three VL HVR sequences selected from (i) HVR-L1 comprising the amino acid sequence of SEQ ID NO:351; (ii) HVR-L2 comprising the amino acid sequence of SEQ ID NO:352 and (c) HVR-L3 comprising the amino acid sequence of SEQ ID NO:353.

In one embodiment, the anti-TIM3 antibody comprises (a) a VH domain comprising (i) HVR-H1 comprising the amino acid sequence of SEQ ID NO:348, (ii) HVR-H2 comprising the amino acid sequence of SEQ ID NO:349, and (iii) HVR-H3 comprising an amino acid sequence selected from SEQ ID NO:350; and (b) a VL domain comprising (i) HVR-L1 comprising the amino acid sequence of SEQ ID NO:351; (ii) HVR-L2 comprising the amino acid sequence of SEQ ID NO:352 and (iii) HVR-L3 comprising the amino acid sequence of SEQ ID NO:353.

In one embodiment such anti-TIM3 antibody comprises
i) comprises a VH sequence of SEQ ID NO:354 and a VL sequence of SEQ ID NO:355;
ii) or humanized variant of the VH and VL of the antibody under i).

In one embodiment, the anti-TIM3 antibody comprises at least one, two, three, four, five, or six HVRs selected from (a) HVR-H1 comprising the amino acid sequence of SEQ ID NO:356; (b) HVR-H2 comprising the amino acid sequence of SEQ ID NO:357; (c) HVR-H3 comprising the amino acid sequence of SEQ ID NO:358; (d) HVR-L1 comprising the amino acid sequence of SEQ ID NO:359; (e) HVR-L2 comprising the amino acid sequence of SEQ ID NO:360; and (f) HVR-L3 comprising the amino acid sequence of SEQ ID NO:361.

In one embodiment, the anti-TIM3 antibody comprises (a) HVR-H1 comprising the amino acid sequence of SEQ ID NO:356; (b) HVR-H2 comprising the amino acid sequence of SEQ ID NO:357; (c) HVR-H3 comprising the amino acid sequence of SEQ ID NO:358; (d) HVR-L1 comprising the amino acid sequence of SEQ ID NO:359; (e) HVR-L2 comprising the amino acid sequence of SEQ ID NO:360; and (f) HVR-L3 comprising the amino acid sequence of SEQ ID NO:361.

In one embodiment, the anti-TIM3 antibody comprises (a) a VH domain comprising at least one, at least two, or all three VH HVR sequences selected from (i) HVR-H1 comprising the amino acid sequence of SEQ ID NO:356, (ii) HVR-H2 comprising the amino acid sequence of SEQ ID NO: 357, and (iii) HVR-H3 comprising an amino acid sequence selected from SEQ ID NO: 358; and (b) a VL domain comprising at least one, at least two, or all three VL HVR sequences selected from (i) HVR-L1 comprising the amino acid sequence of SEQ ID NO: 359; (ii) HVR-L2 comprising the amino acid sequence of SEQ ID NO:360 and (c) HVR-L3 comprising the amino acid sequence of SEQ ID NO:361.

In one embodiment, the anti-TIM3 antibody comprises (a) a VH domain comprising (i) HVR-H1 comprising the amino acid sequence of SEQ ID NO: 356, (ii) HVR-H2 comprising the amino acid sequence of SEQ ID NO: 357, and (iii) HVR-H3 comprising an amino acid sequence selected from SEQ ID NO: 358; and (b) a VL domain comprising (i) HVR-L1 comprising the amino acid sequence of SEQ ID NO: 359; (ii) HVR-L2 comprising the amino acid sequence of SEQ ID NO:360 and (iii) HVR-L3 comprising the amino acid sequence of SEQ ID NO:361.

In one embodiment such anti-TIM3 antibody comprises
i) comprises a VH sequence of SEQ ID NO:362 and a VL sequence of SEQ ID NO:363;
ii) or humanized variant of the VH and VL of the antibody under i).

In one embodiment, the anti-TIM3 antibody comprises at least one, two, three, four, five, or six HVRs selected from (a) HVR-H1 comprising the amino acid sequence of SEQ ID NO:364; (b) HVR-H2 comprising the amino acid sequence of SEQ ID NO:365; (c) HVR-H3 comprising the amino acid sequence of SEQ ID NO:366; (d) HVR-L1 comprising the amino acid sequence of SEQ ID NO:367; (e) HVR-L2 comprising the amino acid sequence of SEQ ID NO:368; and (f) HVR-L3 comprising the amino acid sequence of SEQ ID NO:369.

In one embodiment, the anti-TIM3 antibody comprises (a) HVR-H1 comprising the amino acid sequence of SEQ ID NO:364; (b) HVR-H2 comprising the amino acid sequence of SEQ ID NO:365; (c) HVR-H3 comprising the amino acid sequence of SEQ ID NO:366; (d) HVR-L1 comprising the amino acid sequence of SEQ ID NO:367; (e) HVR-L2 comprising the amino acid sequence of SEQ ID NO:368; and (f) HVR-L3 comprising the amino acid sequence of SEQ ID NO:369.

In one embodiment, the anti-TIM3 antibody comprises (a) a VH domain comprising at least one, at least two, or all three VH HVR sequences selected from (i) HVR-H1 comprising the amino acid sequence of SEQ ID NO:364, (ii) HVR-H2 comprising the amino acid sequence of SEQ ID NO:365, and (iii) HVR-H3 comprising an amino acid sequence selected from SEQ ID NO:366; and (b) a VL domain comprising at least one, at least two, or all three VL HVR sequences selected from (i) HVR-L1 comprising the amino acid sequence of SEQ ID NO:367; (ii) HVR-L2 comprising the amino acid sequence of SEQ ID NO:368 and (c) HVR-L3 comprising the amino acid sequence of SEQ ID NO:369.

In one embodiment, the anti-TIM3 antibody comprises (a) a VH domain comprising (i) HVR-H1 comprising the amino acid sequence of SEQ ID NO:364, (ii) HVR-H2 comprising the amino acid sequence of SEQ ID NO:365, and (iii) HVR-H3 comprising an amino acid sequence selected from SEQ ID NO:366; and (b) a VL domain comprising (i) HVR-L1 comprising the amino acid sequence of SEQ ID NO:367; (ii) HVR-L2 comprising the amino acid sequence of SEQ ID NO:368 and (iii) HVR-L3 comprising the amino acid sequence of SEQ ID NO:369.

In one embodiment such anti-TIM3 antibody comprises
i) comprises a VH sequence of SEQ ID NO:370 and a VL sequence of SEQ ID NO:371;
ii) or humanized variant of the VH and VL of the antibody under i).

In any of the above embodiments, an anti-TIM3 antibody is humanized. In one embodiment, an anti-TIM3 antibody comprises HVRs as in any of the above embodiments, and further comprises an acceptor human framework, e.g. a human immunoglobulin framework or a human consensus framework. In another embodiment, an anti-TIM3 antibody comprises HVRs as in any of the above embodiments, and further comprises a VH and VL comprising such HVRs. In a further aspect, the anti-TIM3 antibody binds to the same epitope as an anti-TIM3 antibody provided herein. For example, in certain embodiments, anti-TIM3 antibody binds to the same epitope as anti-TIM3 antibody comprising a VH sequence of SEQ ID NO:310 and a VL sequence of SEQ ID NO:311, or anti-TIM3 antibody binds to the same epitope as anti-TIM3 antibody comprising a VH sequence of SEQ ID NO:312 and a VL sequence of SEQ ID NO:313, or an antibody is provided that binds to the same epitope as anti-TIM3 antibody comprising a VH sequence of SEQ ID NO:322 and a VL sequence of SEQ ID NO:323, or an antibody is provided that binds to the same epitope as anti-TIM3 antibody comprising a VH sequence of SEQ ID NO:330 and a VL sequence of SEQ ID NO:331, or an antibody is provided that binds to the same epitope as anti-TIM3 antibody comprising a VH sequence of SEQ ID NO:338 and a VL sequence of SEQ ID N0339, or an antibody is provided that binds to the same epitope as anti-TIM3 antibody comprising a VH sequence of SEQ ID NO:346 and a VL sequence of SEQ ID NO:347, or an antibody is provided that binds to the same epitope as anti-TIM3 antibody comprising a VH sequence of SEQ ID NO:354 and a VL sequence of SEQ ID NO:355, or an antibody is provided that binds to the same epitope as anti-TIM3 antibody comprising a VH sequence of SEQ ID NO:362 and a VL sequence of SEQ ID NO:363, or an antibody is provided that binds to the same epitope as anti-TIM3 antibody comprising a VH sequence of SEQ ID NO:370 and a VL sequence of SEQ ID NO:371. In one preferred embodiment an antibody is provided that binds to the same epitope as an anti-TIM3 antibody comprising a VH sequence of SEQ ID NO:310 and a VL sequence of SEQ ID NO:311.

In one embodiment, the anti-TIM3 competes for binding to human TIM3 with an anti-TIM3 antibody comprising a VH sequence of SEQ ID NO:310 and a VL sequence of SEQ ID NO:311 as determined in a competition assay using TIM3 expressing RPMI-8226 cells (ATCC® CCL-155™).

In one embodiment, the anti-TIM3 antibody according to any of the above embodiments is a monoclonal antibody, including a chimeric, humanized or human antibody. In one embodiment, an anti-TIM3 antibody is an antibody fragment, e.g., a Fv, Fab, Fab', scFv, diabody, or F(ab')$_2$ fragment. In another embodiment, the antibody is a full length antibody, e.g., an intact IgG1 or IgG4 antibody or other antibody class or isotype as defined herein.

In a further aspect, an anti-TIM3 antibody according to any of the above embodiments may incorporate any of the features, singly or in combination, as described herein.

In one embodiment, the anti-TIM3 antibody is any of the antibodies described in WO 2011/155607, WO 2013/

006490, WO 03/063792, WO 2009/097394, or WO 2011/159877. In one embodiment, the anti-TIM3 antibody is F38-2E2. In some embodiments, the anti-TIM-3 antibodies are antibodies from hybridomas 8B.2C12 and 25F.1D6 and prepared as disclosed in U. S. Patent application Nos: 2004/0005322 and 2005/0191721, Sabatos, C. A. et al., Nature Immunol. 4:1102-1110, 2003, and Sanchez-Fueyo, A. et al., Nature Immunol. 4:1093-1012003, all of which are hereby incorporated by reference as if set forth in their entirety. Other antibodies to TIM-3 are specifically contemplated and can be produced, e.g., with the methods disclosed herein. The nucleotide and protein sequences of TIM3 human sequences can be found at Genbank accession number AF251707.1 and Uniprot accession number Q8TDQ0. An exemplary human TIM3 amino acid sequence is set forth at SEQ ID NO:380; an exemplary human TIM3 extracellular domain amino acid sequence is set forth at SEQ ID NO:381.

Antibody Preparation

As described above, in some embodiments, the PD-1 binding antagonist is an antibody (e.g., an anti-PD-1 antibody, an anti-PDL1 antibody, or an anti-PDL2 antibody). In some embodiments, the TIM3 antagonist is an antibody (e.g., an anti-TIM3 antagonist antibody). The antibodies described herein may be prepared using techniques available in the art for generating antibodies, exemplary methods of which are described in more detail in the following sections.

The antibody is directed against an antigen of interest. For example, the antibody may be directed against PD-1 (such as human PD-1), PDL1 (such as human PDL1), PDL2 (such as human PDL2), an TIM3 (such as human TIM3). Preferably, the antigen is a biologically important polypeptide and administration of the antibody to a mammal suffering from a disorder can result in a therapeutic benefit in that mammal.

In certain embodiments, an antibody described herein has a dissociation constant (Kd) of 1 µM, 150 nM, 100 nM, 50 nM, 10 nM, 1 nM, 0.1 nM, 0.01 nM, or 0.001 nM (e.g. 10-8 M or less, e.g. from 10-8 M to 10-13 M, e.g., from 10-9 M to 10-13 M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of (125I)-labeled antigen in the presence of a titration series of unlabeled antigen, then capturing bound antigen with an anti-Fab antibody-coated plate (see, e.g., Chen et al., J. Mol. Biol. 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH9.6), and subsequently blocked with 2% (w/v) bovine serum albumin in PBS for two to five hours at room temperature (approximately 23° C.). In a non-adsorbent plate (Nunc #269620), 100 pM or 26 pM [125I]-antigen are mixed with serial dilutions of a Fab of interest. The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT TM gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein.

Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates (kon) and dissociation rates (koff) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio koff/kon. See, e.g., Chen et al., J. Mol. Biol. 293:865-881 (1999). If the on-rate exceeds 106 M-1 s-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

In some embodiments, an anti-TIM3 antibody as described herein exhibits a binding affinity of at least 100 pM or less against human TIM3, a binding affinity of at least 300 pM or less against human TIM3, a binding affinity of at least 400 pM or less against human TIM3, a neutralizing ability of at least 40 nM or less against the human TIM3, a neutralizing ability of at least 120 nM or less against the human TIM3, and a neutralizing ability of at least 31 nM or less against the human TIM3. In these embodiments, binding affinity may be measured by surface plasmon resonance as described in U.S. Pat. No. 8,771,697, Antibody Fragments In certain embodiments, an antibody described herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. Nat. Med 9:129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med 9:129-134 (2003); and Hollinger et al., Proc. Natl. Acad Sci.

USA 90: 6444-6448 (1993). Triabodies and tetrabodies are also described in Hudson et al., *Nat. Med* 9:129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). Antibody fragments can be made by various techniques, including but not limited to proteolytic digestion of an intact antibody as well as production by recombinant host cells (e.g. *E. coli* or phage), as described herein.

Chimeric and Humanized Antibodies

In certain embodiments, an antibody described herein is a chimeric antibody. Certain chimeric antibodies are described, e.g., in U.S. Pat. No. 4,816,567; and Morrison et al., *Proc. Nat. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof. In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity. Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Nat. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

Human Antibodies

In certain embodiments, an antibody described herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region. Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Nat. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005). Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Library-Derived Antibodies

Antibodies may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA*

101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single chain Fv (scFv) fragments or as Fab fragments. Libraries from immunized sources provide high affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360. Antibodies or antibody fragments isolated from human antibody libraries are considered human antibodies or human antibody fragments herein.

Multispecific Antibodies

In certain embodiments, an antibody described herein is a multispecific antibody, e.g. a bispecific antibody. Multispecific antibodies are monoclonal antibodies that have binding specificities for at least two different sites. Examples of T cell activating bispecific antigen binding molecules specific for FolR1 and CD3 are described herein. In some embodiments, the PD1 axis component antagonist is multispecific. In one of the binding specificities is for a PD-1 axis component (e.g., PD-1, PDL1, or PDL2) and the other is for any other antigen. In some embodiments, one of the binding specificities is for IL-17 or IL-17R and the other is for any other antigen. In certain embodiments, bispecific antibodies may bind to two different epitopes of a PD-1 axis component (e.g., PD-1, PDL1, or PDL2), IL-17, or IL-17R. Bispecific antibodies can be prepared as full length antibodies or antibody fragments.

In some embodiments, one of the binding specificities is for a PD-1 axis component (e.g., PD-1, PDL1, or PDL2) and the other is for IL-17 or IL-17R. Provided herein are methods for treating or delaying progression of cancer in an individual comprising administering to the individual an effective amount of a multispecific antibody, wherein the multispecific antibody comprises a first binding specificity for a PD-1 axis component (e.g., PD-1, PDL1, or PDL2) and a second binding specificity for IL-17 or IL-17R. In some embodiments, a multispecific antibody may be made by any of the techniques described herein and below.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); crosslinking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:64446448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1). The antibody or fragment herein also includes a "Dual Acting FAb" or "DAF" comprising an antigen binding site that binds to a PD-1 axis component (e.g., PD-1, PDL1, or PDL2), IL-17, or IL-17R as well as another, different antigen (see, US 2008/0069820, for example).

C. Nucleic Acid Sequences, Vectors and Methods of Production

Polynucleotides encoding a T cell activating bispecific antigen binding molecule, e.g., a T cell activating bispecific antigen binding molecule comprising a first antigen binding site specific for Folate Receptor 1 (FolR1) and a second antigen binding site specific for CD3, and antibodies may be used for production of the T cell activating bispecific antigen binding molecule and antibodies described herein. The T cell activating bispecific antigen binding molecule and antibodies of the invention may be expressed as a single polynucleotide that encodes the entire bispecific antigen binding molecule or as multiple (e.g., two or more) polynucleotides that are co-expressed. Polypeptides encoded by polynucleotides that are co-expressed may associate through, e.g., disulfide bonds or other means to form a functional T cell activating bispecific antigen binding molecule and antibody. For example, the light chain portion of a Fab fragment may be encoded by a separate polynucleotide from the portion of the bispecific antibody or the antibody binding to FolR1 comprising the heavy chain portion of the Fab fragment, an Fc domain subunit and optionally (part of) another Fab fragment. When co-expressed, the heavy chain polypeptides will associate with the light chain polypeptides to form the Fab fragment. In another example, the portion of the T cell activating bispecific antigen binding molecule or the FolR1 antigen binding portion provided therein comprising one of the two Fc domain subunits and optionally (part of) one or more Fab fragments could be encoded by a separate polynucleotide from the portion of the bispecific antibody or the antibody binding to FolR1 provided therein comprising the other of the two Fc domain subunits and optionally (part of) a Fab fragment. When co-expressed, the Fc domain subunits will associate to form the Fc domain.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

D. Antibody Variants

In certain embodiments, amino acid sequence variants of the T cell activating bispecific antigen binding molecule specific for FolR1 and CD3 provided herein and antibodies are contemplated, in addition to those described above. For example, it may be desirable to improve the binding affinity and/or other biological properties of the T cell activating bispecific antigen binding molecule. Amino acid sequence variants of a T cell activating bispecific antigen binding molecule and antibody may be prepared by introducing appropriate modifications into the nucleotide sequence encoding the T cell activating bispecific antigen binding molecule or antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

1. Substitution, Insertion, and Deletion Variants

In certain embodiments, variants having one or more amino acid substitutions are provided. Sites of interest for substitutional mutagenesis include the HVRs and FRs. Conservative substitutions are shown in Table B under the heading of "conservative substitutions." More substantial changes are provided in Table B under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE B

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gn;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

2. Glycosylation Variants

In certain embodiments, a T cell activating bispecific antigen binding molecule or an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the T cell activating bispecific antigen binding molecule or the antibody used with the invention comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in a bispecific antibody or an antibody binding to DR5 of the invention may be made in order to create antibody variants with certain improved properties.

In one embodiment, bispecific antibody variants or variants of antibodies are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

T cell activating bispecific antigen binding molecule variants and antibody variants are further provided with bisected oligosaccharides, e.g., in which a biantennary oligosaccharide attached to the Fc region of the T cell activating bispecific antigen binding molecule binding to FolR1 is bisected by GlcNAc. Such T cell activating bispecific antigen binding molecule variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

3. Cysteine Engineered Antibody Variants

In certain embodiments, it may be desirable to create cysteine engineered T cell activating bispecific antigen binding molecule and antibodies, e.g., THIOMABS, in which one or more residues of the T cell activating bispecific antigen binding molecule are substituted with cysteine residues. In particular embodiments, the substituted residues occur at accessible sites of the T cell activating bispecific antigen binding molecule. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

E. Recombinant Methods and Compositions

T cell activating bispecific antigen binding molecule and antibodies of the invention may be obtained, for example, by solid-state peptide synthesis (e.g. Merrifield solid phase synthesis) or recombinant production. For recombinant production one or more polynucleotide encoding the T cell activating bispecific antigen binding molecule or antibodies (or fragments), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of a T cell activating bispecific antigen binding molecule or an antibody along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y (1989). The expression vector can be part of a plasmid, virus, or may be a nucleic acid fragment. The expression vector includes an expression cassette into which the polynucleotide encoding T cell activating bispecific antigen binding molecule (fragment) or an antibody (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the T cell activating bispecific antigen binding molecule (fragment) or an antibody, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells.

Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the T cell activating bispecific antigen binding molecule or the antibody is desired, DNA encoding a signal sequence may be placed upstream of the nucleic acid encoding a bispecific antibody of the invention or the antibody binding to DR5 of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the T cell activating bispecific antigen binding molecule may be included within or at the ends of the T cell activating bispecific antigen binding molecule (fragment) or the antibody (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) a vector comprising a polynucleotide that encodes a T cell activating bispecific antigen binding molecule or an antibody of the invention or a part thereof. As used herein, the term "host cell" refers to any kind of cellular system which can be engineered to generate the T cell activating bispecific antigen binding molecule, e.g., the FolR1 T cell activating bispecific antigen binding molecules disclosed herein, or antibody, e.g., anti-PD-1 antibodies, anti-PD-L1 antibodies, and anti-TIM3 antibodies of the invention or fragments thereof. Host cells suitable for replicating and for supporting expression of T cell activating bispecific antigen binding molecule and antibodies of the invention are well known in the art. Such cells may be transfected or transduced as appropriate with the particular expression vector and large quantities of vector containing cells can be grown for seeding large scale fermenters to obtain sufficient quantities of the T cell activating bispecific antigen binding molecule and antibodies for clinical applications. Suitable host cells include prokaryotic microorganisms, such as *E. coli*, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B.K.C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., YO, NS0, Sp20 cell).

Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain.

Any animal species of antibody, antibody fragment, antigen binding domain or variable region can be used in the T cell activating bispecific antigen binding molecules of the invention. Non-limiting antibodies, antibody fragments, antigen binding domains or variable regions useful in the present invention can be of murine, primate, or human origin. If the T cell activating bispecific antigen binding molecule is intended for human use, a chimeric form of antibody may be used wherein the constant regions of the antibody are from a human. A humanized or fully human form of the antibody can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain embodiments, the antigen binding moieties useful in the present invention are engineered to have enhanced binding affinity according to, for example, the methods disclosed in U.S. Pat. Appl. Publ. No. 2004/0132066, the entire contents of which are hereby incorporated by reference. The ability of the T cell activating bispecific antigen binding molecule of the invention to bind to a specific antigenic determinant can be measured either through an enzyme-linked immunosorbent assay (ELISA) or other techniques familiar to one of skill in the art, e.g. surface plasmon resonance technique (analyzed on a BIACORE T100 system) (Liljeblad, et al., Glyco J 17, 323-329 (2000)), and traditional binding assays (Heeley, Endocr Res 28, 217-229 (2002)). Competition assays may be used to identify an antibody, antibody fragment, antigen binding domain or variable domain that competes with a reference antibody for binding to a particular antigen, e.g. an antibody that competes with the V9 antibody for binding to CD3. In certain embodiments, such a competing antibody binds to the same epitope (e.g. a linear or a conformational epitope) that is bound by the reference antibody. Detailed exemplary methods for mapping an epitope to which an antibody binds are provided in Morris (1996) "Epitope Mapping Protocols," in Methods in Molecular Biology vol. 66 (Humana Press, Totowa, N.J.). In an exemplary competition assay, immobilized antigen (e.g. CD3) is incubated in a solution comprising a first labeled antibody that binds to the antigen (e.g. V9 antibody, described in U.S. Pat. No. 6,054,297) and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch. 14 (Cold Spring Harbor Laboratory, Cold Spring Harbor, N.Y.).

In certain embodiments, the antigen binding moieties useful in the present invention are engineered to have enhanced binding affinity according to, for example, the methods disclosed in U.S. Pat. Appl. Publ. No. 2004/0132066, the entire contents of which are hereby incorporated by reference. The ability of the T cell activating bispecific antigen binding molecule or the antibody of the invention to bind to a specific antigenic determinant can be measured either through an enzyme-linked immunosorbent assay (ELISA) or other techniques familiar to one of skill in the art, e.g. surface plasmon resonance technique (analyzed on a BIACORE T100 system) (Liljeblad, et al., Glyco J 17, 323-329 (2000)), and traditional binding assays (Heeley, Endocr Res 28, 217-229 (2002)). Competition assays may be used to identify an antibody, antibody fragment, antigen binding domain or variable domain that competes with a reference antibody for binding to a particular antigen. In certain embodiments, such a competing antibody binds to the same epitope (e.g. a linear or a conformational epitope) that is bound by the reference antibody. Detailed exemplary methods for mapping an epitope to which an antibody binds are provided in Morris (1996) "Epitope Mapping Protocols," in Methods in Molecular Biology vol. 66 (Humana Press, Totowa, N.J.). In an exemplary competition assay, immobilized antigen is incubated in a solution comprising a first labeled antibody that binds to the antigen and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch. 14 (Cold Spring Harbor Laboratory, Cold Spring Harbor, N.Y.).

T cell activating bispecific antigen binding molecules and antibodies prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the bispecific antibody or the antibody binding to DR5 binds. For example, for affinity chromatography purification of bispecific antibodies of the invention, a matrix with protein A or protein G may be used. Sequential Protein A or G affinity chromatography and size exclusion chromatography can be used to isolate a bispecific antibody essentially as described in the Examples. The purity of the bispecific antibody or the antibody binding to DR5 can be determined by any of a variety of well-known analytical methods including gel electrophoresis, high pressure liquid chromatography, and the like.

F. Assays

T cell activating bispecific antigen binding molecules, e.g., a T cell activating bispecific antigen binding molecules comprising a first antigen binding site specific for Folate Receptor 1 (FolR1) and a second antigen binding site specific for CD3, and antibodies, e.g., anti-PD-1 axis binding antagonist antibodies and anti-TIM3 antagonist antibodies provided herein may be identified, screened for, or characterized for their physical/chemical properties and/or biological activities by various assays known in the art.

1. Affinity Assays

The affinity of the T cell activating bispecific antigen binding molecules, e.g., a T cell activating bispecific antigen binding molecules comprising a first antigen binding site specific for Folate Receptor 1 (FolR1) and a second antigen binding site specific for CD3, and antibodies, e.g., anti-PD-1 axis binding antagonist antibodies and anti-TIM3 antagonist antibodies provided herein for their respective antigen, e.g., FolR1, PD-1, PD-L1, TIM3, can be determined in accordance with the methods set forth in the Examples by surface plasmon resonance (SPR), using standard instrumentation such as a BIAcore instrument (GE Healthcare), and receptors or target proteins such as may be obtained by recombinant expression. Alternatively, binding of T cell activating bispecific antigen binding molecules and antibodies provided therein to their respective antigen may be evaluated using cell lines expressing the particular receptor or target antigen, for example by flow cytometry (FACS).

$K_D$ may be measured by surface plasmon resonance using a BIACORE® T100 machine (GE Healthcare) at 25° C. To analyze the interaction between the Fc-portion and Fc receptors, His-tagged recombinant Fc-receptor is captured by an anti-Penta His antibody (Qiagen) ("Penta His" disclosed as SEQ ID NO: 392) immobilized on CM5 chips and the bispecific constructs are used as analytes. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Anti Penta-His antibody ("Penta His" disclosed as SEQ ID NO: 392) is diluted with 10 mM sodium acetate, pH 5.0, to 40 µg/ml before injection at a flow rate of 5 µl/min to achieve approximately 6500 response units (RU) of coupled protein. Following the injection of the ligand, 1 M ethanolamine is injected to block unreacted groups. Subsequently the Fc-receptor is captured for 60 s at 4 or 10 nM. For kinetic measurements, four-fold serial dilutions of the bispecific construct (range between 500 nM and 4000 nM) are injected in HBS-EP (GE Healthcare, 10 mM HEPES, 150 mM NaCl, 3 mM EDTA, 0.05% Surfactant P20, pH 7.4) at 25° C. at a flow rate of 30 µl/min for 120 s.

To determine the affinity to the target antigen, bispecific constructs are captured by an anti human Fab specific antibody (GE Healthcare) that is immobilized on an activated CM5-sensor chip surface as described for the anti Penta-His antibody ("Penta His" disclosed as SEQ ID NO: 392). The final amount of coupled protein is approximately 12000 RU. The bispecific constructs are captured for 90 s at 300 nM. The target antigens are passed through the flow cells for 180 s at a concentration range from 250 to 1000 nM with a flowrate of 30 µl/min. The dissociation is monitored for 180 s.

Bulk refractive index differences are corrected for by subtracting the response obtained on reference flow cell. The steady state response was used to derive the dissociation constant $K_D$ by non-linear curve fitting of the Langmuir binding isotherm. Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999).

2. Binding Assays and Other Assays

In one aspect, a T cell activating bispecific antigen binding molecules, e.g., a T cell activating bispecific antigen binding molecules comprising a first antigen binding site specific for Folate Receptor 1 (FolR1) and a second antigen binding site specific for CD3, and antibodies, e.g., anti-PD-1 axis binding antagonist antibodies and anti-TIM3 antagonist antibodies of the invention is tested for its antigen binding activity, e.g., by known methods such as ELISA, Western blot, etc.

In another aspect, competition assays may be used to identify an antibody or fragment that competes with a specific reference antibody for binding to the respective antigens. In certain embodiments, such a competing antibody binds to the same epitope (e.g., a linear or a conformational epitope) that is bound by a specific reference antibody. Detailed exemplary methods for mapping an epitope to which an antibody binds are provided in Morris (1996) "Epitope Mapping Protocols," in *Methods in Molecular Biology* vol. 66 (Humana Press, Totowa, N.J.). Further methods are described in the example section.

3. Activity Assays

In one aspect, assays are provided for identifying T cell activating bispecific antigen binding molecules, e.g., a T cell activating bispecific antigen binding molecules comprising a first antigen binding site specific for Folate Receptor 1 (FolR1) and a second antigen binding site specific for CD3, and antibodies, e.g., anti-PD-1 axis binding antagonist antibodies and anti-TIM3 antagonist antibodies provided herein having biological activity. Biological activity may include, e.g., inducing DNA fragmentation, induction of apoptosis and lysis of targeted cells. Antibodies having such biological activity in vivo and/or in vitro are also provided.

In certain embodiments, T cell activating antigen binding molecule and antibody of the invention is tested for such biological activity. Assays for detecting cell lysis (e.g. by measurement of LDH release) or apoptosis (e.g. using the TUNEL assay) are well known in the art. Assays for measuring ADCC or CDC are also described in WO 2004/065540 (see Example 1 therein), the entire content of which is incorporated herein by reference.

G. Pharmaceutical Formulations

Pharmaceutical formulations of a T cell activating bispecific antigen binding molecules, e.g., a T cell activating bispecific antigen binding molecule comprising a first antigen binding site specific for Folate Receptor 1 (FolR1) and a second antigen binding site specific for CD3, and antibodies, e.g., anti-PD-1 axis binding antagonist antibodies and anti-TIM3 antagonist antibodies as described herein are prepared by mixing such T cell activating bispecific antigen binding molecules or antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

H. Therapeutic Methods and Compositions

The therapeutic combinations comprising one or more of the T cell activating bispecific antigen binding molecules and the anti-PD-1 axis binding antagonist antibody and, optionally, the TIM3 antagonist provided herein may be used in therapeutic methods.

In one aspect, a T cell activating bispecific antigen binding molecules that binds to Folate Receptor 1 (FolR1) and CD3 for use as a medicament is provided for use in combination with an anti-PD-1 axis binding antagonist antibody. In certain embodiments, a T cell activating bispecific antigen binding molecules that binds to FolR1 and CD3 for use in combination with an anti-PD-1 axis binding antagonist antibody is provided for use in a method of treatment. In certain embodiments, the combination further comprises a TIM3 antagonist, e.g., an anti-TIM3 antagonist antibody. In certain embodiments, the invention provides a T cell activating bispecific antigen binding molecules that binds to FolR1 and CD3 and an anti-PD-1 axis binding antagonist antibody for use in a method of treating an individual having cancer comprising administering to the individual an effective amount of the T cell activating bispecific antigen binding molecules that binds to FolR1 and CD3 and the anti-PD-1 axis binding antagonist antibody. In one such embodiment, the method further comprises administering to the individual an effective amount of at least one TIM3 antagonist, e.g., as described below. An "individual" according to any of the above embodiments is preferably a human. In one preferred embodiment, said cancer is pancreatic cancer, sarcoma or colorectal carcinoma. In other embodiments, the cancer is colorectal cancer, sarcoma, head and neck cancers, squamous cell carcinomas, breast cancer, pancreatic cancer, gastric cancer, non-small-cell lung carcinoma, small-cell lung cancer or mesothelioma. In embodiments in which the cancer is breast cancer, the breast cancer may be triple negative breast cancer.

In a further aspect, the invention provides the use of a therapeutic combination comprising a T cell activating bispecific antigen binding molecules that binds to FolR1 and CD3 and an anti-PD-1 axis binding antagonist antibody in the manufacture or preparation of a medicament. In one embodiment, the combination further comprises a TIM3 antagonist. In one embodiment, the medicament is for treatment of cancer. In a further embodiment, the medicament is for use in a method of treating cancer comprising administering to an individual having cancer an effective amount of the medicament. In one such embodiment, the method further comprises administering to the individual an effective amount of at least one additional therapeutic agent, e.g., as described below. An "individual" according to any of the above embodiments may be a human.

In a further aspect, the invention provides a method for treating cancer. In one embodiment, the method comprises administering to an individual having cancer an effective amount of a therapeutic combination comprising a T cell activating bispecific antigen binding molecules that binds to FolR1 and CD3 and an anti-PD-1 axis binding antagonist antibody. In one such embodiment, the method further comprises administering to the individual an effective amount of at least one additional therapeutic agent, as described below. In one such embodiment, the at least one additional therapeutic agent is an anti-TIM3 antagonist antibody. An "individual" according to any of the above embodiments may be a human. In one preferred embodiment said cancer is pancreatic cancer, sarcoma or colorectal carcinoma. In other embodiments, the cancer is colorectal cancer, sarcoma, head and neck cancers, squamous cell carcinomas, breast cancer, pancreatic cancer, gastric cancer, non-small-cell lung carcinoma, small-cell lung cancer or mesothelioma.

In a further aspect, the invention provides pharmaceutical formulations comprising any of the T cell activating bispecific antigen binding molecules that binds to FolR1 and CD3 provided herein, e.g., for use in any of the above therapeutic methods, and an anti-PD-1 axis binding antagonist antibody. In one embodiment, a pharmaceutical formulation comprises any of the T cell activating bispecific antigen binding molecules that binds to FolR1 provided herein and a pharmaceutically acceptable carrier. In another embodiment, a pharmaceutical formulation comprises any of T cell activating bispecific antigen binding molecules that binds to FolR1 and CD3 and an anti-PD-1 axis binding antagonist antibody provided herein and at least one additional therapeutic agent, e.g., as described below.

A bispecific antibody can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Bispecific antibodies may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The bispecific antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a bispecific antibody will depend on the type of disease to be treated, the type of antibody, the severity and course of the disease, whether the bispecific antibody is administered for preventive or therapeutic purposes, previous therapy, the patient's clinical history and response to the bispecific antibody and the discretion of the attending physician. The bispecific antibody is suitably administered to the patient at one time or over a series of treatments. Depending on the type and severity of the disease, about 1 µg/kg to 15 mg/kg (e.g. 0.1 mg/kg-10 mg/kg) of the bispecific antibody or the novel antibody binding to DR5 can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the bispecific would be in the range from about 0.05 mg/kg to about 10 mg/kg. Thus, one or more doses of about 0.5 mg/kg, 2.0 mg/kg, 4.0 mg/kg or 10 mg/kg may be administered to the patient. Such doses may be administered intermittently, e.g. every week or every three weeks (e.g. such that the patient receives from about two to about twenty, or e.g. about six doses of the bispecific antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to the T cell activating bispecific antigen binding molecules that binds to FolR1 and CD3 and the anti-PD-1 axis binding antagonist antibody, and, optionally, the anti-TIM3 antagonist antibody.

I. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a bispecific antibody and an additional active agent is the further chemotherapeutic agent as described herein. The label or package insert indicates that the composition is used for treating the condition of choice. Moreover, the article of manufacture may comprise (a) a first container with a composition contained therein, wherein the composition comprises a bispecific antibody; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to the T cell activating bispecific antigen binding molecules that binds to FolR1 and CD3 and the anti-PD-1 axis binding antagonist antibody and, optionally, the anti-TIM3 antagonist antibody.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

III. Examples

The following are examples of methods and compositions of the invention. It is understood that various other embodiments may be practiced, given the general description provided above.

General Methods

Recombinant DNA Techniques

Standard methods were used to manipulate DNA as described in Sambrook et al., Molecular cloning: A laboratory manual; Cold Spring Harbor Laboratory Press, Cold Spring Harbor, N.Y., 1989. The molecular biological reagents were used according to the manufacturers' instructions. General information regarding the nucleotide sequences of human immunoglobulins light and heavy chains is given in: Kabat, E. A. et al., (1991) Sequences of Proteins of Immunological Interest, $5^{th}$ ed., NIH Publication No. 91-3242.

DNA Sequencing

DNA sequences were determined by double strand sequencing.

Gene Synthesis

Desired gene segments where required were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Isolation of Primary Human Pan T Cells from PBMCs

Peripheral blood mononuclear cells (PBMCs) were prepared by Histopaque density centrifugation from enriched lymphocyte preparations (buffy coats) obtained from local blood banks or from fresh blood from healthy human donors. Briefly, blood was diluted with sterile PBS and carefully layered over a Histopaque gradient (Sigma, H8889). After centrifugation for 30 minutes at 450×g at room temperature (brake switched off), part of the plasma above the PBMC containing interphase was discarded. The PBMCs were transferred into new 50 ml Falcon tubes and tubes were filled up with PBS to a total volume of 50 ml. The mixture was centrifuged at room temperature for 10 minutes at 400×g (brake switched on). The supernatant was discarded and the PBMC pellet washed twice with sterile PBS (centrifugation steps at 4° C. for 10 minutes at 350×g). The resulting PBMC population was counted automatically (ViCell) and stored in RPMI640 medium, containing 10% FCS and 1% L-alanyl-L-glutamine (Biochrom, K0302) at 37° C., 5% $CO_2$ in the incubator until assay start.

T cell enrichment from PBMCs was performed using the Pan T Cell Isolation Kit II (Miltenyi Biotec #130-091-156), according to the manufacturer's instructions. Briefly, the cell pellets were diluted in 40 µl cold buffer per 10 million cells (PBS with 0.5% BSA, 2 mM EDTA, sterile filtered) and incubated with 10 µl Biotin-Antibody Cocktail per 10 million cells for 10 min at 4° C. 30 µl cold buffer and 20 µl Anti-Biotin magnetic beads per 10 million cells were added, and the mixture incubated for another 15 min at 4° C. Cells were washed by adding 10-20× the current volume and a subsequent centrifugation step at 300×g for 10 min. Up to 100 million cells were resuspended in 500 µl buffer. Magnetic separation of unlabeled human pan T cells was performed using LS columns (Miltenyi Biotec #130-042-401) according to the manufacturer's instructions. The resulting T cell population was counted automatically (ViCell) and stored in AIM-V medium at 37° C., 5% $CO_2$ in the incubator until assay start (not longer than 24 h).

Isolation of Primary Human Naive T Cells from PBMCs

Peripheral blood mononuclear cells (PBMCs) were prepared by Histopaque density centrifugation from enriched lymphocyte preparations (buffy coats) obtained from local blood banks or from fresh blood from healthy human donors. T-cell enrichment from PBMCs was performed using the Naive CD8+ T cell isolation Kit from Miltenyi Biotec (#130-093-244), according to the manufacturer's instructions, but skipping the last isolation step of CD8+ T cells (also see description for the isolation of primary human pan T cells).

Isolation of Murine Pan T Cells from Splenocytes

Spleens were isolated from C57BL/6 mice, transferred into a GentleMACS C-tube (Miltenyi Biotech #130-093-237) containing MACS buffer (PBS+0.5% BSA+2 mM EDTA) and dissociated with the GentleMACS Dissociator to obtain single-cell suspensions according to the manufacturer's instructions. The cell suspension was passed through a pre-separation filter to remove remaining undissociated tissue particles. After centrifugation at 400×g for 4 min at 4° C., ACK Lysis Buffer was added to lyse red blood cells (incubation for 5 min at room temperature). The remaining cells were washed with MACS buffer twice, counted and used for the isolation of murine pan T cells. The negative (magnetic) selection was performed using the Pan T Cell Isolation Kit from Miltenyi Biotec (#130-090-861), following the manufacturer's instructions. The resulting T cell population was automatically counted (ViCell) and immediately used for further assays.

Isolation of Primary Cynomolgus PBMCs from Heparinized Blood

Peripheral blood mononuclar cells (PBMCs) were prepared by density centrifugation from fresh blood from healthy cynomolgus donors, as follows: Heparinized blood was diluted 1:3 with sterile PBS, and Lymphoprep medium (Axon Lab #1114545) was diluted to 90% with sterile PBS. Two volumes of the diluted blood were layered over one volume of the diluted density gradient and the PBMC fraction was separated by centrifugation for 30 min at 520×g, without brake, at room temperature. The PBMC band was transferred into a fresh 50 ml Falcon tube and washed with sterile PBS by centrifugation for 10 min at 400×g at 4° C. One low-speed centrifugation was performed to remove the platelets (15 min at 150×g, 4° C.), and the resulting PBMC population was automatically counted (ViCell) and immediately used for further assays.

Example 1

Purification of Biotinylated Folate Receptor-Fc Fusions

To generate new antibodies against human FolR1 the following antigens and screening tools were generated as monovalent Fc fusion proteins (the extracellular domain of the antigen linked to the hinge region of Fc-knob which is co-expressed with an Fc-hole molecule). The antigen genes were synthesized (Geneart, Regensburg, Germany) based on sequences obtained from GenBank or SwissProt and inserted into expression vectors to generate fusion proteins with Fc-knob with a C-terminal Avi-tag for in vivo or in vitro biotinylation. In vivo biotinylation was achieved by co-expression of the bacterial birA gene encoding a bacterial biotin ligase during production. Expression of all genes was under control of a chimeric MPSV promoter on a plasmid containing an oriP element for stable maintenance of the plasmids in EBNA containing cell lines.

For preparation of the biotinylated monomeric antigen/Fc fusion molecules, exponentially growing suspension HEK293 EBNA cells were co-transfected with three vectors encoding the two components of fusion protein (knob and hole chains) as well as BirA, an enzyme necessary for the biotinylation reaction. The corresponding vectors were used at a 9.5:9.5:1 ratio ("antigen ECD-Fc knob-avi tag": "Fc hole": "BirA").

For protein production in 500 ml shake flasks, 400 million HEK293 EBNA cells were seeded 24 hours before transfection. For transfection cells were centrifuged for 5 minutes at 210 g, and supernatant was replaced by pre-warmed CD CHO medium. Expression vectors were resuspended in 20 mL of CD CHO medium containing 200 pg of vector DNA. After addition of 540 µL of polyethylenimine (PEI), the solution was mixed for 15 seconds and incubated for 10 minutes at room temperature. Afterwards, cells were mixed with the DNA/PEI solution, transferred to a 500 mL shake flask and incubated for 3 hours at 37° C. in an incubator with a 5% $CO_2$ atmosphere. After the incubation, 160 mL of F17 medium was added and cells were cultured for 24 hours. One day after transfection, 1 mM valproic acid and 7% Feed 1 (Lonza) were added to the culture. The production medium was also supplemented with 100 µM biotin. After 7 days of culturing, the cell supernatant was collected by spinning down cells for 15 min at 210 g. The solution was sterile filtered (0.22 μm filter), supplemented with sodium azide to a final concentration of 0.01% (w/v), and kept at 4° C.

Secreted proteins were purified from cell culture supernatants by affinity chromatography using Protein A, followed by size exclusion chromatography. For affinity chromatography, the supernatant was loaded on a HiTrap ProteinA HP column (CV=5 mL, GE Healthcare) equilibrated with 40 mL 20 mM sodium phosphate, 20 mM sodium citrate pH 7.5. Unbound protein was removed by washing with at least 10 column volumes of 20 mM sodium phosphate, 20 mM sodium citrate pH 7.5. The bound protein was eluted using a linear pH-gradient created over 20 column volumes of 20 mM sodium citrate, 100 mM sodium chloride, 100 mM glycine, pH 3.0. The column was then washed with 10 column volumes of 20 mM sodium citrate, 100 mM sodium chloride, 100 mM glycine, pH 3.0. pH of collected fractions was adjusted by adding 1/10 (v/v) of 0.5 M sodium phosphate, pH 8.0. The protein was concentrated and filtered prior to loading on a HiLoad Superdex 200 column (GE Healthcare) equilibrated with 20 mM histidine, 140 mM sodium chloride, pH 6.0.

The protein concentration was determined by measuring the optical density (OD) at 280 nm, using the molar extinction coefficient calculated on the basis of the amino acid sequence. Purity and molecular weight of the FolR1-Fc-fusion was analyzed by SDS capillary electrophoresis in the presence and absence of a reducing agent following the manufacturer instructions (instrument Caliper LabChipGX, Perkin Elmer). The aggregate content of samples was analyzed using a TSKgel G3000 SW XL analytical size-exclusion column (Tosoh) equilibrated in 25 mM K2HPO4, 125 mM NaCl, 200 mM L-arginine monohydrochloride, 0.02% (w/v) NaN3, pH 6.7 running buffer at 25° C.

Purified antigen-Fc-fusion proteins were analyzed by surface plasmon resonance assays using commercially available antibodies to confirm correct and natural conformation of the antigens (data not shown).

TABLE 1

Antigens produced for isolation, selection and counter selection of human FolR1 antibodies

| Antigen | ECD (aa) | Accession number | Sequence | Seq ID No |
|---|---|---|---|---|
| human FolR1 | 25-234 | P15328 | RIAWARTELLNVCMNAKHHKEKPGPEDKLHEQCRPWR KNACCSTNTSQEAHKDVSYLYRFNWNHCGEMAPACKR HFIQDTCLYECSPNLGPWIQQVDQSWRKERVLNVPLC KEDCEQWWEDCRTSYTCKSNWHKGWNWTSGFNKCAVG AACQPFHFYFPTPTVLCNEIWTHSYKVSNYSRGSGRC IQMWFDPAQGNPNEEVARFYAAAM | 227 |
| human FolR2 | 17-230 | P14207 | TMCSAQDRTDLLNVCMDAKHHKTKPGPEDKLHDQCSP WKKNACCTASTSQELHKDTSRLYNFNWDHCGKMEPAC KRHFIQDTCLYECSPNLGPWIQQVNQSWRKERFLDVP LCKEDCQRWWEDCHTSHTCKSNWHRGWDTSGVNKCP AGALCRTFESYFPTPAALCEGLWSHSYKVSNYSRGSG RCIQMWFDSAQGNPNEEVARFYAAAMHVN | 228 |
| human FolR3 | 24-243 | P41439 | SARARTDLLNVCMNAKHHKTQPSPEDELYGQCSPWKK NACCTASTSQELHKDTSRLYNFNWDHCGKMEPTCKRH FIQDSCLYECSPNLGPWIRQVNQSWRKERILNVPLCK EDCERWWEDCRTSYTCKSNWHKGWNWTSGINECPAGA LCSTFESYFPTPAALCEGLWSHSFKVSNYSRGSGRCI QMWFDSAQGNPNEEVAKFYAAAMNAGAPSRGIIDS | 229 |
| murine FolR1 | 25-232 | P35846 | TRARTELLNVCMDAKHHKEKPGPEDNLHDQCSPWKTN SCCSTNTSQEAHKDISYLYRFNWNHCGTMTSECKRHF IQDTCLYECSPNLGPWIQQVDQSWRKERILDVPLCKE DCQQWWEDCQSSFTCKSNWHKGWNWSSGHNECPVGAS CHPFTFYFPTSAALCEEIWSHSYKLSNYSRGSGRCIQ MWFDPAQGNPNEEVARFYAEAMS | 230 |
| cynomolgus FolR1 | 25-234 | G7PR14 | EAQTRTARARTELLNVCMNAKHHKEKPGPEDKLHEQC RPWKKNACCSTNTSQEAHKDVSYLYRFNWNHCGEMAP ACKRHFIQDTCLYECSPNLGPWIQQVDQSWRKERVLN VPLCKEDCERWWEDCRTSYCKSNWHKGWNWTSGFNKC PVGAACQPFHFYFPTPTVLCNEIWTYSYKVSNYSRGS GRCIQMWFDPAQGNPNEEVARFYAAAMS | 231 |

TABLE 2

Summary of the yield and final monomer content of the FolR-Fc-fusions.

| Antigen | Monomer [%] (SEC) | Yield |
|---|---|---|
| huFolR1 | 100 | 30 mg/L |
| cyFolR1 | 100 | 32 mg/L |
| muFolR1 | 100 | 31 mg/L |
| huFolR2 | 100 | 16 mg/L |
| huFolR3 | 95 | 38 mg/L |

Example 2

Generation of Common Light Chain with CD3ε Specificity

The T cell activating bispecific molecules described herein comprise at least one CD3 binding moiety. This moiety can be generated by immunizing laboratory animals, screening phage library or using known anti-CD3 antibodies. The common light chain with CD3ε specificity was generated by humanizing the light chain of a murine parental anti-CD3ε antibody (CH2527). For humanization of an antibody of non-human origin, the CDR residues from the non-human antibody (donor) have to be transplanted onto the framework of a human (acceptor) antibody. Generally, acceptor framework sequences are selected by aligning the sequence of the donor to a collection of potential acceptor sequences and choosing one that has either reasonable homology to the donor, or shows similar amino acids at some positions critical for structure and activity. In the present case, the search for the antibody acceptor framework was performed by aligning the mouse VL-domain sequence of the parental antibody to a collection of human germline sequences and choosing the human sequence that showed high sequence identity. Surprisingly, a good match in terms of framework sequence homology was found in a rather infrequent human light chain belonging to the V-domain family 7 of the lambda type, more precisely, hVL_7_46 (IMGT nomenclature, GenBank Acc No. Z73674). This infrequent human light chain was subsequently chosen as acceptor framework for humanization of the light chain of CH2527. The three complementarity determining regions (CDRs) of the mouse light chain variable domain were grafted onto this acceptor framework. Since the framework 4 region is not part of the variable region of the germline V-gene, the alignment for this region (J-element) was done individually. Hence the IGU3-02 sequence was chosen for humanization of this light chain.

Thirteen humanized variants were generated (CH2527-VL7_46-1 to VL7_46-10, VL7_46-12 to VL7_46-14). These differ in framework residues (and combinations thereof) that were back-mutated to the murine V-domain sequence or in CDR-residues (Kabat definition) that could be kept identical to the human germline sequence. The following framework residues outside the CDRs were back-mutated to the murine residues in the final humanized VL-domain variant VL7_46-13 (murine residues listed): V36, E38, F44, G46, G49, and G57, respectively. The human J-element IGU3-02 was 100% identical to the J-element of the murine parental antibody.

Example 3

SPR Assessment of Humanized Variants with CD3ε Specificity

Humanized VL variants were assessed as chimera in a 2+1 TCB format, i.e. humanized light chain V-domains were paired with murine heavy chain V-domains. SPR assessment was carried out on a ProteOn XPR36 instrument (Bio-Rad). More precisely, the variants were captured directly from the culture supernatant on an anti-Fab derivatized GLM sensorchip (Goat Anti-Human IgG, F(ab')$_2$ Fragment Specific, Jackson ImmunoResearch) in vertical orientation. The following analytes were subsequently injected horizontally as single concentrations to assess binding to human and cynomolgus CD3ε: 3 µM hu CD3ε(−1-26)-Fc(knob)-avi (ID807) and 2.5 µM cy CD3ε-(-1-26)-Fc(knob)-Avi-Fc(hole) (ID873), respectively. Binding responses were qualitatively compared to binding of the murine control construct and graded + (comparable binding observed), +/−(reduced binding observed) and − (no binding observed). The capture antibody was regenerated after each cycle of ligand capture and analyte binding and the murine construct was re-injected at the end of the study to confirm the activity of the capture surface. The results are summarized in Table 3.

TABLE 3

Qualitative binding assessment based on SPR for the humanized light chain variants combined with the murine heavy chain of CH2527. Only the humanized light chain variant that was finally chosen, CH2527-VL7_46-13, highlighted in bold letters, exhibited comparable binding to human and cynomolgus CD3ε.

| humanized VL variant | binding to CD3ε |
|---|---|
| murine_CH2527-VL | + |
| CH2527-VL7_46-1 | − |
| CH2527-VL7_46-2 | − |
| CH2527-VL7_46-3 | − |
| CH2527-VL7_46-4 | − |
| CH2527-VL7_46-5 | − |
| CH2527-VL7_46-6 | − |
| CH2527-VL7_46-7 | − |
| CH2527-VL7_46-8 | − |
| CH2527-VL7_46-9 | − |
| CH2527-VL7_46-10 | − |
| CH2527-VL7_46-12 | +/− |
| CH2527-VL7_46-13 | + |
| CH2527-VL7_46-14 | − |

Example 4

Properties of Humanized Common Light Chain with CD3ε Specificity

The light chain V-domain variant that was chosen for the humanized lead molecule is VL7_46-13. The degree of humanness, i.e. the sequence homology of the humanized V-domain to the human germline V-domain sequence was determined. For VL7_46-13, the overall sequence identity with the closest human germline homolog is 65% before humanization and 80% afterwards. Omitting the CDR regions, the sequence identity is 92% to the closest human germline homolog. As can be seen from Table 3, VL7_46-13 is the only humanized VL variant out of a panel of 13 variants that showed comparable binding to the parental murine antibody and also retained its cross-reactivity to cynomolgus CD3ε. This result indicates that it was not trivial to humanize the murine VL-domain without losing binding affinity to CD3ε which required several back-mutations to murine framework residues (in particular G46) while retaining G24 in CDR1. In addition, this result shows that the VL-domain plays a crucial role in target recognition. Importantly, the humanized VL-domain VL7_46-13 based on an infrequent human germline belonging to the V-domain family 7 of the lambda type and retaining affinity and specificity for CD3ε, is also suitable to be used as a common light chain in phage-displayed antibody libraries of the Fab-format and enables successful selection for novel specificities which greatly facilitates the generation and production of bispecific molecules binding to CD3ε and e.g. a tumor target and sharing the same 'common' light chain.

Example 5

Generation of a Phage Displayed Antibody Library Using a Human Germ-Line Common Light Chain Derived from HVK1-39

Several approaches to generate bispecific antibodies that resemble full length human IgG utilize modifications in the Fc region that induce heterodimerization of two distinct heavy chains. Such examples include knobs-into-holes (Merchant et al., Nat Biotechnol. 1998 July; 16(7):677-81) SEED (Davis et al., Protein Eng Des Sel. 2010 April; 23(4):195-202) and electrostatic steering technologies (Gunasekaran et al., J Biol Chem. 2010 Jun. 18; 285(25):19637-46). Although these approaches enable effective heterodimerization of two distinct heavy chains, appropriate pairing of cognate light and heavy chains remains a problem. Usage of a common light chain (LC) can solve this issue (Merchant, et al. Nat Biotech 16, 677-681 (1998)).

Here, we describe the generation of an antibody library for the display on a M13 phage. Essentially, we designed a multi framework library for the heavy chain with one constant (or "common") light chain. This library is designed for generating multispecific antibodies without the need to use sophisticated technologies to avoid light chain mispairing.

By using a common light chain the production of these molecules can be facilitated as no mispairing occurs any longer and the isolation of a highly pure bispecific antibody is facilitated. As compared to other formats the use of Fab fragments as building blocks as opposed to e.g. the use of scFv fragments results in higher thermal stability and the lack of scFv aggregation and intermolecular scFv formation.

Library Generation

In the following the generation of an antibody library for the display on M13 phage is described. Essentially, we designed a multi framework library for the heavy chain with one constant (or "common") light chain.

We used these heavy chains in the library (GenBank Accession Numbers in brackets):
IGHV1-46*01 (X92343) (SEQ ID NO:104),
IGHV1-69*06 (L22583), (SEQ ID NO:105)
IGHV3-15*01 (X92216), (SEQ ID NO:106)
IGHV3-23*01 (M99660), (SEQ ID NO:107)
IGHV4-59*01 (AB019438), (SEQ ID NO:108)
IGHV5-51*01 (M99686), (SEQ ID NO:109)

All heavy chains use the IGHJ2 as J-element, except the IGHV1-69*06 which uses IGHJ6 sequence. The design of the randomization included the CDR-H1, CDR-H2, and CDR-H3. For CDR-H1 and CDR-H2 a "soft" randomization strategy was chosen, and the randomization oligonucleotides were such that the codon for the amino acid of the germ-line sequence was present at 50%. All other amino acids, except cysteine, were summing up for the remaining 50%. In CDR-H3, where no germ-line amino acid is present due to the presence of the genetic D-element, oligonucleotides were designed that allow for the usage of randomized inserts between the V-element and the J-element of 4 to 9 amino acids in length. Those oligonucleotides contained in their randomized part e.g. The three amino acids G/Y/S are present to 15% each, those amino acids A/D/T/R/P/L/V/W/F/I/E are present to 4.6% each.

Exemplary methods for generation of antibody libraries are described in Hoogenboom et al., Nucleic Acids Res. 1991, 19, 4133-413; Le et. al, J. Mol. Biol. (2004) 340, 1073-1093.

The light chain is derived from the human sequence hVK1-39, and is used in an unmodified and non-randomized fashion. This will ensure that the same light chain can be used for other projects without additional modifications.

Exemplary Library Selection:

Selections with all affinity maturation libraries are carried out in solution according to the following procedure using a monomeric and biotinylated extracellular domain of a target antigen X.

1. $10^{12}$ phagemid particles of each library are bound to 100 nM biotinylated soluble antigen for 0.5 h in a total volume of 1 ml. 2. Biotinylated antigen is captured and specifically bound phage particles are isolated by addition of $\sim 5 \times 10^{7}$ streptavidin-coated magnetic beads for 10 min. 3. Beads are washed using 5-10×1 ml PBSTween20 and 5-10×1 ml PBS. 4. Elution of phage particles is done by addition of 1 ml 100 mM TEA (triethylamine) for 10 min and neutralization by addition of 500 ul 1M Tris/HCl pH 7.4 and 5. Re-infection of exponentially growing E. coli TG1 bacteria, infection with helper phage VCSM13 and subsequent PEG/NaCl precipitation of phagemid particles is applied in subsequent selection rounds. Selections are carried out over 3-5 rounds using either constant or decreasing (from $10^{-7}M$ to $2 \times 10^{-9}M$) antigen concentrations. In round 2, capture of antigen/phage complexes is performed using neutravidin plates instead of streptavidin beads. All binding reactions are supplemented either with 100 nM bovine serum albumin, or with non-fat milk powder in order to compete for unwanted clones arising from mere sticky binding of the antibodies to the plastic support.

Selections are being carried out over three or four rounds using decreasing antigen concentrations of the antigen starting from 100 nM and going down to 5 nM in the final selection round. Specific binders are defined as signals ca. 5× higher than background and are identified by ELISA. Specific binders are identified by ELISA as follows: 100 μl of 10 nM biotinylated antigen per well are coated on neutravidin plates. Fab-containing bacterial supernatants are added and binding Fabs are detected via their Flag-tags by using an anti-Flag/HRP secondary antibody. ELISA-positive clones are bacterially expressed as soluble Fab fragments in 96-well format and supernatants are subjected to a kinetic screening experiment by SPR-analysis using ProteOn XPR36 (BioRad). Clones expressing Fabs with the highest affinity constants are identified and the corresponding phagemids are sequenced. For further characterization, the Fab sequences are amplified via PCR from the phagemid and cloned via appropriate restriction sites into human IgG1 expression vectors for mammalian production.

Generation of a Phage Displayed Antibody Library Using a Humanized CD3ε Specific Common Light Chain Here, the generation of an antibody library for the display on M13 phage is described. Essentially, we designed a multi framework library for the heavy chain with one constant (or "common") light chain. This library was designed for the generation of Fc-containing, but FcgR binding inactive T cell bispecific antibodies of IgG1 P329G LALA or IgG4 SPLE PG isotype in which one or two Fab recognize a tumor surface antigen expressed on a tumor cell whereas the remaining Fab arm of the antibody recognizes CD3e on a T cell.

Library Generation

In the following the generation of an antibody library for the display on M13 phage is described. Essentially, we designed a multi framework library for the heavy chain with one constant (or "common") light chain. This library is designed solely for the generation of Fc-containing, but FcgR binding inactive T cell bispecific antibodies of IgG1 P329G LALA or IgG4 SPLE PG isotype.

Diversity was introduced via randomization oligonucleotides only in the CDR3 of the different heavy chains. Methods for generation of antibody libraries are well known in the art and are described in (Hoogenboom et al., Nucleic Acids Res. 1991, 19, 4133-413; or in: Le et. al, J. Mol. Biol. (2004) 340, 1073-1093).

We used these heavy chains in the library:
IGHV1-46*01 (X92343), (SEQ ID NO:104)
IGHV1-69*06 (L22583), (SEQ ID NO:105)
IGHV3-15*01 (X92216), (SEQ ID NO:106)
IGHV3-23*01 (M99660), (SEQ ID NO:107)
IGHV4-59*01 (AB019438), (SEQ ID NO:108)
IGHV5-51*01 (M99686), (SEQ ID NO:109)

We used the light chain derived from the humanized human and Cynomolgus CD3 ε specific antibody CH2527 in the library: (VL7_46-13; SEQ ID NO:112). This light chain was not randomized and used without any further modifications in order to ensure compatibility with different bispecific binders.

All heavy chains use the IGHJ2 as J-element, except the IGHV1-69*06 which uses IGHJ6 sequence. The design of the randomization focused on the CDR-H3 only, and PCR oligonucleotides were designed that allow for the usage of randomized inserts between the V-element and the J-element of 4 to 9 amino acids in length.

Example 6

Selection of Antibody Fragments from Common Light Chain Libraries (Comprising Light Chain with CD3ε Specificity) to FolR1

The antibodies 16A3, 15A1, 18D3, 19E5, 19A4, 15H7, 15B6, 16D5, 15E12, 21D1, 16F12, 21A5, 21G8, 19H3, 20G6, and 20H7 comprising the common light chain VL7_46-13 with CD3ε specificity were obtained by phage display selections against different species (human, cynomolgus and murine) of FolR1. Clones 16A3, 15A1, 18D3, 19E5, 19A4, 15H7, 15B6, 21D1, 16F12, 19H3, 20G6, and 20H7 were selected from a sub-library in which the common light chain was paired with a heavy chain repertoire based on the human germline VH1_46. In this sub-library, CDR3 of VH1_46 has been randomized based on 6 different CDR3 lengths. Clones 16D5, 15E12, 21A5, and 21G8 were selected from a sub-library in which the common light chain was paired with a heavy chain repertoire based on the human germline VH3_15. In this sub-library, CDR3 of VH3_15 has been randomized based on 6 different CDR3 lengths. In order to obtain species cross-reactive (or murine FolR1-reactive) antibodies, the different species of FolR1 were alternated (or kept constant) in different ways over 3 rounds of biopanning: 16A3 and 15A11 (human-cynomolgus-human FolR1); 18D3 (cynomolgus-human-murine FolR1); 19E5 and 19A4 (3 rounds against murine FolR1); 15H7, 15B6, 16D5, 15E12, 21D1, 16F12, 21A5, 21G8 (human-cynomolgus-human FolR1); 19H3, 20G6, and 20H7 (3 rounds against murine FolR1).

Human, murine and cynomolgus FolR1 as antigens for the phage display selections as well as ELISA- and SPR-based screenings were transiently expressed as N-terminal monomeric Fc-fusion in HEK EBNA cells and in vivo site-specifically biotinylated via co-expression of BirA biotin ligase at the avi-tag recognition sequence located at the C-terminus of the Fc portion carrying the receptor chain (Fc knob chain). In order to assess the specificity to FolR1, two related receptors, human FolR2 and FolR3 were generated in the same way.

Selection rounds (biopanning) were performed in solution according to the following pattern:
1. Pre-clearing of ~$10^{12}$ phagemid particles on maxisorp plates coated with 10 ug/ml of an unrelated human IgG to deplete the libraries of antibodies recognizing the Fc-portion of the antigen.
2. Incubating the non-Fc-binding phagemid particles with 100 nM biotinylated human, cynomolgus, or murine FolR1 for 0.5 h in the presence of 100 nM unrelated non-biotinylated Fc knob-into-hole construct for further depletion of Fc-binders in a total volume of 1 ml.
3. Capturing the biotinylated FolR1 and attached specifically binding phage by transfer to 4 wells of a neutravidin pre-coated microtiter plate for 10 min (in rounds 1 & 3).
4. Washing the respective wells using 5×PBS/Tween20 and 5×PBS.
5. Eluting the phage particles by addition of 250 ul 100 mM TEA (triethylamine) per well for 10 min and neutralization by addition of 500 ul 1 M Tris/HCl pH 7.4 to the pooled eluates from 4 wells.
6. Post-clearing of neutralized eluates by incubation on neutravidin pre-coated microtiter plate with 100 nM biotin-captured FolR2 or FolR3 for final removal of Fc- and unspecific binders.
7. Re-infection of log-phase E. coli TG1 cells with the supernatant of eluted phage particles, infection with helperphage VCSM13, incubation on a shaker at 30° C. over night and subsequent PEG/NaCl precipitation of phagemid particles to be used in the next selection round.

Selections were carried out over 3 rounds using constant antigen concentrations of 100 nM. In round 2, in order to avoid enrichment of binders to neutravidin, capture of antigen: phage complexes was performed by addition of $5.4 \times 10^7$ streptavidin-coated magnetic beads. Specific binders were identified by ELISA as follows: 100 ul of 25 nM biotinylated human, cynomolgus, or murine FolR1 and 10 ug/ml of human IgG were coated on neutravidin plates and maxisorp plates, respectively. Fab-containing bacterial supernatants were added and binding Fabs were detected via their Flag-tags using an anti-Flag/HRP secondary antibody. Clones exhibiting signals on human FolR1 and being negative on human IgG were short-listed for further analyses and were also tested in a similar fashion against the remaining two species of FolR. They were bacterially expressed in a 0.5 liter culture volume, affinity purified and further characterized by SPR-analysis using BioRad's ProteOn XPR36 biosensor.

Affinities ($K_D$) of selected clones were measured by surface plasmon resonance (SPR) using a ProteOn XPR36 instrument (Biorad) at 25° C. with biotinylated human, cynomolgus, and murine FolR1 as well as human FolR2 and FolR3 (negative controls) immobilized on NLC chips by neutravidin capture. Immobilization of antigens (ligand): Recombinant antigens were diluted with PBST (10 mM phosphate, 150 mM sodium chloride pH 7.4, 0.005% Tween 20) to 10 µg/ml, then injected at 30 µl/minute in vertical orientation.

Injection of analytes: For 'one-shot kinetics' measurements, injection direction was changed to horizontal orientation, two-fold dilution series of purified Fab (varying concentration ranges) were injected simultaneously along separate channels 1-5, with association times of 200 s, and dissociation times of 600 s. Buffer (PBST) was injected along the sixth channel to provide an "in-line" blank for referencing. Association rate constants ($k_{on}$) and dissociation rate constants ($k_{off}$) were calculated using a simple one-to-one Langmuir binding model in ProteOn Manager v3.1 software by simultaneously fitting the association and dissociation sensorgrams. The equilibrium dissociation constant ($K_D$) was calculated as the ratio $k_{off}/k_{on}$. Table 4 lists the equilibrium dissociation constants ($K_D$) of the selected clones specific for FolR1.

TABLE 4

Equilibrium dissociation constants (KD) for anti-FolR1 antibodies (Fab-format) selected by phage display from common light chain sub-libraries comprising VL7_46-13, a humanized light chain specific for CD3ε. KD in nM.

| Clone | huFolR1 [nM] | cyFolR1 [nM] | muFolR1 [nM] | huFolR2 [nM] | huFolR3 [nM] |
|---|---|---|---|---|---|
| 16A3 | 21.7 | 18 | very weak | no binding | no binding |
| 15A1 | 30.9 | 17.3 | very weak | no binding | no binding |
| 18D3 | 93.6 | 40.2 | very weak | no binding | no binding |
| 19E5 | 522 | 276 | 19.4 | no binding | no binding |
| 19A4 | 2050 | 4250 | 43.1 | no binding | no binding |
| 15H7 | 13.4 | 72.5 | no binding | no binding | no binding |
| 15B6 | 19.1 | 13.9 | no binding | no binding | no binding |
| 16D5 | 39.5 | 114 | no binding | no binding | no binding |
| 15E12 | 55.7 | 137 | no binding | no binding | no binding |
| 21D1 | 62.6 | 32.1 | no binding | no binding | no binding |
| 16F12 | 68 | 90.9 | no binding | no binding | no binding |
| 21A5 | 68.8 | 131 | no binding | no binding | no binding |
| 21G8 | 130 | 261 | no binding | no binding | no binding |
| 19H3 | no binding | no binding | 89.7 | no binding | no binding |
| 20G6 | no binding | no binding | 78.5 | no binding | no binding |

Example 7

Selection of Antibody Fragments from Generic Multi-Framework Libraries to FolR1

The antibodies 11F8, 36F2, 9D11, 5D9, 6B6, and 14E4 were obtained by phage display selections based on generic multi-framework sub-libraries against different species (human, cynomolgus and murine) of FolR. In these multi-framework sub-libraries, different VL-domains with randomized CDR3 (3 different lengths) are paired with different VH-domains with randomized CDR3 (6 different lengths). The selected clones are of the following VL/VH pairings: 11F8 (Vk_1_5/VH_1_69), 36F2 (Vk_3_20/VH_1_46), 9D11 (Vk2D_28/VH1_46), 5D9 (Vk3_20/VH1_46), 6B6 (Vk3_20/VH1_46), and 14E4 (Vk3_20/VH3_23). In order to obtain species cross-reactive (or murine FolR1-reactive) antibodies, the different species of FolR1 were alternated (or kept constant) in different ways over 3 or 4 rounds of biopanning: 11F8 (cynomolgus-murine-human FolR1); 36F2 (human-murine-cynomolgus-murine FolR1); 9D11 (cynomolgus-human-cynomolgus FolR1); 5D9 (human-cynomolgus-human FolR1); 6B6 (human-cynomolgus-human FolR1) and 14E4 (3 rounds against murine FolR1).

Human, murine and cynomolgus FolR1 as antigens for the phage display selections as well as ELISA- and SPR-based screenings were transiently expressed as N-terminal monomeric Fc-fusion in HEK EBNA cells and in vivo site-specifically biotinylated via co-expression of BirA biotin ligase at the avi-tag recognition sequence located at the C-terminus of the Fc portion carrying the receptor chain (Fc knob chain). In order to assess the specificity to FolR1, two related receptors, human FolR2 and FolR3 were generated in the same way.

Selection rounds (biopanning) were performed in solution according to the following pattern:
1. Pre-clearing of ~10$^{12}$ phagemid particles on maxisorp plates coated with 10 ug/ml of an unrelated human IgG to deplete the libraries of antibodies recognizing the Fc-portion of the antigen.
2. Incubating the non-Fc-binding phagemid particles with 100 nM biotinylated human, cynomolgus, or murine FolR1 for 0.5 h in the presence of 100 nM unrelated non-biotinylated Fc knob-into-hole construct for further depletion of Fc-binders in a total volume of 1 ml.
3. Capturing the biotinylated FolR1 and attached specifically binding phage by transfer to 4 wells of a neutravidin pre-coated microtiter plate for 10 min (in rounds 1 & 3).
4. Washing the respective wells using 5×PBS/Tween20 and 5×PBS.
5. Eluting the phage particles by addition of 250 ul 100 mM TEA (triethylamine) per well for 10 min and neutralization by addition of 500 ul 1 M Tris/HCl pH 7.4 to the pooled eluates from 4 wells.
6. Post-clearing of neutralized eluates by incubation on neutravidin pre-coated microtiter plate with 100 nM biotin-captured FolR2 or FolR3 for final removal of Fc- and unspecific binders.
7. Re-infection of log-phase E. coli TG1 cells with the supernatant of eluted phage particles, infection with help-erphage VCSM13, incubation on a shaker at 30° C. over night and subsequent PEG/NaCl precipitation of phagemid particles to be used in the next selection round.

Selections were carried out over 3 rounds using constant antigen concentrations of 100 nM. In round 2 and 4, in order to avoid enrichment of binders to neutravidin, capture of antigen: phage complexes was performed by addition of 5.4×10$^7$ streptavidin-coated magnetic beads. Specific binders were identified by ELISA as follows: 100 ul of 25 nM biotinylated human, cynomolgus, or murine FolR1 and 10 ug/ml of human IgG were coated on neutravidin plates and maxisorp plates, respectively. Fab-containing bacterial supernatants were added and binding Fabs were detected via their Flag-tags using an anti-Flag/HRP secondary antibody. Clones exhibiting signals on human FolR1 and being negative on human IgG were short-listed for further analyses and were also tested in a similar fashion against the remaining two species of FolR. They were bacterially expressed in a 0.5 liter culture volume, affinity purified and further characterized by SPR-analysis using BioRad's ProteOn XPR36 biosensor.

Affinities ($K_D$) of selected clones were measured by surface plasmon resonance (SPR) using a ProteOn XPR36 instrument (Biorad) at 25° C. with biotinylated human, cynomolgus, and murine FolR1 as well as human FolR2 and FolR3 (negative controls) immobilized on NLC chips by neutravidin capture. Immobilization of antigens (ligand): Recombinant antigens were diluted with PBST (10 mM phosphate, 150 mM sodium chloride pH 7.4, 0.005% Tween 20) to 10 µg/ml, then injected at 30 µl/minute in vertical orientation. Injection of analytes: For 'one-shot kinetics' measurements, injection direction was changed to horizontal orientation, two-fold dilution series of purified Fab (varying concentration ranges) were injected simultaneously along separate channels 1-5, with association times of 150 or 200 s, and dissociation times of 200 or 600 s, respectively. Buffer (PBST) was injected along the sixth channel to provide an "in-line" blank for referencing. Association rate constants ($k_{on}$) and dissociation rate constants ($k_{off}$) were calculated using a simple one-to-one Langmuir binding model in ProteOn Manager v3.1 software by simultaneously fitting the association and dissociation sensorgrams. The equilibrium dissociation constant ($K_D$) was calculated as the ratio $k_{off}/k_{on}$. Table 5 lists the equilibrium dissociation constants ($K_D$) of the selected clones specific for FolR1.

TABLE 5

Equilibrium dissociation constants ($K_D$) for anti-FolR1 antibodies (Fab-format) selected by phage display from generic multi-framework sub-libraries. $K_D$ in nM.

| Clone | $K_D$ (nM) | | | | |
|---|---|---|---|---|---|
| | huFolR1 | cyFolR1 | muFolR1 | huFolR2 | huFolR3 |
| 11F8 | 632 | 794 | 1200 | no binding | no binding |
| 36F2 | 1810 | 1640 | 737 | no binding | no binding |
| 9D11 | 8.64 | 5.29 | no binding | no binding | no binding |
| 5D9 | 8.6 | 5.9 | no binding | no binding | no binding |
| 6B6 | 14.5 | 9.4 | no binding | no binding | no binding |
| 14E4 | no binding | no binding | 6.09 | no binding | no binding. |

Example 8

Production and Purification of Novel FolR1 Binders in IgG and T-Cell Bispecific Formats To identify FolR1 binders which are able to induce T-cell dependent killing of selected target cells the antibodies isolated from a common light chain- or Fab-library were converted into the corresponding human IgG1 format. In brief, the variable heavy and variable light chains of unique FolR1 binders from phage display were amplified by standard PCR reactions using the Fab clones as the template. The PCR products were purified and inserted (either by restriction endonuclease and ligase based cloning, or by 'recombineering' using the InFusion kit from Invitrogen) into suitable expression vectors in which they are fused to the appropriate human constant heavy or human constant light chain. The expression cassettes in these vectors consist of a chimeric MPSV promoter and a synthetic polyadenylation site. In addition, the plasmids contain the oriP region from the Epstein Barr virus for the stable maintenance of the plasmids in HEK293 cells harboring the EBV nuclear antigen (EBNA). After PEI mediated transfection the antibodies were transiently produced in HEK293 EBNA cells and purified by standard ProteinA affinity chromatography followed by size exclusion chromatography as described:

Transient Transfection and Production

All (bispecific) antibodies (if not obtained from a commercial source) used herein were transiently produced in HEK293 EBNA cells using a PEI mediated transfection procedure for the required vectors as described below. HEK293 EBNA cells are cultivated in suspension serum free in CD CHO culture medium. For the production in 500 ml shake flask 400 million HEK293 EBNA cells are seeded 24 hours before transfection (for alternative scales all amounts were adjusted accordingly). For transfection cells are centrifuged for 5 min by 210×g, supernatant is replaced by pre-warmed 20 ml CD CHO medium. Expression vectors are mixed in 20 ml CD CHO medium to a final amount of 200 µg DNA. After addition of 540 µl PEI solution is vortexed for 15 s and subsequently incubated for 10 min at room temperature. Afterwards cells are mixed with the DNA/PEI solution, transferred to a 500 ml shake flask and incubated for 3 hours by 37° C. in an incubator with a 5% CO2 atmosphere. After incubation time 160 ml F17 medium is added and cell are cultivated for 24 hours. One day after transfection 1 mM valporic acid and 7% Feed 1 is added. After 7 days cultivation supernatant is collected for purification by centrifugation for 15 min at 210×g, the solution is sterile filtered (0.22 µm filter) and sodium azide in a final concentration of 0.01% w/v is added, and kept at 4° C. After production the supernatants were harvested and the antibody containing supernatants were filtered through 0.22 µm sterile filters and stored at 4° C. until purification.

Antibody Purification

All molecules were purified in two steps using standard procedures, such as protein A affinity purification (Äkta Explorer) and size exclusion chromatography. The supernatant obtained from transient production was adjusted to pH 8.0 (using 2 M TRIS pH 8.0) and applied to HiTrap PA FF (GE Healthcare, column volume (cv)=5 ml) equilibrated with 8 column volumes (cv) buffer A (20 mM sodium phosphate, 20 mM sodium citrate, pH 7.5). After washing with 10 cv of buffer A, the protein was eluted using a pH gradient to buffer B (20 mM sodium citrate pH 3, 100 mM NaCl, 100 mM glycine) over 12 cv. Fractions containing the protein of interest were pooled and the pH of the solution was gently adjusted to pH 6.0 (using 0.5 M $Na_2HPO_4$ pH 8.0). Samples were concentrated to 2 ml using ultra-concentrators (Vivaspin 15R 30.000 MWCO HY, Sartorius) and subsequently applied to a HiLoad™ 16/60 Superdex™ 200 preparative grade (GE Healthcare) equilibrated with 20 mM Histidine, pH 6.0, 140 mM NaCl, 0.01% Tween-20. The aggregate content of eluted fractions was analyzed by analytical size exclusion chromatography. Therefore, 30 µl of each fraction was applied to a TSKgel G3000 SW XL analytical size-exclusion column (Tosoh) equilibrated in 25 mM $K_2HPO_4$, 125 mM NaCl, 200 mM L-arginine monohydrochloride, 0.02% (w/v) $NaN_3$, pH 6.7 running buffer at 25° C. Fractions containing less than 2% oligomers were pooled and concentrated to final concentration of 1-1.5 mg/ml using ultra concentrators (Vivaspin 15R 30.000 MWCO HY, Sartorius). The protein concentration was determined by measuring the optical density (OD) at 280 nm, using the molar extinction coefficient calculated on the basis of the amino acid sequence. Purity and molecular weight of the constructs were analyzed by SDS capillary electrophoresis in the presence and absence of a reducing agent following the manufacturer instructions (instrument Caliper LabChipGX, Perkin Elmer). Purified proteins were frozen in liquid N2 and stored at −80° C.

Based on in vitro characterization results selected binders we converted into a T-cell bispecific format. In these molecules the FolR1:CD3 binding moieties are arranged in a 2:1 order with the FolR11 Fabs being located at the N-terminus. For clones isolated from the standard Fab library the CD3 binding part was generated as a CrossFab (CH1Cκ crossing) while for the clones from the common light chain library no crossing was necessary. These bispecific molecules were produced and purified analogously to the IgGs.

TABLE 6

Yield and monomer content of novel FolR1 binders in IgG and TCB format, respectively.

| | | | IgG | | TCB | |
|---|---|---|---|---|---|---|
| # | Clone | Library | Yield [mg/L] | Monomer [%] | Yield [mg/L} | Monomer [%] |
| 1 | 11F8 | Fab | 8.03 | 96.26 | — | — |
| 2 | 14E4 | Fab | 8.90 | 98.12 | — | — |
| 3 | 15B6 | CLC | 7.72 | 100.00 | — | — |
| 4 | 15E12 | CLC | 6.19 | 100.00 | — | — |
| 5 | 15H7 | CLC | 8.94 | 100.00 | — | — |
| 6 | 16A3 | CLC | 0.60 | n.d. | — | — |
| 7 | 16D5 | CLC | 36.50 | 96.96 | 4.36 | 97.19 |
| 8 | 16F12 | CLC | 5.73 | 97.17 | — | — |
| 9 | 18D3 | CLC | 0.90 | n.d. | — | — |

TABLE 6-continued

Yield and monomer content of novel FolR1 binders in IgG and TCB format, respectively.

| | | | IgG | | TCB | |
|---|---|---|---|---|---|---|
| # | Clone | Library | Yield [mg/L] | Monomer [%] | Yield [mg/L] | Monomer [%] |
| 10 | 19A4 | CLC | 38.32 | 100.00 | 37.50 | 100.00 |
| 11 | 19E5 | CLC | 46.09 | 100.00 | — | — |
| 12 | 19H3 | CLC | 7.64 | 100.00 | — | — |
| 13 | 20G6 | CLC | 24.00 | 100.00 | — | — |
| 14 | 20H7 | CLC | 45.39 | 100.00 | — | — |
| 15 | 21A5 | CLC | 1.38 | 98.56 | 47.31 | 95.08 |
| 16 | 21D1 | CLC | 5.47 | 100.00 | — | — |
| 17 | 21G8 | CLC | 6.14 | 97.28 | 9.27 | 100.00 |
| 18 | 36F2 | Fab | 11.22 | 100.00 | 18.00 | 100.00 |
| 19 | 5D9 | Fab | 20.50 | 100.00 | 0.93 | 97.32 |
| 20 | 6B6 | Fab | 3.83 | 100.00 | 4.17 | 91.53 |
| 21 | 9D11 | Fab | 14.61 | 100.00 | 2.63 | 100.00 |

CLC: Common light chain

Example 9

2+1 and 1+1 T-Cell Bispecific Formats

Four different T-cell bispecific formats were prepared for one common light chain binder (16D5) and three formats for one binder from the Fab library (9D11) to compare their killing properties in vitro.

The standard format is the 2+1 inverted format as already described (FolR1:CD3 binding moieties arranged in a 2:1 order with the FolR1 Fabs located at the N-terminus). In the 2+1 classical format the FolR1:CD3 binding moieties are arranged in a 2:1 order with the CD3 Fab being located at the N-terminus. Two monovalent formats were also prepared. The 1+1 head-to-tail has the FolR1:CD3 binding moieties arranged in a 1:1 order on the same arm of the molecule with the FolR1 Fab located at the N-terminus. In the 1+1 classical format the FolR1:CD3 binding moieties are present once, each on one arm of the molecule. For the 9D11 clone isolated from the standard Fab library the CD3 binding part was generated as a CrossFab (CH1Cκ crossing) while for the 16D5 from the common light chain library no crossing was necessary. These bispecific molecules were produced and purified analogously to the standard inverted T-cell bispecific format.

TABLE 7

Summary of the yield and final monomer content of the different T-cell bispecific formats.

| Construct | Monomer [%] (SEC) | Yield |
|---|---|---|
| 16D5 FolR1 TCB 2 + 1 (inverted) | 96% | 5.4 mg/L |
| 16D5 FolR1 TCB 2 + 1 (classical) | 90% | 4.6 mg/L |
| 16D5 FolR1 TCB 1 + 1 (head-to-tail) | 100 % | 5.4 mg/L |
| 16D5 FolR1 TCB 1 + 1 (classical) | 100% | 0.7 mg/L |
| 9D11 FolR1 TCB 2 + 1 (inverted) | 100% | 2.6 mg/L |
| 9D11 FolR1 TCB 1 + 1 (head-to-tail) | 100% | 6.1 mg/L |
| 9D11 FolR1 TCB 1 + 1 (classical) | 96% | 1.3 mg/L |
| Mov19 FolR1 TCB 2 + 1 (inverted) | 98% | 3 mg/L |
| Mov19 FolR1 TCB 1 + 1 (head-to-tail) | 100% | 5.2 mg/L |

Example 10

Biochemical Characterization of FolR1 Binders by Surface Plasmon Resonance

Binding of FolR1 binders as IgG or in the T-cell bispecific format to different recombinant folate receptors (human FolR1, 2 and 3, murine FolR1 and cynomolgus FolR1; all as Fc fusions) was assessed by surface plasmon resonance (SPR). All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany).

Single Injections

First the anti-FolR1 IgGs were analyzed by single injections (Table 1) to characterize their crossreactivity (to human, murine and cyno FolR1) and specificity (to human FolR1, human FolR2, human FolR3). Recombinant biotinylated monomeric Fc fusions of human, cynomolgus and murine Folate Receptor 1 (FolR1-Fc) or human Folate Receptor 2 and 3 (FolR2-Fc, FolR3-Fc) were directly coupled on a SA chip using the standard coupling instruction (Biacore, Freiburg/Germany). The immobilization level was about 300-400 RU. The IgGs were injected for 60 seconds at a concentration of 500 nM. IgGs binding to huFolR2 and huFolR3 were rejected for lack of specificity. Most of the binders are only crossreactive between human and cyno FolR1, additional crossreactivity to murine FolR1 went most of the time hand in hand with loss of specificity.

TABLE 8

Crossreactivity and specificity of 25 new folate receptor 1 binders (as IgGs) as well as of two control IgGs (Mov19 and Farletuzumab). + means binding, – means no binding, +/– means weak binding.

| Clone name | Binding to huFolR1 | Binding to cyFolR1 | Binding to muFolR1 | Binding to huFolR2 | Binding to huFolR3 |
|---|---|---|---|---|---|
| Mov19 | + | + | – | – | – |
| Farletuzumab | + | + | – | – | – |
| 16A3 | + | + | +/– | – | – |
| 18D3 | + | + | – | – | – |
| 19E5 | + | + | + | + | + |
| 19A4 | – | – | + | + | + |
| 15H7 | + | + | + | – | – |
| 15B6 | + | + | – | – | – |
| 16D5 | + | + | – | – | – |
| 15E12 | + | + | +/– | + | + |
| 21D1 | + | + | +/– | – | – |
| 16F12 | + | + | – | – | – |
| 21A5 | + | + | – | – | +/– |
| 21G8 | + | + | – | + | + |
| 19H3 | – | – | + | – | – |
| 20G6 | – | – | + | – | – |
| 20H7 | – | – | + | – | – |
| 9D11 | + | + | – | – | – |
| 5D9 | + | + | – | + | + |
| 6B6 | + | + | – | + | + |
| 11F8 | + | + | + | + | + |
| 36F2 | + | + | + | – | – |
| 14E4 | – | – | + | – | – |

Avidity to Folate Receptor 1

The avidity of the interaction between the anti-FolR1 IgGs or T cell bispecifics and the recombinant folate receptors was determined as described below (Table 9).

Recombinant biotinylated monomeric Fc fusions of human, cynomolgus and murine Folate Receptor 1 (FolR1-Fc) were directly coupled on a SA chip using the standard coupling instruction (Biacore, Freiburg/Germany). The immobilization level was about 300-400 RU. The anti- FolR1 IgGs or T cell bispecifics were passed at a concentration range from 2.1 to 500 nM with a flow of 30 μL/minutes through the flow cells over 180 seconds. The dissociation was monitored for 600 seconds. Bulk refractive index differences were corrected for by subtracting the response obtained on reference flow cell immobilized with recombinant biotinylated IL2 receptor Fc fusion. For the analysis of the interaction of 19H3 IgG and murine folate receptor 1, folate (Sigma F7876) was added in the HBS-EP running buffer at a concentration of 2.3 μM. The binding curves resulting from the bivalent binding of the IgGs or T cell bispecifics were approximated to a 1:1 Langmuir binding and fitted with that model (which is not correct, but gives an idea of the avidity). The apparent avidity constants for the interactions were derived from the rate constants of the fitting using the Bia Evaluation software (GE Healthcare).

TABLE 9

Bivalent binding (avidity with apparent KD) of selected FolR1 binders as IgGs or as T-cell bispecifics (TCB) on human and cyno FolR1.

| Analyte | Ligand | ka (1/Ms) | kd (Vs) | Apparent KD (M) |
|---|---|---|---|---|
| 16D5 TCB | huFolR1 | 8.31E+04 | 3.53E−04 | 4.24E−09 |
| | cyFolR1 | 1.07E+05 | 3.70E−04 | 3.45E−09 |
| 9D11 TCB | huFolR1 | 1.83E+05 | 9.83E−05 | 5.36E−10 |
| | cyFolR1 | 2.90E+05 | 6.80E−05 | 2.35E−10 |
| 21A5 TCB | huFolR1 | 2.43E+05 | 2.64E−04 | 1.09E−09 |
| | cyFolR1 | 2.96E+05 | 2.76E−04 | 9.32E−10 |
| 36F2 IgG | huFolR1 | 2.62E+06 | 1.51E−02 | 5.74E−9 |
| | cyFolR1 | 3.02E+06 | 1.60E−02 | 5.31E−9 |
| | muFolR1 | 3.7E+05 | 6.03E−04 | 1.63E−9 |
| Mov19 IgG | huFolR1 | 8.61E+05 | 1.21E−04 | 1.4E−10 |
| | cyFolR1 | 1.29E+06 | 1.39E−04 | 1.08E−10 |
| Farletuzumab | huFolR1 | 1.23E+06 | 9E−04 | 7.3E−10 |
| | cyFolR1 | 1.33E+06 | 8.68E−04 | 6.5E−10 |
| 19H3 IgG | muFolR1 | 7.1E+05 | 1.1E−03 | 1.55E−09 |

1. Affinity to Folate Receptor 1

The affinity of the interaction between the anti-FolR1 IgGs or the T cell bispecifics and the recombinant folate receptors was determined as described below (Table 10).

For affinity measurement, direct coupling of around 6000-7000 resonance units (RU) of the anti-human Fab specific antibody (Fab capture kit, GE Healthcare) was performed on a CM5 chip at pH5.0 using the standard amine coupling kit (GE Healthcare). Anti-FolR1 IgGs or T cell bispecifics were captured at 20 nM with a flow rate of 10 μl/min for 20 or 40 sec, the reference flow cell was left without capture. Dilution series (6.17 to 500 nM or 12.35 to 3000 nM) of human or cyno Folate Receptor 1Fc fusion were passed on all flow cells at 30 μl/min for 120 or 240 sec to record the association phase. The dissociation phase was monitored for 240 sand triggered by switching from the sample solution to HBS-EP. The chip surface was regenerated after every cycle using a double injection of 60 sec 10 mM Glycine-HCl pH 2.1 or pH1.5. Bulk refractive index differences were corrected for by subtracting the response obtained on the reference flow cell 1. The affinity constants for the interactions were derived from the rate constants by fitting to a 1:1 Langmuir binding using the Bia Evaluation software (GE Healthcare).

TABLE 10

Monovalent binding (affinity) of selected FolR1 binders as IgGs or as T-cell bispecifics (TCB) on human and cyno FolR1.

| Ligand | Analyte | ka (1/Ms) | kd (1/s) | KD (M) |
|---|---|---|---|---|
| 16D5 TCB | huFolR1 | 1.53E+04 | 6.88E−04 | 4.49E−08 |
| | cyFolR1 | 1.32E+04 | 1.59E−03 | 1.21E−07 |

TABLE 10-continued

Monovalent binding (affinity) of selected FolR1 binders as IgGs or as T-cell bispecifics (TCB) on human and cyno FolR1.

| Ligand | Analyte | ka (1/Ms) | kd (1/s) | KD (M) |
|---|---|---|---|---|
| 9D11 TCB | huFolR1 | 3.69E+04 | 3.00E−04 | 8.13E−09 |
| | cyFolR1 | 3.54E+04 | 2.06E−04 | 5.82E−09 |
| 21A5 TCB | huFolR1 | 1.79E+04 | 1.1E−03 | 6.16E−08 |
| | cyFolR1 | 1.48E+04 | 2.06E−03 | 1.4E−07 |
| Mov19 IgG | huFolR1 | 2.89E+05 | 1.59E−04 | 5.5E−10 |
| | cyFolR1 | 2.97E+05 | 1.93E−04 | 6.5E−10 |
| Farletuzumab | huFolR1 | 4.17E+05 | 2.30E−02 | 5.53E−08 |
| | cyFolR1 | 5.53E+05 | 3.73E−02 | 6.73E−08 |

2. Affinity to CD3

The affinity of the interaction between the anti-FolR1 T cell bispecifics and the recombinant human CD3εδ-Fc was determined as described below (Table 11).

For affinity measurement, direct coupling of around 9000 resonance units (RU) of the anti-human Fab specific antibody (Fab capture kit, GE Healthcare) was performed on a CM5 chip at pH 5.0 using the standard amine coupling kit (GE Healthcare). Anti-FolR1 T cell bispecifics were captured at 20 nM with a flow rate of 10 μl/min for 40 sec, the reference flow cell was left without capture. Dilution series (6.17 to 500 nM) of human CD3εδ-Fc fusion were passed on all flow cells at 30 μl/min for 240 sec to record the association phase. The dissociation phase was monitored for 240 s and triggered by switching from the sample solution to HBS-EP. The chip surface was regenerated after every cycle using a double injection of 60 sec 10 mM Glycine-HCl pH 2.1. Bulk refractive index differences were corrected for by subtracting the response obtained on the reference flow cell 1. The affinity constants for the interactions were derived from the rate constants by fitting to a 1:1 Langmuir binding using the Bia Evaluation software (GE Healthcare).

TABLE 11

Monovalent binding (affinity) of selected FolR1 T-cell bispecifics (TCB) on human CD3-Fc.

| Ligand | Analyte | ka (1/Ms) | kd (1/s) | KD (M) |
|---|---|---|---|---|
| 16D5 TCB | huCD3 | 4.25E+04 | 3.46E−03 | 8.14E−08 |
| 21A5 TCB | huCD3 | 3.72E+04 | 3.29E−03 | 8.8E−08 |

The CD3 binding part is identical for all constructs and the affinity is similar for the measured T cell bispecifics ($K_D$ range between 60 and 90 nM).

Example 11

Simultaneous Binding T Cell Bispecifics on Folate Receptor 1 and CD3

Simultaneous binding of the anti-FolR1 T cell bispecifics on recombinant Folate Receptor 1 and recombinant human CD3εδ-Fc was determined as described below.

Recombinant biotinylated monomeric Fc fusions of human, cynomolgus and murine Folate Receptor 1 (FolR1-Fc) were directly coupled on a SA chip using the standard coupling instruction (Biacore, Freiburg/Germany). The immobilization level was about 300-400 RU. The anti-FolR1 T cell bispecifics were injected for 60 s at 500 nM with a flow of 30 μl/minutes through the flow cells, followed by an injection of hu CDεδ-Fc for 60 s at 500 nM. Bulk refractive index differences were corrected for by subtracting the response obtained on reference flow cell immobilized with recombinant biotinylated IL2 receptor Fc fusion. The four T cell bispecifics tested (16D5 TCB, 21A5 TCB, 51C7 TCB and 45D2 TCB) were able to bind simultaneously to Folate Receptor 1 and human CD3 as expected.

Example 12

Epitope Binning

For epitope binning, the anti-FolR1 IgGs or T cell bispecifics were directly immobilized on a CM5 chip at pH 5.0 using the standard amine coupling kit (GE Healthcare), with a final response around 700 RU. 500 nM huFolR1-Fc was then captured for 60 s, followed by 500 nM of the different binders for 30 s. The surface was regenerated with two injections of 10 mM glycine pH 2 for 30 s each. It is assessed if the different binders can bind to huFolR1 captured on immobilized binders (Table 12).

TABLE 12

Epitope characterization of selected FolR1 binders as IgGs or as T-cell bispecifics (TCB) on human FolR1. +means binding, −means no binding, +/−means weak binding

| | | Analytes in solution | | | | | |
|---|---|---|---|---|---|---|---|
| | On huFolR1 | 16D5 TCB | 21A5 TCB | 9D11 TCB | 36F2 IgG | Mov19 IgG | Farletuzumab |
| Immobilized | 16D5 TCB | − | − | − | + | + | + |
| | 21A5 TCB | − | − | − | + | + | + |
| | 9D11 TCB | No additional binding on FolR1 possible once captured on 9D11 | | | | | |
| | 36F2 IgG | Measure not possible, huFolR1 dissociates too rapidly | | | | | |
| | Mov19 IgG | + | + | +/− | − | − | − |

Based on these results and additional data with simultaneous binding on immobilized huFolR1, the binders were separated in three groups. It is not clear if 9D11 has a separate epitope because it displaces all the other binders. 16D5 and 21A5 seem to be in the same group and Mov9, Farletuzumab (Coney et al., Cancer Res. 1991 Nov. 15; 51(22):6125-32; Kalli et al., Curr Opin Investig Drugs. 2007 December; 8(12):1067-73) and 36F2 in another (Table 13). However, 36F2 binds to a different epitope than Mov 19 and Farletuzumab as it binds to human, cynomous and murine FolR1.

TABLE 13

Epitope grouping of selected FolR1 binders as IgGs or as T-cell bispecifics (TCB) on human FolR1

| Epitope 1 | Epitope 2 | Epitope 3 |
|---|---|---|
| 16D5 | 9D11 | Mov19 |
| 21A5 | | Farletuzumab |
| | | 36F2 |

Example 13

Selection of Binders

FolR1 binders in the IgG formats were screened by surface plasmon resonance (SPR) and by in vitro assay on cells to select the best candidates.

The anti-FolR1 IgGs were analyzed by SPR to characterize their crossreactivity (to human, murine and cynomolgus FolR1) and specificity (to human FolR1, human FolR2, human FolR3). Unspecific binding to human FolR2 and 3 was considered an exclusion factor. Binding and specificity to human FolR1 was confirmed on cells. Some binders did not bind on cells expressing FolR1 even though they recognized the recombinant human FolR1 in SPR. Aggregation temperature was determined but was not an exclusion factor because the selected binders were all stable. Selected binders were tested in a polyreactivity ELISA to check for unspecific binding, which led to the exclusion of four binders. This process resulted in an initial selection of three binders: 36F2 (Fab library), 9D11 (Fab library) and 16D5 (common light chain). 36F2 dissociated rapidly from huFolR1 and was, therefore, initially not favored.

Example 14

Figure 5:
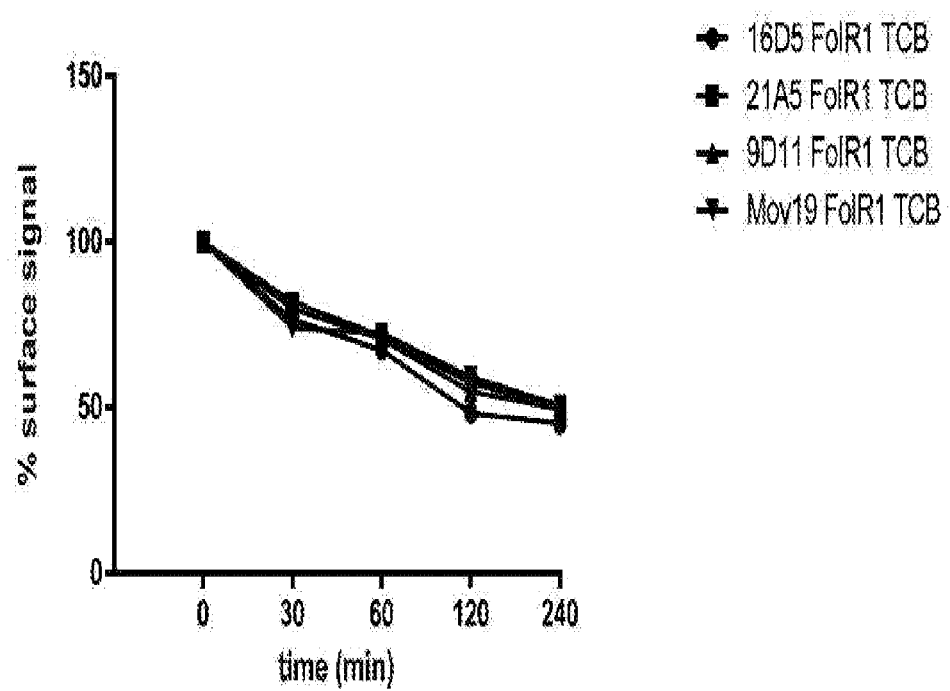
FIG. 5 depicts a graph illustrating internalization of FolR1 TCBs after binding. Internalization of the four FolR1 TCBs after binding to FolR1 was tested on HeLa cells. Remaining FolR1 TCBs on the surface were detected with a fluorescently labeled anti-human secondary antibody after indicated time points of incubation at 37° C. Percentage of internalization was calculated.
Figure 6A:
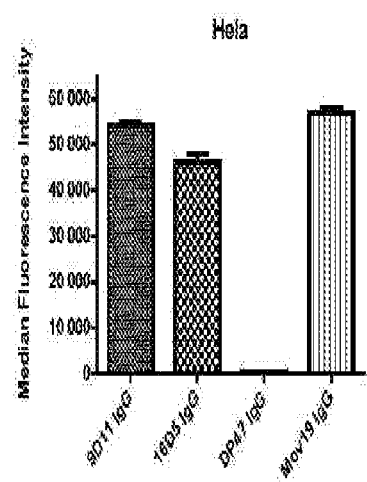
FIGS. 6A-E depict graphs summarizing binding of FolR1 IgGs to cells with different FolR1 expression levels. Binding of 9D11, 16D5 and Mov19 IgG to tumor cells with different FolR1 expression levels was analyzed by flow cytometry. DP47 IgG was included as isotype control and MKN-45 were included as FolR1 negative cell line. The antibodies were detected with a fluorescently labeled anti-human secondary antibody.
Figure 6B:
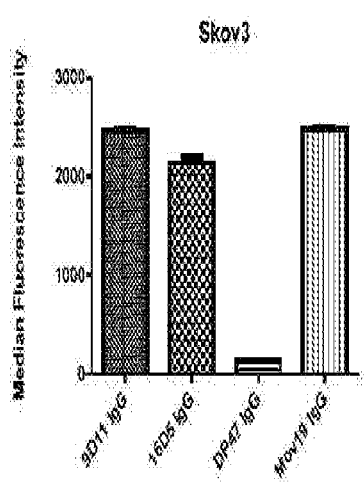
Figure 6C:
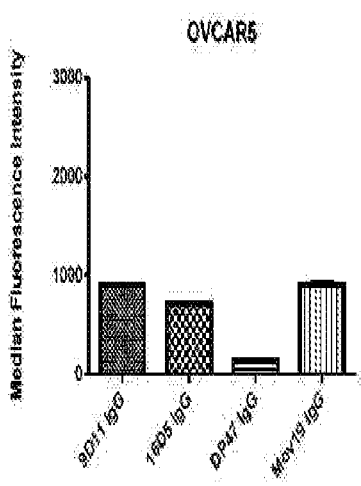
Figure 6D:
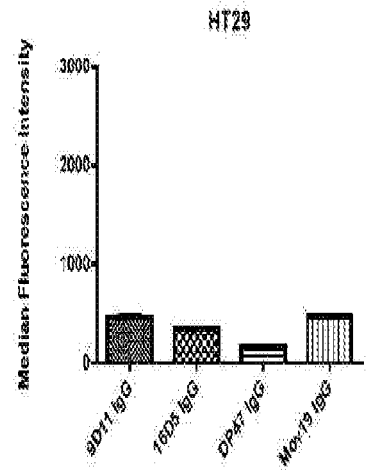
Figure 6E:
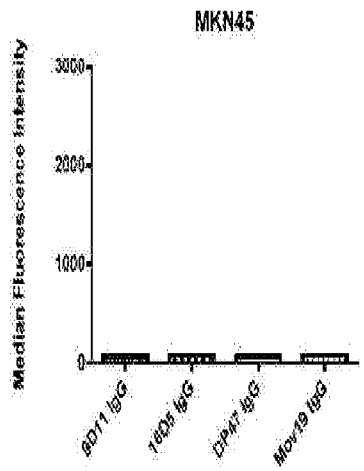
Figure 7A:
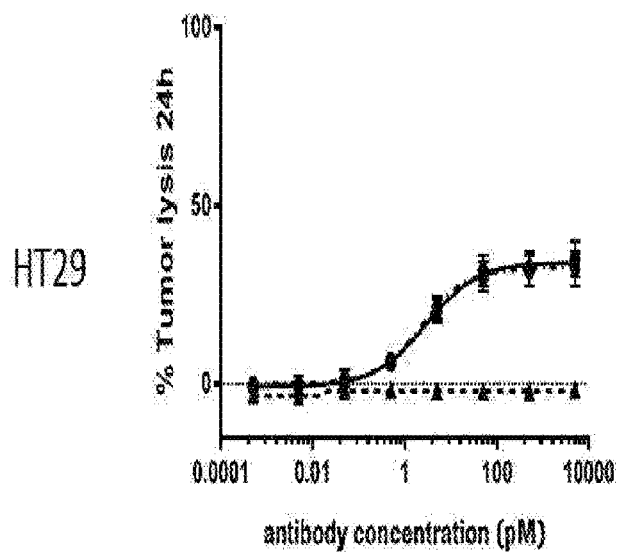
Figure 7B:
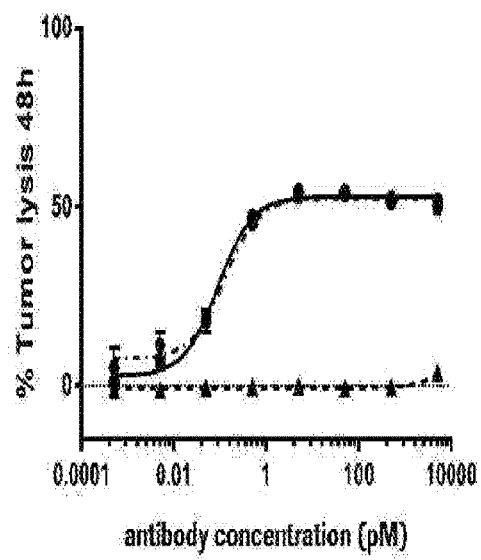
Figure 7C:
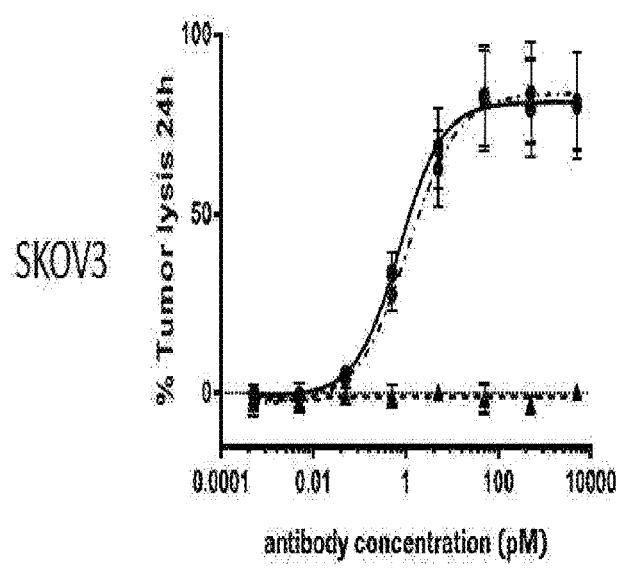
Figure 7D:
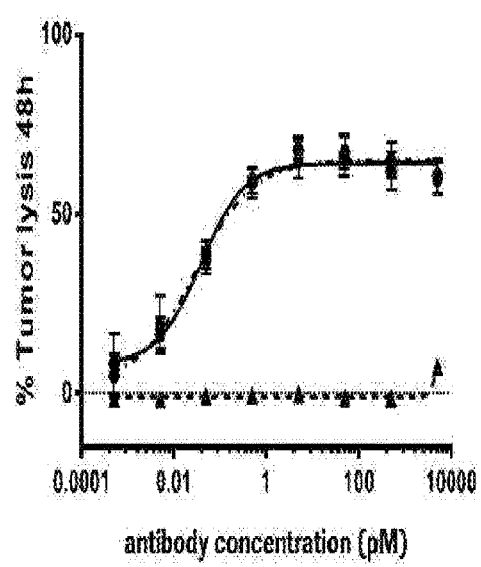
Figure 7E:
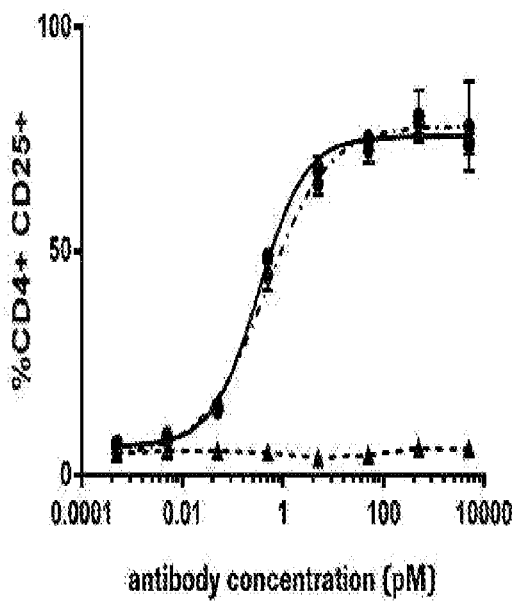
Figure 7F:
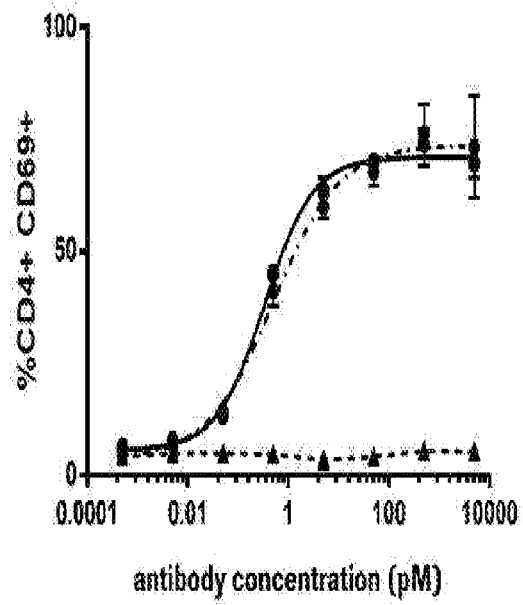
Figure 7G:
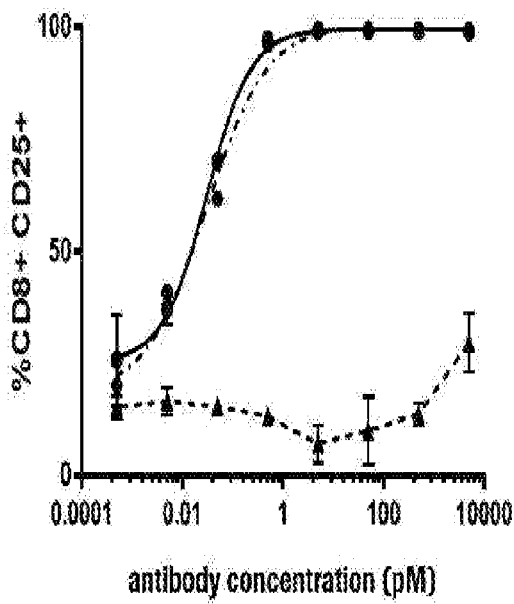
Figure 7H:
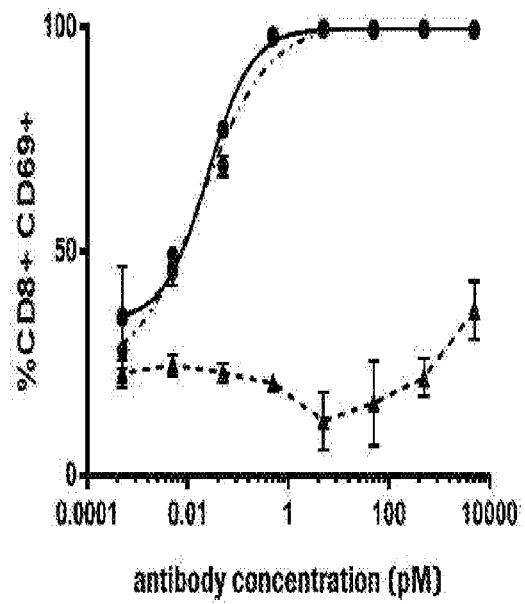

Specific Binding of Newly Generated FolR1 Binders to Human FolR1 Positive Tumor Cells New FolR1 binders were generated via Phage Display using either a Fab library or a common light chain library using the CD3 light chain. The identified binders were converted into a human IgG1 format and binding to FolR1 high expressing HeLa cells was addressed. As reference molecule the human FolR1 binder Mov19 was included. Most of the binders tested in this assay showed intermediate to good binding to FolR1 with some clones binding equally well as Mov19 (see FIG. 2). The clones 16A3, 18D3, 15H7, 15B6, 21D1, 14E4 and 16F12 were excluded because binding to FolR1 on cells could not be confirmed by flow cytometry. In a next step the selected clones were tested for specificity to human FolR1 by excluding binding to the closely related human FolR2. HEK cells were transiently transfected with either human FolR1 or human FolR2 to address specificity. The clones 36F2 and 9D11 derived from the Fab library and the clones 16D5 and 21A5 derived from the CLC library bind specifically to human FolR1 and not to human FolR2 (see FIGS. 3A-B). All the other tested clones showed at least some binding to human FolR2 (see FIGS. 3A-B). Therefore these clones were excluded from further characterization. In parallel cross-reactivity of the FolR1 clones to cyno FolR1 was addressed by performing binding studies to HEK cells transiently transfected with cyno FolR1. All tested clones were able to bind cyno FolR1 and the four selected human FoLR1 specific clones 36F2, 9D11, 16D5 and 21A5 bind comparably well human and cyno FoLR1 (FIG. 4). Subsequently three human FoLR1 specific cyno cross-reactive binders were converted into TCB format and tested for induction of T cell killing and T cell activation. These clones were 9D11 from the Fab library and 16D5 and 21A5 from the CLC library. As reference molecule Mov19 FolR1 TCB was included in all studies. These FolR1 TCBs were then used to compare induction of internalization after binding to FolR1 on HeLa cells. All three tested clones are internalized upon binding to FolR1 comparable to internalization upon binding of Mov19 FoLR1 TCB (FIG. 5). 21A5 FolR1 TCB was discontinued due to signs of polyreactivity.

The intermediate expressing cell line SKOV3 and the low expressing cell line HT-29 were further on used to test T cell mediated killing and T cell activation using 16D5 TCB and 9D11 TCB; DP47 TCB was included as negative control. Both cell lines were killed in the presence of already very low levels of 16D5 TCB and 9D11 TCB and there was no difference in activity between both TCBs even though 9D11 TCB binds stronger to FolR1 than 16D5 TCB. Overall killing of SKOV3 cells was higher compared to HT-29 which reflects the higher expression levels of FolR1 on SKOV3 cells (FIGS. 7A-D). In line with this, a strong upregulation of the activation marker CD25 and CD69 on CD4$^+$ T cells and CD8$^+$ T cells was detected. Activation of T cells was very similar in the presence of SKOV3 cells and HT-29 cells. The negative control DP47 TCB does not induce any killing at the used concentrations and there was no significant upregulation of CD25 and CD69 on T cells.

TABLE 15

| | EC50 values of tumor cell killing and T cell activation with SKOV3 cells | | | | | |
|---|---|---|---|---|---|---|
| Construct | Killing 24 h (pM) | Killing 48 h (pM) | CD4 + CD69 + (%) | CD4 + CD25 + (%) | CD8 + CD69 + (%) | CD8 + CD25 + (%) |
| 9D11 FolR1 TCB | 1.1 | 0.03 | 0.51 | 0.46 | 0.019 | 0.03 |
| 16D5 FolR1 TCB | 0.7 | 0.04 | 0.34 | 0.33 | 0.025 | 0.031 |

Example 15

T Cell-Mediated Killing of FolR1-Expressing Tumor Target Cells Induced by FolR1 TCB Antibodies The FolR1 TCBs were used to determine T cell mediated killing of tumor cells expressing FoLR1. A panel of potential target cell lines was used to determine FoLR1 binding sites by Qifikit analysis.

The used panel of tumor cells contains FolR1 high, intermediate and low expressing tumor cells and a FolR1 negative cell line.

TABLE 14

| FolR1 binding sites on tumor cells | | |
|---|---|---|
| Cell line | Origin | FolR1 binding sites |
| Hela | Cervix adenocarcinoma | 2'240'716 |
| Skov3 | Ovarian adenocarcinoma | 91'510 |
| OVCAR5 | Ovarian adenocarcinoma | 22'077 |
| HT29 | Colorectal adenocarcinoma | 10'135 |
| MKN45 | Gastric adenocarcinoma | 54 |

Binding of the three different FoLR1 TCBs (containing 9D11, 16D5 and Mov19 binders) to this panel of tumor cell lines was determined showing that the FoLR1 TCBs bind specifically to FolR1 expressing tumor cells and not to a FoLR1 negative tumor cell line. The amount of bound construct is proportional to the FoLR1 expression level and there is still good binding of the constructs to the FolR1 low cell line HT-29 detectable. In addition there is no binding of the negative control DP47 TCB to any of the used cell lines (FIGS. 6A-E). DP47 TCB is an untargeted TCB and was prepared as described in WO2014/131712.

TABLE 16

| | EC50 values of tumor cell killing and T cell activation with HT-29 cells | | | | | |
|---|---|---|---|---|---|---|
| Construct | Killing 24 h (pM) | Killing 48 h (pM) | CD4 + CD69 + (%) | CD4 + CD25 + (%) | CD8 + CD69 + (%) | CD8 + CD25 + (%) |
| 9D11 FolR1 TCB | 2.3 | 0.1 | 1.22 | 1.11 | 0.071 | 0.084 |
| 16D5 FolR1 TCB | 2.8 | 0.1 | 0.69 | 0.62 | 0.021 | 0.028 |

Example 16

Figure 8:
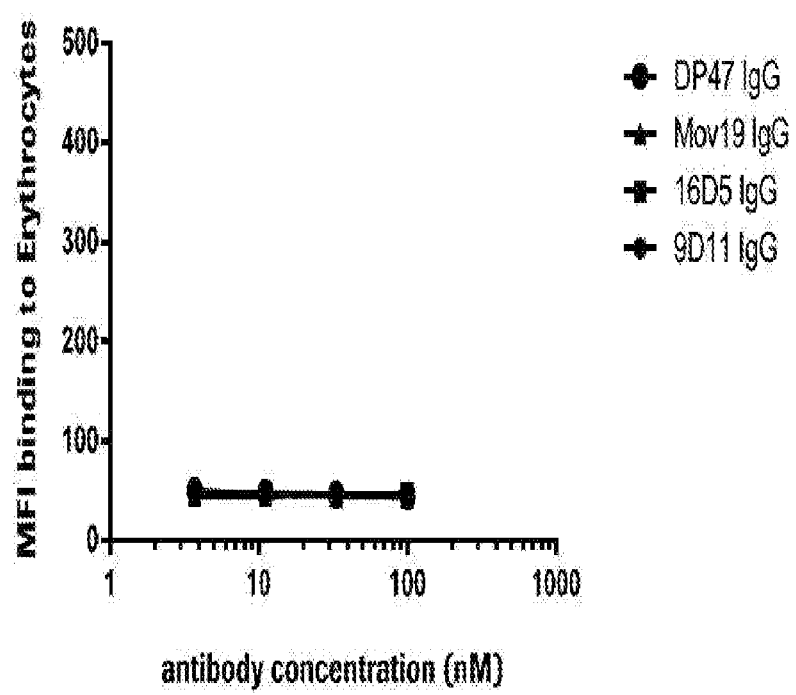
FIG. 8 depicts a graph showing absence of anti-FolR1 binding to erythrocytes. Erythrocytes were gated as CD235a positive population and binding of 9D11 IgG, 16D5 IgG, Mov19 IgG and DP47 IgG to this population was determined by flow cytometry. The antibodies were detected with a fluorescently labeled anti-human secondary antibody.
Figure 9A:
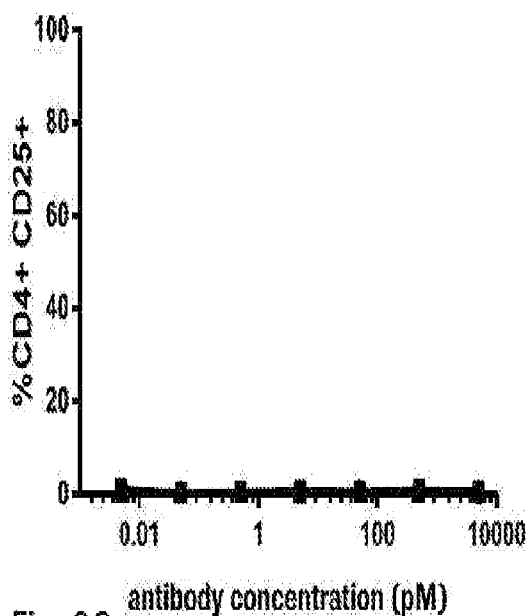
FIGS. 9A-D depict graphs summarizing activation marker upregulation in whole blood. CD25 and CD69 activation marker upregulation of CD4 T cells and CD8 T cells 24 h after addition of 9D11 FolR1 TCB, 16D5 FolR1 TCB, Mov19 FolR1 TCB and DP47 TCB was analyzed by flow cytometry.
Figure 9B:
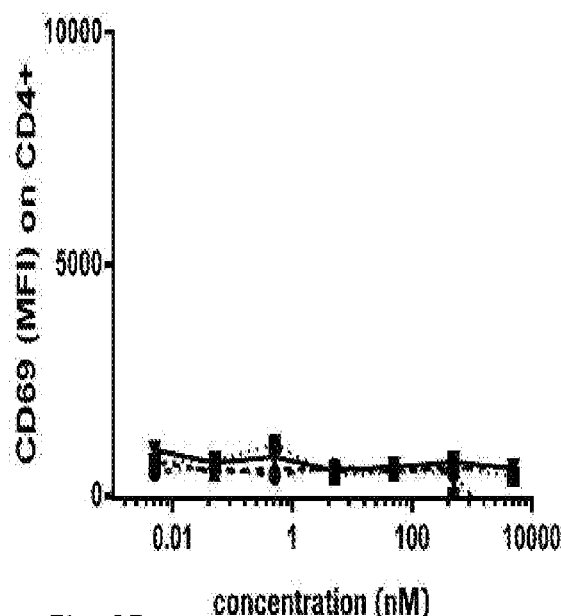
Figure 9C:
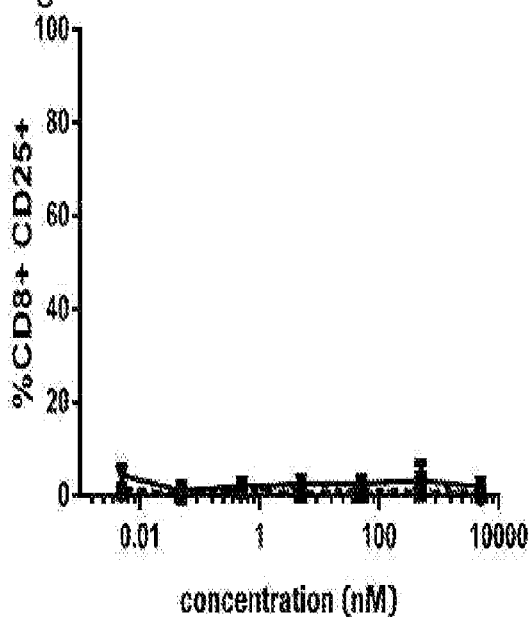
Figure 9D:
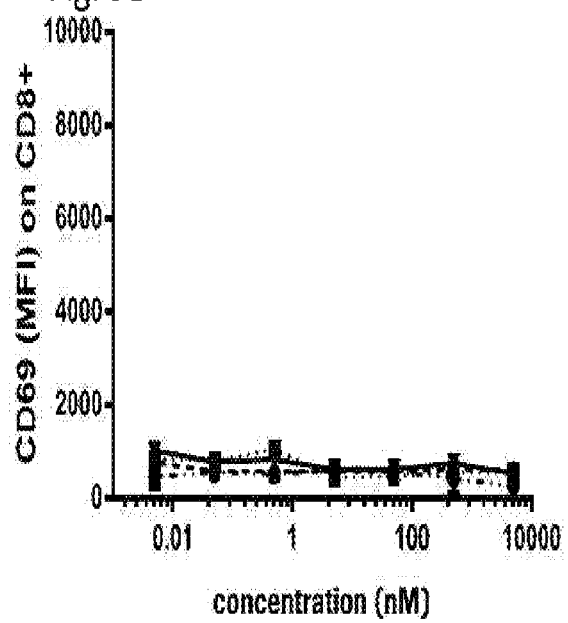

Binding of FolR1 TCB Antibodies to Erythrocytes and T Cell Activation in Whole Blood To prove that there is no spontaneous activation in the absence of FoLR1 expressing tumor cells we tested if there is binding of the FolR1 clones to erythrocytes which might potentially express FolR1. We could not observe any specific binding of 9D11 IgG, 16D5 IgG and Mov19 IgG to erythrocytes, as negative control DP47 IgG was included (FIG. 8).

To exclude any further unspecific binding to blood cells or unspecific activation via FoLR1 TCB, 9D11 TCB, 16D5 TCB and Mov19 TCB were added into whole blood and upregulation of CD25 and CD69 on CD4$^+$ T cells and CD8$^+$ T cells was analyzed by flow cytometry. DP47 TCB was included as negative control. No activation of T cells with any of the tested constructs could be observed by analyzing upregulation of CD25 and CD69 on CD4$^+$ T cells and CD8$^+$ T cells (FIG. 9).

Example 17

Figure 10A:
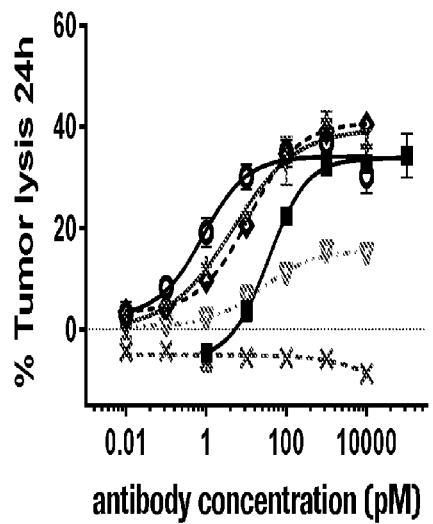
FIGS. 10A-C depict T-cell killing induced by 36F2 TCB, 16D5 TCB, 16D5 TCB classical, 16D5 TCB 1+1 and 16D5 TCB HT of Hela (high FolR1) (FIG. 24A), Skov-3 (medium FolR1) (FIG. 24B) and HT-29 (low FolR1) (FIG. 24C) human tumor cells (E:T=10:1, effectors human PBMCs, incubation time 24 h). DP47 TCB was included as non-binding control.
Figure 10B:
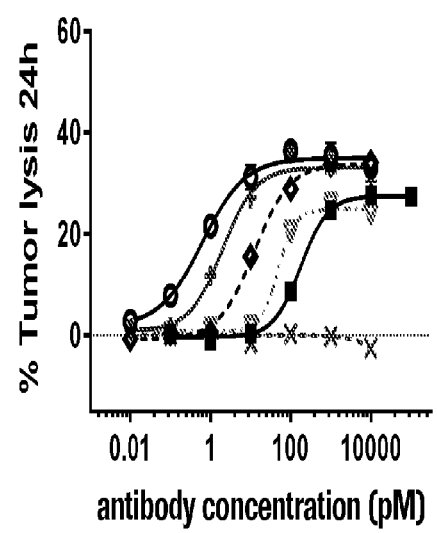
Figure 10C:
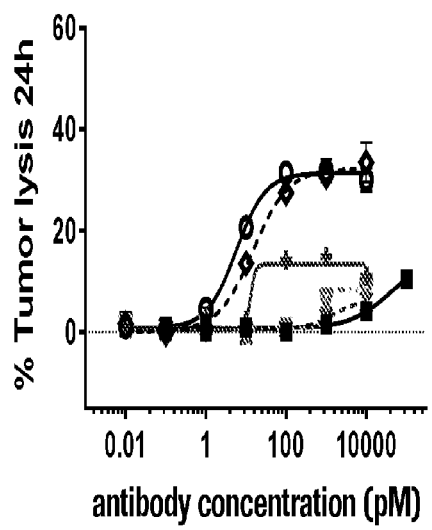

T-Cell Killing Induced by 36F2 TCB and 16D5 TCB in Different Monovalent and Bivalent T-Cell Bispecific Formats T-cell killing mediated by 36F2 TCB, 16D5 TCB, 16D5 TCB classical, 16D5 TCB 1+1 and 16D5 TCB HT antibodies of Hela, Skov-3 (medium FolR1, about 70000-90000 copies) and HT-29 (low FolR1, about 10000) human tumor cells was assessed. DP47 TCB antibody was included as negative control. Human PBMCs were used as effectors and the killing was detected at 24 h of incubation with the bispecific antibody. Briefly, target cells were harvested with Trypsin/EDTA, washed, and plated at density of 25 000 cells/well using flat-bottom 96-well plates. Cells were left to adhere overnight. Peripheral blood mononuclear cells (PBMCs) were prepared by Histopaque density centrifugation of enriched lymphocyte preparations (buffy coats) obtained from healthy human donors. Fresh blood was diluted with sterile PBS and layered over Histopaque gradient (Sigma, #H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (ViCell) and stored in RPMI1640 medium containing 10% FCS and 1% L-alanyl-L-glutamine (Biochrom, K0302) at 37° C., 5% CO2 in cell incubator until further use (no longer than 24 h). For the killing assay, the antibody was added at the indicated concentrations (range of 0.01 μM-100 nM in triplicates). PBMCs were added to target cells at final E:T ratio of 10:1. Target cell killing was assessed after 24 h of incubation at 37° C., 5% CO2 by quantification of LDH released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific construct. The results show target-specific killing of all three FolR1+ target cell lines induced by 36F2 TCB and 16D5 TCB (FIG. 10).

Example 18

Generation of Anti-TIM3 Antibodies

Immunization of mice NMRI mice were immunized genetically, using a plasmid expression vector coding for full-length human Tim-3 by intradermal application of 100 ug vector DNA (plasmid 15304_hTIM3-fl), followed by Electroporation (2 square pulses of 1000 V/cm, duration 0.1 ms, interval 0.125 s; followed by 4 square pulses of 287.5 V/cm, duration 10 ms, interval 0.125 s. Mice received either 6 consecutive immunizations at days 0, 14, 28, 42, 56, 70, and 84. Blood was taken at days 36, 78 and 92 and serum prepared, which was used for titer determination by ELISA (see below). Animals with highest titers were selected for boosting at day 96, by intravenous injection of 50 ug of recombinant human Tim-3 human Fc chimera, and monoclonal antibodies were isolated by hybridoma technology, by fusion of splenocytes to myeloma cell line 3 days after boost.

Determination of serum titers (ELISA) Human recombinant Tim-3 human Fc chimera was immobilized on a 96-well NUNC Maxisorp plate at 0.3 ug/ml, 100 ul/well, in PBS, followed by: blocking of the plate with 2% Crotein C in PBS, 200 ul/well; application of serial dilutions of antisera, in duplicates, in 0.5% Crotein C in PBS, 100 ul/well; detection with HRP-conjugated goat anti-mouse antibody (Jackson Immunoresearch/Dianova 115-036-071; 1/16 000). For all steps, plates were incubated for 1 h at 37° C. Between all steps, plates were washed 3 times with 0.05% Tween 20 in PBS. Signal was developed by addition of BM Blue POD Substrate soluble (Roche), 100 ul/well; and stopped by addition of 1 M HCl, 100 ul/well. Absorbance was read out at 450 nm, against 690 nm as reference. Titer was defined as dilution of antisera resulting in half-maximal signal.

Example 19

Characterization Anti-Tim3 Antibodies

ELISA for Tim3 Nunc-Maxi Sorp Streptavidine plates (MicroCoat #11974998/MC1099) were coated by 25 μl/well with Tim3-ECD-His-Biotin (biotinylated with BirA Ligase) and incubated at RT for 1 h while shaking at 400 rpm rotation. After washing (3×90 μl/well with PBST-buffer) 25 μl aTim3 samples or diluted (1:2 steps) reference antibody aTim3 F38-2E2 (Biolegend) was added and incubated 1 h at RT. After washing (3×90 μl/well with PBST-buffer) 25 μl/well sheep-anti-mouse-POD (GE NA9310V) was added in 1:9000 dilution and incubated at RT for 1 h while shaking at 400 rpm rotation. After washing (4×90 μl/well with PBST-buffer) 25 μl/well TMB substrate (Calbiochem, #CL07) was added and incubated until OD 1.5-2.5. Then the reaction was stopped by addition of 25 μl/well 1N HCL-solution. Measurement took place at 370/492 nm. ELISA results are listed as EC50-values [ng/ml] in summary Table 17 below.

Cell ELISA for Tim3 Adherent CHO-K1 cell line stably transfected with plasmid 15312_hTIM3-fl_pUC_Neo coding for full-length human Tim3 and selection with G418 (Neomycin resistance marker on plasmid) were seeded at a concentration of 1.2×10E6 cells/ml into 384-well flat bottom plates and grown over night.

At the next day 25 μl/well Tim3 sample or aTim3 reference antibody F38-2E2 Azide free (Biolegend, 354004) was added and incubated for 2 h at 4 C (to avoid internalization). After washing (3×90 μl/well PBST (BIOTEK Washer: Prog. 29, 1×90) cells were fixed by flicking out residual buffer and addition of 50 μl/well 0.05% Glutaraldehyde: Dilution 1:500 of 25% Glutaraldehyde (Sigma Cat. No: G5882) in 1×PBS-buffer and incubated for 1 h at RT. After washing (3×90 μl/well PBST (BIOTEK Washer: Prog. 21, 3×90 GreinLysin) 25 μl/well secondary antibody was added for detection (Sheep-anti-mouse-POD; Horseradish POD linked F(ab')$_2$ Fragment; GE NA9310) followed by 2 h incubation at RT while shaking at 400 rpm. After washing (3×90 μl/well PBST (BIOTEK Washer: Prog. 21, 3×90 GreinLysin) 25 μl/well TMB substrate solution (Roche 11835033001) was added and incubated until OD 1.5-2.5. Then the reaction was stopped by addition of 25 μl/well 1N HCL-solution. Measurement took place at 370/492 nm. Cell ELISA results are listed as "EC50 CHO-Tim3"-values [ng/ml] in summary table Table 17 below.

TABLE 17

Binding Affinites of exemplary antibodies ( ELISA and BIACORE)

| Assay | Tim3_0018 | Tim3_0021 | Tim3_0028 | Tim3_0026 | Tim3_0033 | Tim3_0038 |
|---|---|---|---|---|---|---|
| Affinity KD [nM] mono/bivalent Tim3 | 3.4/1.1 | 204/4.1 | 173/2.8 | 6.2/1.5 | n.f./3.1 | 7.6/0.6 |
| EC50 ELISA [nM] | 0.56 | | 0.22 | | | 0.501 |
| EC50 ELISA [ng/ml] | 94 | 47 | 37 | 47 | 1321 | 83 |
| EC50 CHO-Tim3 [nM] | 0.52 | | 0.32 | | | 0.17 |
| EC50 CHO-Tim3 [ng/ml] | 87 | 73 | 53 | 69 | 3710 | 29 |

Biacore characterization of the Tim3 ABs A surface plasmon resonance (SPR) based assay has been used to determine the kinetic parameters of the binding between several murine Tim3 binders as well as commercial human Tim3 binding references. Therefore, an anti-mouse IgG was immobilized by amine coupling to the surface of a (Biacore) CM5 sensor chip. The samples were then captured and hu/cy Tim3-ECD was bound to them. The sensor chip surface was regenerated after each analysis cycle. The equilibrium constant $K_D$ was finally gained by fitting the data to a 1:1 langmuir interaction model. About 12000 response units (RU) of 30 µg/ml anti-mouse IgG (GE Healthcare #BR-1008-38) were coupled onto the spots 1, 2, 4 and 5 of the flow cells 1-4 (spots 1,5 are active and spots 2,4 are reference spots) of a CM5 sensor chip in a Biacore B4000 at pH 5.0 by using an amine coupling kit supplied by GE Healthcare.

The sample and running buffer was HBS-EP+ (0.01 M HEPES, 0.15 M NaCl, 3 mM EDTA, 0.05% v/v Surfactant P20, pH 7.4). Flow cell temperature was set to 25° C. and sample compartment temperature to 12° C. The system was primed with running buffer. The samples were injected for 30 seconds with a concentration of 200 µg/ml and bound to the spots 1 and 5 of each flow cell, allowing the measurement of eight samples in parallel. Then a complete set of different (monomeric cyno, monomeric human and huFc fused dimeric human Tim3-ECD) concentrations (s. Table X) was injected over each sample for 240 s followed by a dissociation time of 30/1800 s (s. Table 1). Each analysis cycle (sample capture, spot 1 and 5—Tim3 ECD injection) was then regenerated with a 30 seconds long injection of Glycine-HCl pH 1.7. The flow rate was set to 30 µl/min for the whole run. Finally, the double referenced data was fitted to a 1:1 langmuir interaction model with the Biacore B4000 Evaluation Software. Resulting $K_D$ values are shown in Table 17 and 18.

TABLE 18

Binding affinities determined by Biacore-KD values gained by a kinetic SPR measurement.-n.f. means no fit possible, most likely due to no or weak binding.

| Sample | huTim3 $K_D$ (25° C.) [M] | huTim3Fc $K_D$ (25° C.) [M] | cyTim3 $K_D$ (25° C.) [M] |
|---|---|---|---|
| TIM3-0016 | 3.29E−09 | 1.09E−09 | 2.16E−08 |
| TIM3-0016 variant (0018) | 3.40E−09 | 1.11E−09 | 4.19E−08 |
| TIM3-0021 | 2.04E−07 | 4.07E−09 | n.f. |
| TIM3-0022 | 1.26E−07 | 1.52E−09 | 2.84E−08 |
| TIM3-0026 | 6.23E−09 | 1.52E−09 | n.f. |
| TIM3-0028 | 1.73E−07 | 2.77E−09 | n.f. |
| TIM3-0030 | 3.11E−09 | 1.28E−09 | n.f. |
| TIM3-0033 | n.f. | 3.05E−09 | n.f. |
| TIM3-0038 | 7.56E−09 | 5.69E−10 | n.f. |

TABLE 18-continued

Binding affinities determined by Biacore-KD values gained by a kinetic SPR measurement.-n.f. means no fit possible, most likely due to no or weak binding.

| Sample | huTim3 $K_D$ (25° C.) [M] | huTim3Fc $K_D$ (25° C.) [M] | cyTim3 $K_D$ (25° C.) [M] |
|---|---|---|---|
| Reference antibody Biolegend F38-2E2 | 1.36E−08 | 7.50E−09 | 1.68E−07 |
| Reference antibody USB 11E365 | 1.34E−08 | 7.73E−09 | 1.41E−07 |

Example 20

Generation of Anti-Tim3 Antibody Derivatives

Chimeric antibodies derivatives Chimeric Tim3 antibodies were generated by amplifying the variable heavy and light chain regions of the anti-TIM3 mouse antibodies Tim3-0016, Tim3-0016 variant (0018), Tim3-0021, Tim3-0022, Tim3-0026, Tim3-0028, Tim3-0030, and Tim3-0033, Tim3-0038 from via PCR and cloning them into heavy chain expression vectors as fusion proteins with human IgG1 backbones/human CH1-Hinge-CH2-CH3 with LALA and PG mutations (Leucine 234 to Alanine, Leucine 235 to Alanine, Proline 329 to Glycine) abrogating effector functions and light chain expression vectors as fusion proteins to human C-kappa. LC and HC Plasmids were then cotransfected into HEK293 and purified after 7 days from supernatants by standard methods for antibody purification.

Removal of glycosylation site NYT: Modifying 1 HVR-L1 position in Tim3-0016, Tim3_0016 variant (named 0018 or Tim3_0018) by substitution of N by Q or S Mutations within the variable light vchain region of Tim3_0016 and Tim3_0016 variant (0018) were generated by in vitro mutagenesis using Agilent "Quick Change Lightning Site-directed Mutagenesis Kit" according manufacturer's instructions. By this method the asparagine (N) of the glycoslyation site motif NYT in the light chain HVR-L1 (SEQ ID NO: 4) was replaced by glutamine (Q) (resulting in SEQ ID NO: 11=Tim3_0016_HVR-L1 variant 1_NQ) or, alternatively, the asparagine (N) was replaced by serine (S) (resulting in SEQ ID NO: 12=Tim3_0016_HVR-L1 variant 2_NS). In both glycoslyation site motif NYT was successfully modified. LC and HC Plasmids coding for the variants were then cotransfected into HEK293 and purified after 7 days from supernatants by standard methods for antibody purification. The generated mutants were tested by ELISA on human Tim3, ELISA on cynomolgus Tim3 and cellular ELISA on adherent CHO-K1 cells expressing full-length human Tim3. All mutants generated were found to show even more functional binding to human TIM3 (human), cyno TIM3 (cyno) or human TIMR on CHO cells than the parental antibodies Tim3_0016 or the Tim3_0016 antibody variant Tim3_0018 respectively.

TABLE 19

| Mutants tested | Biochem Human | | Biochem Cyno | | cellular bindg. CHO-Tim3 | |
|---|---|---|---|---|---|---|
| | EC50 [ng/ml] values in relation to the sample's max value | inflexion point [ng/ml] | EC50 [ng/ml] values in relation to the sample's max value | inflexion point [ng/ml] | EC50 [ng/ml] values in relation to the sample's max value | inflexion point [ng/ml] |
| aTim3 F38 2E2 | 73.2 | 86.3 | 423.0 | 209878.3 | 350.2 | 224.3 |
| aTim3 0018 | 16.1 | 15.3 | 14.6 | 14.6 | 26.4 | 29.4 |
| aT3m3 0018MutNQ | 12.0 | 10.8 | 13.2 | 10.8 | 13.4 | 12.8 |
| aT3m3 0018MutNS | 10.3 | 6.5 | 11.9 | 6.5 | 11.2 | 11.1 |
| aTim3 0016 MutNQ | 7.6 | 5.7 | 8.3 | 5.7 | 6.8 | 5.4 |
| aTim3 0016MutNS | 8.5 | 6.5 | 9.7 | 5.5 | 9.1 | 8.5 |

Example 21

Fluorescent Labeling of Purified Monoclonal Antibody

The fluorescent labeling of the hybridoma derived monoclonal antibody was carried out by using Alexa Fluor 488 Monoclonal Antibody Labeling Kit (manufactured by Invitrogen) according to the manufacturer's instructions. After the labeling, each antibody was confirmed to be positively labeled with Alexa Fluor 488 (hereinafter referred to as "Alexa-488") by FACSCalibur (manufactured by BD Biosciences) analysis for TIM-3 expressing RPMI-8226 and Pfeiffer cells.

Example 22

Classification of Binding Epitope Groups Using FACS Based Competition Assay

The relation of epitopes between generated anti-TIM3 antibodies and six anti-TIM3 reference antibodies was analyzed by a FACS based binding competition assay. The TIM3 reference antibodies were the following: antibodies 4177 and 8213 as described in US2012/189617, antibodies 1.7E10 and 27.12E12 as described in WO2013/06490; antibody 344823 (Clone 344823, manufactured by R&D Systems) and antibody F38-2E2 (Clone F38-2E2, manufactured by BioLegend and R&D Systems). In brief, the test antibody was allowed to interact and bind with the TIM-3 expressing RPMI-8226 cells (ATCC® CCL-155™) and then it was evaluated by flow cytometry method whether another anti-TIM-3 antibody could also bind to TIM-3 expressing cells.

In short human TIM3 expressing RPMI-8226 cells were incubated with BD human Fc Block for 10 min at RT and stained in two different experimental setups to exclude the impact of the difference in the affinity of the tested antibodies on the binding:
1) with disclosed purified anti-TIM3 (10 µg/ml in BD staining buffer for 0.5 h at 4° C.), which were conjugated with Alexa*488 according to the manufacturer's instructions (Molecular Probes A-20181) with an average of 2.7 fluorophores per antibody. Then a) unlabeled (1-4) reference recombinant anti-TIM3 antibodies or Isotype control were added (10 µg/ml) for 0.5 h at 4° C. in BD SB and after washing with BD SB stained with PE-labeled anti-huFcγ Abs (JIR, 109-116-098, 1:200, 0.5 h at 4° C. in BD SB) or b) PE labeled (5-6) available reference anti-TIM3 antibodies or appropriate Isotype controls were added (10 µg/ml) for 0.5 h at 4° C. in BD SB. After washing and centrifugation MFI signals of stained RPMI-8226 cells were analyzed by BD Biosciences FACSCanto flow cytometer.

TABLE 20

Summary of epitope characterzation.

| | Max % inhibition of Binding | | | | | |
|---|---|---|---|---|---|---|
| | Epitope Group 1 | | | Epitope Group 3 | | |
| | 1a | | 1b | 3a | 3b | |
| | TIM3-0016 | TIM3-0018 | TIM3-0026 | TIM3-0022 | TIM3-0028 | TIM3-0038 |
| clone 4177 | 1 | −9 | 29 | 79 | −3 | 0 |
| clone 8213 | −2 | 9 | 9 | 9 | 38 | 29 |
| clone 1-7E10 | −5 | 15 | 24 | 0 | 20 | 7 |
| clone 27-12E12 | −1 | 4 | 22 | 40 | 82 | 94 |
| clone 344823 | 0 | 0 | 3 | 102 | 107 | 99 |
| clone F38-2E2 | −7 | −6 | 2 | 77 | 75 | 94 |
| 100 | >90 | | | | | |
| 100 | >50 | | | | | |
| 100 | >30 | | | | | |
| 100 | >20 | | | | | |

Results from the FACS based epitope groups mapping show that Tim3_0016 and Tim3_0016 variant Tim3_0018 show no binding competition with any tested anti-TIM-3 reference antibodies and it was suggested that these Abs recognized the new epitope different from the epitopes to which all previous described TIM3 reference antibodies recognized whereas Tim3_0022, Tim3_0026, Tim3_0028 and Tim3_0038 compete to different extend for binding to surface expressed TIM3 on JRPMI-8226 cells with various competitors.

Example 23

Effect of Human Anti-TIM-3 Antibodies on Cytokine Production in a Mixed Lymphocyte Reaction (MLR)

A mixed lymphocyte reaction was used to demonstrate the effect of blocking ther TIM-3 pathway to lymphocyte effector cells. T cells in the assay were tested for activation and theier IFN-gamma secretion in the presence or absence of an anti-TIM-3 mAbs.

Human Lymphocytes were isolated from peripheral blood of healthy donor by density gradient centrifugation using Leukosep (Greiner Bio One, 227 288). Briefly, heparinized blood were diluted with the three fold volume of PBS and 25 ml aliquots of the diluted blood were layered in 50 ml Leukosep tubes. After centrifugation at 800×g for 15 min at room temperature (w/o break) the lymphocyte containing fractions were harvested, washed in PBS and used directly in functional assay or resuspended in freezing medium (10% DMSO, 90% FCS) at 1.0E+07 cells/ml and stored in liquid nitrogen. 1:1 target/responder cell ratio was used in MLR assay (i.e. each MLR culture contained ~2.0E+05 PBMCs from each donor in a total volume of 200 µl. Anti-TIM3 monoclonal antibodies Tim3_0016, Tim3_0016 variant (Tim3_0018), Tim3_0021, Tim3_0022, Tim3_0026, Tim3_0028, Tim3_0030, Tim3_0033, Tim3_0038 and F38-2E2 (BioLegend), were added to each culture at different antibody concentrations. Either no antibody or an isotype control antibody was used as a negative control and rec hu IL-2 (20 EU/ml) was used as positive control. The cells were cultured for 6 days at 37° C. After day 6 100 µl of medium was taken from each culture for cytokine measurement. The levels of IFN-gamma were measured using OptEIA ELISA kit (BD Biosciences).

The results are shown in Table 21 (IFN-g secretion/release). The anti-TIM-3 monoclonal antibodies promoted T cell activation and IFN-gamma secretion in concentration dependent manner. The anti-TIM3 antibodies Tim3_0021, Tim3_0022, Tim3_0028, and Tim3_0038 reduce release of the inflammatory cytokine IFN-gamma) more than the F38-2E2 antibody. Tim3_0016, Tim3_0016 variant (Tim3_0018), Tim3_0033 and Tim3_0038 showed a similar release when compared the F38-2E2 antibody. In contrast, cultures containing the isotype control antibody did not show an increase in IFN-gamma secretion.

TABLE 21

Percentage anti-Tim3 antibody induced IFNgamma release in comparison to rec hu IL-2 (20 EU/ml) ( = 100%) as positive control and no antibody as negative control (Donors

| Compound concentration | MLR + IL-220 U/ml | Isotype IgG2a | F38-2E2 | Tim3 0016 | Tim3 0018 | Tim3 0021 | Tim3 0022 | Tim3 0026 | Tim3 0028 | Tim3 0030 | Tim3 0033 | Tim3 0038 | Isotype hIgG1 |
|---|---|---|---|---|---|---|---|---|---|---|---|---|---|
| 40 µg/ml | | 2 | 36 | 33 | 36 | 112 | 58 | 25 | 40 | 14 | 35 | 51 | 0 |
| 10 µg/ml | 100 | 0 | 26 | 22 | 30 | 108 | 38 | 16 | 38 | 4 | 30 | 38 | 5 |
| 1 µg/ml | | 0 | 7 | 7 | 12 | 101 | 18 | 18 | 12 | 3 | 0 | 1 | 0 |

Example 24

Internalization of Anti-TIM-3 Antibodies into TIM-3 Expressing Cells

TIM-3-specific antibodies described herein can be internalized into TIM-3-expressing cells, including TIM-3 expressing lymphoma, multiple myeloma and AML cells. For example, the disclosed TIM-3 specific antibodies and fragments thereof are shown to be internalized into rec TIM3 CHO cells stabile expressing human TIM-3 as evaluated by cell based ELISA, flow cytometry (FACS) and confocal microscopy.

Stable Tim3-transfected CHO-K1 cells (clone 8) (4×104 cells/well/100 µl) were seeded into 98 well-MTP using fresh culture medium. After overnight cell attachment, cell culture medium was removed and the test antibodies were added to the cells (10 µg/ml in cell culture medium) and incubated for 0.5 hour at 4° C. As reference, a commercial mouse-anti-human antibody (TIM3 MAB 11E365 (US Biological, T5469-92P) was used. After washing (2× with cell culture medium) and centrifugation cells were incubated for 3 h at a) 4° C. or b) 37° C. in 200 µl cell culture medium. Internalization typically occurs at 37° C., but not at 4° C., which provides another control for the reaction. Then cells were fixated with 100 µl/well 0.05% glutharaldehyde (Sigma Cat. No: G5882) in 1×PBS for 10 min at room temperature (RT). This was followed by three washing steps with 200 µl PBS-T and secondary antibody sheep-anti-mouse-POD (Horseradish POD linked F(ab')$_2$ Fragment; GE NA9310)) were added for 1 hour at RT. After the final washing steps (3×PBS-T), TMB substrate was added (Roche order no. 11835033001) for 15 min and color development was stopped using 1N HCl. Final ODs were determined by measurement at 450/620 nm in an ELISA reader. This cellular ELISA procedure was used for medium throughput evaluation of the internalizing capacity of the testing antibodies which were purified from hybridoma supernatants.

The percentage of internalization was calculated as follow:

Internalization[%]=(1−ODsample_37° C./OD sample_4° C.)*100

Figure 29A:
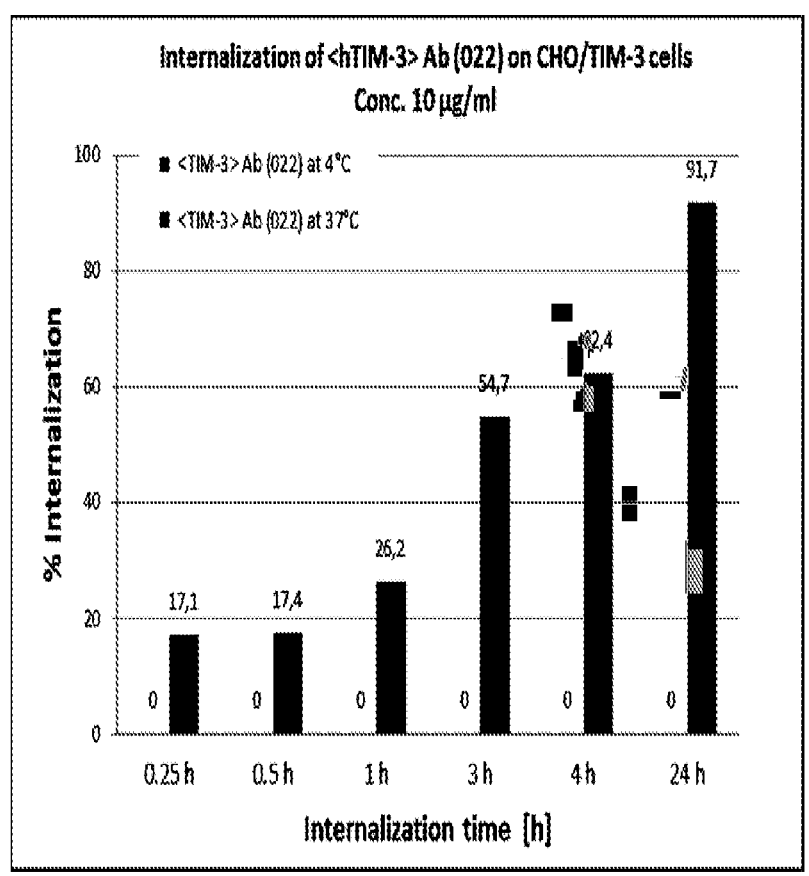
FIGS. 29A-B show results from a FACS based internalization assay. The data show that the Fab fragment (<TIM-3> Fab) of anti-TIM3 antibody Tim3_0022 (abbreviated as <TIM-3> Ab(022)) internalized into rec CHOK1 cells expressing huTIM-3 after incubation at 37° C. with similar kinetic as the antibody in the full IgG format.
Figure 29B:
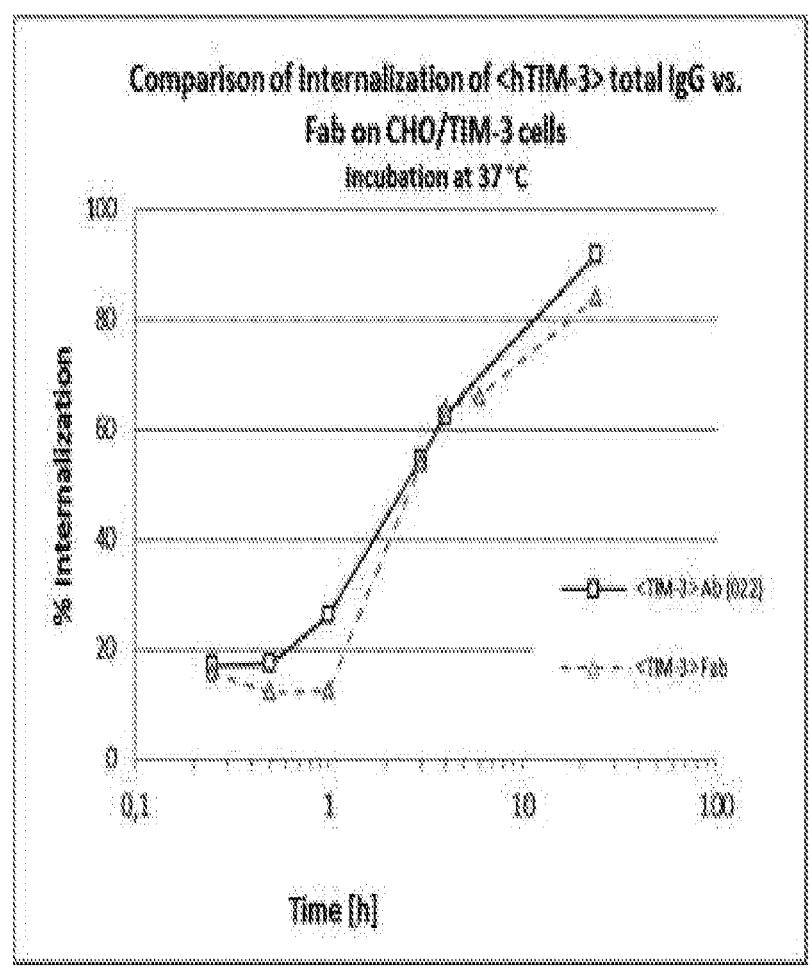
Figure 30A:
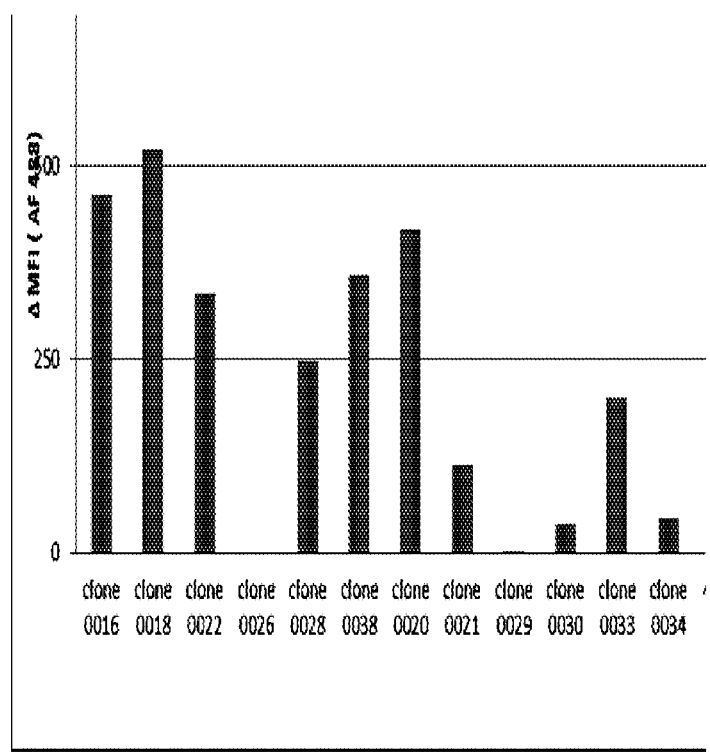
FIGS. 30A-B show binding of anti-TIM3 antibodies to RPMI-8226 cells (antibody desigantion clone 0016 refers to antibody Tim3_0016, clone 0016 refers to antibody Tim3_0016 variant (antibody Tim3_0018), clone 0022 refers to antibody Tim3_00122, etc.).
Figure 30B:
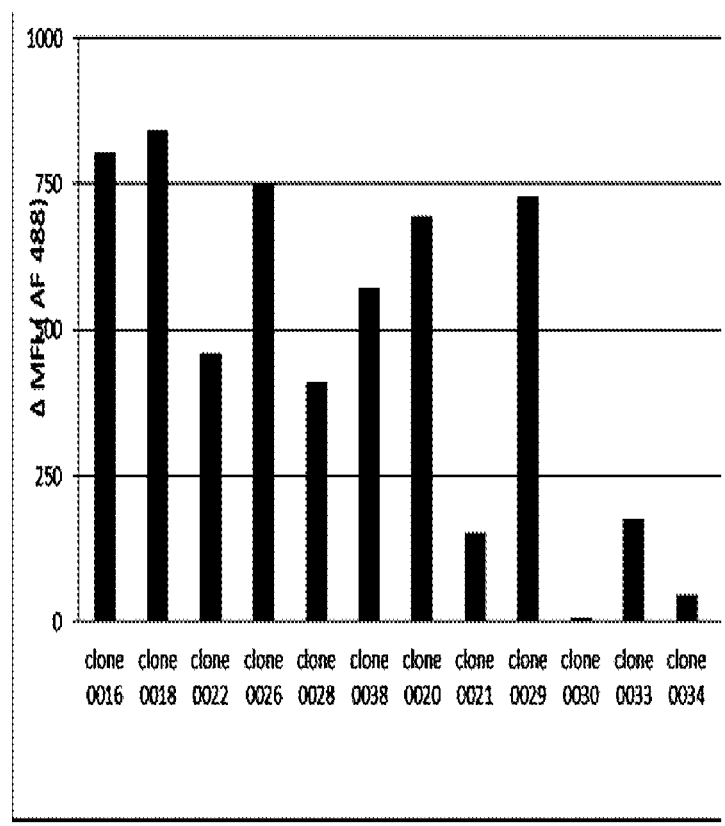

The results are shown in FIGS. 29A and B for (Internalization). Almost all tested anti-TIM-3 monoclonal antibodies were similar well internalized into stable Tim3-transfected CHO-K1 cells after 3 h incubation at 37° C. (not all data shown).

The determination of EC50 internalizing values (time dependency) as well as comparison of the kinetics of the internalization depending on mono-vs. bivalency was estimated by FACS for selected candidates.

In short, human TIM3 stable expressing CHO-K1 cells were seeded ($4\times10^5$ cells/well/50 µl) into 98 well-v bottom MTP using fresh culture medium and incubated with Redimune® NF Liquid for 10 min at RT to block unspecific binding. Then 50 µl/well of selected purified anti-TIM3 (10 µg/ml in cell culture medium) were added and incubated for 1 h at 4° C. After washing (with cell culture medium) and centrifugation cells were incubated for 0.25, 0.5, 1, 2, 3, 4, 6 and 24 h at a) 4° C. or b) 37° C. in 200 µl cell culture medium. Than cells were washed with PBS/1 % BSA and secondary antibody Alexa Fluor 488 Goat-anti-mouseIgG, $F(ab)_2$ were added for 1 hour at 4° C. After washing and centrifugation 125 µl of CellFix (BD Bioscience, 1:1000) were added and MFI signals of stained cells were analyzed by BD Biosciences FACSCanto flow cytometer.

The percentage of internalization was calculated as follow:

$$\text{Internalization}[\%]=(1-\text{MFIsample\_37}^\circ\text{C.}/\text{MFIsample\_4}^\circ\text{C.})*100$$

Example for the evaluation of time dependent internalization of anti-TIM3 antibodies Tim3_0016, Tim3_0016 variant (Tim3_0018), Tim3_0021, Tim3_0028, Tim3_0030, Tim3_0033, Tim3_0038 on RPMI-8226 cells (ATCC® CCL-155™): The presently disclosed anti-TIM3 antibodies are internalized rapidly into TIM3 expressing RPMI-8226 cells (ATCC® CCL-155™) at a high level. The experiments were conducted as described above with TIM3 expressing RPMI-8226 cells (ATCC® CCL-155™) instead of rec CHOK1 cells expressing huTIM-3. Results are shown in the Table 22. The following antibodies were used as TIM3 reference antibodies: antibody 8213 as described in US2012/189617, antibody 27.12E12 as described in WO2013/06490. Tim3_0016, Tim3_0016 variant (Tim3_0018), Tim3_0038 were used as human IgG1 chimeric versions.

TABLE 22

Percentage internalization at the indicated time point (0 min set as 0 percent).

| Antibody | Percentage internalization of anti-TIM3 antibodies | | | | |
|---|---|---|---|---|---|
| | 30 Min | 60 Min | 120 Min | 240 Min | 26 h |
| 8213 | 22 | 22 | 43 | 52 | 72 |
| 27.12E12 | 19 | 22 | 25 | 46 | 59 |
| Tim3_0016 | 33 | 52 | 55 | 66 | 87 |
| Tim3_0018 | 39 | 41 | 80 | 70 | 88 |
| Tim3_0021 | 70 | 75 | 74 | 78 | 77 |
| Tim3_0028 | 50 | 59 | 67 | 68 | 83 |
| Tim3_0033 | 75 | 81 | 82 | 82 | 80 |
| Tim3_0038 | 22 | 20 | 45 | 46 | 63 |

The results show that the tested antibodies are rapidly internalized at high percentage compared to reference antibodies on RPMI-8226 cells (ATCC® CCL-155™).

Example 25

Binding of Anti-TIM-3 Antibodies to Isolated Human Monocytes Expressing TIM-3

CD14+ Monocytes were isolated from anticoagulated peripheral blood of healthy donors by density gradient centrifugation using Ficoll-Paque (GE Healthcare) (see General Protocols in the User Manuals or visit www.milte-nyibiotec.com/protocols) and subsequent positive selection via CD14 MicroBeads. First the CD14+ cells are magnetically labeled with CD14 MicroBeads. Then the cell suspension is loaded onto a MACS® Column which is placed in the magnetic field of a MACS Separator. The magnetically labeled CD14+ cells are retained in the column. The unlabeled cells run through, this cell fraction is depleted of CD14+ cells. After removal of the column from the magnetic field, the magnetically retained CD14+ cells can be eluted as the positively selected cell fraction. After centrifugation at 200×g for 10 min at room temperature the monocytes were harvested and used directly in binding assay or resuspended in freezing medium (10% DMSO, 90% FCS) at 1.0E+07 cells/ml and stored in liquid nitrogen.

As shown in the literature Monocytes express constitutively TIM3 on their surface. $1\times10^5$ CD14+ isolated human monocytes (50 µl/well) were put into 98 well-v bottom MTP in fresh culture medium and incubated with Redimune® NF Liquid for 15 min at RT to block unspecific binding. Than 50 µl/well of disclosed anti-TIM3 mAbs or reference anti-TIM-3 mAbs 344823 (R&D) and F38-2E2 (BioLegend) (10 µg/ml in cell culture medium) were added and incubated for 1 h at 4° C. Than cells were washed with PBS/1 % BSA and secondary antibody PE-labeled Goat-anti-mouse F(ab')2 were (Jackson Lab 115-006-072) added for 1 hour at 4° C. After washing and centrifugation MFI signals of stained cells were analyzed by BD Biosciences FACSCanto flow cytometer.

The specific binding was calculated as follow:

$$\text{Specific Binding [MFI]} = \text{Geom. Mean MFIsample} - \text{Geom. Mean MFIisotype control}$$

The results are shown in Table 8: (Binding to human Monocytes). TIM3 clones Tim3_0016, Tim3_0018, Tim3_0020, Tim3_0028 and Tim3_0038 bind to human monocytes of different donors even better than the reference anti-TIM-3 Abs.

TABLE 23

Binding to human Monocytes.

| | donor1 (CD14+) | donor2 (CD14+) | donor3 (CD14+) |
|---|---|---|---|
| Tim3 0016 | 2122 | 1634 | 1690 |
| Tim3 0018 | 2326 | 1818 | 1943 |
| Tim3 0020 | 1917 | 1377 | 1462 |
| Tim3 0021 | 1134 | 951 | 1197 |
| Tim3 0022 | 1468 | 1111 | 1235 |
| Tim3 0026 | 1665 | 1016 | 900 |
| Tim3 0030 | 1411 | 419 | 466 |
| Tim3 0038 | 1637 | 1368 | 1401 |
| Tim3 0028 | 1351 | 950 | 1607 |
| Tim3 0033 | 480 | 328 | 595 |
| M-IgG2b | 0 | 13 | 0 |
| M-IgG1 | 144 | 55 | 213 |
| <TIM-3>PE Mab, M-IgG1 (Cl F38-2E2; Biolegend) | 516 | 493 | 460 |
| <TIM-3>PE Mab, Rat IgG2A (Clone 344823, R&D) | 1010 | 917 | 814 |
| Rat-IgG2A-PE | 71 | 68 | 70 |

Example 26

Binding of Anti-TIM-3 Antibodies to Isolated Cyno Monocytes Expressing TIM-3

CD14+ Monocytes were isolated from cynomolgus monkey anticoagulated peripheral blood (Covance) by density gradient centrifugation using Ficoll-Paque (GE Healthcare) (see General Protocols in the User Manuals or visit www.m-iltenyibiotec.com/protocols) and subsequent positive selection via NHP CD14 MicroBeads. First the CD14+ cells are magnetically labeled with CD14 MicroBeads. Then the cell suspension is loaded onto a MACS® Column which is placed in the magnetic field of a MACS Separator. The magnetically labeled CD14+ cells are retained in the column. The unlabeled cells run through, this cell fraction is depleted of CD14+ cells. After removal of the column from the magnetic field, the magnetically retained CD14+ cells can be eluted as the positively selected cell fraction. After centrifugation at 200×g for 10 min at room temperature the monocytes were harvested and used directly in binding assay or resuspended in freezing medium (10% DMSO, 90% FCS) at 1.0E+07 cells/ml and stored in liquid nitrogen.

As shown in the literature Monocytes express constitutively TIM3 on their surface. $1\times10^5$ CD14+ isolated cyno monocytes (50 µl/well) were put into 98 well-v bottom MTP in fresh culture medium and incubated with Redimune® NF Liquid for 15 min at RT to block unspecific binding. Than 50 µl/well of Alexa488 labeled anti-TIM3 (10 µg/ml in cell culture medium) were added and incubated for 1 h at 4° C. After washing and centrifugation MFI signals of stained cells were analyzed by BD Biosciences FACSCanto flow cytometer.

The specific binding was calculated as follow:

Specific Binding [MFI]=Geom. Mean MFIsample−
Geom. Mean MFIisotype control

The results are shown in Table 9 (Binding to Cyno Monocytes). TIM3 clones Tim3_0016, Tim3_0018, Tim3_0026, Tim3_0028 and, Tim3_0030 bind to cyno monocytes of different cyno donors.

TABLE 24

Binding to Cyno Monocytes.

| | cyno1 (16719M) CD14+ | cyno2 (17435M) CD14+ | cyno3 (30085F) CD14+ |
|---|---|---|---|
| AF + PI | 75 | 83 | 84 |
| HumTIM-3 Alexa488 R&D (34482) | 158 | 121 | 143 |
| Rat-IgG2A-Alexa488 | 84 | 86 | 91 |
| hum TIM-3 A488 F38-2E2 (NOVUS Biol) | 135 | 136 | 124 |
| M-IgG1-Alexa 488 | 72 | 82 | 83 |
| Tim3 _0016-A488 | 157 | 177 | 187 |
| Tim3 _0016 variant 0018-A488 | 301 | 480 | 417 |
| Tim3 0022-A488 | 115 | 134 | 138 |
| Tim3 0026-A488 | 137 | 184 | 197 |
| Tim3 0028-A488 | 3936 | 2996 | 4090 |
| Tim3 0038-A488 | 97 | 107 | 120 |
| Tim3_0020-A488 | 274 | 378 | 354 |
| Tim3 0021 A488 | 348 | 473 | 399 |
| Tim3 0030 A488 | 119 | 163 | 144 |
| Tim3 0033 A488 | 71 | 81 | 83 |
| TIM-3 (4177) A488 | 78 | 83 | 85 |
| TIM-3 (8213) A488 | 75 | 83 | 87 |

Example 27

Binding of Anti-TIM-3 Antibodies to NHL and MM Cell Lines Expressing TIM-3

The binding capacity of disclosed anti-TIM3 antibodies and two anti-TIM3 reference antibodies clones (1) 4177 and (2) 8213 (Kyowa) was analyzed by a FACS. In short human TIM3 expressing B cell lymphoma cells (exemplified as Pfeiffer cells) and multiple myeloma cells (exemplified as RPMI-8226 cells) were incubated with BD human Fc Block for 10 min at RT to block unspecific binding. Then $2\times10^5$ cells (50 µl/well) were put into 98 well-v bottom MTP and 50 µl/well of Alexa488 labeled anti-TIM3 (10 µg/ml in BD Staining buffer) were added and incubated for 1 h at 4° C. After washing and centrifugation MFI signals of stained cells were analyzed by BD Biosciences FACSCanto flow cytometer.

The specific binding was calculated as follow:

Specific Binding [MFI]=Geom. Mean MFIsample−
Geom. Mean MFIisotype control

Figure 2A:
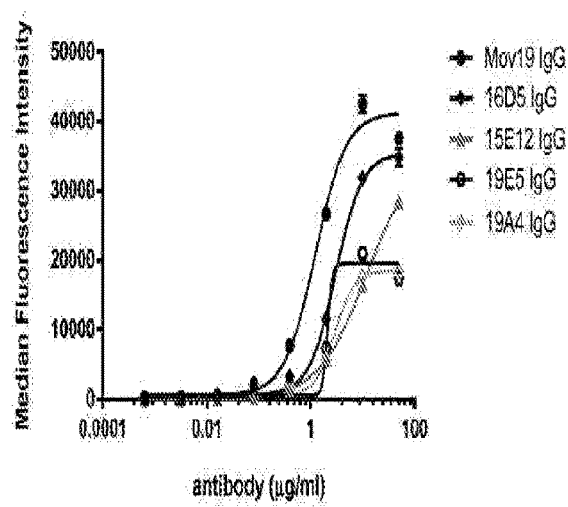
FIGS. 2A-C depict graphs summarizing Binding of FoLR1 IgG binders to HeLa cells. Binding of newly generated FolR1 binders to FolR1 expressed on HeLa cells were determined by flow cytometry. Bound antibodies were detected with a fluorescently labeled anti-human secondary antibody.
Figure 2B:
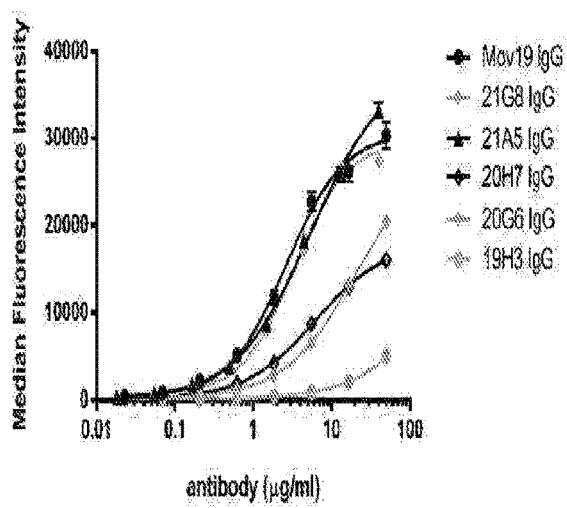
Figure 2C:
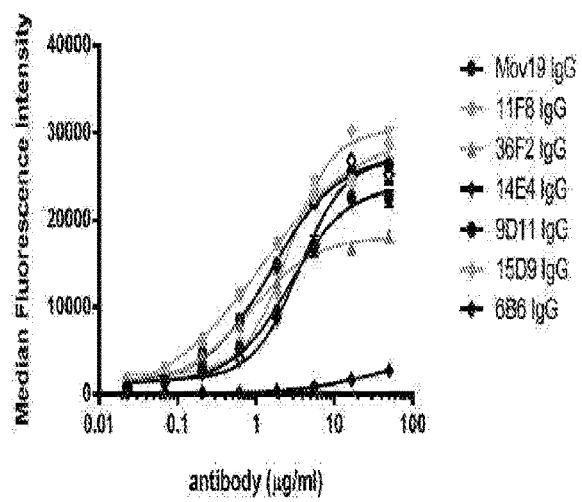
Figure 3A:
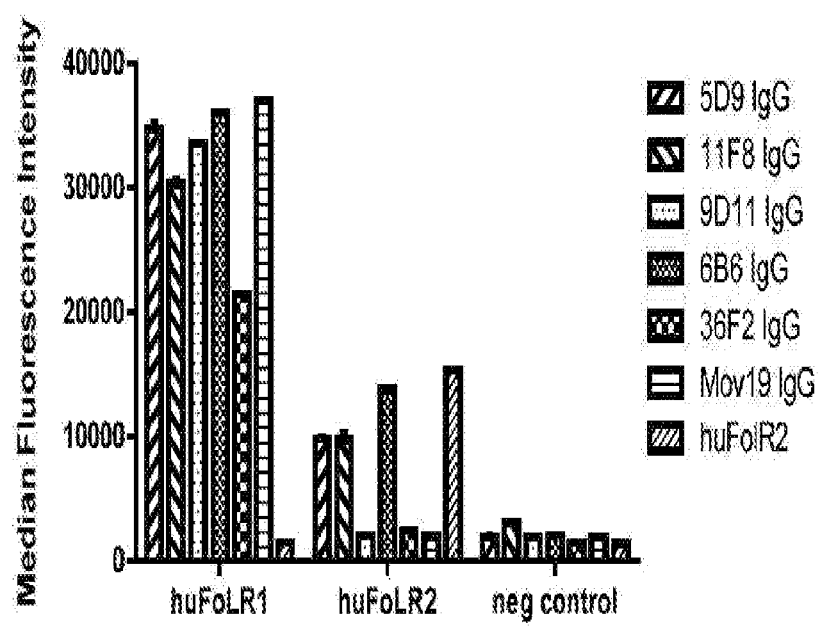
FIGS. 3A-B depict graphs summarizing specificity of FolR1 binders for FolR1. Binding of FolR1 IgGs to HEK cells transiently transfected with either FolR1 or FolR2 was analyzed by flow cytometry to identify clones which bind specifically to FolR1 and not to FolR2. The antibodies were detected with a fluorescently labeled anti-human secondary antibody.
Figure 3B:
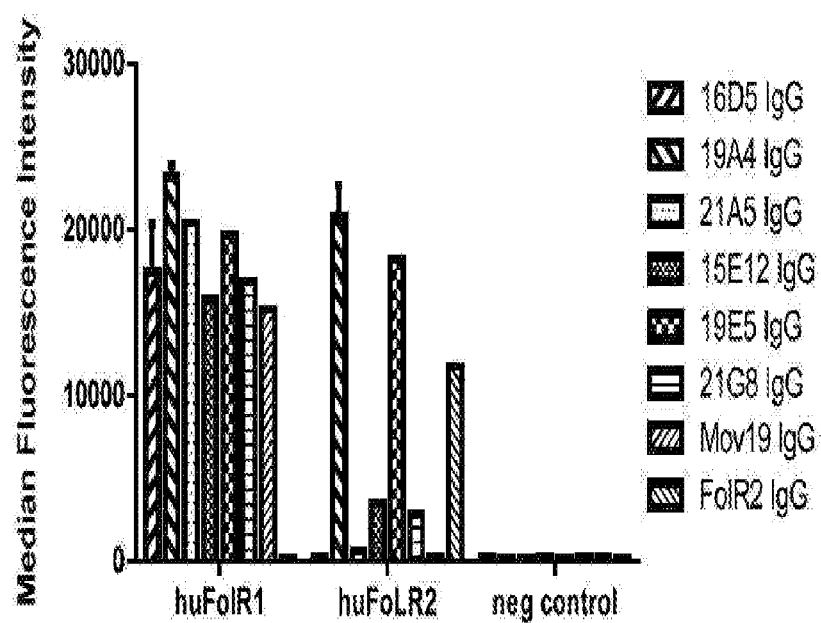

The results are shown in FIGS. 2A and 2B (Binding to RPMI-8226 and Pfeiffer cells).

Example 10: Cytotoxic Activity of Anti-TIM-3 Antibodies on TIM-3 Expressing NHL and MM Cells TIM3-specific antibodies conjugated with *Pseudomonas* exotoxin (PE 24) effectively kill TIM3-expressing cells. The cytotoxic activity of disclosed anti-TIM3 antibodies and one commercial available anti-TIM3 reference antibody clone 11E365 (available from US Biological) was analysed with Promega CellTiter-Glo Luminescent Cell Viability Assay. In short to 5×103 (50 µl/well in 98 well MTP, in triplicate) recombinant CHO K1 stabile expressing human TIM-3 or 2 x104 cells (50 µl/well in 98 well MTP, in triplicate) human TIM3 expressing B cell lymphoma cells (exemplified as Pfeiffer cells) or multiple myeloma cells (exemplified as RPMI-8226 cells) were added 25 µl/well 1:5 serial dilution of disclosed anti-TIM-3 antibodies with the highest concentration of 10 µg/ml or appropriate media to untreated cells or Isotype control to untargeted treated cells. Treatment ranges from 10 µg/ml to 1 ng/ml in triplicate. All antibodies were used as full length mouse Fcγ versions. For conjugation of the conjugation of the *Pseudomonas* exotoxin 10 µg/ml of mouse Fcγ fragment specific Fabs conjugated with PE 24 were added and incubated for 3 days at 37° C. Cycloheximide as a known protein synthesis inhibitor in eukaryotes was used as positive control. Viability of treated cells were measured with Promega CellTiter-Glo Luminescent Cell Viability Assay.

The cytotoxic activity was calculated as follow:

Rel. Inhibition [%]=(1−(Esampel−E negative control)/(E positive control−E negative control))*100

The results are shown in Table 25.

TABLE 25

Cytotoxic activity of anti-TIM3 mAbs on TIM-3 expressing recombinant, NHL and MM cell lines in sandwich format.

| Antibodies and references (all anti TIM3 antibodies conjugated to a deimunized Pseudomonas exotoxin A) | IC50 [nM] | | |
|---|---|---|---|
| | recTIM-3 CHO cells | Pfeiffer cells | RPMI-8226 |
| Tim3_0016 | 0.04 | 0.09 | 0.55 |
| Tim3_0016 variant 1 (Tim3_0018) | 0.05 | 0.10 | 0.66 |
| Tim3_0020 | 0.07 | 0.11 | >64 |
| Tim3_0021 | 0.04 | 0.10 | 5.9 |
| Tim3_0022 | 0.02 | 0.07 | 0.36 |

TABLE 25-continued

Cytotoxic activity of anti-TIM3 mAbs on
TIM-3 expressing recombinant, NHL
and MM cell lines in sandwich format.

| Antibodies and references (all anti TIM3 antibodies conjugated to a deimunized Pseudomonas exotoxin A) | IC50 [nM] | | |
|---|---|---|---|
| | recTIM-3 CHO cells | Pfeiffer cells | RPMI-8226 |
| Tim3_0023 | 0.03 | 0.08 | >64 |
| Tim3_0026 | 0.03 | 0.08 | >64 |
| Tim3_0030 | 0.03 | 0.10 | >64 |
| Tim3_0033 | 0.11 | 0.20 | 0.79 |
| Tim3_0038 | 0.01 | <0.002 | 0.16 |
| US Biol. Clone 11E365 | 0.7 | 1.2 | 1.1 |
| Cells w/o Ab | — | — | — |
| Cells + <mFc> Fab PE | — | — | — |
| IgG2A + <mFc> Fab PE | — | — | — |
| Cycloheximide | 135 | 181 | 245 |

All tested TIM3 clones are highly potent (IC50 range 0.01-0.2 nM) on recombinant CHO K1 stabile expressing human TIM-3 and Pfeiffer cells expressing high and moderate levels of TIM-3 and even more potent in their cytotoxic activity than the strong internalizing reference anti-TIM-3 Ab clone 11E365, US Biological. TIM3 clones 0016, 0018, 0021, 0022, 0033 and 0038 are also potent on RPMI-8226 cells expressing 5 fold lower TIM-3 level compare to recombinant CHO TIM-3 cells.

Example 28: Comparison of the Cytotoxic Activity of Disclosed Anti-TIM3 Antibodies Vs. Two Anti-TIM3 Reference Antibodies 1.7.E10 and 27-12E12 (as Described in WO2013/06490)

The cytotoxic activity of disclosed anti-TIM3 antibodies and two anti-TIM3 reference antibodies the TIM3 reference antibodies 1.7E10 and 27.12E12 as described in WO2013/06490 was analysed with Promega CellTiter-Glo Luminescent Cell Viability Assay as described above. All antibodies were used as full length human IgG1 format including the human Fcgamma part. In this experiment conjugation of the Pseudomonas exotoxin was achieved via human Fcγ fragment specific Fabs conjugated with PE 24 (10 µg/ml) which were added and incubated for 5 days at 37° C.

The results are shown in Table 26.

TABLE 26

Comparison of cytotoxic activity of anti-TIM3 mAbs
on TIM-3 expressing NHL and MM cell lines.

| Antibodies and references (all anti TIM3 antibodies conjugated to a deimunized Pseudomonas exotoxin A) | Pfeiffer cells | | RPMI-8226 cells | |
|---|---|---|---|---|
| | Max. killing | Rel. IC50 [nM] | Max. killing | Rel. IC50 [nM] |
| Cycloheximide | 100 [%] | 271 | 100 [%] | 111 |
| 1.7E10 | 60.3 [%] | 0.68 | 65.7 [%] | 2.544 |
| 27-12E12 | 75.7 [%] | 0.02 | 86.6 [%] | 0.111 |
| Tim3_0016 | 84.9 [%] | 0.05 | 86.6 [%] | 0.063 |
| Tim3_0016 variant (Tim3_0018) | 82.9 [%] | 0.06 | 88.1 [%] | 0.081 |
| Tim3_0026 | 78.3 [%] | <0.02 | 83.1 [%] | 0.067 |
| Tim3_002 | 82.6 [%] | <0.02 | 83.8 [%] | 0.047 |
| Isotype Control hIgG1 | 3.2 [%] | N.A | 0.4 [%] | N.A |

All disclosed TIM3 clones are highly active (IC50 range 0.02-0.08 nM) on Pfeiffer and RPMI-8226 cells expressing TIM-3 and even more potent in their cytotoxic activity than the strong internalizing reference anti-TIM-3 Ab clone 27-12E12. All antibodies were compared as Pseudomonas exotoxin (PE24) conjugates using the same Pseudomonas exotoxin under the same conditions.

Example 28

Cytotoxic Activity of Fab-PE24 Constructs of Disclosed Anti-TIM3 Antibodies on MM, NHL and AML Cell Lines (Expressing TIM3, but not PSMA)

The cytotoxic activity was analysed with Promega CellTiter-Glo Luminescent Cell Viability Assay as described above. 1:5 serial dilutions of Fab-fragments of disclosed anti-TIM3 antibodies directly conjugated to PE24 with the highest concentration of 50 µg/ml or appropriate media to untreated cells or non-binding anti-PSMA Fab-PE24 control to untargeted treated cells were incubated with 7.5×10³ Pfeiffer cells or 2×10³ RPMI-8226 cells (50 µl/well in 98 well MTP) for 4 days at 37° C. Treatment ranges from 50 µg/ml to 8 ng/ml in triplicate. Cycloheximide was used as positive control.

The results are shown in Table 27.

TABLE 27

Cytotoxic activity of Fab-PE24 constructs of disclosed anti-
TIM3 antibodies on MM, NHL and AML cell lines.

| | RPMI-8226 | | Karpas-299 | | CMK | | TF-1 | | MOLM-13 | |
|---|---|---|---|---|---|---|---|---|---|---|
| Antibodies and references (all anti TIM3 antibodies conjugated to a deimunized Pseudomonas exotoxin A) | Max. killing | IC50 [nM] | Max. killing | IC50 [nM] | Max. killing | IC50 [nM] | Max. killing | IC50 [nM] | Max. killing | IC50 [nM] |
| Cycloheximide | 100 [%] | 281 | 100 [%] | 113 | 100 [%] | 149.0 | 100 [%] | 207 | 100 [%] | 156 |
| Anti_PSMA | 10.5 [%] | N.A. | 40.1 [%] | N.A. | 8.98 [%] | N.A. | 5.27 [%] | N.A. | 18.9 [%] | N.A. |
| Tim3_0022 | 99.1 [%] | 1.9 | 98.8 [%] | 10 | 67.1 [%] | 255 | 58.6 [%] | 299 | 58.5 [%] | 579 |
| Tim3_0016 | 99.3 [%] | 1.1 | 99.2 [%] | 4 | 64.8 [%] | 225 | 54.2 [%] | 534 | 62.7 [%] | 459 |

All tested Fab-PE24 constructs of disclosed anti-TIM3 antibodies are highly potent (IC50 range 1-10 nM) on MM (RPMI-8226) and NHL (Karpas-299) cells expressing moderate level of TIM-3 and demonstrate significant cytotoxic activity on AML cell lines (CMK, TF-1, MOLM-13) expressing very low levels of TIM-3.

Example 29

Figure 31:
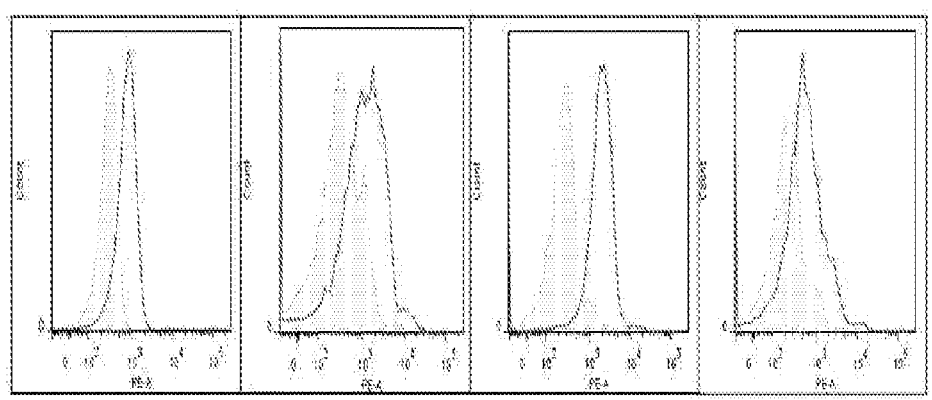
FIG. 31 shows expression level of TIM-3 on different patient AML cell samples by FACS using anti-TIM-3 mAbs.

Cytotoxic Activity of Immuno Conjugates (*Pseudomonas* Exotoxin A Conjugates (Fab-PE24 Constructs) of Disclosed Anti-TIM3 on Primary Leukemic Stem/Progenitor AML Cells from Relapsed/Refractory Patients CD34+ cells from peripheral blood of relapsed/refractory patients were obtained from AllCells, LLC, Alameda, Calif. After confirmation of purity and viability of all samples (purity range 84-94% and viability range 95-99%) the expression level of TIM-3 was evaluated by FACS as described in Example 7 using anti-TIM-3 mAbs 344823 (R&D). (see FIG. 31). All tested (4/4) primary leukemic stem/progenitor (CD34+) AML samples from relapsed/refractory patients demonstrate homogeneous expression of TIM-3 at different levels.

For the evaluation of cytotoxic activity of Fab-PE24 constructs of disclosed anti-TIM3 clones 0016 and 0022 on primary CD34+ AML cells 1×10$^4$ cells (50 µl/well in 98 well MTP, in triplicate) were incubated with 1:5 serial dilutions of Fab-fragments with the highest concentration of 50 µg/ml or appropriate media to untreated cells or non-binding anti-PSMA Fab-PE24 control to untargeted treated cells for 3 days at 37° C. Cycloheximide was used as positive control. Cytotoxic activity was analysed with Promega CellTiter-Glo Luminescent Cell Viability Assay as described above in Example 28.

The results are shown in Table 28. (Cytotoxic activity of Fab-PE24 constructs of disclosed anti-TIM3 antibodies on primary CD34+ AML cells).

Fab-PE24 constructs of anti-TIM3 antibodies Tim3_0016 and Tim3_0022 are highly potent on (2/4) primary AML samples (PB0142 and PB0135) (IC50 range 30-116 nM) and demonstrate significant cytotoxic activity on all (4/4) primary leukemic stem/progenitor (CD34+) AML cells expressing different levels of TIM-3.

Example 30

Comparison of Potency of Fab-PE24 Constructs of Selected Anti-TIM3 Antibodies on NHL and MM Cell Lines The evaluation of cytotoxic activity of sortase coupled Fab-PE24 constructs of selected disclosed anti-TIM3 antibodies was analysed with Promega CellTiter-Glo Luminescent Cell Viability Assay as described above in Example 28.

The results are shown in Table 29.

TABLE 29

Cytotoxic activity of Fab-PE24 constructs of selected anti-TIM3 antibodies on NHL and MM cells.

| Antibodies and references (all anti TIM3 antibodies conjugated to a deimunized Pseudomonas exotoxin A) | Pfeiffer cells | | RPMI-8226 cells | |
|---|---|---|---|---|
| | Max. killing | IC50 [nM] | Max. killing | IC50 [nM] |
| Cycloheximide | 100 [%] | 271.1 | 100 [%] | 153 |
| anti-PSMA | 25.2 [%] | N.A. | 21.5 [%] | N.A. |
| TIM-3 0022 | 99.9 [%] | 1.58 | 99.6 [%] | 2.14 |
| TIM-3 0016 | 99.6 [%] | 0.77 | 99.2 [%] | 0.61 |
| TIM-3 0021 | 98.4 [%] | 2.15 | 99.1 [%] | 3.61 |
| TIM-3 0033 | 99.8 [%] | 5.30 | 99.7 [%] | 5.73 |
| TIM-3 0038 | 99.6 [%] | 0.47 | 98.3 [%] | 0.32 |

High cytotoxic potency was demonstrated with Fab-PE24 constructs of all selected disclosed anti-TIM3 antibodies (IC50 range 0.3-5 nM) on NHL (Pfeiffer) and MM (RPMI-8226) cells expressing moderate level of TIM-3.

The highest cytotoxic activity was observed with Fab-PE24 constructs of disclosed anti-TIM3 antibodies Tim3_0016 and Tim3_0038.

TABLE 28

Cytotoxic activity of Fab-PE24 constructs of disclosed anti-TIM3 antibodies on primary CD34 + AML cells).

| | D1; AML CD34 + PB0136 cells | | D2; AML CD34 + PB0142 cells | | D3; AML CD34 + PB0135 cells | | D4; AML CD34 + PB0193 cells | |
|---|---|---|---|---|---|---|---|---|
| Antibodies and references (all anti TIM3 antibodies conjugated to a deimunized Pseudomonas exotoxin A) | Max. killing | IC50 [nM] | Max. killing | IC50 [nM] | Max. killing | IC50 [nM] | Max. killing | IC50 [nM] |
| Cycloheximide | 100 [%] | 212 | 100 [%] | 262 | 100 [%] | 121 | 100 [%] | 208 |
| anti-PSMA | 2 [%] | N.A. | 8 [%] | N.A. | 18 [%] | N.A. | 12 [%] | N.A. |
| TIM-3 0022-cFP | 38 [%] | >691 | 75 [%] | 107 | 31 [%] | >691 | 57 [%] | 375 |
| TIM-3 0016-cFP | 48 [%] | >691 | 79 [%] | 30 | 44 [%] | >691 | 69 [%] | 116 |

Example 31

Comparison of Cytotoxic Activity of Fab-PE24 Construct Vs. Total-IgG-Amatoxin Conjugate of the Same Clone of Disclosed Anti-TIM-3 Antibody on Pfeiffer Cells The evaluation of cytotoxic activity of conjugated Fab-PE24 construct of disclosed anti-TIM3 clone 0016 vs. total IgG of the same clone conjugated with Amatoxin (according to the procedures described in WO2012/041504 (conjugated via the 6'C-atom of amatoxin amino acid 4, particularly via an oxygen atom bound to the 6'C-atom of amatoxin amino acid, and wherein the TIM3 antibody is connected by a linker via a urea moiety) was analysed with Promega CellTiter-Glo Luminescent Cell Viability Assay as described above in Example 12. The results are shown in Table 30.

TABLE 30

Cytotoxic activity of Fab-PE24 construct vs. total IgG-Amatoxin conjugate of anti-TIM3 clone 0016 on NHL cells

| Pfeiffer cells | Max. killing | IC50 [nM] |
| --- | --- | --- |
| Cycloheximide | 100 [%] | 163 |
| Isotype hIgG1 Amatoxin | 28 [%] | N.A. |
| TIM-3 0016- Amatoxin | 93.3 [%] | 0.81 |
| TIM-3 0016-PE24 | 99.8 [%] | 0.25 |

Example 32

Patients and Tumor Sample Processing

Freshly excised solid tumor lesions and malignant effusions were collected from 34 patients with non-small cell lung cancer, 7 patients with ovarian cancer and 1 patient with renal cell carcinoma (RCC) between. The solid tumor lesions were dissociated mechanically and digested using accutase (PAA), collagenase IV (Worthington), hyaluronidase (Sigma), and DNAse type IV (Sigma) directly after excision. Single-cell suspensions were prepared. The cellular fraction of malignant effusions was isolated by density gradient centrifugation using Histopaque-1119 (Sigma). All samples were stored in liquid nitrogen until further usage. The study was approved by the local Ethical Review Board (Ethikkommission Nordwestschweiz).

Example 33

Tumor Sample Characterization

All tumor samples were comprehensively characterized by multicolor flow cytometry.

The following antibodies were used for flow cytometric analysis: α-CD4-PE, α-CD8-PE-Cy7, α-CD11b-PerCP-eFluor710, α-CD45-PE-Cy7, α-CD45-PerCP-Cy5.5, α-CD137-FITC, α-BTLA-Biotin, α-CTLA-4-PE, α-ICOS-FITC, α-IFN-γ-FITC, α-Lag-3-APC (all eBioscience), α-CD3-PECF594, α-CD25-BV605, α-CD69-FTC, α-Epcam-FITC, α-granzyme B-PE, α-active caspase 3-PE, α-PD-1-BV605, Steptavidin-BV711 (all BD Bioscience), α-CD45RA-BV421, α-CCR7-AlexaFluor647, α-FoxP3-AlexaFluor647, α-Tim-3-BV421, α-Tim-3-BV605 (all Biolegend). Dead cells were stained with LIVE/DEAD® Fixable Near-IR Dead Cell Stain Kit or LIVE/DEAD® Fixable Blue Dead Cell Stain Kit (Invitrogen). For intracellular stainings Fixation and Permabilization Buffers from eBioscience were used. Samples were acquired for flow cytometric analysis on a BD LSR Fortessa. The human IL-2, IFN-γ and TNF ELISA sets were all obtained from BD Bioscience.

$CD8^+$ and $CD4^+$ T cells (CD45+CD3+) were characterized for the expression of the surface markers PD-1, Tim-3, CTLA-4, Lag-3, BTLA, CD25, CD69, CD137, ICOS, CD45RA and CCR7. Tumor cells ($CD45\text{-}Epcam^+$) were characterized for the expression of FolR1 comparing the binding of a FolR1 specific antibody with its matched isotype control. Only samples that were positive for FolR1 expression were used for treatment with FolR1-TCB, and samples expressing EpCAM for treatment with catumaxomab, respectively.

Example 34

Ex Vivo Treatment of Tumor Samples with FolR1-TCB

FolR1 positive tumor digests or malignant effusions were thawed, washed and plated in 96-well flat bottom cell culture plates (BD Falcon) with a density of 3×10 cells/200 μl/well in complete medium (DMEM+Sodium Pyruvate (1 mM)+MEM non essential AA (1×)+L-Glutamin (2 mM)+Penicillin/Streptomycin (100 ng/ml)+2-Mercaptoethanol (50 nM)+Ciproxin (1 mg/ml)+10% human Serum). The samples were cultured in the presence or absence of FolR1-TCB or DP47 TCB at a concentration of 2 nM for 24 h. Activation of $CD8^+$ and $CD4^+$ T cells ($CD45^+CD3^+$) upon FolR1-TCB treatment was determined by multicolor flow cytometry by measuring the expression of the cell surface markers CD25, CD69, CD137, ICOS, PD-1 and Tim-3. Furthermore the expression of granzyme B and IFN-γ was determined by intracellular staining. The concentration of IL-2 in the cell culture supernatants was measured by ELISA (human IL-2 ELISA set, BD OptEIA) following the instructions of the manufacturer.

Example 35

Ex Vivo Treatment of Tumor Samples with Catumaxomab

The trifunctional TCB catumaxomab (Removab®) was obtained from Fresenius. The experimental conditions were similar as indicated above for FolR1-TCB. Briefly, EpCAM positive tumor digests or malignant effusions were cultured in the presence or absence of catumaxomab at a concentration of 10 ng/ml for 24 h. Analysis of $CD8^+$ and $CD4^+$ positive T cells (CD45+CD3+) was performed as described above.

Example 36

Killing Assay

To determine the FolR1-TCB induced tumor cell killing, $3 \times 10^4$ CFSE-labelled Skov3 cells were cocultured with tumor samples in the presence or absence of FolR1-TCB at a concentration of 2 nM for 24 h in 96-well flat bottom cell culture plates. The E:T ratio (E: effector CD45+CD3+ cells; T: target $FolR1^+$ cells from tumor and added Skov3 cells) was adjusted to 1:1 in each well and the cell number of the added tumor samples was calculated for each sample according to prior characterization by flow cytometry. Cell death of Skov3 cells was determined by flow cytometry by measuring activated caspase 3 and the live/dead marker Live/Dead-near-IR. The assay was performed in triplicates. The FolR1-TCB mediated killing was calculated according to the following equation: % of specific killing=100−[(% of Skov3 live cells in FolR1-TCB treated sample/% of Skov3 live cells in untreated sample)×100].

To compare the FolR1-TCB-induced killing capacity of T-cells between tumor samples, and to exclude additional factors suppressing T-cell functionality, such as expression of PD-L1 on the tumor cells, we exogenously added CFSE-labeled FolR1$^+$ Skov3 cells to the tumor digests and adjusted the E:T ratio to 1:1, essentially as described above. We then measured the FolR1-TCB-induced killing of CFSE-labeled Skov3 cells, which allowed us to also include FolR1$^−$ tumor samples into the analysis. As some tumors from the initial cohort could not be used to characterize TCB-mediated tumor cell killing due to a very low amount of effector cells, a separate cohort of 12 tumor digests and 5 malignant effusions from 15 non-small cell lung cancer (NSCLC) and two epithelial ovarian carcinoma (EOC) patients was analyzed. All samples were characterized for their CD3$^+$ effector and FolR1$^+$ target cell content (FIG. 39). Tumor cell killing of CD3$^+$ T-cells from patients was compared with PBMC-derived T-cells from healthy donors. A substantial heterogeneity in tumor cell killing between individual patients was observed (26±11.8%) after 24 h (FIG. 12O). Of note, CD3$^+$ T-cells from healthy donors induced a significantly better killing than TILs (42.8±9.7%, p=0.013). Exposure to a control TCB with no binding to a tumor antigen (DP47-TCB) did not induce any tumor cell killing.

Example 37

Polyclonal Stimulation with Anti-CD3/CD28 Antibodies

A 96-well flat-bottom plate was precoated with 0.5 μg/ml anti-CD3ε (clone OKT3, Biolegend) for 2 hrs at 37° C. Afterwards, the antibody solution was removed and the plate washed extensively. Frozen tumor suspensions were thawed, washed and cultured at 3×10$^5$ cells/200 μl/well in complete medium with 2 μg/ml anti-CD28 antibody (clone 28.2, eBioscience) for 24 hrs. After 24 hrs of incubation cells were collected, washed and analyzed by flow cytometry for expression of activation markers e.g. CD25 and T cell effector functions e.g. granzyme B and IFN-γ on CD8$^+$ T cells. Supernatants were collected for IL-2, IFN-γ and TNF-α ELISA which was performed according to the manufacturer's instructions.

Example 38

Restoring of T Cell Function by PD-1 Blockade

Tumor digests were stimulated by agonistic anti-CD3 and anti-CD28 antibodies as described above in the presence or absence of 10 μg/ml anti-PD-1 antibody (MDX5C4) per well and incubated for 24 hrs. After 24 hrs cells were collected, washed and analyzed by flow cytometry. Supernatants were collected for IL-2, IFN-γ and TNF-α ELISA which was performed according to the manufacturer's instructions.

Example 39

Activation of T Cells in Tumor Digests and Malignant Effusions by FolR1 TCB

Figure 11A:
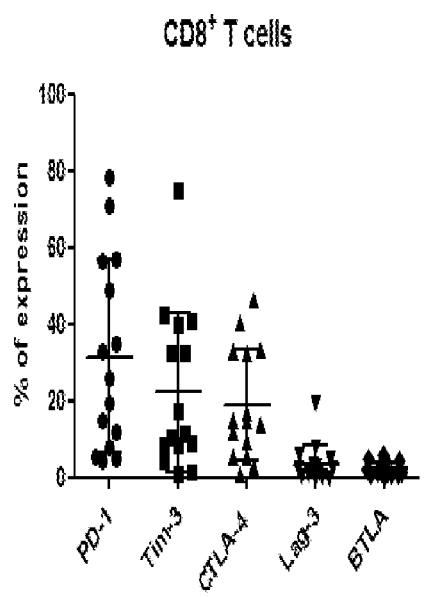
FIGS. 11A-B show expression of inhibitory receptors on tumor-infiltrating T cells. $CD8^+$ and $CD4^+$ T cells in tumor samples were characterized by flow cytometry for their expression of inhibitory receptors.
Figure 11B:
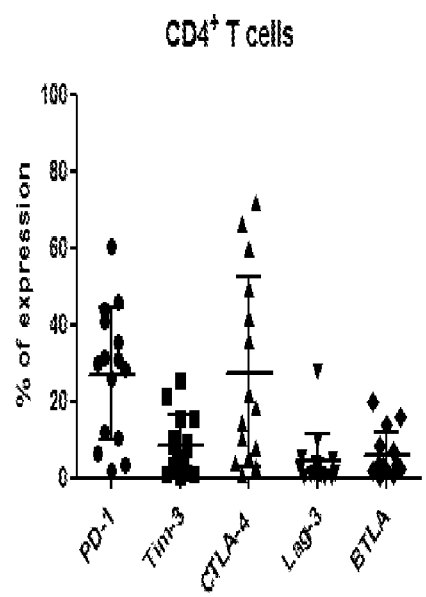

The T cell bispecific antibodies engaging CD3 and folate receptor 1 (Mov19 based FolR1-TCB and the control antibody DP47-TCB were provided by Roche Glycart. The anti-PD-1 antibody 5C4 is described in U.S. Pat. No. 8,008,449. The anti-Tim3 antibody F38-2EL was used. For flow cytometric characterization of FolR1 expression the antibody anti-FolR1-APC (aa25-233) from LifeSpanBiosciences and its matched isotype control (Biolegend) were used. Tumor lesions from 15 patients with FolR1$^+$ tumors were characterized for T cell activation induced by FolR1 TCB. The samples consisted of 9 single cell suspensions and 6 malignant effusions derived from patients with NSCLC (n=7), ovarian cancer (n=7), and renal cell cancer (n=1). The amount of CD3$^+$ T cells and of FolR1$^+$ tumor cells was highly variable between patients (CD3+: mean 33.9% t standard deviation of 16.6%, FolR1$^+$: 17.1% t 16.8%). Characterization of the expression of the inhibitory receptors PD-1, Tim-3, CTLA-4, Lag- and BTLA on T cells revealed a large heterogeneity among patients (FIG. 11A-B). While the tumor-infiltrating CD8$^+$ T cells showed high levels of PD-1, Tim-3 and CTLA-4 (31.6%±25%; 22.2%±20.8% and 18.7%±14.4%, respectively), Lag-3 and BTLA were only expressed on a minority of cells in all patients of this cohort (3.5%±4.9% and 2.3%±1.7%, respectively). Inhibitory receptors on CD4$^+$ T cells were distributed similarly, with a slightly more prominent expression of CTLA-4.

Figure 12A:
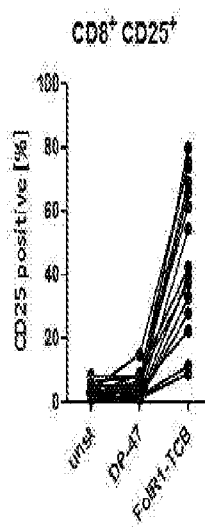
FIGS. 12A-O show activation of $CD8^+$ T cells in tumor digests and malignant effusions upon exposure to FolR1-TCB. Tumor digests or malignant effusions were cultured for 24 h in the presence or absence of FolR1-TCB or the control TCB DP-47. The expression of activation markers or markers of T cell function on $CD8^+$ T cells was determined by flow cytometry (FIG. 12A-M).
Figure 12B:
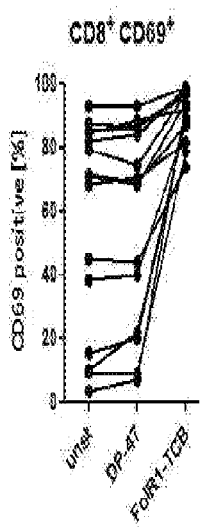
FIG. 12J-K show representative FACS plots showing FolR1-TCB-induced T cell activation in a high responding (BS-269) or a low responding patient (BS-212).
FIG. 12L depicts FACS plots showing FolR1-TCB-induced activation marker expression in T cells from a representative patient. The graphs in FIG. 12M depict the increase in marker expression after FolR1-TCB treatment with mean and standard deviations. As comparison, PBMC from healthy donors were co-cultured with the Skov3 tumor cell line and stimulated with FolR1-TCB.
FIG. 12N depicts IFN-γ, IL-2, TNF and perforin in the cell culture supernatants as determined by Cytometric Bead Array or ELISA and normalized to the amount of $1\times10^5$ $CD3^+$ T-cells (IFN-γ, TNF, IL-2) or $CD3^+$ $CD8^+$ T-cells (perforin) in the culture.
Figure 12C:
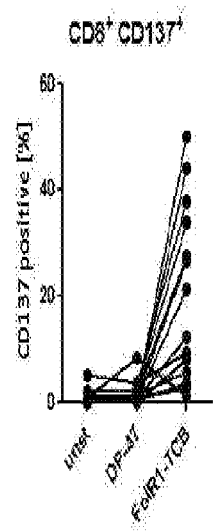
Figure 12D:
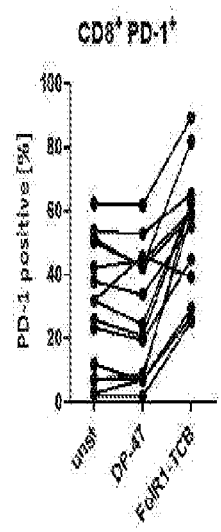
Figure 12E:
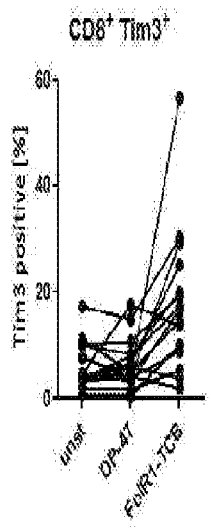
Figure 12F:
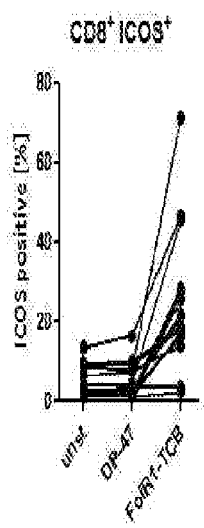
Figure 12G:
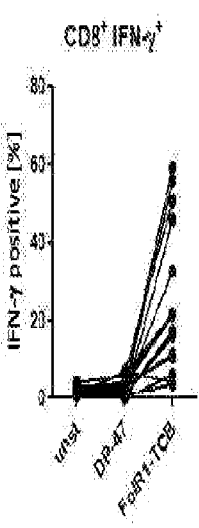
Figure 12H:
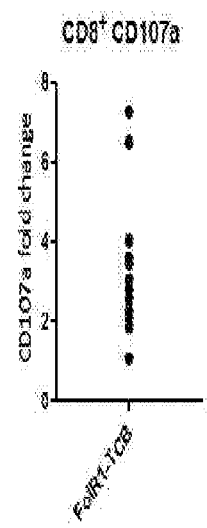
Figure 12I:
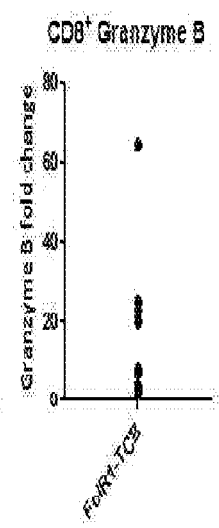
Figure 12J:
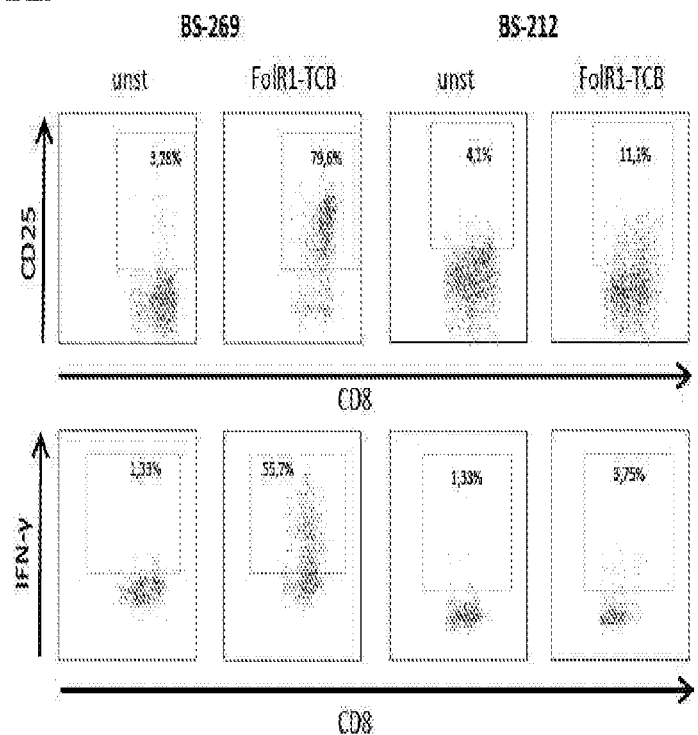
Figure 12K:
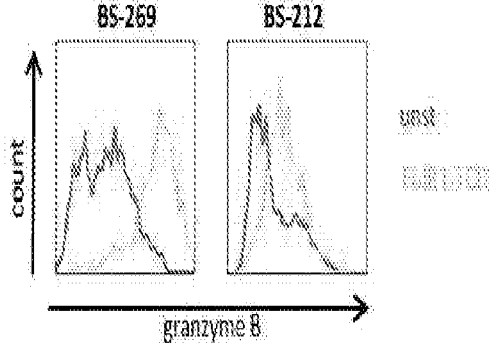
Figure 12L:
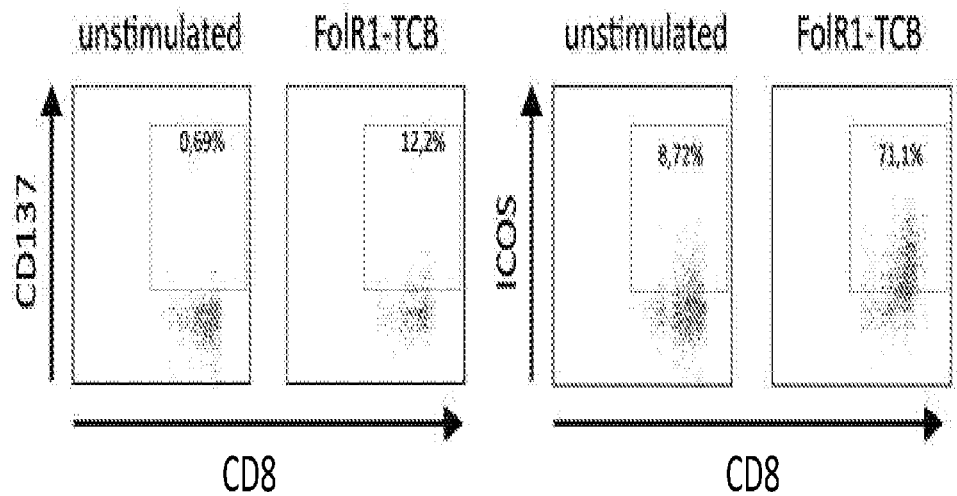
Figure 12M:
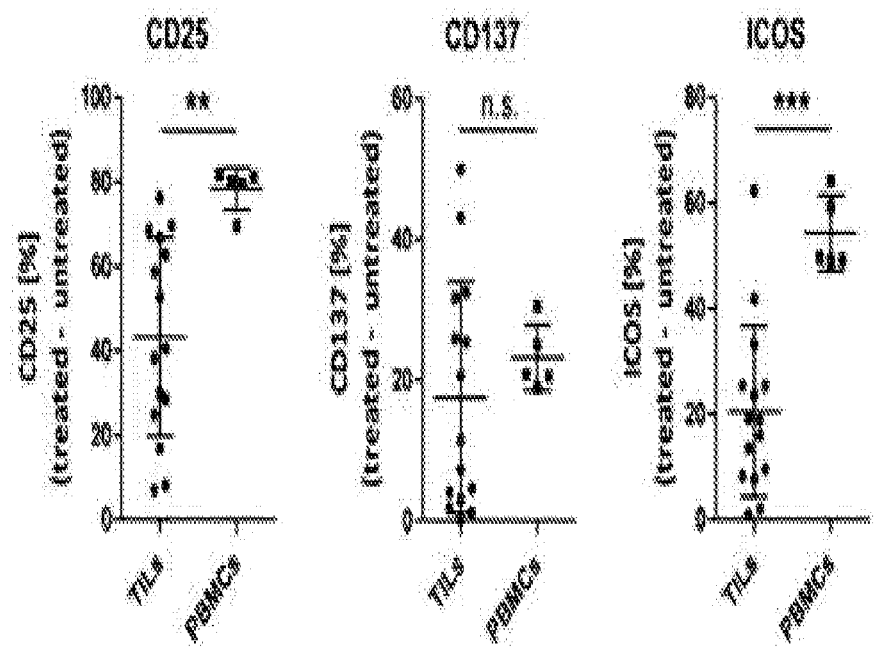
Figure 12N:
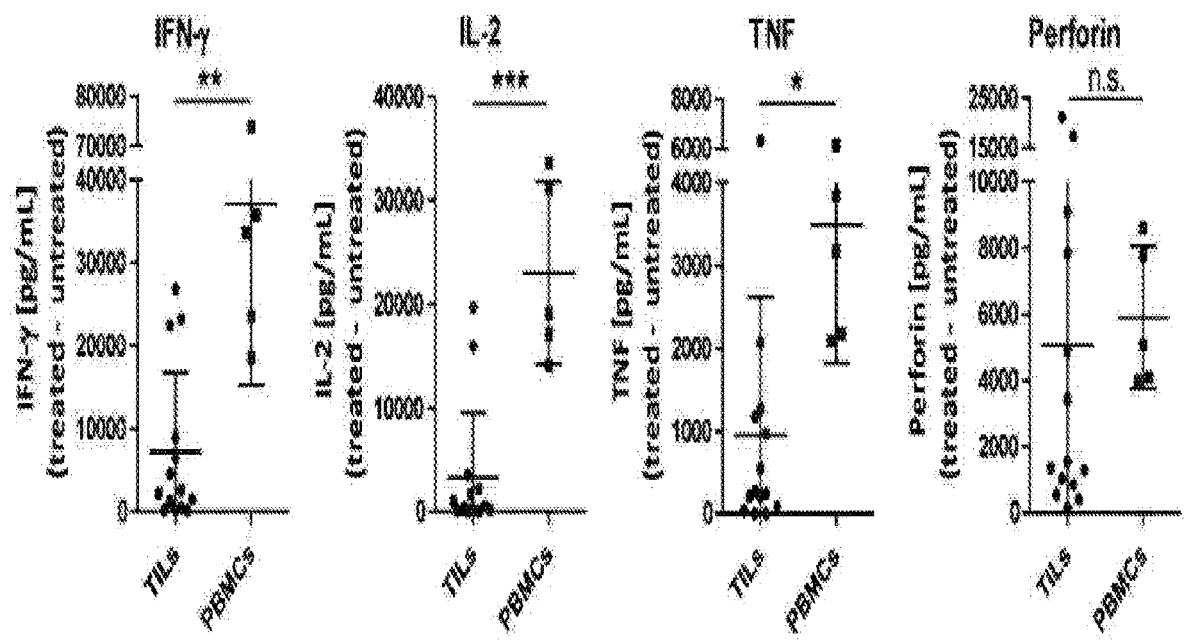
Figure 120:
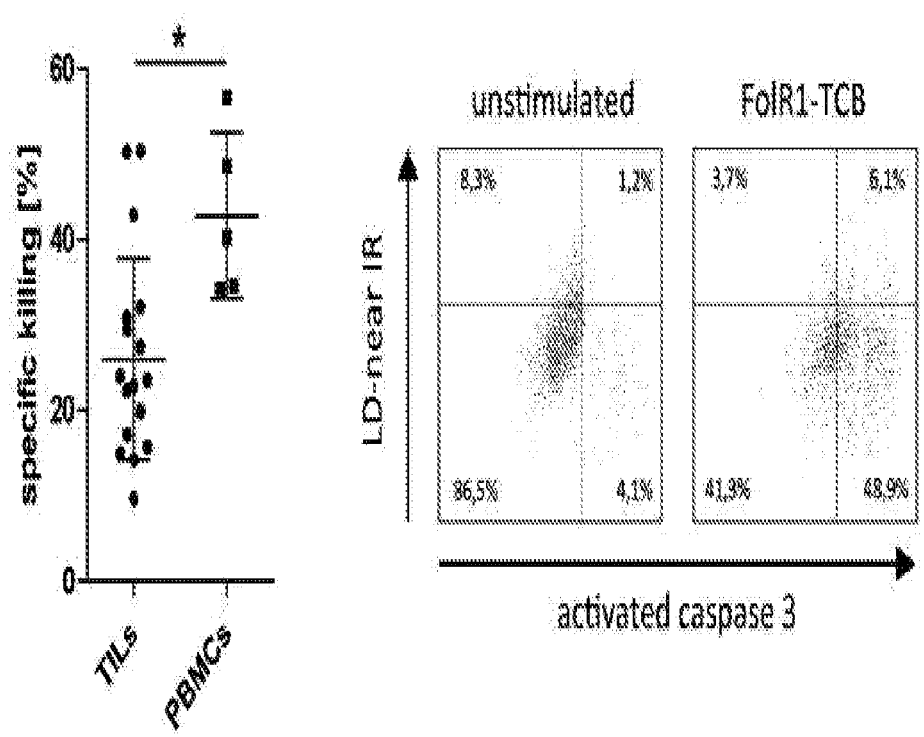

To determine FolR1-TCB induced T cell activation, tumor samples were cultured in the presence or absence of FolR1-TCB or the control TCB DP-47. Then, T cells were characterized by multicolor flow cytometry for expression of activation markers and T cell effector functions, as described above. FIG. 12A-O reveals a large heterogeneity in FolR1-TCB induced T cell activation between patients. In particular, while the vast majority of patients expressed CD69 already at baseline, upregulation of CD25, CD137, and ICOS, varying from 9-80%, 2.5-50% and 3.5-71%, respectively was observed. Acquisition of effector functions such as IFN-γ secretion, CD107 degranulation and expression of granzyme B was observed, ranging from 3.7-59%, a fold change of 1-7 or 1.3-64, respectively (FIG. 12A-I). The inhibitory receptors PD-1 and Tim-3 were further upregulated as a marker of activation upon FolR1-TCB treatment, irrespective of their baseline expression. Exposure to TCB DP-47 did not induce any T cell activation. The upregulation of CD25 and ICOS induced by FolR1-TCB stimulation was significantly stronger in peripheral CD8$^+$ T-cells from healthy donors than for tumor-derived CD8$^+$ cells (p=0.002 and p<0.001, respectively; FIG. 12J, FIG. 12L, FIG. 12M). The secretion of T-cell effector cytokines IFN-γ, IL-2, and TNF upon FolR1-TCB stimulation was largely diminished amongst TILs in the majority of tumors compared with PBMCs from healthy donors (p=0.0047, p<0.001, and p=0.006, respectively; FIG. 12N). FolR1-TCB-induced perforin secretion was highly variable in TILs, and severely impaired in a subset of patients (FIG. 12N).

Figure 13A:
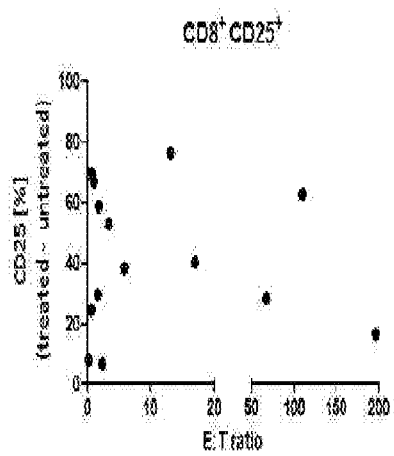
FIGS. 13A-C show that FolR1-TCB-induced T cell activation shows no correlation with E:T ratio (FIG. 13A) or the amount of $FolR1^+$ tumor cells (FIG. 13B). Tumor digests or malignant effusions were cultured for 24 h in the presence or absence of FolR1-TCB. The FolR1-TCB induced expression of CD25 was correlated to E:T ratio or the amount of target cells. MFI: mean fluorescence intensity.
Figure 13B:
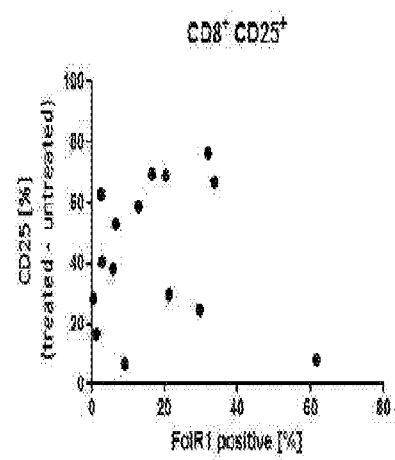
Figure 13C:
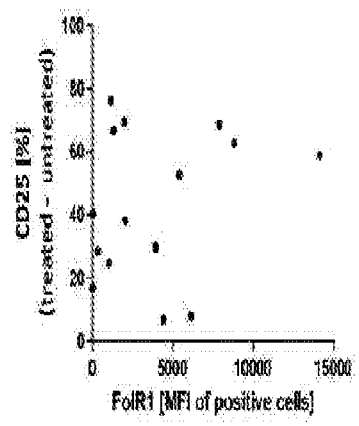

Similarly, despite a lower upregulation of granzyme B, FolR1-TCB induced activation and acquisition of effector functions of CD4$^+$ T cells (FIG. 25A-I). To assess whether the abundance of intra-tumoral T cells or FolR1 expression impacts on T cell activation upon TCB exposure, the upregulation of activation markers was correlated to the E:T ratio (E: effector CD45$^+$CD3$^+$ T cells; T: FolR1$^+$ cells) and to the percentage and to the level of tumor antigen expression of FolR1$^+$ cells (FIG. 13A-C). The latter was determined by the mean fluorescence intensity of FolR1 on tumor cells (CD45$^−$ EpCAM$^+$) using flow cytometry (FIG. 13C). However, neither of these parameters did influence T cell activation, i.e., even low amounts of FolR1$^+$ cells, high E:T ratios, or poor T-cell infiltration have been sufficient for an efficient upregulation of activation and functional markers. In addition, the presence of potentially immune-suppressive cell populations such as regulatory T-cells or immature myeloid cells did not influence T-cell activation or T-cell function.

Example 40

FolR1-TCB Induced T Cell Activation Inversely Correlates with Expression of PD-1 and Tim-3

Figure 14G:
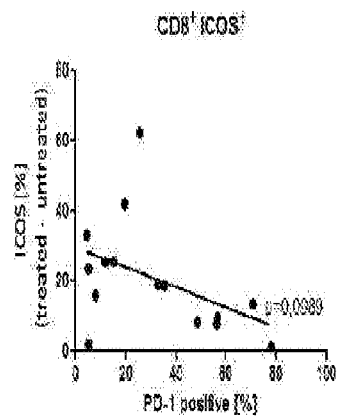
Figure 14H:
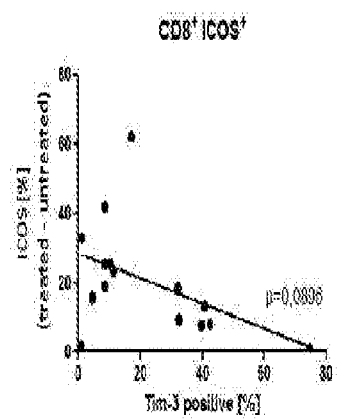
Figure 14I:
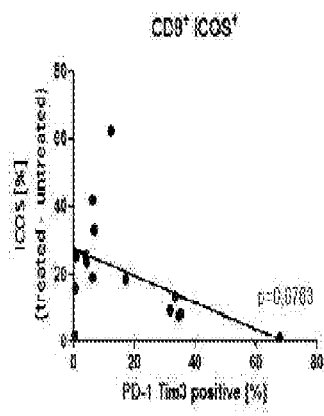
Figure 14J:
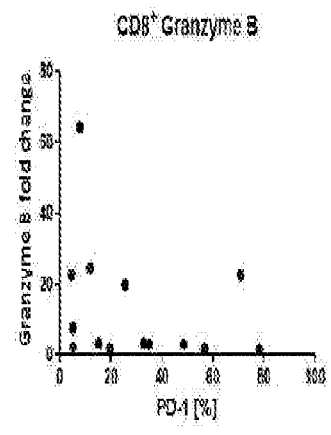
Figure 14K:
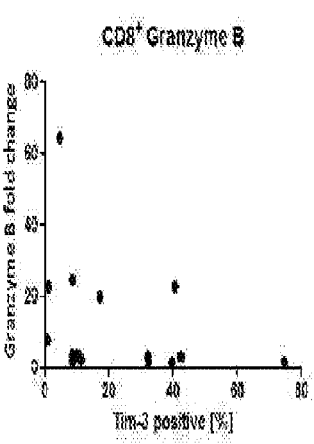
Figure 14L:
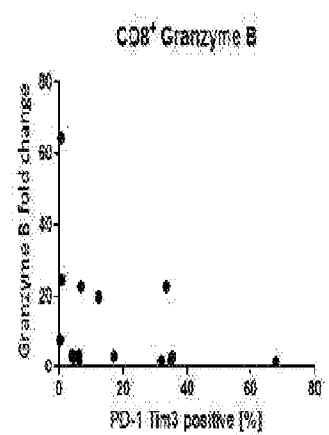
Figure 15A:
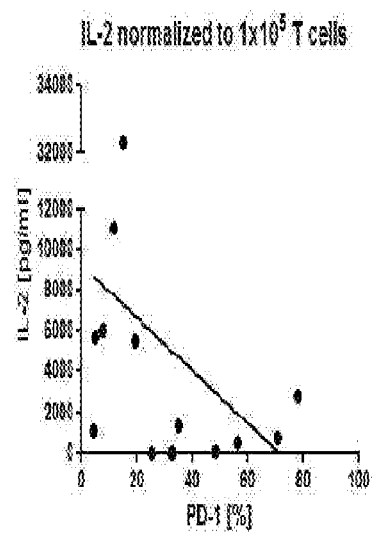
FIGS. 15A-C show FolR1-TCB induced IL-2 secretion inversely correlates with co-expression of PD-1 and Tim-3. Tumor digests or malignant effusions were cultured for 24 h in the presence or absence of FolR1 TCB. IL-2 in the cell culture supernatants was determined by ELISA and normalized to the amount of T cells. The FolR1 TCB induced IL-2 secretion was correlated to baseline single- or co-expression of the inhibitory receptors PD-1 and Tim-3.
Figure 15B:
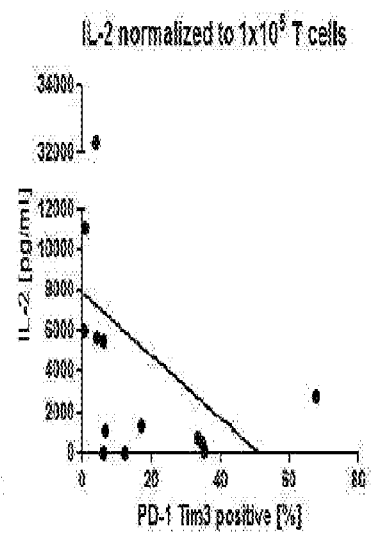
Figure 15C:
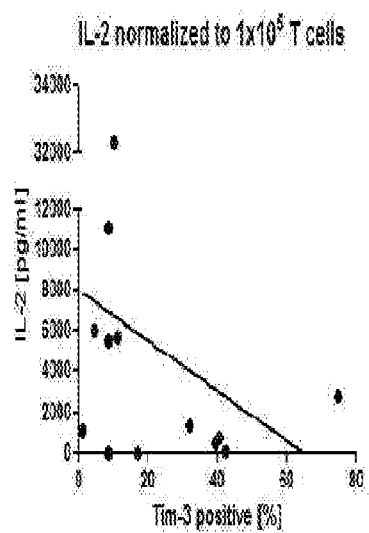
Figure 16A:
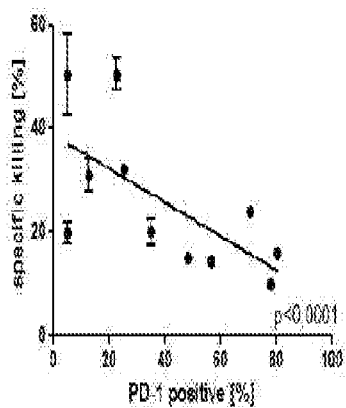
Figure 16B:
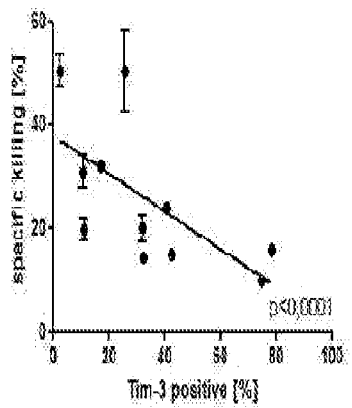
Figure 16C:
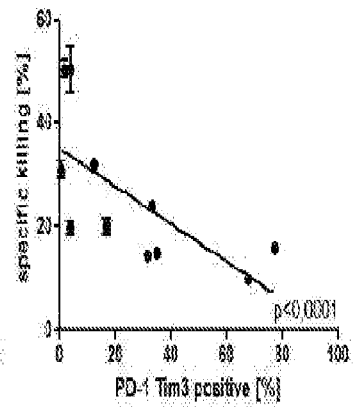
Figure 16D:
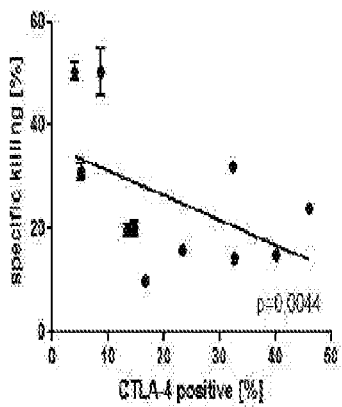
Figure 16E:
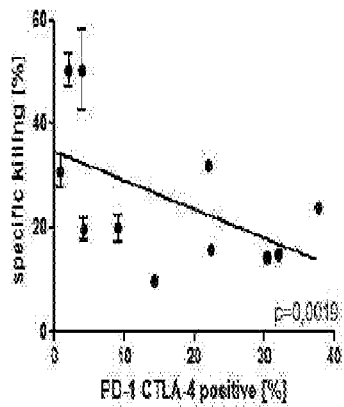
Figure 17A:
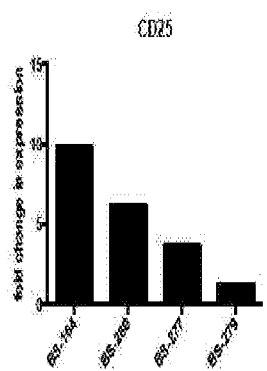
FIGS. 17A-H show activation of tumor-infiltrating $CD8^+$ T cells upon exposure to catumaxomab. Tumor digests or malignant effusions were cultured for 24 h in the presence or absence of catumaxomab.
Figure 17B:
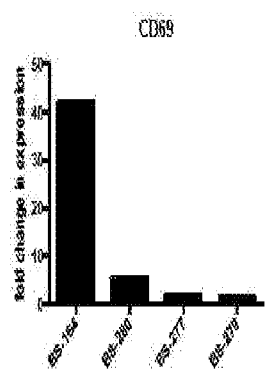
Figure 17C:
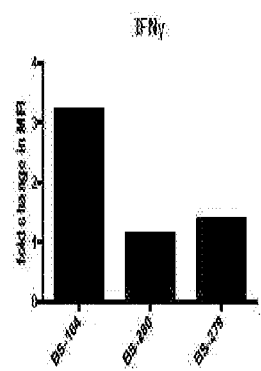
Figure 17D:
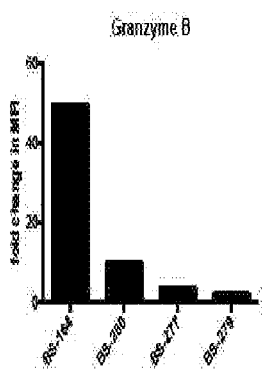
Figure 17E:
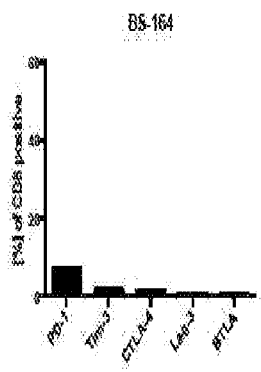
Figure 17F:
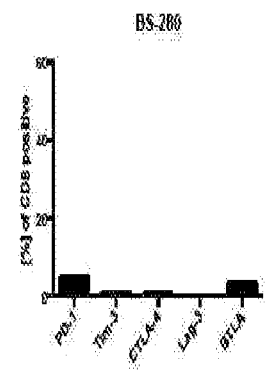
Figure 17G:
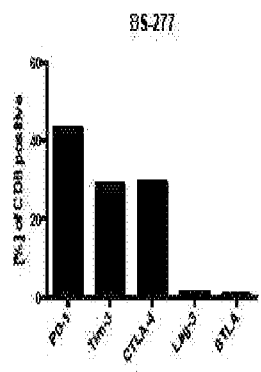
Figure 17H:
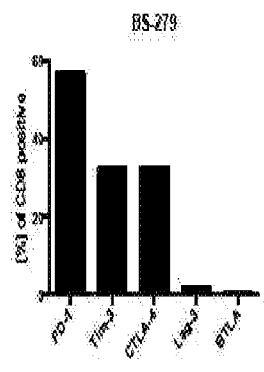
Figure 26A:
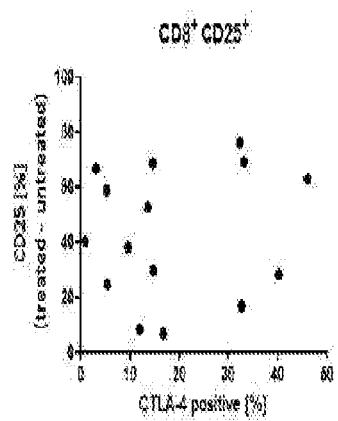
FIGS. 26A-C show FolR1-TCB induced T cell activation is independent of CTLA-4, Lag-3 and BTLA expression. Tumor digests or malignant effusions were cultured for 24 h in the presence or absence of FolR1-TCB. The expression of CD25 on CD8$^+$ T cells was determined by flow cytometry. The FolR1-TCB induced expression of CD25 was correlated to baseline expression of CTLA-4, Lag-3 and BTLA.
Figure 26B:
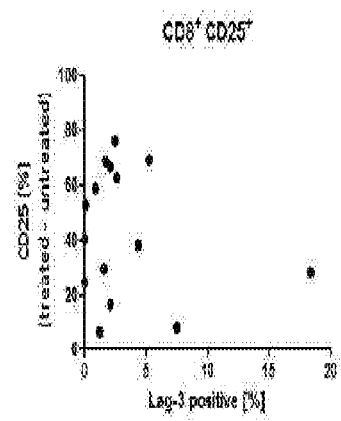
Figure 26C:
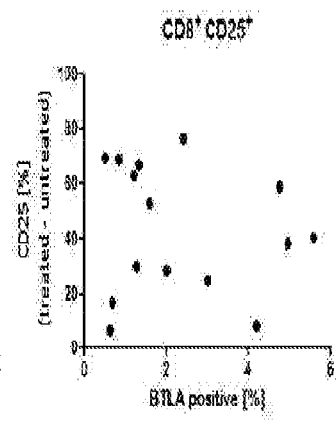

High expression of inhibitory receptors has been described as a hallmark of exhausted T cells. Therefore, a dysfunctional state of tumor-infiltrating T cells may impact efficacy of the FolR1 TCB and may be responsible, at least in part, for heterogeneous T cell activation upon TCB exposure. To this end, the co-expression of inhibitory receptors, as determined at baseline, was correlated to FolR1 TCB induced upregulation of activation markers and T cell effector functions. Both PD-1 and Tim-3 expression on $CD8^+$ T cells thereby negatively correlated with T cell activation determined by expression of CD25, CD137 and ICOS. $CD8^+$ T cells with a high expression of PD-1 or Tim-3 showed a marginal effect upon FolR1-TCB treatment, while T cells with a low expression of these inhibitory receptors could be strongly activated upon treatment with FolR1-TCB (FIG. 14A-I). Measurement of FolR1-TCB induced IL-2 secretion normalized to the content of T cells in the samples revealed the same dependencies on PD-1 and Tim-3 expression (FIG. 15A-C), while FolR1-TCB induced upregulation of granzyme B was less dependent on prior expression of these inhibitory receptors (FIG. 14J-L). Interestingly, the baseline expression of CTLA-4, Lag-3 and BTLA on $CD8^+$ T cells did not correlate with FolR1-TCB induced T cell activation (FIG. 26A-C). Expression of inhibitory receptors on $CD4^+$ T cells was much less predictive for FolR1-TCB induced $CD4^+$ T cell activation compared to the expression of the same receptors on $CD8^+$ T cells.

Example 41

FolR1-TCB Induced Tumor Cell Killing Inversely Correlates with Expression of PD-1 and Tim-3

To investigate FolR1-TCB induced killing of tumor cells at an adjusted E:T ratio of 1:1, CFSE-labelled Skov3 cells were exogenously added to the tumor digests which contain a previously determined amount of $CD3^+$ T cells using multicolor flow cytometry. FolR1-TCB induced killing of Skov3 cells was determined by measuring activated caspase 3 and a live/dead marker. In line with the FolR1-TCB induced T cell activation as measured by CD25 up-regulation, the specific killing upon FolR1-TCB exposure negatively correlated with single or co-expression of PD-1 and Tim-3 on $CD8^+$ T cells. Furthermore, FolR1-TCB induced killing was also influenced by the baseline expression of CTLA-4 and the co-expression of PD-1 and CTLA-4. However, the impact of CTLA-4 expression on FolR1-TCB induced tumor cell killing was less pronounced compared to PD-1 and Tim-3 expression.

Example 42

Treatment of Fresh Tumor Lesions with Catumaxomab—Activation of Tumor-Infiltrating T Cells Using Catumaxomab and Correlation with Expression of Inhibitory Receptors To determine to which extent catumaxomab induces T cell activation and to confirm the findings described above using a second, independent T cell bispecific molecule, 4 tumor digests from patients with NSCLC were exposed to catumaxomab, a trifunctional bispecific antibody recognizing CD3 on T cells and EpCAM on tumor cells. Then, T cells were characterized by flow cytometry for expression of activation markers and T cell effector functions (FIG. 17A-D). Validating our data above for FolR1-TCB, we observed a striking heterogeneity in catumaxomab induced T cell activation. Accordingly, the baseline expression of inhibitory receptors differed between the patients (FIG. 17E-H).

Figure 18A:
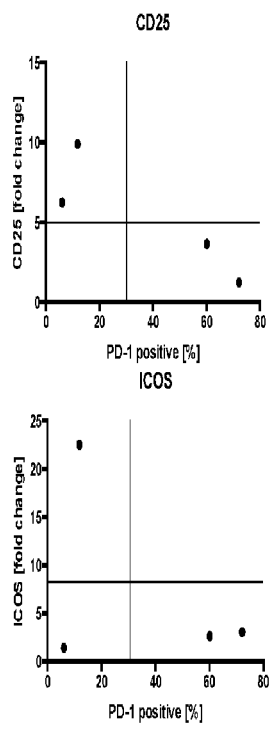
FIGS. 18A-R show Catumaxomab-induced T cell activation inversely correlates with co-expression of inhibitory receptors. Tumor digests or malignant effusions were cultured for 24 h in the presence or absence of catumaxomab. T cell activation and effector functions were correlated to the expression of PD-1 (FIG. 18A-F), Tim-3 (FIG. 18G-L) or of the combination of PD-1 and Tim-3 (FIG. 18M-R).
Figure 18B:
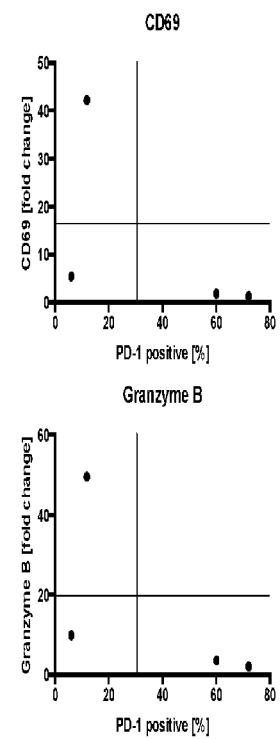
Figure 18C:
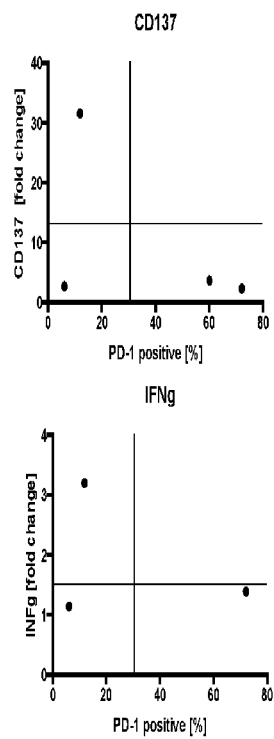
Figure 18D:
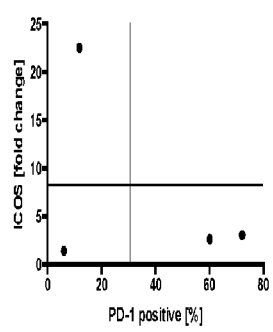
Figure 18E:
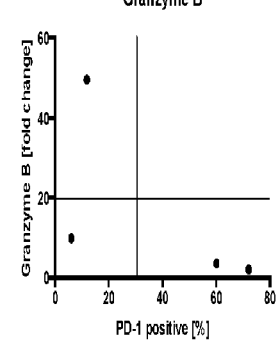
Figure 18F:
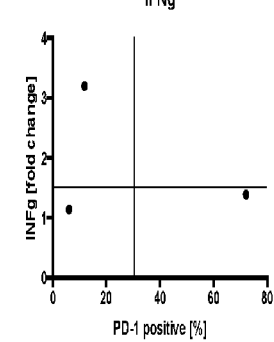

Analysis of T cell activation and effector function upon treatment with catumaxomab revealed two groups of patients according to PD-1 and/or Tim-3 expression on $CD8^+$ T cells confirming our findings with FolR1-TCB (FIG. 18A-R). $PD-1^{low}$, $Tim-3^{low}$, and, even more pronounced, both $PD-1^{low}/Tim-3^{low}$ expressing cells, failed to be activated by catumaxomab, whereas $PD-1_{high}$, $Tim-3^{high}$, and $PD-1^{high}/Tim-3^{high}$ T cells substantially upregulated CD25, CD69, CD137, ICOS, granzyme B and IFN-γ.

Example 43

Figure 19A:
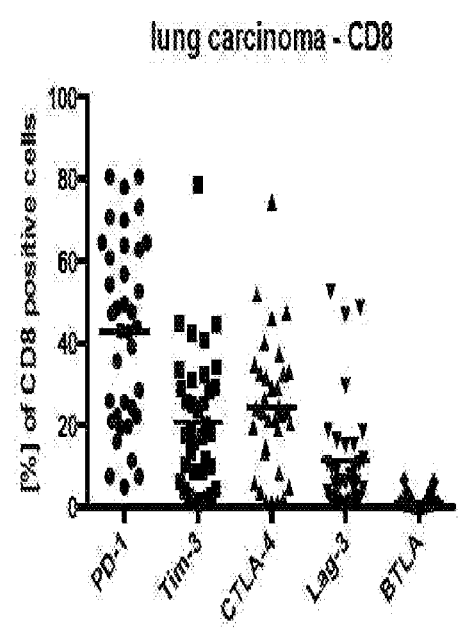
FIGS. 19A-H show expression of inhibitory receptors on tumor-infiltrating T cells in Non-small cell lung cancer patients. $CD8^+$ and $CD4^+$ T cells in tumor samples were characterized by flow cytometry for their expression of inhibitory receptors (FIG. 19A-F).
Figure 19B:
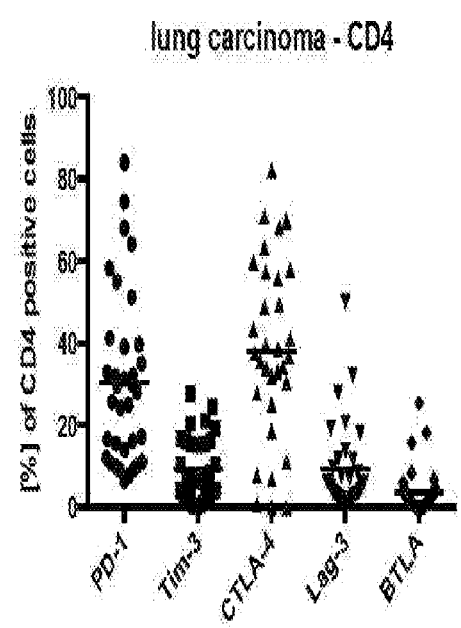
Figure 19C:
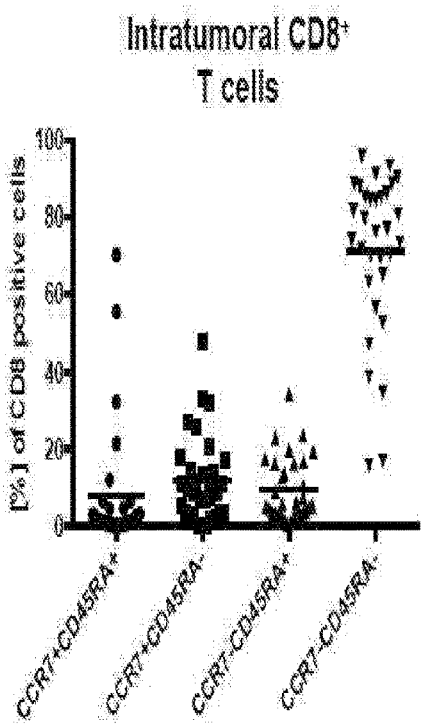
Figure 19D:
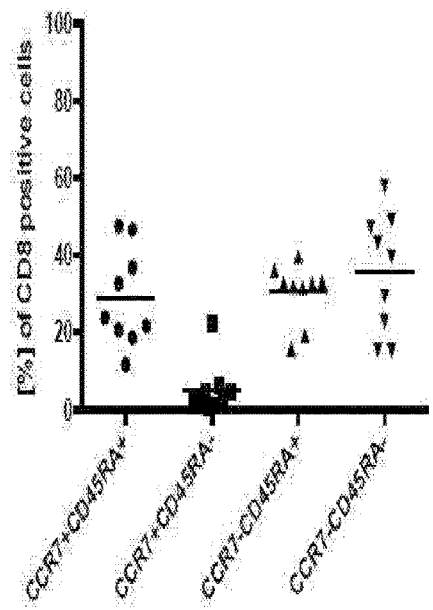
Figure 19E:
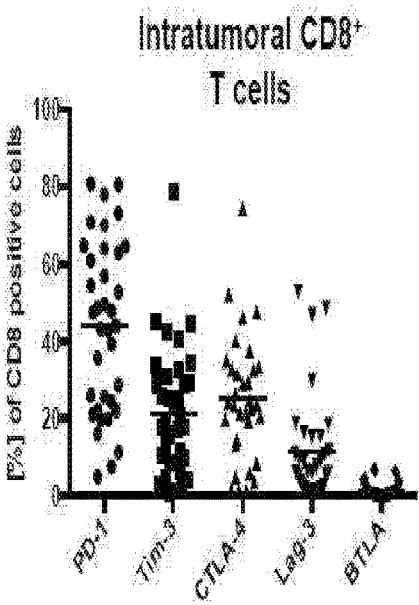
Figure 19F:
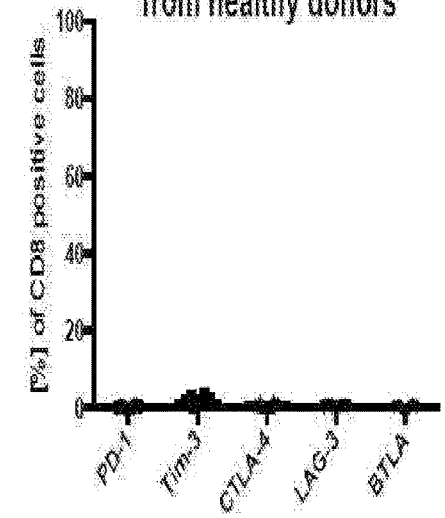
Figure 19G:
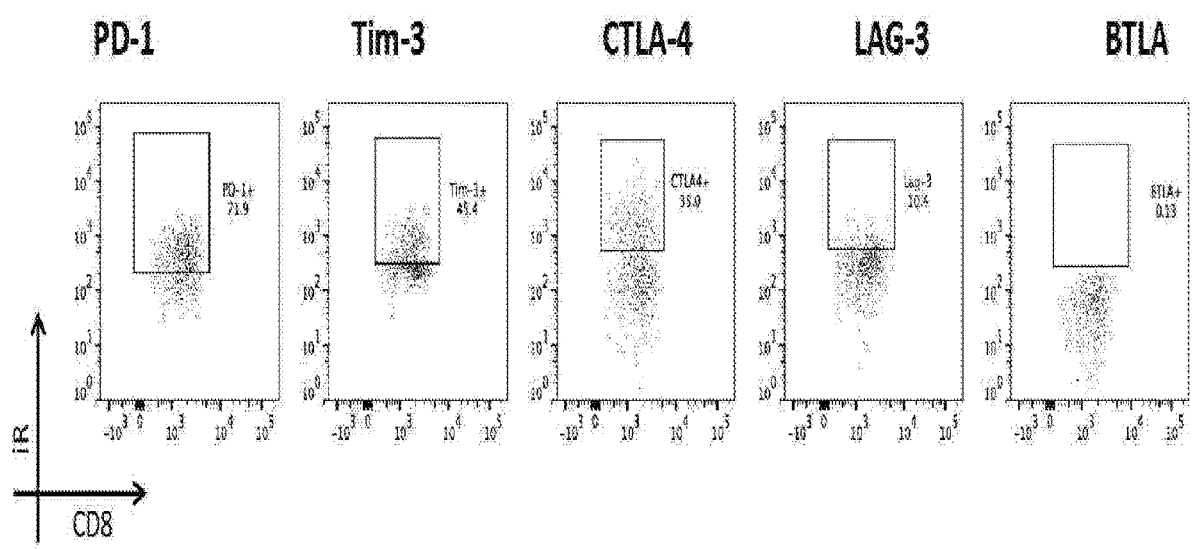
Figure 19H:
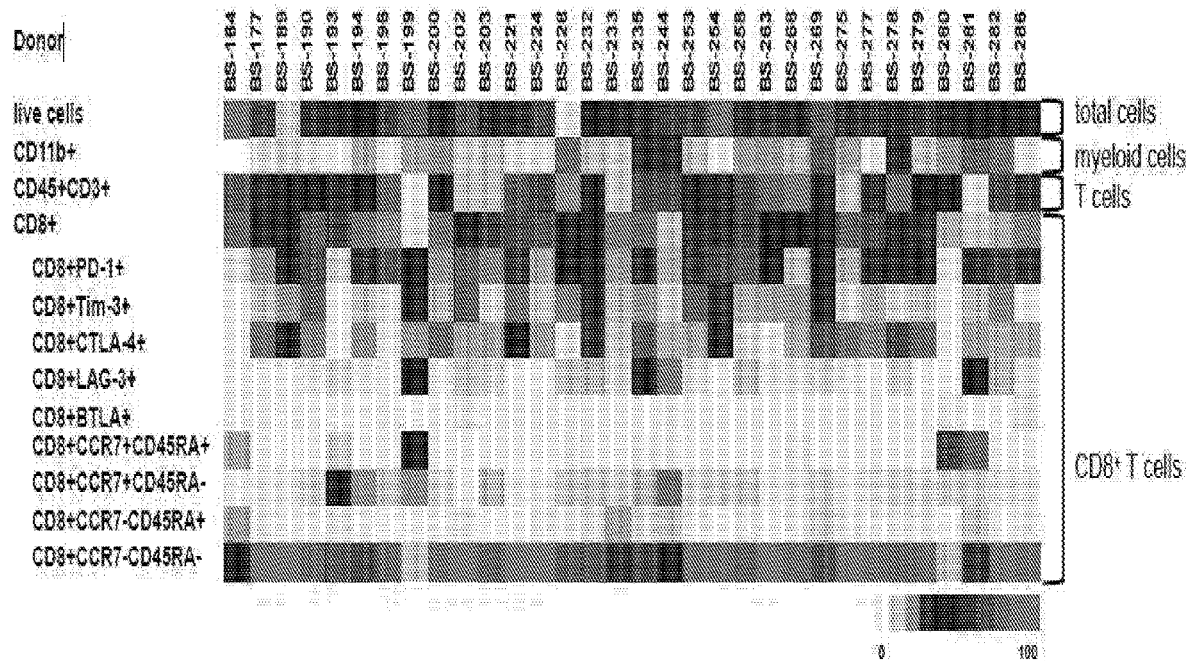

Polyclonal Stimulation of Tumor-Infiltrating T Cells by CD3/CD28—Immune Phenotyping of Tumor-Infiltrating T Cell Subsets in Non-Small Cell Lung Cancer Samples We investigated the expression of co-inhibitory T cell receptors and differentiation markers on tumor-infiltrating $CD3+CD8^+$ and $CD3+CD4^+$ T cell subsets from 34 patients NSCLC using multicolor flow cytometry. The majority of tumors showed a high expression of the inhibitory receptor PD-1 (FIG. 19A-B), a major regulator of T cell exhaustion. Of note, expression of other checkpoint inhibitors such as Tim-3, CTLA-4, LAG-3 or BTLA showed substantial variation between T cells obtained from different tumors (FIG. 19A-B).

Example 44

Cumulative Expression of Inhibitory Receptors Defines T Cell Dysfunction

Figure 20A:
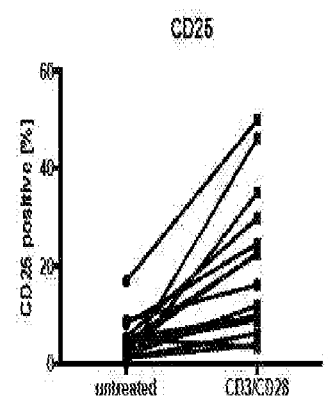
FIGS. 20A-E show T cell activation and effector functions upon polyclonal stimulation by CD3/CD28 antibodies. Expression of CD25 and Granzyme B (FIG. 20A-B) as well as IL-2, IFN-γ and TNF-α (FIG. 20C-E) as markers for T cell activation and effector function, respectively, was analyzed in T cells from digested tumor samples after stimulation of whole tumor digests with agonistic CD3 and CD28 antibodies.
Figure 20B:
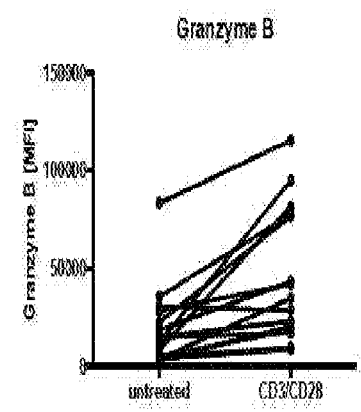
Figure 20C:
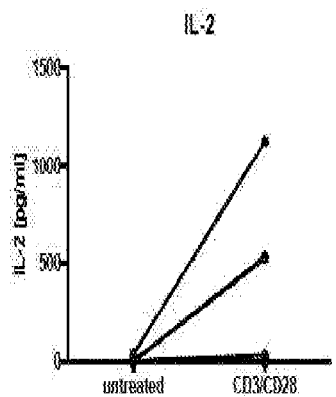
Figure 20D:
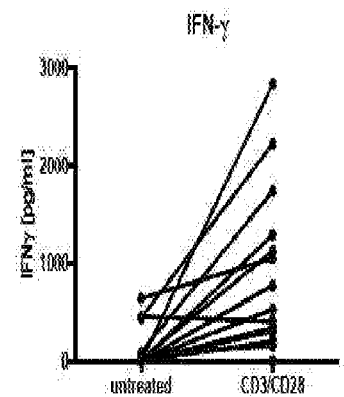
Figure 20E:
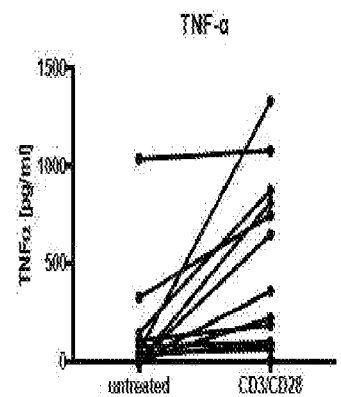

In this Example, polyclonal stimulation was used in a sub-optimal dose to assess the impact of inhibitory receptors on T cell function. The effect of stimulation with agonistic anti-CD3 and anti-CD28 antibodies on T cell activation, as exemplified by CD25 expression, and on T cell effector function as analyzed by IFN-γ, TNF-α and IL-2 production as well as granzyme B expression varied substantially between patients as determined by flow cytometry (FIG. 20A-B) and ELISA (FIG. 20C-E). Of note, we observed different levels of T cell function, varying from T cell populations that exhibit a largely preserved T cell function (i.e., sustained CD25 and granzyme B expression, as well as IL-2, IFN-γ and TNF-α production) to those with abrogated T cell function (loss of CD25 and granzyme B expression and of cytokine production).

Figure 21A:
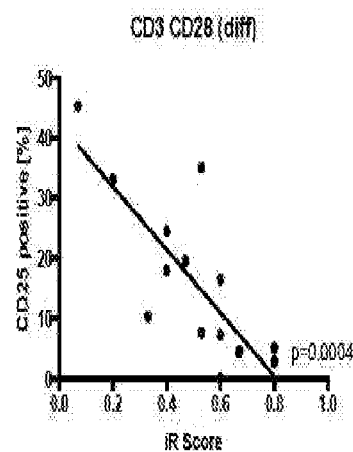
FIGS. 21A-N show expression of inhibitory receptors and T cell dysfunction. Expression of CD25 and Granzyme B (FIG. 21A-B) as well as IL-2, IFN-γ and TNF-α (FIG. 21C-E) upon polyclonal stimulation by an anti-CD3/anti- CD28 antibodies correlates with the cumulative expression of inhibitory receptors indicated by the iR Score.
Figure 21B:
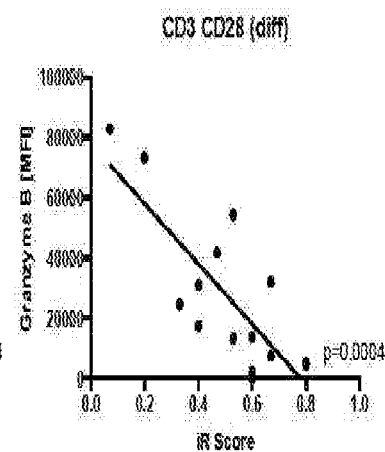
Figure 21C:
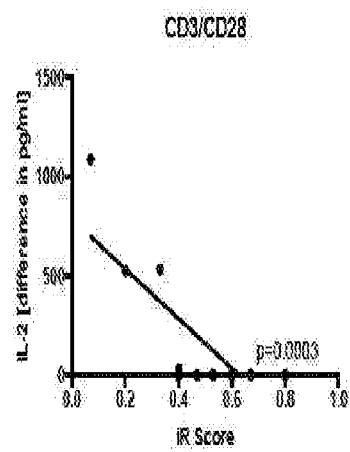
Figure 21D:
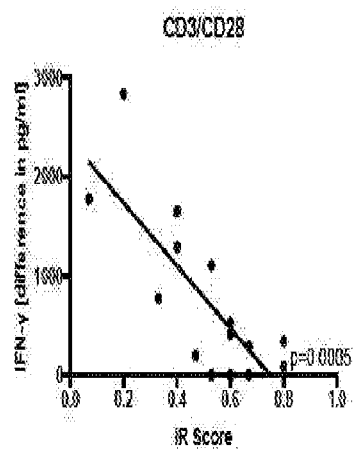
Figure 21E:
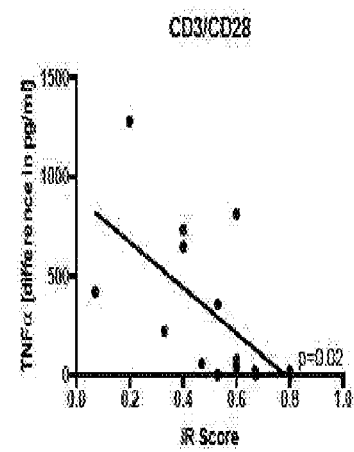
Figure 21F:
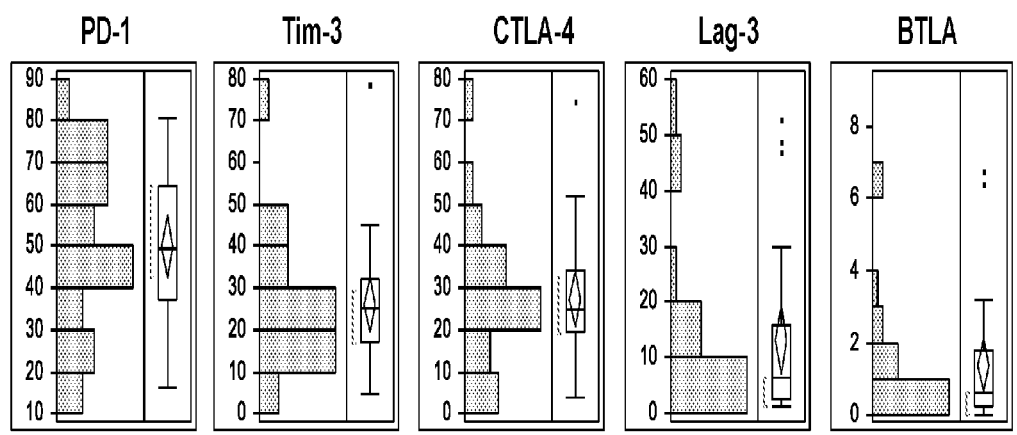
FIG. 21F shows an exemplary calculation of iR scores. The percentage of expression of PD-1, Tim-3, CTLA-4, LAG-3 and BTLA was analyzed in all NSCLC samples and the median as well as interquartile ranges were determined. For the calculation of the iR score each patient received points for the expression of each of the determined inhibitory receptors based on the quartile within which the expression coincided. A maximum of 15 points could be reached; the calculated score of each sample was normalized to this maximum amount of points.
Figure 21G:
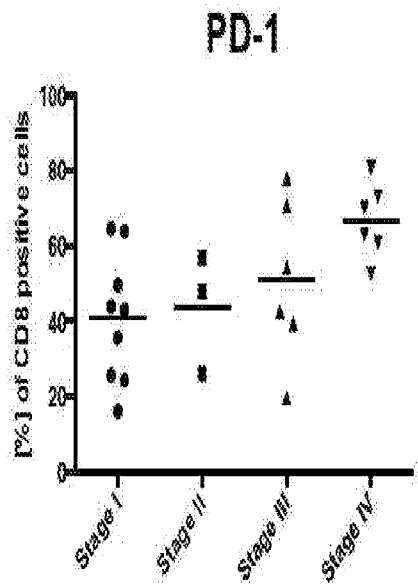
FIG. 21G-K show expression of inhibitory receptors increases with tumor stage. Expression of inhibitory receptors on CD8$^+$ tumor infiltrating T-cells was correlated to the TNM stage.
Figure 21H:
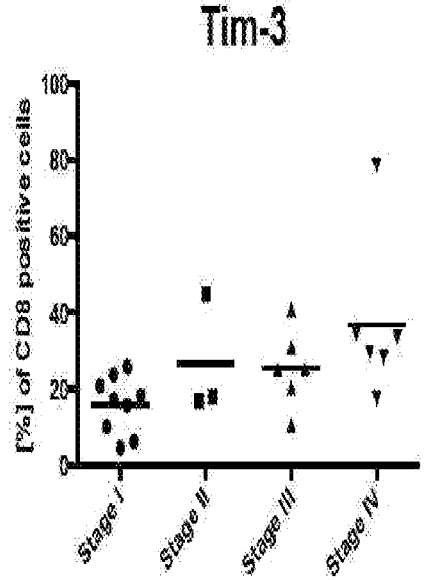
Figure 21I:
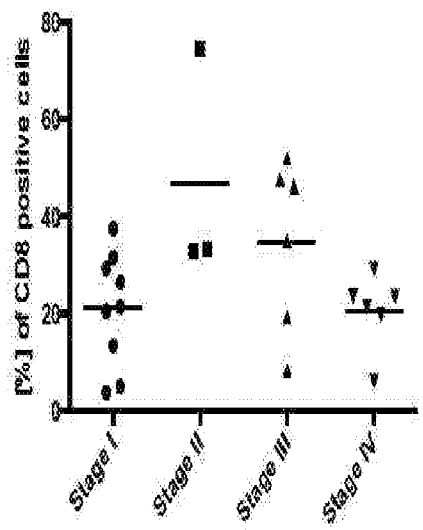
Figure 21J:
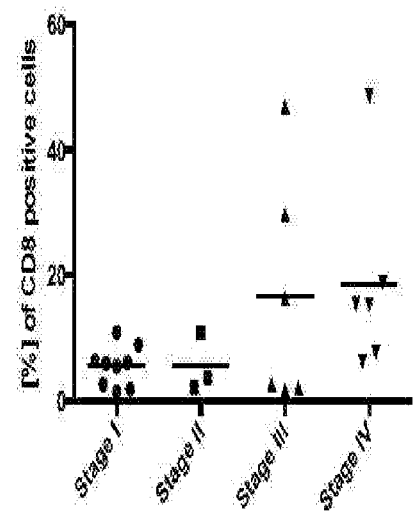

To analyze the impact of multiple inhibitory receptors on T cell functionality we defined the inhibitory receptor (iR) score as a marker for the cumulative expression of inhibitory receptors on T cells. To this end, the percentage of expression of PD-1, Tim-3, CTLA-4, Lag-3 and BTLA was analysed in all NSCLC samples and a score based on the median and interquartile ranges of each expressed receptor was defined and calculated for each sample (e.g., FIG. 21F). Tumor-infiltrating $CD8^+$ T cells expressing a high iR score indicating expression of multiple inhibitory receptors showed a marginal effect upon polyclonal stimulation, correlating with their highly dysfunctional state, whereas T cells with a low iR score could be strongly activated upon polyclonal stimulation (FIG. 21A-E). Upregulation of T cell effector functions, indicated by IL-2, IFN-γ and TNF-α production, not only correlated with the cumulative expression of inhibitory receptors but similarly with PD-1 and Tim-3 expression as well with the co-expression of both receptors (FIG. 22A-I), indicating a significant contribution of PD-1 and Tim-3 to T cell dysfunction.

Example 45

Inhibitory Receptor Expression

Figure 21K:
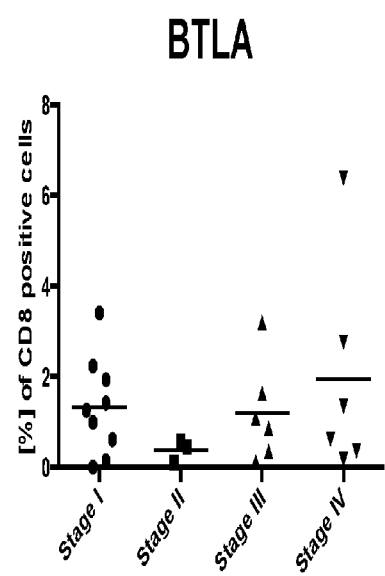
Figure 21L:
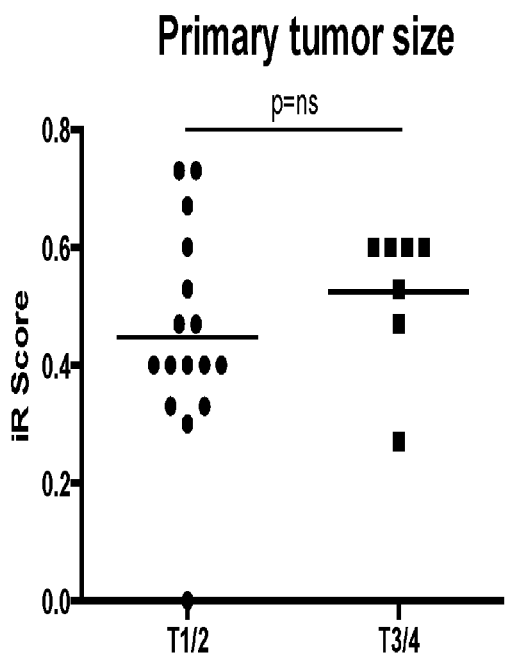
Figure 21M:
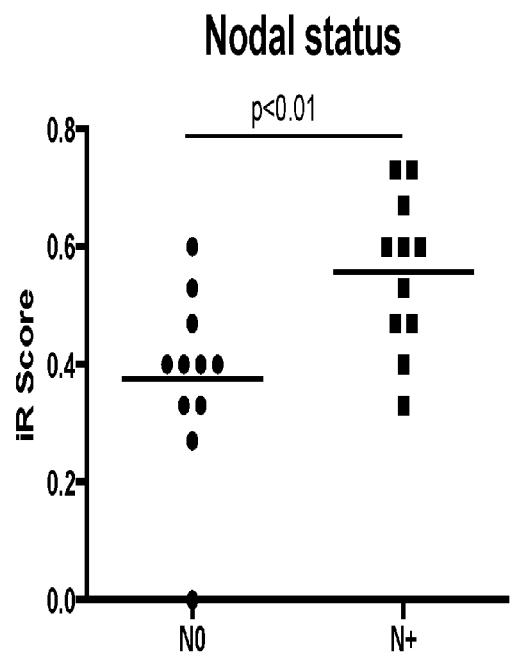
Figure 21N:
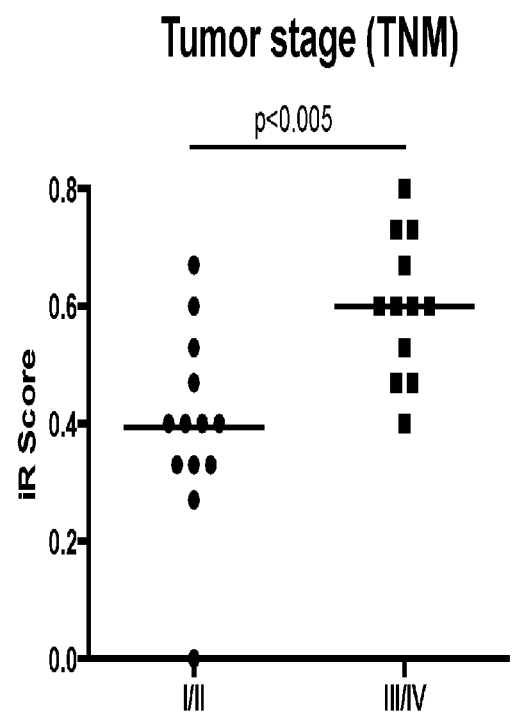
Figure 22A:
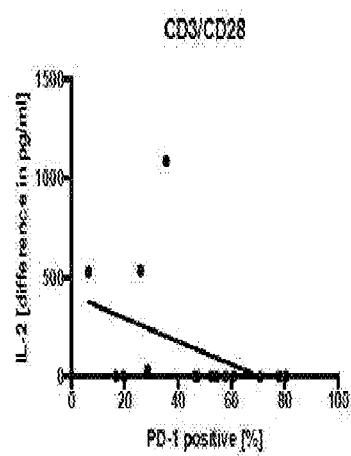
FIGS. 22A-I show expression of PD-1 and Tim-3 correlates with T cell dysfunction. Expression of CD25 and Granzyme B (FIG. 22A-C) as well as IL-2, IFN-γ and TNF-α (FIG. 22D-F) upon polyclonal stimulation by CD3/CD28 correlates with the expression of PD-1 (FIG. 22A-C), Tim-3 (FIG. 22D-F) or PD-Tim-3 (FIG. 22G-I) on tumor-infiltrating T cells.
Figure 22B:
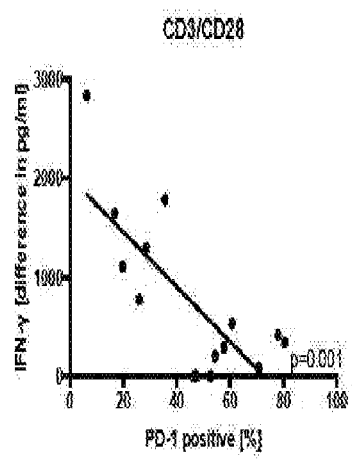
Figure 22C:
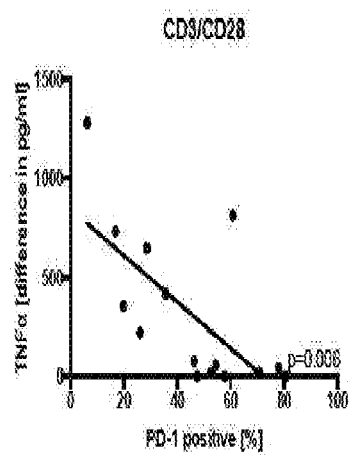
Figure 22D:
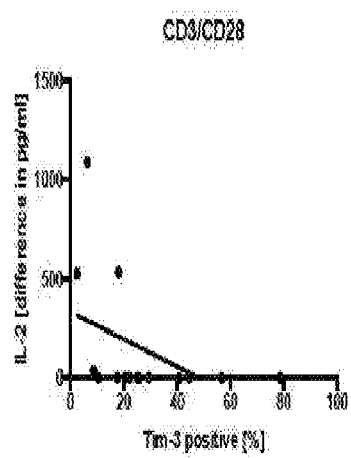
Figure 22E:
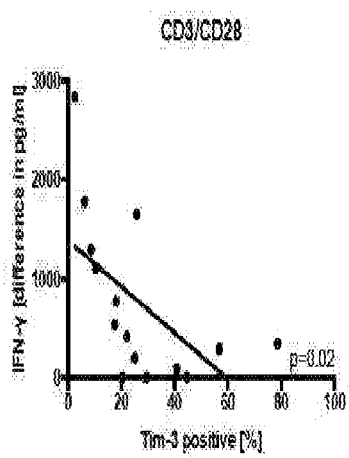
Figure 22F:
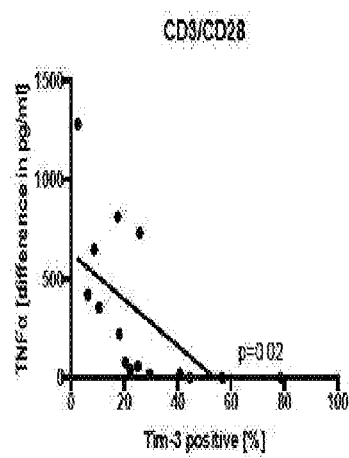
Figure 22G:
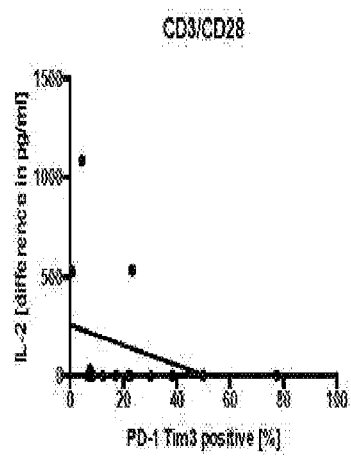
Figure 22H:
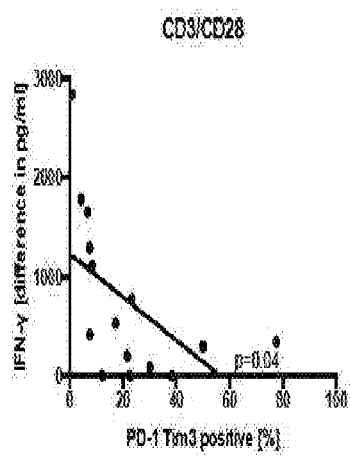
Figure 22I:
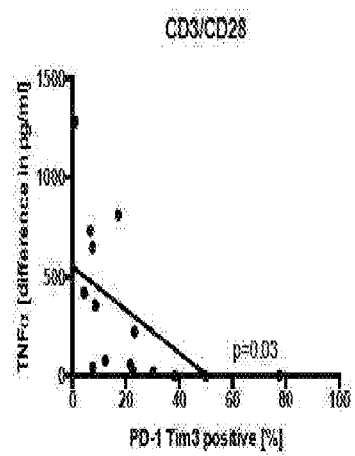
Figure 23A:
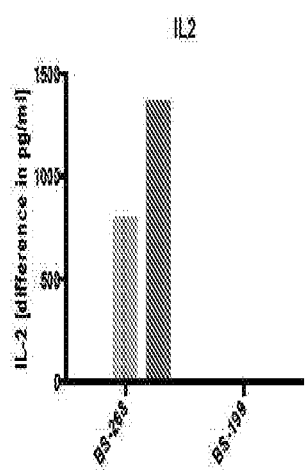
Figure 23B:
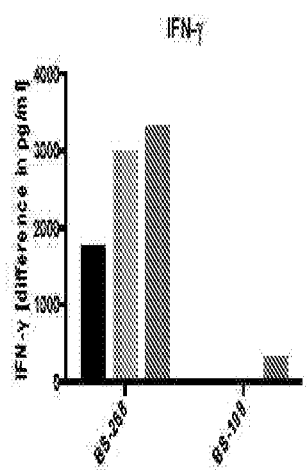
Figure 23C:
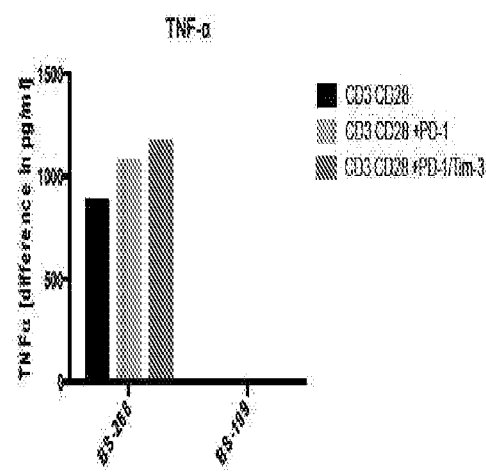
Figure 23E:
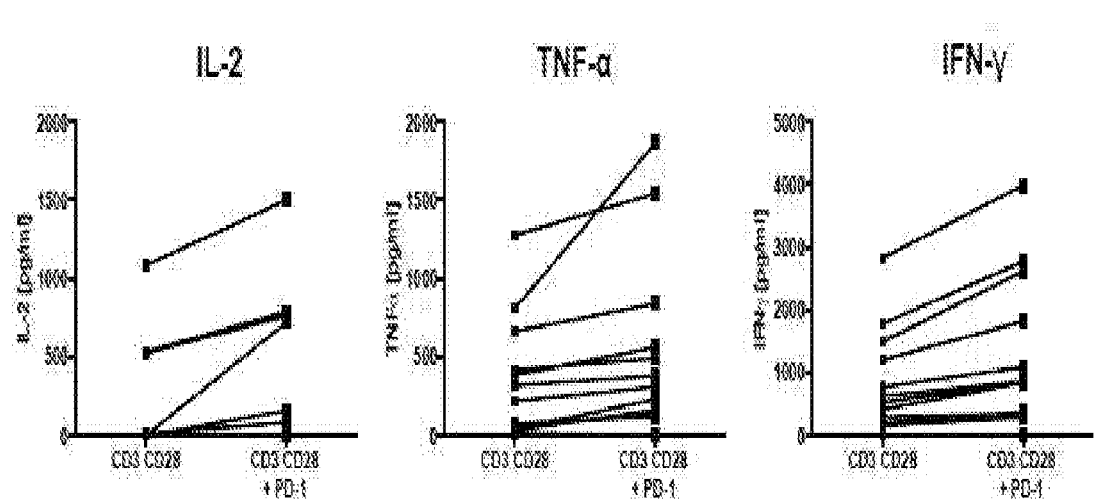

Single and cumulative expression of inhibitory receptors increases with tumor progression. The expression of inhibitory receptors correlated with tumor stage and tumor progression. The number of PD-1, Tim-3 and LAG-3 positive cells was clearly increased in advanced tumor stages (FIG. 21G-K). No clear correlation was observed for the expression of CTLA-4, which may indicate that this receptor acts via a different inhibitory mechanism. BTLA was generally expressed at a low level and only a small increase was found in advanced tumor stages (FIG. 21K). A significant increase in the cumulative expression of inhibitory receptors, as reflected by the iR score, was observed in patients with nodal positive cancers and advanced tumor stages whereas primary tumor size did not significantly correlate with the iR score (FIG. 21L-M). These data suggest a gradual and continuous upregulation of inhibitory receptors, during tumor progression, which are most likely involved in T cell exhaustion in NSCLC.

Figure 32:
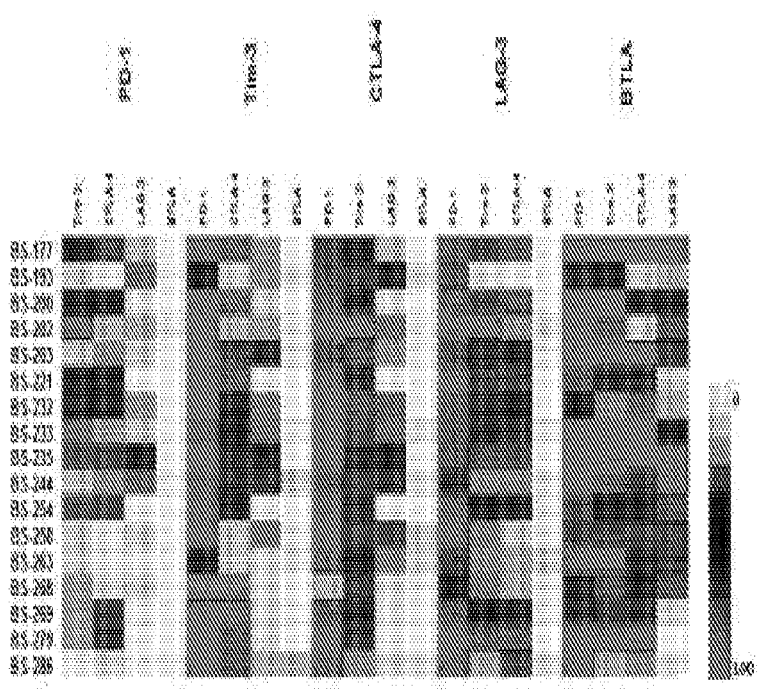
FIG. 32 shows a heat map of expression of inhibitory receptors on NSCLC associated TILs. Co-expression of inhibitory receptors on tumor-infiltrating CD8$^+$ T-cells positive for the indicated immune checkpoint is shown as a heat map displaying the percentage of expression for the additional receptors.

Inhibitory receptors are gradually expressed on tumor-infiltrating T cells. To explore the role of simultaneous expression of distinct inhibitory receptors on single T cells, the concomitant expression of these receptors in CD8$^+$ T cells (FIGS. 32, 33) relative to the expression of any of the five analyzed receptors was analyzed. Expression is shown as heat map, displaying the percentage of expression for the individual patients (FIG. 32) or as a radar plot, which shows the expression as mean and standard deviation of the four respective receptors on CD8$^+$ T cells, pregated for the fifth, indicated immune checkpoint (FIG. 33). CD8$^+$PD-1$^+$ T cells on average expressed the lowest percentages of other inhibitory receptors, whereas CD8$^+$BTLA$^+$ T cells expressed all of the four other inhibitory receptors at high levels, indicating that BTLA marks a particularly exhausted T cell subset (FIGS. 32, 33). An increase in the number of co-expressed inhibitory receptors was observed from CD8$^+$Tim-3$^+$ T cells over CD8$^+$CTLA-4$^+$ T cells to CD8$^+$LAG-3$^+$ T cells (FIGS. 32, 33). These findings suggest a gradual acquisition of inhibitory receptors with PD-1 as a broadly expressed, early marker, while BTLA is upregulated rather late during T cell exhaustion.

Example 46

Blockade of PD-1 can Partially Restore T Cell Function

Rescue of T cell function by PD-1 blocking antibodies depends on the level of PD-1 expression. As we found a clear correlation between the expression of inhibitory receptors, particularly PD-1 and Tim-3, and T cell activation upon polyclonal stimulation, blockade of the PD-1 or PD-1/Tim-3 pathways might restore T cell function. However, addition of a blocking antibody to PD-1 (5C4) or combined blockade of PD-1 and Tim-3 upon stimulation with agonistic anti-CD3 and anti-CD28 antibodies could restore T cell effector function such as production and secretion of IL-2, IFN-γ and TNF-α only in some patients whereas in other patients only a marginal effect was seen (FIG. 23A-D). As observed in a chronic murine LCMV infection model (Blackburn et al., PNAS 105(39):15016 (2008)), we identified PD-1$^{hi}$ and PD-1$^{int}$ subsets in tumor-infiltrating CD8$^+$ T cells from NSCLC patients. In brief, PD-1$^{hi}$, PD-1$^{int}$, and PD-1$^{neg}$ subsets could be identified based on their measured fluorescence intensity. Cells from 33 patients were analysed for PD-1 expression to define uniform parameters for reproducible discernment of the three subsets. The analysis covered the whole spectrum of PD-1 expression levels and included tumor samples with clearly distinguished PD-1$^{neg}$ or PD-1$^{hi}$ populations. This allowed to set the gates for this analysis, which was then applied to all samples.

Only PD-1$^{int}$ expressing T cell subsets appeared to be rescued in activation upon PD-1 or combined PD-1/Tim-3 blockade, while no effect in T cell activation was observed upon blockade in PD-1$^{hi}$ cells (FIG. 24). The latter may exhibit a more exhausted phenotype which appears to be resistant to PD-1 blockade alone.

This finding was confirmed in T cells activated by FolR1 TCB. T cells were stimulated with FolR1 as described above. Blockade of PD-1 further strengthened FolR1-TCB induced T cell activation of T cells from a subset of patients.

Figure 27A:
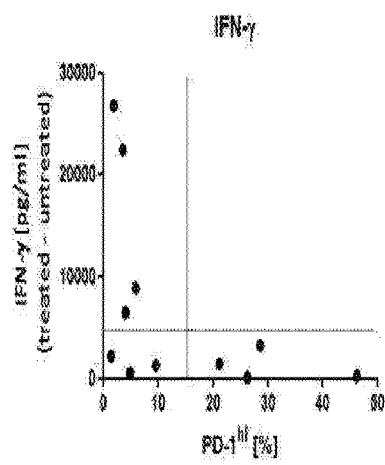
FIGS. 27A-C show FolR1-TCB induces cytokine secretion only in patients with a low percentage of PD-1$^h$ expressing CD8$^+$ T cells. Tumor digests or malignant effusions were cultured for 24 h in the presence or absence of FolR1-TCB. IFN-γ, TNF and IL-2 in the cell culture supernatants was determined and normalized to the amount of $1 \times 10^5$ T cells in the culture. The FolR1-TCB induced cytokine secretion was correlated to baseline PD-1$^{hi}$ expression.
Figure 27B:
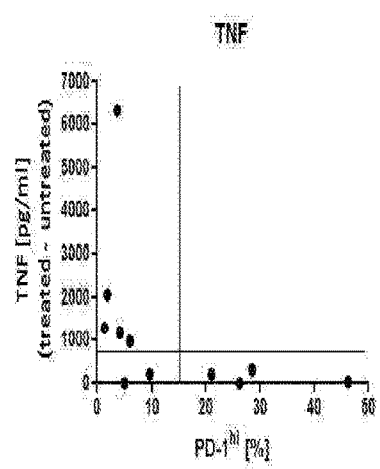
Figure 27C:
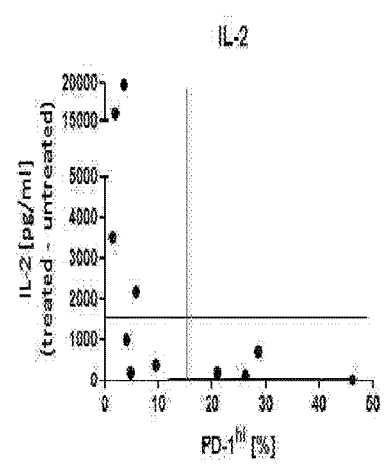
Figure 28A:
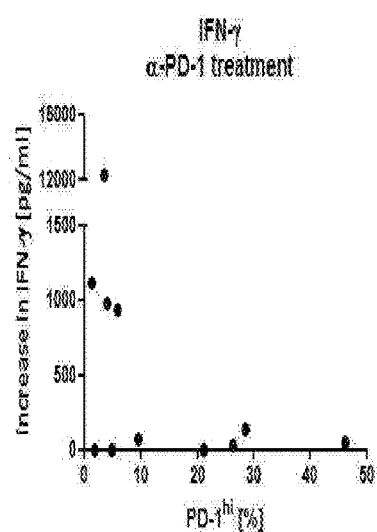
FIGS. 28A-F show that treatment with a PD-blocking antibody fails to induce cytokine secretion in tumor digests or malignant effusions from patients with lung and ovarian cancer with a low percentage of PD-1$^{hi}$ expressing cells. Tumor digests or malignant effusions were cultured for 24 h with FolR1-TCB in the presence or absence of PD-1 blocking antibody (FIG. 28A-C) or the combination of PD-1 and Tim-3 blocking antibodies (FIG. 28D-F). IFN-γ, TNF and IL-2 in the cell culture supernatants was determined and normalized to the amount of $1 \times 10^5$ T cells in the culture. The cytokine secretion induced by the blocking antibodies compared to FolR1-TCB treatment alone was correlated to baseline PD-1$^{hi}$ expression.
Figure 28B:
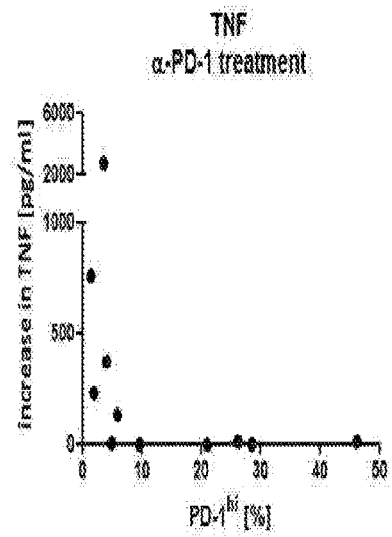
Figure 28C:
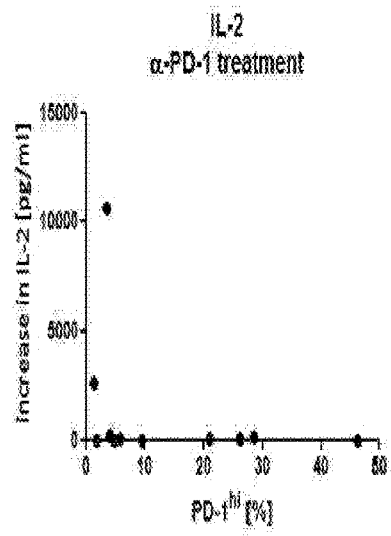
Figure 28D:
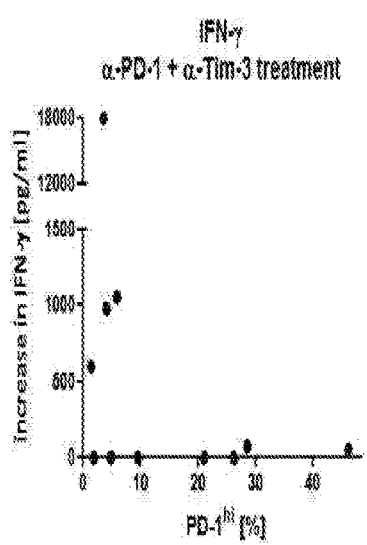
Figure 28E:
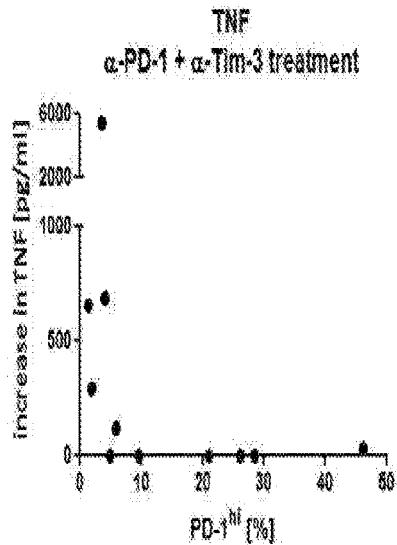
Figure 28F:
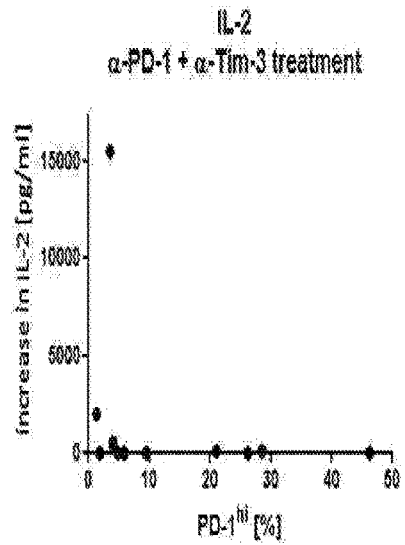

Measurement of FolR1-TCB induced IFN-γ, TNF and IL-2 secretion normalized to the content of T cells in the samples revealed that in patient cell populations with a substantial amount of PD-1$^{hi}$ expressing (approximately >15%) cells were not able to secrete these cytokines. In contrast, cytokine secretion could be induced in most patient cell populations with a lower amount of PD-1$^{hi}$ expressing (approximately <15%) cells (FIG. 27A-C). In the latter group, addition of a blocking antibody to PD-1 or combined blockade of PD-1 and Tim-3 upon stimulation by FolR1-TCB stimulation increased production of IL-2, IFN-γ and TNF-α (FIG. 28A-F). The PD-1$^{hi}$ expressing subset therefore may exhibit a more exhausted phenotype which appears to be resistant to PD-1 blockade alone.

Figure 24A:
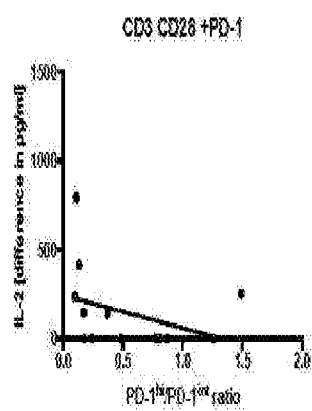
FIGS. 24A-F show that the effect of PD-1 or combined PD-Tim-3 blockade differs in PD-1$^{hi}$ and PD-1$^{int}$ subsets. Correlation of the increase in cytokine production by PD-1 or combined PD-1/Tim-3 blockade with PD-1$^{hi}$ and PD-1$^{int}$ subsets are indicated by PD-1$^{hi}$/PD-1$^{int}$ ratio.
Figure 24B:
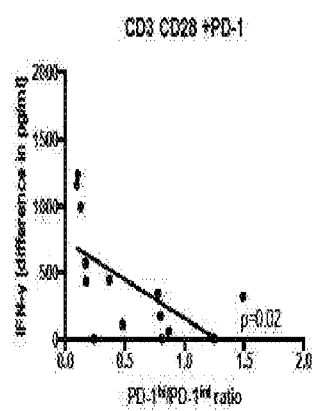
Figure 24C:
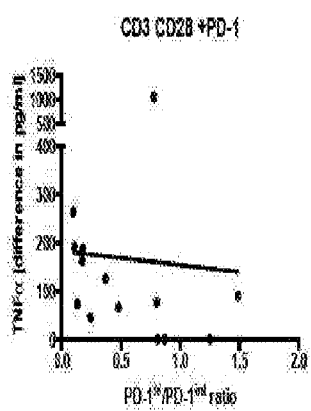
Figure 24D:
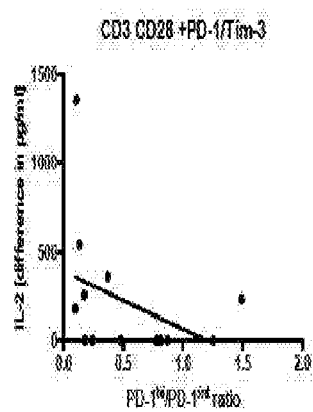
Figure 24E:
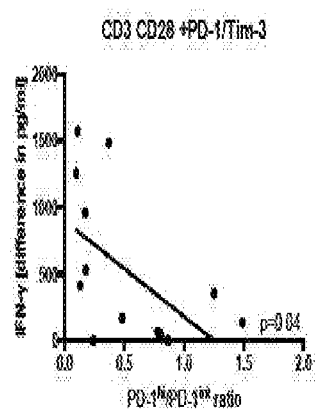
Figure 24F:
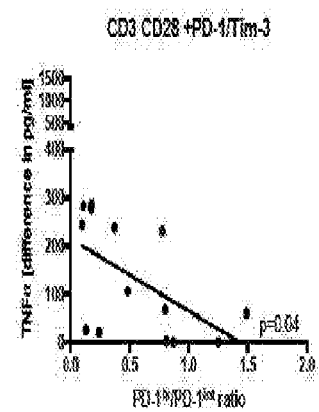

Thus, T cell effector functions such as production of IL-2, IFN-γ and TNF-α could be restored in TILs from some NSCLC patients, whereas in other patients only a marginal recovery of T cell functions could be achieved. The increase in cytokine production upon exposure to anti-CD3/CD28 stimulation in combination with the PD-1 blocking antibody was compared to the percentage of PD-1$^{hi}$ CD8$^+$ T cells from the PD-1 positive population per patient. The increase in cytokine expression upon PD-1 blockade inversely correlated with the percentage of PD-1$^{hi}$ T cells, indicating that patients expressing larger numbers of PD-1$^{hi}$ T cells respond poorly to PD-1 blockade alone (FIG. 24A-C). As T cell dysfunction correlates with the expression of multiple inhibitory receptors (i.e., patients with a high iR score) and response to a PD-1 directed therapy correlates with the expression levels of PD-1 on CD8$^+$ T cells, we further analyzed the expression of Tim-3, CTLA-4, LAG-3 and BTLA in PD-1$^{hi}$ and PD-1$^{int}$ CD8$^+$ T cells. Remarkably, PD-1$^{hi}$ T cells expressed significantly higher levels of additional receptors compared to PD-1$^{int}$ subsets (FIG. 34). Thus, PD-1$^{hi}$ and PD-1$^{int}$ may identify two distinct T cell populations where PD-1$^{hi}$ T cells may exhibit a more exhausted phenotype, which cannot be recovered by PD-1 blockade alone.

The data presented herein for the first time provides a comprehensive phenotypical and functional analysis of tumor-infiltrating CD8$^+$ T cells from patients with NSCLC. The data shows that these cells mainly possess an effector memory phenotype (CCR7-CD45RAlow) and show large heterogeneity in expression of inhibitory receptors such as PD-1, Tim-3, CTLA-4, LAG-3 and BTLA. Nevertheless, a clear increase in the number of receptors expressed on tumor-infiltrating lymphocytes (TILs) from late stage tumors was observed, which reflects the progress of T cell dysfunction during tumor development. The data presented herein shows that the effector functions of TILs were impaired in the vast majority of patients, and that impairment correlated with the expression of inhibitory receptors. To recover T cell function in a clinically relevant setting we combined polyclonal T cell stimulation with antibody-mediated inhibition of PD-1. The effect of PD-1 blockade on T cell functionality varied between TILs from different patients, but could be predicted by assessing the percentage of CD8$^+$ T cells expressing PD-1 at high levels. Here, we could demonstrate that the functionality of TILs can be correlated with and is largely affected by the number and expression level of inhibitory receptors. Of note, even T cells expressing low levels of inhibitory receptors showed some degree of impaired functionality, as the secretion of IL-2 was impaired in the vast majority of patients. Overall the activation and effector function of CD8$^+$ T cells inversely correlated with the cumulative expression of inhibitory receptors, indicating a direct contribution of different inhibitory pathways to T cell dysfunction in NSCLC.

Our analysis of five inhibitory receptors on tumor infiltrating CD8$^+$ T cells showed a clear increase of the single and cumulative expression of these inhibitory receptors in tumor tissues from NSCLC patients presenting with tumor-positive lymph nodes and advanced tumor stages. Expression of CTLA-4 differed from the other four receptors with the highest percentage of positive cells at early stages, which may indicate a distinct role of CTLA-4 in regulating T cell immunity (Topalian et al., Safety, activity, and immune correlates of anti-PD-1 antibody in cancer. N. Engl. J. Med. 366, 2443 (Jun. 28, 2012)). Co-expression analysis of additional inhibitory receptors on single cells, relative to the expression of one given receptor, showed a gradual expression, with early and late upregulation of PD-1 and BTLA, respectively. This may reflect the dynamic process of T cell exhaustion.

The findings presented herein underscore the clinical relevance of inhibitory receptor expression during NSCLC tumor progression, associated with progressive failure of immune control of tumor growth. We document here two populations of CD8$^+$ tumor-infiltrating T cells characterized by different levels of PD-1 expression (PD-1$^{hi}$ and PD-1int subsets). The occurrence of PD-1$^{hi}$ T cells did not correlate with the percentage of PD-1 expression. Interestingly, we observed that the effect of PD-1 blockade correlated with the levels of PD-1 expression, with minimal effects on responsiveness of TILs with high proportions of PD-1hi subpopulations. These findings are in line with experiments in a murine, chronic LCMV infection model where the subset of PD-1$^{int}$ DbGP33-specific CD8$^+$ T cells could be restored upon PD-1 blockade. In contrast, the PD-1$^{hi}$ subset appeared more "exhausted," i.e., exhibited signs of functional exhaustion, and responded poorly to PD-1 blockade. Thus, the level of PD-1 expression may represent a novel marker to define distinct T cell subsets in human cancers and, may serve as a predictor of responses to treatment with PD-1 blocking antibodies.

Example 47

Activation of T-Cells from Healthy Donors and Cancer Patients by FolR1-TCB

Figure 40A:
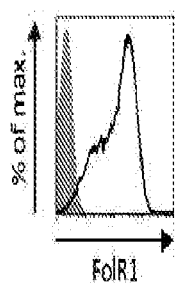
FIGS. 40A-C show activation of CD8$^+$ T-cells upon exposure to increasing concentrations of FolR1-TCB. PBMCs were co-cultured with Skov3 cells for 24 h in the presence or absence of FolR1-TCB or the unspecific control DP-47-TCB.
Figure 40B:
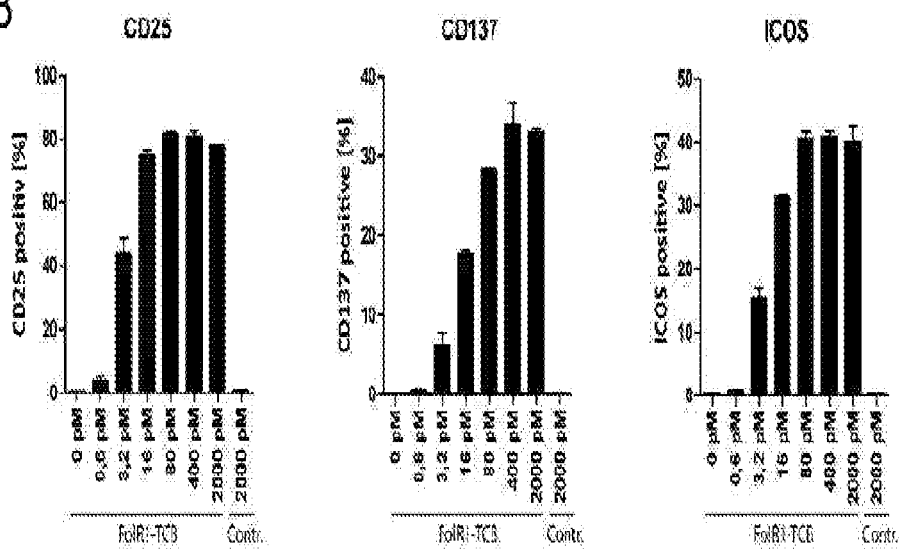

To assess the effect of FolR1-TCB on T-cell activation peripheral blood mononuclear cells (PBMCs) from healthy donors were co-cultured with the FolR1$^+$ ovarian cancer cell line Skov3 (FIG. 40A). Upon exposure to increasing concentrations of FolR1-TCB ranging from 0.6 pM to 2 nM for 24 h we observed a strong activation of CD8$^+$ T-cells with upregulation of CD25, CD137, and ICOS. In addition, T-cells secreted IL-2, IFN-γ, and TNF. Exposure to DP47-TCB, a TCB directed against an irrelevant antigen, did not induce any T-cell activation (FIGS. 40B and C).

Example 48

Inhibitory Receptor Expression is Highly Diverse in Tumor-Infiltrating CD8$^+$ T-Cells As tumor-resident T-cells frequently display a highly dysfunctional phenotype, the observed heterogeneity in T-cell activation among different patients after FolR1-TCB stimulation may be due to an impaired TIL functionality. A hallmark of dysfunctional T-cells in both chronic viral infections and in tumors is the overexpression of inhibitory receptors. To this end, we determined the expression of the immune checkpoints PD-1, Tim-3, CTLA-4, Lag-3, and BTLA on tumor-infiltrating CD8$^+$ T-cells in all tumor samples. We observed a high diversity in frequency and combined expression of these receptors amongst different tumors; PD-1 was found to be the most prominent inhibitory receptor with the highest percentage of expression (60.2±30%), followed by Tim-3 (29.5±24.4%), CTLA-4 (24.6±17.6%), Lag-3 (7.0±5.9%), and BTLA (3.9±2.6%) (FIG. 35F). As described previously in a murine chronic viral infection model (Blackburn et al., Proc Natl Acad Sci USA 2008; 105(39):15016-21) and, as shown herein, in human tumors, the PD-1$^+$ population could be divided into a PD-1$^{hi}$ and a PD-1$^{int}$ expressing subpopulation (FIG. 35A). Analysis of additional inhibitory receptors expressed on these particular subsets showed a significantly higher expression of all other inhibitory receptors, including Tim-3, CTLA-4, Lag-3, and BTLA, in the PD-1$^{hi}$ subpopulation as compared with the expression of these receptors in the PD-1$^{int}$ and PD-1$^{neg}$ subsets (FIG. 36A-D). Therefore, we used the percentage of PD-1$^{hi}$ T-cells in the CD8$^+$ subset as a surrogate marker for the cumulative expression of inhibitory receptors. The tumor samples were divided according to the frequency of PD-1$^{hi}$ cells into two groups with high (PD-1$^{hi}$ abundant tumors) and low frequencies of PD-1$^{hi}$ expressing T-cells (PD-1$^{hi}$ scarce tumors), respectively. A cut-off value of 30% PD-1$^{hi}$ expression was chosen to separate the two groups. The percentage of PD-1$^{hi}$ cells ranged from 39.1-60.5% in the PD-1$^{hi}$ abundant (49.5±7.9%) and from 2.65-19.5% in the PD-1$^{hi}$ scarce group (8.4±5.7%; FIG. 36E). The cut-off value was validated in a second cohort of 14 NSCLC and 2 ovarian cancer patients with a similar distribution in the frequency of PD-1$^{hi}$ cells, where we observed comparable results upon polyclonal stimulation by anti-CD3/anti-CD28 antibodies (FIG. 39).

Example 49

Figure 37A:
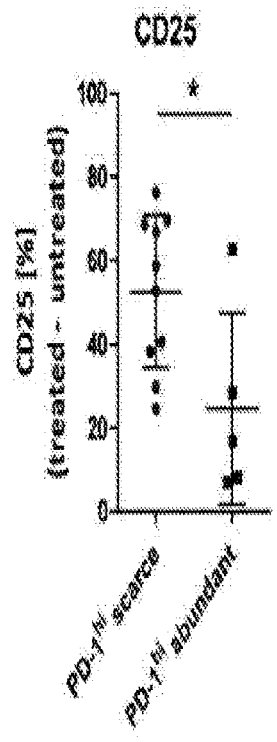
FIGS. 37A-H show that FolR1-TCB-induced T-cell functions depend on the PD-1 expression level of CD8$^+$ T-cells. FolR1$^+$ tumor digests and malignant effusions were cultured for 24 h in the presence or absence of FolR1-TCB. The increase in the expression of activation markers on CD8$^+$ T-cells (FIG. 37A-C) and the increase in the effector cytokines IFN-γ, IL-2, TNF, and perforin (FIG. 37D-G) was determined in PD-1$^{hi}$ scarce and abundant tumors.
Figure 37B:
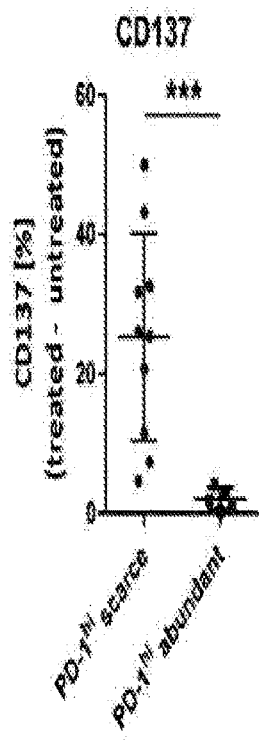
Figure 37C:
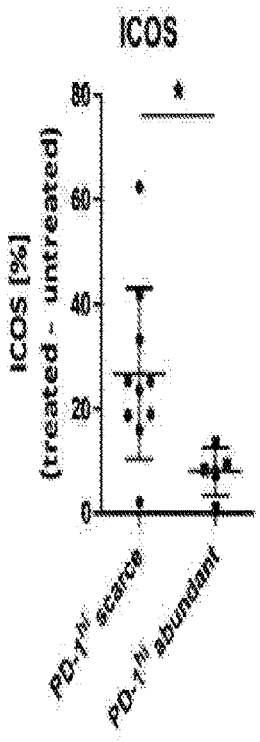
Figure 37D:
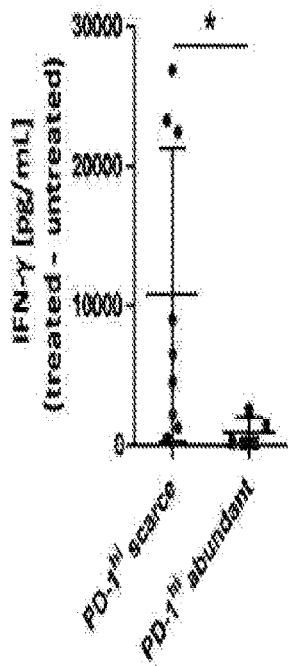
Figure 37E:
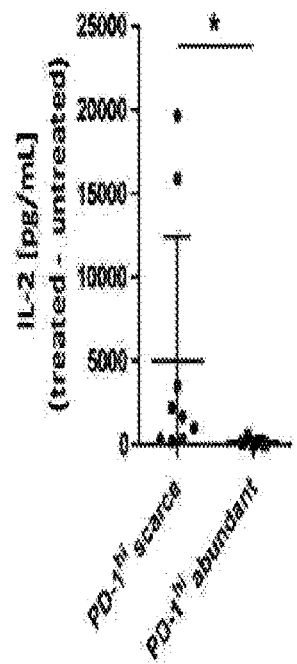
Figure 37F:
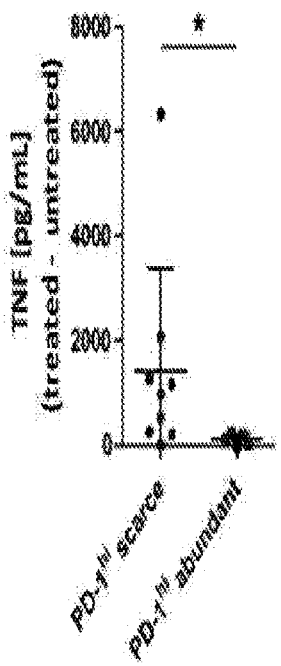
Figure 37G:
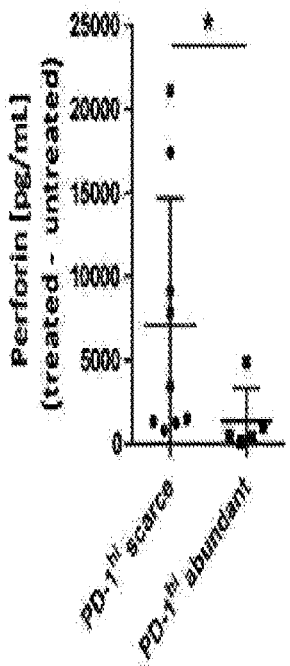
Figure 37H:
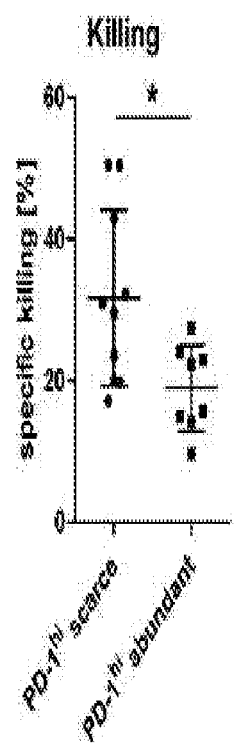

FolR1-TCB-Induced T-Cell Activation Largely Depends on the Level of PD-1 Expression on CD8+ T-Cells We analyzed whether the expression of inhibitory receptors could be correlated with a diminished T-cell functionality upon FolR1-TCB treatment. Consistent with the results described in Example 41 above, FolR1-TCB-induced T-cell activation, as exemplified by CD25, CD137, and ICOS expression (p=0.028; p<0.001, and p=0.008, respectively), and T-cell effector functions, indicated by IFN-γ, IL-2, TNF, as well as perforin secretion, were significantly impaired in PD-1$^{hi}$ abundant tumors compared with PD-1 scarce tumors (p=0.019; p=0.007; p=0.028, and p=0.029, respectively; FIG. 37A-G). Similarly, PD-1$^{hi}$ abundant tumors displayed a significantly reduced cytotoxicity upon FolR1-TCB stimulation whereas a strong tumor cell killing could be observed in the majority of PD-1$^{hi}$ scarce tumors (p=0.021; FIG. 37H).

Example 50

PD-1 Blockade Restores FolR1-TCB-Induced T-Cell Function Only in PD-1$^{hi}$ Scarce Tumors As the level of PD-1 expression on TILs correlates with the efficacy of FolR1-TCB, we analyzed whether blockade of the PD-1/PD-L1 axis in combination with FolR1-TCB treatment might be able to restore T-cell function. We found that upon combined treatment with FolR1-TCB and the PD-1 blocking antibody nivolumab (MDX5C4) secretion of the effector cytokines IFN-γ, TNF, and IL-2 as well as perforin could be increased only in some of the PD-hi scarce tumors. In contrast, in PD-1$^{hi}$ abundant tumors PD-1 blockade failed to elicit any response (FIG. 38A-D). Of note, cytotoxic tumor cell killing could neither be improved in T-cells from PD-1$^{hi}$ scarce nor from PD-1$^{hi}$ abundant tumors by the additional PD-1 blockade (FIG. 38E).

The examples set forth herein describe the immunomodulatory capacity of a CD3×FolR1-specific TCB in primary cancer lesions from patients with non-small cell lung cancer (NSCLC), epithelial ovarian carcinoma (EOC) and renal cell carcinoma (RCC). Compared with fully functional peripheral T-cells from healthy donors, we observed a substantial heterogeneity in FolR1-TCB-induced tumor cell killing and T-cell activation among different human tumor samples, resulting in partial or complete impairment of T-cell function in the majority of patients. Comprehensive analysis of inhibitory receptor expression on the cell surface of intratumoral T-cells revealed that the efficacy of T-cell activation by FolR1-TCB inversely correlated with the expression levels of PD-1. Patients with PD-1$^{hi}$ abundant tumors displayed impaired T-cell activation and effector function upon FolR1-TCB treatment. Additionally, these patients did not respond to PD-1 blockade in contrast to their PD-1$^{hi}$ scarce expressing counterparts. Thus, the bioactivity of bispecific antibodies is considerably hampered by T-cell dysfunction, which is orchestrated, at least in part, by the sustained and highly diverse expression of inhibitory receptors.

Figure 40C:
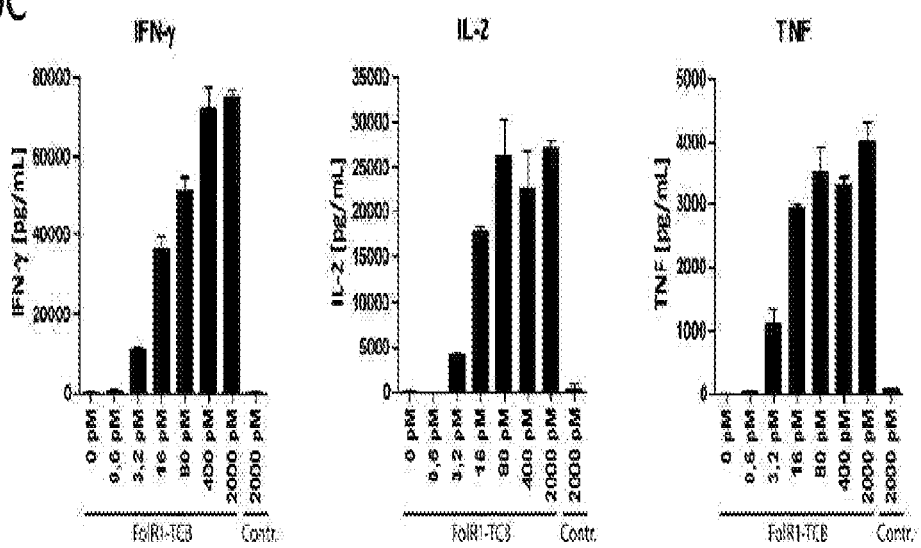

We observed a strong upregulation of T-cell activation markers, effector cytokine secretion and tumor cell killing upon FolR1-TCB stimulation in PBMCs from healthy donors (FIG. 40). In stark contrast, however, T-cell effector functions largely varied and were generally diminished in intratumoral T-cells. Particularly, killing capacity and effector cytokine production was significantly lower in TILs with complete loss of IL-2 production and severely impaired TNF and IFN-γ secretion in the majority of tumors. We documented the expression of the inhibitory receptors PD-1, Tim-3, CTLA-4, Lag-3, and BTLA on intratumoral CD8+ T-cells. PD-1 displayed the broadest expression of all analyzed inhibitory receptors. Observations from chronic murine LCMV infections by Blackburn suggest the presence of functionally distinct PD-1 positive T-cell subsets, which can be separated on the basis of MFI levels, using flow cytometry (Blackburn et al., PNAS 105(39):15016 (2008)). Of note, PD-1$^{hi}$ T-cell subsets displayed a high co-expression of Tim-3 and CTLA-4 and to a lesser extent of Lag-3 and BTLA, while their PD-1$^{int}$ counterparts expressed only low levels of other inhibitory receptors, comparable to PD-1$^{neg}$ T-cells. The frequency of PD-1$^{hi}$ CD8+ T-cells differed largely between patients and allowed us to discriminate between PD-1$^{hi}$ abundant and scarce tumors. In contrast to patients with a PD-1$^{hi}$ scarce phenotype, FolR1-TCB-mediated T-cell activation and tumor cell killing was significantly impaired in tumors displaying a PD-1$^{hi}$ abundant phenotype. These data extend and confirm previous observations that the activation and effector function of CD8+ T-cells correlates with the co-expression of multiple immune checkpoints (Sakuishi et al., J Exp Med 2010; 207(10):2187-94; Fourcade et al., J Exp Med 2010; 207(10):2175-86; Grosso et al., J Immunol 2009; 182(11):6659-69; Matsuzaki et al., Proc Natl Acad Sci USA 2010; 107(17):7875-80; Fourcade et al., Cancer Res 2012; 72(4):887-96). The frequency of PD-1$^{hi}$ T-cells may therefore be useful as a surrogate marker for the functionality of TILs upon TCB activation as well as serve as a predictive marker for the therapeutic responses to TCB treatment. This immune profile could guide the selection of patients who are likely to respond to immunotherapy such as TCBs. Its correlation with clinical benefits remains to be determined in prospective clinical interventions.

A promising avenue to improve the therapeutic efficacy of TCBs lies in the blockade of inhibitory signals on T-cells. As PD-1 was the most prominently expressed inhibitory receptor in all tumors analyzed we assessed whether PD-1 blockade could enhance T-cell effector functions upon TCB activation. Of note, we observed increased secretion of effector cytokines upon combined FolR1-TCB and anti-PD-1 treatment, though only in PD-1$^{hi}$ scarce tumors. Thus, novel therapeutic strategies, exploring the transformation of PD-1$^{hi}$ into PD-1$^{int}$T-cells to increase the susceptibility to PD-1/PD-L1 blockade, are clearly needed.

Remarkably, we observed no improvement on tumor cell killing upon concomitant PD-1 blockade in all of the tumor samples. Thus, blockade of a single immune checkpoint may not be sufficient to restore the cytolytic capacity of TILs. In a mouse tumor model, however, blockade of the PD-1/PD-L1 axis has been shown to increase T-cell infiltration into tumors (Curran et al., Proc Natl Acad Sci USA 2010; 107(9):4275-80), a characteristic of this treatment, which could not be addressed by our in vitro approach. Thus, the therapeutic effect of PD-1 blockade in vivo might not only result from improving T-cell cytotoxicity of residual intratumoral T-cells, but from the sustained functionality of newly infiltrating T-cells. TCB-induced T-cell activation has been shown to upregulate PD-1 expression, which may lead to secondary resistance in the presence of PD-L1 expressed on both tumor cells and infiltrating immune cells as recently demonstrated both with a Her2-specific TCB and with a carcinoembryonic antigen-(CEA) specific TCB (Junttila et al., Cancer Res 2014; 74(19):5561-71; Osada et al., Cancer Immunol Immunother 2015). Importantly, blockade of the PD-1/PD-L1 axis could completely restore TCB-induced T-cell function both in vitro and in a mouse tumor model. These observations indicate that co-administration of checkpoint inhibitors is capable of preventing secondary resistance, which may add to the dysfunctional state of TILs and limit the therapeutic efficacy of TCBs. Further work is clearly needed to determine optimal combination regimens of checkpoint inhibitors and TCBs. It will also be crucial to identify inhibitory and activating T-cell-receptors with non-redundant functions as potential therapeutic targets.

Our findings clearly indicate that bispecific antibodies such as FolR1-TCB are capable of causing T-cells to upregulate co-stimulatory molecules, produce inflammatory cytokines, and acquire cytolytic function. We have observed different states of T-cell dysfunction, which are orchestrated, at least in part, by the expression of inhibitory receptors and, in some instances, reduce the effectiveness of the TCB. As FolR1-TCB-induced effector functions could only be partially restored by PD-1 blockade, our results suggest a rather complex immune regulation, which utilizes multiple and eventually non-redundant pathways to maintain T-cell dysfunction within the tumor environment.

SEQUENCES

Amino Acid Sequences of Exemplary Embodiments

1) FolR binders useful in common light chain format, variable heavy chain

| Description | Sequence | Seq ID No |
|---|---|---|
| 16A3 | QVQLVQSGAEVKKPGASVKVSCKASGYTFT<u>SYYMH</u>WVRQAPGQGLE WMG<u>IINPSGGSTSYAQKFQG</u>RVTMTRDTSTSTVYMELSSLRSEDTA VYYCAR<u>NYYAGVTPFDY</u>WGQGTLVTVSS | 1 |
| 18D3 | QVQLVQSGAEVKKPGASVKVSCKASGYTFT<u>SYYMH</u>WVRQAPGQGLE WMG<u>IINPSGGSTSYAQKFQG</u>RVTMTRDTSTSTVYMELSSLRSEDTA VYYCAR<u>NYYTGGSSAFDY</u>WGQGTLVTVS | 2 |
| 15H7 | QVQLVQSGAEVKKPGASVKVSCKASGYTFT<u>SYYMH</u>WVRQAPGQGLE WMG<u>IINPSGGSTSYAQKFQG</u>RVTMTRDTSTSTVYMELSSLRSEDTA VYYCAR<u>NYYLFSTSFDY</u>WGQGTLVTVSS | 3 |
| 15B6 | QVQLVQSGAEVKKPGASVKVSCKASGYTFT<u>SYYMH</u>WVRQAPGQGLE WMG<u>IINPSGGSTSYAQKFQG</u>RVTMTRDTSTSTVYMELSSLRSEDTA VYYCAR<u>NYYIGIVPFDY</u>WGQGTLVTVSS | 4 |
| 21D1 | QVQLVQSGAEVKKPGASVKVSCKASGYTFT<u>SYYMH</u>WVRQAPGQGLE WMG<u>IINPSGGSTSYAQKFQG</u>RVTMTRDTSTSTVYMELSSLRSEDTA VYYCAR<u>NYYVGVSPFDY</u>WGQGTLVTVSS | 5 |
| 16F12 | QVQLVQSGAEVKKPGASVKVSCKASGYTFT<u>SYYMH</u>WVRQAPGQGLE WMG<u>IINPSGGSTSYAQKFQG</u>RVTMTRDTSTSTVYMELSSLRSEDTA VYYCAR<u>NFTVLRVPFDY</u>WGQGTLVTVSS | 6 |
| 15A1 | QVQLVQSGAEVKKPGASVKVSCKASGYTFT<u>SYYMH</u>WVRQAPGQGLE WMG<u>IINPSGGSTSYAQKFQG</u>RVTMTRDTSTSTVYMELSSLRSEDTA VYYCAR<u>NYYIGVVTFDY</u>WGQGTLVTVSS | 7 |
| 15A1_CDR1 | SYYMH | 8 |
| 15A1_CDR2 | IINPSGGSTSYAQKFQG | 9 |
| 15A1_CDR3 | NYYIGVVTFDY | 10 |
| 19E5 | QVQLVQSGAEVKKPGASVKVSCKASGYTFT<u>SYYMH</u>WVRQAPGQGLE WMG<u>IINPSGGSTSYAQKFQG</u>RVTMTRDTSTSTVYMELSSLRSEDTA VYYCAR<u>GEWRRYTSFDY</u>WGQGTLVTVSS | 11 |
| 19E5_CDR1 | SYYMH | 8 |
| 19E5_CDR2 | IINPSGGSTSYAQKFQG | 9 |
| 19E5_CDR3 | GEWRRYTSFDY | 12 |
| 19A4 | QVQLVQSGAEVKKPGASVKVSCKASGYTFT<u>SYYMH</u>WVRQAPGQGLE WMG<u>IINPSGGSTSYAQKFQG</u>RVTMTRDTSTSTVYMELSSLRSEDTA VYYCAR<u>GGWIRWEHFDY</u>WGQGTLVTVSS | 13 |
| 19A4_CDR1 | SYYMH | 8 |
| 19A4_CDR2 | IINPSGGSTSYAQKFQG | 9 |
| 19A4_CDR3 | GGWIRWEHFDY | 14 |
| 16D5 | EVQLVESGGGLVKPGGSLRLSCAASGFTFS<u>NAWMS</u>WVRQAPGKGLE WVG<u>RIKSKIDGGITDYAAPVKG</u>RFTISRDDSKNTLYLQMNSLKTED TAVYYCTT<u>PWEWSWYDY</u>WGQGTLVTVSS | 15 |

| Description | Sequence | Seq ID No |
| --- | --- | --- |
| 16D5_CDR1 | NAWMS | 16 |
| 16D5_CDR2 | RIKSKIDGGITDYAAPVKG | 17 |
| 16D5_CDR3 | PWEWSWYDY | 18 |
| 15E12 | EVQLVESGGGLVKPGGSLRLSCAASGFTFSNAWMSWVRQAPGKGLE WVGRIKSKIDGGITDYAAPVKGRFTISRDDSKNTLYLQMNSLKTED TAVYYCTTPWEWSYFDYWGQGTLVTVSS | 19 |
| 15E12_CDR1 | NAWMS | 16 |
| 15E12_CDR2 | RIKSKIDGGITDYAAPVKG | 17 |
| 15E12_CDR3 | PWEWSYFDY | 20 |
| 21A5 | EVQLVESGGGLVKPGGSLRLSCAASGFTFSNAWMSWVRQAPGKGLE WVGRIKSKIDGGITDYAAPVKGRFTISRDDSKNTLYLQMNSLKTED TAVYYCTTPWEWAWFDYWGQGTLVTVSS | 21 |
| 21A5_CDR1 | NAWMS | 16 |
| 21A5_CDR2 | RIKSKIDGGITDYAAPVKG | 17 |
| 21A5_CDR3 | PWEWAWFDY | 22 |
| 21G8 | EVQLVESGGGLVKPGGSLRLSCAASGFTFSNAWMSWVRQAPGKGLE WVGRIKSKIDGGITDYAAPVKGRFTISRDDSKNTLYLQMNSLKTED TAVYYCTTPWEWAYFDYWGQGTLVTVSS | 23 |
| 21G8_CDR1 | NAWMS | 16 |
| 21G8_CDR2 | RIKSKIDGGITDYAAPVKG | 17 |
| 21G8_CDR3 | PWEWAYFDY | 24 |
| 19H3 | QVQLVQSGAEVKKPGASVKVSCKASGYTFTSYYMHWVRQAPGQGLE WMGIINPSGGSTSYAQKFQGRVIMIRDTSTSTVYMELSSLRSEDTA VYYCARTGWSRWGYMDYWGQGTLVTVSS | 25 |
| 19H3_CDR1 | SYYMH | 8 |
| 19H3_CDR2 | IINPSGGSTSYAQKFQG | 9 |
| 19H3_CDR3 | TGWSRWGYMDY | 26 |
| 20G6 | QVQLVQSGAEVKKPGASVKVSCKASGYTFTSYYMHWVRQAPGQGLE WMGIINPSGGSTSYAQKFQGRVTMTRDTSTSTVYMELSSLRSEDTA VYYCARGEWIRYYHFDYWGQGTLVTVSS | 27 |
| 20G6_CDR1 | SYYMH | 8 |
| 20G6_CDR2 | IINPSGGSTSYAQKFQG | 9 |
| 20G6_CDR3 | GEWIRYYHFDY | 28 |
| 20H7 | QVQLVQSGAEVKKPGASVKVSCKASGYTFTSYYMHWVRQAPGQGLE WMGIINPSGGSTSYAQKFQGRVTMTRDTSTSTVYMELSSLRSEDTA VYYCARVGWYRWGYMDYWGQGTLVTVSS | 29 |
| 20H7_CDR1 | SYYMH | 8 |
| 20H7_CDR2 | IINPSGGSTSYAQKFQG | 9 |
| 20H7_CDR3 | VGWYRWGYMDY | 30 |

2) CD3 binder common light chain (CLC)

| Description | Sequence | Seq ID No |
|---|---|---|
| common CD3 light chain (VL) | QAVVTQEPSLTVSPGGTVTLTC<u>GSSTGA VTTSNYAN</u>WVQEKPGQAFRGLIGG<u>TNKR</u> <u>AP</u>GTPARFSGSLLGGKAALTLSGAQPED EAEYYC<u>ALWYSNLWV</u>FGGGTKLTVL | 31 |
| common CD3 light chain_CDR1 | GSSTGAVTTSNYAN | 32 |
| common CD3 light chain_CDR2 | GTNKRAP | 33 |
| common CD3 light chain_CDR3 | ALWYSNLWV | 34 |
| common CD3 light chain (VLCL) | QAVVTQEPSLTVSPGGTVTLTC<u>GSSTGA</u> <u>VTTSNYAN</u>WVQEKPGQAFRGLIGG<u>TNKR</u> <u>AP</u>GTPARFSGSLLGGKAALTLSGAQPED EAEYYC<u>ALWYSNLWV</u>FGGGTKLTVLGQP KAAPSVTLFPPSSEELQANKATLVCLIS DFYPGAVTVAWKADSSPVKAGVETTTPS KQSNNKYAASSYLSLTPEQWKSHRSYSC QVTHEGSTVEKTVAPTECS | 35 |

3) CD3 binder, heavy chain

| Description | Sequence | Seq ID No |
|---|---|---|
| CD3 variable heavy chain (VH) | EVQLLESGGGLVQPGGSLRLSCAAS GFTFSTYAMNWVRQAPGKGLEWVSR IRSKYNNYATYYADSVKGRFTISRD DSKNTLYLQMNSLRAEDTAVYYCVR HGNFGNSYVSWFAYWGQGTLVTVSS | 36 |
| CD3 heavy chain (VH)_CDR1 | TYAMN | 37 |
| CD3 heavy chain (VH)_CDR2 | RIRSKYNNYATYYADSVKG | 38 |
| CD3 heavy chain (VH)_CDR3 | HGNFGNSYVSWFAY | 39 |
| CD3 full heavy chain (VHCH1) | EVQLLESGGGLVQPGGSLRLSCAAS GFTFS<u>TYAMN</u>WVRQAPGKGLEWV<u>SR</u> <u>IRSKYNNYATYYADSVKG</u>RFTISRD DSKNTLYLQMNSLRAEDTAVYYCVR <u>HGNFGNSYVSWFAY</u>WGQGTLVTVSS ASTKGPSVFPLAPSSKSTSGGTAAL GCLVKDYFPEPVTVSWNSGALTSGV HTFPAVLQSSGLYSLSSVVTVPSSS LGTQTYICNVNHKPSNTKVDKKVEP KSC | 40 |
| CD3 constant heavy chain CH1 | ASTKGPSVFPLAPSSKSTSGGTAAL GCLVKDYFPEPVTVSWNSGALTSGV HTFPAVLQSSGLYSLSSVVTVPSSS LGTQTYICNVNHKPSNTKVDKKVEP KSC | 84 |

4) FolR binders useful for crossfab Format

| Description | Sequence | Seq ID No |
|---|---|---|
| 11F8_VH | QVQLVQSGAEVKKPGSSVKVSCKASGGTFS<u>SYAIS</u>WVRQAPGQGLE WMGG<u>IIPIFGTANYAQKFQG</u>RVTITADKSTSTAYMELSSLRSEDTA VYYCAR<u>AVFYRAWYSFDY</u>WGQGTTVTVSS | 41 |
| 11F8_VH_CDR1 | SYAIS | 42 |
| 11F8_VH_CDR2 | GIIPIFGTANYAQKFQG | 43 |
| 11F8_VH_CDR3 | AVFYRAWYSFDY | 44 |
| 11F8_VL | DIQMTQSPSTLSASVGDRVTITC<u>RASQSISSWLA</u>WYQQKPGKAPKL LIY<u>DASSLES</u>GVPSRFSGSGSGTEFTLTISSLQPDDFATYYC<u>QQYT</u> <u>SPPPT</u>FGQGTKVEIK | 45 |
| 11F8_VL_CDR1 | RASQSISSWLA | 46 |
| 11F8_VL_CDR2 | DASSLES | 47 |
| 11F8_VL_CDR3 | QQYTSPPPT | 48 |
| 36F2_VH | QVQLVQSGAEVKKPGASVKVSCKASGYTFT<u>SYYMH</u>WVRQAPGQGLE WMGI<u>IINPSGGSTSYAQKFQG</u>RVTMTHDTSTSTVYMELSSLRSEDTA VYYCARS<u>FFTGFHLDY</u>WGQGTLVTVSS | 49 |
| 36F2_VH_CDR1 | SYYMH | 8 |
| 36F2_VH_CDR2 | IINPSGGSTSYAQKFQG | 9 |
| 36F2_VH_CDR3 | SFFTGFHLDY | 50 |
| 36F2_VL | EIVLTQSPGTLSLSPGERATLSC<u>RASQSVSSSYLA</u>WYQQKPGQAPR LLIY<u>GASSRAT</u>GIPDRFSGSGSGTDFTLTISRLEPEDFAVYYC<u>QQY</u> <u>TNEHYYT</u>FGQGTKVEIK | 51 |

| Description | Sequence | Seq ID No |
|---|---|---|
| 36F2_VL_CDR1 | RASQSVSSSYLA | 52 |
| 36F2_VL_CDR2 | GASSRAT | 53 |
| 36F2_VL_CDR3 | QQYTNEHYYT | 54 |
| 9D11_VH | QVQLVQSGAEVKKPGASVKVSCKASGYTFT<u>SYYMH</u>WVRQAPGQGLE WMG<u>IINPSGGPTSYAQKFQG</u>RVTMTRDTSTSTVYMELSSLRSEDTA VYYCAR<u>GDFAWLDY</u>WGQGTLVTVSS | 55 |
| 9D11_VH_CDR1 | SYYMH | 8 |
| 9D11_VH_CDR2 | IINPSGGPTSYAQKFQG | 56 |
| 9D11_VH_CDR3 | GDFAWLDY | 57 |
| 9D11_VL | DIVMTQSPLSLPVTPGEPASISC<u>RSSQSLLHSNGYNYLD</u>WYLQKPG QSPQLLIY<u>LGSNRAS</u>GVPDRFSGSGSGTDFTLKISRVEAEDVGVYY C<u>MQASIMNRT</u>FGQGTKVEIK | 58 |
| 9D11_VL_CDR1 | RSSQSLLHSNGYNYLD | 59 |
| 9D11_VL_CDR2 | LGSNRAS | 60 |
| 9D11_VL_CDR3 | MQASIMNRT | 61 |
| 9D11_VL N95S | DIVMTQSPLSLPVTPGEPASISC<u>RSSQSLLHSNGYNYLD</u>WYLQKPG QSPQLLIY<u>LGSNRAS</u>GVPDRFSGSGSGTDFTLKISRVEAEDVGVYY C<u>MQASIMSRT</u>FGQGTKVEIK | 62 |
| 9D11_VL N95S_CDR3 | MQASIMSRT | 63 |
| 9D11_VL N95Q | DIVMTQSPLSLPVTPGEPASISC<u>RSSQSLLHSNGYNYLD</u>WYLQKPG QSPQLLIY<u>LGSNRAS</u>GVPDRFSGSGSGTDFTLKISRVEAEDVGVYY C<u>MQASIMQRT</u>FGQGTKVEIK | 64 |
| 9D11_VL N95Q_CDR3 | MQASIMQRT | 65 |
| 9D11_VL T97A | DIVMTQSPLSLPVTPGEPASISC<u>RSSQSLLHSNGYNYLD</u>WYLQKPG QSPQLLIY<u>LGSNRAS</u>GVPDRFSGSGSGTDFTLKISRVEAEDVGVYY C<u>MQASIMNRA</u>FGQGTKVEIK | 66 |
| 9D11_VL T97A | MQASIMNRA | 67 |
| 9D11_VL T97N | DIVMTQSPLSLPVTPGEPASISC<u>RSSQSLLHSNGYNYLD</u>WYLQKPG QSPQLLIY<u>LGSNRAS</u>GVPDRFSGSGSGTDFTLKISRVEAEDVGVYY C<u>MQASIMNRN</u>FGQGTKVEIK | 68 |
| 9D11_VL T97N_CDR3 | MQASIMNRN | 69 |
| 5D9_VH | QVQLVQSGAEVKKPGASVKVSCKASGYTFT<u>SYYMH</u>WVRQAPGQGLE WMG<u>IINPSGGSTSYAQKFQG</u>RVTMTRDTSTSTVYMELSSLRSEDTA VYYCAR<u>SYIDMDY</u>WGQGTLVTVSS | 70 |
| 5D9_VH_CDR1 | SYYMH | 8 |
| 5D9_VH_CDR2 | IINPSGGSTSYAQKFQG | 9 |
| 5D9_VH_CDR3 | SYIDMDY | 71 |
| 5D9_VL | EIVLTQSPGTLSLSPGERATLSC<u>RASQSVSSSYLA</u>WYQQKPGQAPR LLIY<u>GASSRAT</u>GIPDRFSGSGSGTDFTLTISRLEPEDFAVYYC<u>QQD NWSPT</u>FGQGTKVEIK | 72 |
| 5D9_VL_CDR1 | RASQSVSSSYLA | 52 |
| 5D9_VL_CDR2 | GASSRAT | 53 |
| 5D9_VL_CDR3 | QQDNWSPT | 73 |

| Description | Sequence | Seq ID No |
|---|---|---|
| 6B6_VH | QVQLVQSGAEVKKPGASVKVSCKASGYTFT<u>SYYMH</u>WVRQAPGQGLE WMGI<u>IINPSGGSTSYAQKFQG</u>RVTMTRDTSTSTVYMELSSLRSEDTA VYYCAR<u>SYVDMDY</u>WGQGTLVTVSS | 74 |
| 6B6_VH_CDR1 | SYYMH | 8 |
| 6B6_VH_CDR2 | IINPSGGSTSYAQKFQG | 9 |
| 6B6_VH_CDR3 | SYVDMDY | 75 |
| 6B6_VL | EIVLTQSPGTLSLSPGERATLSC<u>RASQSVSSSYLA</u>WYQQKPGQAPR LLIY<u>GASSRAT</u>GIPDRFSGSGSGTDFTLTISRLEPEDFAVYYC<u>QQD IWSPT</u>FGQGTKVEIK | 76 |
| 6B6_VL_CDR1 | RASQSVSSSYLA | 52 |
| 6B6_VL_CDR2 | GASSRAT | 53 |
| 6B6_VL_CDR3 | QQDIWSPT | 77 |
| 14E4_VH | EVQLLESGGGLVQPGGSLRLSCAASGFTFS<u>SYAMS</u>WVRQAPGKGLE WVS<u>AISGSGGSTYYADSVKG</u>RFTISRDNSKNTLYLQMNSLRAEDTA VYYCAK<u>DSSYVEWYAFDY</u>WGQGTLVTVSS | 78 |
| 14E4_VH_CDR1 | SYAMS | 79 |
| 14E4_VH_CDR2 | AISGSGGSTYYADSVKG | 80 |
| 14E4_VH_CDR3 | DSSYVEWYAFDY | 81 |
| 14E4_VL | EIVLTQSPGTLSLSPGERATLSC<u>RASQSVSSSYLA</u>WYQQKPGQAPR LLIY<u>GASSRAT</u>GIPDRFSGSGSGTDSTLTISRLEPEDFAVYYC<u>QQP TSSPIT</u>FG QGTKVEIK | 82 |
| 14E4_VL_CDR1 | RASQSVSSSYLA | 52 |
| 14E4_VL_CDR2 | GASSRAT | 53 |
| 14E4_VL_CDR3 | QQPISSPIT | 83 |

5) CD3 binder useful in crossfab Format

| Description | Sequence | Seq ID No |
|---|---|---|
| CD3 heavy chain(VH) | EVQLLESGGGLVQPGGSLRLSCAASGFTFSTYAMNWVRQAPGKGLEWV SRIRSKYNNYATYYADSVKGRFTISRDDSKNTLYLQMNSLRAEDTAVY YCVRHGNFGNSYVSWFAYWGQGTLVTVSS | 36 |
| CD3 heavy chain (VH)_CDR1 | TYAMN | 37 |
| CD3 heavy chain (VH)_CDR2 | RIRSKYNNYATYYADSVKG | 38 |
| CD3 heavy chain (VH)_CDR3 | HGNFGNSYVSWFAY | 39 |
| CD3 light chain (VL) | QAVVTQEPSLTVSPGGTVTLTC<u>GSSTGAVTTSNYAN</u>WVQEKPGQAFRG LIG<u>GTNKRAP</u>GTPARFSGSLLGGKAALTLSGAQPEDEAEYYCALWYSN LWVFGGGTKLTVL | 31 |
| CD3 light chain_CDR1 | GSSTGAVTTSNYAN | 32 |
| CD3 light chain_CDR2 | GTNKRAP | 33 |

-continued

| Description | Sequence | Seq ID No |
|---|---|---|
| CD3 light chain_CDR3 | ALWYSNLWV | 34 |
| pETR12940: crossed common CD3 light chain (VLCH1) | QAVVTQEPSLTVSPGGTVTLTCGSSTGAVTTSNYANWVQEKPGQAFRG LIGGTNKRAPGTPARFSGSLLGGKAALTLSGAQPEDEAEYYCALWYSN LWVFGGGTKLTVLSSASTKGPSVFPLAPSSKSTSGGTAALGCLVKDYF PEPVTVSWNSGALTSGVHTFPAVLQSSGLYSLSSVVTVPSSSLGTQTY ICNVNHKPSNTKVDKKVEPKSC | 86 |
| Crossed CD3 heavy chain (VHCκ); e.g. in pCON1057 | EVQLLESGGGLVQPGGSLRLSCAASGFTFSTYAMNWVRQAPGKGLEWV SRIRSKYNNYATYYADSVKGRFTISRDDSKNTLYLQMNSLRAEDTAVY YCVRHGNFGNSYVSWFAYWGQGTLVTVSSASVAAPSVFIFPPSDEQLK SGTASVVCLLNNFYPREAKVQWKVDNALQSGNSQESVTEQDSKDSTYS LSSTLTLSKADYEKHKVYACEVTHQGLSSPVTKSFNRGEC | 87 |
| CD3-CH1 | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KVEPKSC | 85 |
| CD3-ckappa | VAAPSVFIFPPSDEQLKSGTASVVCLLNNFYPREAKVQWKVDNALQSG NSQESVTEQDSKDSTYSLSSTLTLSKADYEKHKVYACEVTHQGLSSPV TKSFNRGEC | 88 |

6) Exemplary amino acid sequences of CD3-FolR bispecific antibodies 2+1 inverted crossfab formal

| Description | Sequence | Seq ID No |
|---|---|---|
| VHCH1[9D11]_VHC [CD3]_Fcknob_PGLALA pCON1057 | QVQLVQSGAEVKKPGASVKVSCKASGYTFTSYYMHWVRQAP GQGLEWMGIINPSGGPTSYAQKFQGRVTMTRDTSTSTVYME LSSLRSEDTAVYYCARGDFAWLDYWGQGTLVTVSSASTKGP SVFPLAPSSKSTSGGTAALGCLVKDYFPEPVTVSWNSGALT SGVHTFPAVLQSSGLYSLSSVVTVPSSSLGTQTYICNVNHK PSNTKVDKKVEPKSCDGGGGSGGGGSEVQLLESGGGLVQPG GSLRLSCAASGFTFSTYAMNWVRQAPGKGLEWVSRIRSKYN NYATYYADSVKGRFTISRDDSKNTLYLQMNSLRAEDTAVYY CVRHGNFGNSYVSWFAYWGQGTLVTVSSASVAAPSVFIFPP SDEQLKSGTASVVCLLNNFYPREAKVQWKVDNALQSGNSQE SVTEQDSKDSTYSLSSTLTLSKADYEKHKVYACEVTHQGLS SPVTKSFNRGECDKTHTCPPCPAPEAAGGPSVFLFPPKPKD TLMISRTPEVTCVVVDVSHEDPEVKFNWYVDGVEVHNAKTK PREEQYNSTYRVVSVLTVLHQDWLNGKEYKCKVSNKALGAP IEKTISKAKGQPREPQVYTLPPCRDELTKNQVSLWCLVKGF YPSDIAVEWESNGQPENNYKTTPPVLDSDGSFFLYSKLTVD KSRWQQGNVFSCSVMHEALHNHYTQKSLSLSPGK | 94 |
| 9D11_Fchole_PGLALA_HYRF | QVQLVQSGAEVKKPGASVKVSCKASGYTFTSYYMHWVRQAP GQGLEWMGIINPSGGPTSYAQKFQGRVTMTRDTSTSTVYME LSSLRSEDTAVYYCARGDFAWLDYWGQGTLVTVSSASTKGP SVFPLAPSSKSTSGGTAALGCLVKDYFPEPVTVSWNSGALT SGVHTFPAVLQSSGLYSLSSVVTVPSSSLGTQTYICNVNHK PSNTKVDKKVEPKSCDKTHTCPPCPAPEAAGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL GAPIEKTISKAKGQPREPQVCTLPPSRDELTKNQVSLSCAV KGFYPSDIAVEWESNGQPENNYKTTPPVLDSDGSFFLVSKL TVDKSRWQQGNVFSCSVMHEALHNHYTQKSLSLSPGK | 95 |
| 9D11_LC pCON1063 | DIVMTQSPLSLPVTPGEPASISCRSSQSLLHSNGYNYLDWY LQKPGQSPQLLIYLGSNRASGVPDRFSGSGSGTDFTLKISR VEAEDVGVYYCMQASIMNRTFGQGTKVEIKRTVAAPSVFIF PPSDEQLKSGTASVVCLLNNFYPREAKVQWKVDNALQSGNS QESVTEQDSKDSTYSLSSILTLSKADYEKHKVYACEVTHQG LSSPVTKSFNRGEC | 96 |
| VLCH1[CD3] pETR12940 | QAVVTQEPSLTVSPGGTVTLTCGSSTGAVTTSNYANWVQEK PGQAFRGLIGGTNKRAPGTPARFSGSLLGGKAALTLSGAQP EDEAEYYCALWYSNLWVFGGGTKLTVLSSASTKGPSVFPLA PSSKSTSGGTAALGCLVKDYFPEPVTVSWNSGALTSGVHTF | 86 |

| Description | Sequence | Seq ID No |
|---|---|---|
| | PAVLQSSGLYSLSSVVTVPSSSLGTQTYICNVNHKPSNTKV DKKVEPKSC | |
| CH1 | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNIKVDKKVEPKSCD | 428 |
| VHCH1[36F2]_VHCL [CD3]_Fcknob_PGLALA pCON1056 | QVQLVQSGAEVKKPGASVKVSCKASGYTFTSYYMHWVRQAP GQGLEWMGIINPSGGSTSYAQKFQGRVTMTHDTSTSTVYME LSSLRSEDTAVYYCARSFFTGFHLDYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKKVEPKSCDGGGGSGGGGSEVQLLESGGGLVQ PGGSLRLSCAASGFTFSTYAMNWVRQAPGKGLEWVSRIRSK YNNYATYYADSVKGRFTISRDDSKNTLYLQMNSLRAEDTAV YYCVRHGNFGNSYVSWFAYWGQGTLVTVSSASVAAPSVFIF PPSDEQLKSGTASVVCLLNNFYPREAKVQWKVDNALQSGNS QESVTEQDSKDSTYSLSSTLTLSKADYEKHKVYACEVTHQG LSSPVTKSFNRGECDKTHTCPPCPAPEAAGGPSVFLFPPKP KDTLMISRTPEVTCVVVDVSHEDPEVKFNWYVDGVEVHNAK TKPREEQYNSTYRVVSVLTVLHQDWLNGKEYKCKVSNKALG APIEKTISKAKGQPREPQVYTLPPCRDELTKNQVSLWCLVK GFYPSDIAVEWESNGQPENNYKTTPPVLDSDGSFFLYSKLT VDKSRWQQGNVFSCSVMHEALHNHYTQKSLSLSPGK | 393 |
| 36F2-Fc hole PGLALA pCON1050 | QVQLVQSGAEVKKPGASVKVSCKASGYTFTSYYMHWVRQAP GQGLEWMGIINPSGGSTSYAQKFQGRVTMTHDTSTSTVYME LSSLRSEDTAVYYCARSFFTGFHLDYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKKVEPKSCDKTHTCPPCPAPEAAGGPSVFLFP PKPKDTLMISRTPEVTCVVVDVSHEDPEVKFNWYVDGVEVH NAKTKPREEQYNSTYRVVSVLTVLHQDWLNGKEYKCKVSNK ALGAPIEKTISKAKGQPREPQVCTLPPSRDELTKNQVSLSC AVKGFYPSDIAVEWESNGQPENNYKTTPPVLDSDGSFFLVS KLTVDKSRWQQGNVFSCSVMHEALHNHYTQKSLSLSPGK | 394 |
| 36F2 LC pCON1062 | EIVLTQSPGTLSLSPGERATLSCRASQSVSSSYLAWYQQKP GQAPRLLIYGASSRATGIPDRFSGSGSGTDFTLTISRLEPE DFAVYYCQQYTNEHYYTFGQGTKVEIKRTVAAPSVFIFPPS DEQLKSGTASVVCLLNNFYPREAKVQWKVDNALQSGNSQES VTEQDSKDSTYSLSSTLTLSKADYEKHKVYACEVTHXGLSS PVIKSENRGEC | 395 |
| CD3 VLCH1 pETR12940 | QAVVTQEPSLTVSPGGTVTLTCGSSTGAVTTSNYANWVQEK PGQAFRGLIGGTNKRAPGTPARFSGSLLGGKAALTLSGAQP EDEAEYYCALWYSNLWVFGGGTKLTVLSSASTKGPSVFPLA PSSKSTSGGTAALGCLVKDYFPEPVTVSWNSGALTSGVHTF PAVLQSSGLYSLSSVVTVPSSSLGTQTYICNVNHKPSNTKV DKKVEPKSC | 86 |

7) Exemplary amino acid sequences of CD3-FolR bispecific antibodies with common light chain

| | | |
|---|---|---|
| VHCH1[16D5]_VHCH1[CD3]_Fcknob pCON999 | EVQLVESGGGLVKPGGSLRLSCAASGFTFSN AWMSWVRQAPGKGLEWVGRIKSKTDGGITDY AAPVKGRFTISRDDSKNTLYLQMNSLKTEDT AVYYCTTPWEWSWYDYWGQGTLVTVSSASTK GPSVFPLAPSSKSTSGGTAALGCLVKDYFPE PVTVSWNSGALTSGVHTFPAVLQSSGLYSLS SVVTVPSSSLGTQTYICNVNHKPSNTKVDKK VEPKSCDGGGGSGGGGSEVQLLESGGGLVQP GGSLRLSCAASGFTFSTYAMNWVRQAPGKGL EWVSRIRSKYNNYATYYADSVKGRFTISRDD SKNTLYLQMNSLRAEDTAVYYCVRHGNFGNS YVSWFAYWGQGTLVTVSSASTKGPSVFPLAP SSKSTSGGTAALGCLVKDYFPEPVTVSWNSG ALTSGVHTFPAVLQSSGLYSLSSVVTVPSSS LGTQTYICNVNHKPSNTKVDKKVEPKSCDKT HTCPPCPAPEAAGGPSVFLFPPKPKDTLMIS RTPEVTCVVVDVSHEDPEVKFNWYVDGVEVH NAKTKPREEQYNSTYRVVSVLTVLHQDWLNG KEYKCKVSNKALGAPIEKTISKAKGQPREPQ | 89 |

-continued

| | | |
|---|---|---|
| | VYTLPPCRDELTKNQVSLWCLVKGFYPSDIA<br>VEWESNGQPENNYKTTPPVLDSDGSFFLYSK<br>LTVDKSRWQQGNVFSCSVMHEALHNHYTQKS<br>LSLSPGK | |
| VHCH1[16D5]_Fchole pCON983 | EVQLVESGGGLVKPGGSLRLSCAASGFTFSN<br>AWMSWVRQAPGKGLEWVGRIKSKTDGGITDY<br>AAPVKGRFTISRDDSKNTLYLQMNSLKTEDT<br>AVYYCTTPWEWSWYDYWGQGTLVTVSSASTK<br>GPSVFPLAPSSKSTSGGTAALGCLVKDYFPE<br>PVTVSWNSGALTSGVHTFPAVLQSSGLYSLS<br>SVVTVPSSSLGTQTYICNVNHKPSNTKVDKK<br>VEPKSCDKTHTCPPCPAPEAAGGPSVFLFPP<br>KPKDTLMISRTPEVTCVVVDVSHEDPEVKFN<br>WYVDGVEVHNAKTKPREEQYNSTYRVVSVLT<br>VLHQDWLNGKEYKCKVSNKALGAPIEKTISK<br>AKGQPREPQVCTLPPSRDELTKNQVSLSCAV<br>KGFYPSDIAVEWESNGQPENNYKTTPPVLDS<br>DGSFFLVSKLTVDKSRWQQGNVFSCSVMHEA<br>LHNRFTQKSLSLSPGK | 90 |
| CD3_common light chain pETR13197 | QAVVTQEPSLTVSPGGTVTLTCGSSTGAVTT<br>SNYANWVQEKPGQAFRGLIGGTNKRAPGTPA<br>RFSGSLLGGKAALTLSGAQPEDEAEYYCALW<br>YSNLWVFGGGTKLTVLGQPKAAPSVTLFPPS<br>SEELQANKATLVCLISDFYPGAVTVAWKADS<br>SPVKAGVETTTPSKQSNNKYAASSYLSLTPE<br>QWKSHRSYSCQVTHEGSTVEKTVAPTECS | 35 |
| VHCH1[CD3]_VHCH1[16D5]_Fcknob_PGLALA<br>pETR13932 | EVQLLESGGGLVQPGGSLRLSCAASGFTFST<br>YAMNWVRQAPGKGLEWVSRIRSKYNNYATYY<br>ADSVKGRFTISRDDSKNTLYLQMNSLRAEDT<br>AVYYCVRHGNFGNSYVSWFAYWGQGTLVTVS<br>SASTKGPSVFPLAPSSKSTSGGTAALGCLVK<br>DYFPEPVTVSWNSGALTSGVHTFPAVLQSSG<br>LYSLSSVVTVPSSSLGTQTYICNVNHKPSNT<br>KVDKKVEPKSCDGGGGSGGGGSEVQLVESGG<br>GLVKPGGSLRLSCAASGFTFSNAWMSWVRQA<br>PGKGLEWVGRIKSKTDGGTTDYAAPVKGRFT<br>ISRDDSKNTLYLQMNSLKTEDTAVYYCTTPW<br>EWSWYDYWGQGTLVTVSSASTKGPSVFPLAP<br>SSKSTSGGTAALGCLVKDYFPEPVTVSWNSG<br>ALTSGVHTFPAVLQSSGLYSLSSVVTVPSSS<br>LGTQTYICNVNHKPSNTKVDKKVEPKSCDKT<br>HTCPPCPAPEAAGGPSVFLFPPKPKDTLMIS<br>RTPEVTCVVVDVSHEDPEVKFNWYVDGVEVH<br>NAKTKPREEQYNSTYRVVSVLTVLHQDWLNG<br>KEYKCKVSNKALGAPIEKTISKAKGQPREPQ<br>VYTLPPCRDELTKNQVSLWCLVKGFYPSDIA<br>VEWESNGQPENNYKTTPPVLDSDGSFFLYSK<br>LTVDKSRWQQGNVFSCSVMHEALHNHYTQKS<br>LSLSPGK | 91 |
| CD3_Fcknob_PGLALA pETR13917 | EVQLLESGGGLVQPGGSLRLSCAASGFTFST<br>YAMNWVRQAPGKGLEWVSRIRSKYNNYATYY<br>ADSVKGRFTISRDDSKNTLYLQMNSLRAEDT<br>AVYYCVRHGNFGNSYVSWFAYWGQGTLVTVS<br>SASTKGPSVFPLAPSSKSTSGGTAALGCLVK<br>DYFPEPVTVSWNSGALTSGVHTFPAVLQSSG<br>LYSLSSVVTVPSSSLGTQTYICNVNHKPSNT<br>KVDKKVEPKSCDKTHTCPPCPAPEAAGGPSV<br>FLFPPKPKDTLMISRTPEVTCVVVDVSHEDP<br>EVKFNWYVDGVEVHNAKTKPREEQYNSTYRV<br>VSVLTVLHQDWLNGKEYKCKVSNKALGAPIE<br>KTISKAKGQPREPQVYTLPPCRDELTKNQVS<br>LWCLVKGFYPSDIAVEWESNGQPENNYKTTP<br>PVLDSDGSFFLYSKLTVDKSRWQQGNVFSCS<br>VMHEALHNHYTQKSLSLSPGK | 92 |
| Fc_hole_PGLALA_HYRF pETR10755 | DKTHTCPPCPAPELLGGPSVFLFPPKPKDTL<br>MISRTPEVTCVVVDVSHEDPEVKFNWYVDGV<br>EVHNAKTKPREEQYNSTYRVVSVLTVLHQDW<br>LNGKEYKCKVSNKALPAPIEKTISKAKGQPR<br>EPQVCTLPPSRDELTKNQVSLSCAVKGFYPS<br>DIAVEWESNGQPENNYKTTPPVLDSDGSFFL<br>VSKLTVDKSRWQQGNVFSCSVMHEALHNRFT<br>QKSLSLSPGK | 93 |

| | | |
|---|---|---|
| VHCL[CD3]_Fcknob_PGLALA pETR13378 | EVQLLESGGGLVQPGGSLRLSCAASGFTFST YAMNWVRQAPGKGLEWVSRIRSKYNNYATYY ADSVKGRFTISRDDSKNTLYLQMNSLRAEDT AVYYCVRHGNFGNSYVSWFAYWGQGTLVTVS SASVAAPSVFIFPPSDEQLKSGTASVVCLLN NFYPREAKVQWKVDNALQSGNSQESVTEQDS KDSTYSLSSTLTLSKADYEKHKVYACEVTHQ GLSSPVTKSFNRGECDKTHTCPPCPAPEAAG GPSVFLFPPKPKDTLMISRTPEVTCVVVDVS HEDPEVKFNWYVDGVEVHNAKTKPREEQYNS TYRVVSVLTVLHQDWLNGKEYKCKVSNKALG APIEKTISKAKGQPREPQVYTLPPCRDELTK NQVSLWCLVKGFYPSDIAVEWESNGQPENNY KTTPPVLDSDGSFFLYSKLTVDKSRWQQGNV FSCSVMHEALHNHYTQKSLSLSPGK | 98 |
| 16D5 inverted 2 + 1 with N100A in CDR H3 pETR14096 | EVQLVESGGGLVKPGGSLRLSCAASGFTFSN AWMSWVRQAPGKGLEWVGRIKSKIDGGITDY AAPVKGRFTISRDDSKNTLYLQMNSLKTEDT AVYYCTTPWEWSWYDYWGQGTLVTVSSASTK GPSVFPLAPSSKSTSGGTAALGCLVKDYFPE PVTVSWNSGALTSGVHTFPAVLQSSGLYSLS SVVTVPSSSLGTQTYICNVNHKPSNTKVDKK VEPKSCDGGGGSGGGGSEVQLLESGGGLVQP GGSLRLSCAASGFTFSTYAMNWVRQAPGKGL EWVSRIRSKYNNYATYYADSVKGRFTISRDD SKNTLYLQMNSLRAEDTAVYYCVRHGNFGAS YVSWFAYWGQGTLVTVSSASTKGPSVFPLAP SSKSTSGGTAALGCLVKDYFPEPVTVSWNSG ALTSGVHTFPAVLQSSGLYSLSSVVTVPSSS LGTQTYICNVNHKPSNTKVDKKVEPKSCDKT HTCPPCPAPEAAGGPSVFLFPPKPKDTLMIS RTPEVTCVVVDVSHEDPEVKFNWYVDGVEVH NAKTKPREEQYNSTYRVVSVLTVLHQDWLNG KEYKCKVSNKALGAPIEKTISKAKGQPREPQ VYTLPPCRDELTKNQVSLWCLVKGFYPSDIA VEWESNGQPENNYKTTPPVLDSDGSFFLYSK LTVDKSRWQQGNVFSCSVMHEALHNHYTQKS LSLSPGK | 99 |
| 16D5 inverted 2 + 1 with S100aA in CDR H3 pETR14097 | EVQLVESGGGLVKPGGSLRLSCAASGFTFSN AWMSWVRQAPGKGLEWVGRIKSKIDGGITDY AAPVKGRFTISRDDSKNTLYLQMNSLKTEDT AVYYCTTPWEWSWYDYWGQGTLVTVSSASTK GPSVFPLAPSSKSTSGGTAALGCLVKDYFPE PVTVSWNSGALTSGVHTFPAVLQSSGLYSLS SVVTVPSSSLGTQTYICNVNHKPSNTKVDKK VEPKSCDGGGGSGGGGSEVQLLESGGGLVQP GGSLRLSCAASGFTFSTYAMNWVRQAPGKGL EWVSRIRSKYNNYATYYADSVKGRFTISRDD SKNTLYLQMNSLRAEDTAVYYCVRHGNFGNA YVSWFAYWGQGTLVTVSSASTKGPSVFPLAP SSKSTSGGTAALGCLVKDYFPEPVTVSWNSG ALTSGVHTFPAVLQSSGLYSLSSVVTVPSSS LGTQTYICNVNHKPSNTKVDKKVEPKSCDKT HTCPPCPAPEAAGGPSVFLFPPKPKDTLMIS RTPEVTCVVVDVSHEDPEVKFNWYVDGVEVH NAKTKPREEQYNSTYRVVSVLTVLHQDWLNG KEYKCKVSNKALGAPIEKTISKAKGQPREPQ VYTLPPCRDELTKNQVSLWCLVKGFYPSDIA VEWESNGQPENNYKTTPPVLDSDGSFFLYSK LTVDKSRWQQGNVFSCSVMHEALHNHYTQKS LSLSPGK | 100 |
| CD3 light chain fused to CH1; Fc_PGLALA; pETR13862 | QAVVTQEPSLTVSPGGTVTLTCGSSTGAVTT SNYANWVQEKPGQAFRGLIGGTNKRAPGTPA RFSGSLLGGKAALTLSGAQPEDEAEYYCALW YSNLWVFGGGTKLTVLSSASTKGPSVFPLAP SSKSTSGGTAALGCLVKDYFPEPVTVSWNSG ALTSGVHTFPAVLQSSGLYSLSSVVTVPSSS LGTQTYICNVNHKPSNTKVDKKVEPKSCDKT HTCPPCPAPEAAGGPSVFLFPPKPKDTLMIS RTPEVTCVVVDVSHEDPEVKFNWYVDGVEVH NAKTKPREEQYNSTYRVVSVLTVLHQDWLNG KEYKCKVSNKALGAPIEKTISKAKGQPREPQ VYTLPPSRDELTKNQVSLTCLVKGFYPSDIA | 101 |

| Name | Sequence | Seq ID No |
|---|---|---|
| | VEWESNGQPENNYKTTPPVLDSDGSFFLYSK LTVDKSRWQQGNVFSCSVMHEALHNHYTQKS LSLSPGK | |
| 16D5 VH fused to constant kappa chain; pETR13859 | EVQLVESGGGLVKPGGSLRLSCAASGFTFSN AWMSWVRQAPGKGLEWVGRIKSKIDGGITDY AAPVKGRFTISRDDSKNTLYLQMNSLKTEDT AVYYCTTPWEWSWYDYWGQGTLVTVSSASVA APSVFIFPPSDEQLKSGTASVVCLLNNFYPR EAKVQWKVDNALQSGNSQESVTEQDSKDSTY SLSSTLTLSKADYEKHKVYACEVTHQGLSSP VTKSFNRGEC | 102 |
| CD3 VH fused to constant lambda chain; pETR13860 | EVQLLESGGGLVQPGGSLRLSCAASGFTFST YAMNWVRQAPGKGLEWVSRIRSKYNNYATYY ADSVKGRFTISRDDSKNTLYLQMNSLRAEDT AVYYCVRHGNFGNSYVSWFAYWGQGTLVTVS SASPKAAPSVTLFPPSSEELQANKATLVCLI SDFYPGAVTVAWKADSSPVKAGVETTTPSKQ SNNKYAASSYLSLTPEQWKSHRSYSCQVTHE GSTVEKTVAPTECS | 103 |
| IGHV1-46*01(X92343), plus JH4 element | QVQLVQSGAEVKKPGASVKVSCKASGYTFTS YYMHWVRQAPGQGLEWMGIINPSGGSTSYAQ KFQGRVTMTRDTSTSTVYMELSSLRSEDTAV YYCARGGSGGSFDYWGQGTLVTVSS | 104 |
| IGHV1-69*06(L22583), plus JH6 element | QVQLVQSGAEVKKPGSSVKVSCKASGGTFSS YAISWVRQAPGQGLEWMGGIIPIFGTANYAQ KFQGRVTITADKSTSTAYMELSSLRSEDTAV YYCARGGSGGSMDAWGQGTTVTVSS | 105 |
| IGHV3-15*01(X92216), plus JH4 element | EVQLVESGGGLVKPGGSLRLSCAASGFTFSN AWMSWVRQAPGKGLEWVGRIKSKTDGGTTDY AAPVKGRFTISRDDSKNTLYLQMNSLKTEDT AVYYCTTGGSGGSFDYWGQGTLVTVSS | 106 |
| IGHV3-23*01(M99660), plus JH4 element | EVQLLESGGGLVQPGGSLRLSCAASGFTFSS YAMSWVRQAPGKGLEWVSAISGSGGSTYYAD SVKGRFTISRDNSKNTLYLQMNSLRAEDTAV YYCAKGGSGGSPDYWGQGTLVTVSS | 107 |
| IGHV4-59*01(AB019438), plus JH4 element | QVQLQESGPGLVKPSETLSLTCTVSGGSISS YYWSWIRQPPGKGLEWIGYIYYSGSTNYNPS LKSRVTISVDTSKNQFSLKLSSVTAADTAVY YCARGGSGGSFDYWGQGTLVTVSS | 108 |
| IGHV5-51*01(M99686), plus JH4 element | EVQLVQSGAEVKKPGESLKISCKGSGYSFTS YWIGWVRQMPGKGLEWMGIIYPGDSDTRYSP SFQGQVTISADKSISTAYLQWSSLKASDTAM YYCARGGSGGSFDYWGQGTLVTVSS | 109 |
| CD3 specific antibody based on humanized CH2527 light chain | QTVVTQEPSLTVSPGGTVTLTCGSSTGAVTT SNYANWVQEKPGQAFRGLIGGTNKRAPGTPA RFSGSLLGGKAALTLSGAQPEDEAEYYCALW YSNLWVFGGGTKLTVL | 110 |
| hVK1-39(JK4 J-element) | DIQMTQSPSSLSASVGDRVTITCRASQSISS YLNWYQQKPGKAPKLLIYAASSLQSGVPSRF SGSGSGTDFTLTISSLQPEDFATYYCQQSYS TPLTFGGGTKVEIK | 111 |
| VL7_46-13(humanized anti-CD3 antibody light chain) | QAVVTQEPSLTVSPGGTVTLTCGSSTGAVTT SNYANWVQEKPGQAFRGLIGGTNKRAPGTPA RFSGSLLGGKAALTLSGAQPEDEAEYYCALW YSNLWVFGGGTKLTVL | 112 |

8) Exemplary 16D5 variants with reduced affinity
a. Exemplary light chain variants with reduced affinity

| Name | Sequence | Seq ID No |
|---|---|---|
| K53A aa | QTVVTQEPSLTVSPGGTVTLTCGSSTGAVTTSNYANWVQQKPGQAPRGLIGGTNARA PGTPARFSGSLLGGKAALTLSGVQPEDEAEYYCALWYSNLWVFGGGTKLTVL | 113 |

-continued

| Name | Sequence | Seq ID No |
|---|---|---|
| K53A_VL_CDR1 | GSSTGAVTTSNYAN | 32 |
| K53A_VL_CDR2 | GTNARAP | 396 |
| K53A_VL_CDR3 | ALWYSNLWV | 34 |
| S93A aa | QTVVTQEPSLTVSPGGTVTLTCGSSTGAVTTSNYANWVQQKPGQAPRGLIGGTNKRA<br>PGTPARFSGSLLGGKAALTLSGVQPEDEAEYYCALWYANLWVFGGGTKLTVL | 114 |
| S93A_VL_CDR1 | GSSTGAVTTSNYAN | 32 |
| S93A_VL_CDR2 | GTNKRAP | 33 |
| S93A_VL_CDR3 | ALWYANLWV | 397 | b. Exemplary heavy chain variants with reduced affinity

| Name | Sequence | Seq ID No |
|---|---|---|
| S35H aa | EVQLVESGGGLVKPGGSLRLSCAASGFTFSNAWMHWVRQAPGKGLEWVGRIKSKTDG<br>GTTDYAAPVKGRFTISRDDSKNTLYLQMNSLKTEDTAVYYCTTPWEWSWYDYWGQGT<br>LVTVSSAS | 115 |
| S35H_VH_CDR1 | NAWMH | 398 |
| S35H_VH_CDR2 | RIKSKTDGGTTDYAAPVKG | 17 |
| S35H_VH_CDR3 | PWEWSWYDY | 18 |
| G49S aa | EVQLVESGGGLVKPGGSLRLSCAASGFTFSNAWMSWVRQAPGKGLEWVSRIKSKTDG<br>GTTDYAAPVKGRFTISRDDSKNTLYLQMNSLKTEDTAVYYCTTPWEWSWYDYWGQGT<br>LVTVSSAS | 116 |
| G49S_VH_CDR1 | NAWMS | 16 |
| G49S_VH_CDR2 | RIKSKTDGGTTDYAAPVKG | 17 |
| G49S_VH_CDR3 | PWEWSWYDY | 18 |
| R50S aa | EVQLVESGGGLVKPGGSLRLSCAASGFTFSNAWMSWVRQAPGKGLEWVGSIKSKTDG<br>GTTDYAAPVKGRFTISRDDSKNTLYLQMNSLKTEDTAVYYCTTPWEWSWYDYWGQGT<br>LVTVSSAS | 117 |
| R50S_VH_CDR1 | NAWMS | 16 |
| R50S_VH_CDR2 | SIKSKTDGGTTDYAAPVKG | 399 |
| RSOS_VH_CDR3 | PWEWSWYDY | 18 |
| W96Y aa | EVQLVESGGGLVKPGGSLRLSCAASGFTFSNAWMSWVRQAPGKGLEWVGRIKSKTDG<br>GTTDYAAPVKGRFTISRDDSKNTLYLQMNSLKTEDTAVYYCTTPYEWSWYDYWGQGT<br>LVTVSSAS | 118 |
| W96Y_VH_CDR1 | NAWMS | 16 |
| W96Y_VH_CDR2 | RIKSKTDGGTTDYAAPVKG | 17 |
| W96Y_VH_CDR3 | PYEWSWYDY | 400 |
| W98Y aa | EVQLVESGGGLVKPGGSLRLSCAASGFTFSNAWMSWVRQAPGKGLEWVGRIKSKTDG<br>GTTDYAAPVKGRFTISRDDSKNTLYLQMNSLKTEDTAVYYCTTPWEYSWYDYWGQGT<br>LVTVSSAS | 119 |
| W98Y_VH_CDR1 | NAWMS | 16 |
| W98Y_VH_CDR2 | RIKSKTDGGTTDYAAPVKG | 17 |
| W98Y_VH_CDR3 | PWEYSWYDY | 232 |

9) Additional exemplary embodiments generated from a phage display library (CDRs underlined)

| Name | Sequence | Seq ID No |
|---|---|---|
| 90D7 aa | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARNYTIVVSPFDYWGQGTLVTVSSAS | 120 |
| 90D7_VH_CDR1 | SYYMH | 8 |
| 90D7_VH_CDR2 | IINPSGGSTSYAQKFQG | 9 |
| 90D7_VH_CDR3 | NYTIVVSPFDY | 233 |
| 90C1 aa | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARNYFIGSVAMDYWGQGTLVTVSSAS | 121 |
| 90C1_VH_CDR1 | SYYMH | 8 |
| 90C1_VH_CDR2 | IINPSGGSTSYAQKFQG | 9 |
| 90C1_VH_CDR3 | NYFIGSVAMDY | 234 |
| 5E8 VH aa | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARGLTYSMDYWGQGTLVTVSSAS | 122 |
| 5E8_VH_CDR1 | SYYMH | 8 |
| 5E8_VH_CDR2 | IINPSGGSTSYAQKFQG | 9 |
| 5E8_VH_CDR3 | GLTYSMDY | 235 |
| 5E8 VL aa | DIVMTQSPLSLPVTPGEPASISCRSSQSLLHSNGYNYLDWYLQKPGQSPQLLIYLGSNRASGVFDRFSGSGSGTDFTLKISRVEAEDVGVYYCMQALQIPNTFGQGTKVEIKRT | 123 |
| 5E8_VL_CDR1 | RSSQSLLHSNGYNYLD | 59 |
| 5E8_VL_CDR2 | LGSNRAS | 60 |
| 5E8_VL_CDR3 | MQALQIPNT | 236 |
| 12A4 VH aa | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKYAYALDYWGQGTLVTVSSAS | 124 |
| 12A4_VH_CDR1 | SYAMS | 79 |
| 12A4_VH_CDR2 | AISGSGGSTYYADSVKG | 80 |
| 12A4_VH_CDR3 | YAYALDY | 237 |
| 12A4 VL aa | EIVLTQSPGTLSLSPGERATLSCRASQSVSSSYLAWYQQKPGQAPRLLIYGASSRATGIPDRFSGSGSGTDFTLTISRLEPEDFAVYYCQQHGSSSTFGQGTKVEIKRT | 125 |
| 12A4_VL_CDR1 | RASQSVSSSYLA | 52 |
| 12A4_VL_CDR2 | GASSRAT | 53 |
| 12A4_VL_CDR3 | QQHGSSST | 238 |
| 7A3 VH aa | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARGDFSAGRLMDYWGQGTLVTVSSAS | 126 |
| 7A3_VH_CDR1 | SYYMH | 8 |
| 7A3_VH_CDR2 | IINPSGGSTSYAQKFQG | 9 |
| 7A3_VH_CDR3 | GDFSAGRLMDY | 239 |
| 7A3 VL aa | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPPITFGQGTKVEIKRT | 127 |
| 7A3_VL_CDR1 | RSSQSLLHSNGYNYLD | 59 |
| 7A3_VL_CDR2 | LGSNRAS | 60 |

| Name | Sequence | Seq ID No |
|---|---|---|
| 7A3_VL_CDR3 | MQALQTPPIT | 240 |
| 6E10 VH aa | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARGDYNAFDYWGHGTLVTVSSAS | 128 |
| 6E10_VH_CDR1 | SYYMH | 8 |
| 6E10_VH_CDR2 | IINPSGGSTSYAQKFQG | 9 |
| 6E10_VH_CDR3 | GDYNAFDY | 241 |
| 6E10 VL aa | DIVMTQSPLSLPVTPGEPASISCRSSQSLLHSNGYNYLDWYLQKPGQSPQLLIYLGSNRASGVDDRESGSGSGTDFTLKISRVEAEDVGVYYCMQAWHSPTFGQGTKVEIKRT | 129 |
| 6E10_VL_CDR1 | RSSQSLLHSNGYNYLD | 59 |
| 6E10_VL_CDR2 | LGSNRAS | 60 |
| 6E10_VL_CDR3 | MQAWHSPT | 242 |
| 12F9 VH aa | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARGATYTMDYWGQGTLVTVSSAS | 130 |
| 12F9_VH_CDR1 | SYYMH | 8 |
| 12F9_VH_CDR2 | IINPSGGSTSYAQKFQG | 9 |
| 12F9_VH_CDR3 | GATYTMDY | 243 |
| 12F9 VL aa | DIVMTQSPLSLPVTPGEPASISCRSSQSLLHSNGYNYLDWYLQKPGQSPQLLIYLGSNRASGVDDRESGSGSGTDETLKISRVEAEDVGVYYCMQALQTPITFGQGTKVEIKRT | 131 |
| 12F9_VL_CDR1 | RSSQSLLHSNGYNYLD | 59 |
| 12F9_VL_CDR2 | LGSNRAS | 60 |
| 12F9_VL_CDR3 | MQALQTPIT | 244 |

10) 9D11 Glycosite variants: variable light chain of exemplary embodiments (CDRs underlined)

| Variant | Sequence | Seq ID No |
|---|---|---|
| N95S | DIVMTQSPLSLPVTPGEPASISC<u>RSSQSLLHSNGYNYLD</u>WYLQKPGQSPQLLIY<u>LGSNRAS</u>GVPDRFSGSGSGTDFTLKISRVEAEDVGVYYC<u>MQASIMSRT</u>FGQGTKVEIK | 132 |
| 12F9_VL_CDR1 | RSSQSLLHSNGYNYLD | 59 |
| 12F9_VL_CDR2 | LGSNRAS | 60 |
| 12F9_VL_CDR3 | MQASIMSRT | 63 |
| N95Q | DIVMTQSPLSLPVTPGEPASISC<u>RSSQSLLHSNGYNYLD</u>WYLQKPGQSPQLLIY<u>LGSNRAS</u>GVPDRFSGSGSGTDFTLKISRVEAEDVGVYYC<u>MQASIMQRT</u>FGQGTKVEIK | 133 |
| N95Q_VL_CDR1 | RSSQSLLHSNGYNYLD | 59 |
| N95Q_VL_CDR2 | LGSNRAS | 60 |
| N95Q_VL_CDR3 | MQASIMQRT | 65 |
| T97A | DIVMTQSPLSLPVTPGEPASISC<u>RSSQSLLHSNGYNYLD</u>WYLQKPGQSPQLLIY<u>LGSNRAS</u>GVPDRFSGSGSGTDFTLKISRVEAEDVGVYYC<u>MQASIMNRA</u>FGQGTKVEIK | 134 |
| T97A_VL_CDR1 | RSSQSLLHSNGYNYLD | 59 |
| T97A_VL_CDR2 | LGSNRAS | 60 |
| T97A_VL_CDR3 | MQASIMNRA | 67 |

| Variant | Sequence | Seq ID No |
|---|---|---|
| T97N | DIVMTQSPLSLPVTPGEPASISC<u>RSSQSLLHSNGYNYLD</u>WYLQKPGQSPQLLIY<u>LGS NRAS</u>GVPDRFSGSGSGTDFTLKISRVEAEDVGVYYC<u>MQASIMNRN</u>FGQGTKVEIK | 135 |
| T97N_VL_CDR1 | RSSQSLLHSNGYNYLD | 59 |
| T97N_VL_CDR2 | LGSNRAS | 60 |
| T97N_VL_CDR3 | MQASIMNRN | 69 |

11) Deamination Variants

| Variant | Sequence | Seq ID No |
|---|---|---|
| 16D5 VH_D52dE | EVQLVESGGGLVKPGGSLRLSCAASGFTFSNAWMSWVRQAPGKGLEWVGRIKSKTEG GTTDYAAPVKGRFTISRDDSKNTLYLQMNSLKTEDTAVYYCTTPWEWSWYDYWGQGT LVTVSS | 248 |
| 16D5 VH_D52dQ | EVQLVESGGGLVKPGGSLRLSCAASGFTFSNAWMSWVRQAPGKGLEWVGRIKSKTQG GTTDYAAPVKGRFTISRDDSKNTLYLQMNSLKTEDTAVYYCTTPWEWSWYDYWGQGT LVTVSS | 249 |
| CD3_VH N100A | EVQLLESGGGLVQPGGSLRLSCAASGFTFSTYAMNWVRQAPGKGLEWVSRIRSKYNN YATYYADSVKGRFTISRDDSKNTLYLQMNSLRAEDTAVYYCVRHGNFGASYVSWFAY WGQGTLVTVSS | 250 |
| CD3_VH S100aA | EVQLLESGGGLVQPGGSLRLSCAASGFTFSTYAMNWVRQAPGKGLEWVSRIRSKYNN YATYYADSVKGRFTISRDDSKNTLYLQMNSLRAEDTAVYYCVRHGNFGNAYVSWFAY WGQGTLVTVSS | 251 |
| 16D5 [VHCH1]-CD3[VHCH1-N100A]-Fcknob_PGLALA | EVQLVESGGGLVKPGGSLRLSCAASGFTFSNAWMSWVRQAPGKGLEWVGRIKSKTDG GTTDYAAPVKGRFTISRDDSKNTLYLQMNSLKTEDTAVYYCTTPWEWSWYDYWGQGT LVTVSSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPKSCDGGGG SGGGGSEVQLLESGGGLVQPGGSLRLSCAASGFTFSTYAMNWVRQAPGKGLEWVSRI RSKYNNYATYYADSVKGRFTISRDDSKNTLYLQMNSLRAEDTAVYYCVRHGNFGASY VSWFAYWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTKVDKK VEPKSCDKTHTCPPCPAPEAAGGPSVFLFPPKPKDTLMISRTPEVTCVVVDVSHEDP EVKFNWYVDGVEVHNAKTKPREEQYNSTYRVVSVLTVLHQDWLNGKEYKCKVSNKAL GAPIEKTISKAKGQPREPQVYTLPPCRDELTKNQVSLWCLVKGFYPSDIAVEWESNG QPENNYKTTPPVLDSDGSFFLYSKLTVDKSRWQQGNVFSCSVMHEALHNHYTQKSLS LSPGK | 252 |
| 16D5-Fchole-PGLALA | EVQLVESGGGLVKPGGSLRLSCAASGFTFSNAWMSWVRQAPGKGLEWVGRIKSKTDG GTTDYAAPVKGRFTISRDDSKNTLYLQMNSLKTEDTAVYYCTTPWEWSWYDYWGQGT LVTVSSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPKSCDKTHT CPPCPAPEAAGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALGAPIEKTISKA KGQPREPQVCTLPPSRDELTKNQVSLSCAVKGFYPSDIAVEWESNGQPENNYKTTPP VLDSDGSFFLVSKLTVDKSRWQQGNVFSCSVMHEALHNRFTQKSLSLSPGK | 253 |
| CD3-CLC | QAVVTQEPSLTVSPGGTVTLTCGSSTGAVTTSNYANWVQEKPGQAFRGLIGGTNKRA PGTPARFSGSLLGGKAALTLSGAQPEDEAEYYCALWYSNLWVFGGGTKLTVLGQPKA APSVTLFPPSSEELQANKATLVCLISDFYPGAVTVAWKADSSPVKAGVETTTPSKQS NNKYAASSYLSLTPEQWKSHRSYSCQVTHEGSTVEKTVAPTECS | 254 |
| 16D5 [VHCH1]-CD3[VHCH1-S100aA]-Fcknob_PGLALA | EVQLVESGGGLVKPGGSLRLSCAASGFTFSNAWMSWVRQAPGKGLEWVGRIKSKTDG GTTDYAAPVKGRFTISRDDSKNTLYLQMNSLKTEDTAVYYCTTPWEWSWYDYWGQGT LVTVSSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPKSCDGGGG SGG GGSEVQLLESGGGLVQPGGSLRLSCAASGFTFSTYAMNWVRQAPGKGLEWVSRIRSK YNNYATYYADSVKGRFTISRDDSKNTLYLQMNSLRAEDTAVYYCVRHGNFGNAYVSW FAYWGQGTLVTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKKVEP KSCDKTHTCPPCPAPEAAGGPSVFLFPPKPKDTLMISRTPEVTCVVVDVSHEDPEVK FNWYVDGVEVHNAKTKPREEQYNSTYRVVSVLTVLHQDWLNGKEYKCKVSNKALGAP IEKTISKAKGQPREPQVYTLPPCRDELTKNQVSLWCLVKGFYPSDIAVEWESNGQPE NNYKTTPPVLDSDGSFFLYSKLTVDKSRWQQGNVFSCSVMHEALHNHYTQKSLSLSP GK | 255 |

| Variant | Sequence | Seq ID No |
|---|---|---|
| 9D11 [VHCH1]-CD3[VHCL-N100A]-Fcknob_PGLALA | QVQLVQSGAEVKKPGASVKVSCHASGYTFTSYYMHWVRQAPGQGLEWMGIINPSGGP TSYAQKFQGRVTMTRDTSTSTVYMELSSLRSEDTAVYYCARGDFAWLDYWGQGTLVT VSSASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKKVEPKSCDGGGGSGG GGSEVQLLESGGGLVQPGGSLRLSCAASGFTFSTYAMNWVRQAPGKGLEWVSRIRSK YNNYATYYADSVKGRFTISRDDSKNTLYLQMNSLRAEDTAVYYCVRHGNFGASYVSW FAYWGQGTLVTVSSASVAAPSVFIFPPSDEQLKSGTASVVCLLNNFYPREAKVQWKV DNALQSGNSQESVTEQDSKDSTYSLSSTLTLSKADYEKHKVYACEVTHQGLSSPVTK SFNRGECDKTHTCPPCPAPEAAGGPSVFLFPPKPKDTLMISRTPEVTCVVVDVSHED PEVKFNWYVDGVEVHNAKTKPREEQYNSTYRVVSVLTVLHQDWLNGKEYKCKVSNKA LGAPIEKTISKAKGQPREPQVYTLPPCRDELTKNQVSLWCLVKGFYPSDIAVEWESN GQPENNYKTTPPVLDSDGSFFLYSKLTVDKSRWQQGNVFSCSVMHEALHNHYTQKSL SLSPGK | 256 |
| 9D11-Fchole | QVQLVQSGAEVKKPGASVKVSCHASGYTFTSYYMHWVRQAPGQGLEWMGIINPSGGP TSYAQKFQGRVTMTRDTSTSTVYMELSSLRSEDTAVYYCARGDFAWLDYWGQGTLVT VSSASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKKVEPKSCDKTHTCPP CPAPEAAGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALGAPIEKTISKAKGQ PREPQVCTLPPSRDELTKNQVSLSCAVKGFYPSDIAVEWESNGQPENNYKTTPPVLD SDGSFFLVSKLTVDKSRWQQGNVFSCSVMHEALHNHYTQKSLSLSPGK | 257 |
| 9D11_LC [N95Q] | DIVMTQSPLSLPVTPGEPASISCRSSQSLLHSNGYNYLDWYLQKPGQSPQLLIYLGS NRASGVPDRFSGSGSGTDFTLKISRVEAEDVGVYYCMQASIMQRTFGQGTKVEIKRT VAAPSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC | 258 |
| CD3_VLCH1 | QAVVTQEPSLTVSPGGTVTLTCGSSTGAVTTSNYANWVQEKPGQAFRGLIGGTNKRA PGTPARFSGSLLGGKAALTLSGAQPEDEAEYYCALWYSNLWVFGGGTKLTVLSSAST KGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSC | 259 |
| 9D11 [VHCH1]-CD3[VHCH1-S100aA]-Fcknob_PGLALA | QVQLVQSGAEVKKPGASVKVSCHASGYTFTSYYMHWVRQAPGQGLEWMGIINPSGGP TSYAQKFQGRVTMTRDTSTSTVYMELSSLRSEDTAVYYCARGDFAWLDYWGQGTLVT VSSASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKKVEPKSCDGGGGSGG GGSEVQLLESGGGLVQPGGSLRLSCAASGFTFSTYAMNWVRQAPGKGLEWVSRIRSK YNNYATYYADSVKGRFTISRDDSKNTLYLQMNSLRAEDTAVYYCVRHGNFGNAYVSW FAYWGQGTLVTVSSASVAAPSVFIFPPSDEQLKSGTASVVCLLNNFYPREAKVQWKV DNALQSGNSQESVTEQDSKDSTYSLSSTLTLSKADYEKHKVYACEVTHQGLSSPVTK SFNRGECDKTHTCPPCPAPEAAGGPSVFLFPPKPKDTLMISRTPEVTCVVVDVSHED PEVKFNWYVDGVEVHNAKTKPREEQYNSTYRVVSVLTVLHQDWLNGKEYKCKVSNKA LGAPIEKTISKAKGQPREPQVYTLPPCRDELTKNQVSLWCLVKGFYPSDIAVEWESN GQPENNYKTTPPVLDSDGSFFLYSKLTVDKSRWQQGNVFSCSVMHEALHNHYTQKSL SLSPGK | 260 |

12) Mov19 based FolR1 TCBs pf exemplary embodiments (CDRs underlined)

| Name | Sequence | Seq ID No |
|---|---|---|
| pETR11646 Mov19 VH-CH1-Fchole PG/LALA | QVQLQQSGAELVKPGASVKISCKASGYSFTGYFMNW VKQSHGKSLEWIGRIHPYDGDTFYNQNFKDKATLTV DKSSNTAHMELLSLTSEDFAVYYCTRYDGSRAMDYW GQGTTVTVSSASTKGPSVFPLAPSSKSTSGGTAALG CLVKDYFPEPVTVSWNSGALTSGVHTFPAVLQSSGL YSLSSVVTVPSSSLGTQTYICNVNHKPSNTKVDKKV EPKSCDKTHTCPPCPAPEAAGGPSVFLFPPKPKDTL MISRTPEVTCVVVDVSHEDPEVKFNWYVDGVEVHNA KTKPREEQYNSTYRVVSVLTVLHQDWLNGKEYKCKV SNKALGAPIEKTISKAKGQPREPQVCTLPPSRDELT KNQVSLSCAVKGFYPSDIAVEWESNGQPENNYKTTP PVLDSDGSFFLVSKLTVDKSRWQQGNVFSCSVMHEA LHNHYTQKSLSLSPGK | 136 |
| pETR11647 Mov19 VH-CH1- | QVQLQQSGAELVKPGASVKISCKASGYSFTGYFMNW VKQSHGKSLEWIGRIHPYDGDTFYNQNFKDKATLTV DKSSNTAHMELLSLTSEDFAVYYCTRYDGSRAMDYW GQGTTVTVSSASTKGPSVFPLAPSSKSTSGGTAALG | 137 |
| CD3 VH-CL-Fcknob PG/LALA | CLVKDYFPEPVTVSWNSGALTSGVHTFPAVLQSSGL YSLSSVVTVPSSSLGTQTYICNVNHKPSNTKVDKKV EPKSCDGGGGSGGGGSEVQLVESGGGLVQPGKSLKL SCAASGFTFNTYAMNWVRQAPGKGLEWVARIRSKYN NYATYYADSVKDRFTISRDDSQSILYLQMNNLKTED TAMYYCVRHGNFGNSYVSWFAYWGQGTLVTVSAASV AAPSVFIFPPSDEQLKSGTASVVCLLNNFYPREAKV QWKVDNALQSGNSQESVTEQDSKDSTYSLSSTLTLS KADYEKHKVYACEVTHQGLSSPVTKSFNRGECDKTH TCPPCPAPEAAGGPSVFLFPPKPKDTLMISRTPEVT CVVVDVSHEDPEVKFNWYVDGVEVHNAKTKPREEQY NSTYRVVSVLTVLHQDWLNGKEYKCKVSNKALGAPI EKTISKAKGQPREPQVYTLPPCRDELTKNQVSLWCL VKGFYPSDIAVEWESNGQPENNYKTTPPVLDSDGSF FLYSKLTVDKSRWQQGNVFSCSVMHEALHNHYTQKS LSLSPGK | |

| Name | Sequence | Seq ID No |
|---|---|---|
| pETR11644 Mov19 LC | DIELTQSPASLAVSLGQRAIISCKASQSVSFAGTSL MHWYHQKPGQQPKLLIYRASNLEAGVPTRFSGSGSK TDFTLNIHPVEEEDAATYYCQQSREYPYTFGGGTKL EIKRTVAAPSVFIFPPSDEQLKSGTASVVCLLNNFY PREAKVQWKVDNALQSGNSQESVTEQDSKDSTYSLS STLTLSKADYEKHKVYACEVTHQGLSSPVTKSFNRG EC | 138 |

| Name | Sequence | Seq ID No |
|---|---|---|
| Hu IgG1 Fc | DKTHTCPPCPAPELLGGPSVFLFPPKPKDT LMISRTPEVTCVVVDVSHEDPEVKFNWYVD GVEVHNAKTKPREEQYNSTYRVVSVLTVLH QDWLNGKEYKCKVSNKALPAPIEKTISKAK GQPREPQVYTLPPSRDELTKNQVSLTCLVK GFYPSDIAVEWESNGQPENNYKTTPPVLDS DGSFFLYSKLTVDKSRWQQGNVFSCSVMHE ALHNHYTQKSLSLSPGK | 245 |

13) Additional FolR1 TCBs with intermediate affinity binders (CDRs according to Kabat, underlined)

| Name | Sequence | Seq ID No |
|---|---|---|
| 16D5 variant W96Y/D5 2E VH | EVQLVESGGGLVKPGGSLRLSCAASGFTFS <u>NAWMS</u>WVRQAPGKGLEWVG<u>RIKSKTEGGTT DYAAPVKG</u>RFTISRDDSKNTLYLQMNSLKT EDTAVYYCTT<u>PYEWSWYDY</u>WGQGTLVTSS | 401 |
| W96Y/D5 2E VH CDR1 | NAWMS | 16 |
| W96Y/D5 2E VH CDR2 | RIKSKTEGGTTDYAAPVKG | 402 |
| W96Y/D5 2E VH CDR3 | PYEWSWYDY | 400 |
| 16D5 variant W96Y/D5 2E VL | QAVVTQEPSLTVSPGGTVTLTC<u>GSSTGAVT TSNYAN</u>WVQEKPGQAFRGLIG<u>GTNKRAP</u>AGT PARFSGSLLGGKAALTLSGAQPEDEAEYYC <u>ALWYSNLWV</u>FGGGTKLTVL | 31 |
| W96Y/D5 2E_CD3-VHCH1_Fc-knob_PGLALA pETR14945 | EVQLVESGGGLVKPGGSLRLSCAASGFTFS NAWMSWVRQAPGRGLEWVGRIKSKTEGGTT DYAAPVKGRFTISRDDSKNTLYLQMNSLKT EDTAVYYCTTPYEWSWYDYWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDGGGGSGGGGSEVQLLE SGGGLVQPGGSLRLSCAASGFTFSTYAMNW VRQAPGKGLEWVSRIRSKYNNYATYYADSV KGRFTISRDDSKNTLYLQMNSLRAEDTAVY YCVRHGNFGNSYVSWFAYWGQGTLVTVSSA STKGPSVFPLAPSSKSTSGGTAALGCLVKD YFPEPVTVSWNSGALTSGVHTFPAVLQSSG LYSLSSVVTVPSSSLGTQTYICNVNHKPSN TKVDKKVEPKSCDKTHTCPPCPAPEAAGGP SVFLFPPKPKDTLMISRTPEVTCVVVDVSH EDPEVKFNWYVDGVEVHNAKTKPREEQYNS TYRVVSVLTVLHQDWLNGKEYKCKVSNKAL GAPIEKTISKAKGQPREPQVYTLPPCRDEL TKNQVSLWCLVKGFYPSDIAVEWESNGQPE NNYKTTPPVLDSDGSFFLYSKLTVDKSRWQ QGNVFSCSVMHEALHNHYTQKSLSLSPGK | 403 |
| W96Y/D5 2E_Fc-hole_PGLALA_HYRF pETR14946 | EVQLVESGGGLVKPGGSLRLSCAASGFTFS NAWMSWVRQAPGKGLEWVGRIKSKTEGGTT DYAAPVKGRFTISRDDSKNTLYLQMNSLKT EDTAVYYCTTPYEWSWYDYWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPEAAGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LGAPIEKTISKAKGQPREPQVCTLPPSRDE LTKNQVSLSCAVKGFYPSDIAVEWESNGQP ENNYKTTPPVLDSDGSFFLVSKLTVDKSRW QQGNVFSCSVMHEALHNRFTQKSLSLSPGK | 404 |

| Name | Sequence | Seq ID No |
|---|---|---|
| 14B1 VH | EVQLLESGGGLVQPGGSLRLSCAASGFTFS SYAMSWVRQAPGKGLEWVSAISGSGGSTYY ADSVKGRFTISRDNSKNTLYLQMNSLRAED TAVYYCARGDYRYRYFDYWGQGTLVTVSS | 405 |
| 14B1 VL | SSELTQDPAVSVALGQTVRITCQGDSLRSY YASWYQQKPGQAPVLVIYGKENRPSGIPDR FSGSSSGNTASLTITGAQAEDEADYYCNSR ESPPTGLVVFGGGTKLTVL | 406 |
| 14B1[EE]_CD3[VLCH1]_Fc-knob_PGLALA pETR14976 | EVQLLESGGGLVQPGGSLRLSCAASGFTFS SYAMSWVRQAPGKGLEWVSAISGSGGSTYY ADSVKGRFTISRDNSKNTLYLQMNSLRAED TAVYYCARGDYRYRYFDYWGQGTLVTVSSA STKGPSVFPLAPSSKSTSGGTAALGCLVED YFPEPVTVSWNSGALTSGVHTFPAVLQSSG LYSLSSVVTVPSSSLGTQTYICNVNHKPSN TKVDEKVEPKSCDGGGGSGGGGSQAVVTQE PSLTVSPGGTVTLTCGSSTGAVTTSNYANW VQEKPGQAFRGLIGGTNKRAPGTPARFSGS LLGGKAALTLSGAQPEDEAEYYCALWYSNL WVFGGGTKLTVLSSASTKGPSVFPLAPSSK STSGGTAALGCLVKDYFPEPVTVSWNSGAL TSGVHTFPAVLQSSGLYSLSSVVTVPSSSL GTQTYICNVNHKPSNTKVDKKVEPKSCDKT HTCPPCPAPEAAGGPSVFLFPPKPKDTLMI SRTPEVTCVVVDVSHEDPEVKFNWYVDGVE VHNAKTKREEQYNSTYRVVSVLTVLHQDWL NPGKEYKCKVSNKALGAPIEKTISKAKGQP REPQVYTLPPCRDELTKNQVSLWCLVKGFY PSDIAVEWESNGQPENNYKTTPPVLDSDGS FFLYSKLTVDKSRWQQGNVFSCSVMHEALH NHYTQKSLSLSPGK | 407 |
| 14B1[EE]_Fc-hole_PGLALA pETR14977 | EVQLLESGGGLVQPGGSLRLSCAASGFTFS SYAMSWVRQAPGKGLEWVSAISGSGGSTYY ADSVKGRFTISRDNSKNTLYLQMNSLRAED TAVYYCARGDYRYRYFDYWGQGTLVTVSSA STKGPSVFPLAPSSKSTSGGTAALGCLVED YFPEPVTVSWNSGALTSGVHTFPAVLQSSG LYSLSSVVTVPSSSLGTQTYICNVNHKPSN TKVDEKVEPKSCDKTHTCPPCPAPEAAGGP SVFLFPPKPKDTLMISRTPEVTCVVVDVSH EDPEVKFNWYVDGVEVHNAKTKPREEQYNS TYRVVSVLTVLHQDWLNGKEYKCKVSNKAL GAPIEKTISKAKGQPREPQVCTLPPSRDEL TKNQVSLSCAVKGFYPSDIAVEWESNGQPE NNYKTTPPVLDSDGSFFLVSKLTVDKSRWQ QGNVFSCSVMHEALHNHYTQKSLSLSPGK | 408 |
| 14B1 LC [KK] Constant lambda pETR14979 | SSELTQDPAVSVALGQTVRITCQGDSLRSY YASWYQQKPGQAPVLVIYGKNNRPSGIPDR FSGSSSGNTASLTITGAQAEDEADYYCNSR ESPPTGLVVFGGGTKLTVLGQPKAAPSVTL FPPSSKKLQANKATLVCLISDFYPGAVTVA WKADSSPVKAGVETTTPSKQSNNKYAASSY LSLTPEQWKSHRSYSCQVTHEGSTVEKTVA PTECS | 409 |
| 9C7 VH | QVQLVQSGAEVKKPGASVKVSCKASGYTFT SYYMHWVRQAPGQGLEWMGIINPSGGSTSY AQKFQGRVTMTRDTSTSTVYMELSSLRSED TAVYYCARGDWSYYMDYWGQGTLVTVSS | 410 |
| 9C7 VL | DIVMTQSPLSLPVTPGEPASISCRSSQSLL HSNGYNYLDWYLQKPGQSPQLLIYLGSNRA SGVPDRFSGSGSGTDFTLKISRVEAEDVGV YYCMQARQTPTFGQGTKVEIK | 411 |
| 9C7[EE]_CD3[VLCH1]_Fc-knob_PGLALA pETR14974 | QVQLVQSGAEVKKPGASVKVSCKASGYTFT SYYMHWVRQAPGQGLEWMGIINPSGGSTSY AQKFQGRVTMTRDTSTSTVYMELSSLRSED TAVYYCARGDWSYYMDYWGQGTLVTVSSAS TKGPSVFPLAPSSKSTSGGTAALGCLVEDY FPEPVTVSWNSGALTSGVHTFPAVLQSSGL | 412 |

-continued

| Name | Sequence | Seq ID No |
|---|---|---|
| | YSLSSVVTVPSSSLGTQTYICNVNHKPSNT KVDEKVEPKSCDGGGGSGGGGSQAVVTQEP SLTVSPGGTVTLTCGSSTGAVTTSNYANWV QEKPGQAFRGLIGGTNKRAPGTPARFSGSL LGGKAALTLSGAQPEDEAEYYCALWYSNLW VFGGGTKLTVLSSASTKGPSVFPLAPSSKS TSGGTAALGCLVKDYFPEPVTVSWNSGALT SGVHTFPAVLQSSGLYSLSSVVTVPSSSLG TQTYICNVNHKPSNTKVDKKVEPKSCDKTH TCPPCPAPEAAGGPSVFLFPPKPKDTLMIS RTPEVTCVVVDVSHEDPEVKFNWYVDGVEV HNAKTKPREEQYNSTYRVVSVLTVLHQDWL NGKEYKCKVSNKALGAPIEKTISKAKGQPR EPQVYTLPPCRDELTKNQVSLWCLVKGFYP SDIAVEWESNGQPENNYKTTPPVLDSDGSF FLYSKLTVDKSRWQQGNVFSCSVMHEALHN HYTQKSLSLSPGK | |
| 9C7[EE]_Fc-hole_PGLALA pETR14975 | QVQLVQSGAEVKKPGASVKVSCKASGYTFT SYYMHWVRQAPGQGLEWMGIINPSGGSTSY AQKFQGRVTMTRDTSTSTVYMELSSLRSED TAVYYCARGDWSYYMDYWGQGTLVTVSSAS TKGPSVFPLAPSSKSTSGGTAALGCLVEDY FPEPVTVSWNSGALTSGVHTFPAVLQSSGL YSLSSVVTVPSSSLGTQTYICNVNHKPSNT KVDEKVEPKSCDKTHTCPPCPAPEAAGGPS VFLFPPKPKDTLMISRTPEVTCVVVDVSHE DPEVKFNWYVDGVEVHNAKTKPREEQYNST YRVVSVLTVLHQDWLNGKEYKCKVSNKALG APIEKTISKAKGQPREPQVCTLPPSRDELT KNQVSLSCAVKGFYPSDIAVEWESNGQPEN NYKTTPPVLDSDGSFFLVSKLTVDKSRWQQ GNVFSCSVMHEALHNHYTQKSLSLSPGK | 413 |
| 9C7 LC [RK] pETR14980 | DIVMTQSPLSLPVTPGEPASISCRSSQSLL HSNGYNYLDWYLQKPGQSPQLLIYLGSNRA SGVPDRFSGSGSGTDFTLKISRVEAEDVGV YYCMQARQTPTFGQGTKVEIKRTVAAPSVF IFPPSDRKLKSGTASVVCLLNNFYPREAKV QWKVDNALQSGNSQESVTEQDSKDSTYSLS STLTLSKADYEKHKVYACEVTHQGLSSPVT KSFNRGEC | 414 |

14) Antigen Sequences

| Antigen | Sequence | Seq ID No |
|---|---|---|
| hu FolR1 | MAQRMTTQLLLLLVWVAVVGEAQTRIAWARTELL NVCMNAKHHKEKPGPEDKLHEQCRPWRKNACCST NTSQEAHKDVSYLYRFNWNHCGEMAPACKRHFIQ DTCLYECSPNLGPWIQQVDQSWRKERVLNVPLCK EDCEQWWEDCRTSYTCKSNWHKGWNWTSGFNKCA VGAACQPFHFYFPTPTVLCNEIWTHSYKVSNYSR GSGRCIQMWFDPAQGNPNEEVARFYAAAMSGAGP WAAWPFLLSLALMLLWLLS | 139 |
| huFolR1 ECD-AcTev-Fcknob-Avi tag | RIAWARTELLNVCMNAKHHKEKPGPEDKLHEQCR PWRKNACCSTNTSQEAHKDVSYLYRFNWNHCGEM APACKRHFIQDTCLYECSPNLGPWIQQVDQSWRK ERVLNVPLCKEDCEQWWEDCRTSYTCKSNWHKGW NWTSGFNKCAVGAACQPFHFYFPTPTVLCNEIWT HSYKVSNYSRGSGRCIQMWFDPAQGNPNEEVARF YAAAMVD<u>EQLYFQG</u>GSPKSADKTHTCPPCPAPEL LGGPSVFLFPPKPKDTLMISRTPEVTCVVVDVSH EDPEVKFNWYVDGVEVHNAKTKPREEQYNSTYRV VSVLTVLHQDWLNGKEYKCKVSNKALPAPIEKTI SKAKGQPREPQVYTLPPCRDELTKNQVSLWCLVK GFYPSDIAVEWESNGQPENNYKTTPPVLDSDGSF FLYSKLTVDKSRWQQGNVFSCSVMHEALHNHYTQ KSLSLSPGKSGGLNDIFEAQKIEWHE | 140 |
| Fchole | DKTHTCPPCPAPELLGGPSVFLFPPKPKDTLMIS RTPEVTCVVVDVSHEDPEVKFNWYVDGVEVHNAK TKPREEQYNSTYRVVSVLTVLHQDWLNGKEYKCK VSNKALPAPIEKTISKAKGQPREPQVCTLPPSRD ELTKNQVSLSCAVKGFYPSDIAVEWESNGQPENN YKTTPPVLDSDGSFFLVSKLTVDKSRWQQGNVFS CSVMHEALHNRFTQKSLSLSPGK | 141 |
| mu FolR1 | MAHLMTVQLLLLLVMWMAECAQSRATRARTELLNV CMDAKHHKEKPGPEDNLHDQCSPWKTNSCCSTNT SQEAHKDISYLYRFNWNHCGTMTSECKRHFIQDT CLYECSPNLGPWIQQVDQSWRKERILDVPLCKED CQQWWEDCQSSFTCKSNWHKGWNWSSGHNECPVG ASCHPFTFYFPTSAALCEEIWSHSYKLSNYSRGS GRCIQMWFDPAQGNPNEEVARFYAEAMSGAGLHG TWPLLCSLSLVLLWVIS | 142 |
| mu FolR1 ECD-AcTev-Fcknob-Avitag | TRARTELLNVCMDAKHHKEKPGPEDNLHDQCSPW KTNSCCSTNTSQEAHKDISYLYRFNWNHCGTMTS ECKRHFIQDTCLYECSPNLGPWIQQVDQSWRKER ILDVPLCKEDCQQWWEDCQSSFTCKSNWHKGWNW SSGHNECPVGASCHPFTFYFPTSAALCEEIWSHS YKLSNYSRGSGRCIQMWFDPAQGNPNEEVARFYA EAMVD<u>EQLYFQG</u>GSPKSADKTHTCPPCPAPELLG GPSVFLFPPKPKDTLMISRTPEVTCVVVDVSHED | 143 |

| Antigen | Sequence | Seq ID No |
|---|---|---|
| | PEVKFNWYVDGVEVHNAKTKPREEQYNSTYRVVS VLTVLHQDWLNGKEYKCKVSNKALPAPIEKTISK AKGQPREPQVYTLPPCRDELTKNQVSLWCLVKGF YPSDIAVEWESNGQPENNYKTTPPVLDSDGSFFL YSKLTVDKSRWQQGNVFSCSVMHEALHNHYTQKS LSLSPGKSGGLNDIFEAQKIEWHE | |
| cy FolR1 | MAQRMTTQLLLLLVWVAVVGEAQTRTARARTELL NVCMNAKHHKEKPGPEDKLHEQCRPWKKNACCST NTSQEAHKDVSYLYRFNWNHCGEMAPACKRHFIQ DTCLYECSPNLGPWIQQVDQSWRKERVLNVPLCK EDCERWWEDCRTSYTCKSNWHKGWNWTSGFNKCP VGAACQPFHFYFPTPTVLCNEIWTYSYKVSNYSR GSGRCIQMWFDPAQGNPNEEVARFYAAAMSGAGP WAAWPLLLSLALTLLWLLS | 144 |
| cy FolR1 ECD-AcTev-Fcknob-Avi tag | RTARARTELLNVCMNAKHHKEKPGPEDKLHEQCR PWKKNACCSTNTSQEAHKDVSYLYRFNWNHCGEM APACKRHFIQDTCLYECSPNLGPWIQQVDQSWRK ERVLNVPLCKEDCEQWWEDCRTSYTCKSNWHKGW NWTSGFNKCPVGAACQPFHFYFPTPTVLCNEIWT YSYKVSNYSRGSGRCIQMWFDPAQGNPNEEVARF YAAAMVDEQLYFQGGSPKSADKTHTCPPCPAPEL LGGPSVFLFPPKPKDTLMISRTPEVTCVVVDVSH EDPEVKFNWYVDGVEVHNAKTKPREEQYNSTYRV VSVLTVLHQDWLNGKEYKCKVSNKALPAPIEKTI SKAKGQPREPQVYTLPPCRDELTKNQVSLWCLVK GFYPSDIAVEWESNGQPENNYKTTPPVLDSDGSF FLYSKLTVDKSRWQQGNVFSCSVMHEALHNHYTQ KSLSLSPGKSGGLNDIFEAQKIEWHE | 145 |
| hu FolR2 | MVWKWMPLLLLLVCVATMCSAQDRTDLLNVCMDA KHHKTKPGPEDKLHDQCSPWKKNACCTASTSQEL HKDTSRLYNFNWDHCGKMEPACKRHFIQDTCLYE CSPNLGPWIQQVNQSWRKERFLDVPLCKEDCQRW WEDCHTSHTCKSNWHRGWDWTSGVNKCPAGALCR TFESYFPTPAALCEGLWSHSYKVSNYSRGSGRCI QMWFDSAQGNPNEEVARFYAAAMHVNAGEMLHGT GGLLLSLALMLQLWLLG | 146 |
| hu FolR2 ECD-AcTev-Fcknob- | TMCSAQDRTDLLNVCMDAKHHKTKPGPEDKLHDQ CSPWKKNACCTASTSQELHKDTSRLYNFNWDHCG KMEPACKRHFIQDTCLYECSPNLGPWIQQVNQSW RKERFLDVPLCKEDCQRWWEDCHTSHTCKSNWHR GWDWTSGVNKCPAGALCRTFESYFPTPAALCEGL | 147 |

| Antigen | Sequence | Seq ID No |
|---|---|---|
| Avi tag | WSHSYKVSNYSRGSGRCIQMWFDSAQGNPNEEVA RFYAAAMHVVDEQLYFQGGSPKSADKTHTCPPCP APELLGGPSVFLFPPKPKDTLMISRTPEVTCVVV DVSHEDPEVKFNWYVDGVEVHNAKTKPREEQYNS TYRVVSVLTVLHQDWLNGKEYKCKVSNKALPAPI EKTISKAKGQPREPQVYTLPPCRDELTKNQVSLW CLVKGFYPSDIAVEWESNGQPENNYKTTPPVLDS DGSFFLYSKLTVDKSRWQQGNVFSCSVMHEALHN HYTQKSLSLSPGKSGGLNDIFEAQKIEWHE | |
| hu FolR3 | MAWQMMQLLLLLALVTAAGSAQPRSARARTDLLNV CMNAKHHKTQPSPEDELYGQCSPWKKNACCTAST SQELHKDTSRLYNFNWDHCGKMEPTCKRHFIQDS CLYECSPNLGPWIRQVNQSWRKERILNVPLCKED CERWWEDCRTSYTCKSNWHKGWNWTSGINECPAG ALCSTFESYFPTPAALCEGLWSHSFKVSNYSRGS GRCIQMWFDSAQGNPNEEVAKFYAAAMNAGAPSR GIIDS | 148 |
| hu FolR3 ECD-AcTev-Fcknob-Avi tag | SARARTDLLNVCMNAKHHKTQPSPEDELYGQCSP WKKNACCTASTSQELHKDTSRLYNFNWDHCGKME PTCKRHFIQDSCLYECSPNLGPWIRQVNQSWRKE RILNVPLCKEDCERWWEDCRTSYTCKSNWHKGWN WTSGINECPAGALCSTFESYFPTPAALCEGLWSH SFKVSNYSRGSGRCIQMWFDSAQGNPNEEVAKFY AAAMNAGAPSRGIIDSDEQLYFQGGSPKSADKT HTCPPCPAPELLGGPSVFLFPPKPKDTLMISRTP EVTCVVVDVSHEDPEVKFNWYVDGVEVHNAKTKP REEQYNSTYRVVSVLTVLHQDWLNGKEYKCKVSN KALPAPIEKTISKAKGQPREPQVYTLPPCRDELT KNQVSLWCLVKGFYPSDIAVEWESNGQPENNYKT TPPVLDSDGSFFLYSKLTVDKSRWQQGNVFSCSV MHEALHNHYTQKSLSLSPGKSGGLNDIFEAQKIE WHE | 149 |
| hu CD3ε | MQSGTHWRVLGLCLLSVGVWGQDGNEEMGGITQT PYKVSISGTTVILTCPQYPGSEILWQHNDKNIGG DEDDKNIGSDEDHLSLKEFSELEQSGYYVCYPRG SKPEDANFYLYLRARVCENCMEMDVMSVATIVIV DICITGGLLLLVYYWSKNRKAKAKPVTRGAGAGGR QRGQNKERPPPVPNPDYEPIRKGQRDLYSGLNQRR I | 150 |

2) Nucleotide sequences of exemplary embodiments

| Description | Sequence | Seq ID No |
|---|---|---|
| 16A3 | CAGGTGCAATTGGTTCAATCTGGTGCTGAAGTAAAAAAACCGGGCGCTTCC GTTAAAGTGAGCTGCAAAGCATCCGGATACACCTTCACTTCCTATTACATG CACTGGGTTCGTCAAGCCCCGGGCCAGGGTCTGGAATGGATGGGCATCATT AACCCAAGCGGTGGCTCTACCTCCTACGCGCAGAAATTCCAGGGTCGCGTC ACGATGACCCGTGACACTAGCACCTCTACCGTTTATATGGAGCTGTCCAGC CTGCGTTCTGAAGATACTGCAGTGTACTACTGTGCACGCAACTACTACGCT GGTGTTACTCCGTTCGACTATTGGGGTCAAGGCACCCTCGTAACGGTTTCT TCT | 151 |
| 15A1 | CAGGTGCAATTGGTTCAATCTGGTGCTGAAGTAAAAAAACCGGGCGCTTCC GTTAAAGTGAGCTGCAAAGCATCCGGATACACCTTCACTTCCTATTACATG CACTGGGTTCGTCAAGCCCCGGGCCAGGGTCTGGAATGGATGGGCATCATT AACCCAAGCGGTGGCTCTACCTCCTACGCGCAGAAATTCCAGGGTCGCGTC ACGATGACCCGTGACACTAGCACCTCTACCGTTTATATGGAGCTGTCCAGC CTGCGTTCTGAAGATACTGCAGTGTACTACTGTGCACGCAACTACTACATC GGTGTTGTTACTTTCGACTATTGGGGTCAAGGCACCCTCGTAACGGTTTCT TCT | 152 |
| 18D3 | CAGGTGCAATTGGTTCAATCTGGTGCTGAAGTAAAAAAACCGGGCGCTTCC GTTAAAGTGAGCTGCAAAGCATCCGGATACACCTTCACTTCCTATTACATG CACTGGGTTCGTCAAGCCCCGGGCCAGGGTCTGGAATGGATGGGCATCATT AACCCAAGCGGTGGCTCTACCTCCTACGCGCAGAAATTCCAGGGTCGCGTC ACGATGACCCGTGACACTAGCACCTCTACCGTTTATATGGAGCTGTCCAGC | 153 |

| | |
|---|---|
| | CTGCGTTCTGAAGATACTGCAGTGTACTACTGTGCACGCAACTACTACACT GGTGGTTCTTCTGCTTTCGACTATTGGGGTCAAGGCACCCTCGTAACGGTT TCTTCT |
| 19E5 | CAGGTGCAATTGGTTCAATCTGGTGCTGAAGTAAAAAAACCGGGCGNTTCC 154 GTTAAAGTGAGCTGCAAAGCATCCGGATACACCTTCACTTCCTATTACATG CACTGGGTTCGTCAAGCCCCGGGCCAGGGTCTGGAATGGATGGGCATCATT AACCCAAGCGGTGGCTCTACCTCCTACGCGCAGAAATTCCAGGGTCGCGTC ACGATGACCCGTGACACTAGCACCTCTACCGTTTATATGGAGCTGTCCAGC CTGCGTTCTGAAGATACTGCAGTGTACTACTGTGCACGCGGTGAATGGCGT CGTTACACTTCTTTCGACTATTGGGGTCAAGGCACCCTCGTAACGGTTTCT TCT |
| 19A4 | CAGGTGCAATTGGTTCAATCTGGTGCTGAAGTAAAAAAACCGGGCGCTTCC 155 GTTAAAGTGAGCTGCAAAGCATCCGGATACACCTTCACTTCCTATTACATG CACTGGGTTCGTCAAGCCCCGGGCCAGGGTCTGGAATGGATGGGCATCATT AACCCAAGCGGTGGCTCTACCTCCTACGCGCAGAAATTCCAGGGTCGCGTC ACGATGACCCGTGACACTAGCACCTCTACCGTTTATATGGAGCTGTCCAGC CTGCGTTCTGAAGATACTGCAGTGTACTACTGTGCACGCGGTGGTTGGATC CGTTGGGAACATTTCGACTATTGGGGTCAAGGCACCCTCGTAACGGTTTCT TCT |
| 15H7 | CAGGTGCAATTGGTTCAATCTGGTGCTGAAGTAAAAAAACCGGGCGCTTCC 156 GTTAAAGTGAGCTGCAAAGCATCCGGATACACCTTCACTTCCTATTACATG CACTGGGTTCGTCAAGCCCCGGGCCAGGGTCTGGAATGGATGGGCATCATT AACCCAAGCGGTGGCTCTACCTCCTACGCGCAGAAATTCCAGGGTCGCGTC ACGATGACCCGTGACACTAGCACCTCTACCGTTTATATGGAGCTGTCCAGC CTGCGTTCTGAAGATACTGCAGTGTACTACTGTGCACGCAACTACTACCTG TTCTCTACTTCTTTCGACTATTGGGGTCAAGGCACCCTCGTAACGGTTTCT TCT |
| 15E6 | CAGGTGCAATTGGTTCAATCTGGTGCTGAGGTAAAAAAACCGGGCGCTTCC 157 GTTAAAGTGAGCTGCAAAGCATCCGGATACACCTTCACTTCCTATTACATG CACTGGGTTCGTCAAGCCCCGGGCCAGGGTCTGGAATGGATGGGCATCATT AACCCAAGCGGTGGCTCTACCTCCTACGCGCAGAAATTCCAGGGTCGCGTC ACGATGACCCGTGACACTAGCACCTCTACCGTTTATATGGAGCTGTCCAGC CTGCGTTCTGAAGATACTGCAGTGTACTACTGTGCACGCAACTACTACATC GGTATCGTTCCGTTCGACTATTGGGGTCAAGGCACCCTCGTAACGGTTTCT TCT |
| 16D5 | GAGGTGCAATTGGTTGAATCTGGTGGTGGTCTGGTAAAACCGGGCGGTTCC 158 CTGCGTCTGAGCTGCGCGGCTTCCGGATTCACCTTCTCCAACGCGTGGATG AGCTGGGTTCGCCAGGCCCCGGGCAAAGGCCTCGAGTGGGTTGGTCGTATC AAGTCTAAAACTGACGGTGGCACCACGGATTACGCGGCTCCAGTTAAAGGT CGTTTTACCATTTCCCGCGACGATAGCAAAAACACTCTGTATCTGCAGATG AACTCTCTGAAAACTGAAGACACCGCAGTCTACTACTGTACTACCCCGTGG GAATGGTCTTGGTACGATTATTGGGCCAGGGCACGCTGGTTACGGTGTCT TCC |
| 15E12 | GAGGTGCAATTGGTTGAATCTGGTGGTGGTCTGGTAAAACCGGGCGGTTCC 159 CNGCGTCTGAGCTGCGCGGCTTCCGGATTCACCTTCTCCAACGCGTGGATG AGCTGGGTTCGCCAGGCCCCGGGCAAAGGCCTCGAGTGGGTTGGTCGTATC AAGTCTAAAACTGACGGTGGCACCACGGATTACGCGGCTCCAGTTAAAGGT CGTTTTACCATTTCCCGCGACGATAGCAAAAACACTCTGTATCTGCAGATG AACTCTCTGAAAACCGAAGACACCGCAGTCTACTACTGTACTACCCCGTGG GAATGGTCTTACTTCGATTATTGGGCCAGGGCACGCTGGTTACGGTGTCT TCC |
| 21D1 | CAGGTGCAATTGGTTCAATCTGGTGCTGAAGTAAAAAAACCGGGCGCTTCC 160 GTTAAAGTGAGCTGCAAAGCATCCGGATACACCTTCACTTCCTATTACATG CACTGGGTTCGTCAAGCCCCGGGCCAGGGTCTGGAATGGATGGGCATCATT AACCCAAGCGGTGGCTCTACCTCCTACGCGCAGAAATTCCAGGGTCGCGTC ACGATGACCCGTGACACTAGCACCTCTACCGTTTATATGGAGCTGTCCAGC CTGCGTTCTGAAGATACTGCAGTGTACTACTGTGCACGCAACTACTACGTT GGTGTTTCTCCGTTCGACTATTGGGGTCAAGGCACCCTCGTAACGGTTTCT TCT |
| 16F12 | CAGGTGCAATTGGTTCAATCTGGTGCTGAAGTAAAAAAACCGGGCGNTTCC 161 GTTAAAGTGAGCTGCAAAGCATCCGGATACACCTTCACTTCCTATTACATG CACTGGGTTCGTCAAGCCCCGGGCCAGGGTCTGGAATGGATGGGCATCATT AACCCAAGCGGTGGCTCTACCTCNTACGCGCAGAAATTCCAGGGTCGCGTC ACGATGACCCGTGACACTAGCACCTCTACCGTTTATATGGAGCTGTCCAGC CTGCGTTCTGAAGATACTGCAGTGTACTACTGTGCACGCAACTTCACTGTT CTGCGTGTTCCGTTCGACTATTGGGGTCAAGGCACCCTCGTAACGGTTTCT TCT |
| 21A5 | GAGGTGCAATTGGTTGAATCTGGTGGTGGTCTGGTAAAACCGGGCGGTTCC 162 CTGCGTCTGAGCTGCGCGGCTTCCGGATTCACCTTCTCCAACGCGTGGATG AGCTGGGTTCGCCAGGCCCCGGGCAAAGGCCTCGAGTGGGTTGGTCGTATC |

|  |  |
|---|---|
|  | AAGTCTAAAACTGACGGTGGCACCACGGATTACGCGGCTCCAGTTAAAGGT<br>CGTTTTACCATTTCCCGCGACGATAGCAAAAACACTCTGTATCTGCAGATG<br>AACTCTCTGAAAACTGAAGACACCGCAGTCTACTACTGTACTACCCCGTGG<br>GAATGGGCTTGGTTCGATTATTGGGGCCAGGGCACGCTGGTTACGGTGTCT<br>TCC |
| 21G8 | GAGGTGCAATTGGTTGAATCTGGTGGTGGTCTGGTAAAACCGGGCGGTTCC 163<br>CTGCGTCTGAGCTGCGCGGCTTCCGGATTCACCTTCTCCAACGCGTGGATG<br>AGCTGGGTTCGCCAGGCCCCGGGCAAAGGCCTCGAGTGGGTTGGTCGTATC<br>AAGTCTAAAACTGACGGTGGCACCACGGATTACGCGGCTCCAGTTAAAGGT<br>CGTTTTACCATTTCCCGCGACGATAGCAAAAACACTCTGTATCTGCAGATG<br>AACTCTCTGAAAACCGAAGACACCGCAGTCTACTACTGTACTACCCCTTGG<br>GAATGGGCTTACTTCGATTATTGGGGCCAGGGCACGCTGGTTACGGTGTCT<br>TCC |
| 19H3 | CAGGTGCAATTGGTTCAATCTGGTGCTGAAGTAAAAAAACCGGGCGCTTCC 164<br>GTTAAAGTGAGCTGCAAAGCATCCGGATACACCTTCACTTCCTATTACATG<br>CACTGGGTTCGTCAAGCCCCGGGCCAGGGTCTGGAATGGATGGGCATCATT<br>AACCCAAGCGGTGGCTCTACCTCCTACGCGCAGAAATTCCAGGGTCGCGTC<br>ACGATGACCCGTGACACTAGCACCTCTACCGTTTATATGGAGCTGTCCAGC<br>CTGCGTTCTGAAGATACTGCAGTGTACTACTGTGCACGCACTGGTTGGTCT<br>CGTTGGGGTTACATGGACTATTGGGGCCAAGGCACCCTCGTAACGGTTTCT<br>TCT |
| 20G6 | CAGGTGCAATTGGTTCAATCTGGTGCTGAAGTAAAAAAACCGGGCGCTTCC 165<br>GTTAAAGTGAGCTGCAAAGCATCCGGATACACCTTCACTTCCTATTACATG<br>CACTGGGTTCGTCAAGCCCCGGGCCAGGGTCTGGAATGGATGGGCATCATT<br>AACCCAAGCGGTGGCTCTACCTCCTACGCGCAGAAATTCCAGGGTCGCGTC<br>ACGATGACCCGTGACACTAGCACCTCTACCGTTTATATGGAGCTGTCCAGC<br>CTGCGTTCTGAAGATACTGCAGTGTACTACTGTGCACGCGGTGAATGGATC<br>CGTTACTACCATTTCGACTATTGGGGTCAAGGCACCCTCGTAACGGTTTCT<br>TCT |
| 20H7 | CAGGTGCAATTGGTTCAATCTGGTGCTGAAGTAAAAAAACCGGGCGCTTCC 166<br>GTTAAAGTGAGCTGCAAAGCATCCGGATACACCTTCACTTCCTATTACATG<br>CACTGGGTTCGTCAAGCCCCGGGCCAGGGTCTGGAATGGATGGGCATCATT<br>AACCCAAGCGGTGGCTCTACCTCCTACGCGCAGAAATTCCAGGGTCGCGTC<br>ACGATGACCCGTGACACTAGCACCTCTACCGTTTATATGGAGCTGTCCAGC<br>CTGCGTTCTGAAGATACTGCAGTGTACTACTGTGCACGCGTTGGTTGGTAC<br>CGTTGGGGTTACATGGACTATTGGGGTCAAGGCACCCTCGTAACGGTTTCT<br>TCT |
| 11F8_VH | CAGGTGCAATTGGTGCAGTCTGGGGCTGAGGTGAAGAAGCCTGGGTCCTCG 167<br>GTGAAGGTCTCCTGCAAGGCCTCCGGAGGCACATTCAGCAGCTACGCTATA<br>AGCTGGGTGCGACAGGCCCCTGGACAAGGGCTCGAGTGGATGGGAGGGATC<br>ATCCCTATCTTTGGTACAGCAAACTACGCACAGAAGTTCCAGGGCAGGGTA<br>ACCATTACTGCAGACAAATCCACGAGCACAGCCTACATGGAGCTGAGCAGC<br>CTGAGATCTGAGGACACCGCCGTGTATTACTGTGCGAGAGCTGTTTTCTAC<br>CGTGCTTGGTACTCTTTCGACTACTGGGGCCAAGGGACCACCGTGACCGTC<br>TCCTCA |
| 11F8_VL | GACATCCAGATGACCCAGTCTCCTTCCACCCTGTCTGCATCTGTAGGAGAC 168<br>CGTGTCACCATCACTTGCCGTGCCAGTCAGAGTATTAGTAGCTGGTTGGCC<br>TGGTATCAGCAGAAACCAGGGAAAGCCCCTAAGCTCCTGATCTATGATGCC<br>TCCAGTTTGGAAAGTGGGGTCCCATCGCGTTTCAGCGGCAGTGGATCCGGG<br>ACAGAATTCACTCTCACCATCAGCAGCTTGCAGCCTGATGATTTTGCAACT<br>TATTACTGCCAACAGTATACCAGCCCACCACCAACGTTTGGCCAGGGCACC<br>AAAGTCGAGATCAAG |
| 36F2_VH | CAGGTGCAATTGGTTCAATCTGGTGCTGAAGTAAAAAAACCGGGCGCTTCC 169<br>GTTAAAGTGAGCTGCAAAGCATCCGGATACACCTTCACTTCCTATTACATG<br>CACTGGGTTCGTCAAGCCCCGGGCCAGGGTCTGGAATGGATGGGCATCATT<br>AACCCAAGCGGTGGCTCTACCTCCTACGCGCAGAAATTCCAGGGTCGCGTC<br>ACGATGACCCATGACACTAGCACCTCTACCGTTTATATGGAGCTGTCCAGC<br>CTGCGTTCTGAAGATACTGCAGTGTACTACTGTGCACGCTCTTTCTTCACT<br>GGTTTCCATCTGGACTATTGGGGTCAAGGCACCCTCGTAACGGTTTCTTCT |
| 36F2_VL | GAAATCGTGTTAACGCAGTCTCCAGGCACCCTGTCTTTGTCTCCAGGGGAA 170<br>AGAGCCACCCTCTCTTGCAGGGCCAGTCAGAGTGTTAGCAGCAGCTACTTA<br>GCCTGGTACCAGCAGAAACCTGGCCAGGCTCCCAGGCTCCTCATCTATGGA<br>GCATCCAGCAGGGCCACTGGCATCCCAGACAGGTTCAGTGGCAGTGGATCC<br>GGGACAGACTTCACTCTCACCATCAGCAGACTGGAGCCTGAAGATTTTGCA<br>GTGTATTACTGTCAGCAGTATACCAACGAACATTATTATACGTTCGGCCAG<br>GGGACCAAAGTGGAAATCAAA |
| 9D11_VH | CAGGTGCAATTGGTTCAATCTGGTGCTGAAGTAAAAAAACCGGGCGCTTCC 171<br>GTTAAAGTGAGCTGCAAAGCATCCGGATACACCTTCACTTCCTATTACATG<br>CACTGGGTTCGTCAAGCCCCGGGCCAGGGTCTGGAATGGATGGGCATCATT<br>AACCCAAGCGGTGGCCCTACCTCCTACGCGCAGAAATTCCAGGGTCGCGTC |

|  |  |  |
|---|---|---|
| | ACGATGACCCGTGACACTAGCACCTCTACCGTTTATATGGAGCTGTCCAGC<br>CTGCGTTCTGAAGATACTGCAGTGTACTACTGTGCACGCGGTGACTTCGCT<br>TGGCTGGACTATTGGGGTCAAGGCACCCTCGTAACGGTTTCTTCT | |
| 9D11_VL | GATATTGTTATGACTCAATCTCCACTGTCTCTGCCGGTGACTCCAGGCGAA<br>CCGGCGAGCATTTCTTGCCGTTCCAGCCAGTCTCTGCTGCACTCCAACGGC<br>TACAACTATCTCGATTGGTACCTGCAAAAACCGGGTCAGAGCCCTCAGCTG<br>CTGATCTACCTGGGCTCTAACCGCGCTTCCGGTGTACCGGACCGTTTCAGC<br>GGCTCTGGATCCGGCACCGATTTCACGTTGAAAATCAGCCGTGTTGAAGCA<br>GAAGACGTGGGCGTTTATTACTGTATGCAGGCAAGCATTATGAACCGGACT<br>TTTGGTCAAGGCACCAAGGTCGAAATTAAA | 172 |
| 9D11_VL<br>N95S | GATATTGTTATGACTCAATCTCCACTGTCTCTGCCGGTGACTCCAGGCGAA<br>CCGGCGAGCATTTCTTGCCGTTCCAGCCAGTCTCTGCTGCACTCCAACGGC<br>TACAACTATCTCGATTGGTACCTGCAAAAACCGGGTCAGAGCCCTCAGCTG<br>CTGATCTACCTGGGCTCTAACCGCGCTTCCGGTGTACCGGACCGTTTCAGC<br>GGCTCTGGATCCGGCACCGATTTCACGTTGAAAATCAGCCGTGTTGAAGCA<br>GAAGACGTGGGCGTTTATTACTGTATGCAGGCAAGCATTATGAGCCGGACT<br>TTTGGTCAAGGCACCAAGGTCGAAATTAAA | 173 |
| 9D11_VL<br>N95Q | GATATTGTTATGACTCAATCTCCACTGTCTCTGCCGGTGACTCCAGGCGAA<br>CCGGCGAGCATTTCTTGCCGTTCCAGCCAGTCTCTGCTGCACTCCAACGGC<br>TACAACTATCTCGATTGGTACCTGCAAAAACCGGGTCAGAGCCCTCAGCTG<br>CTGATCTACCTGGGCTCTAACCGCGCTTCCGGTGTACCGGACCGTTTCAGC<br>GGCTCTGGATCCGGCACCGATTTCACGTTGAAAATCAGCCGTGTTGAAGCA<br>GAAGACGTGGGCGTTTATTACTGTATGCAGGCAAGCATTATGCAGCGGACT<br>TTTGGTCAAGGCACCAAGGTCGAAATTAAA | 174 |
| 9D11_VL<br>T97A | GATATTGTTATGACTCAATCTCCACTGTCTCTGCCGGTGACTCCAGGCGAA<br>CCGGCGAGCATTTCTTGCCGTTCCAGCCAGTCTCTGCTGCACTCCAACGGC<br>TACAACTATCTCGATTGGTACCTGCAAAAACCGGGTCAGAGCCCTCAGCTG<br>CTGATCTACCTGGGCTCTAACCGCGCTTCCGGTGTACCGGACCGTTTCAGC<br>GGCTCTGGATCCGGCACCGATTTCACGTTGAAAATCAGCCGTGTTGAAGCA<br>GAAGACGTGGGCGTTTATTACTGTATGCAGGCAAGCATTATGAACCGGGCT<br>TTTGGTCAAGGCACCAAGGTCGAAATTAAA | 175 |
| 9D11_VL<br>T97N | GATATTGTTATGACTCAATCTCCACTGTCTCTGCCGGTGACTCCAGGCGAA<br>CCGGCGAGCATTTCTTGCCGTTCCAGCCAGTCTCTGCTGCACTCCAACGGC<br>TACAACTATCTCGATTGGTACCTGCAAAAACCGGGTCAGAGCCCTCAGCTG<br>CTGATCTACCTGGGCTCTAACCGCGCTTCCGGTGTACCGGACCGTTTCAGC<br>GGCTCTGGATCCGGCACCGATTTCACGTTGAAAATCAGCCGTGTTGAAGCA<br>GAAGACGTGGGCGTTTATTACTGTATGCAGGCAAGCATTATGAACCGGAAT<br>TTTGGTCAAGGCACCAAGGTCGAAATTAAA | 176 |
| 5D9_VH | CAGGTGCAATTGGTTCAATCTGGTGCTGAAGTAAAAAAACCGGGCGCTTCC<br>GTTAAAGTGAGCTGCAAAGCATCCGGATACACCTTCACTTCCTATTACATG<br>CACTGGGTTCGTCAAGCCCCGGGCCAGGGTCTGGAATGGATGGGCATCATT<br>AACCCAAGCGGTGGCTCTACCTCCTACGCGCAGAAATTCCAGGGTCGCGTC<br>ACGATGACCCGTGACACTAGCACCTCTACCGTTTATATGGAGCTGTCCAGC<br>CTGCGTTCTGAAGATACTGCAGTGTACTACTGTGCACGCTCTTACATCGAC<br>ATGGACTATTGGGGTCAAGGCACCCTCGTAACGGTTTCTTCT | 177 |
| 5D9_VL | GAAATCGTGTTAACGCAGTCTCCAGGCACCCTGTCTTTGTCTCCAGGGGAA<br>AGAGCCACCCTCTCTTGCAGGGCCAGTCAGAGTGTTAGCAGCAGCTACTTA<br>GCCTGGTACCAGCAGAAACCTGGCCAGGCTCCCAGGCTCCTCATCTATGGA<br>GCATCCAGCAGGGCCACTGGCATCCCAGACAGGTTCAGTGGCAGTGGATCC<br>GGGACAGACTTCACTCTCACCATCAGCAGACTGGAGCCTGAAGATTTTGCA<br>GTGTATTACTGTCAGCAGGATAACTGGAGCCCAACGTTCGGCCAGGGGACC<br>AAAGTGGAAATCAAA | 178 |
| 6B6_VH | CAGGTGCAATTGGTTCAATCTGGTGCTGAAGTAAAAAAACCGGGCGCTTCC<br>GTTAAAGTGAGCTGCAAAGCATCCGGATACACCTTCACTTCCTATTACATG<br>CACTGGGTTCGTCAAGCCCCGGGCCAGGGTCTGGAATGGATGGGCATCATT<br>AACCCAAGCGGTGGCTCTACCTCCTACGCGCAGAAATTCCAGGGTCGCGTC<br>ACGATGACCCGTGACACTAGCACCTCTACCGTTTATATGGAGCTGTCCAGC<br>CTGCGTTCTGAAGATACTGCAGTGTACTACTGTGCACGCTCTTACGTTGAC<br>ATGGACTATTGGGGTCAAGGCACCCTCGTAACGGTTTCTTCT | 179 |
| 6B6_VL | GAAATCGTGTTAACGCAGTCTCCAGGCACCCTGTCTTTGTCTCCAGGGGAA<br>AGAGCCACCCTCTCTTGCAGGGCCAGTCAGAGTGTTAGCAGCAGCTACTTA<br>GCCTGGTACCAGCAGAAACCTGGCCAGGCTCCCAGGCTCCTCATCTATGGA<br>GCATCCAGCAGGGCCACTGGCATCCCAGACAGGTTCAGTGGCAGTGGATCC<br>GGGACAGACTTCACTCTCACCATCAGCAGACTGGAGCCTGAAGATTTTGCA<br>GTGTATTACTGTCAGCAGGATATTTGGAGCCCAACGTTCGGCCAGGGGACC<br>AAAGTGGAAATCAAA | 180 |
| 14E4_VH | GAGGTGCAATTGTTGGAGTCTGGGGGAGGCTTGGTACAGCCTGGGGGGTCC<br>CTGAGACTCTCCTGTGCAGCCTCCGGATTCACCTTTAGCAGTTATGCCATG<br>AGCTGGGTCCGCCAGGCTCCAGGGAAGGGGCTGGAGTGGGTCTCAGCTATT | 181 |

-continued

|  |  |  |
|---|---|---|
|  | AGTGGTAGTGGTGGTAGCACATACTACGCAGACTCCGTGAAGGGCCGGTTC<br>ACCATCTCCAGAGACAATTCCAAGAACACGCTGTATCTGCAGATGAACAGC<br>CTGAGAGCCGAGGACACGGCCGTATATTACTGTGCGAAAGACTCTTCTTAC<br>GTTGAATGGTACGCTTTCGACTACTGGGGCCAAGGAACCCTGGTCACCGTC<br>TCGAGT |  |
| 14E4_VL | GAAATCGTGTTAACGCAGTCTCCAGGCACCCTGTCTTTGTCTCCAGGGGAA<br>AGAGCCACCCTCTCTTGCAGGGCCAGTCAGAGTGTTAGCAGCAGCTACTTA<br>GCCTGGTACCAGCAGAAACCTGGCCAGGCTCCCAGGCTCCTCATCTATGGA<br>GCATCCAGCAGGGCCACTGGCATCCCAGACAGGTTCAGTGGCAGTGGATCC<br>GGGACAGACTCCACTCTCACCATCAGCAGACTGGAGCCTGAAGATTTTGCA<br>GTGTATTACTGTCAGCAGCCAACCAGCAGCCCAATTACGTTCGGCCAGGGG<br>ACCAAAGTGGAAATCAAA | 182 |
| CD3 heavy chain (VHCH1) | GAGGTGCAGCTGCTGGAATCTGGCGGCGGACTGGTGCAGCCTGGCGGATCT<br>CTGAGACTGAGCTGTGCCGCCAGCGGCTTCACCTTCAGCACCTACGCCATG<br>AACTGGGTGCGCCAGGCCCCTGGCAAAGGCCTGGAATGGGTGTCCCGGATC<br>AGAAGCAAGTACAACAACTACGCCACCTACTACGCCGACAGCGTGAAGGGC<br>CGGTTCACCATCAGCCGGGACGACAGCAAGAACACCCTGTACCTGCAGATG<br>AACAGCCTGCGGGCCGAGGACACCGCCGTGTACTATTGTGTGCGGCACGGC<br>AACTTCGGCAACAGCTATGTGTCTTGGTTTGCCTACTGGGGCCAGGGCACC<br>CTCGTGACCGTGTCAAGCGCTAGTACCAAGGGCCCCAGCGTGTTCCCCCTG<br>GCACCCAGCAGCAAGAGCACATCTGGCGGAACAGCCGCTCTGGGCTGTCTG<br>GTGAAAGACTACTTCCCCGAGCCCGTGACCGTGTCTTGGAACTCTGGCGCC<br>CTGACCAGCGGCGTGCACACCTTTCCAGCCGTGCTGCAGAGCAGCGGCCTG<br>TACTCCCTGTCCTCCGTGGTCACCGTGCCCTCTAGCTCCCTGGGAACACAG<br>ACATATATCTGTAATGTCAATCACAAGCCTTCCAACACCAAAGTCGATAAG<br>AAAGTCGAGCCCAAGAGCTGC | 183 |
| Crossed CD3 heavy chain (VHCκ) | GAGGTGCAGCTGCTGGAATCTGGCGGCGGACTGGTGCAGCCTGGCGGATCT<br>CTGAGACTGAGCTGTGCCGCCAGCGGCTTCACCTTCAGCACCTACGCCATG<br>AACTGGGTGCGCCAGGCCCCTGGCAAAGGCCTGGAATGGGTGTCCCGGATC<br>AGAAGCAAGTACAACAACTACGCCACCTACTACGCCGACAGCGTGAAGGGC<br>CGGTTCACCATCAGCCGGGACGACAGCAAGAACACCCTGTACCTGCAGATG<br>AACAGCCTGCGGGCCGAGGACACCGCCGTGTACTATTGTGTGCGGCACGGC<br>AACTTCGGCAACAGCTATGTGTCTTGGTTTGCCTACTGGGGCCAGGGCACC<br>CTCGTGACCGTGTCAAGCGCTAGTGTGGCCGCTCCCTCCGTGTTTATCTTT<br>CCCCCATCCGATGAACAGCTGAAAAGCGGCACCGCCTCCGTCGTGTGTCTG<br>CTGAACAATTTTTACCCTAGGGAAGCTAAAGTGCAGTGGAAAGTGGATAAC<br>GCACTGCAGTCCGGCAACTCCCAGGAATCTGTGACAGAACAGGACTCCAAG<br>GACAGCACCTACTCCCTGTCCTCCACCCTGACACTGTCTAAGGCTGATTAT<br>GAGAAACACAAAGTCTACGCCTGCGAAGTCACCCATCAGGGCCTGAGCTCG<br>CCCGTCACAAAGAGCTTCAACAGGGGAGAGTGT | 184 |
| Mutagenesis primer GAB7734 N95Q | GCAGGCAAGCATTATGCAGCGGACTTTTGGTCAAGG | 185 |
| Mutagenesis primer GAB7735 N95S | CAGGCAAGCATTATGAGCCGGACTTTTGGTCAAGG | 186 |
| Mutagenesis primer GAB7736 T97A | CATTATGAACCGGGCTTTTGGTCAAGGCACCAAGGTC | 187 |
| Mutagenesis primer GAB7737 T97N | CATTATGAACCGGAATTTTGGTCAAGGCACCAAGGTC | 188 |
| VHCH1[16D5]_VHCH1[CD3]_Fcknob_PGLALA<br>pCON999 (Inverted TCB with 16D5 2 +<br>1: pCON999 + pCON983 + pETR13197) | GAGGTGCAATTGGTTGAATCTGGTGGTGGTCTGGTAAAACCGGGCGGTTCC<br>CTGCGTCTGAGCTGCGCGGCTTCCGGATTCACCTTCTCCAACGCGTGGATG<br>AGCTGGGTTCGCCAGGCCCCGGGCAAAGGCCTCGAGTGGGTTGGTCGTATC<br>AAGTCTAAAACTGACGGTGGCACCACGGATTACGCGGCTCCAGTTAAAGGT<br>CGTTTTACCATTTCCCGCGACGATAGCAAAAACACTCTGTATCTGCAGATG<br>AACTCTCTGAAAACTGAAGACACCGCAGTCTACTACTGTACTACCCCGTGG<br>GAATGGTCTTGGTACGATTATTGGGGCCAGGGCACGCTGGTTACGGTGTCT<br>TCCGCTAGCACAAAGGGCCCTAGCGTGTTCCCTCTGGCCCCCAGCAGCAAG<br>AGCACAAGCGGCGGAACAGCCGCCCTGGGCTGCCTCGTGAAGGACTACTTC<br>CCCGAGCCCGTGACAGTGTCTTGGAACAGCGGAGCCCTGACAAGCGGCGTG<br>CACACTTTCCCTGCCGTGCTGCAGAGCAGCGGCCTGTACTCCCTGAGCAGC<br>GTGGTCACCGTGCCTAGCAGCAGCCTGGGCACCCAGACCTACATCTGCAAC<br>GTGAACCACAAGCCCAGCAACACCAAAGTGGACAAGAAGGTGGAGCCCAAG<br>AGCTGTGATGGCGGAGGAGGGTCCGGAGGCGGAGGATCCGAGGTGCAGCTG<br>CTGGAATCTGGCGGCGGACTGGTGCAGCCTGGCGGATCTCTGAGACTGAGC<br>TGTGCCGCCAGCGGCTTCACCTTCAGCACCTACGCCATGAACTGGGTGCGC<br>CAGGCCCCTGGCAAAGGCCTGGAATGGGTGTCCCGGATCAGAAGCAAGTAC<br>AACAACTACGCCACCTACTACGCCGACAGCGTGAAGGGCCGGTTCACCATC<br>AGCCGGGACGACAGCAAGAACACCCTGTACCTGCAGATGAACAGCCTGCGG<br>GCCGAGGACACCGCCGTGTACTATTGTGTGCGGCACGGCAACTTCGGCAAC<br>AGCTATGTGTCTTGGTTTGCCTACTGGGGCCAGGGCACCCTCGTGACCGTG<br>TCAAGCGCTAGTACCAAGGGCCCCAGCGTGTTCCCCCTGGCACCCAGCAGC<br>AAGAGCACATCTGGCGGAACAGCCGCTCTGGGCTGTCTGGTGAAAGACTAC<br>TTCCCCGAGCCCGTGACCGTGTCTTGGAACTCTGGCGCCCTGACCAGCGGC<br>GTGCACACCTTTCCAGCCGTGCTGCAGAGCAGCGGCCTGTACTCCCTGTCC<br>TCCGTGGTCACCGTGCCCTCTAGCTCCCTGGGAACACAGACATATATCTGT<br>AATGTCAATCACAAGCCTTCCAACACCAAAGTCGATAAGAAAGTCGAGCCC | 189 |

| | |
|---|---|
| | AAGAGCTGCGACAAAACTCACACATGCCCACCGTGCCCAGCACCTGAAGCT<br>GCAGGGGACCGTCAGTCTTCCTCTTCCCCCCAAAACCCAAGGACACCCTC<br>ATGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCAT<br>AATGCCAAGACAAAGCCGCGGGAGGAGCAGTACAACAGCACGTACCGTGTG<br>GTCAGCGTCCTCACCGTCCTGCACCAGGACTGGCTGAATGGCAAGGAGTAC<br>AAGTGCAAGGTCTCCAACAAAGCCCTCGGCGCCCCCATCGAGAAAACCATC<br>TCCAAAGCCAAAGGGCAGCCCCGAGAACCACAGGTGTACACCCTGCCCCCA<br>TGCCCGGATGAGCTGACCAAGAACCAGGTCAGCCTGTGGTGCCTGGTCAAA<br>GGCTTCTATCCCAGCGACATCGCCGTGGAGTGGGAGAGCAATGGGCAGCCG<br>GAGAACAACTACAAGACCACGCCTCCCGTGCTGGACTCCGACGGCTCCTTC<br>TTCCTCTACAGCAAGCTCACCGTGGACAAGAGCAGGTGGCAGCAGGGGAAC<br>GTCTTCTCATGCTCCGTGATGCATGAGGCTCTGCACAACCACTACACGCAG<br>AAGAGCCTCTCCCTGTCTCCGGGTAAA |
| VHCH1[16D5]_Fchole_PGLALA_HYRF<br>pCON983 | GAGGTGCAATTGGTTGAATCTGGTGGTGGTCTGGTAAAACCGGGCGGTTCC 190<br>CTGCGTCTGAGCTGCGCGGCTTCCGGATTCACCTTCTCCAACGCGTGGATG<br>AGCTGGGTTCGCCAGGCCCCGGGCAAAGGCCTCGAGTGGGTTGGTCGTATC<br>AAGTCTAAAACTGACGGTGGCACCACGGATTACGCGGCTCCAGTTAAAGGT<br>CGTTTTACCATTTCCCGCGACGATAGCAAAAACACTCTGTATCTGCAGATG<br>AACTCTCTGAAAACTGAAGACACCGCAGTCTACTACTGTACTACCCCGTGG<br>GAATGGTCTTGGTACGATTATTGGGGCCAGGGCACGCTGGTTACGGTGTCT<br>TCCGCTAGCACCAAGGGCCCCTCCGTGTTCCCCCTGGCCCCCAGCAGCAAG<br>AGCACCAGCGGCGGCACAGCCGCTCTGGGCTGCCTGGTCAAGGACTACTTC<br>CCCGAGCCCGTGACCGTGTCCTGGAACAGCGGAGCCCTGACCTCCGGCGTG<br>CACACCTTCCCCGCCGTGCTGCAGAGTTCTGGCCTGTATAGCCTGAGCAGC<br>GTGGTCACCGTGCCTTCTAGCAGCCTGGGCACCCAGACCTACATCTGCAAC<br>GTGAACCACAAGCCCAGCAACACCAAGGTGGACAAGAAGGTGGAGCCCAAG<br>AGCTGCGACAAAACTCACACATGCCCACCGTGCCCAGCACCTGAAGCTGCA<br>GGGGGACCGTCAGTCTTCCTCTTCCCCCCAAAACCCAAGGACACCCTCATG<br>ATCTCCCGGACCCCTGAGGTCACATGCGTGGTGGTGGACGTGAGCCACGAA<br>GACCCTGAGGTCAAGTTCAACTGGTACGTGGACGGCGTGGAGGTGCATAAT<br>GCCAAGACAAAGCCGCGGGAGGAGCAGTACAACAGCACGTACCGTGTGGTC<br>AGCGTCCTCACCGTCCTGCACCAGGACTGGCTGAATGGCAAGGAGTACAAG<br>TGCAAGGTCTCCAACAAAGCCCTCGGCGCCCCCATCGAGAAAACCATCTCC<br>AAAGCCAAAGGGCAGCCCCGAGAACCACAGGTGTGCACCCTGCCCCCATCC<br>CGGGATGAGCTGACCAAGAACCAGGTCAGCCTCTCGTGCGCAGTCAAAGGC<br>TTCTATCCCAGCGACATCGCCGTGGAGTGGGAGAGCAATGGGCAGCCGGAG<br>AACAACTACAAGACCACGCCTCCCGTGCTGGACTCCGACGGCTCCTTCTTC<br>CTCGTGAGCAAGCTCACCGTGGACAAGAGCAGGTGGCAGCAGGGGAACGTC<br>TTCTCATGCTCCGTGATGCATGAGGCTCTGCACAACCGCTTCACGCAGAAG<br>AGCCTCTCCCTGTCTCCGGGTAAA |
| CD3_common light chain pETR13197 | CAGGCCGTCGTGACCCAGGAACCCAGCCTGACAGTGTCTCCTGGCGGCACC 191<br>GTGACCCTGACATGTGGCAGTTCTACAGGCGCCGTGACCACCAGCAACTAC<br>GCCAACTGGGTGCAGGAAAAGCCCGGCCAGGCCTTCAGAGGACTGATCGGC<br>GGCACCAACAAGAGAGCCCCTGGCACCCCTGCCAGATTCAGCGGATCTCTG<br>CTGGGAGGAAAGGCCGCCCTGACACTGTCTGGCGCCCAGCCAGAAGATGAG<br>GCCGAGTACTACTGCGCCCTGTGGTACAGCAACCTGTGGGTGTTCGGCGGA<br>GGCACCAAGCTGACAGTCCTAGGTCAACCCAAGGCTGCCCCCAGCGTGACC<br>CTGTTCCCCCCCAGCAGCGAGGAACTGCAGGCCAACAAGGCCACCCTGGTC<br>TGCCTGATCAGCGACTTCTACCCAGGCGCCGTGACCGTGGCCTGGAAGGCC<br>GACAGCAGCCCCGTGAAGGCCGGCGTGGAGACCACCACCCCCAGCAAGCAG<br>AGCAACAACAAGTACGCCGCCAGCAGCTACCTGAGCCTGACCCCCGAGCAG<br>TGGAAGAGCCACAGGTCCTACAGCTGCCAGGTGACCCACGAGGGCAGCACC<br>GTGGAGAAAACCGTGGCCCCCACCGAGTGCAGC |
| VHCH1[CD3]_VHCH1[16D5]_Fcknob_PGLALA<br>pETR13932 (Classical TCB with 16D5;<br>2 + 1: pETR13932 + pCON983 +<br>pETR13197) | GAGGTGCAGCTGCTGGAATCTGGCGGCGGACTGGTGCAGCCTGGCGGATCT 192<br>CTGAGACTGAGCTGTGCCGCCAGCGGCTTCACCTTCAGCACCTACGCCATG<br>AACTGGGTGCGCCAGGCCCCTGGCAAAGGCCTGGAATGGGTGTCCCGGATC<br>AGAAGCAAGTACAACAACTACGCCACCTACTACGCCGACAGCGTGAAGGGC<br>CGGTTCACCATCAGCCGGGACGACAGCAAGAACACCCTGTACCTGCAGATG<br>AACAGCCTGCGGGCCGAGGACACCGCCGTGTACTATTGTGTGCGGCACGGC<br>AACTTCGGCAACAGCTATGTGTCTTGGTTTGCCTACTGGGGCCAGGGCACC<br>CTCGTGACCGTGTCATCTGCTAGCACCAAAGGGCCCTAGCGTGTTCCCTCTG<br>GCCCCCAGCAGCAAGAGCACAAGCGGCGGAACAGCCGCCTGGGCTGCCTC<br>GTGAAGGACTACTTCCCCGAGCCCGTGACAGTGTCTTGGAACAGCGGAGCC<br>CTGACAAGCGGCGTGCACACCTTCCCTGCCGTGCTGCAGAGCAGCGGCCTG<br>TACTCCCTGAGCAGCGTGGTCACCGTGCCTAGCAGCAGCCTGGGCACCCAG<br>ACCTACATCTGCAACGTGAACCACAAGCCCAGCAACACCAAAGTGGACAAG<br>AAGGTGGAGCCCAAGAGCTGTGATGGCGGAGGAGGGTCCGGAGGCGGAGGA<br>TCCGAGGTGCAATTGGTTGAATCTGGTGGTGGTCTGGTAAAACCGGGCGGT<br>TCCCTGCGTCTGAGCTGCGCGGCTTCCGGATTCACCTTCTCCAACGCGTGG<br>ATGAGCTGGGTTCGCCAGGCCCCGGGCAAAGGCCTCGAGTGGGTTGGTCGT<br>ATCAAGTCTAAAACTGACGGTGGCACCACGGATTACGCGGCTCCAGTTAAA<br>GGTCGTTTTACCATTTCCCGCGACGATAGCAAAAACACTCTGTATCTGCAG<br>ATGAACTCTCTGAAAACTGAAGACACCGCAGTCTACTACTGTACTACCCCG<br>TGGGAATGGTCTTGGTACGATTATTGGGGCCAGGGCACGCTGGTTACGGTG<br>TCTAGCGCTAGTACCAAGGGCCCCAGCGTGTTCCCCCTGGCACCCAGCAGC |

| | | |
|---|---|---|
| | AAGAGCACATCTGGCGGAACAGCCGCTCTGGGCTGTCTGGTGAAAGACTAC<br>TTCCCCGAGCCCGTGACCGTGTCTTGGAACTCTGGCGCCCTGACCAGCGGC<br>GTGCACACCTTTCCAGCCGTGCTGCAGAGCAGCGGCCTGTACTCCCTGTCC<br>TCCGTGGTCACCGTGCCCTCTAGCTCCCTGGGAACACAGACATATATCTGT<br>AATGTCAATCACAAGCCTTCCAACACCAAAGTCGATAAGAAAGTCGAGCCC<br>AAGAGCTGCGACAAAACTCACACATGCCCACCGTGCCCAGCACCTGAAGCT<br>GCAGGGGGACCGTCAGTCTTCCTCTTCCCCCCAAAACCCAAGGACACCCTC<br>ATGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCAT<br>AATGCCAAGACAAAGCCGCGGGAGGAGCAGTACAACAGCACGTACCGTGTG<br>GTCAGCGTCCTCACCGTCCTGCACCAGGACTGGCTGAATGGCAAGGAGTAC<br>AAGTGCAAGGTCTCCAACAAAGCCCTCGGCGCCCCCATCGAGAAAACCATC<br>TCCAAAGCCAAAGGGCAGCCCCGAGAACCACAGGTGTACACCCTGCCCCCA<br>TGCCGGGATGAGCTGACCAAGAACCAGGTCAGCCTGTGGTGCCTGGTCAAA<br>GGCTTCTATCCCAGCGACATCGCCGTGGAGTGGGAGAGCAATGGGCAGCCG<br>GAGAACAACTACAAGACCACGCCTCCCGTGCTGGACTCCGACGGCTCCTTC<br>TTCCTCTACAGCAAGCTCACCGTGGACAAGAGCAGGTGGCAGCAGGGGAAC<br>GTCTTCTCATGCTCCGTGATGCATGAGGCTCTGCACAACCACTACACGCAG<br>AAGAGCCTCTCCCTGTCTCCGGGTAAA | |
| VHCH1[CD3]_Fcknob_PGLALA<br>pETR13719 (16D5 IgG format, 1 + 1:<br>pETR13719 + pCON983 + pETR13197) | GAGGTGCAGCTGCTGGAATCTGGCGGCGGACTGGTGCAGCCTGGCGGATCT<br>CTGAGACTGAGCTGTGCCGCCAGCGGCTTCACCTTCAGCACCTACGCCATG<br>AACTGGGTGCGCCAGGCCCCTGGCAAAGGCCTGGAATGGGTGTCCCGGATC<br>AGAAGCAAGTACAACAACTACGCCACCTACTACGCCGACAGCGTGAAGGGC<br>CGGTTCACCATCAGCCGGGACGACAGCAAGAACACCCTGTACCTGCAGATG<br>AACAGCCTGCGGGCCGAGGACACCGCCGTGTACTATTGTGTGCGGCACGGC<br>AACTTCGGCAACAGCTATGTGTCTTGGTTTGCCTACTGGGGCCAGGGCACC<br>CTCGTGACCGTGTCATCTGCTAGCACCAAGGGCCCATCGGTCTTCCCCCTG<br>GCACCCTCCTCCAAGAGCACCTCTGGGGGCACAGCGGCCCTGGGCTGCCTG<br>GTCAAGGACTACTTCCCCGAACCGGTGACGGTGTCGTGGAACTCAGGCGCC<br>CTGACCAGCGGCGTGCACACCTTCCCGGCTGTCCTACAGTCCTCAGGACTC<br>TACTCCCTCAGCAGCGTGGTGACCGTGCCCTCCAGCAGCTTGGGCACCCAG<br>ACCTACATCTGCAACGTGAATCACAAGCCCAGCAACACCAAGGTGGACAAG<br>AAAGTTGAGCCCAAATCTTGTGACAAAACTCACACATGCCCACCGTGCCCA<br>GCACCTGAAGCTGCAGGGGGACCGTCAGTCTTCCTCTTCCCCCCAAAACCC<br>AAGGACACCCTCATGATCTCCCGGACCCCTGAGGTCACATGCGTGGTGGTG<br>GACGTGAGCCACGAAGACCCTGAGGTCAAGTTCAACTGGTACGTGGACGGC<br>GTGGAGGTGCATAATGCCAAGACAAAGCCGCGGGAGGAGCAGTACAACAGC<br>ACGTACCGTGTGGTCAGCGTCCTCACCGTCCTGCACCAGGACTGGCTGAAT<br>GGCAAGGAGTACAAGTGCAAGGTCTCCAACAAAGCCCTCGGCGCCCCCATC<br>GAGAAAACCATCTCCAAAGCCAAAGGGCAGCCCCGAGAACCACAGGTGTAC<br>ACCCTGCCCCCATGCCGGGATGAGCTGACCAAGAACCAGGTCAGCCTGTGG<br>TGCCTGGTCAAAGGCTTCTATCCCAGCGACATCGCCGTGGAGTGGGAGAGC<br>AATGGGCAGCCGGAGAACAACTACAAGACCACGCCTCCCGTGCTGGACTCC<br>GACGGCTCCTTCTTCCTCTACAGCAAGCTCACCGTGGACAAGAGCAGGTGG<br>CAGCAGGGGAACGTCTTCTCATGCTCCGTGATGCATGAGGCTCTGCACAAC<br>CACTACACGCAGAAGAGCCTCTCCCTGTCTCCGGGTAAA | 193 |
| Fc_hole_PGLALA_HYRF<br>pETR10755 (16D5 Head-to-tail, 1 + 1:<br>pCON999 + pETR10755 + pETR13197) | GACAAAACTCACACATGCCCACCGTGCCCAGCACCTGAACTCCTGGGGGGA<br>CCGTCAGTCTTCCTCTTCCCCCCAAAACCCAAGGACACCCTCATGATCTCC<br>CGGACCCCTGAGGTCACATGCGTGGTGGTGGACGTGAGCCACGAAGACCCT<br>GAGGTCAAGTTCAACTGGTACGTGGACGGCGTGGAGGTGCATAATGCCAAG<br>ACAAAGCCGCGGGAGGAGCAGTACAACAGCACGTACCGTGTGGTCAGCGTC<br>CTCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGCC<br>AAAGGGCAGCCCCGAGAACCACAGGTGTGCACCCTGCCCCCATCCCGGGAT<br>GAGCTGACCAAGAACCAGGTCAGCCTCTCGTGCGCAGTCAAAGGCTTCTAT<br>CCCAGCGACATCGCCGTGGAGTGGGAGAGCAATGGGCAGCCGGAGAACAAC<br>TACAAGACCACGCCTCCCGTGCTGGACTCCGACGGCTCCTTCTTCCTCGTG<br>AGCAAGCTCACCGTGGACAAGAGCAGGTGGCAGCAGGGGAACGTCTTCTCA<br>TGCTCCGTGATGCATGAGGCTCTGCACAACCGCTTCACGCAGAAGAGCCTC<br>TCCCTGTCTCCGGGTAAA | 194 |
| VHCH1[9D11]_VHCL[CD3]1_Fcknob_PGLALA<br>pCON1057 (9D11 inverted format, 2 +<br>1: pCON1057 + pCON1051 + pCON1063 +<br>pETR12940) | CAGGTGCAATTGGTTCAATCTGGTGCTGAAGTAAAAAAACCGGGCGCTTCC<br>GTTAAAGTGAGCTGCAAAGCATCCGGATACACCTTCACTTCCTATTACATG<br>CACTGGGTTCGTCAAGCCCCGGGCCAGGGTCTGGAATGGATGGGCATCATT<br>AACCCAAGCGGTGGCCCTACCTCCTACGCGCAGAAATTCCAGGGTCGCGTC<br>ACGATGACCCGTGACACTAGCACCTCTACCGTTTATATGGAGCTGTCCAGC<br>CTGCGTTCTGAAGATACTGCAGTGTACTACTGTGCACGCGGTGACTTCGCT<br>TGGCTGGACTATTGGGGTCAAGGCACCCTCGTAACGGTTTCTTCTGCTAGC<br>ACAAAGGGCCCCAGCGTGTTCCCTCTGGCCCCTAGCAGCAAGAGCACATCT<br>GGCGGAACAGCCGCCCTGGGCTGCCTCGTGAAGGACTACTTTCCCGAGCCT<br>GTGACCGTGTCCTGGAACTCTGGCGCCCTGACAAGCGGCGTGCACACCTTT<br>CCAGCCGTGCTGCAGAGCAGCGGCCTGTACTCTCTGAGCAGCGTGGTCACC<br>GTGCCTAGCAGCAGCCTGGGCACCCAGACCTACATCTGCAACGTGAACCAC<br>AAGCCCAGCAACACCAAAGTGGACAAGAAGGTGGAGCCCAAGAGCTGTGAT<br>GGCGGAGGAGGGTCCGGAGGCGGAGGATCCGAGGTGCAGCTGCTGGAATCT<br>GGCGGCGGACTGGTGCAGCCTGGCGGATCTCTGAGACTGAGCTGTGCCGCC<br>AGCGGCTTCACCTTCAGCACCTACGCCATGAACTGGGTGCGCCAGGCCCCT | 195 |

| | |
|---|---|
| | GGCAAAGGCCTGGAATGGGTGTCCCGGATCAGAAGCAAGTACAACAACTAC<br>GCCACCTACTACGCCGACAGCGTGAAGGGCCGGTTCACCATCAGCCGGGAC<br>GACAGCCAAGAACACCCTGTACCTGCAGATGAACAGCCTGCGGGCCGAGGAC<br>ACCGCCGTGTACTATTGTGTGCGGCACGGCAACTTCGGCAACAGCTATGTG<br>TCTTGGTTTGCCTACTGGGGCCAGGGCACCCTCGTGACCGTGTCAAGCGCT<br>AGTGTGGCCGCTCCCTCCGTGTTTATCTTTCCCCCATCCGATGAACAGCTG<br>AAAAGCGGCACCGCCTCCGTCGTGTGTCTGCTGAACAATTTTTACCCTAGG<br>GAAGCTAAAGTGCAGTGGAAAGTGGATAACGCACTGCAGTCCGGCAACTCC<br>CAGGAATCTGTGACAGAACAGGACTCCAAGGACAGCACCTACTCCCTGTCC<br>TCCACCCTGACACTGTCTAAGGCTGATTATGAGAAACACAAAGTCTACGCC<br>TGCGAAGTCACCCATCAGGGCCTGAGCTCGCCCGTCACAAAGAGCTTCAAC<br>AGGGGAGAGTGTGACAAGACCCACACCTGTCCCCCTTGTCCTGCCCCTGAA<br>GCTGCTGGCGGCCCTTCTGTGTTCCTGTTCCCCCCAAAGCCCAAGGACACC<br>CTGATGATCAGCCGGACCCCCGAAGTGACCTGCGTGGTGGTGGATGTGTCC<br>CACGAGGACCCTGAAGTGAAGTTCAATTGGTACGTGGACGGCGTGGAAGTG<br>CACAACGCCAAGACAAAGCCGCGGGAGGAGCAGTACAACAGCACGTACCGT<br>GTGGTCAGCGTCCTCACCGTCCTGCACCAGGACTGGCTGAATGGCAAGGAG<br>TACAAGTGCAAGGTCTCCAACAAAGCCCTCGGCGCCCCCATCGAGAAAACC<br>ATCTCCAAAGCCAAAGGGCAGCCCCGAGAACCACAGGTGTACACCCTGCCC<br>CCATGCCGGGATGAGCTGACCAAGAACCAGGTCAGCCTGTGGTGCCTGGTC<br>AAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCC<br>TTCTTCCTCTACAGCAAGCTCACCGTGGACAAGAGCAGGTGGCAGCAGGGG<br>AACGTCTTCTCATGCTCCGTGATGCATGAGGCTCTGCACAACCACTACACG<br>CAGAAGAGCCTCTCCCTGTCTCCGGGTAAA |
| 9D11_Fchole_PGLALA_HYRF<br>pCON1051 | CAGGTGCAATTGGTTCAATCTGGTGCTGAAGTAAAAAAACCGGGCGCTTCC 196<br>GTTAAAGTGAGCTGCAAAGCATCCGGATACACCTTCACTTCCTATTACATG<br>CACTGGGTTCGTCAAGCCCCGGGCCAGGGTCTGGAATGGATGGGCATCATT<br>AACCCAAGCGGTGGCCCTACCTCCTACGCGCAGAAATTCCAGGGTCGCGTC<br>ACGATGACCCGTGACACTAGCACCTCTACCGTTTATATGGAGCTGTCCAGC<br>CTGCGTTCTGAAGATACTGCAGTGTACTACTGTGCACGCGGTGACTTCGCT<br>TGGCTGGACTATTGGGGTCAAGGCACCCTCGTAACGGTTTCTTCTGCTAGC<br>ACCAAGGGCCCCTCCGTGTTCCCCCTGGCCCCCAGCAGCAAGAGCACCAGC<br>GGCGGCACAGCCGCTCTGGGCTGCCTGGTCAAGGACTACTTCCCCGAGCCC<br>GTGACCGTGTCCTGGAACAGCGGAGCCCTGACCTCCGGCGTGCACACCTTC<br>CCCGCCGTGCTGCAGAGTTCTGGCCTGTATAGCCTGAGCAGCGTGGTCACC<br>GTGCCTTCTAGCAGCCTGGGCACCCAGACCTACATCTGCAACGTGAACCAC<br>AAGCCCAGCAACACCAAGGTGGACAAGAAGGTGGAGCCCAAGAGCTGCGAC<br>AAAACTCACACATGCCCACCGTGCCCAGCACCTGAAGCTGCAGGGGGACCG<br>TCAGTCTTCCTCTTCCCCCCAAAACCCAAGGACACCCTCATGATCTCCCGG<br>ACCCCTGAGGTCACATGCGTGGTGGTGGACGTGAGCCACGAAGACCCTGAG<br>GTCAAGTTCAACTGGTACGTGGACGGCGTGGAGGTGCATAATGCCAAGACA<br>AAGCCGCGGGAGGAGCAGTACAACAGCACGTACCGTGTGGTCAGCGTCCTC<br>ACCGTCCTGCACCAGGACTGGCTGAATGGCAAGGAGTACAAGTGCAAGGTC<br>TCCAACAAAGCCCTCGGCGCCCCCATCGAGAAAACCATCTCCAAAGCCAAA<br>GGGCAGCCCCGAGAACCACAGGTGTGCACCCTGCCCCCATCCCGGGATGAG<br>CTGACCAAGAACCAGGTCAGCCTCTCGTGCGCAGTCAAAGGCTTCTATCCC<br>AGCGACATCGCCGTGGAGTGGGAGAGCAATGGGCAGCCGGAGAACAACTAC<br>AAGACCACGCCTCCCGTGCTGGACTCCGACGGCTCCTTCTTCCTCGTGAGC<br>AAGCTCACCGTGGACAAGAGCAGGTGGCAGCAGGGGAACGTCTTCTCATGC<br>TCCGTGATGCATGAGGCTCTGCACAACCACTACACGCAGAAGAGCCTCTCC<br>CTGTCTCCGGGTAAA |
| 9D11_LC<br>pCON1063 | GATATTGTTATGACTCAATCTCCACTGTCTCTGCCGGTGACTCCAGGCGAA 197<br>CCGGCGAGCATTTCTTGCCGTTCCAGCCAGTCTCTGCTGCACTCCAACGGC<br>TACAACACTATCTCGATTGGTACCTGCAAAAACCGGGTCAGAGCCCTCAGCTG<br>CTGATCTACCTGGGCTCTAACCGCGCTTCCGGTGTACCGGACCGTTTCAGC<br>GGCTCTGGATCCGGCACCGATTTCACGTTGAAAATCAGCCGTGTTGAAGCA<br>GAAGACGTGGGCGTTTATTACTGTATGCAGGCAAGCATTATGAACCGGACT<br>TTTGGTCAAGGCACCAAGGTCGAAATTAAACGTACGGTGGCTGCACCATCT<br>GTCTTCATCTTCCCGCCATCTGATGAGCAGTTGAAATCTGGAACTGCCTCT<br>GTTGTGTGCCTGCTGAATAACTTCTATCCCAGAGAGGCCAAAGTACAGTGG<br>AAGGTGGATAACGCCCTCCAATCGGGTAACTCCCAGGAGAGTGTCACAGAG<br>CAGGACAGCAAGGACAGCACCTACAGCCTCAGCAGCACCCTGACGCTGAGC<br>AAAGCAGACTACGAGAAACACAAAGTCTACGCCTGCGAAGTCACCCATCAG<br>GGCCTGAGCTCGCCCGTCACAAAGAGCTTCAACAGGGGAGAGTGT |
| VLCH1[CD3]<br>pETR12940 | CAGGCCGTCGTGACCCAGGAACCCAGCCTGACAGTGTCTCCTGGCGGCACC 198<br>GTGACCCTGACATGTGGCAGTTCTACAGGCGCCGTGACCACCAGCAACTAC<br>GCCAACTGGGTGCAGGAAAAGCCCGGCCAGGCCTTCAGAGGACTGATCGGC<br>GGCACCAACAAGAGAGCCCCTGGCACCCCTGCCAGATTCAGCGGATCTCTG<br>CTGGGAGGAAAGGCCGCCCTGACACTGTCTGGCGCCCAGCCAGAAGATGAG<br>GCCGAGTACTACTGCGCCCCTGTGGTACAGCAACCTGTGGGTGTTCGGCGGA<br>GGCACCAAGCTGACAGTGCTGAGCAGCGCTTCCACCAAAGGCCCTTCCGTG<br>TTTCCTCTGGCTCCTAGCTCCAAGTCCACCTCTGGAGGCACCGCTGCTCTC<br>GGATGCCTCGTGAAGGATTATTTTCCTGAGCCTGTGACAGTGTCCTGGAAT<br>AGCGGAGCACTGACCTCTGGAGTGCATACTTTCCCCGCTGTGCTGCAGTCC |

| | |
|---|---|
| | TCTGGACTGTACAGCCTGAGCAGCGTGGTGACAGTGCCCAGCAGCAGCCTG<br>GGCACCCAGACCTACATCTGCAACGTGAACCACAAGCCCAGCAACACCAAG<br>GTGGACAAGAAGGTGGAACCCAAGTCTTGT |
| VHCL[CD3]_Fcknob_PGLALA<br>pETR13378 (9D11 CrossMab format,<br>1 + 1: pETR13378 + pCON1051 +<br>pCON1063 + pETR12940) | GAGGTGCAGCTGCTGGAATCTGGCGGCGGACTGGTGCAGCCTGGCGGATCT 199<br>CTGAGACTGAGCTGTGCCGCCAGCGGCTTCACCTTCAGCACCTACGCCATG<br>AACTGGGTGCGCCAGGCCCCTGGCAAAGGCCTGGAATGGGTGTCCCGGATC<br>AGAAGCAAGTACAACAACTACGCCACCTACTACGCCGACAGCGTGAAGGGC<br>CGGTTCACCATCAGCCGGGACGACAGCAAGAACACCCTGTACCTGCAGATG<br>AACAGCCTGCGGGCCGAGGACACCGCCGTGTACTATTGTGTGCGGCACGGC<br>AACTTCGGCAACAGCTATGTGTCTTGGTTTGCCTACTGGGGCCAGGGCACC<br>CTCGTGACCGTGTCATCTGCTAGCGTGGCCGCTCCCTCCGTGTTTATCTTT<br>CCCCCATCCGATGAACAGCTGAAAAGCGGCACCGCCTCCGTCGTGTGTCTG<br>CTGAACAATTTTTACCCTAGGGAAGCTAAAGTGCAGTGGAAAGTGGATAAC<br>GCACTGCAGTCCGGCAACTCCCAGGAATCTGTGACAGAACAGGACTCCAAG<br>GACAGCACCTACTCCCTGTCCTCCACCCTGACACTGTCTAAGGCTGATTAT<br>GAGAAACACAAAGTCTACGCCTGCGAAGTCACCCATCAGGGCCTGAGCTCG<br>CCCGTCACAAAGAGCTTCAACAGGGGAGAGTGTGACAAGACCCACACCTGT<br>CCCCCTTGTCCTGCCCCTGAAGCTGCTGGCGGCCCTTCTGTGTTCCTGTTC<br>CCCCCAAAGCCCAAGGACACCCTGATGATCAGCCGGACCCCCGAAGTGACC<br>TGCGTGGTGGTGGATGTGTCCCACGAGGACCCTGAAGTGAAGTTCAATTGG<br>TACGTGGACGGCGTGGAAGTGCACAACGCCAAGACAAAGCCGCGGGAGGAG<br>CAGTACAACAGCACGTACCGTGTGGTCAGCGTCCTCACCGTCCTGCACCAG<br>GACTGGCTGAATGGCAAGGAGTACAAGTGCAAGGTCTCCAACAAAGCCCTC<br>GGCGCCCCCATCGAGAAAACCATCTCCAAAGCCAAAGGGCAGCCCCGAGAA<br>CCACAGGTGTACACCCTGCCCCCATGCCGGGATGAGCTGACCAAGAACCAG<br>GTCAGCCTGTGGTGCCTGGTCAAAGGCTTCTATCCCAGCGACATCGCCGTG<br>GAGTGGGAGAGCAATGGGCAGCCGGAGAACAACTACAAGACCACGCCTCCC<br>GTGCTGGACTCCGACGGCTCCTTCTTCCTCTACAGCAAGCTCACCGTGGAC<br>AAGAGCAGGTGGCAGCAGGGGAACGTCTTCTCATGCTCCGTGATGCATGAG<br>GCTCTGCACAACCACTACACGCAGAAGAGCCTCTCCCTGTCTCCGGGTAAA |
| 16D5 inverted 2 + 1 with N100A in<br>CDR H3 pETR14096<br>(pETR14096 + pCON983 + pETR13197) | GAGGTGCAATTGGTTGAATCTGGTGGTGGTCTGGTAAAACCGGGCGGTTCC 200<br>CTGCGTCTGAGCTGCGCGGCTTCCGGATTCACCTTCTCCAACGCGTGGATG<br>AGCTGGGTTCGCCAGGCCCCGGGCAAAGGCCTCGAGTGGGTTGGTCGTATC<br>AAGTCTAAAACTGACGGTGGCACCACGGATTACGCGGCTCCAGTTAAAGGT<br>CGTTTTACCATTTCCCGCGACGATAGCAAAAACACTCTGTATCTGCAGATG<br>AACTCTCTGAAAACTGAAGACACCGCAGTCTACTACTGTACTACCCCGTGG<br>GAATGGCTTGGTACGATTATTGGGGCCAGGGCACGCTGGTTACGGTGTCT<br>TCCGCTAGCACAAAGGGCCCTAGCGTGTTCCCTCTGGCCCCCAGCAGCAAG<br>AGCACAAGCGGCGGAACAGCCGCCCTGGGCTGCCTCGTGAAGGACTACTTC<br>CCCGAGCCCGTGACAGTGTCTTGGAACAGCGGAGCCCTGACAAGCGGCGTG<br>CACACTTTCCCTGCCGTGCTGCAGAGCAGCGGCCTGTACTCCCTGAGCAGC<br>GTGGTCACCGTGCCTAGCAGCAGCCTGGGCACCCAGACCTACATCTGCAAC<br>GTGAACCACAAGCCCAGCAACACCAAAGTGGACAAGAAGGTGGAGCCCAAG<br>AGCTGTGATGGCGGAGGAGGGTCCGGAGGCGGAGGATCCGAGGTGCAGCTG<br>CTGGAATCTGGCGGCGGACTGGTGCAGCCTGGCGGATCTCTGAGACTGAGC<br>TGTGCCGCCAGCGGCTTCACCTTCAGCACCTACGCCATGAACTGGGTGCGC<br>CAGGCCCCTGGCAAAGGCCTGGAATGGGTGTCCCGGATCAGAAGCAAGTAC<br>AACAACTACGCCACCTACTACGCCGACAGCGTGAAGGGCCGGTTCACCATC<br>AGCCGGGACGACAGCAAGAACACCCTGTACCTGCAGATGAACAGCCTGCGG<br>GCCGAGGACACCGCCGTGTACTATTGTGTGCGGCACGGCAACTTCGGCGCC<br>AGCTATGTGTCTTGGTTTGCCTACTGGGGCCAGGGCACCCTCGTGACCGTG<br>TCAAGCGCTAGTACCAAGGGCCCCAGCGTGTTCCCCCTGGCACCCAGCAGC<br>AAGAGCACATCTGGCGGAACAGCCGCTCTGGGCTGTCTGGTGAAAGACTAC<br>TTCCCCGAGCCCGTGACCGTGTCTTGGAACTCTGGCGCCCTGACCAGCGGC<br>GTGCACACCTTTCCAGCCGTGCTGCAGAGCAGCGGCCTGTACTCCCTGTCC<br>TCCGTGGTCACCGTGCCCTCTAGCTCCCTGGGAACACAGACATATATCTGT<br>AATGTCAATCACAAGCCTTCCAACACCAAAGTCGATAAGAAAGTCGAGCCC<br>AAGAGCTGCGACAAAACTCACACATGCCCACCGTGCCCAGCACCTGAAGCT<br>GCAGGGGGACCGTCAGTCTTCCTCTTCCCCCCAAAACCCAAGGACACCCTC<br>ATGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCAT<br>AATGCCAAGACAAAGCCGCGGGAGGAGCAGTACAACAGCACGTACCGTGTG<br>GTCAGCGTCCTCACCGTCCTGCACCAGGACTGGCTGAATGGCAAGGAGTAC<br>AAGTGCAAGGTCTCCAACAAAGCCCTCGGCGCCCCCATCGAGAAAACCATC<br>TCCAAAGCCAAAGGGCAGCCCCGAGAACCACAGGTGTACACCCTGCCCCCA<br>TGCCGGGATGAGCTGACCAAGAACCAGGTCAGCCTGTGGTGCCTGGTCAAA<br>GGCTTCTATCCCAGCGACATCGCCGTGGAGTGGGAGAGCAATGGGCAGCCG<br>GAGAACAACTACAAGACCACGCCTCCCGTGCTGGACTCCGACGGCTCCTTC<br>TTCCTCTACAGCAAGCTCACCGTGGACAAGAGCAGGTGGCAGCAGGGGAAC<br>GTCTTCTCATGCTCCGTGATGCATGAGGCTCTGCACAACCACTACACGCAG<br>AAGAGCCTCTCCCTGTCTCCGGGTAAA |
| 16D5 inverted 2 + 1 with S100aA in<br>CDR H3 pETR14097 (pETR14097 +<br>pCON983 + pETR13197) | GAGGTGCAATTGGTTGAATCTGGTGGTGGTCTGGTAAAACCGGGCGGTTCC 201<br>CTGCGTCTGAGCTGCGCGGCTTCCGGATTCACCTTCTCCAACGCGTGGATG<br>AGCTGGGTTCGCCAGGCCCCGGGCAAAGGCCTCGAGTGGGTTGGTCGTATC<br>AAGTCTAAAACTGACGGTGGCACCACGGATTACGCGGCTCCAGTTAAAGGT<br>CGTTTTACCATTTCCCGCGACGATAGCAAAAACACTCTGTATCTGCAGATG |

| | |
|---|---|
| | AACTCTCTGAAAACTGAAGACACCGCAGTCTACTACTGTACTACCCCGTGG<br>GAATGGTCTTGGTACGATTATTGGGGCCAGGGCACGCTGGTTACGGTGTCT<br>TCCGCTAGCACAAAGGGCCCTAGCGTGTTCCCTCTGGCCCCCAGCAGCAAG<br>AGCACAAGCGGCGGAACAGCCGCCCTGGGCTGCCTCGTGAAGGACTACTTC<br>CCCGAGCCCGTGACAGTGTCTTGGAACAGCGGAGCCCTGACAAGCGGCGTG<br>CACACTTTCCCTGCCGTGCTGCAGAGCAGCGGCCTGTACTCCCTGAGCAGC<br>GTGGTCACCGTGCCTAGCAGCAGCCTGGGCACCCAGACCTACATCTGCAAC<br>GTGAACCACAAGCCCAGCAACACCAAAGTGGACAAGAAGGTGGAGCCCAAG<br>AGCTGTGATGGCGGAGGAGGGTCCGGAGGCGGAGGATCCGAGGTGCAGCTG<br>CTGGAATCTGGCGGCGGACTGGTGCAGCCTGGCGGATCTCTGAGACTGAGC<br>TGTGCCGCCAGCGGCTTCACCTTCAGCACCTACGCCATGAACTGGGTGCGC<br>CAGGCCCCTGGCAAAGGCCTGGAATGGGTGTCCCGGATCAGAAGCAAGTAC<br>AACAACTACGCCACCTACTACGCCGACAGCGTGAAGGGCCGGTTCACCATC<br>AGCCGGGACGACAGCAAGAACACCCTGTACCTGCAGATGAACAGCCTGCGG<br>GCCGAGGACACCGCCGTGTACTATTGTGTGCGGCACGGCAACTTCGGCAAC<br>GCCTATGTGTCTTGGTTTGCCTACTGGGGCCAGGGCACCCTCGTGACCGTG<br>TCAAGCGCTAGTACCAAGGGCCCCAGCGTGTTCCCCCTGGCACCCAGCAGC<br>AAGAGCACATCTGGCGGAACAGCCGCTCTGGGCTGTCTGGTGAAAGACTAC<br>TTCCCCGAGCCCGTGACCGTGTCTTGGAACTCTGGCGCCCTGACCAGCGGC<br>GTGCACACCTTTCCAGCCGTGCTGCAGAGCAGCGGCCTGTACTCCCTGTCC<br>TCCGTGGTCACCGTGCCCTCTAGCTCCCTGGGAACACAGACATATATCTGT<br>AATGTCAATCACAAGCCTTCCAACACCAAAGTCGATAAGAAAGTCGAGCCC<br>AAGAGCTGCGACAAAACTCACACATGCCCACCGTGCCCAGCACCTGAAGCT<br>GCAGGGGGACCGTCAGTCTTCCTCTTCCCCCCAAAACCCAAGGACACCCTC<br>ATGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCAT<br>AATGCCAAGACAAAGCCGCGGGAGGAGCAGTACAACAGCACGTACCGTGTG<br>GTCAGCGTCCTCACCGTCCTGCACCAGGACTGGCTGAATGGCAAGGAGTAC<br>AAGTGCAAGGTCTCCAACAAAGCCCTCGGCGCCCCCATCGAGAAAACCATC<br>TCCAAAGCCAAAGGGCAGCCCCGAGAACCACAGGTGTACACCCTGCCCCCA<br>TGCCGGGATGAGCTGACCAAGAACCAGGTCAGCCTGTGGTGCCTGGTCAAA<br>GGCTTCTATCCCAGCGACATCGCCGTGGAGTGGGAGAGCAATGGGCAGCCG<br>GAGAACAACTACAAGACCACGCCTCCCGTGCTGGACTCCGACGGCTCCTTC<br>TTCCTCTACAGCAAGCTCACCGTGGACAAGAGCAGGTGGCAGCAGGGGAAC<br>GTCTTCTCATGCTCCGTGATGCATGAGGCTCTGCACAACCACTACACGCAG<br>AAGAGCCTCTCCCTGTCTCCGGGTAAA |
| CD3 light chain fused to CH1;<br>Fc_PGLALA; pETR13862 (Kappa-lambda<br>antibody with CD3 common light chain<br>fused to CH1 + Fc_PGLALA.<br>VHs fused to kappa or lambda<br>constant chain pETR13859 +<br>pETR13860 + pETR13862) | CAGGCCGTCGTGACCCAGGAACCCAGCCTGACAGTGTCTCCTGGCGGCACC 202<br>GTGACCCTGACATGTGGCAGTTCTACAGGCGCCGTGACCACCAGCAACTAC<br>GCCAACTGGGTGCAGGAAAAGCCCGGCCAGGCCTTCAGAGGACTGATCGGC<br>GGCACCAACAAGAGAGCCCCTGGCACCCCTGCCAGATTCAGCGGATCTCTG<br>CTGGGAGGAAAGGCCGCCCTGACACTGTCTGGCGCCCAGCCAGAAGATGAG<br>GCCGAGTACTACTGCGCCCTGTGGTACAGCAACCTGTGGGTGTTCGGCGGA<br>GGCACCAAGCTGACAGTGCTGAGCAGCGCTAGCACCAAGGGCCCATCGGTC<br>TTCCCCCTGGCACCCTCCTCCAAGAGCACCTCTGGGGGCACAGCGGCCCTG<br>GGCTGCCTGGTCAAGGACTACTTCCCCGAACCGGTGACGGTGTCGTGGAAC<br>TCAGGCGCCCTGACCAGCGGCGTGCACACCTTCCCGGCTGTCCTACAGTCC<br>TCAGGACTCTACTCCCTCAGCAGCGTGGTGACCGTGCCCTCCAGCAGCTTG<br>GGCACCCAGACCTACATCTGCAACGTGAATCACAAGCCCAGCAACACCAAG<br>GTGGACAAGAAAGTTGAGCCCAAATCTTGTGACAAAACTCACACATGCCCA<br>CCGTGCCCAGCACCTGAAGCTGCAGGGGGACCGTCAGTCTTCCTCTTCCCC<br>CCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTAC<br>GTGGACGGCGTGGAGGTGCATAATGCCAAGACAAAGCCGCGGGAGGAGCAG<br>TACAACAGCACGTACCGTGTGGTCAGCGTCCTCACCGTCCTGCACCAGGAC<br>TGGCTGAATGGCAAGGAGTACAAGTGCAAGGTCTCCAACAAAGCCCTCGGC<br>GCCCCCATCGAGAAAACCATCTCCAAAGCCAAAGGGCAGCCCCGAGAACCA<br>CAGGTGTACACCCTGCCCCCATCCCGGGATGAGCTGACCAAGAACCAGGTC<br>AGCCTGACCTGCCTGGTCAAAGGCTTCTATCCCAGCGACATCGCCGTGGAG<br>TGGGAGAGCAATGGGCAGCCGGAGAACAACTACAAGACCACGCCTCCCGTG<br>CTGGACTCCGACGGCTCCTTCTTCCTCTACAGCAAGCTCACCGTGGACAAG<br>AGCAGGTGGCAGCAGGGGAACGTCTTCTCATGCTCCGTGATGCATGAGGCT<br>CTGCACAACCACTACACGCAGAAGAGCCTCTCCCTGTCTCCGGGTAAA |
| 16D5 VH fused to constant kappa<br>chain; pETR13859 | GAGGTGCAATTGGTTGAATCTGGTGGTGGTCTGGTAAAACCGGGCGGTTCC 203<br>CTGCGTCTGAGCTGCGCGGCTTCCGGATTCACCTTCTCCAACGCGTGGATG<br>AGCTGGGTTCGCCAGGCCCCGGGCAAAGGCCTCGAGTGGGTTGGTCGTATC<br>AAGTCTAAAACTGACGGTGGCACCACGGATTACGCGGCTCCAGTTAAAGGT<br>CGTTTTACCATTTCCCGCGACGATAGCAAAAACACTCTGTATCTGCAGATG<br>AACTCTCTGAAAACTGAAGACACCGCAGTCTACTACTGTACTACCCCGTGG<br>GAATGGTCTTGGTACGATTATTGGGGCCAGGGCACGCTGGTTACGGTGTCT<br>TCCGCTAGCGTGGCCGCTCCCTCCGTGTTCATCTTCCCACCTTCCGACGAG<br>CAGCTGAAGTCCGGCACCGCTTCTGTCGTGTGCCTGCTGAACAACTTCTAC<br>CCCCGCGAGGCCAAGGTGCAGTGGAAGGTGGACAACGCCCTGCAGTCCGGC<br>AACAGCCAGGAATCCGTGACCGAGCAGGACTCCAAGGACAGCACCTACTCC<br>CTGTCCTCCACCCTGACCCTGTCCAAGGCCGACTACGAGAAGCACAAGGTG<br>TACGCCTGCGAAGTGACCCACCAGGGCCTGTCTAGCCCCGTGACCAAGTCT<br>TTCAACCGGGGCGAGTGC |

| -continued | |
|---|---|
| CD3 VH fused to constant lambda chain; pETR13860 | GAAGTGCAGCTGCTGGAATCCGGCGGAGGACTGGTGCAGCCTGGCGGATCT 204<br>CTGAGACTGTCTTGTGCCGCCTCCGGCTTCACCTTCTCCACCTACGCCATG<br>AACTGGGTGCGACAGGCTCCTGGCAAGGGCCTGGAATGGGTGTCCCGGATC<br>AGATCCAAGTACAACAACTACGCCACCTACTACGCCGACTCCGTGAAGGGC<br>CGGTTCACCATCTCTCGGGACGACTCCAAGAACACCCTGTACCTGCAGATG<br>AACTCCCTGCGGGCCGAGGACACCGCCGTGTACTATTGTGTGCGGCACGGC<br>AACTTCGGCAACTCCTATGTGTCTTGGTTTGCCTACTGGGGCCAGGGCACC<br>CTCGTGACCGTGTCATCTGCTAGCCCCAAGGCTGCCCCCAGCGTGACCCTG<br>TTTCCCCCCAGCAGCGAGGAACTGCAGGCCAACAAGGCCACCCTGGTCTGC<br>CTGATCAGCGACTTCTACCCAGGCGCCGTGACCGTGGCCTGGAAGGCCGAC<br>AGCAGCCCCGTGAAGGCCGGCGTGGAGACCACCACCCCCAGCAAGCAGAGC<br>AACAACAAGTACGCCGCCAGCAGCTACCTGAGCCTGACCCCCGAGCAGTGG<br>AAGAGCCACAGGTCCTACAGCTGCCAGGTGACCCACGAGGGCAGCACC<br>GTGGAGAAAACCGTGGCCCCCACCGAGTGCAGC |
| VHCH1[36F2]_VHCL[CD3]_Fcknob_PGLALA pCON1056 | CAGGTGCAATTGGTTCAATCTGGTGCTGAAGTAAAAAAACCGGGCGCTTCC 246<br>GTTAAAGTGAGCTGCAAAGCATCCGGATACACCTTCACTTCCTATTACATG<br>CACTGGGTTCGTCAAGCCCCGGGCCAGGGTCTGGAATGGATGGGCATCATT<br>AACCCAAGCGGTGGCTCTACCTCCTACGCGCAGAAATTCCAGGGTCGCGTC<br>ACGATGACCCATGACACTAGCACCTCTACCGTTTATATGGAGCTGTCCAGC<br>CTGCGTTCTGAAGATACTGCAGTGTACTACTGTGCACGCTCTTTCTTCACT<br>GGTTTCCATCTGGACTATTGGGGTCAAGGCACCCTCGTAACGGTTTCTTCT<br>GCTAGCACAAAGGGCCCCAGCGTGTTCCCTCTGGCCCCTAGCAGCAAGAGC<br>ACATCTGGCGGAACAGCCGCCCTGGGCTGCCTCGTGAAGGACTACTTTCCC<br>GAGCCTGTGACCGTGTCCTGGAACTCTGGCGCCCTGACAAGCGGCGTGCAC<br>ACCTTTCCAGCCGTGCTGCAGAGCAGCGGCCTGTACTCTCTGAGCAGCGTG<br>GTCACCGTGCCTAGCAGCAGCCTGGGCACCCAGACCTACATCTGCAACGTG<br>AACCACAAGCCCAGCAACACCAAAGTGGACAAGAAGGTGGAGCCCAAG<br>AGCTGTGATGGCGGAGGAGGGTCCGGAGGCGGAGGATCCGAGGTGCAGCTG<br>CTGGAATCTGGCGGCGGACTGGTGCAGCCTGGCGGATCTCTGAGACTGAGC<br>TGTGCCGCCAGCGGCTTCACCTTCAGCACCTACGCCATGAACTGGGTGCGC<br>CAGGCCCCTGGCAAAGGCCTGGAATGGGTGTCCCGGATCAGAAGCAAGTAC<br>AACAACTACGCCACCTACTACGCCGACAGCGTGAAGGGCCGGTTCACCATC<br>AGCCGGGACGACAGCAAGAACACCCTGTACCTGCAGATGAACAGCCTGCGG<br>GCCGAGGACACCGCCGTGTACTATTGTGTGCGGCACGGCAACTTCGGCAAC<br>AGCTATGTGTCTTGGTTTGCCTACTGGGGCCAGGGCACCCTCGTGACCGTG<br>TCAAGCGCTAGTGTGGCCGCTCCCTCCGTGTTTATCTTTCCCCCATCCGAT<br>GAACAGCTGAAAAGCGGCACCGCCTCCGTCGTGTGTCTGCTGAACAATTTT<br>TACCCTAGGGAAGCTAAAGTGCAGTGGAAAGTGGATAACGCACTGCAGTCC<br>GGCAACTCCCAGGAATCTGTGACAGAACAGGACTCCAAGGACAGCACCTAC<br>TCCCTGTCCTCCACCCTGACACTGTCTAAGGCTGATTATGAGAAACAC<br>AAAGTCTACGCCTGCGAAGTCACCCATCAGGGCCTGAGCTCGCCCGTCACA<br>AAGAGCTTCAACAGGGGAGAGTGTGACAAGACCCACACCTGTCCCCCTTGT<br>CCTGCCCCTGAAGCTGCTGGCGGCCCTTCTGTGTTCCTGTTCCCCCCAAAG<br>CCCAAGGACACCCTGATGATCAGCCGGACCCCCGAAGTGACCTGCGTGGTG<br>GTGGATGTGTCCCACGAGGACCCTGAAGTGAAGTTCAATTGGTACGTGGAC<br>GGCGTGGAAGTGCACAACGCCAAGACAAAGCCGCGGGAGGAGCAGTACAAC<br>AGCACGTACCGTGTGGTCAGCGTCCTCACCGTCCTGCACCAGGACTGGCTG<br>AATGGCAAGGAGTACAAGTGCAAGGTCTCCAACAAAGCCCTCGGCGCCCCC<br>ATCGAGAAAACCATCTCCAAAGCCAAAGGGCAGCCCCGAGAACCACAGGTG<br>TACACCCTGCCCCCATGCCGGGATGAGCTGACCAAGAACCAGGTCAGCCTG<br>TGGTGCCTGGTCAAAGGCTTCTATCCCAGCGACATCGCCGTGGAGTGGGAG<br>AGCAATGGGCAGCCGGAGAACAACTACAAGACCACGCCTCCCGTGCTGGAC<br>TCCGACGGCTCCTTCTTCCTCTACAGCAAGCTCACCGTGGACAAGAGC<br>AGGTGGCAGCAGGGGAACGTCTTCTCATGCTCCGTGATGCATGAGGCTCTG<br>CACAACCACTACACGCAGAAGAGCCTCTCCCTGTCTCCGGGTAAA |
| 36F2-Fc hole PGLALA pCON1050 | CAGGTGCAATTGGTTCAATCTGGTGCTGAAGTAAAAAAACCGGGCGCTTCC 247<br>GTTAAAGTGAGCTGCAAAGCATCCGGATACACCTTCACTTCCTATTACATG<br>CACTGGGTTCGTCAAGCCCCGGGCCAGGGTCTGGAATGGATGGGCATCATT<br>AACCCAAGCGGTGGCTCTACCTCCTACGCGCAGAAATTCCAGGGTCGCGTC<br>ACGATGACCCATGACACTAGCACCTCTACCGTTTATATGGAGCTGTCCAGC<br>CTGCGTTCTGAAGATACTGCAGTGTACTACTGTGCACGCTCTTTCTTCACT<br>GGTTTCCATCTGGACTATTGGGGTCAAGGCACCCTCGTAACGGTTTCTTCT<br>GCTAGCACCAAGGGCCCCTCCGTGTTCCCCCTGGCCCCCAGCAGCAAGAGC<br>ACCAGCGGCGGCACAGCCGCTCTGGGCTGCCTGGTCAAGGACTACTTCCCC<br>GAGCCCGTGACCGTGTCCTGGAACAGCGGAGCCCTGACCTCCGGCGTGCAC<br>ACCTTCCCCGCCGTGCTGCAGAGTTCTGGCCTGTATAGCCTGAGCAGCGTG<br>GTCACCGTGCCTTCTAGCAGCCTGGGCACCCAGACCTACATCTGCAACGTG<br>AACCACAAGCCCAGCAACACCAAGGTGGACAAGAAGGTGGAGCCCAAG<br>AGCTGCGACAAAACTCACACATGCCCACCGTGCCCAGCACCTGAAGCTGCA<br>GGGGGACCGTCAGTCTTCCTCTTCCCCCCAAAACCCAAGGACACCCTCATG<br>ATCTCCCGGACCCCTGAGGTCACATGCGTGGTGGTGGACGTGAGCCACGAA<br>GACCCTGAGGTCAAGTTCAACTGGTACGTGGACGGCGTGGAGGTGCATAAT<br>GCCAAGACAAAGCCGCGGGAGGAGCAGTACAACAGCACGTACCGTGTGGTC<br>AGCGTCCTCACCGTCCTGCACCAGGACTGGCTGAATGGCAAGGAGTACAAG<br>TGCAAGGTCTCCAACAAAGCCCTCGGCGCCCCCATCGAGAAAACCATCTCC<br>AAAGCCAAGGGCAGCCCCGAGAACCACAGGTGTGCACCCTGCCCCCATCC<br>CGGGATGAGCTGACCAAGAACCAGGTCAGCCTCTCCGTGCGCAGTCAAAGGC |

-continued

| Name | Sequence | |
|---|---|---|
| 36F2 LC pCON1062 | TTCTATCCCAGCGACATCGCCGTGGAGTGGGAGAGCAATGGGCAGCCGGAG<br>AACAACTACAAGACCACGCCTCCCGTGCTGGACTCCGACGGCTCCTTCTTC<br>CTCGTGAGCAAGCTCACCGTGGACAAGAGCAGGTGGCAGCAGGGGAACGTC<br>TTCTCATGCTCCGTGATGCATGAGGCTCTGCACAACCACTACACGCAG<br>AAGAGCCTCTCCCTGTCTCCGGGTAAA | |
| 36F2 LC pCON1062 | GAAATCGTGTTAACGCAGTCTCCAGGCACCCTGTCTTTGTCTCCAGGGGAA<br>AGAGCCACCCTCTCTTGCAGGGCCAGTCAGAGTGTTAGCAGCAGCTACTTA<br>GCCTGGTACCAGCAGAAACCTGGCCAGGCTCCCAGGCTCCTCATCTATGGA<br>GCATCCAGCAGGGCCACTGGCATCCCAGACAGGTTCAGTGGCAGTGGATCC<br>GGGACAGACTTCACTCTCACCATCAGCAGACTGGAGCCTGAAGATTTTGCA<br>GTGTATTACTGTCAGCAGTATACCAACGAACATTATTATACGTTCGGCCAG<br>GGGACCAAAGTGGAAATCAAACGTACGGTGGCTGCACCATCTGTCTTCATC<br>TTCCCGCCATCTGATGAGCAGTTGAAATCTGGAACTGCCTCTGTTGTGTGC<br>CTGCTGAATAACTTCTATCCCAGAGAGGCCAAAGTACAGTGGAAGGTGGAT<br>AACGCCCTCCAATCGGGTAACTCCCAGGAGAGTGTCACAGAGCAGGACAGC<br>AAGGACAGCACCTACAGCCTCAGCAGCACCCTGACGCTGAGCAAAGCAGAC<br>TACGAGAAACACAAAGTCTACGCCTGCGAAGTCACCCATCANGGCCTGAGC<br>TCGCCCGTCACAAAGAGCTTCAACAGGGGAGAGTGT | 97 |
| CD3 VLCH1 pETR12940 | CAGGCCGTCGTGACCCAGGAACCCAGCCTGACAGTGTCTCCTGGCGGCACC<br>GTGACACTGTGCCAGTTCTACAGGCGCCGTGACCACCAGCAACTAC<br>GCCAACTGGGTGCAGGAAAAGCCCGGCCAGGCCTTCAGAGGACTGATCGGC<br>GGCACCAACAAGAGAGCCCCTGGCACCCCTGCCAGATTCAGCGGATCTCTG<br>CTGGGAGGAAAGGCCGCCCTGACACTGTCTGGCGCCCAGCCAGAAGATGAG<br>GCCGAGTACTACTGCGCCCTGTGGTACAGCAACCTGTGGGTGTTCGGCGGA<br>GGCACCAAGCTGACAGTGCTGAGCAGCGCTTCCACCAAAGGCCCTTCCGTG<br>TTTCCTCTGGCTCCTAGCTCCAAGTCCACCTCTGGAGGCACCGCTGCTCTC<br>GGATGCCTCGTGAAGGATTATTTTCCTGAGCCTGTGACAGTGTCCTGGAAT<br>AGCGGAGCACTGACCTCTGGAGTGCATACTTTCCCCGCTGTGCTGCAGTCC<br>TCTGGACTGTACAGCCTGAGCAGCGTGGTGACAGTGCCCAGCAGCAGCCTG<br>GGCACCCAGACCTACATCTGCAACGTGAACCACAAGCCCAGCAACACCAAG<br>GTGGACAAGAAGGTGGAACCCAAGTCTTGT | 198 |

| Name | Sequence | Seq ID No |
|---|---|---|
| K53A nt | CAGACCGTCGTGACCCAGGAACCCAGCCTGACAGTGTCTCCTGGCGGCACC<br>GTGACCCTGACATGTGGCAGTTCTACAGGCGCCGTGACCACCAGCAACTAC<br>GCCAACTGGGTGCAGCAGAAGCCAGGCCAGGCTCCCAGAGGACTGATCGGC<br>GGCACCAACGCCAGAGCCCCTGGCACCCCTGCCAGATTCAGCGGATCTCTG<br>CTGGGAGGAAAGGCCGCCCTGACACTGTCTGGCGTGCAGCCTGAAGATGAG<br>GCCGAGTACTACTGCGCCCTGTGGTACAGCAACCTGTGGGTGTTCGGCGGA<br>GGCACCAAGCTGACAGTCCTA | 205 |
| S93A nt | CAGACCGTCGTGACCCAGGAACCCAGCCTGACAGTGTCTCCTGGCGGCACC<br>GTGACCCTGACATGTGGCAGTTCTACAGGCGCCGTGACCACCAGCAACTAC<br>GCCAACTGGGTGCAGCAGAAGCCAGGCCAGGCTCCCAGAGGACTGATCGGC<br>GGCACCAACAAGAGAGCCCCTGGCACCCCTGCCAGATTCAGCGGATCTCTG<br>CTGGGAGGAAAGGCCGCCCTGACACTGTCTGGCGTGCAGCCTGAAGATGAG<br>GCCGAGTACTACTGCGCCCCTGTGGTACGCCAACCTGTGGGTGTTCGGCGGA<br>GGCACCAAGCTGACAGTCCTA | 206 |

| Name | Sequence | Seq ID No |
|---|---|---|
| S35H nt | GAGGTGCAATTGGTGGAAAGCGGAGGCGGCCTCGTGAAGCCTGGCGGATCT<br>CTGAGACTGAGCTGTGCCGCCAGCGGCTTCACCTTCAGCAACGCCTGATG<br>CACTGGGTGCGCCAGGCCCCTGGAAAAGGACTCGAGTGGGTGGGACGGATC<br>AAGAGCAAGACCGATGGCGGCACCACCGACTATGCCGCCCCTGTGAAGGGC<br>CGGTTCACCATCAGCAGGGACGACAGCAAGAACACCCTGTACCTGCAGATG<br>AACAGCCTGAAAACCGAGGACACCGCCGTGTACTACTGCACCACCCCCTGG<br>GAGTGGTCTTGGTACGACTATTGGGGCCAGGGCACCCTCGTGACCGTGTCC<br>TCTGCTAGC | 207 |
| G49S nt | GAGGTGCAATTGGTGGAAAGCGGAGGCGGCCTCGTGAAGCCTGGCGGATCT<br>CTGAGACTGAGCTGTGCCGCCAGCGGCTTCACCTTCAGCAACGCCTGATG<br>AGCTGGGTGCGCCAGGCCCCTGGAAAAGGACTCGAGTGGGTGTCCCGGATC<br>AAGAGCAAGACCGATGGCGGCACCACCGACTATGCCGCCCCTGTGAAGGGC<br>CGGTTCACCATCAGCAGGGACGACAGCAAGAACACCCCGCCGTGTACTACTGCACCACCCCCTGG<br>GAGTGGTCTTGGTACGACTATTGGGGCCAGGGCACCCTCGTGACCGTGTCC<br>TCTGCTAGC | 208 |

-continued

| Name | Sequence | Seq ID No |
|---|---|---|
| R50S nt | GAGGTGCAATTGGTGGAAAGCGGAGGCGGCCTCGTGAAGCCTGGCGGATCT CTGAGACTGAGCTGTGCCGCCAGCGGCTTCACCTTCAGCAACGCCTGGATG AGCTGGGTGCGCCAGGCCCCTGGAAAAGGACTCGAGTGGGTGGGATCTATC AAGAGCAAGACCGACGGCGGCACCACCGACTATGCCGCCCCTGTGAAGGGC CGGTTCACCATCAGCAGGGACGACAGCAAGAACACCCTGTACCTGCAGATG AACAGCCTGAAAACCGAGGACACCGCCGTGTACTACTGCACCACCCCCTGG GAGTGGTCTTGGTACGACTATTGGGGCCAGGGCACCCTCGTGACCGTGTCC TCT GCTAGC | 209 |
| W96Y nt | GAGGTGCAATTGGTGGAAAGCGGAGGCGGCCTCGTGAAGCCTGGCGGATCT CTGAGACTGAGCTGTGCCGCCAGCGGCTTCACCTTCAGCAACGCCTGGATG AGCTGGGTGCGCCAGGCCCCTGGAAAAGGACTCGAGTGGGTGGGACGGATC AAGAGCAAGACCGATGGCGGCACCACCGACTATGCCGCCCCTGTGAAGGGC CGGTTCACCATCAGCAGGGACGACAGCAAGAACACCCTGTACCTGCAGATG AACAGCCTGAAAACCGAGGACACCGCCGTGTACTACTGCACCACCCCCTAC GAGTGGTCTTGGTACGACTACTGGGGCCAGGGCACCCTCGTGACCGTGTCA TCT GCTAGC | 210 |
| W98Y nt | GAGGTGCAATTGGTGGAAAGCGGAGGCGGCCTCGTGAAGCCTGGCGGATCT CTGAGACTGAGCTGTGCCGCCAGCGGCTTCACCTTCAGCAACGCCTGGATG AGCTGGGTGCGCCAGGCCCCTGGAAAAGGACTCGAGTGGGTGGGACGGATC AAGAGCAAGACCGATGGCGGCACCACCGACTATGCCGCCCCTGTGAAGGGC CGGTTCACCATCAGCAGGGACGACAGCAAGAACACCCTGTACCTGCAGATG AACAGCCTGAAAACCGAGGACACCGCCGTGTACTACTGCACCACCCCCTGG GAGTACTCTTGGTACGACTACTGGGGCCAGGGCACCCTCGTGACCGTGTCA TCT GCTAGC | 211 |

| Name | Sequence | Seq ID No |
|---|---|---|
| 90D7 nt | CAGGTGCAATTGGTTCAATCTGGTGCTGAAGTAAAAAAACCGGGCGCTTCC GTTAAAGTGAGCTGCAAAGCATCCGGATACACCTTCACTTCCTATTACATG CACTGGGTTCGTCAAGCCCCGGGCCAGGGTCTGGAATGGATGGGCATCATT AACCCAAGCGGTGGCTCTACCTCCTACGCGCAGAAATTCCAGGGTCGCGTC ACGATGACCCGTGACACTAGCACCTCTACCGTTTATATGGAGCTGTCCAGC CTGCGTTCTGAAGATACTGCAGTGTACTACTGTGCACGCAACTACACTATC GTTGTTTCTCCGTTCGACTATTGGGGTCAAGGCACCCTCGTAACGGTTTCT TCTGCTAGC | 212 |
| 90C1 nt | CAGGTGCAATTGGTTCAATCTGGTGCTGAAGTAAAAAAACCGGGCGCTTCC GTTAAAGTGAGCTGCAAAGCATCCGGATACACCTTCACTTCCTATTACATG CACTGGGTTCGTCAAGCCCCGGGCCAGGGTCTGGAATGGATGGGCATCATT AACCCAAGCGGTGGCTCTACCTCCTACGCGCAGAAATTCCAGGGTCGCGTC ACGATGACCCGTGACACTAGCACCTCTACCGTTTATATGGAGCTGTCCAGC CTGCGTTCTGAAGATACTGCAGTGTACTACTGTGCACGCAACTACTTCATC GGTTCTGTTGCTATGGACTATTGGGGTCAAGGCACCCTCGTAACGGTTTCT TCTGCTAGC | 213 |
| 5E8 VH nt | CAGGTGCAATTGGTTCAATCTGGTGCTGAAGTAAAAAAACCGGGCGCTTCC GTTAAAGTGAGCTGCAAAGCATCCGGATACACCTTCACTTCCTATTACATG CACTGGGTTCGTCAAGCCCCGGGCCAGGGTCTGGAATGGATGGGCATCATT AACCCAAGCGGTGGCTCTACCTCCTACGCGCAGAAATTCCAGGGTCGCGTC ACGATGACCCGTGACACTAGCACCTCTACCGTTTATATGGAGCTGTCCAGC CTGCGTTCTGAAGATACTGCAGTGTACTACTGTGCACGCGGTCTGACTTAC TCTATGGACTATTGGGGTCAAGGCACCCTCGTAACGGTTTCTTCTGCTAGC | 214 |
| 5E8 VL nt | GATATTGTTATGACTCAATCTCCACTGTCTCTGCCGGTGACTCCAGGCGAA CCGGCGAGCATTTCTTGCCGTTCCAGCCAGTCTCTGCTGCACTCCAACGGC TACAACTATCTCGATTGGTACCTGCAAAAACCGGGTCAGAGCCCTCAGCTG CTGATCTACCTGGGCTCTAACCGCGCTTCCGGTGTACCGGACCGTTTCAGC GGCTCTGGATCCGGCACCGATTTCACGTTGAAAATCAGCCGTGTTGAAGCA GAAGACGTGGGCGTTTATTACTGTATGCAGGCACTGCAGATTCCAAACACT TTTGGTCAAGGCACCAAGGTCGAAATTAAACGTACG | 215 |
| 12A4 VH nt | GAGGTGCAATTGTTGGAGTCTGGGGGAGGCTTGGTACAGCCTGGGGGGTCC CTGAGACTCTCCTGTGCAGCCTCCGGATTCACCTTTAGCAGTTATGCCATG AGCTGGGTCCGCCAGGCTCAGGGAAGGGGCTGGAGTGGGTCTCAGCTATT AGTGGTAGTGGTGGTAGCACATACTACGCAGACTCCGTGAAGGGCCGGTTC ACCATCTCCAGAGACAATTCCAAGAACACGCTGTATCTGCAGATGAACAGC | 216 |

-continued

| Name | Sequence | Seq ID No |
|---|---|---|
| | CTGAGAGCCGAGGACACGGCCGTATATTACTGTGCGAAATACGCTTACGCT<br>CTGGACTACTGGGGCCAAGGAACCCTGGTCACCGTCTCGAGTGCTAGC | |
| 12A4 VL nt | GAAATCGTGTTAACGCAGTCTCCAGGCACCCTGTCTTTGTCTCCAGGGGAA<br>AGAGCCACCCTCTCTTGCAGGGCCAGTCAGAGTGTTAGCAGCAGCTACTTA<br>GCCTGGTACCAGCAGAAACCTGGCCAGGCTCCCAGGCTCCTCATCTATGGA<br>GCATCCAGCAGGGCCACTGGCATCCCAGACAGGTTCAGTGGCAGTGGATCC<br>GGGACAGACTTCACTCTCACCATCAGCAGACTGGAGCCTGAAGATTTTGCA<br>GTGTATTACTGTCAGCAGCATGGCAGCAGCAGCACGTTCGGCCAGGGGACC<br>AAAGTGGAAATCAAACGTACG | 217 |
| 7A3 VH nt | CAGGTGCAATTGGTTCAATCTGGTGCTGAAGTAAAAAAACCGGGCGCTTCC<br>GTTAAAGTGAGCTGCAAAGCATCCGGATACACCTTCACTTCCTATTACATG<br>CACTGGGTTCGTCAAGCCCCGGGCCAGGGTCTGGAATGGATGGGCATCATT<br>AACCCAAGCGGTGGCTCTACCTCCTACGCGCAGAAATTCCAGGGTCGCGTC<br>ACGATGACCCGTGACACTAGCACCTCTACCGTTTATATGGAGCTGTCCAGC<br>CTGCGTTCTGAAGATACTGCAGTGTACTACTGTGCACGCGGTGACTTCTCT<br>GCTGGTCGTCTGATGGACTATTGGGGTCAAGGCACCCTCGTAACGGTTTCT<br>TCTGCTAGC | 218 |
| 7A3 VL nt | GATATTGTTATGACTCAATCTCCACTGTCTCTGCCGGTGACTCCAGGCGAA<br>CCGGCGAGCATTTCTTGCCGTTCCAGCCAGTCTCTGCTGCACTCCAACGGC<br>TACAACTATCTCGATTGGTACCTGCAAAAACGGGTCAGAGCCCTCAGCTG<br>CTGATCTACCTGGGCTCTAACCGCGCTTCCGGTGTACCGGACCGTTTCAGC<br>GGCTCTGGATCCGGCACCGATTTCACGTTGAAAATCAGCCGTGTTGAAGCA<br>GAAGACGTGGGCGTTTATTACTGTATGCAGGCACTGCAGACCCCACCAATT<br>ACCTTTGGTCAAGGCACCAAGGTCGAAATTAAACGTACG | 219 |
| 6E10 VH nt | CAGGTGCAATTGGTTCAATCTGGTGCTGAAGTAAAAAAACCGGGCGCTTCC<br>GTTAAAGTGAGCTGCAAAGCATCCGGATACACCTTCACTTCCTATTACATG<br>CACTGGGTTCGTCAAGCCCCGGGCCAGGGTCTGGAATGGATGGGCATCATT<br>AACCCAAGCGGTGGCTCTACCTCCTACGCGCAGAAATTCCAGGGTCGCGTC<br>ACGATGACCCGTGACACTAGCACCTCTACCGTTTATATGGAGCTGTCCAGC<br>CTGCGTTCTGAAGATACTGCAGTGTACTACTGTGCACGCGGTGACTACAAC<br>GCTTTCGACTATTGGGGTCACGGCACCCTCGTAACGGTTTCTTCTGCTAGC | 220 |
| 6E10 VL nt | GATATTGTTATGACTCAATCTCCACTGTCTCTGCCGGTGACTCCAGGCGAA<br>CCGGCGAGCATTTCTTGCCGTTCCAGCCAGTCTCTGCTGCACTCCAACGGC<br>TACAACTATCTCGATTGGTACCTGCAAAAACGGGTCAGAGCCCTCAGCTG<br>CTGATCTACCTGGGCTCTAACCGCGCTTCCGGTGTACCGGACCGTTTCAGC<br>GGCTCTGGATCCGGCACCGATTTCACGTTGAAAATCAGCCGTGTTGAAGCA<br>GAAGACGTGGGCGTTTATTACTGTATGCAGGCATGGCATAGCCCAACTTTT<br>GGTCAAGGCACCAAGGTCGAAATTAAACGTACG | 221 |
| 12F9 VH nt | CAGGTGCAATTGGTTCAATCTGGTGCTGAAGTAAAAAAACCGGGCGCTTCC<br>GTTAAAGTGAGCTGCAAAGCATCCGGATACACCTTCACTTCCTATTACATG<br>CACTGGGTTCGTCAAGCCCCGGGCCAGGGTCTGGAATGGATGGGCATCATT<br>AACCCAAGCGGTGGCTCTACCTCCTACGCGCAGAAATTCCAGGGTCGCGTC<br>ACGATGACCCGTGACACTAGCACCTCTACCGTTTATATGGAGCTGTCCAGC<br>CTGCGTTCTGAAGATACTGCAGTGTACTACTGTGCACGCGGTGCTACTTAC<br>ACTATGGACTATTGGGGTCAAGGCACCCTCGTAACGGTTTCTTCTGCTAGC | 222 |
| 12F9 VL nt | GATATTGTTATGACTCAATCTCCACTGTCTCTGCCGGTGACTCCAGGCGAA<br>CCGGCGAGCATTTCTTGCCGTTCCAGCCAGTCTCTGCTGCACTCCAACGGC<br>TACAACTATCTCGATTGGTACCTGCAAAAACGGGTCAGAGCCCTCAGCTG<br>CTGATCTACCTGGGCTCTAACCGCGCTTCCGGTGTACCGGACCGTTTCAGC<br>GGCTCTGGATCCGGCACCGATTTCACGTTGAAAATCAGCCGTGTTGAAGCA<br>GAAGACGTGGGCGTTTATTACTGTATGCAGGCACTGCAGACCCCAATTACT<br>TTTGGTCAAGGCACCAAGGTCGAAATTAAACGTACG | 223 |

| Name | Sequence | Seq ID No |
|---|---|---|
| pETR11646<br>Mov19 VH-<br>CH1-Fchole<br>PG/LALA | CAGGTGCAGCTGCAGCAGTCTGGCGCCGAGCTCGTGAAACCTGGCGCCTCC<br>GTGAAGATCAGCTGCAAGGCCAGCGGCTACAGCTTCACCGGCTACTTCATG<br>AACTGGGTCAAGCAGAGCCACGGCAAGAGCCTGGAATGGATCGGCAGAATC<br>CACCCCTACGACGGCGACACCTTCTACAACCAGAACTTCAAGGACAAGGCC<br>ACCCTGACCGTGGACAAGAGCAGCAACACCGCCCACATGGAACTGCTGAGC<br>CTGACCAGCGAGGACTTCGCCGTGTACTACTGCACCAGATACGACGGCAGC<br>CGGGCCATGGATTATTGGGGCCAGGGCACCACCGTGACAGTGTCCAGCGCT<br>AGCACCAAGGGCCCCTCCGTGTTCCCCCTGGCCCCCAGCAGCAAGAGCACC<br>AGCGGCGGCACAGCCGCTCTGGGCTGCCTGGTCAAGGACTACTTCCCCGAG<br>CCCGTGACCGTGTCCTGGAACAGCGGAGCCCTGACCTCCGGCGTGCACACC | 224 |

| Name | Sequence | Seq ID No |
|---|---|---|
| | TTCCCCGCCGTGCTGCAGAGTTCTGGCCTGTATAGCCTGAGCAGCGTGGTC<br>ACCGTGCCTTCTAGCAGCCTGGGCACCCAGACCTACATCTGCAACGTGAAC<br>CACAAGCCCAGCAACACCAAGGTGGACAAGAAGGTGGAGCCCAAGAGCTGC<br>GACAAAACTCACACATGCCCACCGTGCCCAGCACCTGAAGCTGCAGGGGGA<br>CCGTCAGTCTTCCTCTTCCCCCCAAAACCCAAGGACACCCTCATGATCTCC<br>CGGACCCCTGAGGTCACATGCGTGGTGGTGGACGTGAGCCACGAAGACCCT<br>GAGGTCAAGTTCAACTGGTACGTGGACGGCGTGGAGGTGCATAATGCCAAG<br>ACAAAGCCGCGGGAGGAGCAGTACAACAGCACGTACCGTGTGGTCAGCGTC<br>CTCACCGTCCTGCACCAGGACTGGCTGAATGGCAAGGAGTACAAGTGCAAG<br>GTCTCCAACAAAGCCCTCGGCGCCCCCATCGAGAAAACCATCTCCAAAGCC<br>AAAGGGCAGCCCCGAGAACCACAGGTGTGCACCCTGCCCCCATCCCGGGAT<br>GAGCTGACCAAGAACCAGGTCAGCCTCTCGTGCGCAGTCAAAGGCTTCTAT<br>CCCAGCGACATCGCCGTGGAGTGGGAGAGCAATGGGCAGCCGGAGAACAAC<br>TACAAGACCACGCCTCCCGTGCTGGACTCCGACGGCTCCTTCTTCCTCGTG<br>AGCAAGCTCACCGTGGACAAGAGCAGGTGGCAGCAGGGGAACGTCTTCTCA<br>TGCTCCGTGATGCATGAGGCTCTGCACAACCACTACACGCAGAAGAGCCTC<br>TCCCTGTCTCCGGGTAAA | |
| pETR11647<br>Mov19 VH-<br>CH1-CD3<br>VH-CL-<br>Fcknob<br>PG/LALA | CAGGTGCAGCTGCAGCAGTCTGGCGCCGAGCTCGTGAAACCTGGCGCCTCC<br>GTGAAGATCAGCTGCAAGGCCAGCGGCTACAGCTTCACCGGCTACTTCATG<br>AACTGGGTCAAGCAGAGCCACGGCAAGAGCCTGGAATGGATCGGCAGAATC<br>CACCCCTACGACGGCGACACCTTCTACAACCAGAACTTCAAGGACAAGGCC<br>ACCCTGACCGTGGACAAGAGCAGCAACACCGCCTACCTGCACATGGAACTGCTGAGC<br>CTGACCAGCGAGGACTTCGCCGTGTACTACTGCACCAGATACGACGGCAGC<br>CGGGCCATGGATTATTGGGGCCAGGGCACCACCGTGACAGTGTCCAGCGCT<br>AGCACAAAGGGCCCCAGCGTGTTCCCTCTGGCCCCTAGCAGCAAGAGCACA<br>TCTGGCGGAACAGCCGCCTGGGCTGCCTCGTGAAGGACTACTTTCCCGAG<br>CCTGTGACCGTGTCCTGGAACTCTGGCGCCCTGACAAGCGGCGTGCACACC<br>TTTCCAGCCGTGCTGCAGAGCAGCGGCCTGTACTCTCTGAGCAGCGTGGTC<br>ACCGTGCCTAGCAGCAGCCTGGGCACCCAGACCTACATCTGCAACGTGAAC<br>CACAAGCCCAGCAACACCAAGGTGGACAAGAAGGTGGAGCCCAAGAGCTGT<br>GATGGCGGAGGAGGGTCCGGAGGCGGAGGATCCGAAGTGCAGCTGGTGGAA<br>AGCGGCGGAGGCCTGGTCAGCCTAAGGGCTCTCTGAAGCTGAGCTGTGCC<br>GCCAGCGGCTTCACCTTCAACACCTACGCCATGAACTGGGTGCGCCAGGCC<br>CCTGGCAAAGGCCTGGAATGGGTGGCCCGGATCAGAAGCAAGTACAACAAT<br>TACGCCACCTACTACGCCGACAGCGTGAAGGACCGGTTCACCATCAGCCGG<br>GACGACAGCCAGAGCATCCTGTACCTGCAGATGAACAACCTGAAAACCGAG<br>GACACCGCCATGTACTACTGCGTGCGGCACGGCAACTTCGGCAACAGCTAT<br>GTGTCTTGGTTTGCCTACTGGGGCCAGGGCACCCTCGTGACAGTGTCTGCT<br>GCTAGCGTGGCCGCTCCCTCCGTGTTTATCTTTCCCCCATCCGATGAACAG<br>CTGAAAAGCGGCACCGCCTCCGTCGTGTGTCTGCTGAACAATTTTTACCCT<br>AGGGAAGCTAAAGTGCAGTGGAAAGTGGATAACGCACTGCAGTCCGGCAAC<br>TCCCAGGAATCTGTGACAGAACAGGACTCCAAGGACAGCACCTACTCCCTG<br>TCCTCCACCCTGACACTGTCTAAGGCTGATTATGAGAAACACAAAGTCTAC<br>GCCTGCGAAGTCACCCATCAGGGCCTGAGCTCGCCCGTCACAAAGAGCTTC<br>AACAGGGGAGAGTGTGACAAGACCCACACCTGTCCCCCTTGTCCTGCCCCT<br>GAAGCTGCTGGCGGCCCTTCTGTGTTCCTGTTCCCCCCAAAGCCCAAGGAC<br>ACCCTGATGATCAGCCGGACCCCCGAAGTGACCTGCGTGGTGGTGGATGTG<br>TCCCACGAGGACCCTGAAGTGAAGTTCAATTGGTACGTGGACGGCGTGGAA<br>GTGCACAACGCCAAGACAAAGCCGCGGGAGGAGCAGTACAACAGCACGTAC<br>CGTGTGGTCAGCGTCCTCACCGTCCTGCACCAGGACTGGCTGAATGGCAAG<br>GAGTACAAGTGCAAGGTCTCCAACAAAGCCCTCGGCGCCCCCATCGAGAAA<br>ACCATCTCCAAAGCCAAAGGGCAGCCCCGAGAACCACAGGTGTACACCCTG<br>CCCCCATGCCGGGATGAGCTGACCAAGAACCAGGTCAGCCTGTGGTGCCTG<br>GTCAAAGGCTTCTATCCCAGCGACATCGCCGTGGAGTGGGAGAGCAATGGG<br>CAGCCGGAGAACAACTACAAGACCACGCCTCCCGTGCTGGACTCCGACGGC<br>TCCTTCTTCCTCTACAGCAAGCTCACCGTGGACAAGAGCAGGTGGCAGCAG<br>GGGAACGTCTTCTCATGCTCCGTGATGCATGAGGCTCTGCACAACCACTAC<br>ACGCAGAAGAGCCTCTCCCTGTCTCCGGGTAAA | 225 |
| pETR11644<br>Mov19 LC | GACATCGAGCTGACCCAGAGCCCTGCCTCTCTGGCCGTGTCTCTGGGACAG<br>AGAGCCATCATCAGCTGCAAGGCCAGCCAGAGCGTGTCCTTTGCCGGCACC<br>TCTCTGATGCACTGGTATCACCAGAAGCCCGGCCAGCAGCCCAAGCTGCTG<br>ATCTACAGAGCCAGCAACCTGGAAGCGGCGTGCCCACAAGATTTTCCGGC<br>AGCGGCAGCAAGACCGACTTCACCCTGAACATCCACCCCGTGGAAGAAGAG<br>GACGCCGCCACCTACTACTGCCAGCAGAGCAGAGTACCCCTACACCTTC<br>GGCGGAGGCACCAAGCTGGAAATCAAGCGTACGGTGGCTGCACCATCTGTC<br>TTCATCTTCCCGCCATCTGATGAGCAGTTGAAATCTGGAACTGCCTCTGTT<br>GTGTGCCTGCTGAATAACTTCTATCCCAGAGAGGCCAAAGTACAGTGGAAG<br>GTGGATAACGCCCTCCAATCGGGTAACTCCCAGGAGAGTGTCACAGAGCAG<br>GACAGCAAGGACAGCACCTACAGCCTCAGCAGCACCCTGACGCTGAGCAAA<br>GCAGACTACGAGAAACACAAAGTCTACGCCTGCGAAGTCACCCATCAGGGC<br>CTGAGCTCGCCCGTCACAAAGAGCTTCAACAGGGGAGAGTGT | 226 |

| Variant | Sequence | Seq ID No |
|---|---|---|
| 16D5 VH_D52dE | GAGGTGCAATTGGTTGAATCTGGTGGTGGTCTGGTAAAACCGGGCGGTTCCC TGCGTCTGAGCTGCGCGGCTTCCGGATTCACCTTCTCCAACGCGTGGATGAG CTGGGTTCGCCAGGCCCCGGGCAAAGGCCTCGAGTGGGTTGGTCGTATCAAG TCTAAAACTGAGGGTGGCACCACGGATTACGCGGCTCCAGTTAAAGGTCGTT TTACCATTTCCCGCGACGATAGCAAAAACACTCTGTATCTGCAGATGAACTC TCTGAAAACTGAAGACACCGCAGTCTACTACTGTACTACCCCGTGGGAATGG TCTTGGTACGATTATTGGGGCCAGGGCACGCTGGTTACGGTGTCTTCC | 261 |
| 16D5 VH_D52dQ | GAGGTGCAATTGGTTGAATCTGGTGGTGGTCTGGTAAAACCGGGCGGTTCCC TGCGTCTGAGCTGCGCGGCTTCCGGATTCACCTTCTCCAACGCGTGGATGAG CTGGGTTCGCCAGGCCCCGGGCAAAGGCCTCGAGTGGGTTGGTCGTATCAAG TCTAAAACTCAGGGTGGCACCACGGATTACGCGGCTCCAGTTAAAGGTCGTT TTACCATTTCCCGCGACGATAGCAAAAACACTCTGTATCTGCAGATGAACTC TCTGAAAACTGAAGACACCGCAGTCTACTACTGTACTACCCCGTGGGAATGG TCTTGGTACGATTATTGGGGCCAGGGCACGCTGGTTACGGTGTCTTCC | 262 |
| CD3_VH N100A | GAGGTGCAGCTGCTGGAATCTGGCGGCGGACTGGTGCAGCCTGGCGGATCTC TGAGACTGAGCTGTGCCGCCAGCGGCTTCACCTTCAGCACCTACGCCATGAA CTGGGTGCGCCAGGCCCCTGGCAAAGGCCTGGAATGGGTGTCCCGGATCAGA AGCAAGTACAACAACTACGCCACCTACTACGCCGACAGCGTGAAGGGCCGGT TCACCATCAGCCGGGACGACAGCAAGAACACCCTGTACCTGCAGATGAACAG CCTGCGGGCCGAGGACACCGCCGTGTACTATTGTGTGCGGCACGGCAACTTC GGCGCCAGCTATGTGTCTTGGTTTGCCTACTGGGGCCAGGGCACCCTCGTGA CCGTGTCAAGC | 263 |
| CD3_VH S100aA | GAGGTGCAGCTGCTGGAATCTGGCGGCGGACTGGTGCAGCCTGGCGGATCTC TGAGACTGAGCTGTGCCGCCAGCGGCTTCACCTTCAGCACCTACGCCATGAA CTGGGTGCGCCAGGCCCCTGGCAAAGGCCTGGAATGGGTGTCCCGGATCAGA AGCAAGTACAACAACTACGCCACCTACTACGCCGACAGCGTGAAGGGCCGGT TCACCATCAGCCGGGACGACAGCAAGAACACCCTGTACCTGCAGATGAACAG CCTGCGGGCCGAGGACACCGCCGTGTACTATTGTGTGCGGCACGGCAACTTC GGCAACGCCTATGTGTCTTGGTTTGCCTACTGGGGCCAGGGCACCCTCGTGA CCGTGTCAAGC | 264 |
| 16D5 [VHCH1]-CD3 [VHCH1-N100A]-Fcknob_PGLALA | GAGGTGCAATTGGTTGAATCTGGTGGTGGTCTGGTAAAACCGGGCGGTTCCC TGCGTCTGAGCTGCGCGGCTTCCGGATTCACCTTCTCCAACGCGTGGATGAG CTGGGTTCGCCAGGCCCCGGGCAAAGGCCTCGAGTGGGTTGGTCGTATCAAG TCTAAAACTGACGGTGGCACCACGGATTACGCGGCTCCAGTTAAAGGTCGTT TTACCATTTCCCGCGACGATAGCAAAAACACTCTGTATCTGCAGATGAACTC TCTGAAAACTGAAGACACCGCAGTCTACTACTGTACTACCCCGTGGGAATGG TCTTGGTACGATTATTGGGGCCAGGGCACGCTGGTTACGGTGTCTTCCGCTA GCACAAAGGGCCCTAGCGTGTTCCCTCTGGCCCCCAGCAGCAAGAGCACAAG CGGCGGAACAGCCGCCCTGGGCTGCCTCGTGAAGGACTACTTCCCCGAGCCC GTGACAGTGTCTTGGAACAGCGGAGCCCTGACAAGCGGCGTGCACACTTTCC CTGCCGTGCTGCAGAGCAGCGGCCTGTACTCCCTGAGCAGCGTGGTCACCGT GCCCTCCAGCAGCCTGGGCACCCAGACCTACATCTGCAACGTGAACCACAAG CCCAGCAACACCAAAGTGGACAAGAAGGTGGAGCCCAAGAGCTGTGATGGCG GAGGAGGGTCCGGAGGCGGAGGATCCGAGGTGCAGCTGCTGGAATCTGGCGG CGGACTGGTGCAGCCTGGCGGATCTCTGAGACTGAGCTGTGCCGCCAGCGGC TTCACCTTCAGCACCTACGCCATGAACTGGGTGCGCCAGGCCCCTGGCAAAG GCCTGGAATGGGTGTCCCGGATCAGAAGCAAGTACAACAACTACGCCACCTA CTACGCCGACAGCGTGAAGGGCCGGTTCACCATCAGCCGGGACGACAGCAAG AACACCCTGTACCTGCAGATGAACAGCCTGCGGGCCGAGGACACCGCCGTGT ACTATTGTGTGCGGCACGGCAACTTCGGCGCCAGCTATGTGTCTTGGTTTGC CTACTGGGGCCAGGGCACCCTCGTGACCGTGTCAAGCGCTAGTACCAAGGGC CCCAGCGTGTTCCCCCTGGCACCCAGCAGCAAGAGCACATCTGGCGGAACAG CCGCTCTGGGCTGTCTGGTGAAAGACTACTTCCCCGAGCCCGTGACCGTGTC TTGGAACTCTGGCGCCCTGACCAGCGGCGTGCACACCTTTCCAGCCGTGCTG CAGAGCAGCGGCCTGTACTCCCTGTCCTCCGTGGTCACCGTGCCCTCTAGCT CCCTGGGAACACAGACATATATCTGTAATGTCAATCACAAGCCTTCCAACAC CAAAGTCGATAAGAAAGTCGAGCCCAAGAGCTGCGACAAAACTCACACATGC CCACCGTGCCCAGCACCTGAAGCTGCAGGGGGACCGTCAGTCTTCCTCTTCC CCCCAAAACCCAAGGACACCCTCATGATCTCCCGGACCCCTGAGGTCACATG CGTGGTGGTGGACGTGAGCCACGAAGACCCTGAGGTCAAGTTCAACTGGTAC GTGGACGGCGTGGAGGTGCATAATGCCAAGACAAAGCCGCGGGAGGAGCAGT ACAACAGCACGTACCGTGTGGTCAGCGTCCTCACCGTCCTGCACCAGGACTG GCTGAATGGCAAGGAGTACAAGTGCAAGGTCTCCAACAAAGCCCTCGGCGCC CCCATCGAGAAAACCATCTCCAAAGCCAAAGGGCAGCCCCGAGAACCACAGG TGTACACCCTGCCCCCATGCCCGGGATGAGCTGACCAAGAACCAGGTCAGCCT GTGGTGCCTGGTCAAAGGCTTCTATCCCAGCGACATCGCCGTGGAGTGGGAG AGCAATGGGCAGCCGGAGAACAACTACAAGACCACGCCTCCCGTGCTGGACT CCGACGGCTCCTTCTTCCTCTACAGCAAGCTCACCGTGGACAAGAGCAGGTG GCAGCAGGGGAACGTCTTCTCATGCTCCGTGATGCATGAGGCTCTGCACAAC CACTACACGCAGAAGAGCCTCTCCCTGTCTCCGGGTAAA | 265 |
| 16D5-Fchole-PGLALA | GAGGTGCAATTGGTTGAATCTGGTGGTGGTCTGGTAAAACCGGGCGGTTCCC TGCGTCTGAGCTGCGCGGCTTCCGGATTCACCTTCTCCAACGCGTGGATGAG CTGGGTTCGCCAGGCCCCGGGCAAAGGCCTCGAGTGGGTTGGTCGTATCAAG | 266 |

-continued

| Variant | Sequence | Seq ID No |
|---|---|---|
| | TCTAAAACTGACGGTGGCACCACGGATTACGCGGCTCCAGTTAAAGGTCGTT<br>TTACCATTTCCCGCGACGATAGCAAAAACACTCTGTATCTGCAGATGAACTC<br>TCTGAAAACTGAAGACACCGCAGTCTACTACTGTACTACCCCGTGGGAATGG<br>TCTTGGTACGATTATTGGGGCCAGGGCACGCTGGTTACGGTGTCTTCCGCTA<br>GCACCAAGGGCCCCTCCGTGTTCCCCCTGGCCCCCAGCAGCAAGAGCACCAG<br>CGGCGGCACAGCCGCTCTGGGCTGCCTGGTCAAGGACTACTTCCCCGAGCCC<br>GTGACCGTGTCCTGGAACAGCGGAGCCCTGACCTCCGGCGTGCACACCTTCC<br>CCGCCGTGCTGCAGAGTTCTGGCCTGTATAGCCTGAGCAGCGTGGTCACCGT<br>GCCTTCTAGCAGCCTGGGCACCCAGACCTACATCTGCAACGTGAACCACAAG<br>CCCAGCAACACCAAGGTGGACAAGAAGGTGGAGCCCAAGAGCTGCGACAAAA<br>CTCACACATGCCCACCGTGCCCAGCACCTGAAGCTGCAGGGGGACCGTCAGT<br>CTTCCTCTTCCCCCCAAAACCCAAGGACACCCTCATGATCTCCCGGACCCCT<br>GAGGTCACATGCGTGGTGGTGGACGTGAGCCACGAAGACCCTGAGGTCAAGT<br>TCAACTGGTACGTGGACGGCGTGGAGGTGCATAATGCCAAGACAAAGCCGCG<br>GGAGGAGCAGTACAACAGCACGTACCGTGTGGTCAGCGTCCTCACCGTCCTG<br>CACCAGGACTGGCTGAATGGCAAGGAGTACAAGTGCAAGGTCTCCAACAAAG<br>CCCTCGGCGCCCCCATCGAGAAAACCATCTCCAAAGCCAAAGGGCAGCCCCG<br>AGAACCACAGGTGTGCACCCTGCCCCCATCCCGGGATGAGCTGACCAAGAAC<br>CAGGTCAGCCTCTCGTGCGCAGTCAAAGGCTTCTATCCCAGCGACATCGCCG<br>TGGAGTGGGAGAGCAATGGGCAGCCGGAGAACAACTACAAGACCACGCCTCC<br>CGTGCTGGACTCCGACGGCTCCTTCTTCCTCGTGAGCAAGCTCACCGTGGAC<br>AAGAGCAGGTGGCAGCAGGGGAACGTCTTCTCATGCTCCGTGATGCATGAGG<br>CTCTGCACAACCGCTTCACGCAGAAGAGCCTCTCCCTGTCTCCGGGTAAA | |
| CD3-CLC | CAGGCCGTCGTGACCCAGGAACCCAGCCTGACAGTGTCTCCTGGCGGCACCG<br>TGACCCTGACATGTGGCAGTTCTACAGGCGCCGTGACCACCAGCAACTACGC<br>CAACTGGGTGCAGGAAAAGCCCGGCCAGGCCTTCAGAGGACTGATCGGCGGC<br>ACCAACAAGAGAGCCCCTGGCACCCCTGCCAGATTCAGCGGATCTCTGCTGG<br>GAGGAAAGGCCGCCCTGACACTGTCTGGCGCCCAGCCAGAAGATGAGGCCGA<br>GTACTACTGCGCCCTGTGGTACAGCAACCTGTGGGTGTTCGGCGGAGGCACC<br>AAGCTGACAGTCCTAGGTCAACCCAAGGCTGCCCCCAGCGTGACCCTGTTCC<br>CCCCCAGCAGCGAGGAACTGCAGGCCAACAAGGCCACCCTGGTCTGCCTGAT<br>CAGCGACTTCTACCCAGGCGCCGTGACCGTGGCCTGGAAGGCCGACAGCAGC<br>CCCGTGAAGGCCGGCGTGGAGACCACCACCCCCAGCAAGCAGAGCAACAACA<br>AGTACGCCGCCAGCAGCTACCTGAGCCTGACCCCCGAGCAGTGGAAGAGCCA<br>CAGGTCCTACAGCTGCCAGGTGACCCACGAGGGCAGCACCGTGGAGAAAACC<br>GTGGCCCCCACCGAGTGCAGC | 267 |
| 16D5<br>[VHCH1]-CD3<br>[VHCH1-S100aA]-<br>Fcknob_PGLALA | GAGGTGCAATTGGTTGAATCTGGTGGTGGTCTGGTAAAACCGGGCGGTTCCC<br>TGCGTCTGAGCTGCGCGGCTTCCGGATTCACCTTCTCCAACGCGTGGATGAG<br>CTGGGTTCGCCAGGCCCCGGGCAAAGGCCTCGAGTGGGTTGGTCGTATCAAG<br>TCTAAAACTGACGGTGGCACCACGGATTACGCGGCTCCAGTTAAAGGTCGTT<br>TTACCATTTCCCGCGACGATAGCAAAAACACTCTGTATCTGCAGATGAACTC<br>TCTGAAAACTGAAGACACCGCAGTCTACTACTGTACTACCCCGTGGGAATGG<br>TCTTGGTACGATTATTGGGGCCAGGGCACGCTGGTTACGGTGTCTTCCGCTA<br>GCACAAAGGGCCCCTAGCGTGTTCCCTCTGGCCCCCAGCAGCAAGAGCACAAG<br>CGGCGGAACAGCCGCCCTGGGCTGCCTCGTGAAGGACTACTTCCCCGAGCCC<br>GTGACAGTGTCTTGGAACAGCGGAGCCCTGACAAGCGGCGTGCACACTTTCC<br>CTGCCGTGCTGCAGAGCAGCGGCCTGTACTCCCTGAGCAGCGTGGTCACCGT<br>GCCTAGCAGCAGCCTGGGCACCCAGACCTACATCTGCAACGTGAACCACAAG<br>CCCAGCAACACCAAAGTGGACAAGAAGGTGGAGCCCAAGAGCTGTGATGGCG<br>GAGGAGGGTCCGGAGGCGGAGGATCCGAGGTGCAGCTGCTGGAATCTGGCGG<br>CGGACTGGTGCAGCCTGGCGGATCTCTGAGACTGAGCTGTGCCGCCAGCGGC<br>TTCACCTTCAGCACCTACGCCATGAACTGGGTGCGCCAGGCCCCTGGCAAAG<br>GCCTGGAATGGGTGTCCCGGATCAGAAGCAAGTACAACAACTACGCCACCTA<br>CTACGCCGACAGCGTGAAGGGCCGGTTCACCATCAGCCGGGACGACAGCAAG<br>AACACCCTGTACCTGCAGATGAACAGCCTGCGGGCCGAGGACACCGCCGTGT<br>ACTATTGTGTGCGGCACGGCAACTTCGGCAACGCCTATGTGTCTTGGTTTGC<br>CTACTGGGGCCAGGGCACCCTCGTGACCGTGTCAAGCGCTAGTACCAAGGGC<br>CCCAGCGTGTTCCCCCTGGCACCCAGCAGCAAGAGCACATCTGGCGGAACAG<br>CCGCTCTGGGCTGTCTGGTGAAAGACTACTTCCCCGAGCCCGTGACCGTGTC<br>TTGGAACTCTGGCGCCCTGACCAGCGGCGTGCACACCTTTCCAGCCGTGCTG<br>CAGAGCAGCGGCCTGTACTCCCTGTCCTCCGTGGTCACCGTGCCCTCTAGCT<br>CCCTGGGAACACAGACATATATCTGTAATGTCAATCACAAGCCTTCCAACAC<br>CAAAGTCGATAAGAAAGTCGAGCCCAAGAGCTGCGACAAAACTCACACATGC<br>CCACCGTGCCCAGCACCTGAAGCTGCAGGGGGACCGTCAGTCTTCCTCTTCC<br>CCCCAAAACCCAAGGACACCCTCATGATCTCCCGGACCCCTGAGGTCACATG<br>CGTGGTGGTGGACGTGAGCCACGAAGACCCTGAGGTCAAGTTCAACTGGTAC<br>GTGGACGGCGTGGAGGTGCATAATGCCAAGACAAAGCCGCGGGAGGAGCAGT<br>ACAACAGCACGTACCGTGTGGTCAGCGTCCTCACCGTCCTGCACCAGGACTG<br>GCTGAATGGCAAGGAGTACAAGTGCAAGGTCTCCAACAAAGCCCTCGGCGCC<br>CCCATCGAGAAAACCATCTCCAAAGCCAAAGGGCAGCCCCGAGAACCACAGG<br>TGTACACCCTGCCCCATGCCGGGATGAGCTGACCAAGAACCAGGTCAGCCT<br>GTGGTGCCTGGTCAAAGGCTTCTATCCCAGCGACATCGCCGTGGAGTGGGAG<br>AGCAATGGGCAGCCGGAGAACAACTACAAGACCACGCCTCCCGTGCTGGACT<br>CCGACGGCTCCTTCTTCCTCTACAGCAAGCTCACCGTGGACAAGAGCAGGTG | 268 |

| Variant | Sequence | Seq ID No |
|---|---|---|
| | GCAGCAGGGGAACGTCTTCTCATGCTCCGTGATGCATGAGGCTCTGCACAAC CACTACACGCAGAAGAGCCTCTCCCTGTCTCCGGGTAAA | |
| 9D11 [VHCH1]-CD3 [VHCL-N100A]- Fcknob_PGLALA | CAGGTGCAATTGGTTCAATCTGGTGCTGAAGTAAAAAAACCGGGCGCTTCCG TTAAAGTGAGCTGCAAAGCATCCGGATACACCTTCACTTCCTATTACATGCA CTGGGTTCGTCAAGCCCGGGCCAGGGTCTGGAATGGATGGGCATCATTAAC CCAAGCGGTGGCCCTACCTCCTACGCGCAGAAATTCCAGGGTCGCGTCACGA TGACCCGTGACACTAGCACCTCTACCGTTTATATGGAGCTGTCCAGCCTGCG TTCTGAAGATACTGCAGTGTACTACTGTGCACGCGGTGACTTCGCTTGGCTG GACTATTGGGGTCAAGGCACCCTCGTAACGGTTTCTTCTGCTAGCACAAAGG GCCCCAGCGTGTTCCCTCTGGCCCCTAGCAGCAAGAGCACATCTGGCGGAAC AGCCGCCCTGGGCTGCCTCGTGAAGGACTACTTTCCCGAGCCTGTGACCGTG TCCTGGAACTCTGGCGCCCTGACAAGCGGCGTGCACACCTTTCCAGCCGTGC TGCAGAGCAGCGGCCTGTACTCTCTGAGCAGCGTGGTCACCGTGCCTAGCAG CAGCCTGGGCACCCAGACCTACATCTGCAACGTGAACCACAAGCCCAGCAAC ACCAAAGTGGACAAGAAGGTGGAGCCCAAGAGCTGTGATGGCGGAGGAGGT CCGGAGGCGGAGGATCCGAGGTGCAGCTGCTGGAATCTGGCGGCGGACTGGT GCAGCCTGGCGGATCTCTGAGACTGAGCTGTGCCGCCAGCGGCTTCACCTTC AGCACCTACGCCATGAACTGGGTGCGCCAGGCCCCTGGCAAAGGCCTGGAAT GGGTGTCCCGGATCAGAAGCAAGTACAACAACTACGCCACCTACTACGCCGA CAGCGTGAAGGGCCGGTTCACCATCAGCCGGGACGACAGCAAGAACACCCTG TACCTGCAGATGAACAGCCTGCGGGCCGAGGACACCGCCGTGTACTATTGTG TGCGGCACGGCAACTTCGGCGCCAGCTATGTGCTTGGTTGCCTACTGGGG CCAGGGCACCCTCGTGACCGTGTCAAGCGCTAGTGTGGCCGCTCCCTCCGTG TTTATCTTTCCCCCATCCGATGAACAGCTGAAAAGCGGCACCGCCTCCGTCG TGTGTCTGCTGAACAATTTTTACCCTAGGGAAGCTAAAGTGCAGTGGAAAGT GGATAACGCACTGCAGTCCGGCAACTCCCAGGAATCTGTGACAGAACAGGAC TCCAAGGACAGCACCTACTCCCTGTCCTCCACCCTGACACTGTCTAAGGCTG ATTATGAGAAACACAAAGTCTACGCCTGCGAAGTCACCCATCAGGGCCTGAG CTCGCCCGTCACAAAGAGCTTCAACAGGGGAGAGTGTGACAAGACCCACACC TGTCCCCCTTGTCCTGCCCCTGAAGCTGCTGGCGGCCCTTCTGTGTTCCTGT TCCCCCCAAAGCCCAAGGACACCCTGATGATCAGCCGGACCCCCGAAGTGAC CTGCGTGGTGGTGGATGTGTCCCACGAGGACCCTGAAGTGAAGTTCAATTGG TACGTGGACGGCGTGGAAGTGCACAACGCCAAGACAAAGCCGCGGGAGGAGC AGTACAACAGCACGTACCGTGTGGTCAGCGTCCTCACCGTCCTGCACCAGGA CTGGCTGAATGGCAAGGAGTACAAGTGCAAGGTCTCCAACAAAGCCCTCGGC GCCCCCATCGAGAAAACCATCTCCAAAGCCAAAGGGCAGCCCCGAGAACCAC AGGTGTACACCCTGCCCCCATGCCGGGATGAGCTGACCAAGAACCAGGTCAG CCTGTGGTGCCTGGTCAAAGGCTTCTATCCCAGCGACATCGCCGTGGAGTGG GAGAGCAATGGGCAGCCGGAGAACAACTACAAGACCACGCCTCCCGTGCTGG ACTCCGACGGCTCCTTCTTCCTCTACAGCAAGCTCACCGTGGACAAGAGCAG GTGGCAGCAGGGGAACGTCTTCTCATGCTCCGTGATGCATGAGGCTCTGCAC AACCACTACACGCAGAAGAGCCTCTCCCTGTCTCCGGGTAAA | 269 |
| 9D11-Fchole | CAGGTGCAATTGGTTCAATCTGGTGCTGAAGTAAAAAAACCGGGCGCTTCCG TTAAAGTGAGCTGCAAAGCATCCGGATACACCTTCACTTCCTATTACATGCA CTGGGTTCGTCAAGCCCGGGCCAGGGTCTGGAATGGATGGGCATCATTAAC CCAAGCGGTGGCCCTACCTCCTACGCGCAGAAATTCCAGGGTCGCGTCACGA TGACCCGTGACACTAGCACCTCTACCGTTTATATGGAGCTGTCCAGCCTGCG TTCTGAAGATACTGCAGTGTACTACTGTGCACGCGGTGACTTCGCTTGGCTG GACTATTGGGGTCAAGGCACCCTCGTAACGGTTTCTTCTGCTAGCACCAAGG GCCCCTCCGTGTTCCCCCTGGCCCCCAGCAGCAAGAGCACCAGCGGCGCCAC AGCCGCTCTGGGCTGCCTGGTCAAGGACTACTTCCCCGAGCCCGTGACCGTG TCCTGGAACAGCGGAGCCCTGACCTCCGGCGTGCACACCTTCCCCGCCGTGC TGCAGAGTTCTGGCCTGTATAGCCTGAGCAGCGTGGTCACCGTGCCTTCTAG CAGCCTGGGCACCCAGACCTACATCTGCAACGTGAACCACAAGCCCAGCAAC ACCAAGGTGGACAAGAAGGTGGAGCCCAAGAGCTGCGACAAAACTCACACAT GCCCACCGTGCCCAGCACCTGAAGCTGCAGGGGGACCGTCAGTCTTCCTCTT CCCCCCAAAACCCAAGGACACCCTCATGATCTCCCGGACCCCTGAGGTCACA TGCGTGGTGGTGGACGTGAGCCACGAAGACCCTGAGGTCAAGTTCAACTGGT ACGTGGACGGCGTGGAGGTGCATAATGCCAAGACAAAGCCGCGGGAGGAGCA GTACAACAGCACGTACCGTGTGGTCAGCGTCCTCACCGTCCTGCACCAGGAC TGGCTGAATGGCAAGGAGTACAAGTGCAAGGTCTCCAACAAAGCCCTCGGCG CCCCCATCGAGAAAACCATCTCCAAAGCCAAAGGGCAGCCCCGAGAACCACA GGTGTACACCCTGCCCCCATCCCGGGATGAGCTGACCAAGAACCAGGTCAGC CTCTCGTGCGCAGTCAAAGGCTTCTATCCCAGCGACATCGCCGTGGAGTGGG AGAGCAATGGGCAGCCGGAGAACAACTACAAGACCACGCCTCCCGTGCTGGA CTCCGACGGCTCCTTCTTCCTCGTGAGCAAGCTCACCGTGGACAAGAGCAGG TGGCAGCAGGGGAACGTCTTCTCATGCTCCGTGATGCATGAGGCTCTGCACA ACCACTACACGCAGAAGAGCCTCTCCCTGTCTCCGGGTAAA | 270 |
| 9D11_LC [N95Q] | GATATTGTTATGACTCAATCTCCACTGTCTCTGCCGGTGACTCCAGGCGAAC CGGCGAGCATTTCTTGCCGTTCCAGCCAGTCTCTGCTGCACTCCAACGGCTA CAACTATCTCGATTGGTACCTGCAAAAACCGGGTCAGAGCCCTCAGCTGCTG ATCTACCTGGGCTCTAACCGCGCTTCCGGTGTACCGGACCGTTTCAGCGGCT CTGGATCCGGCACCGATTTCACGTTGAAAATCAGCCGTGTTGAAGCAGAAGA | 271 |

| Variant | Sequence | Seq ID No |
|---|---|---|
| | CGTGGGCGTTTATTACTGTATGCAGGCAAGCATTATGCAGCGGACTTTTGGT<br>CAAGGCACCAAGGTCGAAATTAAACGTACGGTGGCTGCACCATCTGTCTTCA<br>TCTTCCCGCCATCTGATGAGCAGTTGAAATCTGGAACTGCCTCTGTTGTGTG<br>CCTGCTGAATAACTTCTATCCCAGAGAGGCCAAAGTACAGTGGAAGGTGGAT<br>AACGCCCTCCAATCGGGTAACTCCCAGGAGAGTGTCACAGAGCAGGACAGCA<br>AGGACAGCACCTACAGCCTCAGCAGCACCCTGACGCTGAGCAAAGCAGACTA<br>CGAGAAACACAAAGTCTACGCCTGCGAAGTCACCCATCAGGGCCTGAGCTCG<br>CCCGTCACAAAGAGCTTCAACAGGGGAGAGTGT | |
| CD3_VLCH1 | CAGGCCGTCGTGACCCAGGAACCCAGCCTGACAGTGTCTCCTGGCGGCACCG<br>TGACCCTGACATGTGGCAGTTCTACAGGCGCCGTGACCACCAGCAACTACGC<br>CAACTGGGTGCAGGAAAAGCCCGGCCAGGCCTTCAGAGGACTGATCGGCGGC<br>ACCAACAAGAGAGCCCCTGGCACCCCTGCCAGATTCAGCGGATCTCTGCTGG<br>GAGGAAAGGCCGCCCTGACACTGTCTGGCGCCCAGCCAGAAGATGAGGCCGA<br>GTACTACTGCGCCCTGTGGTACAGCAACCTGTGGGTGTTCGGCGGAGGCACC<br>AAGCTGACAGTGCTGAGCAGCGCTTCCACCAAAGGCCCTTCCGTGTTTCCTC<br>TGGCTCCTAGCTCCAAGTCCACCTCTGGAGGCACCGCTGCTCTCGGATGCCT<br>CGTGAAGGATTATTTTCCTGAGCCTGTGACAGTGTCCTGGAATAGCGGAGCA<br>CTGACCTCTGGAGTGCATACTTTCCCCGCTGTGCTGCAGTCCTCTGGACTGT<br>ACAGCCTGAGCAGCGTGGTGACAGTGCCCAGCAGCAGCCTGGGCACCCAGAC<br>CTACATCTGCAACGTGAACCACAAGCCCAGCAACACCAAGGTGGACAAGAAG<br>GTGGAACCCAAGTCTTGT | 272 |
| 9D11<br>[VHCH1]-CD3<br>[VHCH1-S100aA]-<br>Fcknob_PGLALA | CAGGTGCAATTGGTTCAATCTGGTGCTGAAGTAAAAAAACCGGGGCGCTTCCG<br>TTAAAGTGAGCTGCAAAGCATCCGGATACACCTTCACTTCCTATTACATGCA<br>CTGGGTTCGTCAAGCCCGGGCCAGGGTCTGGAATGGATGGGCATCATTAAC<br>CCAAGCGGTGGCCCTACCTCCTACGCGCAGAAATTCCAGGGTCGCGTCACGA<br>TGACCCGTGACACTAGCACCTCTACCGTTTATATGGAGCTGTCCAGCCTGCG<br>TTCTGAAGATACTGCAGTGTACTACTGTGCACGCGGTGACTTCGCTTGGCTG<br>GACTATTGGGGTCAAGGCACCCTCGTAACGGTTTCTTCTGCTAGCACAAAGG<br>GCCCCAGCGTGTTCCCTCTGGCCCCTAGCAGCAAGAGCACATCGGCGGAAC<br>AGCCGCCCTGGGCTGCCTCGTGAAGGACTACTTTCCCGAGCCTGTGACCGTG<br>TCCTGGAACTCTGGCGCCCTGACAAGCGGCGTGCACACCTTTCCAGCCGTGC<br>TGCAGAGCAGCGGCCTGTACTCTCTGAGCAGCGTGGTCACCGTGCCTAGCAG<br>CAGCCTGGGCACCCAGACCTACATCTGCAACGTGAACCACAAGCCCAGCAAC<br>ACCAAAGTGGACAAGAAGGTGGAGCCCAAGAGCTGTGATGGCGGAGGAGGGT<br>CCGGAGGCGGAGGATCCGAGGTGCAGCTGCTGGAATCTGGCGGCGGACTGGT<br>GCAGCCTGGCGGATCTCTGAGACTGAGCTGTGCCGCCAGCGGCTTCACCTTC<br>AGCACCTACGCCATGAACTGGGTGCGCCAGGCCCCTGGCAAAGGCCTGGAAT<br>GGGTGTCCCGGATCAGAAGCAAGTACAACAACTACGCCACCTACTACGCCGA<br>CAGCGTGAAGGGCCGGTTCACCATCAGCCGGGACGACAGCAAGAACACCCTG<br>TACCTGCAGATGAACAGCCTGCGGGCCGAGGACACCGCCGTGTACTATTGTG<br>TGCGGCACGGCAACTTCGGCAACGCCTATGTGTCTTGGTTTGCCTACTGGGG<br>CCAGGGCACCCTCGTGACCGTGTCAAGCGCTAGTGTGGCCGCTCCCTCCGTG<br>TTTATCTTTCCCCCATCCGATGAACAGCTGAAAAGCGGCACCGCCTCCGTCG<br>TGTGTCTGCTGAACAATTTTTACCCTAGGGAAGCTAAAGTGCAGTGGAAAGT<br>GGATAACGCACTGCAGTCCGGCAACTCCCAGGAATCTGTGACAGAACAGGAC<br>TCCAAGGACAGCACCTACTCCCTGTCCTCCACCCTGACACTGTCTAAGGCTG<br>ATTATGAGAAACACAAAGTCTACGCCTGCGAAGTCACCCATCAGGGCCTGAG<br>CTCGCCCGTCACAAAGAGCTTCAACAGGGGAGAGTGTGACAAGACCCACACC<br>TGTCCCCCTTGTCCTGCCCCTGAAGCTGCTGGCGGCCCTTCTGTGTTCCTGT<br>TCCCCCCAAAGCCCAAGGACACCCTGATGATCAGCCGGACCCCCGAAGTGAC<br>CTGCGTGGTGGTGGATGTGTCCCACGAGGACCCTGAAGTGAAGTTCAATTGG<br>TACGTGGACGGCGTGGAAGTGCACAACGCCAAGACAAAGCCGCGGGAGGAGC<br>AGTACAACAGCACGTACCGTGTGGTCAGCGTCCTCACCGTCCTGCACCAGGA<br>CTGGCTGAATGGCAAGGAGTACAAGTGCAAGGTCTCCAACAAAGCCCTCGGC<br>GCCCCCATCGAGAAAACCATCTCCAAAGCCAAGGGCAGCCCCGAGAACCAC<br>AGGTGTACACCCTGCCCCCATGCCGGGATGAGCTGACCAAGAACCAGGTCAG<br>CCTGTGGTGCCTGGTCAAAGGCTTCTATCCCAGCGACATCGCCGTGGAGTGG<br>GAGAGCAATGGGCAGCCGGAGAACAACTACAAGACCACGCCTCCCGTGCTGA<br>CTCCGACGGCTCCTTCTTCCTCTACAGCAAGCTCACCGTGGACAAGAGCAG<br>GTGGCAGCAGGGGAACGTCTTCTCATGCTCCGTGATGCATGAGGCTCTGCAC<br>AACCACTACACGCAGAAGAGCCTCTCCCTGTCTCCGGGTAAA | 273 |

| Name | Sequence | Seq ID No |
|---|---|---|
| 16D5<br>variant<br>W96Y/<br>D52E | GAGGTGCAATTGGTGGAAAGCGGAGGCGGCCTCGTGAAGCCTGGCGGATCTC<br>TGAGACTGAGCTGTGCCGCCAGCGGCTTCACCTTCAGCAACGCCTGGATGAG<br>CTGGGTGCGCCAGGCCCCTGGAAAAGGACTCGAGTGGGTGGGACGGATCAAG<br>AGCAAGACCGAGGGCGGCACCACCGACTATGCCGCCCCTGTGAAGGGCCGGT | 415 |

| Name | Sequence | Seq ID No |
|---|---|---|
| VH | TCACCATCAGCAGGGACGACAGCAAGAACACCCTGTACCTGCAGATGAACAG CCTGAAAACCGAGGACACCGCCGTGTACTACTGCACCACCCCCTACGAGTGG TCTTGGTACGACTACTGGGGCCAGGGCACCCTCGTGACCGTGTCATCT | |
| W96Y/ D52E-_CD3-VHCH1_Fc-knob_PGLALA pETR14945 | GAGGTGCAATTGGTGGAAAGCGGAGGCGGCCTCGTGAAGCCTGGCGGATCTC TGAGACTGAGCTGTGCCGCCAGCGGCTTCACCTTCAGCAACGCCTGGATGAG CTGGGTGCGCCAGGCCCCTGGAAAAGGACTCGAGTGGGTGGGACGGATCAAG AGCAAGACCGAGGGCGGCACCACCGACTATGCCGCCCCTGTGAAGGGCCGGT TCACCATCAGCAGGGACGACAGCAAGAACACCCTGTACCTGCAGATGAACAG CCTGAAAACCGAGGACACCGCCGTGTACTACTGCACCACCCCCTACGAGTGG TCTTGGTACGACTACTGGGGCCAGGGCACCCTCGTGACCGTGTCATCTGCTA GCACAAAGGGCCCTAGCGTGTTCCCTCTGGCCCCCAGCAGCAAGAGCACAAG CGGCGGAACAGCCGCCCTGGGCTGCCTCGTGAAGGACTACTTCCCCGAGCCC GTGACAGTGTCTTGGAACAGCGGAGCCCTGACAAGCGGCGTGCACACCTTCC CTGCCGTGCTGCAGAGCAGC GGCCTGTACTCCCTGAGCAGCGTGGTCACCGTGCCTAGCAGCAGCCTGGGCA CCCAGACCTACATCTGCAACGTGAACCACAAGCCCAGCAACACCAAAGTGGA CAAGAAGGTGGAGCCCAAGAGCTGTGATGGCGGAGGAGGGTCCGGAGGCGGA GGATCCGAGGTGCAGCTGCTGGAATCTGGCGGCGGAACTGGTGCAGCCTGGCG GATCTCTGAGACTGAGCTGTGCCGCCAGCGGCTTCACCTTCAGCACCTACGC CATGAACTGGGTGCGCCAGGCCCCTGGCAAAGGCCTGGAATGGGTGTCCCGG ATCAGAAGCAAGTACAACAACTACGCCACCTACTACGCCGACAGCGTGAAGG GCCGGTTCACCATCAGCCGGGACGACAGCAAGAACACCCTGTACCTGCAGAT GAACAGCCTGCGGGCCGAGGACACCGCCGTGTACTATTGTGTGCGGCACGGC AACTTCGGCAACAGCTATGTGTCTTGGTTTGCCTACTGGGGCCAGGGCACCC TCGTGACCGTGTCAAGCGCT AGTACCAAGGGCCCCAGCGTGTTCCCCCTGGCACCCAGCAGCAAGAGCACAT CTGGCGGAACAGCCGCTCTGGGCTGTCTGGTGAAAGACTACTTCCCCGAGCC CGTGACCGTGTCTTGGAACTCTGGCGCCCTGACCAGCGGCGTGCACACCTTT CCAGCCGTGCTGCAGAGCAGCGGCCTGTACTCCCTGTCCTCCGTGGTCACCG TGCCCTCTAGCTCCCTGGGAACACAGACATATATCTGTAATGTCAATCACAA GCCTTCCAACACCAAAGTCGATAAGAAAGTCGAGCCCAAGAGCTGCGACAAA ACTCACACATGCCCACCGTGCCCAGCACCTGAAGCTGCAGGGGGACCGTCAG TCTTCCTCTTCCCCCCAAAACCCAAGGACACCCTCATGATCTCCCGGACCCC TGAGGTCACATGCGTGGTGGTGGACGTGAGCCACGAAGACCCTGAGGTCAAG TTCAACTGGTACGTGGACGGCGTGGAGGTGCATAATGCCAAGACAAAGCCGC GGGAGGAGCAGTACAACAGC ACGTACCGTGTGGTCAGCGTCCTCACCGTCCTGCACCAGGACTGGCTGAATG GCAAGGAGTACAAGTGCAAGGTCTCCAACAAAGCCCTCGGCGCCCCCATCGA GAAAACCATCTCCAAAGCCAAAGGGCAGCCCCGAGAACCACAGGTGTACACC CTGCCCCCATGCCGGGATGAGCTGACCAAGAACCAGGTCAGCCTGTGGTGCC TGGTCAAAGGCTTCTATCCCAGCGACATCGCCGTGGAGTGGGAGAGCAATGG GCAGCCGGAGAACAACTACAAGACCACGCCTCCCGTGCTGGACTCCGACGGC TCCTTCTTCCTCTACAGCAAGCTCACCGTGGACAAGAGCAGGTGGCAGCAGG GGAACGTCTTCTCATGCTCCGTGATGCATGAGGCTCTGCACAACCACTACAC GCAGAAGAGCCTCTCCCTGTCTCCGGGTAAA | 416 |
| W96Y/ D52E-_Fc-hole_PGLALA_HYRF pETR14946 | GAGGTGCAATTGGTGGAAAGCGGAGGCGGCCTCGTGAAGCCTGGCGGATCTC TGAGACTGAGCTGTGCCGCCAGCGGCTTCACCTTCAGCAACGCCTGGATGAG CTGGGTGCGCCAGGCCCCTGGAAAAGGACTCGAGTGGGTGGGACGGATCAAG AGCAAGACCGAGGGCGGCACCACCGACTATGCCGCCCCTGTGAAGGGCCGGT TCACCATCAGCAGGGACGACAGCAAGAACACCCTGTACCTGCAGATGAACAG CCTGAAAACCGAGGACACCGCCGTGTACTACTGCACCACCCCCTACGAGTGG TCTTGGTACGACTACTGGGGCCAGGGCACCCTCGTGACCGTGTCATCTGCTA GCACCAAGGGCCCCTCCGTGTTCCCCCTGGCCCCCAGCAGCAAGAGCACCAG CGGCGGCACAGCCGCTCTGGGCTGCCTGGTCAAGGACTACTTCCCCGAGCCC GTGACCGTGTCCTGGAACAGCGGAGCCCTGACCTCCGGCGTGCACACCTTCC CCGCCGTGCTGCAGAGTTCT GGCCTGTATAGCCTGAGCAGCGTGGTCACCGTGCCTTCTAGCAGCCTGGGCA CCCAGACCTACATCTGCAACGTGAACCACAAGCCCAGCAACACCAAGGTGGA CAAGAAGGTGGAGCCCAAGAGCTGCGACAAAACTCACACATGCCCACCGTGC CCAGCACCTGAAGCTGCAGGGGACCGTCAGTCTTCCTCTTCCCCCCAAAAC CCAAGGACACCCTCATGATCTCCCGGACCCCTGAGGTCACATGCGTGGTGGT GGACGTGAGCCACGAAGACCCTGAGGTCAAGTTCAACTGGTACGTGGACGGC GTGGAGGTGCATAATGCCAAGACAAAGCCGCGGGAGGAGCAGTACAACAGCA CGTACCGTGTGGTCAGCGTCCTCACCGTCCTGCACCAGGACTGGCTGAATGG CAAGGAGTACAAGTGCAAGGTCTCCAACAAAGCCCTCGGCGCCCCCATCGAG AAAACCATCTCCAAAGCCAAAGGGCAGCCCCGAGAACCACAGGTGTGCACCC TGCCCCCATCCCGGGATGAG CTGACCAAGAACCAGGTCAGCCTCTCGTGCGCAGTCAAAGGCTTCTATCCCA GCGACATCGCCGTGGAGTGGGAGAGCAATGGGCAGCCGGAGAACAACTACAA GACCACGCCTCCCGTGCTGGACTCCGACGGCTCCTTCTTCCTCGTGAGCAAG CTCACCGTGGACAAGAGCAGGTGGCAGCAGGGGAACGTCTTCTCATGCTCCG TGATGCATGAGGCTCTGCACAACCGCTTCACGCAGAAGAGCCTCTCCCTGTC TCCGGGTAAA | 417 |

| Name | Sequence | Seq ID No |
|---|---|---|
| 14B1 VH | GAGGTGCAATTGTTGGAGTCTGGGGGAGGCTTGGTACAGCCTGGGGGGTCCC<br>TGAGACTCTCCTGTGCAGCCTCCGGATTCACCTTTAGCAGTTATGCCATGAG<br>CTGGGTCCGCCAGGCTCCAGGGAAGGGGCTGGAGTGGGTCTCAGCTATTAGT<br>GGTAGTGGTGGTAGCACATACTACGCAGACTCCGTGAAGGGCCGGTTCACCA<br>TCTCCAGAGACAATTCCAAGAACACGCTGTATCTGCAGATGAACAGCCTGAG<br>AGCCGAGGACACGGCCGTATATTACTGTGCGCGTGGTGACTACCGTTACCGT<br>TACTTCGACTACTGGGGCCAAGGAACCCTGGTCACCGTCTCGAGT | 418 |
| 14B1 VL | TCTTCTGAACTGACTCAAGATCCAGCTGTTAGCGTGGCTCTGGGTCAGACTG<br>TACGTATCACCTGCCAAGGCGATTCTCTGCGCTCCTACTACGCAAGCTGGTA<br>CCAGCAGAAACCGGGTCAGGCCCCAGTTCTGGTGATTTACGGCAAAAACAAC<br>CGTCCGTCTGGGATCCCGGACCGTTTCTCCGGCAGCTCTTCCGGTAACACGG<br>CGAGCCTCACCATCACTGGCGCTCAAGCAGAAGACGAGGCCGACTATTACTG<br>TAACTCTCGGGAAAGCCCACCAACCGGCCTGGTTGTCTTCGGTGGCGGTACC<br>AAGCTGACCGTCCTA | 419 |
| 14B1<br>[EE]_CD3<br>[VLCH1]_Fc-knob_PGLALA<br>pETR14976 | GAGGTGCAATTGTTGGAGTCTGGGGGAGGCTTGGTACAGCCTGGGGGGTCCC<br>TGAGACTCTCCTGTGCAGCCTCCGGATTCACCTTTAGCAGTTATGCCATGAG<br>CTGGGTCCGCCAGGCTCCAGGGAAGGGGCTGGAGTGGGTCTCAGCTATTAGT<br>GGTAGTGGTGGTAGCACATACTACGCAGACTCCGTGAAGGGCCGGTTCACCA<br>TCTCCAGAGACAATTCCAAGAACACGCTGTATCTGCAGATGAACAGCCTGAG<br>AGCCGAGGACACGGCCGTATATTACTGTGCGCGTGGTGACTACCGTTACCGT<br>TACTTCGACTACTGGGGCCAAGGAACCCTGGTCACCGTCTCGAGTGCTAGCA<br>CCAAGGGCCCCTCCGTGTTTCCTCTGGCCCCTTCCAGCAAGTCCACCTCTGG<br>CGGAACTGCCGCTCTGGGCTGCCTGGTGGAAGATTACTTCCCCGAGCCCGTG<br>ACCGTGTCCTGGAATTCTGGCGCTCTGACCTCCGGCGTGCACACCTTTCCAG<br>CTGTGCTGCAGTCCTCCGGCCTGTACTCCCTGTCCGTCGTGACAGTGCC<br>CTCCAGCTCTCTGGGCACCCAGACCTACATCTGCAACGTGAACCACAAGCCC<br>TCCAACACCAAGGTGGACGAGAAGGTGGAACCCAAGTCCTGCGACGGTGGCG<br>GAGGTTCCGGAGGCGGAGGATCCCAGGCTGTCGTGACCCAGGAACCCTCCCT<br>GACAGTGTCTCCTGGCGGCACCGTGACCCTGACCTGTGGATCTTCTACCGGC<br>GCTGTGACCACCTCCAACTACGCCAATTGGGTGCAGGAAAAGCCCGGCCAGG<br>CCTTCAGAGGACTGATCGGCGGCACCAACAAGAGAGCCCCTGGCACCCCTGC<br>CAGATTCTCCGGTTCTCTGCTGGGCGGCAAGGCTGCCCTGACTCTGTCTGGT<br>GCTCAGCCTGAGGACGAGGCCGAGTACTACTGCGCCCTGTGGTACTCCAACC<br>TGTGGGTGTTCGGCGGAGGCACCAAGCTGACCGTGCTGTCCAGCGCTTCCAC<br>CAAGGGACCCAGTGTGTTCCCCCTGGCCCCCAGCTCCAAGTCTACATCCGGT<br>GGCACAGCTGCCCTGGGATGTCTCGTGAAGGACTACTTTCCTGAGCCTGTGA<br>CAGTGTCTTGGAACAGCGGAGCCCTGACCAGCGGAGTGCACACCATTCCCTG<br>CAGTGTCTGCAGAGCAGCGGCCTGTATAGCCTGAGCAGCGTCGTGACCGTGCCT<br>TCCTCTAGCCTGGGAACACAGACATATATCTGTAATGTGAATCATAAGCCCA<br>GTAATACCAAAGTGGATAAGAAAGTGGAACCTAAGAGCTGCGATAAGACCCA<br>CACCTGTCCCCCCTGCCCTGCTCCTGAAGCTGCTGGTGGCCCTAGCGTGTTC<br>CTGTTCCCCCCAAAGCCCAAGGACACCCTGATGATCTCCCGGACCCCCGAAG<br>TGACCTGCGTGGTGGTGGATGTGTCCCACGAGGACCCTGAAGTGAAGTTCAA<br>TTGGTACGTGGACGGCGTGGAAGTGCACAACGCCAAGACCAAGCCTAGAGAG<br>GAACAGTACAACTCCACCTACCGGGTGGTGTCCGTGCTGACAGTGCTGCACC<br>AGGACTGGCTGAACGGCAAAGAGTACAAGTGCAAGGTGTCCAACAAGGCCCT<br>GGGCGCTCCCATCGAAAAGACCATCTCCAAGGCCAAGGGCCAGCCCCGGGAA<br>CCCCAGGTGTACACCCTGCCCCCATGCCGGGATGAGCTGACCAAGAACCAGG<br>TCAGCCTGTGGTGCCTGGTCAAAGGCTTCTATCCCAGCGACATCGCCGTGGA<br>GTGGGAGAGCAATGGGCAGCCGGAGAACAACTACAAGACCACGCCTCCCGTG<br>CTGGACTCCGACGGCTCCTTCTTCCTCTACAGCAAGCTCACCGTGGACAAGA<br>GCAGGTGGCAGCAGGGGAACGTCTTCTCATGCTCCGTGATGCATGAGGCTCT<br>GCACAACCACTACACGCAGAAGAGCCTCTCCCTGTCTCCGGGTAAA | 420 |
| 14B1<br>[EE]_Fc-hole_PGLALA<br>pETR14977 | GAGGTGCAATTGTTGGAGTCTGGGGGAGGCTTGGTACAGCCTGGGGGGTCCC<br>TGAGACTCTCCTGTGCAGCCTCCGGATTCACCTTTAGCAGTTATGCCATGAG<br>CTGGGTCCGCCAGGCTCCAGGGAAGGGGCTGGAGTGGGTCTCAGCTATTAGT<br>GGTAGTGGTGGTAGCACATACTACGCAGACTCCGTGAAGGGCCGGTTCACCA<br>TCTCCAGAGACAATTCCAAGAACACGCTGTATCTGCAGATGAACAGCCTGAG<br>AGCCGAGGACACGGCCGTATATTACTGTGCGCGTGGTGACTACCGTTACCGT<br>TACTTCGACTACTGGGGCCAAGGAACCCTGGTCACCGTCTCGAGTGCTAGCA<br>CCAAGGGCCCCTCCGTGTTCCCCCTGGCCCCCAGCAGCAAGAGCACCAGCGG<br>CGGCACAGCCGCTCTGGGCTGCCTGGTCGAGGACTACTTCCCCGAGCCCGTG<br>ACCGTGTCCTGGAACAGCGGAGCCCTGACCTCCGGCGTGCACACCTTCCCCG<br>CCGTGCTGCAGAGTTCTGGCCTGTATAGCCTGAGCAGCGTGGTCACCGTGCC<br>TTCTAGCAGCCTGGGCACCCAGACCTACATCTGCAACGTGAACCACAAGCCC<br>AGCAACACCAAGGTGGACGAGAAGGTGGAGCCCAAGAGCTGCGACAAAACTC<br>ACACATGCCCACCGTGCCCAGCACCTGAAGCTGCAGGGGGACCGTCAGTCTT<br>CCTCTTCCCCCCAAAACCCAAGGACACCCTCATGATCTCCCGGACCCCTGAG<br>GTCACATGCGTGGTGGTGGACGTGAGCCACGAAGACCCTGAGGTCAAGTTCA<br>ACTGGTACGTGGACGGCGTGGAGGTGCATAATGCCAAGACAAAGCCGCGGGA<br>GGAGCAGTACAACAGCACGTACCGTGTGGTCAGCGTCCTCACCGTCCTGCAC<br>CAGGACTGGCTGAATGGCAAGGAGTACAAGTGCAAGGTCTCCAACAAAGCCC<br>TCGGCGCCCCCATCGAGAAAACCATCTCCAAAGCCAAAGGGCAGCCCCGAGA | 421 |

| Name | Sequence | Seq ID No |
|---|---|---|
| | ACCACAGGTGTGCACCCTGCCCCCATCCCGGGATGAGCTGACCAAGAACCAG<br>GTCAGCCTCTCGTGCGCAGTCAAAGGCTTCTATCCCAGCGACATCGCCGTGG<br>AGTGGGAGAGCAATGGGCAGCCGGAGAACAACTACAAGACCACGCCTCCCGT<br>GCTGGACTCCGACGGCTCCTTCTTCCTCGTGAGCAAGCTCACCGTGGACAAG<br>AGCAGGTGGCAGCAGGGGAACGTCTTCTCATGCTCCGTGATGCATGAGGCTC<br>TGCACAACCACTACACGCAGAAGAGCCTCTCCCTGTCTCCGGGTAAA | |
| 14B1 LC [KK] Constant lambda pETR14979 | TCTTCTGAACTGACTCAAGATCCAGCTGTTAGCGTGGCTCTGGGTCAGACTG<br>TACGTATCACCTGCCAAGGCGATTCTCTGCGCTCCTACTACGCAAGCTGGTA<br>CCAGCAGAAACCGGGTCAGGCCCCAGTTCTGGTGATTTACGGCAAAAACAAC<br>CGTCCGTCTGGGATCCCGGACCGTTTCTCCGGCAGCTCTTCCGGTAACACGG<br>CGAGCCTCACCATCACTGGCGCTCAAGCAGAAGACGAGGCCGACTATTACTG<br>TAACTCTCGGGAAAGCCCACCAACCGGCCTGGTTGTCTTCGGTGGCGGTACC<br>AAGCTGACCGTCCTAGGTCAACCCAAGGCTGCCCCCAGCGTGACCCTGTTCC<br>CCCCCAGCAGCAAGAAACTGCAGGCCAACAAGGCCACCCTGGTCTGCCTGAT<br>CAGCGACTTCTACCCAGGCGCCGTGACCGTGGCCTGGAAGGCCGACAGCAGC<br>CCCGTGAAGGCCGGCGTGGAGACCACCACCCCCAGCAAGCAGAGCAACAACA<br>AGTACGCCGCCAGCAGCTACCTGAGCCTGACCCCCGAGCAGTGGAAGAGCCA<br>CAGGTCCTACAGCTGCCAGGTGACCCACGAGGGCAGCACCGTGGAGAAAACC<br>GTGGCCCCCACCGAGTGCAGC | 422 |
| 9C7 VH | CAGGTGCAATTGGTTCAATCTGGTGCTGAAGTAAAAAAACCGGGCGCTTCCG<br>TTAAAGTGAGCTGCAAAGCATCCGGATACACCTTCACTTCCTATTACATGCA<br>CTGGGTTCGTCAAGCCCCGGGCCAGGGTCTGGAATGGATGGGCATCATTAAC<br>CCAAGCGGTGGCTCTACCTCCTACGCGCAGAAATTCCAGGGTCGCGTCACGA<br>TGACCCGTGACACTAGCACCTCTACCGTTTATATGGAGCTGTCCAGCCTGCG<br>TTCTGAAGATACTGCAGTGTACTACTGTGCACGCGGTGACTGGTCTTACTAC<br>ATGGACTATTGGGGTCAAGGCACCCTCGTAACGGTTTCTTCT | 423 |
| 9C7 VL | GATATTGTTATGACTCAATCTCCACTGTCTCTGCCGGTGACTCCAGGCGAAC<br>CGGCGAGCATTTCTTGCCGTTCCAGCCAGTCTCTGCTGCACTCCAACGGCTA<br>CAACTATCTCGATTGGTACCTGCAAAAACCGGGTCAGAGCCCTCAGCTGCTG<br>ATCTACCTGGGCTCTAACCGCGCTTCCGGTGTACCGGACCGTTTCAGCGGCT<br>CTGGATCCGGCACCGATTTCACGTTGAAAATCAGCCGTGTTGAAGCAGAAGA<br>CGTGGGCGTTTATTACTGTATGCAGGCACGGCAGACCCCAACTTTTGGTCAA<br>GGCACCAAGGTCGAAATTAAA | 424 |
| 9C7[EE]_CD3 [VLCH1]_Fcknob PGLALA pETR14974 | CAGGTGCAATTGGTTCAATCTGGTGCTGAAGTAAAAAAACCGGGCGCTTCCG<br>TTAAAGTGAGCTGCAAAGCATCCGGATACACCTTCACTTCCTATTACATGCA<br>CTGGGTTCGTCAAGCCCCGGGCCAGGGTCTGGAATGGATGGGCATCATTAAC<br>CCAAGCGGTGGCTCTACCTCCTACGCGCAGAAATTCCAGGGTCGCGTCACGA<br>TGACCCGTGACACTAGCACCTCTACCGTTTATATGGAGCTGTCCAGCCTGCG<br>TTCTGAAGATACTGCAGTGTACTACTGTGCACGCGGTGACTGGTCTTACTAC<br>ATGGACTATTGGGGTCAAGGCACCCTCGTAACGGTTTCTTCTGCTAGCACCA<br>AGGGCCCCTCCGTGTTTCCTCTGGCCCCTTCCAGCAAGTCCACCTCTGGCGG<br>AACTGCCGCTCTGGGCTGCCTGGTGAAGGATTACTTCCCCGAGCCCGTGACC<br>GTGTCCTGGAATTCTGGCGCTCTGACCTCCGGCGTGCACACCTTTCCAGCTG<br>TGCTGCAGTCCTCCGGCCTGTACTCCCTGTCCTCCGTCGTGACAGTGCCCTC<br>CAGCTCTCTGGGCACCCAGACCTACATCTGCAACGTGAACCACAAGCCCTCC<br>AACACCAAGGTGGACGAGAAGGTGGAACCCAAGTCCTGCGACGGTGGCGGAG<br>GTTCCGGAGGCGGAGGATCCCAGGCTGTCGTGACCCAGGAACCCTCCCTGAC<br>AGTGTCTCCTGGCGGCACCGTGACCCTGACCTGTGGATCTTCTACCGGCGCT<br>GTGACCACCTCCAACTACGCCAATTGGGTGCAGGAAAAGCCCGGCCAGGCCT<br>TCAGAGGACTGATCGGCGGCACCAACAAGAGAGCCCCTGGCACCCCTGCCAG<br>ATTCTCCGGTTCTCTGCTGGGCGGCAAGGCTGCCCTGACTCTGTCTGGTGCT<br>CAGCCTGAGGACGAGGCCGAGTACTACTGCGCCCTGTGGTACTCCAACCTGT<br>GGGTGTTCGGCGGAGGCACCAAGCTGACCGTGCTGTCCAGCGCTTCCACCAA<br>GGGACCCAGTGTGTTCCCCCTGGCCCCCAGCTCCAAGTCTACATCCGGTGGC<br>ACAGCTGCCCTGGGATGTCTCGTGAAGGACTACTTTCCTGAGCCTGTGACAG<br>TGTCTTGGAACAGCGGAGCCCTGACCAGCGGAGTGCACACATTCCCTGCAGT<br>GCTGCAGAGCAGCGGCCTGTATAGCCTGAGCAGCGTCGTGACCGTGCCTTCC<br>TCTAGCCTGGGAACACAGACATATATCTGTAATGTGAATCATAAGCCCAGTA<br>ATACCAAAGTGGATAAGAAAGTGGAACCTAAGAGCTGCGATAAGACCCACAC<br>CTGTCCCCCCTGCCCTGCTCCTGAAGCTGCTGGTGGCCCTAGCGTGTTCCTG<br>TTCCCCCCAAAGCCCAAGGACACCCTGATGATCTCCCGGACCCCCGAAGTGA<br>CCTGCGTGGTGGTGGATGTGTCCCACGAGGACCCTGAAGTGAAGTTCAATTG<br>GTACGTGGACGGCGTGGAAGTGCACAACGCCAAGACCAAGCCTAGAGAGGAA<br>CAGTACAACTCCACCTACCGGGTGGTGTCCGTGCTGACAGTGCTGCACCAGG<br>ACTGGCTGAACGGCAAAGAGTACAAGTGCAAGGTGTCCAACAAGGCCCTGGG<br>CGCTCCCATCGAAAAGACCATCTCCAAGGCCAAGGGCCAGCCCCGGGAACCC<br>CAGGTGTACACCCTGCCCCCATGCCGGGATGAGCTGACCAAGAACCAGGTCA<br>GCCTGTGGTGCCTGGTCAAAGGCTTCTATCCCAGCGACATCGCCGTGGAGTG<br>GGAGAGCAATGGGCAGCCGGAGAACAACTACAAGACCACGCCTCCCGTGCTG<br>GACTCCGACGGCTCCTTCTTCCTCTACAGCAAGCTCACCGTGGACAAGAGCA<br>GGTGGCAGCAGGGGAACGTCTTCTCATGCTCCGTGATGCATGAGGCTCTGCA<br>CAACCACTACACGCAGAAGAGCCTCTCCCTGTCTCCGGGTAAA | 425 |

| Name | Sequence | Seq ID No |
|---|---|---|
| 9C7[EE]_Fc-hole_PGLALA pETR14975 | CAGGTGCAATTGGTTCAATCTGGTGCTGAAGTAAAAAAACCGGGCGCTTCCG TTAAAGTGAGCTGCAAAGCATCCGGATACACCTTCACTTCCTATTACATGCA CTGGGTTCGTCAAGCCCGGGCCAGGGTCTGGAATGGATGGGCATCATTAAC CCAAGCGGTGGCTCTACCTCCTACGCGCAGAAATTCCAGGGTCGCGTCACGA TGACCCGTGACACTAGCACCTCTACCGTTTATATGGAGCTGTCCAGCCTGCG TTCTGAAGATACTGCAGTGTACTACTGTGCACGCGGTGACTGGTCTTACTAC ATGGACTATTGGGGTCAAGGCACCCTCGTAACGGTTTCTTCTGCTAGCACCA AGGGCCCCTCCGTGTTCCCCCTGGCCCCCAGCAGCAAGAGCACCAGCGGCGG CACAGCCGCTCTGGGCTGCCTGGTCGAGGACTACTTCCCCGAGCCCGTGACC GTGTCCTGGAACAGCGGGAGCCCTGACCTCCGGCGTGCACACCTTCCCCGCCG TGCTGCAGAGTTCTGGCCTGTATAGCCTGAGCAGCGTGGTCACCGTGCCTTC TAGCAGCCTGGGCACCCAGACCTACATCTGCAACGTGAACCACAAGCCCAGC AACACCAAGGTGGACGAGAAGGTGGAGCCCAAGAGCTGCGACAAAACTCACA CATGCCCACCGTGCCCAGCACCTGAAGCTGCAGGGGGACCGTCAGTCTTCCT CTTCCCCCCAAAACCCAAGGACACCCTCATGATCTCCCGGACCCCTGAGGTC ACATGCGTGGTGGTGGACGTGAGCCACGAAGCCCTGAGGTCAAGTTCAACT GGTACGTGGACGGCGTGGAGGTGCATAATGCCAAGACAAAGCCGCGGGAGGA GCAGTACAACAGCACGTACCGTGTGGTCAGCGTCCTCACCGTCCTGCACCAG GACTGGCTGAATGGCAAGGAGTACAAGTGCAAGGTCTCCAACAAAGCCCTCG GCGCCCCCATCGAGAAAACCATCTCCAAAGCCAAAGGGCAGCCCCGAGAACC ACAGGTGTGCACCCTGCCCCCATCCCGGGATGAGCTGACCAAGAACCAGGTC AGCCTCTCGTGCGCAGTCAAAGGCTTCTATCCCAGCGACATCGCCGTGGAGT GGGAGAGCAATGGGCAGCCGGAGAACAACTACAAGACCACGCCTCCCGTGCT GGACTCCGACGGCTCCTTCTTCCTCGTGAGCAAGCTCACCGTGGACAAGAGC AGGTGGCAGCAGGGGAACGTCTTCTCATGCTCCGTGATGCATGAGGCTCTGC ACAACCACTACACGCAGAAGAGCCTCTCCCTGTCTCCGGGTAAA | 426 |
| 9C7 LC [RK] pETR14980 | GATATTGTTATGACTCAATCTCCACTGTCTCTGCCGGTGACTCCAGGCGAAC CGGCGAGCATTCTTGCCGTTCCAGCCAGTCTCTGCTGCACTCCAACGGCTA CAACTATCTCGATTGTACCTGCAAAAACCGGGTCAGAGCCCTCAGCTGCTG ATCTACCTGGGCTCTAACCGCGCTTCCGGTGTACCGGACCGTTTCAGCGGCT CTGGATCCGGCACCGATTTCACGTTGAAAATCAGCCGTGTTGAAGCAGAAGA CGTGGGCGTTTATTACTGTATGCAGGCACGGCAGACCCCAACTTTTGGTCAA GGCACCAAGGTCGAAATTAAACGTACGGTGGCTGCACCATCTGTCTTCATCT TCCCGCCATCTGATCGGAAGTTGAAATCTGGAACTGCCTCTGTTGTGTGCCT GCTGAATAACTTCTATCCCAGAGAGGCAAAGTACAGTGGAAGGTGGATAAC GCCCTCCAATCGGGTAACTCCCAGGAGAGTGTCACAGAGCAGGACAGCAAGG ACAGCACCTACAGCCTCAGCAGCACCCTGACGCTGAGCAAAGCAGACTACGA GAAACACAAAGTCTACGCCTGCGAAGTCACCCATCAGGGCCTGAGCTCGCCC GTCACAAAGAGCTTCAACAGGGGAGAGTGT | 427 |

Exemplary Anti-PD1 Antagonist Sequences

| Description | Sequence | Seq ID No |
|---|---|---|
| anti-PDL1 antibody | QVQLVESGGGVVQPGRSLRLDCKASGITFSNSGMHWVRQAPGKGLE WVAVIWYDGSKRYYADSVKGRFTISRDNSKNTLFLQMNSLRAEDTA VYYCATNDDYWGQGTLVTVSSASTKGPSVFPLAPCSRSTSESTAAL GCLVKDYFPEPVTVSWNSGALTSGVHTFPAVLQSSGLYSLSSVVTV PSSSLGTKTYTCNVDHKPSNTKVDKRVESKYGPPCPPCPAPEFLGG PSVFLFPPKPKDTLMISRTPEVTCVVVDVSQEDPEVQFNWYVDGVE VHNAKTKPREEQFNSTYRVVSVLTVLHQDWLNGKEYKCKVSNKGLP SSIEKTISKAKGQPREPQVYTLPPSQEEMTKNQVSLTCLVKGFYPS DIAVEWESNGQPENNYKTTPPVLDSDGSFFLYSRLTVDKSRWQEGN VFSCSVMHEALHNHYTQKSLSLSLGK | 274 |
| anti-PDL1 antibody | EIVLTQSPATLSLSPGERATLSCRASQSVSSYLAWYQQKPGQAPRL LIYDASNRATGIPARFSGSGSGTDFTLTISSLEPEDFAVYYCQQSS NWPRTFGQGTKVEIKRTVAAPSVFIFPPSDEQLKSGTASVVCLLNN FYPREAKVQWKVDNALQSGNSQESVTEQDSKDSTYSLSSTLTLSKA DYEKHKVYACEVTHQGLSSPVTKSFNRGEC | 275 |
| anti-PDL1 antibody | QVQLVQSGVEVKKPGASVKVSCKASGYTFTNYYMYWVRQAPGQGLE WMGGINPSNGGTNFNEKFKNRVTLTTDSSTTTAYMELKSLQFDDTA VYYCARRDYRFDMGFDYWGQGTTVTVSSASTKGPSVFPLAPCSRST SESTAALGCLVKDYFPEPVTVSWNSGALTSGVHTFPAVLQSSGLYS LSSVVTVPSSSLGTKTYTCNVDHKPSNTKVDKRVESKYGPPCPPCP APEFLGGPSVFLFPPKPKDTLMISRTPEVTCVVVDVSQEDPEVQFN WYVDGVEVHNAKTKPREEQFNSTYRVVSVLTVLHQDWLNGKEYKCK | 276 |

| Description | Sequence | Seq ID No |
|---|---|---|
| | VSNKGLPSSIEKTISKAKGQPREPQVYTLPPSQEEMTKNQVSLTCL VKGFYPSDIAVEWESNGQPENNYKTTPPVLDSDGSFFLYSRLTVDK SRWQEGNVFSCSVMHEALHNHYTQKSLSLSLGK | |
| anti-PDL1 antibody | EIVLTQSPATLSLSPGERATLSCRASKGVSTSGYSYLHWYQQKPGQ APRLLIYLASYLESGVPARFSGSGSGTDFTLTISSLEPEDFAVYYC QHSRDLPLTFGGGTKVEIKRTVAAPSVFIFPPSDEQLKSGTASVVC LLNNFYPREAKVQWKVDNALQSGNSQESVTEQDSKDSTYSLSSTLT LSKADYEKHKVYACEVTHQGLSSPVT KSFNRGEC | 277 |
| heavy | EVQLVESGGGLVQPGGSLRLSCAASGFTFSDSWIHWVRQAPGKGLE WVAWISPYGGSTYYADSVKGRFTISADTSKNTAYLQMNSLRAEDTA VYYCARRHWPGGFDYWGQGTLVTVSSASTKGPSVFPLAPSSKSTSG GTAALGCLVKDYFPEPVTVSWNSGALTSGVHTFPAVLQSSGLYSLS SVVTVPSSSLGTQTYICNVNHKPSNTKVDKKVEPKSCDKTHTCPPC PAPELLGGPSVFLFPPKPKDTLMISRTPEVTCVVVDVSHEDPEVKF NWYVDGVEVHNAKTKPREEQYASTYRVVSVLTVLHQDWLNGKEYKC KVSNKALPAPIEKTISKAKGQPREPQVYTLPPSREEMTKNQVSLTC LVKGFYPSDIAVEWESNGQPENNYKTTPPVLDSDGSFFLYSKLTVD KSRWQQGNVFSCSVMHEALHNHYTQKSLSLSPG | 278 |
| light | DIQMTQSPSSLSASVGDRVTITCRASQDVSTAVAWYQQKPGKAPKL LIYSASFLYSGVPSRFSGSGSGTDFTLTISSLQPEDFATYYCQQYL YHPATFGQGTKVEIKRTVAAPSVFIFPPSDEQLKSGTASVVCLLNN FYPREAKVQWKVDNALQSGNSQESVTEQDSKDSTYSLSSTLTLSKA DYEKHKVYACEVTHQGLSSPVTKSFNRGEC | 279 |
| anti-PDL1 antibody VH | EVQLVESGGGLVQPGGSLRLSCAASGFTFSDSWIHWVRQAPGKGLE WVAWISPYGGSTYYADSVKGRFTISADTSKNTAYLQMNSLRAEDTA VYYCARRHWPGGFDYWGQGTLVTVSS | 280 |
| anti-PDL1 antibody VH | EVQLVESGGGLVQPGGSLRLSCAASGFTFSDSWIHWVRQAPGKGLE WVAWISPYGGSTYYADSVKGRFTISADTSKNTAYLQMNSLRAEDTA VYYCARRHWPGGFDYWGQGTLVTVSSASTK | 281 |
| anti-PDL1 antibody VL | DIQMTQSPSSLSASVGDRVTITCRASQDVSTAVAWYQQKPGKAPKL LIYSASFLYSGVPSRFSGSGSGTDFTLTISSLQPEDFATYYCQQYL YHPATFGQGTKVEIKR | 282 |
| HVR-H1 | GFTFSX1SWIH | 283 |
| HVR-H2 | AWIX2PYGGSX3YYADSVKG | 284 |
| HVR-H3 | RHWPGGFDY | 285 |
| HVR-L1 | RASQX4X5X6TX7X8A | 286 |
| HVR-L2 | SASX9LX10S | 287 |
| HVR-L3 | QQX11X12X13X14PX15T | 288 |
| HVR-H1 | GFTFSDSWIH | 289 |
| HVR-H2 | AWISPYGGSTYYADSVKG | 290 |
| HVR-H3 | RHWPGGFDY | 291 |
| HVR-L1 | RASQDVSTAVA | 292 |
| HVR-L2 | SASFLYS | 293 |
| HVR-L3 | QQYLYHPAT | 294 |
| anti-PDL1 antibody HC-FR1 | EVQLVESGGGLVQPGGSLRLSCAAS | 295 |
| anti-PDL1 antibody HC-FR2 | HC-FR2 is WVRQAPGKGLEWV | 296 |
| anti-PDL1 antibody HC-FR3 | RFTISADTSKNTAYLQMNSLRAEDTAVYYCAR | 297 |

| Description | Sequence | Seq ID No |
|---|---|---|
| anti-PDL1 antibody HC-FR4 | WGQGTLVTVSA | 298 |
| anti-PDL1 antibody HC-FR4 | WGQGTLVTVSS | 299 |
| LC-FR1 | DIQMTQSPSSLSASVGDRVTITC | 300 |
| LC-FR2 | WYQQKPGKAPKLLIY | 301 |
| LC-FR3 | GVPSRFSGSGSGTDFTLTISSLQPEDFATYYC | 302 |
| LC-FR4 | FGQGTKVEIKR | 303 |
| anti-PDL1 antibody VH | EVQLVESGGGLVQPGGSLRLSCAASGFTFSDSWIHWVRQAPGKGLEWVAWISPYGGSTYYADSVKGRFTISADTSKNTAYLQMNSLRAEDTAVYYCARRHWPGGFDYWGQGTLVTVSA | 382 |
| anti-PDL1 antibody VL | DIQMTQSPSSLSASVGDRVTITCRASQDVSTAVAWYQQKPGKAPKLLIYSASFLYSGVPSRFSGSGSGTDFTLTISSLQPEDFATYYCQQYLYHPATFGQGTKVEIKR | 383 |

Exemplary Anti-TIM3 Antibody Sequences
    Sequences of exemplary anti-TIM3 antibody amino acid sequences and exemplary TIM3 sequences are set forth in the sequence listing below as follows:

```
SEQ ID NO: 304   heavy chain HVR-H1, Tim3_0016

SEQ ID NO: 305   heavy chain HVR-H2, Tim3_0016

SEQ ID NO: 306   heavy chain HVR-H3, Tim3_0016

SEQ ID NO: 307   light chain HVR-L1, Tim3_0016

SEQ ID NO: 308   light chain HVR-L2, Tim3_0016

SEQ ID NO: 309   light chain HVR-L3, Tim3_0016

SEQ ID NO: 310   heavy chain variable domain VH, Tim3_0016

SEQ ID NO: 311   light chain variable domain VL, Tim3_0016

SEQ ID NO: 312   heavy chain variable domain VH, Tim3_0016 variant (0018)

SEQ ID NO: 313   light chain variable domain VL, Tim3_0016 variant (0018)

SEQ ID NO: 314   light chain HVR-L1, Tim3_0016_HVR-L1 variant 1_NQ
                 (removal of glycosylation sity by N to Q mutation)

SEQ ID NO: 315   light chain HVR-L1, Tim3_0016_HVR-L1 variant 2_NS
                 (removal of glycosylation sity by N to S mutation)

SEQ ID NO: 316   heavy chain HVR-H1, Tim3_0021

SEQ ID NO: 317   heavy chain HVR-H2, Tim3_0021

SEQ ID NO: 318   heavy chain HVR-H3, Tim3_0021

SEQ ID NO: 319   light chain HVR-L1, Tim3_0021

SEQ ID NO: 320   light chain HVR-L2, Tim3_0021

SEQ ID NO: 321   light chain HVR-L3, Tim3_0021

SEQ ID NO: 322   heavy chain variable domain VH, Tim3_0021

SEQ ID NO: 323   light chain variable domain VL, Tim3_0021

SEQ ID NO: 324   heavy chain HVR-H1, Tim3_0022
```

-continued

```
SEQ ID NO: 325    heavy chain HVR-H2, Tim3_0022
SEQ ID NO: 326    heavy chain HVR-H3, Tim3_0022
SEQ ID NO: 327    light chain HVR-L1, Tim3_0022
SEQ ID NO: 328    light chain HVR-L2, Tim3_0022
SEQ ID NO: 329    light chain HVR-L3, Tim3_0022
SEQ ID NO: 330    heavy chain variable domain VH, Tim3_0022
SEQ ID NO: 331    light chain variable domain VL, Tim3_0022
SEQ ID NO: 332    heavy chain HVR-H1, Tim3_0026
SEQ ID NO: 333    heavy chain HVR-H2, Tim3_0026
SEQ ID NO: 334    heavy chain HVR-H3, Tim3_0026
SEQ ID NO: 335    light chain HVR-L1, Tim3_0026
SEQ ID NO: 336    light chain HVR-L2, Tim3_0026
SEQ ID NO: 337    light chain HVR-L3, Tim3_0026
SEQ ID NO: 338    heavy chain variable domain VH, Tim3_0026
SEQ ID NO: 339    light chain variable domain VL, Tim3_0026
SEQ ID NO: 340    heavy chain HVR-H1, Tim3_0028
SEQ ID NO: 341    heavy chain HVR-H2, Tim3_0028
SEQ ID NO: 342    heavy chain HVR-H3, Tim3_0028
SEQ ID NO: 343    light chain HVR-L1, Tim3_0028
SEQ ID NO: 344    light chain HVR-L2, Tim3_0028
SEQ ID NO: 345    light chain HVR-L3, Tim3_0028
SEQ ID NO: 346    heavy chain variable domain VH, Tim3_0028
SEQ ID NO: 347    light chain variable domain VL, Tim3_0028
SEQ ID NO: 348    heavy chain HVR-H1, Tim3_0030
SEQ ID NO: 349    heavy chain HVR-H2, Tim3_0030
SEQ ID NO: 350    heavy chain HVR-H3, Tim3_0030
SEQ ID NO: 351    light chain HVR-L1, Tim3_0030
SEQ ID NO: 352    light chain HVR-L2, Tim3_0030
SEQ ID NO: 353    light chain HVR-L3, Tim3_0030
SEQ ID NO: 354    heavy chain variable domain VH, Tim3_0030
SEQ ID NO: 355    light chain variable domain VL, Tim3_0030
SEQ ID NO: 356    heavy chain HVR-H1, Tim3_0033
SEQ ID NO: 357    heavy chain HVR-H2, Tim3_0033
SEQ ID NO: 358    heavy chain HVR-H3, Tim3_0033
SEQ ID NO: 359    light chain HVR-L1, Tim3_0033
SEQ ID NO: 360    light chain HVR-L2, Tim3_0033
SEQ ID NO: 361    light chain HVR-L3, Tim3_0033
SEQ ID NO: 362    heavy chain variable domain VH, Tim3_0033
SEQ ID NO: 363    light chain variable domain VL, Tim3_0033
```

-continued

```
SEQ ID NO: 364    heavy chain HVR-H1, Tim3_0038

SEQ ID NO: 365    heavy chain HVR-H2, Tim3_0038

SEQ ID NO: 366    heavy chain HVR-H3, Tim3_0038

SEQ ID NO: 367    light chain HVR-L1, Tim3_0038

SEQ ID NO: 368    light chain HVR-L2, Tim3_0038

SEQ ID NO: 369    light chain HVR-L3, Tim3_0038

SEQ ID NO: 370    heavy chain variable domain VH, Tim3_0038

SEQ ID NO: 371    light chain variable domain VL, Tim3_0038

SEQ ID NO: 372    an exemplary Pseudomonas exotoxin A variant 1
                  (deimunized PE24 example)

SEQ ID NO: 373    an exemplary Pseudomonas exotoxin A variant 2
                  (deimunized PE24 example)

SEQ ID NO: 374    human kappa light chain constant region

SEQ ID NO: 375    human lambda light chain constant region

SEQ ID NO: 376    human heavy chain constant region derived from IgG1

SEQ ID NO: 377    human heavy chain constant region derived from IgG1 with
                  mutations L234A and L235A SEQ ID NO: 378    human heavy chain constant region derived from IgG1 with
                  mutations L234A, L235A and P329G SEQ ID NO: 379    human heavy chain constant region derived from IgG4

SEQ ID NO: 380    exemplary human TIM3 sequences

SEQ ID NO: 381    human TIM3 Extracellular Domain (ECD)

<210> 304
<211>   9
<212> PRT
<213> Mus musculus

<400> 304

Gly Phe Ser Leu Ser Thr Ser Gly Met
1               5

<210> 305
<211>   3
<212> PRT
<213> Mus musculus

<400> 305

Leu Asn Asp
1

<210> 306
<211>   8
<212> PRT
<213> Mus musculus

<400> 306

Asn Gly Tyr Leu Tyr Ala Leu Asp
1               5

<210> 307
<211>   6
<212> PRT
<213> Mus musculus

<400> 307

Ser Ser Ser Val Asn Tyr
1               5
```

```
<210> 308
<211>   3
<212> PRT
<213> Mus musculus

<400> 308

Asp Ala Phe
1

<210> 309
<211>   7
<212> PRT
<213> Mus musculus

<400> 309

Trp Ser Ser Tyr Pro Trp Thr
1               5

<210> 310
<211> 120
<212> PRT
<213> Mus musculus

<400> 310

Gln Val Thr Leu Lys Glu Ser Gly Pro Gly Ile Leu Gln Pro Ser Gln
1               5                  10                  15

Thr Leu Arg Leu Thr Cys Ser Phe Ser Gly Phe Ser Leu Ser Thr Ser
            20                  25                  30

Gly Met Ser Val Gly Trp Ile Arg Gln Pro Ser Gly Lys Gly Leu Glu
        35                  40                  45

Trp Leu Ala His Ile Trp Leu Asn Asp Asp Val Phe Phe Asn Pro Ala
    50                  55                  60

Leu Lys Ser Arg Leu Thr Ile Ser Lys Asp Thr Ser Asn Asn Gln Val
65                  70                  75                  80

Phe Leu Gln Ile Ala Ser Val Val Thr Ala Asp Thr Ala Thr Tyr Tyr
                85                  90                  95

Cys Val Arg Ala Asn Gly Tyr Leu Tyr Ala Leu Asp Tyr Trp Gly Gln
            100                 105                 110

Gly Thr Ser Val Thr Val Ser Ser
        115                 120

<210> 311
<211> 106
<212> PRT
<213> Mus musculus

<400> 311

Gln Ile Val Leu Thr Gln Ser Pro Ala Ile Met Ser Ala Ser Pro Gly
1               5                  10                  15

Gln Lys Val Thr Ile Thr Cys Ser Ala Ser Ser Ser Val Asn Tyr Thr
            20                  25                  30

Gln Trp Tyr Gln Gln Lys Leu Gly Ser Ser Pro Lys Leu Trp Ile Tyr
        35                  40                  45

Asp Ala Phe Lys Leu Ala Pro Gly Val Pro Ala Arg Phe Ser Gly Ser
    50                  55                  60

Gly Thr Gly Thr Ser Tyr Ser Leu Thr Ile Ser Ser Met Glu Ala Glu
65                  70                  75                  80

Asp Ala Ala Ser Tyr Phe Cys His Gln Trp Ser Ser Tyr Pro Trp Thr
                85                  90                  95

Phe Gly Gly Gly Thr Lys Leu Glu Ile Lys
            100                 105
```

```
<210> 312
<211> 120
<212> PRT
<213> Mus musculus

<400> 312

Gln Val Thr Leu Lys Glu Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Ser Val Gly Trp Ile Arg Gln Pro Ser Gly Lys Gly Leu Glu
        35                  40                  45

Trp Leu Ala His Ile Trp Leu Asn Asp Asp Val Phe Phe Asn Pro Ala
    50                  55                  60

Leu Lys Arg Arg Leu Thr Ile Ser Lys Asp Thr Ser Asn Asn Gln Val
65                  70                  75                  80

Phe Leu Gln Ile Ala Ser Val Val Thr Ala Asp Thr Ala Thr Tyr Tyr
                85                  90                  95

Cys Val Arg Ala Asn Gly Tyr Leu Tyr Ala Leu Asp Tyr Trp Gly Gln
            100                 105                 110

Gly Ile Ser Val Thr Val Ser Ser
        115                 120

<210> 313
<211> 106
<212> PRT
<213> Mus musculus

<400> 313

Gln Ile Val Leu Thr Gln Ser Pro Ala Ile Met Ser Ala Ser Pro Gly
1               5                   10                  15

Gln Lys Val Thr Ile Thr Cys Ser Ala Ser Ser Ser Val Asn Tyr Thr
            20                  25                  30

Gln Trp Tyr Gln Gln Lys Leu Gly Ser Ser Pro Lys Leu Trp Ile Tyr
        35                  40                  45

Asp Ala Phe Lys Leu Ala Pro Gly Val Pro Ala Arg Phe Ser Gly Ser
    50                  55                  60

Gly Thr Gly Thr Ser Tyr Ser Leu Thr Ile Ser Ser Met Glu Ala Glu
65                  70                  75                  80

Asp Ala Ala Ser Tyr Phe Cys His Gln Trp Ser Ser Tyr Pro Trp Thr
                85                  90                  95

Phe Gly Gly Gly Thr Lys Leu Glu Ile Lys
            100                 105

<210> 314
<211> 6
<212> PRT
<213> Mus musculus

<400> 314

Ser Ser Ser Val Gln Tyr
1               5

<210> 315
<211> 6
<212> PRT
<213> Mus musculus

<400> 315

Ser Ser Ser Val Ser Tyr
1               5
```

<210> 316
<211> 7
<212> PRT
<213> Mus musculus

<400> 316

Gly Tyr Ser Phe Thr Ser Tyr
1               5

<210> 317
<211> 3
<212> PRT
<213> Mus musculus

<400> 317

Ser Asp Ser
1

<210> 318
<211> 9
<212> PRT
<213> Mus musculus

<400> 318

Gly Tyr Tyr Ala Trp Tyr Tyr Phe Asp
1               5

<210> 319
<211> 7
<212> PRT
<213> Mus musculus

<400> 319

Ser Gln Ser Ile Gly Asn Asn
1               5

<210> 320
<211> 3
<212> PRT
<213> Mus musculus

<400> 320

Tyr Ala Ser
1

<210> 321
<211> 6
<212> PRT
<213> Mus musculus

<400> 321

Ser Asn Ser Trp Pro Leu
1               5

<210> 322
<211> 120
<212> PRT
<213> Mus musculus

<400> 322

Gln Val Gln Leu Gln Gln Ser Gly Pro Gln Leu Val Arg Pro Gly Ala
1               5                   10                  15

Ser Val Gln Ile Ser Cys Lys Ala Ser Gly Tyr Ser Phe Thr Ser Tyr
            20                  25                  30

Leu Leu His Trp Leu Lys Gln Arg Pro Gly Gln Gly Leu Glu Trp Ile
        35                  40                  45

Gly Met Ile Asp Pro Ser Asp Ser Glu Thr Arg Leu Asn Gln Lys Phe
    50                  55                  60

-continued

```
Lys Asp Lys Ala Thr Leu Thr Val Asp Lys Ser Ser Thr Ala Tyr
 65                  70                  75                  80

Met Gln Leu Ser Ser Pro Thr Ser Glu Asp Ser Ala Val Tyr Tyr Cys
                 85                  90                  95

Ala Arg Asp Gly Tyr Tyr Ala Trp Tyr Tyr Phe Asp Cys Trp Gly Gln
            100                 105                 110

Gly Thr Thr Leu Thr Val Ser Ser
            115                 120

<210> 323
<211> 107
<212> PRT
<213> Mus musculus

<400> 323

Asp Ile Val Leu Thr Gln Ser Pro Ala Thr Leu Ser Val Thr Pro Gly
  1               5                  10                  15

Asp Arg Val Ser Leu Ser Cys Arg Ala Ser Gln Ser Ile Gly Asn Asn
                 20                  25                  30

Leu His Trp Tyr Gln Gln Lys Ser His Glu Ser Pro Arg Leu Leu Ile
             35                  40                  45

Lys Tyr Ala Ser His Ser Ile Ser Gly Ile Pro Ser Lys Phe Ser Gly
 50                  55                  60

Thr Gly Ser Gly Thr Asp Phe Thr Leu Ser Phe Asn Ser Val Glu Thr
 65                  70                  75                  80

Glu Asp Phe Gly Met Tyr Phe Cys Gln Gln Ser Asn Ser Trp Pro Leu
                 85                  90                  95

Thr Phe Gly Ala Gly Thr Lys Leu Glu Leu Lys
            100                 105

<210> 324
<211>   5
<212> PRT
<213> Mus musculus

<400> 324

Gly Asp Ser Ile Ala
  1               5

<210> 325
<211>   3
<212> PRT
<213> Mus musculus

<400> 325

Tyr Ser Gly
  1

<210> 326
<211>   4
<212> PRT
<213> Mus musculus

<400> 326

Asp Tyr Phe Asp
  1

<210> 327
<211>   7
<212> PRT
<213> Mus musculus

<400> 327

Arg Gln Asp Val Arg Lys Asn
```

```
<210> 328
<211>   3
<212> PRT
<213> Mus musculus

<400> 328

Tyr Thr Ser
1

<210> 329
<211>   6
<212> PRT
<213> Mus musculus

<400> 329

Tyr Asp Asn Leu Pro Phe
1               5

<210> 330
<211> 114
<212> PRT
<213> Mus musculus

<400> 330

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Ala Ser Ala
            20                  25                  30

Tyr Trp Asn Trp Ile Arg Lys Phe Pro Gly Asn Lys Leu Glu Tyr Met
        35                  40                  45

Gly Tyr Ile Asn Tyr Ser Gly Ser Thr Tyr Tyr Asn Pro Ser Leu Lys
    50                  55                  60

Ser Arg Ile Ser Ile Thr Arg Asp Thr Ser Gln Asn Gln Tyr Tyr Leu
65                  70                  75                  80

Gln Leu Asn Ser Val Thr Thr Glu Asp Thr Ala Thr Tyr Tyr Cys Val
                85                  90                  95

Thr Gly Asp Tyr Phe Asp Tyr Trp Gly Arg Gly Thr Thr Leu Thr Val
            100                 105                 110

Ser Ser

<210> 331
<211> 107
<212> PRT
<213> Mus musculus

<400> 331

Asp Ile Gln Met Thr Gln Ser Pro Ser Ser Leu Ser Ala Tyr Leu Gly
1               5                   10                  15

Gly Lys Val Thr Ile Thr Cys Lys Ala Arg Gln Asp Val Arg Lys Asn
            20                  25                  30

Ile Gly Trp Tyr Gln His Lys Pro Gly Lys Gly Pro Arg Leu Leu Ile
        35                  40                  45

Trp Tyr Thr Ser Thr Leu Gln Ser Gly Ile Pro Ser Arg Phe Ser Gly
    50                  55                  60

Ser Gly Ser Gly Arg Asp Tyr Ser Phe Asn Ile Asn Asn Leu Glu Pro
65                  70                  75                  80

Glu Asp Ile Ala Thr Tyr Tyr Cys Leu Gln Tyr Asp Asn Leu Pro Phe
                85                  90                  95

Thr Phe Gly Thr Gly Thr Lys Leu Glu Ile Arg
            100                 105
```

```
<210> 332
<211>   5
<212> PRT
<213> Mus musculus

<400> 332

Gly Tyr Thr Phe Thr
1               5

<210> 333
<211>   3
<212> PRT
<213> Mus musculus

<400> 333

Glu Thr Tyr
1

<210> 334
<211>   4
<212> PRT
<213> Mus musculus

<400> 334

Gly Tyr Pro Ala
1

<210> 335
<211>  12
<212> PRT
<213> Mus musculus

<400> 335

Ser Arg Thr Ile Leu His Ser Ser Gly Asn Thr Tyr
1               5                   10

<210> 336
<211>   3
<212> PRT
<213> Mus musculus

<400> 336

Lys Val Ser
1

<210> 337
<211>   6
<212> PRT
<213> Mus musculus

<400> 337

Asp Ser His Val Pro Phe
1               5

<210> 338
<211> 115
<212> PRT
<213> Mus musculus

<400> 338

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Arg Gly Leu Lys Trp Met
        35                  40                  45

Gly Tyr Ile Asn Thr Glu Thr Tyr Glu Pro Thr Phe Gly Ala Asp Phe
    50                  55                  60
```

```
Lys Gly Arg Phe Ala Phe Ser Leu Asp Thr Ser Ala Thr Ala Tyr
 65                  70                  75                  80

Leu Gln Ile Asn Ser Leu Lys Thr Glu Asp Thr Ala Thr Phe Phe Cys
                 85                  90                  95

Gly Gly Gly Gly Tyr Pro Ala Tyr Trp Gly Gln Gly Thr Val Val Ile
            100                 105                 110

Val Ser Ala
        115

<210> 339
<211> 112
<212> PRT
<213> Mus musculus

<400> 339

Asp Val Leu Met Thr Gln Thr Pro Leu Ser Leu Pro Val Ser Leu Gly
1               5                   10                  15

Asp Gln Ala Ser Ile Ser Cys Arg Ser Ser Arg Thr Ile Leu His Ser
            20                  25                  30

Ser Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Asn Ile
65                  70                  75                  80

Ser Arg Val Glu Ala Glu Asp Leu Gly Val Tyr Tyr Cys Phe Gln Asp
                85                  90                  95

Ser His Val Pro Phe Thr Phe Gly Thr Gly Thr Lys Leu Glu Ile Lys
            100                 105                 110

<210> 340
<211>   7
<212> PRT
<213> Mus musculus

<400> 340

Gly Phe Asn Ile Lys Thr Thr
1               5

<210> 341
<211>   3
<212> PRT
<213> Mus musculus

<400> 341

Ala Asp Asp
1

<210> 342
<211>   8
<212> PRT
<213> Mus musculus

<400> 342

Phe Gly Tyr Val Ala Trp Phe Ala
1               5

<210> 343
<211>   7
<212> PRT
<213> Mus musculus

<400> 343

Ser Gln Ser Val Asp Asn Tyr
```

<210> 344
<211> 3
<212> PRT
<213> Mus musculus

<400> 344

Tyr Ala Ser
1

<210> 345
<211> 6
<212> PRT
<213> Mus musculus

<400> 345

His Tyr Ser Ser Pro Tyr
1               5

<210> 346
<211> 119
<212> PRT
<213> Mus musculus

<400> 346

Glu Val Gln Leu Gln Gln Ser Val Ala Glu Leu Val Arg Pro Gly Ala
1               5                   10                  15

Ser Val Lys Leu Ser Cys Thr Ala Ser Gly Phe Asn Ile Lys Thr Thr
            20                  25                  30

Tyr Met His Trp Val Lys Gln Arg Pro Glu Gln Gly Leu Glu Trp Ile
        35                  40                  45

Gly Arg Ile Asp Pro Ala Asp Asp Asn Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Ala Ala Ile Tyr Tyr Cys
                85                  90                  95

Val Arg Asp Phe Gly Tyr Val Ala Trp Phe Ala Tyr Trp Gly Gln Gly
            100                 105                 110

Thr Leu Val Thr Phe Ser Ala
        115

<210> 347
<211> 107
<212> PRT
<213> Mus musculus

<400> 347

Asn Ile Val Met Thr Pro Thr Pro Lys Phe Leu Pro Val Ser Ser Gly
1               5                   10                  15

Asp Arg Val Thr Met Thr Cys Arg Ala Ser Gln Ser Val Asp Asn Tyr
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Ile Gly Val Pro Asp Arg Phe Thr Gly
    50                  55                  60

Ser Gly Ser Gly Thr Asp Phe Thr Phe Thr Ile Ser Ser Val Gln Val
65                  70                  75                  80

Glu Asp Leu Ala Val Tyr Phe Cys Gln Gln His Tyr Ser Ser Pro Tyr
                85                  90                  95

Thr Phe Gly Ser Gly Thr Lys Leu Glu Ile Lys

```
<210> 348
<211> 7
<212> PRT
<213> Mus musculus

<400> 348

Gly Tyr Pro Phe Ser Glu Tyr
1               5

<210> 349
<211> 3
<212> PRT
<213> Mus musculus

<400> 349

Glu Thr Gly
1

<210> 350
<211> 4
<212> PRT
<213> Mus musculus

<400> 350

Gly Tyr Pro Ala
1

<210> 351
<211> 12
<212> PRT
<213> Mus musculus

<400> 351

Ser Arg Ser Ile Val His Ser Ser Gly Asn Thr Tyr
1               5                   10

<210> 352
<211> 3
<212> PRT
<213> Mus musculus

<400> 352

Lys Val Ser
1

<210> 353
<211> 5
<212> PRT
<213> Mus musculus

<400> 353

Asp Ser His Val Pro
1               5

<210> 354
<211> 115
<212> PRT
<213> Mus musculus

<400> 354

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Pro Phe Ser Glu Tyr
                20                  25                  30

Ser Ile His Trp Val Lys Gln Ala Pro Gly Lys Gly Leu Lys Trp Met
            35                  40                  45

Val Tyr Val Asn Thr Glu Thr Gly Gln Pro Ile Val Gly Asp Asp Phe
```

```
            50                  55                  60
Arg Gly Arg Phe Val Leu Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Gly Gly Gly Gly Tyr Pro Ala Tyr Trp Gly Gln Gly Thr Leu Val Thr
            100                 105                 110

Val Ser Ala
        115

<210> 355
<211> 112
<212> PRT
<213> Mus musculus

<400> 355

Asp Val Leu Met Thr Gln Thr Pro Leu Ser Leu Pro Val Ser Leu Gly
  1               5                  10                  15

Asp Gln Ala Ser Ile Ser Cys Arg Ser Ser Arg Ser Ile Val His Ser
                 20                  25                  30

Ser Gly Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Asn Ile
 65                  70                  75                  80

Ser Arg Val Glu Ala Glu Asp Leu Gly Val Tyr Tyr Cys Phe Gln Asp
                 85                  90                  95

Ser His Val Pro Phe Thr Phe Gly Thr Gly Thr Lys Leu Glu Ile Lys
            100                 105                 110

<210> 356
<211>   7
<212> PRT
<213> Mus musculus

<400> 356

Gly Phe Thr Phe Ser Ser Ser
  1               5

<210> 357
<211>   3
<212> PRT
<213> Mus musculus

<400> 357

Ala Thr Gly
  1

<210> 358
<211>   8
<212> PRT
<213> Mus musculus

<400> 358

Tyr Pro His Tyr Tyr Ala Met Asp
  1               5

<210> 359
<211>   7
<212> PRT
<213> Mus musculus

<400> 359
```

Ser Glu Asn Ile Phe Ser Asn
1               5

<210> 360
<211>   3
<212> PRT
<213> *Mus musculus*

<400> 360

Ser Ala Thr
1

<210> 361
<211>   6
<212> PRT
<213> *Mus musculus*

<400> 361

Phe Tyr Lys Ile Pro Phe
1               5

<210> 362
<211> 121
<212> PRT
<213> *Mus musculus*

<400> 362

Gln Gly Gln Met His Gln Ser Gly Ala Glu Leu Val Lys Pro Gly Ser
1               5                   10                  15

Ser Val Lys Leu Ser Cys Lys Thr Ser Gly Phe Thr Phe Ser Ser Ser
            20                  25                  30

Phe Ile Ser Trp Leu Lys Gln Lys Pro Gly Gln Ser Leu Glu Trp Ile
        35                  40                  45

Ala Trp Ile Tyr Ala Ala Thr Gly Ser Thr Ser Tyr Asn Gln Lys Phe
    50                  55                  60

Thr Asn Lys Ala Gln Leu Thr Val Asp Thr Ser Ser Ser Ala Ala Tyr
65                  70                  75                  80

Met Gln Phe Ser Ser Leu Thr Thr Glu Asp Ser Ala Ile Tyr Tyr Cys
                85                  90                  95

Ala Arg His Ala Gly Tyr Pro His Tyr Tyr Ala Met Asp Tyr Trp Gly
            100                 105                 110

Gln Gly Thr Ser Val Thr Val Ser Ser
        115                 120

<210> 363
<211> 107
<212> PRT
<213> *Mus musculus*

<400> 363

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Phe Ser Asn
            20                  25                  30

Leu Ala Trp Tyr Gln Gln Lys Gln Gly Lys Ser Pro Gln Leu Leu Val
        35                  40                  45

Tyr Ser Ala Thr Asn Leu Gly Asp Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Asn Tyr Tyr Cys Gln His Tyr Lys Ile Pro Phe
                85                  90                  95

```
Thr Phe Gly Thr Gly Thr Lys Leu Glu Ile Lys
            100                 105

<210> 364
<211> 7
<212> PRT
<213> Mus musculus

<400> 364

Gly Phe Asn Ile Lys Asp Tyr
1               5

<210> 365
<211> 3
<212> PRT
<213> Mus musculus

<400> 365

Glu Asp Gly
1

<210> 366
<211> 8
<212> PRT
<213> Mus musculus

<400> 366

His Gly Tyr Val Gly Trp Phe Ala
1               5

<210> 367
<211> 8
<212> PRT
<213> Mus musculus

<400> 367

Ala Ser Glu Asn Val Asp Thr Tyr
1               5

<210> 368
<211> 3
<212> PRT
<213> Mus musculus

<400> 368

Gly Ala Ser
1

<210> 369
<211> 6
<212> PRT
<213> Mus musculus

<400> 369

Ser Tyr Ser Tyr Pro Trp
1               5

<210> 370
<211> 119
<212> PRT
<213> Mus musculus

<400> 370

Glu Val Gln Leu Gln Gln Ser Gly Ala Glu Pro Leu Lys Pro Gly Ala
1               5                   10                  15

Ser Val Lys Leu Thr Cys Thr Thr Ser Gly Phe Asn Ile Lys Asp Tyr
            20                  25                  30

Tyr Ile His Trp Val Lys Gln Arg Ser Asp Gln Gly Leu Glu Trp Ile
        35                  40                  45
```

Gly Arg Ile Asp Pro Glu Asp Gly Glu Leu Ile Tyr Ala Pro Lys Phe
        50                  55                  60

Gln Asp Lys Ala Thr Ile Thr Val Asp Thr Ser Ser Asn Ile Ala Tyr
65                  70                  75                  80

Leu Gln Leu Asn Ser Leu Thr Ser Glu Asp Thr Ala Val Tyr Tyr Cys
                85                  90                  95

Ser Arg Asp His Gly Tyr Val Gly Trp Phe Ala Tyr Trp Gly Gln Gly
            100                 105                 110

Thr Leu Val Thr Val Ser Ala
        115

<210> 371
<211> 107
<212> PRT
<213> Mus musculus

<400> 371

Asn Val Val Met Thr Gln Ser Pro Lys Ser Met Ile Met Ser Val Gly
1               5                   10                  15

Gln Arg Val Thr Leu Asn Cys Lys Ala Ser Glu Asn Val Asp Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Arg Ser Ala Thr Asp Phe Thr Leu Thr Ile Ser Ser Val Gln Ala
65                  70                  75                  80

Glu Asp Leu Ala Val Tyr Tyr Cys Gly Gln Ser Tyr Ser Tyr Pro Trp
                85                  90                  95

Thr Phe Gly Gly Gly Thr Lys Leu Glu Phe Arg
            100                 105

<210> 372
<211> 219
<212> PRT
<213> Artificial

<220>
<223> an exemplary Pseudomonas exotoxin A variant 1(deim

```
Leu Asp Ala Ile Thr Gly Pro Glu Glu Gly Arg Leu Glu Thr
145                 150                 155                 160

Ile Leu Gly Trp Pro Leu Ala Glu Arg Thr Val Val Ile Pro Ser Ala
                165                 170                 175

Ile Pro Thr Asp Pro Arg Asn Val Gly Gly Asp Leu Asp Pro Ser Ser
            180                 185                 190

Ile Pro Asp Lys Glu Gln Ala Ile Ser Ala Leu Pro Asp Tyr Ala Ser
        195                 200                 205

Gln Pro Gly Lys Pro Pro Arg Glu Asp Leu Lys
    210                 215

<210> 373
<211> 219
<212> PRT
<213> Artificial

<220>
<223> an exemplary Pseudomonas exotoxin A variant 2(deimunized PE24 example)

<400> 373

Pro Thr Gly Ala Glu Phe Leu Gly Asp Gly Gly Asp Val Ser Phe Ser
1               5                   10                  15

Thr Arg Gly Thr Gln Asn Trp Thr Val Glu Arg Leu Leu Gln Ala His
            20                  25                  30

Ala Gln Leu Glu Glu Arg Gly Tyr Val Phe Val Gly Tyr His Gly Thr
        35                  40                  45

Ala Leu Glu Ala Ala Gln Ser Ile Val Phe Gly Gly Val Arg Ala Arg
    50                  55                  60

Ser Gln Asp Leu Arg Ala Ile Trp Arg Gly Phe Tyr Ile Ala Gly Asp
65                  70                  75                  80

Pro Ala His Ala Tyr Gly Tyr Ala Gln Asp Gln Glu Pro Asp Ala Arg
                85                  90                  95

Gly Arg Ile Ala Asn Gly Ala Leu Leu Arg Val Tyr Val Pro Ala Ser
            100                 105                 110

Ser Leu Pro Gly Phe Tyr Arg Thr Ser Leu Thr Leu Ala Ala Pro Glu
        115                 120                 125

Ala Ala Gly Glu Val Glu Arg Leu Ile Gly His Pro Leu Pro Leu Arg
    130                 135                 140

Leu Asp Ala Ile Thr Gly Pro Glu Glu Gly Gly Arg Glu Glu Thr
145                 150                 155                 160

Ile Leu Gly Trp Pro Leu Ala Glu Arg Thr Val Val Ile Pro Ser Ala
                165                 170                 175

Ile Pro Thr Asp Pro Arg Asn Val Gly Gly Asp Leu Asp Pro Ser Ser
            180                 185                 190

Ile Pro Asp Lys Glu Gln Ala Ile Ser Ala Leu Pro Asp Tyr Ala Ser
        195                 200                 205

Gln Pro Gly Lys Pro Pro Arg Glu Asp Leu Lys
    210                 215

<210> 374
<211> 107
<212> PRT
<213> Homo Sapiens

<400> 374

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
```

```
                    20                  25                  30

Tyr Pro Arg Glu Ala Lys Val Gln Trp Lys Val Asp Asn Ala Leu Gln
                35                  40                  45

Ser Gly Asn Ser Gln Glu Ser Val Thr Glu Gln Asp Ser Lys Asp Ser
            50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                        85                  90                  95

Pro Val Thr Lys Ser Phe Asn Arg Gly Glu Cys
                100                 105

<210> 375
<211> 105
<212> PRT
<213> Homo Sapiens

<400> 375

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
        50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                    85                  90                  95

Lys Thr Val Ala Pro Thr Glu Cys Ser
                100                 105

<210> 376
<211> 330
<212> PRT
<213> Homo Sapiens

<400> 376

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140
```

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> 377
<211> 330
<212> PRT
<213> homo sapiens

<400> 377

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

```
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> 378
<211> 330
<212> PRT
<213> homo sapiens

<400> 378

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> 379
<211> 327
<212> PRT
<213> Homo Sapiens

<400> 379

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> 380
<211> 280
<212> PRT
<213> homo sapiens

<400> 380

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
                20                  25                  30

Gly Lys Gly Ala Cys Pro Val Phe Glu Cys Gly Asn Val Val Leu Arg
            35                  40                  45

Thr Asp Glu Arg Asp Val Asn Tyr Trp Thr Ser Arg Tyr Trp Leu Asn
        50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

Met Asn Asp Glu Lys Phe Asn Leu Lys Leu Val Ile Lys Pro Ala Lys
                100                 105                 110

Val Thr Pro Ala Pro Thr Arg Gln Arg Asp Phe Thr Ala Ala Phe Pro
                115                 120                 125

Arg Met Leu Thr Thr Arg Gly His Gly Pro Ala Glu Thr Gln Thr Leu
130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg Ile Gly Ile Tyr Ile Gly Ala Gly Ile Cys Ala Gly Leu
                180                 185                 190

Ala Leu Ala Leu Ile Phe Gly Ala Leu Ile Phe Lys Trp Tyr Ser His
            195                 200                 205

Ser Lys Glu Lys Ile Gln Asn Leu Ser Leu Ile Ser Leu Ala Asn Leu
            210                 215                 220

Pro Pro Ser Gly Leu Ala Asn Ala Val Ala Glu Gly Ile Arg Ser Glu
225                 230                 235                 240

Glu Asn Ile Tyr Thr Ile Glu Glu Asn Val Tyr Glu Val Glu Glu Pro
                245                 250                 255

Asn Glu Tyr Tyr Cys Tyr Val Ser Ser Arg Gln Gln Pro Ser Gln Pro
                260                 265                 270

Leu Gly Cys Arg Phe Ala Met Pro
            275                 280

<210> 381
<211> 181
<212> PRT
<213> homo sapiens

<400> 381

Ser Glu Val Glu Tyr Arg Ala Glu Val Gly Gln Asn Ala Tyr Leu Pro
1               5                   10                  15

```
Cys Phe Tyr Thr Pro Ala Ala Pro Gly Asn Leu Val Pro Val Cys Trp
            20                  25                  30

Gly Lys Gly Ala Cys Pro Val Phe Glu Cys Gly Asn Val Val Leu Arg
            35                  40                  45

Thr Asp Glu Arg Asp Val Asn Tyr Trp Thr Ser Arg Tyr Trp Leu Asn
    50                  55                  60

Gly Asp Phe Arg Lys Gly Asp Val Ser Leu Thr Ile Glu Asn Val Thr
 65                  70                  75                  80

Leu Ala Asp Ser Gly Ile Tyr Cys Cys Arg Ile Gln Ile Pro Gly Ile
                85                  90                  95

Met Asn Asp Glu Lys Phe Asn Leu Lys Leu Val Ile Lys Pro Ala Lys
            100                 105                 110

Val Thr Pro Ala Pro Thr Arg Gln Arg Asp Phe Thr Ala Ala Phe Pro
            115                 120                 125

Arg Met Leu Thr Thr Arg Gly His Gly Pro Ala Glu Thr Gln Thr Leu
            130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg Ile Gly
            180
```

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

SEQUENCE LISTING

<160> NUMBER OF SEQ ID NOS: 430

<210> SEQ ID NO 1
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 1

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95
```

```
Ala Arg Asn Tyr Tyr Ala Gly Val Thr Pro Phe Asp Tyr Trp Gly Gln
            100                 105                 110

Gly Thr Leu Val Thr Val Ser Ser
        115                 120
```

<210> SEQ ID NO 2
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Tyr Tyr Thr Gly Gly Ser Ser Ala Phe Asp Tyr Trp Gly
            100                 105                 110

Gln Gly Thr Leu Val Thr Val Ser
        115                 120
```

<210> SEQ ID NO 3
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Tyr Tyr Leu Phe Ser Thr Ser Phe Asp Tyr Trp Gly Gln
            100                 105                 110

Gly Thr Leu Val Thr Val Ser Ser
        115                 120
```

```
<210> SEQ ID NO 4
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Tyr Tyr Ile Gly Ile Val Pro Phe Asp Tyr Trp Gly Gln
            100                 105                 110

Gly Thr Leu Val Thr Val Ser Ser
        115                 120

```
<210> SEQ ID NO 5
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Tyr Tyr Val Gly Val Ser Pro Phe Asp Tyr Trp Gly Gln
            100                 105                 110

Gly Thr Leu Val Thr Val Ser Ser
        115                 120

```
<210> SEQ ID NO 6
<211> LENGTH: 120
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Phe Thr Val Leu Arg Val Pro Phe Asp Tyr Trp Gly Gln
            100                 105                 110

Gly Thr Leu Val Thr Val Ser Ser
        115                 120

<210> SEQ ID NO 7
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Tyr Tyr Ile Gly Val Val Thr Phe Asp Tyr Trp Gly Gln
            100                 105                 110

Gly Thr Leu Val Thr Val Ser Ser
        115                 120

<210> SEQ ID NO 8
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ser Tyr Tyr Met His
1               5

<210> SEQ ID NO 9
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ile Ile Asn Pro Ser Gly Gly Ser Thr Ser Tyr Ala Gln Lys Phe Gln
1               5                   10                  15

Gly

<210> SEQ ID NO 10
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Asn Tyr Tyr Ile Gly Val Val Thr Phe Asp Tyr
1               5                   10

<210> SEQ ID NO 11
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Trp Arg Arg Tyr Thr Ser Phe Asp Tyr Trp Gly Gln
                100                 105                 110

Gly Thr Leu Val Thr Val Ser Ser
            115                 120

<210> SEQ ID NO 12
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 12

Gly Glu Trp Arg Arg Tyr Thr Ser Phe Asp Tyr
1               5                   10

<210> SEQ ID NO 13
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Trp Ile Arg Trp Glu His Phe Asp Tyr Trp Gly Gln
            100                 105                 110

Gly Thr Leu Val Thr Val Ser Ser
        115                 120

<210> SEQ ID NO 14
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gly Gly Trp Ile Arg Trp Glu His Phe Asp Tyr
1               5                   10

<210> SEQ ID NO 15
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60
```

```
Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
             85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser
        115                 120

<210> SEQ ID NO 16
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Asn Ala Trp Met Ser
1               5

<210> SEQ ID NO 17
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Arg Ile Lys Ser Lys Thr Asp Gly Gly Thr Thr Asp Tyr Ala Ala Pro
1               5                   10                  15

Val Lys Gly

<210> SEQ ID NO 18
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Pro Trp Glu Trp Ser Trp Tyr Asp Tyr
1               5

<210> SEQ ID NO 19
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
```

```
                35                  40                  45

Gly Arg Ile Lys Ser Lys Thr Asp Gly Gly Thr Thr Asp Tyr Ala Ala
        50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                    85                  90                  95

Tyr Cys Thr Thr Pro Trp Glu Trp Ser Tyr Phe Asp Tyr Trp Gly Gln
                100                 105                 110

Gly Thr Leu Val Thr Val Ser Ser
            115                 120

<210> SEQ ID NO 20
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Pro Trp Glu Trp Ser Tyr Phe Asp Tyr
 1               5

<210> SEQ ID NO 21
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
            35                  40                  45

Gly Arg Ile Lys Ser Lys Thr Asp Gly Gly Thr Thr Asp Tyr Ala Ala
        50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                    85                  90                  95

Tyr Cys Thr Thr Pro Trp Glu Trp Ala Trp Phe Asp Tyr Trp Gly Gln
                100                 105                 110

Gly Thr Leu Val Thr Val Ser Ser
            115                 120

<210> SEQ ID NO 22
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22
```

```
Pro Trp Glu Trp Ala Trp Phe Asp Tyr
1               5
```

<210> SEQ ID NO 23
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ala Tyr Phe Asp Tyr Trp Gly Gln
            100                 105                 110

Gly Thr Leu Val Thr Val Ser Ser
        115                 120
```

<210> SEQ ID NO 24
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

```
Pro Trp Glu Trp Ala Tyr Phe Asp Tyr
1               5
```

<210> SEQ ID NO 25
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60
```

```
Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Gly Trp Ser Arg Trp Gly Tyr Met Asp Tyr Trp Gly Gln
            100                 105                 110

Gly Thr Leu Val Thr Val Ser Ser
        115                 120

<210> SEQ ID NO 26
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Thr Gly Trp Ser Arg Trp Gly Tyr Met Asp Tyr
1               5                   10

<210> SEQ ID NO 27
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Trp Ile Arg Tyr Tyr His Phe Asp Tyr Trp Gly Gln
            100                 105                 110

Gly Thr Leu Val Thr Val Ser Ser
        115                 120

<210> SEQ ID NO 28
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gly Glu Trp Ile Arg Tyr Tyr His Phe Asp Tyr
1               5                   10
```

```
<210> SEQ ID NO 29
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Trp Tyr Arg Trp Gly Tyr Met Asp Tyr Trp Gly Gln
            100                 105                 110

Gly Thr Leu Val Thr Val Ser Ser
        115                 120

<210> SEQ ID NO 30
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Val Gly Trp Tyr Arg Trp Gly Tyr Met Asp Tyr
1               5                   10

<210> SEQ ID NO 31
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95
```

Leu Trp Val Phe Gly Gly Gly Thr Lys Leu Thr Val Leu
            100                 105

<210> SEQ ID NO 32
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gly Ser Ser Thr Gly Ala Val Thr Thr Ser Asn Tyr Ala Asn
1               5                   10

<210> SEQ ID NO 33
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Gly Thr Asn Lys Arg Ala Pro
1               5

<210> SEQ ID NO 34
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ala Leu Trp Tyr Ser Asn Leu Trp Val
1               5

<210> SEQ ID NO 35
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

```
Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 36
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 37
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Thr Tyr Ala Met Asn
1               5

<210> SEQ ID NO 38
<211> LENGTH: 19
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 38

```
Arg Ile Arg Ser Lys Tyr Asn Asn Tyr Ala Thr Tyr Tyr Ala Asp Ser
1               5                   10                  15

Val Lys Gly
```

<210> SEQ ID NO 39
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 39

```
His Gly Asn Phe Gly Asn Ser Tyr Val Ser Trp Phe Ala Tyr
1               5                   10
```

<210> SEQ ID NO 40
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 40

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205
```

```
Asn Val Asn His Lys Pro Ser Asn Thr Lys Val Asp Lys Lys Val Glu
    210                 215                 220

Pro Lys Ser Cys
225

<210> SEQ ID NO 41
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Val Phe Tyr Arg Ala Trp Tyr Ser Phe Asp Tyr Trp Gly
            100                 105                 110

Gln Gly Thr Thr Val Thr Val Ser Ser
        115                 120

<210> SEQ ID NO 42
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ser Tyr Ala Ile Ser
1               5

<210> SEQ ID NO 43
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Gly Ile Ile Pro Ile Phe Gly Thr Ala Asn Tyr Ala Gln Lys Phe Gln
1               5                   10                  15

Gly

<210> SEQ ID NO 44
<211> LENGTH: 12
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 44

Ala Val Phe Tyr Arg Ala Trp Tyr Ser Phe Asp Tyr
1               5                   10

<210> SEQ ID NO 45
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Thr Ser Pro Pro Pro
                85                  90                  95

Thr Phe Gly Gln Gly Thr Lys Val Glu Ile Lys
            100                 105

<210> SEQ ID NO 46
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Arg Ala Ser Gln Ser Ile Ser Ser Trp Leu Ala
1               5                   10

<210> SEQ ID NO 47
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Asp Ala Ser Ser Leu Glu Ser
1               5

<210> SEQ ID NO 48
<211> LENGTH: 9
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 48

Gln Gln Tyr Thr Ser Pro Pro Thr
1               5

<210> SEQ ID NO 49
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr His Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Phe Phe Thr Gly Phe His Leu Asp Tyr Trp Gly Gln Gly
            100                 105                 110

Thr Leu Val Thr Val Ser Ser
        115

<210> SEQ ID NO 50
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Ser Phe Phe Thr Gly Phe His Leu Asp Tyr
1               5                   10

<210> SEQ ID NO 51
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
```

```
            35                  40                  45
Ile Tyr Gly Ala Ser Ser Arg Ala Thr Gly Ile Pro Asp Arg Phe Ser
         50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Thr Asn Glu His
                 85                  90                  95
Tyr Tyr Thr Phe Gly Gln Gly Thr Lys Val Glu Ile Lys
            100                 105

<210> SEQ ID NO 52
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Arg Ala Ser Gln Ser Val Ser Ser Ser Tyr Leu Ala
 1               5                  10

<210> SEQ ID NO 53
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Gly Ala Ser Ser Arg Ala Thr
 1               5

<210> SEQ ID NO 54
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Gln Gln Tyr Thr Asn Glu His Tyr Tyr Thr
 1               5                  10

<210> SEQ ID NO 55
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Ser Tyr
             20                  25                  30
Tyr Met His Trp Val Arg Gln Ala Pro Gly Gln Gly Leu Glu Trp Met
         35                  40                  45
```

```
Gly Ile Ile Asn Pro Ser Gly Gly Pro Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Phe Ala Trp Leu Asp Tyr Trp Gly Gln Gly Thr Leu
            100                 105                 110

Val Thr Val Ser Ser
            115
```

```
<210> SEQ ID NO 56
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Ile Ile Asn Pro Ser Gly Gly Pro Thr Ser Tyr Ala Gln Lys Phe Gln
1               5                   10                  15

Gly
```

```
<210> SEQ ID NO 57
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Gly Asp Phe Ala Trp Leu Asp Tyr
1               5
```

```
<210> SEQ ID NO 58
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Ile Met Asn Arg Thr Phe Gly Gln Gly Thr Lys Val Glu Ile Lys
```

<210> SEQ ID NO 59
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 59

Arg Ser Ser Gln Ser Leu Leu His Ser Asn Gly Tyr Asn Tyr Leu Asp
1               5                   10                  15

<210> SEQ ID NO 60
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 60

Leu Gly Ser Asn Arg Ala Ser
1               5

<210> SEQ ID NO 61
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 61

Met Gln Ala Ser Ile Met Asn Arg Thr
1               5

<210> SEQ ID NO 62
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 62

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Ile Met Asn Arg Thr Phe Gly Gln Gly Thr Lys Val Glu Ile Lys
            100                 105                 110

<210> SEQ ID NO 63
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Met Gln Ala Ser Ile Met Ser Arg Thr
1               5

<210> SEQ ID NO 64
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Ile Met Gln Arg Thr Phe Gly Gln Gly Thr Lys Val Glu Ile Lys
            100                 105                 110

<210> SEQ ID NO 65
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Met Gln Ala Ser Ile Met Gln Arg Thr
1               5

<210> SEQ ID NO 66
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Asp Ile Val Met Thr Gln Ser Pro Leu Ser Leu Pro Val Thr Pro Gly
1               5                   10                  15

```
Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Ile Met Asn Arg Ala Phe Gly Gln Gly Thr Lys Val Glu Ile Lys
            100                 105                 110

<210> SEQ ID NO 67
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Met Gln Ala Ser Ile Met Asn Arg Ala
1               5

<210> SEQ ID NO 68
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Ile Met Asn Arg Asn Phe Gly Gln Gly Thr Lys Val Glu Ile Lys
            100                 105                 110

<210> SEQ ID NO 69
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Met Gln Ala Ser Ile Met Asn Arg Asn
```

<210> SEQ ID NO 70
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Tyr Ile Asp Met Asp Tyr Trp Gly Gln Gly Thr Leu Val
            100                 105                 110

Thr Val Ser Ser
        115

<210> SEQ ID NO 71
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 71

Ser Tyr Ile Asp Met Asp Tyr
1               5

<210> SEQ ID NO 72
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 72

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

```
Pro Glu Asp Phe Ala Val Tyr Tyr Cys Gln Gln Asp Asn Trp Ser Pro
                85                  90                  95
Thr Phe Gly Gln Gly Thr Lys Val Glu Ile Lys
            100                 105

<210> SEQ ID NO 73
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Gln Gln Asp Asn Trp Ser Pro Thr
1               5

<210> SEQ ID NO 74
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
                20                  25                  30
Tyr Met His Trp Val Arg Gln Ala Pro Gly Gln Gly Leu Glu Trp Met
            35                  40                  45
Gly Ile Ile Asn Pro Ser Gly Gly Ser Thr Ser Tyr Ala Gln Lys Phe
        50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Ser Tyr Val Asp Met Asp Tyr Trp Gly Gln Gly Thr Leu Val
            100                 105                 110
Thr Val Ser Ser
        115

<210> SEQ ID NO 75
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Ser Tyr Val Asp Met Asp Tyr
1               5

<210> SEQ ID NO 76
<211> LENGTH: 107
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic polypeptide"

<400> SEQUENCE: 76

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Ile Trp Ser Pro
                85                  90                  95

Thr Phe Gly Gln Gly Thr Lys Val Glu Ile Lys
            100                 105
```

<210> SEQ ID NO 77
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

```
Gln Gln Asp Ile Trp Ser Pro Thr
1               5
```

<210> SEQ ID NO 78
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Ser Tyr Val Glu Trp Tyr Ala Phe Asp Tyr Trp Gly
                100                 105                 110

Gln Gly Thr Leu Val Thr Val Ser Ser
            115                 120
```

```
<210> SEQ ID NO 79
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Ser Tyr Ala Met Ser
1               5

<210> SEQ ID NO 80
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Ala Ile Ser Gly Ser Gly Gly Ser Thr Tyr Tyr Ala Asp Ser Val Lys
1               5                   10                  15

Gly

<210> SEQ ID NO 81
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Asp Ser Ser Tyr Val Glu Trp Tyr Ala Phe Asp Tyr
1               5                   10

<210> SEQ ID NO 82
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Ser Thr Leu Thr Ile Ser Arg Leu Glu
65                  70                  75                  80

Pro Glu Asp Phe Ala Val Tyr Tyr Cys Gln Gln Pro Thr Ser Ser Pro
                85                  90                  95

Ile Thr Phe Gly Gln Gly Thr Lys Val Glu Ile Lys
            100                 105
```

```
<210> SEQ ID NO 83
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Gln Gln Pro Thr Ser Ser Pro Ile Thr
1               5

<210> SEQ ID NO 84
<211> LENGTH: 103
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 85
<211> LENGTH: 103
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
```

```
<210> SEQ ID NO 86
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys
    210

<210> SEQ ID NO 87
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60
```

```
Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 88
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
            100                 105

<210> SEQ ID NO 89
<211> LENGTH: 689
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89
```

-continued

```
Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asn Ala
            20                  25                  30
Trp Met Ser Trp Val Arg Gln Ala Pro Gly Lys Gly Leu Glu Trp Val
        35                  40                  45
Gly Arg Ile Lys Ser Lys Thr Asp Gly Gly Thr Thr Asp Tyr Ala Ala
    50                  55                  60
Pro Val Lys Gly Arg Phe Thr Ile Ser Arg Asp Asp Ser Lys Asn Thr
65                  70                  75                  80
Leu Tyr Leu Gln Met Asn Ser Leu Lys Thr Glu Asp Thr Ala Val Tyr
            85                  90                  95
Tyr Cys Thr Thr Pro Trp Glu Trp Ser Trp Tyr Asp Tyr Trp Gly Gln
        100                 105                 110
Gly Thr Leu Val Thr Val Ser Ser Ala Ser Thr Lys Gly Pro Ser Val
    115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
        180                 185                 190
Ser Ser Ser Leu Gly Thr Gln Thr Tyr Ile Cys Asn Val Asn His Lys
    195                 200                 205
Pro Ser Asn Thr Lys Val Asp Lys Lys Val Glu Pro Lys Ser Cys Asp
210                 215                 220
Gly Gly Gly Gly Ser Gly Gly Gly Ser Glu Val Gln Leu Leu Glu
225                 230                 235                 240
Ser Gly Gly Gly Leu Val Gln Pro Gly Gly Ser Leu Arg Leu Ser Cys
            245                 250                 255
Ala Ala Ser Gly Phe Thr Phe Ser Thr Tyr Ala Met Asn Trp Val Arg
        260                 265                 270
Gln Ala Pro Gly Lys Gly Leu Glu Trp Val Ser Arg Ile Arg Ser Lys
    275                 280                 285
Tyr Asn Asn Tyr Ala Thr Tyr Tyr Ala Asp Ser Val Lys Gly Arg Phe
290                 295                 300
Thr Ile Ser Arg Asp Asp Ser Lys Asn Thr Leu Tyr Leu Gln Met Asn
305                 310                 315                 320
Ser Leu Arg Ala Glu Asp Thr Ala Val Tyr Tyr Cys Val Arg His Gly
            325                 330                 335
Asn Phe Gly Asn Ser Tyr Val Ser Trp Phe Ala Tyr Trp Gly Gln Gly
        340                 345                 350
Thr Leu Val Thr Val Ser Ser Ala Ser Thr Lys Gly Pro Ser Val Phe
    355                 360                 365
Pro Leu Ala Pro Ser Ser Lys Ser Thr Ser Gly Gly Thr Ala Ala Leu
370                 375                 380
Gly Cys Leu Val Lys Asp Tyr Phe Pro Glu Pro Val Thr Val Ser Trp
385                 390                 395                 400
Asn Ser Gly Ala Leu Thr Ser Gly Val His Thr Phe Pro Ala Val Leu
            405                 410                 415
Gln Ser Ser Gly Leu Tyr Ser Leu Ser Ser Val Val Thr Val Pro Ser
```

```
                    420                 425                 430
Ser Ser Leu Gly Thr Gln Thr Tyr Ile Cys Asn Val Asn His Lys Pro
        435                 440                 445

Ser Asn Thr Lys Val Asp Lys Lys Val Glu Pro Lys Ser Cys Asp Lys
        450                 455                 460

Thr His Thr Cys Pro Pro Cys Pro Ala Pro Glu Ala Ala Gly Gly Pro
465                 470                 475                 480

Ser Val Phe Leu Phe Pro Pro Lys Pro Lys Asp Thr Leu Met Ile Ser
                485                 490                 495

Arg Thr Pro Glu Val Thr Cys Val Val Val Asp Val Ser His Glu Asp
                500                 505                 510

Pro Glu Val Lys Phe Asn Trp Tyr Val Asp Gly Val Glu Val His Asn
                515                 520                 525

Ala Lys Thr Lys Pro Arg Glu Glu Gln Tyr Asn Ser Thr Tyr Arg Val
        530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Gly Ala Pro Ile Glu Lys
                565                 570                 575

Thr Ile Ser Lys Ala Lys Gly Gln Pro Arg Glu Pro Gln Val Tyr Thr
                580                 585                 590

Leu Pro Pro Cys Arg Asp Glu Leu Thr Lys Asn Gln Val Ser Leu Trp
                595                 600                 605

Cys Leu Val Lys Gly Phe Tyr Pro Ser Asp Ile Ala Val Glu Trp Glu
        610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
                645                 650                 655

Ser Arg Trp Gln Gln Gly Asn Val Phe Ser Cys Ser Val Met His Glu
                660                 665                 670

Ala Leu His Asn His Tyr Thr Gln Lys Ser Leu Ser Leu Ser Pro Gly
        675                 680                 685

Lys

<210> SEQ ID NO 90
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80
```

```
Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Gly Gly Thr Ala Ala
130             135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn Arg Phe Thr Gln Lys Ser Leu Ser Leu Ser Pro
        435                 440                 445

Gly Lys
    450

<210> SEQ ID NO 91
<211> LENGTH: 689
<212> TYPE: PRT
<213> ORGANISM: Artificial Sequence
<220> FEATURE:
<221> NAME/KEY: source
```

<223> OTHER INFORMATION: /note="Description of Artificial Sequence: Synthetic polypeptide"

<400> SEQUENCE: 91

| | | | | | | | | | | | | | | |
|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Thr | Tyr |
| | | | 20 | | | | | 25 | | | | | 30 | | |
| Ala | Met | Asn | Trp | Val | Arg | Gln | Ala | Pro | Gly | Lys | Gly | Leu | Glu | Trp | Val |
| | | 35 | | | | | 40 | | | | | 45 | | | |
| Ser | Arg | Ile | Arg | Ser | Lys | Tyr | Asn | Asn | Tyr | Ala | Thr | Tyr | Tyr | Ala | Asp |
| 50 | | | | | 55 | | | | | 60 | | | | | |
| Ser | Val | Lys | Gly | Arg | Phe | Thr | Ile | Ser | Arg | Asp | Asp | Ser | Lys | Asn | Thr |
| 65 | | | | | 70 | | | | | 75 | | | | | 80 |
| Leu | Tyr | Leu | Gln | Met | Asn | Ser | Leu | Arg | Ala | Glu | Asp | Thr | Ala | Val | Tyr |
| | | | | 85 | | | | | 90 | | | | | 95 | |
| Tyr | Cys | Val | Arg | His | Gly | Asn | Phe | Gly | Asn | Ser | Tyr | Val | Ser | Trp | Phe |
| | | | 100 | | | | | 105 | | | | | 110 | | |
| Ala | Tyr | Trp | Gly | Gln | Gly | Thr | Leu | Val | Thr | Val | Ser | Ser | Ala | Ser | Thr |
| | | 115 | | | | | 120 | | | | | 125 | | | |
| Lys | Gly | Pro | Ser | Val | Phe | Pro | Leu | Ala | Pro | Ser | Ser | Lys | Ser | Thr | Ser |
| | 130 | | | | | 135 | | | | | 140 | | | | |
| Gly | Gly | Thr | Ala | Ala | Leu | Gly | Cys | Leu | Val | Lys | Asp | Tyr | Phe | Pro | Glu |
| 145 | | | | | 150 | | | | | 155 | | | | | 160 |
| Pro | Val | Thr | Val | Ser | Trp | Asn | Ser | Gly | Ala | Leu | Thr | Ser | Gly | Val | His |
| | | | | 165 | | | | | 170 | | | | | 175 | |
| Thr | Phe | Pro | Ala | Val | Leu | Gln | Ser | Ser | Gly | Leu | Tyr | Ser | Leu | Ser | Ser |
| | | | 180 | | | | | 185 | | | | | 190 | | |
| Val | Val | Thr | Val | Pro | Ser | Ser | Ser | Leu | Gly | Thr | Gln | Thr | Tyr | Ile | Cys |
| | | | 195 | | | | | 200 | | | | | 205 | | |
| Asn | Val | Asn | His | Lys | Pro | Ser | Asn | Thr | Lys | Val | Asp | Lys | Lys | Val | Glu |
| | 210 | | | | | 215 | | | | | 220 | | | | |
| Pro | Lys | Ser | Cys | Asp | Gly | Gly | Gly | Gly | Ser | Gly | Gly | Gly | Gly | Ser | Glu |
| 225 | | | | | 230 | | | | | 235 | | | | | 240 |
| Val | Gln | Leu | Val | Glu | Ser | Gly | Gly | Gly | Leu | Val | Lys | Pro | Gly | Gly | Ser |
| | | | | 245 | | | | | 250 | | | | | 255 | |
| Leu | Arg | Leu | Ser | Cys | Ala | Ala | Ser | Gly | Phe | Thr | Phe | Ser | Asn | Ala | Trp |
| | | | 260 | | | | | 265 | | | | | 270 | | |
| Met | Ser | Trp | Val | Arg | Gln | Ala | Pro | Gly | Lys | Gly | Leu | Glu | Trp | Val | Gly |
| | | 275 | | | | | 280 | | | | | 285 | | | |
| Arg | Ile | Lys | Ser | Lys | Thr | Asp | Gly | Gly | Thr | Thr | Asp | Tyr | Ala | Ala | Pro |
| | 290 | | | | | 295 | | | | | 300 | | | | |
| Val | Lys | Gly | Arg | Phe | Thr | Ile | Ser | Arg | Asp | Asp | Ser | Lys | Asn | Thr | Leu |
| 305 | | | | | 310 | | | | | 315 | | | | | 320 |
| Tyr | Leu | Gln | Met | Asn | Ser | Leu | Lys | Thr | Glu | Asp | Thr | Ala | Val | Tyr | Tyr |
| | | | | 325 | | | | | 330 | | | | | 335 | |
| Cys | Thr | Thr | Pro | Trp | Glu | Trp | Ser | Trp | Tyr | Asp | Tyr | Trp | Gly | Gln | Gly |
| | | | 340 | | | | | 345 | | | | | 350 | | |
| Thr | Leu | Val | Thr | Val | Ser | Ser | Ala | Ser | Thr | Lys | Gly | Pro | Ser | Val | Phe |
| | | 355 | | | | | 360 | | | | | 365 | | | |
| Pro | Leu | Ala | Pro | Ser | Ser | Lys | Ser | Thr | Ser | Gly | Gly | Thr | Ala | Ala | Leu |
| | 370 | | | | | 375 | | | | | 380 | | | | |
| Gly | Cys | Leu | Val | Lys | Asp | Tyr | Phe | Pro | Glu | Pro | Val | Thr | Val | Ser | Trp |
| 385 | | | | | 390 | | | | | 395 | | | | | 400 |

-continued

```
Asn Ser Gly Ala Leu Thr Ser Gly Val His Thr Phe Pro Ala Val Leu
            405                 410                 415

Gln Ser Ser Gly Leu Tyr Ser Leu Ser Ser Val Val Thr Val Pro Ser
        420                 425                 430

Ser Ser Leu Gly Thr Gln Thr Tyr Ile Cys Asn Val Asn His Lys Pro
            435                 440                 445

Ser Asn Thr Lys Val Asp Lys Lys Val Glu Pro Lys Ser Cys Asp Lys
450                 455                 460

Thr His Thr Cys Pro Pro Cys Pro Ala Pro Glu Ala Ala Gly Gly Pro
465                 470                 475                 480

Ser Val Phe Leu Phe Pro Pro Lys Pro Lys Asp Thr Leu Met Ile Ser
            485                 490                 495

Arg Thr Pro Glu Val Thr Cys Val Val Val Asp Val Ser His Glu Asp
            500                 505                 510

Pro Glu Val Lys Phe Asn Trp Tyr Val Asp Gly Val Glu Val His Asn
        515                 520                 525

Ala Lys Thr Lys Pro Arg Glu Glu Gln Tyr Asn Ser Thr Tyr Arg Val
    530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Gly Ala Pro Ile Glu Lys
            565                 570                 575

Thr Ile Ser Lys Ala Lys Gly Gln Pro Arg Glu Pro Gln Val Tyr Thr
        580                 585                 590

Leu Pro Pro Cys Arg Asp Glu Leu Thr Lys Asn Gln Val Ser Leu Trp
            595                 600                 605

Cys Leu Val Lys Gly Phe Tyr Pro Ser Asp Ile Ala Val Glu Trp Glu
610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
            645                 650                 655

Ser Arg Trp Gln Gln Gly Asn Val Phe Ser Cys Ser Val Met His Glu
        660                 665                 670

Ala Leu His Asn His Tyr Thr Gln Lys Ser Leu Ser Leu Ser Pro Gly
            675                 680                 685

Lys
```

```
<210> SEQ ID NO 92
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
```

```
            50                  55                  60
Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
                115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
                195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Gly Ala Pro Ile Glu Lys Thr Ile Ser Lys Ala Lys Gly Gln Pro Arg
                340                 345                 350

Glu Pro Gln Val Tyr Thr Leu Pro Pro Cys Arg Asp Glu Leu Thr Lys
                355                 360                 365

Asn Gln Val Ser Leu Trp Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys
450                 455

<210> SEQ ID NO 93
```

```
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Phe Thr Gln Lys Ser Leu Ser Leu Ser
    210                 215                 220

Pro Gly Lys
225

<210> SEQ ID NO 94
<211> LENGTH: 690
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Pro Thr Ser Tyr Ala Gln Lys Phe
    50                  55                  60
```

```
Gln Gly Arg Val Thr Met Thr Arg Asp Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Asp Phe Ala Trp Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Gly Gly Gly
210                 215                 220

Gly Ser Gly Gly Gly Gly Ser Glu Val Gln Leu Leu Glu Ser Gly Gly
225                 230                 235                 240

Gly Leu Val Gln Pro Gly Gly Ser Leu Arg Leu Ser Cys Ala Ala Ser
                245                 250                 255

Gly Phe Thr Phe Ser Thr Tyr Ala Met Asn Trp Val Arg Gln Ala Pro
            260                 265                 270

Gly Lys Gly Leu Glu Trp Val Ser Arg Ile Arg Ser Lys Tyr Asn Asn
        275                 280                 285

Tyr Ala Thr Tyr Tyr Ala Asp Ser Val Lys Gly Arg Phe Thr Ile Ser
290                 295                 300

Arg Asp Asp Ser Lys Asn Thr Leu Tyr Leu Gln Met Asn Ser Leu Arg
305                 310                 315                 320

Ala Glu Asp Thr Ala Val Tyr Tyr Cys Val Arg His Gly Asn Phe Gly
                325                 330                 335

Asn Ser Tyr Val Ser Trp Phe Ala Tyr Trp Gly Gln Gly Thr Leu Val
            340                 345                 350

Thr Val Ser Ser Ala Ser Val Ala Ala Pro Ser Val Phe Ile Phe Pro
        355                 360                 365

Pro Ser Asp Glu Gln Leu Lys Ser Gly Thr Ala Ser Val Val Cys Leu
370                 375                 380

Leu Asn Asn Phe Tyr Pro Arg Glu Ala Lys Val Gln Trp Lys Val Asp
385                 390                 395                 400

Asn Ala Leu Gln Ser Gly Asn Ser Gln Glu Ser Val Thr Glu Gln Asp
                405                 410                 415

Ser Lys Asp Ser Thr Tyr Ser Leu Ser Ser Thr Leu Thr Leu Ser Lys
            420                 425                 430

Ala Asp Tyr Glu Lys His Lys Val Tyr Ala Cys Glu Val Thr His Gln
        435                 440                 445

Gly Leu Ser Ser Pro Val Thr Lys Ser Phe Asn Arg Gly Glu Cys Asp
450                 455                 460

Lys Thr His Thr Cys Pro Pro Cys Pro Ala Pro Glu Ala Ala Gly Gly
465                 470                 475                 480

Pro Ser Val Phe Leu Phe Pro Pro Lys Pro Lys Asp Thr Leu Met Ile
```

```
                    485                 490                 495

Ser Arg Thr Pro Glu Val Thr Cys Val Val Asp Val Ser His Glu
                500                 505                 510

Asp Pro Glu Val Lys Phe Asn Trp Tyr Val Asp Gly Val Glu Val His
                515                 520                 525

Asn Ala Lys Thr Lys Pro Arg Glu Glu Gln Tyr Asn Ser Thr Tyr Arg
            530                 535                 540

Val Val Ser Val Leu Thr Val Leu His Gln Asp Trp Leu Asn Gly Lys
545                 550                 555                 560

Glu Tyr Lys Cys Lys Val Ser Asn Lys Ala Leu Gly Ala Pro Ile Glu
                565                 570                 575

Lys Thr Ile Ser Lys Ala Lys Gly Gln Pro Arg Glu Pro Gln Val Tyr
                580                 585                 590

Thr Leu Pro Pro Cys Arg Asp Glu Leu Thr Lys Asn Gln Val Ser Leu
                595                 600                 605

Trp Cys Leu Val Lys Gly Phe Tyr Pro Ser Asp Ile Ala Val Glu Trp
            610                 615                 620

Glu Ser Asn Gly Gln Pro Glu Asn Asn Tyr Lys Thr Thr Pro Pro Val
625                 630                 635                 640

Leu Asp Ser Asp Gly Ser Phe Phe Leu Tyr Ser Lys Leu Thr Val Asp
                645                 650                 655

Lys Ser Arg Trp Gln Gln Gly Asn Val Phe Ser Cys Ser Val Met His
                660                 665                 670

Glu Ala Leu His Asn His Tyr Thr Gln Lys Ser Leu Ser Leu Ser Pro
            675                 680                 685

Gly Lys
    690

<210> SEQ ID NO 95
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Pro Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Phe Ala Trp Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140
```

```
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 96
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45
```

```
Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Ser Ile Met Asn Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
210                 215
```

```
<210> SEQ ID NO 97
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (603)..(603)
<223> OTHER INFORMATION: a, c, t, g, unknown or other

<400> SEQUENCE: 97
gaaatcgtgt taacgcagtc tccaggcacc ctgtctttgt ctccagggga aagagccacc    60
ctctcttgca gggccagtca gagtgttagc agcagctact tagcctggta ccagcagaaa   120
cctggccagg ctcccaggct cctcatctat ggagcatcca gcagggccac tggcatccca   180
gacaggttca gtggcagtgg atccgggaca gacttcactc tcaccatcag cagactggag   240
cctgaagatt ttgcagtgta ttactgtcag cagtatacca cgaacatta ttatacgttc    300 ggccagggga ccaaagtgga aatcaaacgt acggtggctg caccatctgt cttcatcttc   360
ccgccatctg atgagcagtt gaaatctgga actgcctctg ttgtgtgcct gctgaataac   420
ttctatccca gagaggccaa agtacagtgg aaggtggata acgccctcca atcgggtaac   480
tcccaggaga gtgtcacaga gcaggacagc aaggacagca cctacagcct cagcagcacc   540
ctgacgctga gcaaagcaga ctacgagaaa cacaaagtct acgcctgcga agtcacccat   600
canggcctga gctcgcccgt cacaaagagc ttcaacaggg gagagtgt              648
```

```
<210> SEQ ID NO 98
<211> LENGTH: 459
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 98

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys Asp Lys Thr His Thr Cys Pro Pro
225                 230                 235                 240

Cys Pro Ala Pro Glu Ala Ala Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Gly Ala Pro Ile Glu Lys Thr Ile Ser Lys Ala Lys
            340                 345                 350

Gly Gln Pro Arg Glu Pro Gln Val Tyr Thr Leu Pro Pro Cys Arg Asp
        355                 360                 365

Glu Leu Thr Lys Asn Gln Val Ser Leu Trp Cys Leu Val Lys Gly Phe
    370                 375                 380

Tyr Pro Ser Asp Ile Ala Val Glu Trp Glu Ser Asn Gly Gln Pro Glu
385                 390                 395                 400
```

-continued

Asn Asn Tyr Lys Thr Thr Pro Pro Val Leu Asp Ser Asp Gly Ser Phe
            405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
            435                 440                 445

Thr Gln Lys Ser Leu Ser Leu Ser Pro Gly Lys
            450                 455

<210> SEQ ID NO 99
<211> LENGTH: 689
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Gly Gly Gly Gly Ser Gly Gly Gly Ser Glu Val Gln Leu Leu Glu
225                 230                 235                 240

Ser Gly Gly Gly Leu Val Gln Pro Gly Gly Ser Leu Arg Leu Ser Cys
                245                 250                 255

Ala Ala Ser Gly Phe Thr Phe Ser Thr Tyr Ala Met Asn Trp Val Arg
            260                 265                 270

Gln Ala Pro Gly Lys Gly Leu Glu Trp Val Ser Arg Ile Arg Ser Lys
        275                 280                 285

Tyr Asn Asn Tyr Ala Thr Tyr Tyr Ala Asp Ser Val Lys Gly Arg Phe

```
            290                 295                 300
Thr Ile Ser Arg Asp Asp Ser Lys Asn Thr Leu Tyr Leu Gln Met Asn
305                 310                 315                 320

Ser Leu Arg Ala Glu Asp Thr Ala Val Tyr Tyr Cys Val Arg His Gly
                325                 330                 335

Asn Phe Gly Ala Ser Tyr Val Ser Trp Phe Ala Tyr Trp Gly Gln Gly
                340                 345                 350

Thr Leu Val Thr Val Ser Ser Ala Ser Thr Lys Gly Pro Ser Val Phe
            355                 360                 365

Pro Leu Ala Pro Ser Ser Lys Ser Thr Ser Gly Gly Thr Ala Ala Leu
        370                 375                 380

Gly Cys Leu Val Lys Asp Tyr Phe Pro Glu Pro Val Thr Val Ser Trp
385                 390                 395                 400

Asn Ser Gly Ala Leu Thr Ser Gly Val His Thr Phe Pro Ala Val Leu
                405                 410                 415

Gln Ser Ser Gly Leu Tyr Ser Leu Ser Ser Val Val Thr Val Pro Ser
                420                 425                 430

Ser Ser Leu Gly Thr Gln Thr Tyr Ile Cys Asn Val Asn His Lys Pro
            435                 440                 445

Ser Asn Thr Lys Val Asp Lys Lys Val Glu Pro Lys Ser Cys Asp Lys
        450                 455                 460

Thr His Thr Cys Pro Pro Cys Pro Ala Pro Glu Ala Ala Gly Gly Pro
465                 470                 475                 480

Ser Val Phe Leu Phe Pro Pro Lys Pro Lys Asp Thr Leu Met Ile Ser
                485                 490                 495

Arg Thr Pro Glu Val Thr Cys Val Val Val Asp Val Ser His Glu Asp
                500                 505                 510

Pro Glu Val Lys Phe Asn Trp Tyr Val Asp Gly Val Glu Val His Asn
            515                 520                 525

Ala Lys Thr Lys Pro Arg Glu Glu Gln Tyr Asn Ser Thr Tyr Arg Val
        530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Gly Ala Pro Ile Glu Lys
                565                 570                 575

Thr Ile Ser Lys Ala Lys Gly Gln Pro Arg Glu Pro Gln Val Tyr Thr
                580                 585                 590

Leu Pro Pro Cys Arg Asp Glu Leu Thr Lys Asn Gln Val Ser Leu Trp
            595                 600                 605

Cys Leu Val Lys Gly Phe Tyr Pro Ser Asp Ile Ala Val Glu Trp Glu
        610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
                645                 650                 655

Ser Arg Trp Gln Gln Gly Asn Val Phe Ser Cys Ser Val Met His Glu
                660                 665                 670

Ala Leu His Asn His Tyr Thr Gln Lys Ser Leu Ser Leu Ser Pro Gly
            675                 680                 685

Lys

<210> SEQ ID NO 100
<211> LENGTH: 689
```

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 100

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Gly Gly Gly Gly Ser Gly Gly Gly Ser Glu Val Gln Leu Leu Glu
225                 230                 235                 240

Ser Gly Gly Gly Leu Val Gln Pro Gly Gly Ser Leu Arg Leu Ser Cys
                245                 250                 255

Ala Ala Ser Gly Phe Thr Phe Ser Thr Tyr Ala Met Asn Trp Val Arg
            260                 265                 270

Gln Ala Pro Gly Lys Gly Leu Glu Trp Val Ser Arg Ile Arg Ser Lys
        275                 280                 285

Tyr Asn Asn Tyr Ala Thr Tyr Tyr Ala Asp Ser Val Lys Gly Arg Phe
    290                 295                 300

Thr Ile Ser Arg Asp Asp Ser Lys Asn Thr Leu Tyr Leu Gln Met Asn
305                 310                 315                 320

Ser Leu Arg Ala Glu Asp Thr Ala Val Tyr Tyr Cys Val Arg His Gly
                325                 330                 335

Asn Phe Gly Asn Ala Tyr Val Ser Trp Phe Ala Tyr Trp Gly Gln Gly
            340                 345                 350

Thr Leu Val Thr Val Ser Ser Ala Ser Thr Lys Gly Pro Ser Val Phe
        355                 360                 365

Pro Leu Ala Pro Ser Ser Lys Ser Thr Ser Gly Gly Thr Ala Ala Leu
```

```
                    370                 375                 380
Gly Cys Leu Val Lys Asp Tyr Phe Pro Glu Pro Val Thr Val Ser Trp
385                 390                 395                 400

Asn Ser Gly Ala Leu Thr Ser Gly Val His Thr Phe Pro Ala Val Leu
                405                 410                 415

Gln Ser Ser Gly Leu Tyr Ser Leu Ser Ser Val Val Thr Val Pro Ser
                420                 425                 430

Ser Ser Leu Gly Thr Gln Thr Tyr Ile Cys Asn Val Asn His Lys Pro
                435                 440                 445

Ser Asn Thr Lys Val Asp Lys Lys Val Glu Pro Lys Ser Cys Asp Lys
                450                 455                 460

Thr His Thr Cys Pro Pro Cys Pro Ala Pro Glu Ala Ala Gly Gly Pro
465                 470                 475                 480

Ser Val Phe Leu Phe Pro Pro Lys Pro Lys Asp Thr Leu Met Ile Ser
                485                 490                 495

Arg Thr Pro Glu Val Thr Cys Val Val Val Asp Val Ser His Glu Asp
                500                 505                 510

Pro Glu Val Lys Phe Asn Trp Tyr Val Asp Gly Val Glu Val His Asn
                515                 520                 525

Ala Lys Thr Lys Pro Arg Glu Glu Gln Tyr Asn Ser Thr Tyr Arg Val
530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Gly Ala Pro Ile Glu Lys
                565                 570                 575

Thr Ile Ser Lys Ala Lys Gly Gln Pro Arg Glu Pro Gln Val Tyr Thr
                580                 585                 590

Leu Pro Pro Cys Arg Asp Glu Leu Thr Lys Asn Gln Val Ser Leu Trp
                595                 600                 605

Cys Leu Val Lys Gly Phe Tyr Pro Ser Asp Ile Ala Val Glu Trp Glu
                610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
                645                 650                 655

Ser Arg Trp Gln Gln Gly Asn Val Phe Ser Cys Ser Val Met His Glu
                660                 665                 670

Ala Leu His Asn His Tyr Thr Gln Lys Ser Leu Ser Leu Ser Pro Gly
                675                 680                 685

Lys

<210> SEQ ID NO 101
<211> LENGTH: 441
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30
```

```
Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
 50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Ser Ser Ala
                100                 105                 110

Ser Thr Lys Gly Pro Ser Val Phe Pro Leu Ala Pro Ser Ser Lys Ser
            115                 120                 125

Thr Ser Gly Gly Thr Ala Ala Leu Gly Cys Leu Val Lys Asp Tyr Phe
130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys Asp Lys Thr His Thr Cys Pro Pro Cys Pro
210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Ala Leu Gly Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440
```

```
<210> SEQ ID NO 102
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
            35                  40                  45

Gly Arg Ile Lys Ser Lys Thr Asp Gly Gly Thr Thr Asp Tyr Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys
225

<210> SEQ ID NO 103
<211> LENGTH: 231
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
            35                  40                  45

Ser Arg Ile Arg Ser Lys Tyr Asn Asn Tyr Ala Thr Tyr Tyr Ala Asp
        50                  55                  60
```

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Pro
            115                 120                 125

Lys Ala Ala Pro Ser Val Thr Leu Phe Pro Pro Ser Ser Glu Glu Leu
130                 135                 140

Gln Ala Asn Lys Ala Thr Leu Val Cys Leu Ile Ser Asp Phe Tyr Pro
145                 150                 155                 160

Gly Ala Val Thr Val Ala Trp Lys Ala Asp Ser Ser Pro Val Lys Ala
                165                 170                 175

Gly Val Glu Thr Thr Thr Pro Ser Lys Gln Ser Asn Asn Lys Tyr Ala
            180                 185                 190

Ala Ser Ser Tyr Leu Ser Leu Thr Pro Glu Gln Trp Lys Ser His Arg
            195                 200                 205

Ser Tyr Ser Cys Gln Val Thr His Glu Gly Ser Thr Val Glu Lys Thr
        210                 215                 220

Val Ala Pro Thr Glu Cys Ser
225                 230

<210> SEQ ID NO 104
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 104

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Gly Gly Ser Phe Asp Tyr Trp Gly Gln Gly Thr
            100                 105                 110

Leu Val Thr Val Ser Ser
        115

<210> SEQ ID NO 105
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

```
<400> SEQUENCE: 105

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Gly Gly Ser Met Asp Ala Trp Gly Gln Gly Thr
            100                 105                 110

Thr Val Thr Val Ser Ser
        115

<210> SEQ ID NO 106
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Gly Gly Ser Gly Gly Ser Phe Asp Tyr Trp Gly Gln
            100                 105                 110

Gly Thr Leu Val Thr Val Ser Ser
        115                 120

<210> SEQ ID NO 107
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                    20                  25                  30
Ala Met Ser Trp Val Arg Gln Ala Pro Gly Lys Gly Leu Glu Trp Val
                35                  40                  45
Ser Ala Ile Ser Gly Ser Gly Gly Ser Thr Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Gly Gly Ser Gly Gly Ser Phe Asp Tyr Trp Gly Gln Gly Thr
            100                 105                 110
Leu Val Thr Val Ser Ser
            115

<210> SEQ ID NO 108
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Tyr
                20                  25                  30
Tyr Trp Ser Trp Ile Arg Gln Pro Pro Gly Lys Gly Leu Glu Trp Ile
                35                  40                  45
Gly Tyr Ile Tyr Tyr Ser Gly Ser Thr Asn Tyr Asn Pro Ser Leu Lys
            50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Gly Gly Ser Gly Gly Ser Phe Asp Tyr Trp Gly Gln Gly Thr Leu
            100                 105                 110
Val Thr Val Ser Ser
            115

<210> SEQ ID NO 109
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 109

Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Thr Ser Tyr
                20                  25                  30
Trp Ile Gly Trp Val Arg Gln Met Pro Gly Lys Gly Leu Glu Trp Met
                35                  40                  45
Gly Ile Ile Tyr Pro Gly Asp Ser Asp Thr Arg Tyr Ser Pro Ser Phe
            50                  55                  60
```

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Ser Gly Gly Ser Phe Asp Tyr Trp Gly Gln Gly Thr
            100                 105                 110

Leu Val Thr Val Ser Ser
        115

<210> SEQ ID NO 110
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 111
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

```
<210> SEQ ID NO 112
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 113
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Ala Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 114
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

Gln Thr Val Val Thr Gln Glu Pro Ser Leu Thr Val Ser Pro Gly Gly
```

```
                1               5                   10                  15
            Thr Val Thr Leu Thr Cys Gly Ser Ser Thr Gly Ala Val Thr Thr Ser
                            20                  25                  30

Asn Tyr Ala Asn Trp Val Gln Gln Lys Pro Gly Gln Ala Pro Arg Gly
                        35                  40                  45

Leu Ile Gly Gly Thr Asn Lys Arg Ala Pro Gly Thr Pro Ala Arg Phe
                    50                  55                  60

Ser Gly Ser Leu Leu Gly Gly Lys Ala Ala Leu Thr Leu Ser Gly Val
            65                  70                  75                  80

Gln Pro Glu Asp Glu Ala Glu Tyr Tyr Cys Ala Leu Trp Tyr Ala Asn
                            85                  90                  95

Leu Trp Val Phe Gly Gly Gly Thr Lys Leu Thr Val Leu
                        100                 105

<210> SEQ ID NO 115
            <211> LENGTH: 122
            <212> TYPE: PRT
            <213> ORGANISM: Artificial Sequence
            <220> FEATURE:
            <221> NAME/KEY: source
            <223> OTHER INFORMATION: /note="Description of Artificial Sequence:
                  Synthetic polypeptide"

<400> SEQUENCE: 115

Glu Val Gln Leu Val Glu Ser Gly Gly Gly Leu Val Lys Pro Gly Gly
            1               5                   10                  15

Ser Leu Arg Leu Ser Cys Ala Ala Ser Gly Phe Thr Phe Ser Asn Ala
                            20                  25                  30

Trp Met His Trp Val Arg Gln Ala Pro Gly Lys Gly Leu Glu Trp Val
                        35                  40                  45

Gly Arg Ile Lys Ser Lys Thr Asp Gly Gly Thr Thr Asp Tyr Ala Ala
                    50                  55                  60

Pro Val Lys Gly Arg Phe Thr Ile Ser Arg Asp Asp Ser Lys Asn Thr
            65                  70                  75                  80

Leu Tyr Leu Gln Met Asn Ser Leu Lys Thr Glu Asp Thr Ala Val Tyr
                            85                  90                  95

Tyr Cys Thr Thr Pro Trp Glu Trp Ser Trp Tyr Asp Tyr Trp Gly Gln
                        100                 105                 110

Gly Thr Leu Val Thr Val Ser Ser Ala Ser
                    115                 120

<210> SEQ ID NO 116
            <211> LENGTH: 122
            <212> TYPE: PRT
            <213> ORGANISM: Artificial Sequence
            <220> FEATURE:
            <221> NAME/KEY: source
            <223> OTHER INFORMATION: /note="Description of Artificial Sequence:
                  Synthetic polypeptide"

<400> SEQUENCE: 116

Glu Val Gln Leu Val Glu Ser Gly Gly Gly Leu Val Lys Pro Gly Gly
            1               5                   10                  15

Ser Leu Arg Leu Ser Cys Ala Ala Ser Gly Phe Thr Phe Ser Asn Ala
                            20                  25                  30

Trp Met Ser Trp Val Arg Gln Ala Pro Gly Lys Gly Leu Glu Trp Val
                        35                  40                  45

Ser Arg Ile Lys Ser Lys Thr Asp Gly Gly Thr Thr Asp Tyr Ala Ala
                    50                  55                  60
```

```
Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser Ala Ser
        115                 120
```

<210> SEQ ID NO 117
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Gly Ser Ile Lys Ser Lys Thr Asp Gly Gly Thr Thr Asp Tyr Ala Ala
     50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser Ala Ser
        115                 120
```

<210> SEQ ID NO 118
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 118

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Gly Arg Ile Lys Ser Lys Thr Asp Gly Gly Thr Thr Asp Tyr Ala Ala
     50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95
```

```
Tyr Cys Thr Thr Pro Tyr Glu Trp Ser Trp Tyr Asp Tyr Trp Gly Gln
                100                 105                 110

Gly Thr Leu Val Thr Val Ser Ser Ala Ser
        115                 120
```

<210> SEQ ID NO 119
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Tyr Ser Trp Tyr Asp Tyr Trp Gly Gln
                100                 105                 110

Gly Thr Leu Val Thr Val Ser Ser Ala Ser
        115                 120
```

<210> SEQ ID NO 120
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Tyr Thr Ile Val Val Ser Pro Phe Asp Tyr Trp Gly Gln
                100                 105                 110

Gly Thr Leu Val Thr Val Ser Ser Ala Ser
        115                 120
```

```
<210> SEQ ID NO 121
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Tyr Phe Ile Gly Ser Val Ala Met Asp Tyr Trp Gly Gln
                100                 105                 110

Gly Thr Leu Val Thr Val Ser Ser Ala Ser
            115                 120

<210> SEQ ID NO 122
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Leu Thr Tyr Ser Met Asp Tyr Trp Gly Gln Gly Thr Leu
                100                 105                 110

Val Thr Val Ser Ser Ala Ser
            115

<210> SEQ ID NO 123
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 123

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Ile Pro Asn Thr Phe Gly Gln Gly Thr Lys Val Glu Ile Lys
            100                 105                 110

Arg Thr

<210> SEQ ID NO 124
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Ala Tyr Ala Leu Asp Tyr Trp Gly Gln Gly Thr Leu Val
            100                 105                 110

Thr Val Ser Ser Ala Ser
        115

<210> SEQ ID NO 125
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 125

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser

```
                    20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Gly Ser Ser Ser
                85                  90                  95

Thr Phe Gly Gln Gly Thr Lys Val Glu Ile Lys Arg Thr
                100                 105

<210> SEQ ID NO 126
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Phe Ser Ala Gly Arg Leu Met Asp Tyr Trp Gly Gln
                100                 105                 110

Gly Thr Leu Val Thr Val Ser Ser Ala Ser
            115                 120

<210> SEQ ID NO 127
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Met Gln Ala
                85                  90                  95

Leu Gln Thr Pro Pro Ile Thr Phe Gly Gln Gly Thr Lys Val Glu Ile
            100                 105                 110

Lys Arg Thr
        115

<210> SEQ ID NO 128
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Asn Ala Phe Asp Tyr Trp Gly His Gly Thr Leu
            100                 105                 110

Val Thr Val Ser Ser Ala Ser
        115

<210> SEQ ID NO 129
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 129

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Trp His Ser Pro Thr Phe Gly Gln Gly Thr Lys Val Glu Ile Lys Arg
            100                 105                 110
```

Thr

```
<210> SEQ ID NO 130
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Thr Tyr Thr Met Asp Tyr Trp Gly Gln Gly Thr Leu
            100                 105                 110

Val Thr Val Ser Ser Ala Ser
        115

```
<210> SEQ ID NO 131
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 131
```

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Lys Val Glu Ile Lys
            100                 105                 110

Arg Thr

```
<210> SEQ ID NO 132
<211> LENGTH: 112
<212> TYPE: PRT
<213> ORGANISM: Artificial Sequence
<220> FEATURE:
```

<221> NAME/KEY: source
<223> OTHER INFORMATION: /note="Description of Artificial Sequence:
    Synthetic polypeptide"

<400> SEQUENCE: 132

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Ile Met Ser Arg Thr Phe Gly Gln Gly Thr Lys Val Glu Ile Lys
            100                 105                 110

<210> SEQ ID NO 133
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 133

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Ile Met Gln Arg Thr Phe Gly Gln Gly Thr Lys Val Glu Ile Lys
            100                 105                 110

<210> SEQ ID NO 134
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 134

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser

```
                35                  40                  45
Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                85                  90                  95

Ser Ile Met Asn Arg Ala Phe Gly Gln Gly Thr Lys Val Glu Ile Lys
               100                 105                 110

<210> SEQ ID NO 135
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 135

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                85                  90                  95

Ser Ile Met Asn Arg Asn Phe Gly Gln Gly Thr Lys Val Glu Ile Lys
               100                 105                 110

<210> SEQ ID NO 136
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 136

Gln Val Gln Leu Gln Gln Ser Gly Ala Glu Leu Val Lys Pro Gly Ala
 1               5                  10                  15

Ser Val Lys Ile Ser Cys Lys Ala Ser Gly Tyr Ser Phe Thr Gly Tyr
                20                  25                  30

Phe Met Asn Trp Val Lys Gln Ser His Gly Lys Ser Leu Glu Trp Ile
            35                  40                  45

Gly Arg Ile His Pro Tyr Asp Gly Asp Thr Phe Tyr Asn Gln Asn Phe
        50                  55                  60

Lys Asp Lys Ala Thr Leu Thr Val Asp Lys Ser Ser Asn Thr Ala His
 65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
               100                 105                 110
```

```
Thr Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Ala Ala Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Gly Ala Pro Ile Glu Lys Thr
                325                 330                 335
Ile Ser Lys Ala Lys Gly Gln Pro Arg Glu Pro Gln Val Cys Thr Leu
            340                 345                 350
Pro Pro Ser Arg Asp Glu Leu Thr Lys Asn Gln Val Ser Leu Ser Cys
        355                 360                 365
Ala Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Val Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 137
<211> LENGTH: 691
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 137

Gln Val Gln Leu Gln Gln Ser Gly Ala Glu Leu Val Lys Pro Gly Ala
1               5                   10                  15
```

Ser Val Lys Ile Ser Cys Lys Ala Ser Gly Tyr Ser Phe Thr Gly Tyr
            20                  25                  30

Phe Met Asn Trp Val Lys Gln Ser His Gly Lys Ser Leu Glu Trp Ile
        35                  40                  45

Gly Arg Ile His Pro Tyr Asp Gly Asp Thr Phe Tyr Asn Gln Asn Phe
    50                  55                  60

Lys Asp Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Gly Gly
    210                 215                 220

Gly Gly Ser Gly Gly Gly Ser Glu Val Gln Leu Val Glu Ser Gly Gly
225                 230                 235                 240

Gly Gly Leu Val Gln Pro Lys Gly Ser Leu Lys Leu Ser Cys Ala Ala
                245                 250                 255

Ser Gly Phe Thr Phe Asn Thr Tyr Ala Met Asn Trp Val Arg Gln Ala
            260                 265                 270

Pro Gly Lys Gly Leu Glu Trp Val Ala Arg Ile Arg Ser Lys Tyr Asn
        275                 280                 285

Asn Tyr Ala Thr Tyr Tyr Ala Asp Ser Val Lys Asp Arg Phe Thr Ile
    290                 295                 300

Ser Arg Asp Asp Ser Gln Ser Ile Leu Tyr Leu Gln Met Asn Asn Leu
305                 310                 315                 320

Lys Thr Glu Asp Thr Ala Met Tyr Tyr Cys Val Arg His Gly Asn Phe
                325                 330                 335

Gly Asn Ser Tyr Val Ser Trp Phe Ala Tyr Trp Gly Gln Gly Thr Leu
            340                 345                 350

Val Thr Val Ser Ala Ala Ser Val Ala Ala Pro Ser Val Phe Ile Phe
        355                 360                 365

Pro Pro Ser Asp Glu Gln Leu Lys Ser Gly Thr Ala Ser Val Val Cys
370                 375                 380

Leu Leu Asn Asn Phe Tyr Pro Arg Glu Ala Lys Val Gln Trp Lys Val
385                 390                 395                 400

Asp Asn Ala Leu Gln Ser Gly Asn Ser Gln Glu Ser Val Thr Glu Gln
                405                 410                 415

Asp Ser Lys Asp Ser Thr Tyr Ser Leu Ser Ser Thr Leu Thr Leu Ser
            420                 425                 430

Lys Ala Asp Tyr Glu Lys His Lys Val Tyr Ala Cys Glu Val Thr His

```
                  435                 440                 445
    Gln Gly Leu Ser Ser Pro Val Thr Lys Ser Phe Asn Arg Gly Glu Cys
        450                 455                 460
    Asp Lys Thr His Thr Cys Pro Pro Cys Pro Ala Pro Glu Ala Ala Gly
    465                 470                 475                 480
    Gly Pro Ser Val Phe Leu Phe Pro Pro Lys Pro Lys Asp Thr Leu Met
                    485                 490                 495
    Ile Ser Arg Thr Pro Glu Val Thr Cys Val Val Val Asp Val Ser His
                500                 505                 510
    Glu Asp Pro Glu Val Lys Phe Asn Trp Tyr Val Asp Gly Val Glu Val
            515                 520                 525
    His Asn Ala Lys Thr Lys Pro Arg Glu Glu Gln Tyr Asn Ser Thr Tyr
        530                 535                 540
    Arg Val Val Ser Val Leu Thr Val Leu His Gln Asp Trp Leu Asn Gly
    545                 550                 555                 560
    Lys Glu Tyr Lys Cys Lys Val Ser Asn Lys Ala Leu Gly Ala Pro Ile
                    565                 570                 575
    Glu Lys Thr Ile Ser Lys Ala Lys Gly Gln Pro Arg Glu Pro Gln Val
                580                 585                 590
    Tyr Thr Leu Pro Pro Cys Arg Asp Glu Leu Thr Lys Asn Gln Val Ser
            595                 600                 605
    Leu Trp Cys Leu Val Lys Gly Phe Tyr Pro Ser Asp Ile Ala Val Glu
    610                 615                 620
    Trp Glu Ser Asn Gly Gln Pro Glu Asn Asn Tyr Lys Thr Thr Pro Pro
    625                 630                 635                 640
    Val Leu Asp Ser Asp Gly Ser Phe Phe Leu Tyr Ser Lys Leu Thr Val
                    645                 650                 655
    Asp Lys Ser Arg Trp Gln Gln Gly Asn Val Phe Ser Cys Ser Val Met
                660                 665                 670
    His Glu Ala Leu His Asn His Tyr Thr Gln Lys Ser Leu Ser Leu Ser
            675                 680                 685
    Pro Gly Lys
        690

<210> SEQ ID NO 138
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 138

Asp Ile Glu Leu Thr Gln Ser Pro Ala Ser Leu Ala Val Ser Leu Gly
1               5                   10                  15

Gln Arg Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Lys Leu Leu Ile Tyr Arg Ala Ser Asn Leu Glu Ala Gly Val Pro Thr
    50                  55                  60

Arg Phe Ser Gly Ser Gly Ser Lys Thr Asp Phe Thr Leu Asn Ile His
65                  70                  75                  80

Pro Val Glu Glu Glu Asp Ala Ala Thr Tyr Tyr Cys Gln Gln Ser Arg
                85                  90                  95
```

```
Glu Tyr Pro Tyr Thr Phe Gly Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 139
<211> LENGTH: 257
<212> TYPE: PRT
<213> ORGANISM: Homo sapiens

<400> SEQUENCE: 139

```
Met Ala Gln Arg Met Thr Thr Gln Leu Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Met Ser Gly Ala Gly Pro Trp Ala
225                 230                 235                 240

Ala Trp Pro Phe Leu Leu Ser Leu Ala Leu Met Leu Leu Trp Leu Leu
```

```
                        245                 250                 255

Ser

<210> SEQ ID NO 140
<211> LENGTH: 468
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 140

Arg Ile Ala Trp Ala Arg Thr Glu Leu Leu Asn Val Cys Met Asn Ala
1               5                   10                  15

Lys His His Lys Glu Lys Pro Gly Pro Glu Asp Lys Leu His Glu Gln
            20                  25                  30

Cys Arg Pro Trp Arg Lys Asn Ala Cys Cys Ser Thr Asn Thr Ser Gln
        35                  40                  45

Glu Ala His Lys Asp Val Ser Tyr Leu Tyr Arg Phe Asn Trp Asn His
    50                  55                  60

Cys Gly Glu Met Ala Pro Ala Cys Lys Arg His Phe Ile Gln Asp Thr
65                  70                  75                  80

Cys Leu Tyr Glu Cys Ser Pro Asn Leu Gly Pro Trp Ile Gln Gln Val
                85                  90                  95

Asp Gln Ser Trp Arg Lys Glu Arg Val Leu Asn Val Pro Leu Cys Lys
            100                 105                 110

Glu Asp Cys Glu Gln Trp Trp Glu Asp Cys Arg Thr Ser Tyr Thr Cys
        115                 120                 125

Lys Ser Asn Trp His Lys Gly Trp Asn Trp Thr Ser Gly Phe Asn Lys
130                 135                 140

Cys Ala Val Gly Ala Ala Cys Gln Pro Phe His Phe Tyr Phe Pro Thr
145                 150                 155                 160

Pro Thr Val Leu Cys Asn Glu Ile Trp Thr His Ser Tyr Lys Val Ser
                165                 170                 175

Asn Tyr Ser Arg Gly Ser Gly Arg Cys Ile Gln Met Trp Phe Asp Pro
            180                 185                 190

Ala Gln Gly Asn Pro Asn Glu Glu Val Ala Arg Phe Tyr Ala Ala Ala
        195                 200                 205

Met Val Asp Glu Gln Leu Tyr Phe Gln Gly Gly Ser Pro Lys Ser Ala
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335
```

-continued

```
Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
        355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Ser Gly Gly Leu Asn Asp Ile Phe Glu Ala Gln Lys Ile
    450                 455                 460

Glu Trp His Glu
465
```

<210> SEQ ID NO 141
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 141

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Phe Thr Gln Lys Ser Leu Ser Leu Ser
```

Pro Gly Lys
225

<210> SEQ ID NO 142
<211> LENGTH: 255
<212> TYPE: PRT
<213> ORGANISM: Mus musculus

<400> SEQUENCE: 142

Met Ala His Leu Met Thr Val Gln Leu Leu Leu Val Met Trp Met
1               5                   10                  15

Ala Glu Cys Ala Gln Ser Arg Ala Thr Arg Ala Arg Thr Glu Leu Leu
                20                  25                  30

Asn Val Cys Met Asp Ala Lys His His Lys Glu Lys Pro Gly Pro Glu
            35                  40                  45

Asp Asn Leu His Asp Gln Cys Ser Pro Trp Lys Thr Asn Ser Cys Cys
        50                  55                  60

Ser Thr Asn Thr Ser Gln Glu Ala His Lys Asp Ile Ser Tyr Leu Tyr
65                  70                  75                  80

Arg Phe Asn Trp Asn His Cys Gly Thr Met Thr Ser Glu Cys Lys Arg
                85                  90                  95

His Phe Ile Gln Asp Thr Cys Leu Tyr Glu Cys Ser Pro Asn Leu Gly
                100                 105                 110

Pro Trp Ile Gln Gln Val Asp Gln Ser Trp Arg Lys Glu Arg Ile Leu
            115                 120                 125

Asp Val Pro Leu Cys Lys Glu Asp Cys Gln Gln Trp Trp Glu Asp Cys
        130                 135                 140

Gln Ser Ser Phe Thr Cys Lys Ser Asn Trp His Lys Gly Trp Asn Trp
145                 150                 155                 160

Ser Ser Gly His Asn Glu Cys Pro Val Gly Ala Ser Cys His Pro Phe
                165                 170                 175

Thr Phe Tyr Phe Pro Thr Ser Ala Ala Leu Cys Glu Glu Ile Trp Ser
                180                 185                 190

His Ser Tyr Lys Leu Ser Asn Tyr Ser Arg Gly Ser Gly Arg Cys Ile
            195                 200                 205

Gln Met Trp Phe Asp Pro Ala Gln Gly Asn Pro Asn Glu Glu Val Ala
        210                 215                 220

Arg Phe Tyr Ala Glu Ala Met Ser Gly Ala Gly Leu His Gly Thr Trp
225                 230                 235                 240

Pro Leu Leu Cys Ser Leu Ser Leu Val Leu Leu Trp Val Ile Ser
                245                 250                 255

<210> SEQ ID NO 143
<211> LENGTH: 466
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 143

Thr Arg Ala Arg Thr Glu Leu Leu Asn Val Cys Met Asp Ala Lys His
1               5                   10                  15

His Lys Glu Lys Pro Gly Pro Glu Asp Asn Leu His Asp Gln Cys Ser
                20                  25                  30

```
Pro Trp Lys Thr Asn Ser Cys Cys Ser Thr Asn Thr Ser Gln Glu Ala
         35                  40                  45

His Lys Asp Ile Ser Tyr Leu Tyr Arg Phe Asn Trp Asn His Cys Gly
     50                  55                  60

Thr Met Thr Ser Glu Cys Lys Arg His Phe Ile Gln Asp Thr Cys Leu
 65                  70                  75                   80

Tyr Glu Cys Ser Pro Asn Leu Gly Pro Trp Ile Gln Gln Val Asp Gln
                 85                  90                  95

Ser Trp Arg Lys Glu Arg Ile Leu Asp Val Pro Leu Cys Lys Glu Asp
             100                 105                 110

Cys Gln Gln Trp Trp Glu Asp Cys Gln Ser Ser Phe Thr Cys Lys Ser
         115                 120                 125

Asn Trp His Lys Gly Trp Asn Trp Ser Ser Gly His Asn Glu Cys Pro
     130                 135                 140

Val Gly Ala Ser Cys His Pro Phe Thr Phe Tyr Phe Pro Thr Ser Ala
145                 150                 155                 160

Ala Leu Cys Glu Glu Ile Trp Ser His Ser Tyr Lys Leu Ser Asn Tyr
                 165                 170                 175

Ser Arg Gly Ser Gly Arg Cys Ile Gln Met Trp Phe Asp Pro Ala Gln
             180                 185                 190

Gly Asn Pro Asn Glu Glu Val Ala Arg Phe Tyr Ala Glu Ala Met Val
         195                 200                 205

Asp Glu Gln Leu Tyr Phe Gln Gly Gly Ser Pro Lys Ser Ala Asp Lys
     210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                 245                 250                 255

Arg Thr Pro Glu Val Thr Cys Val Val Val Asp Val Ser His Glu Asp
             260                 265                 270

Pro Glu Val Lys Phe Asn Trp Tyr Val Asp Gly Val Glu Val His Asn
         275                 280                 285

Ala Lys Thr Lys Pro Arg Glu Glu Gln Tyr Asn Ser Thr Tyr Arg Val
     290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                 325                 330                 335

Thr Ile Ser Lys Ala Lys Gly Gln Pro Arg Glu Pro Gln Val Tyr Thr
             340                 345                 350

Leu Pro Pro Cys Arg Asp Glu Leu Thr Lys Asn Gln Val Ser Leu Trp
         355                 360                 365

Cys Leu Val Lys Gly Phe Tyr Pro Ser Asp Ile Ala Val Glu Trp Glu
     370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                 405                 410                 415

Ser Arg Trp Gln Gln Gly Asn Val Phe Ser Cys Ser Val Met His Glu
             420                 425                 430

Ala Leu His Asn His Tyr Thr Gln Lys Ser Leu Ser Leu Ser Pro Gly
         435                 440                 445

Lys Ser Gly Gly Leu Asn Asp Ile Phe Glu Ala Gln Lys Ile Glu Trp
```

His Glu
465

<210> SEQ ID NO 144
<211> LENGTH: 257
<212> TYPE: PRT
<213> ORGANISM: Macaca fascicularis

<400> SEQUENCE: 144

Met Ala Gln Arg Met Thr Thr Gln Leu Leu Leu Leu Val Trp Val
1               5                   10                  15

Ala Val Val Gly Glu Ala Gln Thr Arg Thr Ala Arg Ala Arg Thr Glu
            20                  25                  30

Leu Leu Asn Val Cys Met Asn Ala Lys His His Lys Glu Lys Pro Gly
            35                  40                  45

Pro Glu Asp Lys Leu His Glu Gln Cys Arg Pro Trp Lys Lys Asn Ala
        50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Arg Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Pro Val Gly Ala Ala Cys Gln
                165                 170                 175

Pro Phe His Phe Tyr Phe Pro Thr Pro Thr Val Leu Cys Asn Glu Ile
            180                 185                 190

Trp Thr Tyr Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Ala Met Ser Gly Ala Gly Pro Trp Ala
225                 230                 235                 240

Ala Trp Pro Leu Leu Leu Ser Leu Ala Leu Thr Leu Leu Trp Leu Leu
                245                 250                 255

Ser

<210> SEQ ID NO 145
<211> LENGTH: 468
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 145

Arg Thr Ala Arg Ala Arg Thr Glu Leu Leu Asn Val Cys Met Asn Ala
1               5                   10                  15

Lys His His Lys Glu Lys Pro Gly Pro Glu Asp Lys Leu His Glu Gln

```
            20                  25                  30
Cys Arg Pro Trp Lys Lys Asn Ala Cys Cys Ser Thr Asn Thr Ser Gln
            35                  40                  45
Glu Ala His Lys Asp Val Ser Tyr Leu Tyr Arg Phe Asn Trp Asn His
            50                  55                  60
Cys Gly Glu Met Ala Pro Ala Cys Lys Arg His Phe Ile Gln Asp Thr
65                  70                  75                  80
Cys Leu Tyr Glu Cys Ser Pro Asn Leu Gly Pro Trp Ile Gln Gln Val
                85                  90                  95
Asp Gln Ser Trp Arg Lys Glu Arg Val Leu Asn Val Pro Leu Cys Lys
            100                 105                 110
Glu Asp Cys Glu Gln Trp Trp Glu Asp Cys Arg Thr Ser Tyr Thr Cys
            115                 120                 125
Lys Ser Asn Trp His Lys Gly Trp Asn Trp Thr Ser Gly Phe Asn Lys
            130                 135                 140
Cys Pro Val Gly Ala Ala Cys Gln Pro Phe His Phe Tyr Phe Pro Thr
145                 150                 155                 160
Pro Thr Val Leu Cys Asn Glu Ile Trp Thr Tyr Ser Tyr Lys Val Ser
                165                 170                 175
Asn Tyr Ser Arg Gly Ser Gly Arg Cys Ile Gln Met Trp Phe Asp Pro
            180                 185                 190
Ala Gln Gly Asn Pro Asn Glu Glu Val Ala Arg Phe Tyr Ala Ala Ala
            195                 200                 205
Met Val Asp Glu Gln Leu Tyr Phe Gln Gly Gly Ser Pro Lys Ser Ala
            210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
            290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Cys Arg Asp Glu Leu Thr Lys Asn Gln Val Ser
            355                 360                 365
Leu Trp Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
            435                 440                 445
```

```
Pro Gly Lys Ser Gly Gly Leu Asn Asp Ile Phe Glu Ala Gln Lys Ile
        450                 455                 460

Glu Trp His Glu
465
```

<210> SEQ ID NO 146
<211> LENGTH: 255
<212> TYPE: PRT
<213> ORGANISM: Homo sapiens

<400> SEQUENCE: 146

```
Met Val Trp Lys Trp Met Pro Leu Leu Leu Leu Val Cys Val Ala
1               5                   10                  15

Thr Met Cys Ser Ala Gln Asp Arg Thr Asp Leu Leu Asn Val Cys Met
                20                  25                  30

Asp Ala Lys His His Lys Thr Lys Pro Gly Pro Glu Asp Lys Leu His
            35                  40                  45

Asp Gln Cys Ser Pro Trp Lys Lys Asn Ala Cys Cys Thr Ala Ser Thr
        50                  55                  60

Ser Gln Glu Leu His Lys Asp Thr Ser Arg Leu Tyr Asn Phe Asn Trp
65                  70                  75                  80

Asp His Cys Gly Lys Met Glu Pro Ala Cys Lys Arg His Phe Ile Gln
                85                  90                  95

Asp Thr Cys Leu Tyr Glu Cys Ser Pro Asn Leu Gly Pro Trp Ile Gln
            100                 105                 110

Gln Val Asn Gln Ser Trp Arg Lys Glu Arg Phe Leu Asp Val Pro Leu
        115                 120                 125

Cys Lys Glu Asp Cys Gln Arg Trp Trp Glu Asp Cys His Thr Ser His
130                 135                 140

Thr Cys Lys Ser Asn Trp His Arg Gly Trp Asp Trp Thr Ser Gly Val
145                 150                 155                 160

Asn Lys Cys Pro Ala Gly Ala Leu Cys Arg Thr Phe Glu Ser Tyr Phe
                165                 170                 175

Pro Thr Pro Ala Ala Leu Cys Glu Gly Leu Trp Ser His Ser Tyr Lys
            180                 185                 190

Val Ser Asn Tyr Ser Arg Gly Ser Gly Arg Cys Ile Gln Met Trp Phe
        195                 200                 205

Asp Ser Ala Gln Gly Asn Pro Asn Glu Glu Val Ala Arg Phe Tyr Ala
210                 215                 220

Ala Ala Met His Val Asn Ala Gly Glu Met Leu His Gly Thr Gly Gly
225                 230                 235                 240

Leu Leu Leu Ser Leu Ala Leu Met Leu Gln Leu Trp Leu Leu Gly
                245                 250                 255
```

<210> SEQ ID NO 147
<211> LENGTH: 472
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 147

```
Thr Met Cys Ser Ala Gln Asp Arg Thr Asp Leu Leu Asn Val Cys Met
1               5                   10                  15

Asp Ala Lys His His Lys Thr Lys Pro Gly Pro Glu Asp Lys Leu His
```

-continued

```
                20                  25                  30
Asp Gln Cys Ser Pro Trp Lys Lys Asn Ala Cys Cys Thr Ala Ser Thr
            35                  40                  45
Ser Gln Glu Leu His Lys Asp Thr Ser Arg Leu Tyr Asn Phe Asn Trp
        50                  55                  60
Asp His Cys Gly Lys Met Glu Pro Ala Cys Lys Arg His Phe Ile Gln
 65                  70                  75                  80
Asp Thr Cys Leu Tyr Glu Cys Ser Pro Asn Leu Gly Pro Trp Ile Gln
                85                  90                  95
Gln Val Asn Gln Ser Trp Arg Lys Glu Arg Phe Leu Asp Val Pro Leu
            100                 105                 110
Cys Lys Glu Asp Cys Gln Arg Trp Trp Glu Asp Cys His Thr Ser His
        115                 120                 125
Thr Cys Lys Ser Asn Trp His Arg Gly Trp Asp Trp Thr Ser Gly Val
        130                 135                 140
Asn Lys Cys Pro Ala Gly Ala Leu Cys Arg Thr Phe Glu Ser Tyr Phe
145                 150                 155                 160
Pro Thr Pro Ala Ala Leu Cys Glu Gly Leu Trp Ser His Ser Tyr Lys
                165                 170                 175
Val Ser Asn Tyr Ser Arg Gly Ser Gly Arg Cys Ile Gln Met Trp Phe
            180                 185                 190
Asp Ser Ala Gln Gly Asn Pro Asn Glu Glu Val Ala Arg Phe Tyr Ala
        195                 200                 205
Ala Ala Met His Val Val Asp Glu Gln Leu Tyr Phe Gln Gly Gly Ser
        210                 215                 220
Pro Lys Ser Ala Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
        290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Cys Arg Asp Glu Leu Thr Lys
        355                 360                 365
Asn Gln Val Ser Leu Trp Cys Leu Val Lys Gly Phe Tyr Pro Ser Asp
        370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
```

```
Leu Ser Leu Ser Pro Gly Lys Ser Gly Gly Leu Asn Asp Ile Phe Glu
    450                 455                 460

Ala Gln Lys Ile Glu Trp His Glu
465                 470

<210> SEQ ID NO 148
<211> LENGTH: 243
<212> TYPE: PRT
<213> ORGANISM: Homo sapiens

<400> SEQUENCE: 148

Met Ala Trp Gln Met Met Gln Leu Leu Leu Ala Leu Val Thr Ala
1               5                   10                  15

Ala Gly Ser Ala Gln Pro Arg Ser Ala Arg Ala Arg Thr Asp Leu Leu
            20                  25                  30

Asn Val Cys Met Asn Ala Lys His His Lys Thr Gln Pro Ser Pro Glu
        35                  40                  45

Asp Glu Leu Tyr Gly Gln Cys Ser Pro Trp Lys Lys Asn Ala Cys Cys
    50                  55                  60

Thr Ala Ser Thr Ser Gln Glu Leu His Lys Asp Thr Ser Arg Leu Tyr
65                  70                  75                  80

Asn Phe Asn Trp Asp His Cys Gly Lys Met Glu Pro Thr Cys Lys Arg
                85                  90                  95

His Phe Ile Gln Asp Ser Cys Leu Tyr Glu Cys Ser Pro Asn Leu Gly
            100                 105                 110

Pro Trp Ile Arg Gln Val Asn Gln Ser Trp Arg Lys Glu Arg Ile Leu
        115                 120                 125

Asn Val Pro Leu Cys Lys Glu Asp Cys Glu Arg Trp Trp Glu Asp Cys
    130                 135                 140

Arg Thr Ser Tyr Thr Cys Lys Ser Asn Trp His Lys Gly Trp Asn Trp
145                 150                 155                 160

Thr Ser Gly Ile Asn Glu Cys Pro Ala Gly Ala Leu Cys Ser Thr Phe
                165                 170                 175

Glu Ser Tyr Phe Pro Thr Pro Ala Ala Leu Cys Glu Gly Leu Trp Ser
            180                 185                 190

His Ser Phe Lys Val Ser Asn Tyr Ser Arg Gly Ser Gly Arg Cys Ile
        195                 200                 205

Gln Met Trp Phe Asp Ser Ala Gln Gly Asn Pro Asn Glu Glu Val Ala
    210                 215                 220

Lys Phe Tyr Ala Ala Met Asn Ala Gly Ala Pro Ser Arg Gly Ile
225                 230                 235                 240

Ile Asp Ser

<210> SEQ ID NO 149
<211> LENGTH: 479
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 149

Ser Ala Arg Ala Arg Thr Asp Leu Leu Asn Val Cys Met Asn Ala Lys
1               5                   10                  15

His His Lys Thr Gln Pro Ser Pro Glu Asp Glu Leu Tyr Gly Gln Cys
            20                  25                  30
```

-continued

```
Ser Pro Trp Lys Lys Asn Ala Cys Cys Thr Ala Ser Thr Ser Gln Glu
    35                  40                  45

Leu His Lys Asp Thr Ser Arg Leu Tyr Asn Phe Asn Trp Asp His Cys
    50                  55                  60

Gly Lys Met Glu Pro Thr Cys Lys Arg His Phe Ile Gln Asp Ser Cys
65                  70                  75                  80

Leu Tyr Glu Cys Ser Pro Asn Leu Gly Pro Trp Ile Arg Gln Val Asn
                85                  90                  95

Gln Ser Trp Arg Lys Glu Arg Ile Leu Asn Val Pro Leu Cys Lys Glu
                100                 105                 110

Asp Cys Glu Arg Trp Trp Glu Asp Cys Arg Thr Ser Tyr Thr Cys Lys
                115                 120                 125

Ser Asn Trp His Lys Gly Trp Asn Trp Thr Ser Gly Ile Asn Glu Cys
    130                 135                 140

Pro Ala Gly Ala Leu Cys Ser Thr Phe Glu Ser Tyr Phe Pro Thr Pro
145                 150                 155                 160

Ala Ala Leu Cys Glu Gly Leu Trp Ser His Ser Phe Lys Val Ser Asn
                165                 170                 175

Tyr Ser Arg Gly Ser Gly Arg Cys Ile Gln Met Trp Phe Asp Ser Ala
                180                 185                 190

Gln Gly Asn Pro Asn Glu Glu Val Ala Lys Phe Tyr Ala Ala Ala Met
                195                 200                 205

Asn Ala Gly Ala Pro Ser Arg Gly Ile Ile Asp Ser Val Asp Glu Gln
    210                 215                 220

Leu Tyr Phe Gln Gly Gly Ser Pro Lys Ser Ala Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
                275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
                355                 360                 365

Cys Arg Asp Glu Leu Thr Lys Asn Gln Val Ser Leu Trp Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
                435                 440                 445
```

```
Asn His Tyr Thr Gln Lys Ser Leu Ser Leu Ser Pro Gly Lys Ser Gly
            450                 455                 460

Gly Leu Asn Asp Ile Phe Glu Ala Gln Lys Ile Glu Trp His Glu
465                 470                 475

<210> SEQ ID NO 150
<211> LENGTH: 207
<212> TYPE: PRT
<213> ORGANISM: Homo sapiens

<400> SEQUENCE: 150

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 151
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 151
caggtgcaat tggttcaatc tggtgctgaa gtaaaaaaac cgggcgcttc cgttaaagtg      60
agctgcaaag catccggata caccttcact tcctattaca tgcactgggt tcgtcaagcc    120
ccgggccagg gtctggaatg gatgggcatc attaacccaa gcggtggctc tacctcctac    180
gcgcagaaat tccagggtcg cgtcacgatg acccgtgaca ctagcacctc taccgtttat    240
atggagctgt ccagcctgcg ttctgaagat actgcagtgt actactgtgc acgcaactac    300
tacgctggtg ttactccgtt cgactattgg ggtcaaggca ccctcgtaac ggtttcttct    360

<210> SEQ ID NO 152
```

<210> SEQ ID NO 152
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 152

```
caggtgcaat tggttcaatc tggtgctgaa gtaaaaaaac cgggcgcttc cgttaaagtg      60
agctgcaaag catccggata caccttcact tcctattaca tgcactgggt tcgtcaagcc     120
ccgggccagg gtctggaatg gatgggcatc attaacccaa gcgtggctc tacctcctac      180
gcgcagaaat tccagggtcg cgtcacgatg acccgtgaca ctagcacctc taccgtttat     240
atggagctgt ccagcctgcg ttctgaagat actgcagtgt actactgtgc acgcaactac     300
tacatcggtg ttgttacttt cgactattgg ggtcaaggca ccctcgtaac ggtttcttct     360
```

<210> SEQ ID NO 153
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 153

```
caggtgcaat tggttcaatc tggtgctgaa gtaaaaaaac cgggcgcttc cgttaaagtg      60
agctgcaaag catccggata caccttcact tcctattaca tgcactgggt tcgtcaagcc     120
ccgggccagg gtctggaatg gatgggcatc attaacccaa gcgtggctc tacctcctac      180
gcgcagaaat tccagggtcg cgtcacgatg acccgtgaca ctagcacctc taccgtttat     240
atggagctgt ccagcctgcg ttctgaagat actgcagtgt actactgtgc acgcaactac     300
tacactggtg gttcttctgc tttcgactat tggggtcaag gcaccctcgt aacggtttct     360
tct                                                                    363
```

<210> SEQ ID NO 154
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (47)..(47)
<223> OTHER INFORMATION: a, c, t, g, unknown or other

<400> SEQUENCE: 154

```
caggtgcaat tggttcaatc tggtgctgaa gtaaaaaaac cgggcgnttc cgttaaagtg      60
agctgcaaag catccggata caccttcact tcctattaca tgcactgggt tcgtcaagcc     120
ccgggccagg gtctggaatg gatgggcatc attaacccaa gcgtggctc tacctcctac      180
gcgcagaaat tccagggtcg cgtcacgatg acccgtgaca ctagcacctc taccgtttat     240
atggagctgt ccagcctgcg ttctgaagat actgcagtgt actactgtgc acgcggtgaa     300
tggcgtcgtt acacttcttt cgactattgg ggtcaaggca ccctcgtaac ggtttcttct     360
```

<210> SEQ ID NO 155
<211> LENGTH: 360

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 155
caggtgcaat tggttcaatc tggtgctgaa gtaaaaaaac cgggcgcttc cgttaaagtg      60
agctgcaaag catccggata caccttcact tcctattaca tgcactgggt tcgtcaagcc     120
ccgggccagg gtctggaatg gatgggcatc attaacccaa gcggtggctc tacctcctac     180
gcgcagaaat tccagggtcg cgtcacgatg acccgtgaca ctagcacctc taccgtttat     240
atggagctgt ccagcctgcg ttctgaagat actgcagtgt actactgtgc acgcggtggt     300
tggatccgtt gggaacattt cgactattgg ggtcaaggca ccctcgtaac ggtttcttct     360

<210> SEQ ID NO 156
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 156
caggtgcaat tggttcaatc tggtgctgaa gtaaaaaaac cgggcgcttc cgttaaagtg      60
agctgcaaag catccggata caccttcact tcctattaca tgcactgggt tcgtcaagcc     120
ccgggccagg gtctggaatg gatgggcatc attaacccaa gcggtggctc tacctcctac     180
gcgcagaaat tccagggtcg cgtcacgatg acccgtgaca ctagcacctc taccgtttat     240
atggagctgt ccagcctgcg ttctgaagat actgcagtgt actactgtgc acgcaactac     300
tacctgttct ctacttcttt cgactattgg ggtcaaggca ccctcgtaac ggtttcttct     360

<210> SEQ ID NO 157
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 157
caggtgcaat tggttcaatc tggtgctgag gtaaaaaaac cgggcgcttc cgttaaagtg      60
agctgcaaag catccggata caccttcact tcctattaca tgcactgggt tcgtcaagcc     120
ccgggccagg gtctggaatg gatgggcatc attaacccaa gcggtggctc tacctcctac     180
gcgcagaaat tccagggtcg cgtcacgatg acccgtgaca ctagcacctc taccgtttat     240
atggagctgt ccagcctgcg ttctgaagat actgcagtgt actactgtgc acgcaactac     300
tacatcggta tcgttccgtt cgactattgg ggtcaaggca ccctcgtaac ggtttcttct     360

<210> SEQ ID NO 158
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 158

```
gaggtgcaat tggttgaatc tggtggtggt ctggtaaaac cgggcggttc cctgcgtctg     60
agctgcgcgg cttccggatt caccttctcc aacgcgtgga tgagctgggt tcgccaggcc    120
ccgggcaaag gcctcgagtg ggttggtcgt atcaagtcta aaactgacgg tggcaccacg    180
gattacgcgg ctccagttaa aggtcgtttt accatttccc gcgacgatag caaaaacact    240
ctgtatctgc agatgaactc tctgaaaact gaagacaccg cagtctacta ctgtactacc    300
ccgtgggaat ggtcttggta cgattattgg ggccagggca cgctggttac ggtgtcttcc    360
```

<210> SEQ ID NO 159
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (53)..(53)
<223> OTHER INFORMATION: a, c, t, g, unknown or other

<400> SEQUENCE: 159

```
gaggtgcaat tggttgaatc tggtggtggt ctggtaaaac cgggcggttc ccngcgtctg     60
agctgcgcgg cttccggatt caccttctcc aacgcgtgga tgagctgggt tcgccaggcc    120
ccgggcaaag gcctcgagtg ggttggtcgt atcaagtcta aaactgacgg tggcaccacg    180
gattacgcgg ctccagttaa aggtcgtttt accatttccc gcgacgatag caaaaacact    240
ctgtatctgc agatgaactc tctgaaaacc gaagacaccg cagtctacta ctgtactacc    300
ccgtgggaat ggtcttactt cgattattgg ggccagggca cgctggttac ggtgtcttcc    360
```

<210> SEQ ID NO 160
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 160

```
caggtgcaat tggttcaatc tggtgctgaa gtaaaaaaac cgggcgcttc cgttaaagtg     60
agctgcaaag catccggata caccttcact tcctattaca tgcactgggt tcgtcaagcc    120
ccgggccagg gtctggaatg gatgggcatc attaacccaa gcggtggctc tacctcctac    180
gcgcagaaat tccagggtcg cgtcacgatg acccgtgaca ctagcacctc taccgtttat    240
atggagctgt ccagcctgcg ttctgaagat actgcagtgt actactgtgc acgcaactac    300
tacgttggtg tttctccgtt cgactattgg ggtcaaggca ccctcgtaac ggtttcttct    360
```

<210> SEQ ID NO 161
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (47)..(47)
<223> OTHER INFORMATION: a, c, t, g, unknown or other

```
<220> FEATURE:
<221> NAME/KEY: modified_base
<222> LOCATION: (177)..(177)
<223> OTHER INFORMATION: a, c, t, g, unknown or other

<400> SEQUENCE: 161
caggtgcaat tggttcaatc tggtgctgaa gtaaaaaaac cgggcgnttc cgttaaagtg     60
agctgcaaag catccggata caccttcact tcctattaca tgcactgggt tcgtcaagcc    120
ccgggccagg gtctggaatg gatgggcatc attaacccaa gcggtggctc tacctcntac    180
gcgcagaaat tccagggtcg cgtcacgatg acccgtgaca ctagcacctc taccgtttat    240
atggagctgt ccagcctgcg ttctgaagat actgcagtgt actactgtgc acgcaacttc    300
actgttctgc gtgttccgtt cgactattgg ggtcaaggca ccctcgtaac ggtttcttct    360

<210> SEQ ID NO 162
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 162
gaggtgcaat tggttgaatc tggtggtggt ctggtaaaac cgggcggttc cctgcgtctg     60
agctgcgcgg cttccggatt caccttctcc aacgcgtgga tgagctgggt tcgccaggcc    120
ccgggcaaag gcctcgagtg ggttggtcgt atcaagtcta aaactgacgg tggcaccacg    180
gattacgcgg ctccagttaa aggtcgtttt accatttccc gcgacgatag caaaaacact    240
ctgtatctgc agatgaactc tctgaaaact gaagacaccg cagtctacta ctgtactacc    300
ccgtgggaat gggcttggtt cgattattgg ggccagggca cgctggttac ggtgtcttcc    360

<210> SEQ ID NO 163
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 163
gaggtgcaat tggttgaatc tggtggtggt ctggtaaaac cgggcggttc cctgcgtctg     60
agctgcgcgg cttccggatt caccttctcc aacgcgtgga tgagctgggt tcgccaggcc    120
ccgggcaaag gcctcgagtg ggttggtcgt atcaagtcta aaactgacgg tggcaccacg    180
gattacgcgg ctccagttaa aggtcgtttt accatttccc gcgacgatag caaaaacact    240
ctgtatctgc agatgaactc tctgaaaacc gaagacaccg cagtctacta ctgtactacc    300
ccttgggaat gggcttactt cgattattgg ggccagggca cgctggttac ggtgtcttcc    360

<210> SEQ ID NO 164
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 164
```

```
caggtgcaat tggttcaatc tggtgctgaa gtaaaaaaac cgggcgcttc cgttaaagtg    60
agctgcaaag catccggata caccttcact tcctattaca tgcactgggt tcgtcaagcc   120
ccgggccagg gtctggaatg gatgggcatc attaacccaa gcggtggctc tacctcctac   180
gcgcagaaat tccagggtcg cgtcacgatg acccgtgaca ctagcacctc taccgtttat   240
atggagctgt ccagcctgcg ttctgaagat actgcagtgt actactgtgc acgcactggt   300
tggtctcgtt ggggttacat ggactattgg ggccaaggca ccctcgtaac ggtttcttct   360
```

<210> SEQ ID NO 165
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 165

```
caggtgcaat tggttcaatc tggtgctgaa gtaaaaaaac cgggcgcttc cgttaaagtg    60
agctgcaaag catccggata caccttcact tcctattaca tgcactgggt tcgtcaagcc   120
ccgggccagg gtctggaatg gatgggcatc attaacccaa gcggtggctc tacctcctac   180
gcgcagaaat tccagggtcg cgtcacgatg acccgtgaca ctagcacctc taccgtttat   240
atggagctgt ccagcctgcg ttctgaagat actgcagtgt actactgtgc acgcggtgaa   300
tggatccgtt actaccattt cgactattgg ggtcaaggca ccctcgtaac ggtttcttct   360
```

<210> SEQ ID NO 166
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 166

```
caggtgcaat tggttcaatc tggtgctgaa gtaaaaaaac cgggcgcttc cgttaaagtg    60
agctgcaaag catccggata caccttcact tcctattaca tgcactgggt tcgtcaagcc   120
ccgggccagg gtctggaatg gatgggcatc attaacccaa gcggtggctc tacctcctac   180
gcgcagaaat tccagggtcg cgtcacgatg acccgtgaca ctagcacctc taccgtttat   240
atggagctgt ccagcctgcg ttctgaagat actgcagtgt actactgtgc acgcgttggt   300
tggtaccgtt ggggttacat ggactattgg ggtcaaggca ccctcgtaac ggtttcttct   360
```

<210> SEQ ID NO 167
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 167

```
caggtgcaat tggtgcagtc tggggctgag gtgaagaagc ctgggtcctc ggtgaaggtc    60
tcctgcaagg cctccggagg cacattcagc agctacgcta taagctgggt gcgacaggcc   120
cctggacaag gctcgagtg gatgggaggg atcatcccta tctttggtac agcaaactac   180
gcacagaagt tccagggcag ggtaaccatt actgcagaca aatccacgag cacagcctac   240
```

```
atggagctga gcagcctgag atctgaggac accgccgtgt attactgtgc gagagctgtt    300
ttctaccgtg cttggtactc tttcgactac tggggccaag ggaccaccgt gaccgtctcc    360
tca                                                                  363
```

<210> SEQ ID NO 168
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 168

```
gacatccaga tgacccagtc tccttccacc ctgtctgcat ctgtaggaga ccgtgtcacc     60
atcacttgcc gtgccagtca gagtattagt agctggttgg cctggtatca gcagaaacca    120
gggaaagccc ctaagctcct gatctatgat gcctccagtt tggaaagtgg ggtcccatca    180
cgtttcagcg gcagtggatc cgggacagaa ttcactctca ccatcagcag cttgcagcct    240
gatgattttg caacttatta ctgccaacag tataccagcc caccaccaac gtttggccag    300
ggcaccaaag tcgagatcaa g                                              321
```

<210> SEQ ID NO 169
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 169

```
caggtgcaat tggttcaatc tggtgctgaa gtaaaaaaac cgggcgcttc cgttaaagtg     60
agctgcaaag catccggata caccttcact tcctattaca tgcactgggt tcgtcaagcc    120
ccgggccagg gtctggaatg gatgggcatc attaacccaa gcggtggctc tacctcctac    180
gcgcagaaat tccagggtcg cgtcacgatg acccatgaca ctagcacctc taccgtttat    240
atggagctgt ccagcctgcg ttctgaagat actgcagtgt actactgtgc acgctctttc    300
ttcactggtt tccatctgga ctattggggt caaggcaccc tcgtaacggt tcttct        357
```

<210> SEQ ID NO 170
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 170

```
gaaatcgtgt taacgcagtc tccaggcacc ctgtctttgt ctccagggga aagagccacc     60
ctctcttgca gggccagtca gagtgttagc agcagctact tagcctggta ccagcagaaa    120
cctggccagg ctcccaggct cctcatctat ggagcatcca gcagggccac tggcatccca    180
gacaggttca gtggcagtgg atccgggaca gacttcactc tcaccatcag cagactggag    240
cctgaagatt ttgcagtgta ttactgtcag cagtatacca cgaacatta ttatacgttc    300 ggccagggga ccaaagtgga aatcaaa                                        327
```

<210> SEQ ID NO 171
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 171

```
caggtgcaat tggttcaatc tggtgctgaa gtaaaaaaac cgggcgcttc cgttaaagtg      60
agctgcaaag catccggata caccttcact tcctattaca tgcactgggt tcgtcaagcc     120
ccgggccagg gtctggaatg gatgggcatc attaacccaa gcggtggccc tacctcctac     180
gcgcagaaat tccagggtcg cgtcacgatg accgtgaca ctagcacctc taccgtttat      240
atggagctgt ccagcctgcg ttctgaagat actgcagtgt actactgtgc acgcggtgac     300
ttcgcttggc tggactattg gggtcaaggc accctcgtaa cggtttcttc t              351
```

<210> SEQ ID NO 172
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 172

```
gatattgtta tgactcaatc tccactgtct ctgccggtga ctccaggcga accggcgagc      60
atttcttgcc gttccagcca gtctctgctg cactccaacg gctacaacta tctcgattgg     120
tacctgcaaa aaccgggtca gagccctcag ctgctgatct acctgggctc taaccgcgct     180
tccggtgtac cggaccgttt cagcggctct ggatccggca ccgatttcac gttgaaaatc     240
agccgtgttg aagcagaaga cgtgggcgtt tattactgta tgcaggcaag cattatgaac     300
cggacttttg gtcaaggcac caaggtcgaa attaaa                                336
```

<210> SEQ ID NO 173
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 173

```
gatattgtta tgactcaatc tccactgtct ctgccggtga ctccaggcga accggcgagc      60
atttcttgcc gttccagcca gtctctgctg cactccaacg gctacaacta tctcgattgg     120
tacctgcaaa aaccgggtca gagccctcag ctgctgatct acctgggctc taaccgcgct     180
tccggtgtac cggaccgttt cagcggctct ggatccggca ccgatttcac gttgaaaatc     240
agccgtgttg aagcagaaga cgtgggcgtt tattactgta tgcaggcaag cattatgagc     300
cggacttttg gtcaaggcac caaggtcgaa attaaa                                336
```

<210> SEQ ID NO 174
<211> LENGTH: 336
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic polynucleotide"

<400> SEQUENCE: 174
gatattgtta tgactcaatc tccactgtct ctgccggtga ctccaggcga accggcgagc      60
atttcttgcc gttccagcca gtctctgctg cactccaacg gctacaacta tctcgattgg    120
tacctgcaaa aaccgggtca gagccctcag ctgctgatct acctgggctc taaccgcgct    180
tccggtgtac cggaccgttt cagcggctct ggatccggca ccgatttcac gttgaaaatc    240
agccgtgttg aagcagaaga cgtgggcgtt tattactgta tgcaggcaag cattatgcag    300
cggacttttg gtcaaggcac caaggtcgaa attaaa                              336

<210> SEQ ID NO 175
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 175
gatattgtta tgactcaatc tccactgtct ctgccggtga ctccaggcga accggcgagc      60
atttcttgcc gttccagcca gtctctgctg cactccaacg gctacaacta tctcgattgg    120
tacctgcaaa aaccgggtca gagccctcag ctgctgatct acctgggctc taaccgcgct    180
tccggtgtac cggaccgttt cagcggctct ggatccggca ccgatttcac gttgaaaatc    240
agccgtgttg aagcagaaga cgtgggcgtt tattactgta tgcaggcaag cattatgaac    300
cgggcttttg gtcaaggcac caaggtcgaa attaaa                              336

<210> SEQ ID NO 176
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 176
gatattgtta tgactcaatc tccactgtct ctgccggtga ctccaggcga accggcgagc      60
atttcttgcc gttccagcca gtctctgctg cactccaacg gctacaacta tctcgattgg    120
tacctgcaaa aaccgggtca gagccctcag ctgctgatct acctgggctc taaccgcgct    180
tccggtgtac cggaccgttt cagcggctct ggatccggca ccgatttcac gttgaaaatc    240
agccgtgttg aagcagaaga cgtgggcgtt tattactgta tgcaggcaag cattatgaac    300
cggaattttg gtcaaggcac caaggtcgaa attaaa                              336

<210> SEQ ID NO 177
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 177
caggtgcaat tggttcaatc tggtgctgaa gtaaaaaaac cgggcgcttc cgttaaagtg      60
```

| | |
|---|---|
| agctgcaaag catccggata caccttcact tcctattaca tgcactgggt tcgtcaagcc | 120 |
| ccgggccagg gtctggaatg gatgggcatc attaacccaa gcggtggctc tacctcctac | 180 |
| gcgcagaaat tccagggtcg cgtcacgatg acccgtgaca ctagcacctc taccgtttat | 240 |
| atggagctgt ccagcctgcg ttctgaagat actgcagtgt actactgtgc acgctcttac | 300 |
| atcgacatgg actattgggg tcaaggcacc ctcgtaacgg tttcttct | 348 |

<210> SEQ ID NO 178
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 178

| | |
|---|---|
| gaaatcgtgt taacgcagtc tccaggcacc ctgtctttgt ctccagggga aagagccacc | 60 |
| ctctcttgca gggccagtca gagtgttagc agcagctact tagcctggta ccagcagaaa | 120 |
| cctggccagg ctcccaggct cctcatctat ggagcatcca gcagggccac tggcatccca | 180 |
| gacaggttca gtggcagtgg atccgggaca gacttcactc tcaccatcag cagactggag | 240 |
| cctgaagatt ttgcagtgta ttactgtcag caggataact ggagcccaac gttcggccag | 300 |
| gggaccaaag tggaaatcaa a | 321 |

<210> SEQ ID NO 179
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 179

| | |
|---|---|
| caggtgcaat tggttcaatc tggtgctgaa gtaaaaaaac cgggcgcttc cgttaaagtg | 60 |
| agctgcaaag catccggata caccttcact tcctattaca tgcactgggt tcgtcaagcc | 120 |
| ccgggccagg gtctggaatg gatgggcatc attaacccaa gcggtggctc tacctcctac | 180 |
| gcgcagaaat tccagggtcg cgtcacgatg acccgtgaca ctagcacctc taccgtttat | 240 |
| atggagctgt ccagcctgcg ttctgaagat actgcagtgt actactgtgc acgctcttac | 300 |
| gttgacatgg actattgggg tcaaggcacc ctcgtaacgg tttcttct | 348 |

<210> SEQ ID NO 180
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 180

| | |
|---|---|
| gaaatcgtgt taacgcagtc tccaggcacc ctgtctttgt ctccagggga aagagccacc | 60 |
| ctctcttgca gggccagtca gagtgttagc agcagctacc tagcctggta ccagcagaaa | 120 |
| cctggccagg ctcccaggct cctcatctat ggagcatcca gcagggccac tggcatccca | 180 |
| gacaggttca gtggcagtgg atccgggaca gacttcactc tcaccatcag cagactggag | 240 |
| cctgaagatt ttgcagtgta ttactgtcag caggatattt ggagcccaac gttcggccag | 300 | gggaccaaag tggaaatcaa a                                                     321

<210> SEQ ID NO 181
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 181
gaggtgcaat tgttggagtc tgggggaggc ttggtacagc ctgggggtc cctgagactc             60 tcctgtgcag cctccggatt cacctttagc agttatgcca tgagctgggt ccgccaggct           120
ccagggaagg ggctggagtg gtctcagct attagtggta gtggtggtag cacatactac            180
gcagactccg tgaagggccg gttcaccatc tccagagaca attccaagaa cacgctgtat           240
ctgcagatga acagcctgag agccgaggac acggccgtat attactgtgc gaaagactct           300
tcttacgttg aatggtacgc tttcgactac tggggccaag aaccctggt caccgtctcg            360 agt                                                                         363

<210> SEQ ID NO 182
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 182
gaaatcgtgt taacgcagtc tccaggcacc ctgtctttgt ctccagggga aagagccacc            60
ctctcttgca gggccagtca gagtgttagc agcagctact tagcctggta ccagcagaaa          120
cctggccagg ctcccaggct cctcatctat ggagcatcca gcagggccac tggcatccca          180
gacaggttca gtggcagtgg atccgggaca gactccactc tcaccatcag cagactggag          240
cctgaagatt ttgcagtgta ttactgtcag cagccaacca gcagcccaat tacgttcggc          300
caggggacca agtggaaat caaa                                                   324

<210> SEQ ID NO 183
<211> LENGTH: 684
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 183
gaggtgcagc tgctggaatc tggcggcgga ctggtgcagc ctggcggatc tctgagactg            60
agctgtgccg ccagcggctt caccttcagc acctacgcca tgaactgggt gcgccaggcc          120
cctggcaaag gcctggaatg ggtgtcccgg atcagaagca gtacaacaa ctacgccacc           180 tactacgccg acagcgtgaa gggccggttc accatcagcc gggacgacag caagaacacc          240
ctgtacctgc agatgaacag cctgcgggcc gaggacaccg ccgtgtacta ttgtgtgcgg          300
cacggcaact cggcaacag ctatgtgtct tggtttgcct actggggcca gggcacccta          360
gtgaccgtgt caagcgctag taccaagggc ccagcgtgt tcccctggc acccagcagc           420

```
aagagcacat ctggcggaac agccgctctg ggctgtctgg tgaaagacta cttccccgag    480
cccgtgaccg tgtcttggaa ctctggcgcc ctgaccagcg gcgtgcacac ctttccagcc    540
gtgctgcaga gcagcggcct gtactccctg tcctccgtgg tcaccgtgcc ctctagctcc    600
ctgggaacac agacatatat ctgtaatgtc aatcacaagc cttccaacac caaagtcgat    660
aagaaagtcg agcccaagag ctgc                                           684
```

<210> SEQ ID NO 184
<211> LENGTH: 696
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 184

```
gaggtgcagc tgctggaatc tggcggcgga ctggtgcagc ctggcggatc tctgagactg     60
agctgtgccg ccagcggctt caccttcagc acctacgcca tgaactgggt cgcgcaggcc    120
cctggcaaag gcctggaatg ggtgtcccgg atcagaagca agtacaacaa ctacgccacc    180
tactacgcca cagcgtgaa gggccggttc accatcagcc gggacgacag caagaacacc    240
ctgtacctgc agatgaacag cctgcgggcc gaggacaccg ccgtgtacta ttgtgtgcgg    300
cacggcaact tcggcaacag ctatgtgtct tggtttgcct actggggcca gggcaccctc    360
gtgaccgtgt caagcgctag tgtggccgct ccctccgtgt ttatctttcc cccatccgat    420
gaacagctga aaagcggcac cgcctccgtc gtgtgtctgc tgaacaattt ttaccctagg    480
gaagctaaag tgcagtggaa agtggataac gcactgcagt ccggcaactc ccaggaatct    540
gtgacagaac aggactccaa ggacagcacc tactccctgt cctccaccct gacactgtct    600
aaggctgatt atgagaaaca caaagtctac gcctgcgaag tcacccatca gggcctgagc    660
tcgcccgtca caaagagctt caacaggga gagtgt                               696
```

<210> SEQ ID NO 185
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 185

```
gcaggcaagc attatgcagc ggacttttgg tcaagg                               36
```

<210> SEQ ID NO 186
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 186

```
caggcaagca ttatgagccg gacttttggt caagg                                35
```

<210> SEQ ID NO 187
<211> LENGTH: 37
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 187
cattatgaac cgggcttttg gtcaaggcac caaggtc                              37

<210> SEQ ID NO 188
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 188
cattatgaac cggaattttg gtcaaggcac caaggtc                              37

<210> SEQ ID NO 189
<211> LENGTH: 2067
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 189
gaggtgcaat tggttgaatc tggtggtggt ctggtaaaac cgggcggttc cctgcgtctg      60
agctgcgcgg cttccggatt caccttctcc aacgcgtgga tgagctgggt tcgccaggcc    120
ccgggcaaag gcctcgagtg ggttggtcgt atcaagtcta aaactgacgg tggcaccacg    180
gattacgcgg ctccagttaa aggtcgtttt accatttccc gcgacgatag caaaaacact    240
ctgtatctgc agatgaactc tctgaaaact gaagacaccg cagtctacta ctgtactacc    300
ccgtgggaat ggtcttggta cgattattgg ggccagggca cgctggttac ggtgtcttcc    360
gctagcacaa agggcccta g cgtgttccct ctggccccca gcagcaagag cacaagcggc    420
ggaacagccg ccctgggctg cctcgtgaag gactacttcc ccgagcccgt gacagtgtct    480
tggaacagcg gagccctgac aagcggcgtg cacactttcc ctgccgtgct gcagagcagc    540
ggcctgtact ccctgagcag cgtggtcacc gtgcctagca gcagcctggg cacccagacc    600
tacatctgca acgtgaacca caagcccagc aacaccaaag tggacaagaa ggtggagccc    660
aagagctgtg atggcggagg agggtccgga ggcggaggat ccgaggtgca gctgctggaa    720
tctggcggcg gactggtgca gcctggcgga tctctgagac tgagctgtgc cgccagcggc    780
ttcaccttca gcacctacgc catgaactgg gtgcgccagg ccctggcaa aggcctggaa    840 tgggtgtccc ggatcagaag caagtacaac aactacgcca cctactacgc cgacagcgtg    900
aagggccggt tcaccatcag ccgggacgac agcaagaaca ccctgtacct gcagatgaac    960
agcctgcggg ccgaggacac cgccgtgtac tattgtgtgc ggcacggcaa cttcggcaac   1020
agctatgtgt cttggtttgc ctactggggc cagggcaccc tcgtgaccgt gtcaagcgct   1080
agtaccaagg gcccagcgt gttcccctg gcacccagca gcaagagcac atctggcgga   1140
acagccgctc tgggctgtct ggtgaaagac tacttccccg agcccgtgac cgtgtcttgg   1200
aactctggcg ccctgaccag cggcgtgcac acctttccag ccgtgctgca gagcagcggc   1260
ctgtactccc tgtcctccgt ggtcaccgtg ccctctagct ccctgggaac acagacatat   1320
```

```
atctgtaatg tcaatcacaa gccttccaac accaaagtcg ataagaaagt cgagcccaag    1380
agctgcgaca aaactcacac atgcccaccg tgcccagcac ctgaagctgc aggggggaccg   1440 tcagtcttcc tcttcccccc aaaacccaag acaccctca tgatctcccg gacccctgag    1500
gtcacatgcg tggtggtgga cgtgagccac gaagacctg aggtcaagtt caactggtac    1560
gtggacggcg tggaggtgca taatgccaag acaaagccgc gggaggagca gtacaacagc   1620
acgtaccgtg tggtcagcgt cctcaccgtc ctgcaccagg actggctgaa tggcaaggag    1680
tacaagtgca aggtctccaa caaagccctc ggcgccccca tcgagaaaac catctccaaa   1740
gccaaagggc agccccgaga accacaggtg tacaccctgc ccccatgccg ggatgagctg   1800
accaagaacc aggtcagcct gtggtgcctg gtcaaaggct tctatcccag cgacatcgcc   1860
gtggagtggg agagcaatgg gcagccggag aacaactaca agaccacgcc tcccgtgctg   1920
gactccgacg gctccttctt cctctacagc aagctcaccg tggacaagag caggtggcag   1980
caggggaacg tcttctcatg ctccgtgatg catgaggctc tgcacaacca ctacacgcag   2040
aagagcctct ccctgtctcc gggtaaa                                       2067
```

<210> SEQ ID NO 190
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 190

```
gaggtgcaat tggttgaatc tggtggtggt ctggtaaaac cgggcggttc cctgcgtctg      60
agctgcgcgg cttccggatt caccttctcc aacgcgtgga tgagctgggt tcgccaggcc    120
ccgggcaaag gctcgagtg ggttggtcgt atcaagtcta aaactgacgg tggcaccacg     180
gattacgcgc tccagttaa aggtcgtttt accatttccc gcgacgatag caaaaacact     240
ctgtatctgc agatgaactc tctgaaaact gaagacaccg cagtctacta ctgtactacc    300
ccgtgggaat ggtcttggta cgattattgg ggccagggca cgctggttac ggtgtcttcc    360
gctagcacca agggccccctc cgtgttcccc ctggccccca gcagcaagag caccagcggc   420
ggcacagccg ctctgggctg cctggtcaag gactacttcc ccgagcccgt gaccgtgtcc    480
tggaacagcg gagccctgac ctccggcgtg cacaccttcc ccgccgtgct gcagagttct    540
ggcctgtata gcctgagcag cgtggtcacc gtgccttcta gcagcctggg cacccagacc    600
tacatctgca acgtgaacca caagcccagc aacaccaagg tggacaagaa ggtggagccc    660
aagagctgcg acaaaactca cacatgccca ccgtgcccag cacctgaagc tgcaggggga   720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcggcgccc ccatcgagaa aaccatctcc   1020
aaagccaaag gcagccccg agaaccacag gtgtgcaccc tgcccccatc ccgggatgag   1080
ctgaccaaga accaggtcag cctctgtgc gcagtcaaag gcttctatcc cagcgacatc    1140
gccgtggagt gggagagcaa tgggcagccg gagaacaact acaagaccac gcctcccgtg   1200
ctggactccg acggctcctt cttcctcgtg agcaagctca ccgtggacaa gagcaggtgg   1260
```
cagcagggga acgtcttctc atgctccgtg atgcatgagg ctctgcacaa ccgcttcacg    1320
cagaagagcc tctccctgtc tccgggtaaa                                    1350

<210> SEQ ID NO 191
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 191
caggccgtcg tgacccagga acccagcctg acagtgtctc ctggcggcac cgtgaccctg      60
acatgtggca gttctacagg cgccgtgacc accagcaact acgccaactg ggtgcaggaa     120
aagcccggcc aggccttcag aggactgatc ggcggcacca acaagagagc ccctggcacc     180
cctgccagat tcagcggatc tctgctggga ggaaaggccg ccctgacact gtctggcgcc     240
cagccagaag atgaggccga gtactactgc gccctgtggt acagcaacct gtgggtgttc     300
ggcggaggca ccaagctgac agtcctaggt caacccaagg ctgcccccag cgtgaccctg     360 ttcccccca gcagcgagga actgcaggcc aacaaggcca cctggtctg cctgatcagc      420 gacttctacc caggcgccgt gaccgtggcc tggaaggccg acagcagccc cgtgaaggcc     480
ggcgtggaga ccaccacccc cagcaagcag agcaacaaca gtacgccgc cagcagctac     540 ctgagcctga cccccgagca gtggaagagc cacaggtcct acagctgcca ggtgacccac     600
gagggcagca ccgtggagaa accgtggcc cccaccgagt gcagc                     645

<210> SEQ ID NO 192
<211> LENGTH: 2067
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 192
gaggtgcagc tgctggaatc tggcggcgga ctggtgcagc ctggcggatc tctgagactg      60
agctgtgccg ccagcggctt caccttcagc acctacgcca tgaactgggt gcgccaggcc    120
cctggcaaag gcctggaatg ggtgtcccgg atcagaagca agtacaacaa ctacgccacc    180
tactacgccg acagcgtgaa gggccggttc accatcagcc gggacgacag caagaacacc    240
ctgtacctgc agatgaacag cctgcgggcc gaggacaccg ccgtgtacta ttgtgtgcgg    300
cacggcaact cggcaacag ctatgtgtct tggtttgcct actggggcca gggcacccctc   360 gtgaccgtgt catctgctag cacaaagggc cctagcgtgt tccctctggc ccccagcagc    420
aagagcacaa gcggcggaac agccgccctg ggctgcctcg tgaaggacta cttccccgag    480
cccgtgacag tgtcttggaa cagcggagcc ctgacaagcg gcgtgcacac cttccctgcc    540
gtgctgcaga gcagcggcct gtactccctg agcagcgtgg tcaccgtgcc tagcagcagc    600
ctgggcaccc agacctacat ctgcaacgtg aaccacaagc ccagcaacac caaagtggac    660
aagaaggtgg agcccaagag ctgtgatggc ggaggagggt ccggaggcgg aggatccgag    720
gtgcaattgg ttgaatctgg tggtggtctg gtaaaccgg gcggtccct gcgtctgagc      780 tgcgcggctt ccggattcac cttctccaac gcgtggatga gctgggttcg ccaggccccg    840

```
ggcaaaggcc tcgagtgggt tggtcgtatc aagtctaaaa ctgacggtgg caccacggat    900
tacgcggctc cagttaaagg tcgttttacc atttcccgcg acgatagcaa aaacactctg    960
tatctgcaga tgaactctct gaaaactgaa gacaccgcag tctactactg tactacccg    1020 tgggaatggt cttggtacga ttattggggc cagggcacgc tggttacggt gtctagcgct   1080
agtaccaagg gccccagcgt gttccccctg gcacccagca gcaagagcac atctggcgga   1140
acagccgctc tgggctgtct ggtgaaagac tacttcccg agcccgtgac cgtgtcttgg    1200
aactctggcg ccctgaccag cggcgtgcac acctttccag ccgtgctgca gagcagcggc   1260
ctgtactccc tgtcctccgt ggtcaccgtg ccctctagct ccctgggaac acagacatat   1320
atctgtaatg tcaatcacaa gccttccaac accaaagtcg ataagaaagt cgagcccaag   1380
agctgcgaca aaactcacac atgcccaccg tgcccagcac ctgaagctgc aggggaccg    1440 tcagtcttcc tcttcccccc aaaacccaag gacaccctca tgatctcccg gacccctgag   1500
gtcacatgcg tggtggtgga cgtgagccac gaagaccctg aggtcaagtt caactggtac   1560
gtggacggcg tggaggtgca taatgccaag acaaagccgc gggaggagca gtacaacagc   1620
acgtaccgtg tggtcagcgt cctcaccgtc ctgcaccagg actggctgaa tggcaaggag   1680
tacaagtgca aggtctccaa caaagccctc ggcgccccca tcgagaaaac catctccaaa   1740 gccaagggc agccccgaga accacaggtg tacaccctgc ccccatgccg ggatgagctg    1800
accaagaacc aggtcagcct gtggtgcctg gtcaaaggct tctatcccag cgacatcgcc   1860
gtggagtggg agagcaatgg gcagccggag aacaactaca agaccacgcc tcccgtgctg   1920
gactccgacg gctccttctt cctctacagc aagctcaccg tggacaagag caggtggcag   1980
caggggaacg tcttctcatg ctccgtgatg catgaggctc tgcacaacca ctacacgcag   2040
aagagcctct ccctgtctcc gggtaaa                                       2067
```

<210> SEQ ID NO 193
<211> LENGTH: 1365
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 193

```
gaggtgcagc tgctggaatc tggcggcgga ctggtgcagc ctggcggatc tctgagactg     60
agctgtgccg ccagcggctt caccttcagc acctacgcca tgaactgggt cgccaggcc    120 cctggcaaag gcctggaatg ggtgtcccgg atcagaagca agtacaacaa ctacgccacc   180
tactacgccg acagcgtgaa gggccggttc accatcagcc gggacgacag caagaacacc   240
ctgtacctgc agatgaacag cctgcgggcc gaggacaccg ccgtgtacta ttgtgtgcgg   300
cacggcaact cggcaacag ctatgtgtct tggtttgcct actggggcca gggcacccct   360
gtgaccgtgt catctgctag caccaagggc ccatcggtct tccccctggc acctcctcc    420 aagagcacct ctgggggcac agcggccctg ggctgcctgg tcaaggacta cttccccgaa   480
ccggtgacgg tgtcgtggaa ctcaggcgcc ctgaccagcg gcgtgcacac cttcccggct   540
gtcctacagt cctcaggact ctactccctc agcagcgtgg tgaccgtgcc ctccagcagc   600
ttgggcaccc agacctacat ctgcaacgtg aatcacaagc ccagcaacac caaggtggac   660
aagaaagttg agcccaaatc ttgtgacaaa actcacacat gcccaccgtg cccagcacct   720
gaagctgcag gggaccgtc agtcttcctc ttccccccaa aacccaagga caccctcatg    780
```

| | |
|---|---|
| atctcccgga cccctgaggt cacatgcgtg gtggtggacg tgagccacga agaccctgag | 840 |
| gtcaagttca actggtacgt ggacggcgtg gaggtgcata atgccaagac aaagccgcgg | 900 |
| gaggagcagt acaacagcac gtaccgtgtg gtcagcgtcc tcaccgtcct gcaccaggac | 960 |
| tggctgaatg gcaaggagta caagtgcaag gtctccaaca aagccctcgg cgcccccatc | 1020 |
| gagaaaacca tctccaaagc caagggcag ccccgagaac acaggtgta caccctgccc | 1080 |
| ccatgccggg atgagctgac caagaaccag gtcagcctgt ggtgcctggt caaaggcttc | 1140 |
| tatcccagcg acatcgccgt ggagtgggag agcaatgggc agccggagaa caactacaag | 1200 |
| accacgcctc ccgtgctgga ctccgacggc tccttcttcc tctacagcaa gctcaccgtg | 1260 |
| gacaagagca ggtggcagca ggggaacgtc ttctcatgct ccgtgatgca tgaggctctg | 1320 |
| cacaaccact acacgcagaa gagcctctcc ctgtctccgg gtaaa | 1365 |

<210> SEQ ID NO 194
<211> LENGTH: 681
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 194

| | |
|---|---|
| gacaaaactc acacatgccc accgtgccca gcacctgaac tcctgggggg accgtcagtc | 60 |
| ttcctcttcc ccccaaaacc caaggacacc ctcatgatct cccggacccc tgaggtcaca | 120 |
| tgcgtggtgg tggacgtgag ccacgaagac cctgaggtca agttcaactg gtacgtggac | 180 |
| ggcgtggagg tgcataatgc caagacaaag ccgcgggagg agcagtacaa cagcacgtac | 240 |
| cgtgtggtca gcgtcctcac cgtcctgcac caggactggc tgaatggcaa ggagtacaag | 300 |
| tgcaaggtct ccaacaaagc cctcccagcc cccatcgaga aaaccatctc caaagccaaa | 360 |
| gggcagcccc gagaaccaca ggtgtgcacc ctgcccccat cccgggatga gctgaccaag | 420 |
| aaccaggtca gcctctcgtg cgcagtcaaa ggcttctatc ccagcgacat cgccgtggag | 480 |
| tgggagagca atgggcagcc ggagaacaac tacaagacca cgcctcccgt gctggactcc | 540 |
| gacggctcct tcttcctcgt gagcaagctc accgtggaca gagcaggtg gcagcagggg | 600 |
| aacgtcttct catgctccgt gatgcatgag gctctgcaca accgcttcac gcagaagagc | 660 |
| ctctcccctgt ctccgggtaa a | 681 |

<210> SEQ ID NO 195
<211> LENGTH: 2070
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 195

| | |
|---|---|
| caggtgcaat tggttcaatc tggtgctgaa gtaaaaaaac cgggcgcttc cgttaaagtg | 60 |
| agctgcaaag catccggata caccttcact tcctattaca tgcactgggt tcgtcaagcc | 120 |
| ccgggccagg gtctggaatg gatgggcatc attaacccaa gcggtggccc tacctcctac | 180 |
| gcgcagaaat tccagggtcg cgtcacgatg acccgtgaca ctagcacctc taccgttat | 240 |
| atggagctgt ccagcctgcg ttctgaagat actgcagtgt actactgtgc acgcggtgac | 300 |

```
ttcgcttggc tggactattg gggtcaaggc accctcgtaa cggtttcttc tgctagcaca     360
aagggcccca gcgtgttccc tctggcccct agcagcaaga gcacatctgg cggaacagcc     420
gccctgggct gcctcgtgaa ggactacttt cccgagcctg tgaccgtgtc ctggaactct     480
ggcgccctga caagcggcgt gcacaccttt ccagccgtgc tgcagagcag cggcctgtac     540
tctctgagca gcgtggtcac cgtgcctagc agcagcctgg gcacccagac ctacatctgc     600
aacgtgaacc acaagcccag caacaccaaa gtggacaaga aggtggagcc caagagctgt     660
gatggcggag agggtccgg aggcggagga tccgaggtgc agctgctgga atctggcggc     720
ggactggtgc agcctggcgg atctctgaga ctgagctgtg ccgccagcgg cttcaccttc     780
agcacctacg ccatgaactg ggtgcgccag gcccctggca aaggcctgga atgggtgtcc     840
cggatcagaa gcaagtacaa caactacgcc acctactacg ccgacagcgt gaagggccgg     900
ttcaccatca gccgggacga cagcaagaac accctgtacc tgcagatgaa cagcctgcgg     960
gccgaggaca ccgccgtgta ctattgtgtg cggcacggca acttcggcaa cagctatgtg    1020
tcttggtttg cctactgggg ccagggcacc ctcgtgaccg tgtcaagcgc tagtgtggcc    1080
gctccctccg tgtttatctt tccccccatcc gatgaacagc tgaaaagcgg caccgcctcc    1140
gtcgtgtgtc tgctgaacaa ttttacccct agggaagcta agtgcagtg aaagtggat     1200 aacgcactgc agtccggcaa ctcccaggaa tctgtgacag aacaggactc caaggacagc    1260
acctactccc tgtcctccac cctgacactg tctaaggctg attatgagaa acacaaagtc    1320
tacgcctgcg aagtcaccca tcagggcctg agctcgcccg tcacaaagag cttcaacagg    1380
ggagagtgtg acaagaccca cacctgtccc ccttgtcctg cccctgaagc tgctggcggc    1440
ccttctgtgt tcctgttccc cccaaagccc aaggacaccc tgatgatcag ccggacccc    1500 gaagtgacct gcgtggtggt ggatgtgtcc cacgaggacc ctgaagtgaa gttcaattgg    1560
tacgtggacg gcgtggaagt gcacaacgcc aagacaaagc cgcgggagga gcagtacaac    1620
agcacgtacc gtgtggtcag cgtcctcacc gtcctgcacc aggactggct gaatggcaag    1680
gagtacaagt gcaaggtctc caacaaagcc ctcggcgccc catcgagaa aaccatctcc    1740 aaagccaaag ggcagccccg agaaccacag gtgtacaccc tgcccccatg ccgggatgag    1800
ctgaccaaga accaggtcag cctgtggtgc ctggtcaaag gcttctatcc cagcgacatc    1860
gccgtggagt gggagagcaa tgggcagccg gagaacaact acaagaccac gcctcccgtg    1920
ctggactccg acggctcctt cttcctctac agcaagctca ccgtggacaa gagcaggtgg    1980
cagcagggga acgtcttctc atgctccgtg atgcatgagg ctctgcacaa ccactacacg    2040
cagaagagcc tctccctgtc tccgggtaaa                                      2070

<210> SEQ ID NO 196
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 196
caggtgcaat tggttcaatc tggtgctgaa gtaaaaaaac cgggcgcttc cgttaaagtg      60
agctgcaaag catccggata caccttcact tcctattaca tgcactgggt tcgtcaagcc     120
ccgggccagg gtctggaatg gatgggcatc attaacccaa gcggtggccc tacctcctac     180
gcgcagaaat tccagggtcg cgtcacgatg accccgtgaca ctagcaccctc taccgtttat     240
```

```
atggagctgt ccagcctgcg ttctgaagat actgcagtgt actactgtgc acgcggtgac      300
ttcgcttggc tggactattg gggtcaaggc accctcgtaa cggtttcttc tgctagcacc      360
aagggcccct ccgtgttccc cctggccccc agcagcaaga gcaccagcgg cggcacagcc      420
gctctgggct gcctggtcaa ggactacttc cccgagcccg tgaccgtgtc ctggaacagc      480
ggagccctga cctccggcgt gcacaccttc ccgccgtgc tgcagagttc tggcctgtat      540
agcctgagca gcgtggtcac cgtgccttct agcagcctgg gcacccagac ctacatctgc      600
aacgtgaacc acaagcccag caacaccaag gtggacaaga aggtggagcc caagagctgc      660
gacaaaactc acacatgccc accgtgccca gcacctgaag ctgcagggg accgtcagtc      720 ttcctcttcc ccccaaaacc caaggacacc ctcatgatct cccggacccc tgaggtcaca      780
tgcgtggtgg tggacgtgag ccacgaagac cctgaggtca agttcaactg gtacgtggac      840
ggcgtggagg tgcataatgc aagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcggcgcc cccatcgaga aaaccatctc caaagccaaa      1020
gggcagcccc gagaaccaca ggtgtgcacc ctgcccccat cccgggatga gctgaccaag      1080
aaccaggtca gcctctcgtg cgcagtcaaa ggcttctatc ccagcgacat cgccgtggag      1140
tgggagagca atgggcagcc ggagaacaac tacaagacca cgcctcccgt gctggactcc      1200
gacggctcct tcttcctcgt gagcaagctc accgtggaca agagcaggtg gcagcagggg      1260
aacgtcttct catgctccgt gatgcatgag gctctgcaca accactacac gcagaagagc      1320
ctctccctgt ctccgggtaa a      1341

<210> SEQ ID NO 197
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 197
gatattgtta tgactcaatc tccactgtct ctgccggtga ctccaggcga accggcgagc      60
atttcttgcc gttccagcca gtctctgctg cactccaacg gctacaacta tctcgattgg      120
tacctgcaaa aaccgggtca gagccctcag ctgctgatct acctgggctc taaccgcgct      180
tccggtgtac cggaccgttt cagcggctct ggatccggca ccgatttcac gttgaaaatc      240
agccgtgttg aagcagaaga cgtgggcgtt tattactgta tgcaggcaag cattatgaac      300 cggactttg gtcaaggcac caaggtcgaa attaaacgta cggtggctgc accatctgtc      360
ttcatcttcc cgccatctga tgagcagttg aaatctggaa ctgcctctgt tgtgtgcctg      420
ctgaataact tctatcccag agaggccaaa gtacagtgga aggtggataa cgccctccaa      480
tcgggtaact cccaggagag tgtcacagag caggacagca aggacagcac ctacagcctc      540
agcagcaccc tgacgctgag caaagcagac tacgagaaac acaaagtcta cgcctgcgaa      600
gtcacccatc agggcctgag ctcgcccgtc acaaagagct tcaacagggg agagtgt      657

<210> SEQ ID NO 198
<211> LENGTH: 642
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic polynucleotide"

<400> SEQUENCE: 198
caggccgtcg tgacccagga acccagcctg acagtgtctc ctggcggcac cgtgaccctg      60
acatgtggca gttctacagg cgccgtgacc accagcaact acgccaactg ggtgcaggaa     120
aagcccggcc aggccttcag aggactgatc ggcggcacca acaagagagc ccctggcacc     180
cctgccagat tcagcggatc tctgctggga ggaaaggccg ccctgacact gtctggcgcc     240
cagccagaag atgaggccga gtactactgc gccctgtggt acagcaacct gtgggtgttc     300
ggcggaggca ccaagctgac agtgctgagc agcgcttcca ccaaaggccc ttccgtgttt     360
cctctggctc ctagctccaa gtccacctct ggaggcaccg ctgctctcgg atgcctcgtg     420
aaggattatt ttcctgagcc tgtgacagtg tcctggaata cggagcact gacctctgga      480 gtgcatactt tccccgctgt gctgcagtcc tctggactgt acagcctgag cagcgtggtg     540
acagtgccca gcagcagcct gggcacccag acctacatct gcaacgtgaa ccacaagccc     600
agcaacacca aggtggacaa gaaggtggaa cccaagtctt gt                        642

<210> SEQ ID NO 199
<211> LENGTH: 1377
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 199
gaggtgcagc tgctggaatc tggcggcgga ctggtgcagc ctggcggatc tctgagactg      60
agctgtgccg ccagcggctt caccttcagc acctacgcca tgaactgggt gcgccaggcc     120
cctggcaaag gcctggaatg ggtgtcccgg atcagaagca agtacaacaa ctacgccacc     180
tactacgccg acagcgtgaa gggccggttc accatcagcc gggacgacag caagaacacc     240
ctgtacctgc agatgaacag cctgcgggcc gaggacaccg ccgtgtacta ttgtgtgcgg     300
cacggcaact tcggcaacag ctatgtgtct tggtttgcct actggggcca gggcacccctc    360 gtgaccgtgt catctgctag cgtggccgct cccctccgtgt ttatctttcc cccatccgat    420
gaacagctga aaagcggcac cgcctccgtc gtgtgtctgc tgaacaattt ttaccctagg    480
gaagctaaag tgcagtggaa agtggataac gcactgcagt ccggcaactc ccaggaatct    540
gtgacagaac aggactccaa ggacagcacc tactccctgt cctccaccct gacactgtct    600
aaggctgatt atgagaaaca caaagtctac gcctgcgaag tcacccatca gggcctgagc    660
tcgcccgtca caaagagctt caacaggggga gagtgtgaca gacccacac ctgtcccct     720 tgtcctgccc ctgaagctgc tggcggccct tctgtgttcc tgttcccccc aaagcccaag    780
gacaccctga tgatcagccg gaccccgaa gtgacctgc tggtggtgga tgtgtcccac     840
gaggaccctg aagtgaagtt caattggtac gtggacggcg tggaagtgca caacgccaag    900
acaaagccgc gggaggagca gtacaacagc acgtaccgtg tggtcagcgt cctcaccgtc    960
ctgcaccagg actggctgaa tggcaaggag tacaagtgca aggtctccaa caaagccctc    1020
ggcgccccca tcgagaaaac catctccaaa gccaagggc agccccgaga accacaggtg    1080
tacaccctgc ccccatgccg ggatgagctg accaagaacc aggtcagcct gtggtgcctg    1140
gtcaaaggct tctatcccag cgacatcgcc gtggagtggg agagcaatgg gcagccggag    1200
```

| | |
|---|---|
| aacaactaca agaccacgcc tcccgtgctg gactccgacg gctccttctt cctctacagc | 1260 |
| aagctcaccg tggacaagag caggtggcag caggggaact tcttctcatg ctccgtgatg | 1320 |
| catgaggctc tgcacaacca ctacacgcag aagagcctct ccctgtctcc gggtaaa | 1377 |

<210> SEQ ID NO 200
<211> LENGTH: 2067
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 200

| | |
|---|---|
| gaggtgcaat tggttgaatc tggtggtggt ctggtaaaac cgggcggttc cctgcgtctg | 60 |
| agctgcgcgg cttccggatt caccttctcc aacgcgtgga tgagctgggt tcgccaggcc | 120 |
| ccgggcaaag gcctcgagtg ggttggtcgt atcaagtcta aaactgacgg tgcaccacg | 180 |
| gattacgcgg ctccagttaa aggtcgtttt accatttccc gcgacgatag caaaaacact | 240 |
| ctgtatctgc agatgaactc tctgaaaact gaagacaccg cagtctacta ctgtactacc | 300 |
| ccgtgggaat ggtcttggta cgattattgg ggccagggca cgctggttac ggtgtcttcc | 360 |
| gctagcacaa agggcccctag cgtgttccct ctggccccca gcagcaagag cacaagcggc | 420 |
| ggaacagccg ccctgggctg cctcgtgaag gactacttcc ccgagcccgt gacagtgtct | 480 |
| tggaacagcg gagccctgac aagcggcgtg cacactttcc ctgccgtgct gcagagcagc | 540 |
| ggcctgtact ccctgagcag cgtggtcacc gtgcctagca gcagcctggg cacccagacc | 600 |
| tacatctgca acgtgaacca caagcccagc aacaccaaag tggacaagaa ggtggagccc | 660 |
| aagagctgtg atggcggagg agggtccgga ggcggaggat ccgaggtgca gctgctggaa | 720 |
| tctggcggcg gactggtgca gcctggcgga tctctgagac tgagctgtgc cgccagcggc | 780 |
| ttcaccttca gcacctacgc catgaactgg gtgcgccagg cccctggcaa aggcctggaa | 840 |
| tgggtgtccc ggatcagaag caagtacaac aactacgcca cctactacgc cgacagcgtg | 900 |
| aagggccggt tcaccatcag ccgggacgac agcaagaaca ccctgtacct gcagatgaac | 960 |
| agcctgcggg ccgaggacac cgccgtgtac tattgtgtgc ggcacggcaa cttcggcgcc | 1020 |
| agctatgtgt cttggtttgc ctactggggc cagggcaccc tcgtgaccgt gtcaagcgct | 1080 |
| agtaccaagg gcccagcgt gttccccctg gcacccagca gcaagagcac atctggcgga | 1140 |
| acagccgctc tgggctgtct ggtgaaagac tactttcccg agcccgtgac cgtgtcttgg | 1200 |
| aactctggcg ccctgaccag cggcgtgcac accttccag ccgtgctgca gagcagcggc | 1260 |
| ctgtactccc tgtcctccgt ggtcaccgtg ccctctagct ccctgggaac acagacatat | 1320 |
| atctgtaatg tcaatcacaa gccttccaac accaaagtcg ataagaaagt cgagcccaag | 1380 |
| agctgcgaca aaactcacac atgcccaccg tgcccagcac ctgaagctgc aggggaccg | 1440 |
| tcagtcttcc tcttcccccc aaaacccaag gacaccctca tgatctcccg gacccctgag | 1500 |
| gtcacatgcg tggtggtgga cgtgagccac gaagaccctg aggtcaagtt caactggtac | 1560 |
| gtggacggcg tggaggtgca taatgccaag acaaagccgc gggaggagca gtacaacagc | 1620 |
| acgtaccgtg tggtcagcgt cctcaccgtc ctgcaccagg actggctgaa tggcaaggag | 1680 |
| tacaagtgca aggtctccaa caaagccctc ggcgccccca tcgagaaaac catctccaaa | 1740 |
| gccaaagggc agccccgaga accacaggtg tacaccctgc ccccatgccg ggatgagctg | 1800 |

| | |
|---|---|
| accaagaacc aggtcagcct gtggtgcctg gtcaaaggct tctatcccag cgacatcgcc | 1860 |
| gtggagtggg agagcaatgg gcagccggag aacaactaca agaccacgcc tcccgtgctg | 1920 |
| gactccgacg gctccttctt cctctacagc aagctcaccg tggacaagag caggtggcag | 1980 |
| caggggaacg tcttctcatg ctccgtgatg catgaggctc tgcacaacca ctacacgcag | 2040 |
| aagagcctct ccctgtctcc gggtaaa | 2067 |

<210> SEQ ID NO 201
<211> LENGTH: 2067
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 201

| | |
|---|---|
| gaggtgcaat tggttgaatc tggtggtggt ctggtaaaac cgggcggttc cctgcgtctg | 60 |
| agctgcgcgg cttccggatt caccttctcc aacgcgtgga tgagctgggt tcgccaggcc | 120 |
| ccgggcaaag gcctcgagtg ggttggtcgt atcaagtcta aaactgacgg tggcaccacg | 180 |
| gattacgcgg ctccagttaa aggtcgtttt accatttccc gcgacgatag caaaaacact | 240 |
| ctgtatctgc agatgaactc tctgaaaact gaagacaccg cagtctacta ctgtactacc | 300 |
| ccgtgggaat ggtcttggta cgattattgg ggccagggca cgctggttac ggtgtcttcc | 360 |
| gctagcacaa agggccctag cgtgttccct ctggccccca gcagcaagag cacaagcggc | 420 |
| ggaacagccg ccctgggctg cctcgtgaag gactacttcc ccgagcccgt gacagtgtct | 480 |
| tggaacagcg gagccctgac aagcggcgtg cacacttcc ctgccgtgct gcagagcagc | 540 |
| ggcctgtact ccctgagcag cgtggtcacc gtgcctagca gcagcctggg cacccagacc | 600 |
| tacatctgca acgtgaacca caagcccagc aacaccaaag tggacaagaa ggtggagccc | 660 |
| aagagctgtg atggcggagg agggtccgga ggcggaggat ccgaggtgca gctgctggaa | 720 |
| tctggcggcg gactggtgca gcctggcgga tctctgagac tgagctgtgc cgccagcggc | 780 |
| ttcaccttca gcacctacgc catgaactgg gtgcgccagg cccctggcaa aggcctggaa | 840 |
| tgggtgtccc ggatcagaag caagtacaac aactacgcca cctactacgc cgacagcgtg | 900 |
| aagggccggt tcaccatcag ccgggacgac agcaagaaca ccctgtacct gcagatgaac | 960 |
| agcctgcggg ccgaggacac cgccgtgtac tattgtgtgc ggcacggcaa cttcggcaac | 1020 |
| gcctatgtgt cttggtttgc ctactgggcc cagggcaccc tcgtgaccgt gtcaagcgct | 1080 |
| agtaccaagg gcccagcgt gttccccctg gcacccagca gcaagagcac atctggcgga | 1140 |
| acagccgctc tgggctgtct ggtgaaagac tacttccccg agcccgtgac cgtgtcttgg | 1200 |
| aactctggcg ccctgaccag cggcgtgcac acctttccag ccgtgctgca gagcagcggc | 1260 |
| ctgtactccc tgtcctccgt ggtcaccgtg ccctctagct ccctgggaac acagacatat | 1320 |
| atctgtaatg tcaatcacaa gccttccaac accaaagtcg ataagaaagt cgagcccaag | 1380 |
| agctgcgaca aaactcacac atgcccaccg tgcccagcac ctgaagctgc aggggaccg | 1440 |
| tcagtcttcc tcttcccccc aaaacccaag gacaccctca tgatctcccg gacccctgag | 1500 |
| gtcacatgcg tggtggtgga cgtgagccac gaagaccctg aggtcaagtt caactggtac | 1560 |
| gtggacggcg tggaggtgca taatgccaag acaaagccgc gggaggagca gtacaacagc | 1620 |
| acgtaccgtg tggtcagcgt cctcaccgtc ctgcaccagg actggctgaa tggcaaggag | 1680 |
| tacaagtgca aggtctccaa caaagccctc ggcgccccca tcgagaaaac catctccaaa | 1740 |

```
gccaaagggc agccccgaga accacaggtg tacaccctgc ccccatgccg ggatgagctg    1800
accaagaacc aggtcagcct gtggtgcctg gtcaaaggct tctatcccag cgacatcgcc    1860
gtggagtggg agagcaatgg gcagccggag aacaactaca agaccacgcc tcccgtgctg    1920
gactccgacg gctccttctt cctctacagc aagctcaccg tggacaagag caggtggcag    1980
caggggaacg tcttctcatg ctccgtgatg catgaggctc tgcacaacca ctacacgcag    2040
aagagcctct ccctgtctcc gggtaaa                                        2067

<210> SEQ ID NO 202
<211> LENGTH: 1323
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 202
caggccgtcg tgacccagga acccagcctg acagtgtctc ctggcggcac cgtgaccctg      60
acatgtggca gttctacagg cgccgtgacc accagcaact acgccaactg ggtgcaggaa     120
aagcccggcc aggccttcag aggactgatc ggcggcacca acaagagagc ccctggcacc     180
cctgccagat tcagcggatc tctgctggga ggaaaggccg ccctgacact gtctggcgcc     240
cagccagaag atgaggccga gtactactgc gccctgtggt acagcaacct gtgggtgttc     300
ggcggaggca ccaagctgac agtgctgagc agcgctagca ccaagggccc atcggtcttc     360
cccctggcac cctcctccaa gagcacctct gggggcacag cggccctggg ctgcctggtc     420
aaggactact tccccgaacc ggtgacggtg tcgtggaact caggcgccct gaccagcggc     480
gtgcacacct tcccggctgt cctacagtcc tcaggactct actccctcag cagcgtggtg     540
accgtgccct ccagcagctt gggcacccag acctacatct gcaacgtgaa tcacaagccc     600
agcaacacca aggtggacaa gaaagttgag cccaaatctt gtgacaaaac tcacacatgc     660
ccaccgtgcc cagcacctga agctgcaggg ggaccgtcag tcttcctctt ccccccaaaa     720
cccaaggaca cctctcatga tctcccggac cctgaggtca catgcgtggt ggtggacgtg     780
agccacgaag accctgaggt caagttcaac tggtacgtgg acggcgtgga ggtgcataat     840
gccaagacaa agccgcggga ggagcagtac aacagcacgt accgtgtggt cagcgtcctc     900
accgtcctgc accaggactg gctgaatggc aaggagtaca agtgcaaggt ctccaacaaa     960
gccctcggcg cccccatcga gaaaaccatc tccaaagcca aagggcagcc ccgagaacca    1020
caggtgtaca ccctgccccc atcccgggat gagctgacca agaaccaggt cagcctgacc    1080
tgcctggtca aaggcttcta tcccagcgac atcgccgtgg agtgggagag caatgggcag    1140
ccggagaaca actacaagac cacgcctccc gtgctggact ccgacggctc cttcttcctc    1200
tacagcaagc tcaccgtgga caagagcagg tggcagcagg ggaacgtctt ctcatgctcc    1260
gtgatgcatg aggctctgca caaccactac acgcagaaga gcctctccct gtctccgggt    1320
aaa                                                                  1323

<210> SEQ ID NO 203
<211> LENGTH: 681
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic polynucleotide"

<400> SEQUENCE: 203

| | | | | | |
|---|---|---|---|---|---|
| gaggtgcaat | tggttgaatc | tggtggtggt | ctggtaaaac | cgggcggttc | cctgcgtctg | 60 |
| agctgcgcgg | cttccggatt | caccttctcc | aacgcgtgga | tgagctgggt | tcgccaggcc | 120 |
| ccgggcaaag | gcctcgagtg | ggttggtcgt | atcaagtcta | aaactgacgg | tggcaccacg | 180 |
| gattacgcgg | ctccagttaa | aggtcgtttt | accatttccc | gcgacgatag | caaaaacact | 240 |
| ctgtatctgc | agatgaactc | tctgaaaact | gaagacaccg | cagtctacta | ctgtactacc | 300 |
| ccgtgggaat | ggtcttggta | cgattattgg | ggccagggca | cgctggttac | ggtgtcttcc | 360 |
| gctagcgtgg | ccgctccctc | cgtgttcatc | ttcccaccct | tccgacgagca | gctgaagtcc | 420 |
| ggcaccgctt | ctgtcgtgtg | cctgctgaac | aacttctacc | cccgcgaggc | caaggtgcag | 480 |
| tggaaggtgg | acaacgccct | gcagtccggc | aacagccagg | aatccgtgac | cgagcaggac | 540 |
| tccaaggaca | gcacctactc | cctgtcctcc | accctgaccc | tgtccaaggc | cgactacgag | 600 |
| aagcacaagg | tgtacgcctg | cgaagtgacc | caccagggcc | tgtctagccc | cgtgaccaag | 660 |
| tctttcaacc | ggggcgagtg | c | | | | 681 |

<210> SEQ ID NO 204
<211> LENGTH: 693
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 204

| | | | | | |
|---|---|---|---|---|---|
| gaagtgcagc | tgctggaatc | cggcggagga | ctggtgcagc | ctggcggatc | tctgagactg | 60 |
| tcttgtgccg | cctccggctt | caccttctcc | acctacgcca | tgaactgggt | gcgacaggct | 120 |
| cctggcaagg | gcctggaatg | ggtgtcccgg | atcagatcca | agtacaacaa | ctacgccacc | 180 |
| tactacgccg | actccgtgaa | gggccggttc | accatctctc | gggacgactc | caagaacacc | 240 |
| ctgtacctgc | agatgaactc | cctgcgggcc | gaggacaccg | ccgtgtacta | ttgtgtgcgg | 300 |
| cacggcaact | tcggcaactc | ctatgtgtct | tggtttgcct | actggggcca | gggcacccctc | 360 |
| gtgaccgtgt | catctgctag | ccccaaggct | gcccccagcg | tgaccctgtt | ccccccagc | 420 |
| agcgaggaac | tgcaggccaa | caaggccacc | ctggtctgcc | tgatcagcga | cttctaccca | 480 |
| ggcgccgtga | ccgtggcctg | gaaggccgac | agcagcccg | tgaaggccgg | cgtggagacc | 540 |
| accaccccca | gcaagcagag | caacaacaag | tacgccgcca | gcagctacct | gagcctgacc | 600 |
| cccgagcagt | ggaagagcca | caggtcctac | agctgccagg | tgacccacga | gggcagcacc | 660 |
| gtggagaaaa | ccgtggcccc | caccgagtgc | agc | | | 693 |

<210> SEQ ID NO 205
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 205

| | | | | | |
|---|---|---|---|---|---|
| cagaccgtcg | tgacccagga | acccagcctg | acagtgtctc | ctggcggcac | cgtgaccctg | 60 |
| acatgtggca | gttctacagg | cgccgtgacc | accagcaact | acgccaactg | ggtgcagcag | 120 |

```
aagccaggcc aggctcccag aggactgatc ggcggcacca acgccagagc ccctggcacc    180
cctgccagat tcagcggatc tctgctggga ggaaaggccg ccctgacact gtctggcgtg    240
cagcctgaag atgaggccga gtactactgc gccctgtggt acagcaacct gtgggtgttc    300
ggcggaggca ccaagctgac agtccta                                        327

<210> SEQ ID NO 206
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 206
cagaccgtcg tgacccagga acccagcctg acagtgtctc ctggcggcac cgtgaccctg     60
acatgtggca gttctacagg cgccgtgacc accagcaact acgccaactg ggtgcagcag    120
aagccaggcc aggctcccag aggactgatc ggcggcacca acaagagagc ccctggcacc    180
cctgccagat tcagcggatc tctgctggga ggaaaggccg ccctgacact gtctggcgtg    240
cagcctgaag atgaggccga gtactactgc gccctgtggt acgccaacct gtgggtgttc    300
ggcggaggca ccaagctgac agtccta                                        327

<210> SEQ ID NO 207
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 207
gaggtgcaat tggtggaaag cggaggcggc ctcgtgaagc ctggcggatc tctgagactg     60
agctgtgccg ccagcggctt caccttcagc aacgcctgga tgcactgggt cgccaggcc    120 cctggaaaag gactcgagtg ggtgggacgg atcaagagca agaccgatgg cggcaccacc    180
gactatgccg cccctgtgaa gggccggttc accatcagca gggacgacag caagaacacc    240
ctgtacctgc agatgaacag cctgaaaacc gaggacaccg ccgtgtacta ctgcaccacc    300
ccctgggagt ggtcttggta cgactattgg ggccagggca cctcgtgac cgtgtcctct    360 gctagc                                                               366

<210> SEQ ID NO 208
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 208
gaggtgcaat tggtggaaag cggaggcggc ctcgtgaagc ctggcggatc tctgagactg     60
agctgtgccg ccagcggctt caccttcagc aacgcctgga tgagctgggt cgccaggcc    120 cctggaaaag gactcgagtg ggtgtcccgg atcaagagca agaccgatgg cggcaccacc    180
gactatgccg cccctgtgaa gggccggttc accatcagca gggacgacag caagaacacc    240
```

```
ctgtacctgc agatgaacag cctgaaaacc gaggacaccg ccgtgtacta ctgcaccacc      300
ccctgggagt ggtcttggta cgactattgg ggccagggca ccctcgtgac cgtgtcctct      360
gctagc                                                                 366
```

<210> SEQ ID NO 209
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 209

```
gaggtgcaat tggtggaaag cggaggcggc ctcgtgaagc ctggcggatc tctgagactg       60
agctgtgccg ccagcggctt caccttcagc aacgcctgga tgagctgggt gcgccaggcc      120
cctggaaaag gactcgagtg ggtgggatct atcaagagca gaccgacgg cggcaccacc       180 gactatgccg cccctgtgaa gggccggttc accatcagca gggacgacag caagaacacc      240
ctgtacctgc agatgaacag cctgaaaacc gaggacaccg ccgtgtacta ctgcaccacc      300
ccctgggagt ggtcttggta cgactattgg ggccagggca ccctcgtgac cgtgtcctct      360
gctagc                                                                 366
```

<210> SEQ ID NO 210
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 210

```
gaggtgcaat tggtggaaag cggaggcggc ctcgtgaagc ctggcggatc tctgagactg       60
agctgtgccg ccagcggctt caccttcagc aacgcctgga tgagctgggt gcgccaggcc      120
cctggaaaag gactcgagtg ggtgggacg atcaagagca gaccgatgg cggcaccacc        180 gactatgccg cccctgtgaa gggccggttc accatcagca gggacgacag caagaacacc      240
ctgtacctgc agatgaacag cctgaaaacc gaggacaccg ccgtgtacta ctgcaccacc      300
ccctacgagt ggtcttggta cgactactgg ggccagggca ccctcgtgac cgtgtcatct      360
gctagc                                                                 366
```

<210> SEQ ID NO 211
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 211

```
gaggtgcaat tggtggaaag cggaggcggc ctcgtgaagc ctggcggatc tctgagactg       60
agctgtgccg ccagcggctt caccttcagc aacgcctgga tgagctgggt gcgccaggcc      120
cctggaaaag gactcgagtg ggtgggacg atcaagagca gaccgatgg cggcaccacc        180 gactatgccg cccctgtgaa gggccggttc accatcagca gggacgacag caagaacacc      240
ctgtacctgc agatgaacag cctgaaaacc gaggacaccg ccgtgtacta ctgcaccacc      300
```

```
                                                                        -continued ccctgggagt actcttggta cgactactgg ggccagggca ccctcgtgac cgtgtcatct        360
gctagc                                                                  366

<210> SEQ ID NO 212
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 212
caggtgcaat tggttcaatc tggtgctgaa gtaaaaaaac cgggcgcttc cgttaaagtg         60
agctgcaaag catccggata caccttcact tcctattaca tgcactgggt tcgtcaagcc        120
ccgggccagg gtctggaatg gatgggcatc attaacccaa gcggtggctc tacctcctac        180
gcgcagaaat tccagggtcg cgtcacgatg acccgtgaca ctagcacctc taccgtttat        240
atggagctgt ccagcctgcg ttctgaagat actgcagtgt actactgtgc acgcaactac        300
actatcgttg tttctccgtt cgactattgg ggtcaaggca ccctcgtaac ggtttcttct        360
gctagc                                                                  366

<210> SEQ ID NO 213
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 213
caggtgcaat tggttcaatc tggtgctgaa gtaaaaaaac cgggcgcttc cgttaaagtg         60
agctgcaaag catccggata caccttcact tcctattaca tgcactgggt tcgtcaagcc        120
ccgggccagg gtctggaatg gatgggcatc attaacccaa gcggtggctc tacctcctac        180
gcgcagaaat tccagggtcg cgtcacgatg acccgtgaca ctagcacctc taccgtttat        240
atggagctgt ccagcctgcg ttctgaagat actgcagtgt actactgtgc acgcaactac        300
ttcatcggtt ctgttgctat ggactattgg ggtcaaggca ccctcgtaac ggtttcttct        360
gctagc                                                                  366

<210> SEQ ID NO 214
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 214
caggtgcaat tggttcaatc tggtgctgaa gtaaaaaaac cgggcgcttc cgttaaagtg         60
agctgcaaag catccggata caccttcact tcctattaca tgcactgggt tcgtcaagcc        120
ccgggccagg gtctggaatg gatgggcatc attaacccaa gcggtggctc tacctcctac        180
gcgcagaaat tccagggtcg cgtcacgatg acccgtgaca ctagcacctc taccgtttat        240
atggagctgt ccagcctgcg ttctgaagat actgcagtgt actactgtgc acgcggtctg        300
```

```
acttactcta tggactattg gggtcaaggc accctcgtaa cggtttcttc tgctagc        357
```

<210> SEQ ID NO 215
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 215

```
gatattgtta tgactcaatc tccactgtct ctgccggtga ctccaggcga accggcgagc     60
atttcttgcc gttccagcca gtctctgctg cactccaacg gctacaacta tctcgattgg    120
tacctgcaaa aaccgggtca gagccctcag ctgctgatct acctgggctc taaccgcgct    180
tccggtgtac cggaccgttt cagcggctct ggatccggca ccgatttcac gttgaaaatc    240
agccgtgttg aagcagaaga cgtgggcgtt tattactgta tgcaggcact gcagattcca    300
aacactttg gtcaaggcac caaggtcgaa attaaacgta cg                        342
```

<210> SEQ ID NO 216
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 216

```
gaggtgcaat tgttggagtc tgggggaggc ttggtacagc ctgggggggtc cctgagactc    60
tcctgtgcag cctccggatt caccttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaatacgct    300
tacgctctgg actactgggg ccaaggaacc ctggtcaccg tctcgagtgc tagc          354
```

<210> SEQ ID NO 217
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 217

```
gaaatcgtgt taacgcagtc tccaggcacc ctgtctttgt ctccagggga agagccacc     60
ctctcttgca gggccagtca gagtgttagc agcagctact tagcctggta ccagcagaaa    120
cctggccagg ctcccaggct cctcatctat ggagcatcca gcagggccac tggcatccca    180
gacaggttca gtggcagtgg atccgggaca gacttcactc tcaccatcag cagactggag    240
cctgaagatt ttgcagtgta ttactgtcag cagcatggca gcagcagcac gttcggccag    300
gggaccaaag tggaaatcaa acgtacg                                        327
```

<210> SEQ ID NO 218
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 218
caggtgcaat tggttcaatc tggtgctgaa gtaaaaaaac cgggcgcttc cgttaaagtg    60
agctgcaaag catccggata caccttcact tcctattaca tgcactgggt tcgtcaagcc   120
ccgggccagg gtctggaatg gatgggcatc attaacccaa gcgtggctc tacctcctac    180 gcgcagaaat tccagggtcg cgtcacgatg acccgtgaca ctagcacctc taccgtttat   240
atggagctgt ccagcctgcg ttctgaagat actgcagtgt actactgtgc acgcggtgac   300
ttctctgctg gtcgtctgat ggactattgg ggtcaaggca ccctcgtaac ggtttcttct   360
gctagc                                                              366

<210> SEQ ID NO 219
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 219
gatattgtta tgactcaatc tccactgtct ctgccggtga ctccaggcga accggcgagc    60
atttcttgcc gttccagcca gtctctgctg cactccaacg gctacaacta tctcgattgg   120
tacctgcaaa aaccgggtca gagccctcag ctgctgatct acctgggctc taaccgcgct   180
tccggtgtac cggaccgttt cagcggctct ggatccggca ccgatttcac gttgaaaatc   240
agccgtgttg aagcagaaga cgtgggcgtt tattactgta tgcaggcact gcagaccccca  300 ccaattacct ttggtcaagg caccaaggtc gaaattaaac gtacg                   345

<210> SEQ ID NO 220
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 220
caggtgcaat tggttcaatc tggtgctgaa gtaaaaaaac cgggcgcttc cgttaaagtg    60
agctgcaaag catccggata caccttcact tcctattaca tgcactgggt tcgtcaagcc   120
ccgggccagg gtctggaatg gatgggcatc attaacccaa gcgtggctc tacctcctac    180 gcgcagaaat tccagggtcg cgtcacgatg acccgtgaca ctagcacctc taccgtttat   240
atggagctgt ccagcctgcg ttctgaagat actgcagtgt actactgtgc acgcggtgac   300
tacaacgctt tcgactattg gggtcacggc accctcgtaa cggtttcttc tgctagc      357

<210> SEQ ID NO 221
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 221

```
gatattgtta tgactcaatc tccactgtct ctgccggtga ctccaggcga accggcgagc    60
atttcttgcc gttccagcca gtctctgctg cactccaacg gctacaacta tctcgattgg   120
tacctgcaaa aaccgggtca gagccctcag ctgctgatct acctgggctc taaccgcgct   180
tccggtgtac cggaccgttt cagcggctct ggatccggca ccgatttcac gttgaaaatc   240
agccgtgttg aagcagaaga cgtgggcgtt tattactgta tgcaggcatg catagccca   300
acttttggtc aaggcaccaa ggtcgaaatt aaacgtacg                           339
```

<210> SEQ ID NO 222
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 222

```
caggtgcaat tggttcaatc tggtgctgaa gtaaaaaaac cgggcgcttc cgttaaagtg    60
agctgcaaag catccggata caccttcact tcctattaca tgcactgggt tcgtcaagcc   120
ccgggccagg gtctggaatg gatgggcatc attaacccaa gcggtggctc tacctcctac   180
gcgcagaaat tccagggtcg cgtcacgatg acccgtgaca ctagcacctc taccgtttat   240
atggagctgt ccagcctgcg ttctgaagat actgcagtgt actactgtgc acgcggtgct   300
acttacacta tggactattg gggtcaaggc accctcgtaa cggtttcttc tgctagc      357
```

<210> SEQ ID NO 223
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 223

```
gatattgtta tgactcaatc tccactgtct ctgccggtga ctccaggcga accggcgagc    60
atttcttgcc gttccagcca gtctctgctg cactccaacg gctacaacta tctcgattgg   120
tacctgcaaa aaccgggtca gagccctcag ctgctgatct acctgggctc taaccgcgct   180
tccggtgtac cggaccgttt cagcggctct ggatccggca ccgatttcac gttgaaaatc   240
agccgtgttg aagcagaaga cgtgggcgtt tattactgta tgcaggcact gcagacccca   300
attactttg tcaaggcac caaggtcgaa attaaacgta cg                        342
```

<210> SEQ ID NO 224
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 224

```
caggtgcagc tgcagcagtc tggcgccgag ctcgtgaaac ctggcgcctc cgtgaagatc    60
agctgcaagg ccagcggcta cagcttcacc ggctacttca tgaactgggt caagcagagc   120
cacggcaaga gcctggaatg gatcggcaga atccacccct acgacggcga caccttctac   180
```

```
aaccagaact tcaaggacaa ggccaccctg accgtggaca agagcagcaa caccgcccac    240
atggaactgc tgagcctgac cagcgaggac ttcgccgtgt actactgcac cagatacgac    300
ggcagccggg ccatggatta ttggggccag ggcaccaccg tgacagtgtc cagcgctagc    360
accaagggcc cctccgtgtt ccccctggcc ccagcagca agagcaccag cggcggcaca    420
gccgctctgg gctgcctggt caaggactac ttccccgagc ccgtgaccgt gtcctggaac    480
agcggagccc tgacctccgg cgtgcacacc ttccccgccg tgctgcagag ttctggcctg    540
tatagcctga gcagcgtggt caccgtgcct tctagcagcc tgggcaccca gacctacatc    600
tgcaacgtga accacaagcc cagcaacacc aaggtggaca gaaggtgga gcccaagagc    660 tgcgacaaaa ctcacacatg cccaccgtgc ccagcacctg aagctgcagg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctcggc gcccccatcg agaaaaccat ctccaaagcc   1020
aaagggcagc ccgagaacc acaggtgtgc accctgcccc catcccggga tgagctgacc    1080
aagaaccagg tcagcctctc gtgcgcagtc aaaggcttct atcccagcga catcgccgtg    1140
gagtgggaga gcaatgggca gccggagaac aactacaaga ccacgcctcc cgtgctggac    1200
tccgacggct ccttcttcct cgtgagcaag ctcaccgtgg acaagagcag gtggcagcag    1260
gggaacgtct tctcatgctc cgtgatgcat gaggctctgc acaaccacta cacgcagaag    1320
agcctctccc tgtctccggg taaa                                          1344
```

<210> SEQ ID NO 225
<211> LENGTH: 2073
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 225

```
caggtgcagc tgcagcagtc tggcgccgag ctcgtgaaac ctggcgcctc cgtgaagatc     60
agctgcaagg ccagcggcta cagcttcacc ggctacttca tgaactgggt caagcagagc    120
cacggcaaga gcctggaatg gatcggcaga atccaccccct acgacggcga caccttctac    180
aaccagaact tcaaggacaa ggccaccctg accgtggaca agagcagcaa caccgcccac    240
atggaactgc tgagcctgac cagcgaggac ttcgccgtgt actactgcac cagatacgac    300
ggcagccggg ccatggatta ttggggccag ggcaccaccg tgacagtgtc cagcgctagc    360
acaaagggcc ccagcgtgtt ccctctggcc cctagcagca agagcacatc tggcggaaca    420
gccgccctgg gctgcctcgt gaaggactac tttcccgagc ctgtgaccgt gtcctggaac    480
tctggcgccc tgacaagcgg cgtgcacacc tttccagccg tgctgcagag cagcggcctg    540
tactctctga gcagcgtggt caccgtgcct agcagcagcc tgggcaccca gacctacatc    600
tgcaacgtga accacaagcc cagcaacacc aaagtggaca gaaggtgga gcccaagagc    660 tgtgatggcg aggagggtc cggaggcgga ggatccgaag tgcagctggt ggaaagcggc    720
ggaggcctgg tgcagcctaa gggctctctg aagctgagct gtgccgccag cggcttcacc    780
```

```
ttcaacacct acgccatgaa ctgggtgcgc caggcccctg gcaaaggcct ggaatgggtg      840
gcccggatca gaagcaagta caacaattac gccacctact acgccgacag cgtgaaggac      900
cggttcacca tcagccggga cgacagccag agcatcctgt acctgcagat gaacaacctg      960
aaaaccgagg acaccgccat gtactactgc gtgcggcacg gcaacttcgg caacagctat     1020
gtgtcttggt ttgcctactg gggccagggc accctcgtga cagtgtctgc tgctagcgtg     1080
gccgctccct ccgtgtttat ctttccccca tccgatgaac agctgaaaag cggcaccgcc     1140
tccgtcgtgt gtctgctgaa caatttttac cctagggaag ctaaagtgca gtggaaagtg     1200
gataacgcac tgcagtccgg caactcccag gaatctgtga cagaacagga ctccaaggac     1260
agcacctact ccctgtcctc caccctgaca ctgtctaagg ctgattatga gaaacacaaa     1320
gtctacgcct gcgaagtcac ccatcagggc ctgagctcgc ccgtcacaaa gagcttcaac     1380
aggggagagt gtgacaagac ccacacctgt cccccttgtc ctgcccctga agctgctggc     1440
ggcccttctg tgttcctgtt ccccccaaag cccaaggaca ccctgatgat cagccggacc     1500
cccgaagtga cctgcgtggt ggtggatgtg tcccacgagg accctgaagt gaagttcaat     1560
tggtacgtgg acggcgtgga agtgcacaac gccaagacaa agccgcggga ggagcagtac     1620
aacagcacgt accgtgtggt cagcgtcctc accgtcctgc accaggactg gctgaatggc     1680
aaggagtaca agtgcaaggt ctccaacaaa gccctcggcg cccccatcga gaaaaccatc     1740
tccaaagcca agggcagcc ccgagaacca caggtgtaca ccctgccccc atgccgggat      1800
gagctgacca agaaccaggt cagcctgtgg tgcctggtca aaggcttcta tcccagcgac     1860
atcgccgtgg agtgggagag caatgggcag ccggagaaca actacaagac cacgcctccc     1920
gtgctggact ccgacggctc cttcttcctc tacagcaagc tcaccgtgga caagagcagg     1980
tggcagcagg ggaacgtctt ctcatgctcc gtgatgcatg aggctctgca caaccactac     2040
acgcagaaga gcctctccct gtctccgggt aaa                                  2073
```

<210> SEQ ID NO 226
<211> LENGTH: 654
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 226

```
gacatcgagc tgacccagag ccctgcctct ctggccgtgt ctctgggaca gagagccatc       60
atcagctgca aggccagcca gagcgtgtcc tttgccggca cctctctgat gcactggtat      120
caccagaagc ccggccagca gcccaagctg ctgatctaca gagccagcaa cctggaagcc      180
ggcgtgccca agatttttc ggcagcggc agcaagaccg acttcaccct gaacatccac      240
cccgtggaag aagaggacgc cgccacctac tactgccagc agagcagaga gtaccccctac      300
accttcggcg gaggcaccaa gctggaaatc aagcgtacgg tggctgcacc atctgtcttc      360
atcttcccgc catctgatga gcagttgaaa tctggaactg cctctgttgt gtgcctgctg      420
aataacttct atcccagaga ggccaaagta cagtggaagg tggataacgc cctccaatcg     480
ggtaactccc aggagagtgt cacagagcag gacagcaagg acagcaccta cagcctcagc      540
agcaccctga cgctgagcaa agcagactac gagaaacaca agtctacgcc tgcgaagtc      600
acccatcagg gcctgagctc gcccgtcaca aagagcttca caggggaga gtgt            654
```

```
<210> SEQ ID NO 227
<211> LENGTH: 209
<212> TYPE: PRT
<213> ORGANISM: Homo sapiens

<400> SEQUENCE: 227

Arg Ile Ala Trp Ala Arg Thr Glu Leu Leu Asn Val Cys Met Asn Ala
1               5                   10                  15

Lys His His Lys Glu Lys Pro Gly Pro Glu Asp Lys Leu His Glu Gln
            20                  25                  30

Cys Arg Pro Trp Arg Lys Asn Ala Cys Cys Ser Thr Asn Thr Ser Gln
        35                  40                  45

Glu Ala His Lys Asp Val Ser Tyr Leu Tyr Arg Phe Asn Trp Asn His
    50                  55                  60

Cys Gly Glu Met Ala Pro Ala Cys Lys Arg His Phe Ile Gln Asp Thr
65                  70                  75                  80

Cys Leu Tyr Glu Cys Ser Pro Asn Leu Gly Pro Trp Ile Gln Gln Val
                85                  90                  95

Asp Gln Ser Trp Arg Lys Glu Arg Val Leu Asn Val Pro Leu Cys Lys
            100                 105                 110

Glu Asp Cys Glu Gln Trp Trp Glu Asp Cys Arg Thr Ser Tyr Thr Cys
        115                 120                 125

Lys Ser Asn Trp His Lys Gly Trp Asn Trp Thr Ser Gly Phe Asn Lys
130                 135                 140

Cys Ala Val Gly Ala Ala Cys Gln Pro Phe His Phe Tyr Phe Pro Thr
145                 150                 155                 160

Pro Thr Val Leu Cys Asn Glu Ile Trp Thr His Ser Tyr Lys Val Ser
                165                 170                 175

Asn Tyr Ser Arg Gly Ser Gly Arg Cys Ile Gln Met Trp Phe Asp Pro
            180                 185                 190

Ala Gln Gly Asn Pro Asn Glu Glu Val Ala Arg Phe Tyr Ala Ala Ala
        195                 200                 205

Met

<210> SEQ ID NO 228
<211> LENGTH: 214
<212> TYPE: PRT
<213> ORGANISM: Homo sapiens

<400> SEQUENCE: 228

Thr Met Cys Ser Ala Gln Asp Arg Thr Asp Leu Leu Asn Val Cys Met
1               5                   10                  15

Asp Ala Lys His His Lys Thr Lys Pro Gly Pro Glu Asp Lys Leu His
            20                  25                  30

Asp Gln Cys Ser Pro Trp Lys Lys Asn Ala Cys Cys Thr Ala Ser Thr
        35                  40                  45

Ser Gln Glu Leu His Lys Asp Thr Ser Arg Leu Tyr Asn Phe Asn Trp
    50                  55                  60

Asp His Cys Gly Lys Met Glu Pro Ala Cys Lys Arg His Phe Ile Gln
65                  70                  75                  80

Asp Thr Cys Leu Tyr Glu Cys Ser Pro Asn Leu Gly Pro Trp Ile Gln
                85                  90                  95

Gln Val Asn Gln Ser Trp Arg Lys Glu Arg Phe Leu Asp Val Pro Leu
            100                 105                 110

Cys Lys Glu Asp Cys Gln Arg Trp Trp Glu Asp Cys His Thr Ser His
        115                 120                 125
```

```
Thr Cys Lys Ser Asn Trp His Arg Gly Trp Asp Trp Thr Ser Gly Val
            130                 135                 140

Asn Lys Cys Pro Ala Gly Ala Leu Cys Arg Thr Phe Glu Ser Tyr Phe
145                 150                 155                 160

Pro Thr Pro Ala Ala Leu Cys Glu Gly Leu Trp Ser His Ser Tyr Lys
                    165                 170                 175

Val Ser Asn Tyr Ser Arg Gly Ser Gly Arg Cys Ile Gln Met Trp Phe
                180                 185                 190

Asp Ser Ala Gln Gly Asn Pro Asn Glu Glu Val Ala Arg Phe Tyr Ala
            195                 200                 205

Ala Ala Met His Val Asn
        210

<210> SEQ ID NO 229
<211> LENGTH: 220
<212> TYPE: PRT
<213> ORGANISM: Homo sapiens

<400> SEQUENCE: 229

Ser Ala Arg Ala Arg Thr Asp Leu Leu Asn Val Cys Met Asn Ala Lys
1               5                   10                  15

His His Lys Thr Gln Pro Ser Pro Glu Asp Leu Tyr Gly Gln Cys
            20                  25                  30

Ser Pro Trp Lys Lys Asn Ala Cys Cys Thr Ala Ser Thr Ser Gln Glu
        35                  40                  45

Leu His Lys Asp Thr Ser Arg Leu Tyr Asn Phe Asn Trp Asp His Cys
    50                  55                  60

Gly Lys Met Glu Pro Thr Cys Lys Arg His Phe Ile Gln Asp Ser Cys
65                  70                  75                  80

Leu Tyr Glu Cys Ser Pro Asn Leu Gly Pro Trp Ile Arg Gln Val Asn
                85                  90                  95

Gln Ser Trp Arg Lys Glu Arg Ile Leu Asn Val Pro Leu Cys Lys Glu
            100                 105                 110

Asp Cys Glu Arg Trp Trp Glu Asp Cys Arg Thr Ser Tyr Thr Cys Lys
        115                 120                 125

Ser Asn Trp His Lys Gly Trp Asn Trp Thr Ser Gly Ile Asn Glu Cys
    130                 135                 140

Pro Ala Gly Ala Leu Cys Ser Thr Phe Glu Ser Tyr Phe Pro Thr Pro
145                 150                 155                 160

Ala Ala Leu Cys Glu Gly Leu Trp Ser His Ser Phe Lys Val Ser Asn
                165                 170                 175

Tyr Ser Arg Gly Ser Gly Arg Cys Ile Gln Met Trp Phe Asp Ser Ala
            180                 185                 190

Gln Gly Asn Pro Asn Glu Glu Val Ala Lys Phe Tyr Ala Ala Ala Met
        195                 200                 205

Asn Ala Gly Ala Pro Ser Arg Gly Ile Ile Asp Ser
    210                 215                 220

<210> SEQ ID NO 230
<211> LENGTH: 208
<212> TYPE: PRT
<213> ORGANISM: Mus musculus

<400> SEQUENCE: 230

Thr Arg Ala Arg Thr Glu Leu Leu Asn Val Cys Met Asp Ala Lys His
1               5                   10                  15
```

```
His Lys Glu Lys Pro Gly Pro Glu Asp Asn Leu His Asp Gln Cys Ser
            20                  25                  30

Pro Trp Lys Thr Asn Ser Cys Cys Ser Thr Asn Thr Ser Gln Glu Ala
         35                  40                  45

His Lys Asp Ile Ser Tyr Leu Tyr Arg Phe Asn Trp Asn His Cys Gly
 50                  55                  60

Thr Met Thr Ser Glu Cys Lys Arg His Phe Ile Gln Asp Thr Cys Leu
65                  70                  75                  80

Tyr Glu Cys Ser Pro Asn Leu Gly Pro Trp Ile Gln Gln Val Asp Gln
                 85                  90                  95

Ser Trp Arg Lys Glu Arg Ile Leu Asp Val Pro Leu Cys Lys Glu Asp
            100                 105                 110

Cys Gln Gln Trp Trp Glu Asp Cys Gln Ser Ser Phe Thr Cys Lys Ser
        115                 120                 125

Asn Trp His Lys Gly Trp Asn Trp Ser Ser Gly His Asn Glu Cys Pro
130                 135                 140

Val Gly Ala Ser Cys His Pro Phe Thr Phe Tyr Phe Pro Thr Ser Ala
145                 150                 155                 160

Ala Leu Cys Glu Glu Ile Trp Ser His Ser Tyr Lys Leu Ser Asn Tyr
                165                 170                 175

Ser Arg Gly Ser Gly Arg Cys Ile Gln Met Trp Phe Asp Pro Ala Gln
            180                 185                 190

Gly Asn Pro Asn Glu Glu Val Ala Arg Phe Tyr Ala Glu Ala Met Ser
        195                 200                 205

<210> SEQ ID NO 231
<211> LENGTH: 213
<212> TYPE: PRT
<213> ORGANISM: Macaca fascicularis

<400> SEQUENCE: 231

Glu Ala Gln Thr Arg Thr Ala Arg Ala Arg Thr Glu Leu Leu Asn Val
1               5                   10                  15

Cys Met Asn Ala Lys His His Lys Glu Lys Pro Gly Pro Glu Asp Lys
            20                  25                  30

Leu His Glu Gln Cys Arg Pro Trp Lys Lys Asn Ala Cys Cys Ser Thr
        35                  40                  45

Asn Thr Ser Gln Glu Ala His Lys Asp Val Ser Tyr Leu Tyr Arg Phe
 50                  55                  60

Asn Trp Asn His Cys Gly Glu Met Ala Pro Ala Cys Lys Arg His Phe
65                  70                  75                  80

Ile Gln Asp Thr Cys Leu Tyr Glu Cys Ser Pro Asn Leu Gly Pro Trp
                 85                  90                  95

Ile Gln Gln Val Asp Gln Ser Trp Arg Lys Glu Arg Val Leu Asn Val
            100                 105                 110

Pro Leu Cys Lys Glu Asp Cys Glu Arg Trp Trp Glu Asp Cys Arg Thr
        115                 120                 125

Ser Tyr Cys Lys Ser Asn Trp His Lys Gly Trp Asn Trp Thr Ser Gly
130                 135                 140

Phe Asn Lys Cys Pro Val Gly Ala Ala Cys Gln Pro Phe His Phe Tyr
145                 150                 155                 160

Phe Pro Thr Pro Thr Val Leu Cys Asn Glu Ile Trp Thr Tyr Ser Tyr
                165                 170                 175

Lys Val Ser Asn Tyr Ser Arg Gly Ser Gly Arg Cys Ile Gln Met Trp
```

```
                180                 185                 190
Phe Asp Pro Ala Gln Gly Asn Pro Asn Glu Glu Val Ala Arg Phe Tyr
            195                 200                 205

Ala Ala Ala Met Ser
        210

<210> SEQ ID NO 232
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 232

Pro Trp Glu Tyr Ser Trp Tyr Asp Tyr
1               5

<210> SEQ ID NO 233
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Asn Tyr Thr Ile Val Val Ser Pro Phe Asp Tyr
1               5                   10

<210> SEQ ID NO 234
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 234

Asn Tyr Phe Ile Gly Ser Val Ala Met Asp Tyr
1               5                   10

<210> SEQ ID NO 235
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 235

Gly Leu Thr Tyr Ser Met Asp Tyr
1               5

<210> SEQ ID NO 236
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 236
```

```
Met Gln Ala Leu Gln Ile Pro Asn Thr
1               5

<210> SEQ ID NO 237
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 237

Tyr Ala Tyr Ala Leu Asp Tyr
1               5

<210> SEQ ID NO 238
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238

Gln Gln His Gly Ser Ser Ser Thr
1               5

<210> SEQ ID NO 239
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Gly Asp Phe Ser Ala Gly Arg Leu Met Asp Tyr
1               5                   10

<210> SEQ ID NO 240
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

Met Gln Ala Leu Gln Thr Pro Pro Ile Thr
1               5                   10

<210> SEQ ID NO 241
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 241

Gly Asp Tyr Asn Ala Phe Asp Tyr
1               5
```

```
<210> SEQ ID NO 242
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 242

Met Gln Ala Trp His Ser Pro Thr
1               5

<210> SEQ ID NO 243
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 243

Gly Ala Thr Tyr Thr Met Asp Tyr
1               5

<210> SEQ ID NO 244
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 244

Met Gln Ala Leu Gln Thr Pro Ile Thr
1               5

<210> SEQ ID NO 245
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 245

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
```

```
                115                 120                 125
Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 246
<211> LENGTH: 2076
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 246
caggtgcaat tggttcaatc tggtgctgaa gtaaaaaaac cgggcgcttc cgttaaagtg      60
agctgcaaag catccggata caccttcact tcctattaca tgcactgggt tcgtcaagcc     120
ccgggccagg gtctggaatg gatgggcatc attaacccaa gcgtggctc  tacctcctac     180 gcgcagaaat tccagggtcg cgtcacgatg acccatgaca ctagcacctc taccgtttat     240
atggagctgt ccagcctgcg ttctgaagat actgcagtgt actactgtgc acgtctcttc     300
ttcactggtt tccatctgga ctattgggt  caaggcaccc tcgtaacggt ttcttctgct     360
agcacaaagg gccccagcgt gttccctctg gcccctagca gcaagagcac atctggcgga     420
acagccgccc tgggctgcct cgtgaaggac tactttcccg agcctgtgac cgtgtcctgg     480
aactctggcg ccctgacaag cggcgtgcac acctttccag ccgtgctgca gagcagcggc     540
ctgtactctc tgagcagcgt ggtcaccgtg cctagcagca gcctgggcac ccagacctac     600
atctgcaacg tgaaccacaa gcccagcaac accaaagtgg acaagaaggt ggagcccaag     660
agctgtgatg cggaggagg  gtccggaggc ggaggatccg aggtgcagct gctggaatct     720
ggcggcggac tggtgcagcc tggcggatct ctgagactga gctgtgccgc agcggcttc      780 accttcagca cctacgccat gaactgggtg cgccaggccc tggcaaagg  cctggaatgg     840 gtgtcccgga tcagaagcaa gtacaacaac tacgccacct actacgccga cagcgtgaag     900
ggccggttca ccatcagccg ggacgacagc aagaacaccc tgtacctgca gatgaacagc     960
ctgcgggccg aggacaccgc cgtgtactat tgtgtgcggc acggcaactt cggcaacagc    1020
tatgtgtctt ggtttgccta ctggggccag ggcacccctg tgaccgtgtc aagcgctagt    1080
gtggccgctc cctccgtgtt tatctttccc ccatccgatg aacagctgaa agcggcacc     1140 gcctccgtcg tgtgtctgct gaacaatttt taccctaggg aagctaaagt gcagtggaaa    1200
gtggataacg cactgcagtc cggcaactcc caggaatctg tgacagaaca ggactccaag    1260
gacagcacct actccctgtc ctccaccctg acactgtcta aggctgatta tgagaaacac    1320
```

| | |
|---|---|
| aaagtctacg cctgcgaagt cacccatcag ggcctgagct cgcccgtcac aaagagcttc | 1380 |
| aacaggggag agtgtgacaa gacccacacc tgtcccccctt gtcctgcccc tgaagctgct | 1440 |
| ggcggcccctt ctgtgttcct gttccccccca agcccaagg acaccctgat gatcagccgg | 1500 |
| acccccgaag tgacctgcgt ggtggtggat gtgtcccacg aggaccctga agtgaagttc | 1560 |
| aattggtacg tggacggcgt ggaagtgcac aacgccaaga caaagccgcg ggaggagcag | 1620 |
| tacaacagca cgtaccgtgt ggtcagcgtc ctcaccgtcc tgcaccagga ctggctgaat | 1680 |
| ggcaaggagt acaagtgcaa ggtctccaac aaagccctcg gcgcccccat cgagaaaacc | 1740 |
| atctccaaag ccaaagggca gccccgagaa ccacaggtgt acaccctgcc cccatgccgg | 1800 |
| gatgagctga ccaagaacca ggtcagcctg tggtgcctgg tcaaaggctt ctatcccagc | 1860 |
| gacatcgccg tggagtggga gagcaatggg cagccggaga acaactacaa gaccacgcct | 1920 |
| cccgtgctgg actccgacgg ctccttcttc ctctacagca agctcaccgt ggacaagagc | 1980 |
| aggtggcagc aggggaacgt cttctcatgc tccgtgatgc atgaggctct gcacaaccac | 2040 |
| tacacgcaga agagcctctc cctgtctccg ggtaaa | 2076 |

<210> SEQ ID NO 247
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 247

| | |
|---|---|
| caggtgcaat tggttcaatc tggtgctgaa gtaaaaaaac cgggcgcttc cgttaaagtg | 60 |
| agctgcaaag catccggata caccttcact tcctattaca tgcactgggt tcgtcaagcc | 120 |
| ccgggccagg gtctggaatg gatgggcatc attaacccaa gcggtggctc tacctcctac | 180 |
| gcgcagaaat tccagggtcg cgtcacgatg acccatgaca ctagcacctc taccgtttat | 240 |
| atggagctgt ccagcctgcg ttctgaagat actgcagtgt actactgtgc acgctctttc | 300 |
| ttcactggtt tccatctgga ctattggggt caaggcaccc tcgtaacggt tcttctgct | 360 |
| agcaccaagg gcccctccgt gttccccctg gcccccagca gcaagagcac cagcggcggc | 420 |
| acagccgctc tgggctgcct ggtcaaggac tacttccccg agcccgtgac cgtgtcctgg | 480 |
| aacagcggag ccctgacctc cggcgtgcac accttccccg ccgtgctgca gagttctggc | 540 |
| ctgtatagcc tgagcagcgt ggtcaccgtg ccttctagca gcctgggcac ccagacctac | 600 |
| atctgcaacg tgaaccacaa gcccagcaac accaaggtgg acaagaaggt ggagcccaag | 660 |
| agctgcgaca aaactcacac atgcccaccg tgcccagcac ctgaagctgc aggggaccg | 720 |
| tcagtcttcc tcttcccccc aaaacccaag gacaccctca tgatctcccg gacccctgag | 780 |
| gtcacatgcg tggtggtgga cgtgagccac gaagaccctg aggtcaagtt caactggtac | 840 |
| gtggacggcg tggaggtgca taatgccaag acaaagccgc gggaggagca gtacaacagc | 900 |
| acgtaccgtg tggtcagcgt cctcaccgtc ctgcaccagg actggctgaa tggcaaggag | 960 |
| tacaagtgca aggtctccaa caaagccctc ggcgccccca tcgagaaaac catctccaaa | 1020 |
| gccaaagggc agccccgaga accacaggtg tgcaccctgc cccatcccg ggatgagctg | 1080 |
| accaagaacc aggtcagcct ctcgtgcgca gtcaaaggct tctatcccag cgacatcgcc | 1140 |
| gtggagtggg agagcaatgg gcagccggag aacaactaca agaccacgcc tcccgtgctg | 1200 |
| gactccgacg gctccttctt cctcgtgagc aagctcaccg tggacaagag caggtggcag | 1260 | cagggaacg tcttctcatg ctccgtgatg catgaggctc tgcacaacca ctacacgcag    1320 aagagcctct ccctgtctcc gggtaaa                                       1347

<210> SEQ ID NO 248
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 248

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Glu Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser
        115                 120

<210> SEQ ID NO 249
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 249

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Gln Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser
        115                 120

<210> SEQ ID NO 250

<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 250

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Ala Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 251
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 251

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ala Tyr Val Ser Trp Phe
            100                 105                 110

Ala Tyr Trp Gly Gln Gly Thr Leu Val Thr Val Ser Ser
        115                 120                 125
```

<210> SEQ ID NO 252
<211> LENGTH: 689
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 252

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Gly Gly Gly Gly Ser Gly Gly Gly Ser Glu Val Gln Leu Leu Glu
225                 230                 235                 240

Ser Gly Gly Gly Leu Val Gln Pro Gly Gly Ser Leu Arg Leu Ser Cys
                245                 250                 255

Ala Ala Ser Gly Phe Thr Phe Ser Thr Tyr Ala Met Asn Trp Val Arg
            260                 265                 270

Gln Ala Pro Gly Lys Gly Leu Glu Trp Val Ser Arg Ile Arg Ser Lys
        275                 280                 285

Tyr Asn Asn Tyr Ala Thr Tyr Tyr Ala Asp Ser Val Lys Gly Arg Phe
    290                 295                 300

Thr Ile Ser Arg Asp Asp Ser Lys Asn Thr Leu Tyr Leu Gln Met Asn
305                 310                 315                 320

Ser Leu Arg Ala Glu Asp Thr Ala Val Tyr Tyr Cys Val Arg His Gly
                325                 330                 335

Asn Phe Gly Ala Ser Tyr Val Ser Trp Phe Ala Tyr Trp Gly Gln Gly
            340                 345                 350

Thr Leu Val Thr Val Ser Ser Ala Ser Thr Lys Gly Pro Ser Val Phe
        355                 360                 365

Pro Leu Ala Pro Ser Ser Lys Ser Thr Ser Gly Gly Thr Ala Ala Leu
    370                 375                 380

Gly Cys Leu Val Lys Asp Tyr Phe Pro Glu Pro Val Thr Val Ser Trp
385                 390                 395                 400

Asn Ser Gly Ala Leu Thr Ser Gly Val His Thr Phe Pro Ala Val Leu

```
                  405                 410                 415
Gln Ser Ser Gly Leu Tyr Ser Leu Ser Ser Val Val Thr Val Pro Ser
            420                 425                 430

Ser Ser Leu Gly Thr Gln Thr Tyr Ile Cys Asn Val Asn His Lys Pro
            435                 440                 445

Ser Asn Thr Lys Val Asp Lys Lys Val Glu Pro Lys Ser Cys Asp Lys
        450                 455                 460

Thr His Thr Cys Pro Pro Cys Pro Ala Pro Glu Ala Ala Gly Gly Pro
465                 470                 475                 480

Ser Val Phe Leu Phe Pro Pro Lys Pro Lys Asp Thr Leu Met Ile Ser
                485                 490                 495

Arg Thr Pro Glu Val Thr Cys Val Val Val Asp Val Ser His Glu Asp
            500                 505                 510

Pro Glu Val Lys Phe Asn Trp Tyr Val Asp Gly Val Glu Val His Asn
        515                 520                 525

Ala Lys Thr Lys Pro Arg Glu Glu Gln Tyr Asn Ser Thr Tyr Arg Val
    530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Gly Ala Pro Ile Glu Lys
                565                 570                 575

Thr Ile Ser Lys Ala Lys Gly Gln Pro Arg Glu Pro Gln Val Tyr Thr
            580                 585                 590

Leu Pro Pro Cys Arg Asp Glu Leu Thr Lys Asn Gln Val Ser Leu Trp
        595                 600                 605

Cys Leu Val Lys Gly Phe Tyr Pro Ser Asp Ile Ala Val Glu Trp Glu
610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
                645                 650                 655

Ser Arg Trp Gln Gln Gly Asn Val Phe Ser Cys Ser Val Met His Glu
            660                 665                 670

Ala Leu His Asn His Tyr Thr Gln Lys Ser Leu Ser Leu Ser Pro Gly
        675                 680                 685

Lys

<210> SEQ ID NO 253
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 253

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60
```

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
            85                  90                  95

Tyr Cys Thr Thr Pro Trp Glu Trp Ser Trp Tyr Asp Tyr Trp Gly Gln
        100                 105                 110

Gly Thr Leu Val Thr Val Ser Ser Ala Ser Thr Lys Gly Pro Ser Val
    115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn Arg Phe Thr Gln Lys Ser Leu Ser Leu Ser Pro
        435                 440                 445

Gly Lys
    450

<210> SEQ ID NO 254
<211> LENGTH: 215
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 254

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 255
<211> LENGTH: 689
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 255

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95
```

```
Tyr Cys Thr Thr Pro Trp Glu Trp Ser Trp Tyr Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Gly Gly Gly Gly Ser Gly Gly Gly Ser Glu Val Gln Leu Leu Glu
225                 230                 235                 240

Ser Gly Gly Gly Leu Val Gln Pro Gly Gly Ser Leu Arg Leu Ser Cys
                245                 250                 255

Ala Ala Ser Gly Phe Thr Phe Ser Thr Tyr Ala Met Asn Trp Val Arg
            260                 265                 270

Gln Ala Pro Gly Lys Gly Leu Glu Trp Val Ser Arg Ile Arg Ser Lys
        275                 280                 285

Tyr Asn Asn Tyr Ala Thr Tyr Tyr Ala Asp Ser Val Lys Gly Arg Phe
290                 295                 300

Thr Ile Ser Arg Asp Asp Ser Lys Asn Thr Leu Tyr Leu Gln Met Asn
305                 310                 315                 320

Ser Leu Arg Ala Glu Asp Thr Ala Val Tyr Tyr Cys Val Arg His Gly
                325                 330                 335

Asn Phe Gly Asn Ala Tyr Val Ser Trp Phe Ala Tyr Trp Gly Gln Gly
            340                 345                 350

Thr Leu Val Thr Val Ser Ser Ala Ser Thr Lys Gly Pro Ser Val Phe
        355                 360                 365

Pro Leu Ala Pro Ser Ser Lys Ser Thr Ser Gly Gly Thr Ala Ala Leu
370                 375                 380

Gly Cys Leu Val Lys Asp Tyr Phe Pro Glu Pro Val Thr Val Ser Trp
385                 390                 395                 400

Asn Ser Gly Ala Leu Thr Ser Gly Val His Thr Phe Pro Ala Val Leu
                405                 410                 415

Gln Ser Ser Gly Leu Tyr Ser Leu Ser Ser Val Val Thr Val Pro Ser
            420                 425                 430

Ser Ser Leu Gly Thr Gln Thr Tyr Ile Cys Asn Val Asn His Lys Pro
        435                 440                 445

Ser Asn Thr Lys Val Asp Lys Lys Val Glu Pro Lys Ser Cys Asp Lys
450                 455                 460

Thr His Thr Cys Pro Pro Cys Pro Ala Pro Glu Ala Ala Gly Gly Pro
465                 470                 475                 480

Ser Val Phe Leu Phe Pro Pro Lys Pro Lys Asp Thr Leu Met Ile Ser
                485                 490                 495

Arg Thr Pro Glu Val Thr Cys Val Val Val Asp Val Ser His Glu Asp
            500                 505                 510
```

```
Pro Glu Val Lys Phe Asn Trp Tyr Val Asp Gly Val Glu Val His Asn
            515                 520                 525

Ala Lys Thr Lys Pro Arg Glu Glu Gln Tyr Asn Ser Thr Tyr Arg Val
        530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Gly Ala Pro Ile Glu Lys
                565                 570                 575

Thr Ile Ser Lys Ala Lys Gly Gln Pro Arg Glu Pro Gln Val Tyr Thr
            580                 585                 590

Leu Pro Pro Cys Arg Asp Glu Leu Thr Lys Asn Gln Val Ser Leu Trp
        595                 600                 605

Cys Leu Val Lys Gly Phe Tyr Pro Ser Asp Ile Ala Val Glu Trp Glu
610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
                645                 650                 655

Ser Arg Trp Gln Gln Gly Asn Val Phe Ser Cys Ser Val Met His Glu
            660                 665                 670

Ala Leu His Asn His Tyr Thr Gln Lys Ser Leu Ser Leu Ser Pro Gly
        675                 680                 685

Lys

<210> SEQ ID NO 256
<211> LENGTH: 690
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 256

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Pro Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Phe Ala Trp Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

```
Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Gly Gly Gly
210                 215                 220

Gly Ser Gly Gly Gly Gly Ser Glu Val Gln Leu Leu Glu Ser Gly Gly
225                 230                 235                 240

Gly Leu Val Gln Pro Gly Gly Ser Leu Arg Leu Ser Cys Ala Ala Ser
            245                 250                 255

Gly Phe Thr Phe Ser Thr Tyr Ala Met Asn Trp Val Arg Gln Ala Pro
            260                 265                 270

Gly Lys Gly Leu Glu Trp Val Ser Arg Ile Arg Ser Lys Tyr Asn Asn
            275                 280                 285

Tyr Ala Thr Tyr Tyr Ala Asp Ser Val Lys Gly Arg Phe Thr Ile Ser
            290                 295                 300

Arg Asp Asp Ser Lys Asn Thr Leu Tyr Leu Gln Met Asn Ser Leu Arg
305                 310                 315                 320

Ala Glu Asp Thr Ala Val Tyr Tyr Cys Val Arg His Gly Asn Phe Gly
                325                 330                 335

Ala Ser Tyr Val Ser Trp Phe Ala Tyr Trp Gly Gln Gly Thr Leu Val
            340                 345                 350

Thr Val Ser Ser Ala Ser Val Ala Ala Pro Ser Val Phe Ile Phe Pro
            355                 360                 365

Pro Ser Asp Glu Gln Leu Lys Ser Gly Thr Ala Ser Val Val Cys Leu
            370                 375                 380

Leu Asn Asn Phe Tyr Pro Arg Glu Ala Lys Val Gln Trp Lys Val Asp
385                 390                 395                 400

Asn Ala Leu Gln Ser Gly Asn Ser Gln Glu Ser Val Thr Glu Gln Asp
                405                 410                 415

Ser Lys Asp Ser Thr Tyr Ser Leu Ser Ser Thr Leu Thr Leu Ser Lys
            420                 425                 430

Ala Asp Tyr Glu Lys His Lys Val Tyr Ala Cys Glu Val Thr His Gln
            435                 440                 445

Gly Leu Ser Ser Pro Val Thr Lys Ser Phe Asn Arg Gly Glu Cys Asp
450                 455                 460

Lys Thr His Thr Cys Pro Pro Cys Pro Ala Pro Glu Ala Ala Gly Gly
465                 470                 475                 480

Pro Ser Val Phe Leu Phe Pro Pro Lys Pro Lys Asp Thr Leu Met Ile
                485                 490                 495

Ser Arg Thr Pro Glu Val Thr Cys Val Val Val Asp Val Ser His Glu
            500                 505                 510

Asp Pro Glu Val Lys Phe Asn Trp Tyr Val Asp Gly Val Glu Val His
            515                 520                 525

Asn Ala Lys Thr Lys Pro Arg Glu Glu Gln Tyr Asn Ser Thr Tyr Arg
530                 535                 540

Val Val Ser Val Leu Thr Val Leu His Gln Asp Trp Leu Asn Gly Lys
545                 550                 555                 560

Glu Tyr Lys Cys Lys Val Ser Asn Lys Ala Leu Gly Ala Pro Ile Glu
                565                 570                 575

Lys Thr Ile Ser Lys Ala Lys Gly Gln Pro Arg Glu Pro Gln Val Tyr
            580                 585                 590
```

```
Thr Leu Pro Pro Cys Arg Asp Glu Leu Thr Lys Asn Gln Val Ser Leu
            595                 600                 605

Trp Cys Leu Val Lys Gly Phe Tyr Pro Ser Asp Ile Ala Val Glu Trp
610                 615                 620

Glu Ser Asn Gly Gln Pro Glu Asn Asn Tyr Lys Thr Thr Pro Pro Val
625                 630                 635                 640

Leu Asp Ser Asp Gly Ser Phe Phe Leu Tyr Ser Lys Leu Thr Val Asp
                645                 650                 655

Lys Ser Arg Trp Gln Gln Gly Asn Val Phe Ser Cys Ser Val Met His
            660                 665                 670

Glu Ala Leu His Asn His Tyr Thr Gln Lys Ser Leu Ser Leu Ser Pro
            675                 680                 685

Gly Lys
    690

<210> SEQ ID NO 257
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 257

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Pro Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Phe Ala Trp Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
            210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
```

```
                    245                 250                 255

Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 258
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 258

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Ile Met Gln Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

```
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 259
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 259

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys
    210

<210> SEQ ID NO 260
<211> LENGTH: 690
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 260
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Pro Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Phe Ala Trp Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Gly Gly Gly
    210                 215                 220

Gly Ser Gly Gly Gly Gly Ser Glu Val Gln Leu Leu Glu Ser Gly Gly
225                 230                 235                 240

Gly Leu Val Gln Pro Gly Gly Ser Leu Arg Leu Ser Cys Ala Ala Ser
                245                 250                 255

Gly Phe Thr Phe Ser Thr Tyr Ala Met Asn Trp Val Arg Gln Ala Pro
            260                 265                 270

Gly Lys Gly Leu Glu Trp Val Ser Arg Ile Arg Ser Lys Tyr Asn Asn
        275                 280                 285

Tyr Ala Thr Tyr Tyr Ala Asp Ser Val Lys Gly Arg Phe Thr Ile Ser
    290                 295                 300

Arg Asp Asp Ser Lys Asn Thr Leu Tyr Leu Gln Met Asn Ser Leu Arg
305                 310                 315                 320

Ala Glu Asp Thr Ala Val Tyr Tyr Cys Val Arg His Gly Asn Phe Gly
                325                 330                 335

Asn Ala Tyr Val Ser Trp Phe Ala Tyr Trp Gly Gln Gly Thr Leu Val
            340                 345                 350

Thr Val Ser Ser Ala Ser Val Ala Ala Pro Ser Val Phe Ile Phe Pro
        355                 360                 365

Pro Ser Asp Glu Gln Leu Lys Ser Gly Thr Ala Ser Val Val Cys Leu
    370                 375                 380

Leu Asn Asn Phe Tyr Pro Arg Glu Ala Lys Val Gln Trp Lys Val Asp
385                 390                 395                 400

Asn Ala Leu Gln Ser Gly Asn Ser Gln Glu Ser Val Thr Glu Gln Asp
                405                 410                 415

Ser Lys Asp Ser Thr Tyr Ser Leu Ser Ser Thr Leu Thr Leu Ser Lys
```

| | | 420 | | | | 425 | | | | 430 | |
|---|---|---|---|---|---|---|---|---|---|---|---|

Ala Asp Tyr Glu Lys His Lys Val Tyr Ala Cys Glu Val Thr His Gln
                         435                             440                          445

Gly Leu Ser Ser Pro Val Thr Lys Ser Phe Asn Arg Gly Glu Cys Asp
                       450                             455                          460

Lys Thr His Thr Cys Pro Pro Cys Pro Ala Pro Glu Ala Ala Gly Gly
465                       470                       475                       480

Pro Ser Val Phe Leu Phe Pro Pro Lys Pro Lys Asp Thr Leu Met Ile
                    485                       490                          495

Ser Arg Thr Pro Glu Val Thr Cys Val Val Val Asp Val Ser His Glu
             500                       505                        510

Asp Pro Glu Val Lys Phe Asn Trp Tyr Val Asp Gly Val Glu Val His
            515                  520                   525

Asn Ala Lys Thr Lys Pro Arg Glu Glu Gln Tyr Asn Ser Thr Tyr Arg
530                       535                       540

Val Val Ser Val Leu Thr Val Leu His Gln Asp Trp Leu Asn Gly Lys
545                       550                       555                   560

Glu Tyr Lys Cys Lys Val Ser Asn Lys Ala Leu Gly Ala Pro Ile Glu
             565                  570                   575

Lys Thr Ile Ser Lys Ala Lys Gly Gln Pro Arg Glu Pro Gln Val Tyr
            580                       585                       590

Thr Leu Pro Pro Cys Arg Asp Glu Leu Thr Lys Asn Gln Val Ser Leu
            595                  600                       605

Trp Cys Leu Val Lys Gly Phe Tyr Pro Ser Asp Ile Ala Val Glu Trp
610                       615                       620

Glu Ser Asn Gly Gln Pro Glu Asn Asn Tyr Lys Thr Thr Pro Pro Val
625                       630                       635                   640

Leu Asp Ser Asp Gly Ser Phe Phe Leu Tyr Ser Lys Leu Thr Val Asp
                    645                       650                       655

Lys Ser Arg Trp Gln Gln Gly Asn Val Phe Ser Cys Ser Val Met His
            660                       665                       670

Glu Ala Leu His Asn His Tyr Thr Gln Lys Ser Leu Ser Leu Ser Pro
            675                  680                   685

Gly Lys
690

```
<210> SEQ ID NO 261
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 261
gaggtgcaat tggttgaatc tggtggtggt ctggtaaaac cgggcggttc cctgcgtctg      60
agctgcgcgg cttccggatt caccttctcc aacgcgtgga tgagctgggt tcgccaggcc     120
ccgggcaaag cctcgagtg gttggtcgt atcaagtcta aaactgaggg tggcaccacg     180
gattacgcgg ctccagttaa aggtcgtttt accatttccc gcgacgatag caaaaacact     240
ctgtatctgc agatgaactc tctgaaaact gaagacaccg cagtctacta ctgtactacc     300
ccgtgggaat ggtcttggta cgattattgg ggccagggca cgctggttac ggtgtcttcc     360

<210> SEQ ID NO 262
```

```
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 262
gaggtgcaat tggttgaatc tggtggtggt ctggtaaaac cgggcggttc cctgcgtctg      60
agctgcgcgg cttccggatt caccttctcc aacgcgtgga tgagctgggt tcgccaggcc     120
ccgggcaaag gcctcgagtg ggttggtcgt atcaagtcta aaactcaggg tggcaccacg     180
gattacgcgg ctccagttaa aggtcgtttt accatttccc gcgacgatag caaaaacact     240
ctgtatctgc agatgaactc tctgaaaact gaagacaccg cagtctacta ctgtactacc     300
ccgtgggaat ggtcttggta cgattattgg ggccagggca cgctggttac ggtgtcttcc     360

<210> SEQ ID NO 263
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 263
gaggtgcagc tgctggaatc tggcggcgga ctggtgcagc ctggcggatc tctgagactg      60
agctgtgccg ccagcggctt caccttcagc acctacgcca tgaactgggt gcgccaggcc     120
cctggcaaag gcctggaatg ggtgtcccgg atcagaagca agtacaacaa ctacgccacc     180
tactacgccg acagcgtgaa gggccggttc accatcagcc gggacgacag caagaacacc     240
ctgtacctgc agatgaacag cctgcgggcc gaggacaccg ccgtgtacta ttgtgtgcgg     300
cacggcaact cggcgccag ctatgtgtct tggtttgcct actggggcca gggcacccyc     360
gtgaccgtgt caagc                                                      375

<210> SEQ ID NO 264
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 264
gaggtgcagc tgctggaatc tggcggcgga ctggtgcagc ctggcggatc tctgagactg      60
agctgtgccg ccagcggctt caccttcagc acctacgcca tgaactgggt gcgccaggcc     120
cctggcaaag gcctggaatg ggtgtcccgg atcagaagca agtacaacaa ctacgccacc     180
tactacgccg acagcgtgaa gggccggttc accatcagcc gggacgacag caagaacacc     240
ctgtacctgc agatgaacag cctgcgggcc gaggacaccg ccgtgtacta ttgtgtgcgg     300
cacggcaact cggcaacgc ctatgtgtct tggtttgcct actggggcca gggcacccyc     360
gtgaccgtgt caagc                                                      375

<210> SEQ ID NO 265
<211> LENGTH: 2067
<212> TYPE: DNA
<213> ORGANISM: Artificial Sequence
```

<220> FEATURE:
<221> NAME/KEY: source
<223> OTHER INFORMATION: /note="Description of Artificial Sequence: Synthetic polynucleotide"

<400> SEQUENCE: 265

```
gaggtgcaat tggttgaatc tggtggtggt ctggtaaaac cgggcggttc cctgcgtctg      60
agctgcgcgg cttccggatt caccttctcc aacgcgtgga tgagctgggt tcgccaggcc     120
ccgggcaaag gcctcgagtg ggttggtcgt atcaagtcta aaactgacgg tgcaccacg      180
gattacgcgg ctccagttaa aggtcgtttt accatttccc gcgacgatag caaaaacact     240
ctgtatctgc agatgaactc tctgaaaact gaagacaccg cagtctacta ctgtactacc     300
ccgtgggaat ggtcttggta cgattattgg ggccagggca cgctggttac ggtgtcttcc     360
gctagcacaa agggcccctag cgtgttccct ctggccccca gcagcaagag cacaagcggc     420
ggaacagccg ccctgggctg cctcgtgaag gactacttcc ccgagcccgt gacagtgtct     480
tggaacagcg gagccctgac aagcggcgtg cacactttcc ctgccgtgct gcagagcagc     540
ggcctgtact ccctgagcag cgtggtcacc gtgcctagca gcagcctggg cacccagacc     600
tacatctgca acgtgaacca caagcccagc aacaccaaag tggacaagaa ggtgagcccc     660
aagagctgtg atggcggagg agggtccgga ggcggaggat ccgaggtgca gctgctggaa     720
tctggcggcg gactggtgca gcctggcgga tctctgagac tgagctgtgc cgccagcggc     780
ttcaccttca gcacctacgc catgaactgg gtgcgccagg cccctggcaa aggcctggaa     840
tgggtgtccc ggatcagaag caagtacaac aactacgcca cctactacgc cgacagcgtg     900
aagggccggt tcaccatcag ccgggacgac agcaagaaca ccctgtacct gcagatgaac     960
agcctgcggg ccgaggacac cgccgtgtac tattgtgtgc ggcacggcaa cttcggcgcc    1020
agctatgtgt cttggtttgc ctactgggcc agggcaccc tcgtgaccgt gtcaagcgct    1080
agtaccaagg gcccccagcgt gttcccctg gcacccagca gcaagagcac atctggcgga    1140
acagccgctc tgggctgtct ggtgaaagac tacttccccg agcccgtgac cgtgtcttgg    1200
aactctggcg ccctgaccag cggcgtgcac acctttccag ccgtgctgca gagcagcggc    1260
ctgtactccc tgtcctccgt ggtcaccgtg ccctctagct ccctgggaac acagacatat    1320
atctgtaatg tcaatcacaa gccttccaac accaaagtcg ataagaaagt cgagcccaag    1380
agctgcgaca aaactcacac atgcccaccg tgcccagcac ctgaagctgc aggggaccg    1440
tcagtcttcc tcttcccccc aaaacccaag gacaccctca tgatctcccg gaccctgag    1500
gtcacatgcg tggtggtgga cgtgagccac gaagaccctg aggtcaagtt caactggtac    1560
gtggacggcg tggaggtgca taatgccaag acaaagccgc gggaggagca gtacaacagc    1620
acgtaccgtg tggtcagcgt cctcaccgtc ctgcaccagg actggctgaa tggcaaggag    1680
tacaagtgca aggtctccaa caaagccctc ggcgccccca tcgagaaaac catctccaaa    1740
gccaaagggc agccccgaga accacaggtg tacaccctgc ccccatgccg ggatgagctg    1800
accaagaacc aggtcagcct gtggtgcctg gtcaaaggct tctatcccag cgacatcgcc    1860
gtggagtggg agagcaatgg gcagccggag aacaactaca agaccacgcc tcccgtgctg    1920
gactccgacg gctccttctt cctctacagc aagctcaccg tggacaagag caggtggcag    1980
caggggaacg tcttctcatg ctccgtgatg catgaggctc tgcacaacca ctacacgcag    2040
aagagcctct ccctgtctcc gggtaaa                                        2067
```

<210> SEQ ID NO 266

```
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 266
gaggtgcaat tggttgaatc tggtggtggt ctggtaaaac cgggcggttc cctgcgtctg      60
agctgcgcgg cttccggatt caccttctcc aacgcgtgga tgagctgggt tcgccaggcc     120
ccgggcaaag gcctcgagtg ggttggtcgt atcaagtcta aaactgacgg tggcaccacg     180
gattacgcgg ctccagttaa aggtcgtttt accatttccc gcgacgatag caaaaacact     240
ctgtatctgc agatgaactc tctgaaaact gaagacaccg cagtctacta ctgtactacc     300
ccgtgggaat ggtcttggta cgattattgg ggccagggca cgctggttac ggtgtcttcc     360
gctagcacca agggcccctc cgtgttcccc ctggccccca gcagcaagag caccagcggc     420
ggcacagccg ctctgggctg cctggtcaag gactacttcc ccgagcccgt gaccgtgtcc     480
tggaacagcg gagccctgac ctccggcgtg cacaccttcc ccgccgtgct gcagagttct     540
ggcctgtata gcctgagcag cgtggtcacc gtgccttcta gcagcctggg cacccagacc     600
tacatctgca acgtgaacca caagcccagc aacaccaagg tggacaagaa ggtggagccc     660
aagagctgcg acaaaactca catgcccacc gtgcccag cacctgaagc tgcaggggga      720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcggcgccc catcgagaa aaccatctcc    1020 aaagccaaag gcagccccg agaaccacag gtgtgcaccc tgcccccatc ccggatgag    1080 ctgaccaaga accaggtcag cctctcgtgc gcagtcaaag gcttctatcc cagcgacatc    1140
gccgtggagt gggagagcaa tgggcagccg gagaacaact acaagaccac gcctcccgtg    1200
ctggactccg acggctcctt cttcctcgtg agcaagctca ccgtggacaa gagcaggtgg    1260
cagcagggga acgtcttctc atgctccgtg atgcatgagg ctctgcacaa ccgcttcacg    1320
cagaagagcc tctccctgtc tccgggtaaa                                    1350

<210> SEQ ID NO 267
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 267
caggccgtcg tgacccagga acccagcctg acagtgtctc ctggcggcac cgtgaccctg     60
acatgtggca gttctacagg cgccgtgacc accagcaact acgccaactg ggtgcaggaa    120
aagcccggcc aggccttcag aggactgatc ggcggcacca acaagagagc ccctggcacc    180
cctgccagat tcagcggatc tctgctggga ggaaaggccg ccctgacact gtctggcgcc    240
cagccagaag atgaggccga gtactactgc gccctgtggt acagcaacct gtgggtgttc    300
ggcggaggca ccaagctgac agtcctaggt caacccaagg ctgcccccag cgtgaccctg    360
```

```
ttcccccca gcagcgagga actgcaggcc aacaaggcca ccctggtctg cctgatcagc      420
gacttctacc caggcgccgt gaccgtggcc tggaaggcca cagcagccc cgtgaaggcc       480 ggcgtggaga ccaccacccc cagcaagcag agcaacaaca agtacgccgc cagcagctac     540
ctgagcctga cccccgagca gtggaagagc cacaggtcct acagctgcca ggtgaccccac    600 gagggcagca ccgtggagaa accgtggcc cccaccgagt gcagc                      645
```

<210> SEQ ID NO 268
<211> LENGTH: 2067
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 268

```
gaggtgcaat tggttgaatc tggtggtggt ctggtaaaac cgggcggttc cctgcgtctg      60
agctgcgcgg cttccggatt caccttctcc aacgcgtgga tgagctgggt tcgccaggcc     120
ccgggcaaag gcctcgagtg ggttggtcgt atcaagtcta aaactgacgg tgccaccacg     180
gattacgcgg ctccagttaa aggtcgtttt accatttccc gcgacgatag caaaaacact     240
ctgtatctgc agatgaactc tctgaaaact gaagacaccg cagtctacta ctgtactacc     300
ccgtgggaat ggtcttggta cgattattgg ggccagggca cgctggttac ggtgtcttcc     360
gctagcacaa agggcccag cgtgttccct ctggcccca gcagcaagag cacaagcggc       420
ggaacagccg ccctgggctg cctcgtgaag gactacttcc ccgagcccgt gacagtgtct     480
tggaacagcg gagccctgac aagcggcgtg cacactttcc ctgccgtgct gcagagcagc    540
ggcctgtact cctgagcag cgtggtcacc gtgcctagca gcagcctggg cacccagacc    600
tacatctgca acgtgaacca caagcccagc aacaccaaag tggacaagaa ggtggagccc   660
aagagctgtg atggcggagg agggtccgga ggcggaggat ccgaggtgca gctgctggaa     720
tctggcggcg gactggtgca gcctggcgga tctctgagac tgagctgtgc cgccagcggc    780
ttcaccttca gcacctacgc catgaactgg gtgcgccagg cccctggcaa aggcctggaa    840
tgggtgtccc ggatcagaag caagtacaac aactacgcca cctactacgc cgacagcgtg    900
aagggccggt tcaccatcag ccgggacgac agcaagaaca ccctgtacct gcagatgaac    960
agcctgcggg ccgaggacac cgccgtgtac tattgtgtgc ggcacggcaa cttcggcaac  1020
gcctatgtgt cttggtttgc ctactgggc cagggcaccc tcgtgaccgt gtcaagcgct   1080
agtaccaagg gccccagcgt gttccccctg gcacccagca gcaagagcac atctggcgga   1140
acagccgctc tgggctgtct ggtgaaagac tacttcccg agcccgtgac cgtgtcttgg    1200
aactctggcg ccctgaccag cggcgtgcac accttccag ccgtgctgca gagcagcggc    1260
ctgtactccc tgtcctccgt ggtcaccgtg ccctctagct ccctgggaac acagacatat   1320
atctgtaatg tcaatcacaa gccttccaac accaaagtcg ataagaaagt cgagcccaag   1380
agctgcgaca aaactcacac atgcccaccg tgcccagcac ctgaagctgc aggggggaccg   1440 tcagtcttcc tcttccccc aaaacccaag gacaccctca tgatctcccg gacccctgag    1500
gtcacatgcg tggtggtgga cgtgagccac gaagaccctg aggtcaagtt caactggtac   1560
gtggacggcg tggaggtgca taatgccaag acaaagccgc gggaggagca gtacaacagc   1620
acgtaccgtg tggtcagcgt cctcaccgtc ctgcaccagg actggctgaa tggcaaggag   1680
```

```
tacaagtgca aggtctccaa caaagccctc ggcgccccca tcgagaaaac catctccaaa      1740
gccaaagggc agccccgaga accacaggtg tacaccctgc ccccatgccg ggatgagctg      1800
accaagaacc aggtcagcct gtggtgcctg gtcaaaggct tctatcccag cgacatcgcc      1860
gtggagtggg agagcaatgg gcagccggag aacaactaca agaccacgcc tcccgtgctg      1920
gactccgacg gctccttctt cctctacagc aagctcaccg tggacaagag caggtggcag      1980
caggggaacg tcttctcatg ctccgtgatg catgaggctc tgcacaacca ctacacgcag      2040
aagagcctct ccctgtctcc gggtaaa                                         2067

<210> SEQ ID NO 269
<211> LENGTH: 2070
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 269
caggtgcaat tggttcaatc tggtgctgaa gtaaaaaaac cgggcgcttc cgttaaagtg        60
agctgcaaag catccggata caccttcact tcctattaca tgcactgggt tcgtcaagcc       120
ccgggccagg gtctggaatg gatgggcatc attaacccaa gcggtggccc tacctcctac       180
gcgcagaaat tccagggtcg cgtcacgatg acccgtgaca ctagcacctc taccgtttat       240
atggagctgt ccagcctgcg ttctgaagat actgcagtgt actactgtgc acgcggtgac       300
ttcgcttggc tggactattg gggtcaaggc accctcgtaa cggtttcttc tgctagcaca       360
aagggcccca gcgtgttccc tctggcccct agcagcaaga gcacatctgg cggaacagcc       420
gccctgggct gcctcgtgaa ggactacttt cccgagcctg tgaccgtgtc ctggaactct       480
ggcgccctga caagcggcgt gcacaccttt ccagccgtgc tgcagagcag cggcctgtac       540
tctctgagca gcgtggtcac cgtgcctagc agcagcctgg gcacccagac ctacatctgc       600
aacgtgaacc acaagcccag caacaccaaa gtggacaaga aggtggagcc caagagctgt       660
gatggcggag gagggtccgg aggcggagga tccgaggtgc agctgctgga atctggcggc       720
ggactggtgc agcctggcgg atctctgaga ctgagctgtg ccgccagcgg cttcaccttc       780
agcacctacg ccatgaactg ggtgcgccag gcccctggca aaggcctgga atgggtgtcc       840
cggatcagaa gcaagtacaa caactacgcc acctactacg ccgacagcgt gaagggccgg       900
ttcaccatca gccgggacga cagcaagaac accctgtacc tgcagatgaa cagcctgcgg       960
gccgaggaca ccgccgtgta ctattgtgtg cggcacggca acttcggcgc cagctatgtg      1020
tcttggtttg cctactgggg ccagggcacc ctcgtgaccg tgtcaagcgc tagtgtggcc      1080
gctccctccg tgtttatctt ccccccatcc gatgaacagc tgaaaagcgg caccgcctcc      1140
gtcgtgtgtc tgctgaacaa tttttaccct agggaagcta agtgcagtg gaaagtggat      1200 aacgcactgc agtccggcaa ctcccaggaa tctgtgacag aacaggactc caaggacagc      1260
acctactccc tgtcctccac cctgacactg tctaaggctg attatgagaa acacaaagtc      1320
tacgcctgcg aagtcaccca tcagggcctg agctcgcccg tcacaaagag cttcaacagg      1380
ggagagtgtg acaagaccca cacctgtccc ccttgtcctg cccctgaagc tgctggcggc      1440
ccttctgtgt tcctgttccc cccaaagccc aaggacaccc tgatgatcag ccggaccccc      1500
gaagtgacct gcgtggtggt ggatgtgtcc cacgaggacc ctgaagtgaa gttcaattgg      1560
tacgtggacg gcgtggaagt gcacaacgcc aagacaaagc cgcgggagga gcagtacaac      1620
```

```
agcacgtacc gtgtggtcag cgtcctcacc gtcctgcacc aggactggct gaatggcaag    1680
gagtacaagt gcaaggtctc caacaaagcc ctcggcgccc ccatcgagaa aaccatctcc    1740
aaagccaaag ggcagccccg agaaccacag gtgtacaccc tgcccccatg ccgggatgag    1800
ctgaccaaga accaggtcag cctgtggtgc ctggtcaaag gcttctatcc cagcgacatc    1860
gccgtggagt gggagagcaa tgggcagccg gagaacaact acaagaccac gcctcccgtg    1920
ctggactccg acggctcctt cttcctctac agcaagctca ccgtggacaa gagcaggtgg    1980
cagcagggga acgtcttctc atgctccgtg atgcatgagg ctctgcacaa ccactacacg    2040
cagaagagcc tctccctgtc tccgggtaaa                                     2070
```

<210> SEQ ID NO 270
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 270

```
caggtgcaat tggttcaatc tggtgctgaa gtaaaaaaac cgggcgcttc cgttaaagtg     60
agctgcaaag catccggata caccttcact tcctattaca tgcactgggt tcgtcaagcc    120
ccgggccagg gtctggaatg gatgggcatc attaacccaa gcggtggccc tacctcctac    180
gcgcagaaat tccagggtcg cgtcacgatg accgtgacta ctagcacctc taccgtttat    240
atggagctgt ccagcctgcg ttctgaagat actgcagtgt actactgtgc acgcggtgac    300
ttcgcttggc tggactattg gggtcaaggc accctcgtaa cggtttcttc tgctagcacc    360
aagggcccct ccgtgttccc cctggccccc agcagcaaga gcaccagcgg cggcacagcc    420
gctctgggct gcctggtcaa ggactacttc cccgagcccg tgaccgtgtc ctggaacagc    480
ggagccctga cctccggcgt gcacaccttc cccgccgtgc tgcagagttc tggcctgtat    540
agcctgagca gcgtggtcac cgtgccttct agcagcctgg gcacccagac ctacatctgc    600
aacgtgaacc acaagcccag caacaccaag gtggacaaga aggtggagcc caagagctgc    660
gacaaaactc acacatgccc accgtgccca gcacctgaag ctgcaggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcggcgcc ccatcgaga aaaccatctc caagccaaa    1020 gggcagcccc gagaaccaca ggtgtgcacc ctgcccccat cccgggatga gctgaccaag   1080
aaccaggtca gcctctcgtg cgcagtcaaa ggcttctatc cagcgacat cgccgtggag   1140 tgggagagca atgggcagcc ggagaacaac tacaagacca cgcctcccgt gctggactcc   1200
gacggctcct tcttcctcgt gagcaagctc accgtggaca agagcaggtg gcagcagggg   1260
aacgtcttct catgctccgt gatgcatgag gctctgcaca accactacac gcagaagagc   1320
ctctccctgt ctccgggtaa a                                             1341
```

<210> SEQ ID NO 271
<211> LENGTH: 657
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 271

```
gatattgtta tgactcaatc tccactgtct ctgccggtga ctccaggcga accggcgagc      60
atttcttgcc gttccagcca gtctctgctg cactccaacg gctacaacta tctcgattgg    120
tacctgcaaa aaccgggtca gagccctcag ctgctgatct acctgggctc taaccgcgct    180
tccggtgtac cggaccgttt cagcggctct ggatccggca ccgatttcac gttgaaaatc    240
agccgtgttg aagcagaaga cgtgggcgtt tattactgta tgcaggcaag cattatgcag    300
cggactttg tcaaggcac caaggtcgaa attaaacgta cggtggctgc accatctgtc    360
ttcatcttcc cgccatctga tgagcagttg aaatctggaa ctgcctctgt tgtgtgcctg    420
ctgaataact ctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct caacagggg agagtgt        657
```

<210> SEQ ID NO 272
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 272

```
caggccgtcg tgacccagga acccagcctg acagtgtctc ctggcggcac cgtgaccctg      60
acatgtggca gttctacagg cgccgtgacc accagcaact acgccaactg ggtgcaggaa    120
aagcccggcc aggccttcag aggactgatc ggcggcacca caagagagc ccctggcacc    180
cctgccagat tcagcggatc tctgctggga ggaaaggccg ccctgacact gtctggcgcc    240
cagccagaag atgaggccga gtactactgc gccctgtggt acagcaacct gtgggtgttc    300
ggcggaggca ccaagctgac agtgctgagc agcgcttcca ccaaaggccc ttccgtgttt    360
cctctggctc ctagctccaa gtccacctct ggaggcaccg ctgctctcgg atgcctcgtg    420
aaggattatt ttcctgagcc tgtgacagtg tcctggaata cggagcact gacctctgga    480
gtgcatactt tccccgctgt gctgcagtcc tctggactgt acagcctgag cagcgtggtg    540
acagtgccca gcagcagcct gggcacccag acctacatct gcaacgtgaa ccacaagccc    600
agcaacacca aggtggacaa gaaggtggaa cccaagtctt gt                       642
```

<210> SEQ ID NO 273
<211> LENGTH: 2070
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 273

```
caggtgcaat tggttcaatc tggtgctgaa gtaaaaaaac cgggcgcttc cgttaaagtg      60
agctgcaaag catccggata caccttcact tcctattaca tgcactgggt tcgtcaagcc    120
```

```
ccgggccagg gtctggaatg gatgggcatc attaacccaa gcggtggccc tacctcctac    180
gcgcagaaat tccagggtcg cgtcacgatg acccgtgaca ctagcacctc taccgttat     240 atggagctgt ccagcctgcg ttctgaagat actgcagtgt actactgtgc acgcggtgac    300
ttcgcttggc tggactattg gggtcaaggc accctcgtaa cggtttcttc tgctagcaca    360
aagggcccca gcgtgttccc tctggcccct agcagcaaga gcacatctgg cggaacagcc    420
gccctgggct gcctcgtgaa ggactacttt cccgagcctg tgaccgtgtc ctggaactct    480
ggcgccctga agcggcgt gcacaccttt ccagccgtgc tgcagagcag cggcctgtac      540
tctctgagca gcgtggtcac cgtgcctagc agcagcctgg caccagac ctacatctgc      600 aacgtgaacc acaagcccag caacaccaaa gtggacaaga aggtggagcc caagagctgt    660
gatggcggag agggtccgg aggcggagga tccgaggtgc agctgctgga atctggcggc     720
ggactggtgc agcctggcgg atctctgaga ctgagctgtg ccgccagcgg cttcaccttc    780
agcacctacg ccatgaactg ggtgcgccag gcccctggca aaggcctgga atgggtgtcc    840
cggatcagaa gcaagtacaa caactacgcc acctactacg ccgacagcgt gaagggccgg    900
ttcaccatca gccgggacga cagcaagaac accctgtacc tgcagatgaa cagcctgcgg    960
gccgaggaca ccgccgtgta ctattgtgtg cggcacggca acttcggcaa cgcctatgtg   1020
tcttggtttg cctactgggg ccagggcacc ctcgtgaccg tgtcaagcgc tagtgtggcc   1080
gctccctccg tgtttatctt tccccccatcc gatgaacagc tgaaaagcgg caccgcctcc   1140
gtcgtgtgtc tgctgaacaa ttttttaccct agggaagcta agtgcagtg gaaagtggat   1200 aacgcactgc agtccggcaa ctcccaggaa tctgtgacag aacaggactc caaggacagc   1260
acctactccc tgtcctccac cctgacactg tctaaggctg attatgagaa acacaaagtc   1320
tacgcctgcg aagtcaccca tcagggcctg agctcgcccg tcacaaagag cttcaacagg   1380
ggagagtgtg acaagaccca cacctgtccc ccttgtcctg cccctgaagc tgctggcggc   1440
ccttctgtgt tcctgttccc cccaaagccc aaggacaccc tgatgatcag ccggacccc    1500 gaagtgacct gcgtggtggt ggatgtgtcc cacgaggacc ctgaagtgaa gttcaattgg   1560
tacgtggacg gcgtggaagt gcacaacgcc aagacaaagc cgcgggagga gcagtacaac   1620
agcacgtacc gtgtggtcag cgtcctcacc gtcctgcacc aggactggct gaatggcaag   1680
gagtacaagt gcaaggtctc caacaaagcc ctcggcgccc catcgagaa aaccatctcc    1740 aaagccaaag gcagccccg agaaccacag gtgtacaccc tgcccccatg ccgggatgag   1800
ctgaccaaga accaggtcag cctgtggtgc ctggtcaaag gcttctatcc cagcgacatc   1860
gccgtggagt gggagagcaa tgggcagccg gagaacaact acaagaccac gcctcccgtg   1920
ctggactccg acggctcctt cttcctctac agcaagctca ccgtggacaa gagcaggtgg   1980
cagcagggga acgtcttctc atgctccgtg atgcatgagg ctctgcacaa ccactacacg   2040
cagaagagcc tctccctgtc tccgggtaaa                                     2070
```

<210> SEQ ID NO 274
<211> LENGTH: 440
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 274

```
Gln Val Gln Leu Val Glu Ser Gly Gly Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
```

```
                420                 425                 430

Ser Leu Ser Leu Ser Leu Gly Lys
        435                 440

<210> SEQ ID NO 275
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 275

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 276
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 276

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45
```

```
Gly Gly Ile Asn Pro Ser Asn Gly Gly Thr Asn Phe Asn Glu Lys Phe
 50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Asp Thr Ala Val Tyr Tyr Cys
                 85                  90                  95

Ala Arg Arg Asp Tyr Arg Phe Asp Met Gly Phe Asp Tyr Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 277
<211> LENGTH: 218
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 277

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 278
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 278

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
```

```
            85                  90                  95
Ala Arg Arg His Trp Pro Gly Gly Phe Asp Tyr Trp Gln Gly Thr
            100                 105                 110
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
                180                 185                 190
Ser Leu Gly Thr Gln Thr Tyr Ile Cys Asn Val Asn His Lys Pro Ser
                195                 200                 205
Asn Thr Lys Val Asp Lys Lys Val Glu Pro Lys Ser Cys Asp Lys Thr
        210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Ala Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly
            435                 440                 445

<210> SEQ ID NO 279
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 279
```

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Ser Thr Ala
             20                  25                  30

Val Ala Trp Tyr Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Leu Tyr His Pro Ala
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 280
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 280

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Ser
             20                  25                  30

Trp Ile His Trp Val Arg Gln Ala Pro Gly Lys Gly Leu Glu Trp Val
         35                  40                  45

Ala Trp Ile Ser Pro Tyr Gly Gly Ser Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
                100                 105                 110

Leu Val Thr Val Ser Ser
            115
```

```
<210> SEQ ID NO 281
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 281

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys
        115                 120

<210> SEQ ID NO 282
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 282

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 283
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: VARIANT
<222> LOCATION: (6)..(6)
<223> OTHER INFORMATION: /replace="Gly"
<220> FEATURE:
<221> NAME/KEY: MISC_FEATURE
<222> LOCATION: (1)..(10)
<223> OTHER INFORMATION: /note="Variant residues given in the sequence
      have no preference with respect to those in the annotations
      for variant positions"

<400> SEQUENCE: 283

Gly Phe Thr Phe Ser Asp Ser Trp Ile His
1               5                   10

<210> SEQ ID NO 284
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="Leu"
<220> FEATURE:
<221> NAME/KEY: VARIANT
<222> LOCATION: (10)..(10)
<223> OTHER INFORMATION: /replace="Ser"
<220> FEATURE:
<221> NAME/KEY: MISC_FEATURE
<222> LOCATION: (1)..(18)
<223> OTHER INFORMATION: /note="Variant residues given in the sequence
      have no preference with respect to those in the annotations
      for variant positions"

<400> SEQUENCE: 284

Ala Trp Ile Ser Pro Tyr Gly Gly Ser Thr Tyr Tyr Ala Asp Ser Val
1               5                   10                  15

Lys Gly

<210> SEQ ID NO 285
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 285

Arg His Trp Pro Gly Gly Phe Asp Tyr
1               5

<210> SEQ ID NO 286
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: /replace="Val"
<220> FEATURE:
<221> NAME/KEY: MOD_RES
<222> LOCATION: (6)..(6)
<223> OTHER INFORMATION: /replace="Ile"
<220> FEATURE:
```

```
<221> NAME/KEY: MOD_RES
<222> LOCATION: (7)..(7)
<223> OTHER INFORMATION: /replace="Asn"
<220> FEATURE:
<221> NAME/KEY: MOD_RES
<222> LOCATION: (9)..(9)
<223> OTHER INFORMATION: /replace="Phe"
<220> FEATURE:
<221> NAME/KEY: MOD_RES
<222> LOCATION: (10)..(10)
<223> OTHER INFORMATION: /replace="Leu"
<220> FEATURE:
<221> NAME/KEY: misc_feature
<222> LOCATION: (1)..(11)
<223> OTHER INFORMATION: /note="Variant residues given in the sequence
      have no preference with respect to those in the annotations
      for variant positions"

<400> SEQUENCE: 286

Arg Ala Ser Gln Asp Val Ser Thr Ala Val Ala
1               5                   10

<210> SEQ ID NO 287
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: /replace="Thr"
<220> FEATURE:
<221> NAME/KEY: MOD_RES
<222> LOCATION: (6)..(6)
<223> OTHER INFORMATION: /replace="Ala"
<220> FEATURE:
<221> NAME/KEY: misc_feature
<222> LOCATION: (1)..(7)
<223> OTHER INFORMATION: /note="Variant residues given in the sequence
      have no preference with respect to those in the annotations
      for variant positions"

<400> SEQUENCE: 287

Ser Ala Ser Phe Leu Tyr Ser
1               5

<210> SEQ ID NO 288
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: /replace="Gly" or "Phe" or "Ser"
<220> FEATURE:
<221> NAME/KEY: MOD_RES
<222> LOCATION: (4)..(4)
<223> OTHER INFORMATION: /replace="Tyr" or "Phe" or "Trp"
<220> FEATURE:
<221> NAME/KEY: MOD_RES
<222> LOCATION: (5)..(5)
<223> OTHER INFORMATION: /replace="Asn" or "Ala" or "Thr" or "Gly" or
      "Phe" or "Ile"
<220> FEATURE:
<221> NAME/KEY: MOD_RES
<222> LOCATION: (6)..(6)
<223> OTHER INFORMATION: /replace="Val" or "Pro" or "Thr" or "Ile"
<220> FEATURE:
```

```
<221> NAME/KEY: MOD_RES
<222> LOCATION: (8)..(8)
<223> OTHER INFORMATION: /replace="Trp" or "Arg" or "Pro" or "Thr"
<220> FEATURE:
<221> NAME/KEY: misc_feature
<222> LOCATION: (1)..(9)
<223> OTHER INFORMATION: /note="Variant residues given in the sequence
      have no preference with respect to those in the annotations
      for variant positions"

<400> SEQUENCE: 288

Gln Gln Tyr Leu Tyr His Pro Ala Thr
1               5

<210> SEQ ID NO 289
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 289

Gly Phe Thr Phe Ser Asp Ser Trp Ile His
1               5                   10

<210> SEQ ID NO 290
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 290

Ala Trp Ile Ser Pro Tyr Gly Gly Ser Thr Tyr Tyr Ala Asp Ser Val
1               5                   10                  15

Lys Gly

<210> SEQ ID NO 291
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 291

Arg His Trp Pro Gly Gly Phe Asp Tyr
1               5

<210> SEQ ID NO 292
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 292

Arg Ala Ser Gln Asp Val Ser Thr Ala Val Ala
1               5                   10

<210> SEQ ID NO 293
```

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 293

Ser Ala Ser Phe Leu Tyr Ser
1               5

<210> SEQ ID NO 294
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 294

Gln Gln Tyr Leu Tyr His Pro Ala Thr
1               5

<210> SEQ ID NO 295
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 295

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 296
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 296

Trp Val Arg Gln Ala Pro Gly Lys Gly Leu Glu Trp Val
1               5                   10

<210> SEQ ID NO 297
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 297

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30
```

```
<210> SEQ ID NO 298
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 298

Trp Gly Gln Gly Thr Leu Val Thr Val Ser Ala
1               5                   10

<210> SEQ ID NO 299
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 299

Trp Gly Gln Gly Thr Leu Val Thr Val Ser Ser
1               5                   10

<210> SEQ ID NO 300
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 300

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 301
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 301

Trp Tyr Gln Gln Lys Pro Gly Lys Ala Pro Lys Leu Leu Ile Tyr
1               5                   10                  15

<210> SEQ ID NO 302
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 302

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
```

-continued

<210> SEQ ID NO 303
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 303

Phe Gly Gln Gly Thr Lys Val Glu Ile Lys Arg
1               5                   10

<210> SEQ ID NO 304
<211> LENGTH: 9
<212> TYPE: PRT
<213> ORGANISM: Mus musculus

<400> SEQUENCE: 304

Gly Phe Ser Leu Ser Thr Ser Gly Met
1               5

<210> SEQ ID NO 305
<211> LENGTH: 3
<212> TYPE: PRT
<213> ORGANISM: Mus musculus

<400> SEQUENCE: 305

Leu Asn Asp
1

<210> SEQ ID NO 306
<211> LENGTH: 8
<212> TYPE: PRT
<213> ORGANISM: Mus musculus

<400> SEQUENCE: 306

Asn Gly Tyr Leu Tyr Ala Leu Asp
1               5

<210> SEQ ID NO 307
<211> LENGTH: 6
<212> TYPE: PRT
<213> ORGANISM: Mus musculus

<400> SEQUENCE: 307

Ser Ser Ser Val Asn Tyr
1               5

<210> SEQ ID NO 308
<211> LENGTH: 3
<212> TYPE: PRT
<213> ORGANISM: Mus musculus

<400> SEQUENCE: 308

Asp Ala Phe
1

<210> SEQ ID NO 309
<211> LENGTH: 7
<212> TYPE: PRT
<213> ORGANISM: Mus musculus

<400> SEQUENCE: 309

-continued

Trp Ser Ser Tyr Pro Trp Thr
1               5

<210> SEQ ID NO 310
<211> LENGTH: 120
<212> TYPE: PRT
<213> ORGANISM: Mus musculus

<400> SEQUENCE: 310

Gln Val Thr Leu Lys Glu Ser Gly Pro Gly Ile Leu Gln Pro Ser Gln
1               5                   10                  15

Thr Leu Arg Leu Thr Cys Ser Phe Ser Gly Phe Ser Leu Ser Thr Ser
            20                  25                  30

Gly Met Ser Val Gly Trp Ile Arg Gln Pro Ser Gly Lys Gly Leu Glu
        35                  40                  45

Trp Leu Ala His Ile Trp Leu Asn Asp Asp Val Phe Phe Asn Pro Ala
    50                  55                  60

Leu Lys Ser Arg Leu Thr Ile Ser Lys Asp Thr Ser Asn Asn Gln Val
65                  70                  75                  80

Phe Leu Gln Ile Ala Ser Val Val Thr Ala Asp Thr Ala Thr Tyr Tyr
                85                  90                  95

Cys Val Arg Ala Asn Gly Tyr Leu Tyr Ala Leu Asp Tyr Trp Gly Gln
            100                 105                 110

Gly Thr Ser Val Thr Val Ser Ser
            115                 120

<210> SEQ ID NO 311
<211> LENGTH: 106
<212> TYPE: PRT
<213> ORGANISM: Mus musculus

<400> SEQUENCE: 311

Gln Ile Val Leu Thr Gln Ser Pro Ala Ile Met Ser Ala Ser Pro Gly
1               5                   10                  15

Gln Lys Val Thr Ile Thr Cys Ser Ala Ser Ser Ser Val Asn Tyr Thr
            20                  25                  30

Gln Trp Tyr Gln Gln Lys Leu Gly Ser Ser Pro Lys Leu Trp Ile Tyr
        35                  40                  45

Asp Ala Phe Lys Leu Ala Pro Gly Val Pro Ala Arg Phe Ser Gly Ser
    50                  55                  60

Gly Thr Gly Thr Ser Tyr Ser Leu Thr Ile Ser Ser Met Glu Ala Glu
65                  70                  75                  80

Asp Ala Ala Ser Tyr Phe Cys His Gln Trp Ser Ser Tyr Pro Trp Thr
                85                  90                  95

Phe Gly Gly Gly Thr Lys Leu Glu Ile Lys
            100                 105

<210> SEQ ID NO 312
<211> LENGTH: 120
<212> TYPE: PRT
<213> ORGANISM: Mus musculus

<400> SEQUENCE: 312

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Ser Val Gly Trp Ile Arg Gln Pro Ser Gly Lys Gly Leu Glu
         35                  40                  45

Trp Leu Ala His Ile Trp Leu Asn Asp Asp Val Phe Phe Asn Pro Ala
 50                  55                  60

Leu Lys Arg Arg Leu Thr Ile Ser Lys Asp Thr Ser Asn Asn Gln Val
 65                  70                  75                  80

Phe Leu Gln Ile Ala Ser Val Val Thr Ala Asp Thr Ala Thr Tyr Tyr
                 85                  90                  95

Cys Val Arg Ala Asn Gly Tyr Leu Tyr Ala Leu Asp Tyr Trp Gly Gln
                 100                 105                 110

Gly Ile Ser Val Thr Val Ser Ser
        115                 120

<210> SEQ ID NO 313
<211> LENGTH: 106
<212> TYPE: PRT
<213> ORGANISM: Mus musculus

<400> SEQUENCE: 313

Gln Ile Val Leu Thr Gln Ser Pro Ala Ile Met Ser Ala Ser Pro Gly
 1               5                   10                  15

Gln Lys Val Thr Ile Thr Cys Ser Ala Ser Ser Ser Val Asn Tyr Thr
                 20                  25                  30

Gln Trp Tyr Gln Gln Lys Leu Gly Ser Ser Pro Lys Leu Trp Ile Tyr
         35                  40                  45

Asp Ala Phe Lys Leu Ala Pro Gly Val Pro Ala Arg Phe Ser Gly Ser
 50                  55                  60

Gly Thr Gly Thr Ser Tyr Ser Leu Thr Ile Ser Ser Met Glu Ala Glu
 65                  70                  75                  80

Asp Ala Ala Ser Tyr Phe Cys His Gln Trp Ser Tyr Pro Trp Thr
                 85                  90                  95

Phe Gly Gly Gly Thr Lys Leu Glu Ile Lys
                 100                 105

<210> SEQ ID NO 314
<211> LENGTH: 6
<212> TYPE: PRT
<213> ORGANISM: Mus musculus

<400> SEQUENCE: 314

Ser Ser Ser Val Gln Tyr
 1               5

<210> SEQ ID NO 315
<211> LENGTH: 6
<212> TYPE: PRT
<213> ORGANISM: Mus musculus

<400> SEQUENCE: 315

Ser Ser Ser Val Ser Tyr
 1               5

<210> SEQ ID NO 316
<211> LENGTH: 7
<212> TYPE: PRT
<213> ORGANISM: Mus musculus

<400> SEQUENCE: 316

Gly Tyr Ser Phe Thr Ser Tyr
 1               5

```
<210> SEQ ID NO 317
<211> LENGTH: 3
<212> TYPE: PRT
<213> ORGANISM: Mus musculus

<400> SEQUENCE: 317

Ser Asp Ser
1

<210> SEQ ID NO 318
<211> LENGTH: 9
<212> TYPE: PRT
<213> ORGANISM: Mus musculus

<400> SEQUENCE: 318

Gly Tyr Tyr Ala Trp Tyr Tyr Phe Asp
1               5

<210> SEQ ID NO 319
<211> LENGTH: 7
<212> TYPE: PRT
<213> ORGANISM: Mus musculus

<400> SEQUENCE: 319

Ser Gln Ser Ile Gly Asn Asn
1               5

<210> SEQ ID NO 320
<211> LENGTH: 3
<212> TYPE: PRT
<213> ORGANISM: Mus musculus

<400> SEQUENCE: 320

Tyr Ala Ser
1

<210> SEQ ID NO 321
<211> LENGTH: 6
<212> TYPE: PRT
<213> ORGANISM: Mus musculus

<400> SEQUENCE: 321

Ser Asn Ser Trp Pro Leu
1               5

<210> SEQ ID NO 322
<211> LENGTH: 120
<212> TYPE: PRT
<213> ORGANISM: Mus musculus

<400> SEQUENCE: 322

Gln Val Gln Leu Gln Gln Ser Gly Pro Gln Leu Val Arg Pro Gly Ala
1               5                   10                  15

Ser Val Gln Ile Ser Cys Lys Ala Ser Gly Tyr Ser Phe Thr Ser Tyr
                20                  25                  30

Leu Leu His Trp Leu Lys Gln Arg Pro Gly Gln Gly Leu Glu Trp Ile
            35                  40                  45

Gly Met Ile Asp Pro Ser Asp Ser Glu Thr Arg Leu Asn Gln Lys Phe
        50                  55                  60

Lys Asp Lys Ala Thr Leu Thr Val Asp Lys Ser Ser Ser Thr Ala Tyr
65                  70                  75                  80
```

```
Met Gln Leu Ser Ser Pro Thr Ser Glu Asp Ser Ala Val Tyr Tyr Cys
                85                  90                  95

Ala Arg Asp Gly Tyr Tyr Ala Trp Tyr Tyr Phe Asp Cys Trp Gly Gln
            100                 105                 110

Gly Thr Thr Leu Thr Val Ser Ser
        115                 120

<210> SEQ ID NO 323
<211> LENGTH: 107
<212> TYPE: PRT
<213> ORGANISM: Mus musculus

<400> SEQUENCE: 323

Asp Ile Val Leu Thr Gln Ser Pro Ala Thr Leu Ser Val Thr Pro Gly
1               5                   10                  15

Asp Arg Val Ser Leu Ser Cys Arg Ala Ser Gln Ser Ile Gly Asn Asn
            20                  25                  30

Leu His Trp Tyr Gln Gln Lys Ser His Glu Ser Pro Arg Leu Leu Ile
        35                  40                  45

Lys Tyr Ala Ser His Ser Ile Ser Gly Ile Pro Ser Lys Phe Ser Gly
    50                  55                  60

Thr Gly Ser Gly Thr Asp Phe Thr Leu Ser Phe Asn Ser Val Glu Thr
65                  70                  75                  80

Glu Asp Phe Gly Met Tyr Phe Cys Gln Gln Ser Asn Ser Trp Pro Leu
                85                  90                  95

Thr Phe Gly Ala Gly Thr Lys Leu Glu Leu Lys
            100                 105

<210> SEQ ID NO 324
<211> LENGTH: 5
<212> TYPE: PRT
<213> ORGANISM: Mus musculus

<400> SEQUENCE: 324

Gly Asp Ser Ile Ala
1               5

<210> SEQ ID NO 325
<211> LENGTH: 3
<212> TYPE: PRT
<213> ORGANISM: Mus musculus

<400> SEQUENCE: 325

Tyr Ser Gly
1

<210> SEQ ID NO 326
<211> LENGTH: 4
<212> TYPE: PRT
<213> ORGANISM: Mus musculus

<400> SEQUENCE: 326

Asp Tyr Phe Asp
1

<210> SEQ ID NO 327
<211> LENGTH: 7
<212> TYPE: PRT
<213> ORGANISM: Mus musculus

<400> SEQUENCE: 327
```

Arg Gln Asp Val Arg Lys Asn
1               5

<210> SEQ ID NO 328
<211> LENGTH: 3
<212> TYPE: PRT
<213> ORGANISM: Mus musculus

<400> SEQUENCE: 328

Tyr Thr Ser
1

<210> SEQ ID NO 329
<211> LENGTH: 6
<212> TYPE: PRT
<213> ORGANISM: Mus musculus

<400> SEQUENCE: 329

Tyr Asp Asn Leu Pro Phe
1               5

<210> SEQ ID NO 330
<211> LENGTH: 114
<212> TYPE: PRT
<213> ORGANISM: Mus musculus

<400> SEQUENCE: 330

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Ala Ser Ala
            20                  25                  30

Tyr Trp Asn Trp Ile Arg Lys Phe Pro Gly Asn Lys Leu Glu Tyr Met
        35                  40                  45

Gly Tyr Ile Asn Tyr Ser Gly Ser Thr Tyr Tyr Asn Pro Ser Leu Lys
    50                  55                  60

Ser Arg Ile Ser Ile Thr Arg Asp Thr Ser Gln Asn Gln Tyr Tyr Leu
65                  70                  75                  80

Gln Leu Asn Ser Val Thr Thr Glu Asp Thr Ala Thr Tyr Tyr Cys Val
                85                  90                  95

Thr Gly Asp Tyr Phe Asp Tyr Trp Gly Arg Gly Thr Thr Leu Thr Val
            100                 105                 110

Ser Ser

<210> SEQ ID NO 331
<211> LENGTH: 107
<212> TYPE: PRT
<213> ORGANISM: Mus musculus

<400> SEQUENCE: 331

Asp Ile Gln Met Thr Gln Ser Pro Ser Ser Leu Ser Ala Tyr Leu Gly
1               5                   10                  15

Gly Lys Val Thr Ile Thr Cys Lys Ala Arg Gln Asp Val Arg Lys Asn
            20                  25                  30

Ile Gly Trp Tyr Gln His Lys Pro Gly Lys Gly Pro Arg Leu Leu Ile
        35                  40                  45

Trp Tyr Thr Ser Thr Leu Gln Ser Gly Ile Pro Ser Arg Phe Ser Gly
    50                  55                  60

Ser Gly Ser Gly Arg Asp Tyr Ser Phe Asn Ile Asn Asn Leu Glu Pro
65                  70                  75                  80

Glu Asp Ile Ala Thr Tyr Tyr Cys Leu Gln Tyr Asp Asn Leu Pro Phe
            85                  90                  95
Thr Phe Gly Thr Gly Thr Lys Leu Glu Ile Arg
            100                 105

<210> SEQ ID NO 332
<211> LENGTH: 5
<212> TYPE: PRT
<213> ORGANISM: Mus musculus

<400> SEQUENCE: 332

Gly Tyr Thr Phe Thr
1               5

<210> SEQ ID NO 333
<211> LENGTH: 3
<212> TYPE: PRT
<213> ORGANISM: Mus musculus

<400> SEQUENCE: 333

Glu Thr Tyr
1

<210> SEQ ID NO 334
<211> LENGTH: 4
<212> TYPE: PRT
<213> ORGANISM: Mus musculus

<400> SEQUENCE: 334

Gly Tyr Pro Ala
1

<210> SEQ ID NO 335
<211> LENGTH: 12
<212> TYPE: PRT
<213> ORGANISM: Mus musculus

<400> SEQUENCE: 335

Ser Arg Thr Ile Leu His Ser Ser Gly Asn Thr Tyr
1               5                   10

<210> SEQ ID NO 336
<211> LENGTH: 3
<212> TYPE: PRT
<213> ORGANISM: Mus musculus

<400> SEQUENCE: 336

Lys Val Ser
1

<210> SEQ ID NO 337
<211> LENGTH: 6
<212> TYPE: PRT
<213> ORGANISM: Mus musculus

<400> SEQUENCE: 337

Asp Ser His Val Pro Phe
1               5

<210> SEQ ID NO 338
<211> LENGTH: 115
<212> TYPE: PRT
<213> ORGANISM: Mus musculus

<400> SEQUENCE: 338

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Arg Gly Leu Lys Trp Met
        35                  40                  45

Gly Tyr Ile Asn Thr Glu Thr Tyr Glu Pro Thr Phe Gly Ala Asp Phe
    50                  55                  60

Lys Gly Arg Phe Ala Phe Ser Leu Asp Thr Ser Ala Thr Thr Ala Tyr
65                  70                  75                  80

Leu Gln Ile Asn Ser Leu Lys Thr Glu Asp Thr Ala Thr Phe Phe Cys
                85                  90                  95

Gly Gly Gly Gly Tyr Pro Ala Tyr Trp Gly Gln Gly Thr Val Val Ile
                100                 105                 110

Val Ser Ala
        115

<210> SEQ ID NO 339
<211> LENGTH: 112
<212> TYPE: PRT
<213> ORGANISM: Mus musculus

<400> SEQUENCE: 339

Asp Val Leu Met Thr Gln Thr Pro Leu Ser Leu Pro Val Ser Leu Gly
1               5                   10                  15

Asp Gln Ala Ser Ile Ser Cys Arg Ser Ser Arg Thr Ile Leu His Ser
            20                  25                  30

Ser Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Asn Ile
65                  70                  75                  80

Ser Arg Val Glu Ala Glu Asp Leu Gly Val Tyr Tyr Cys Phe Gln Asp
                85                  90                  95

Ser His Val Pro Phe Thr Phe Gly Thr Gly Thr Lys Leu Glu Ile Lys
                100                 105                 110

<210> SEQ ID NO 340
<211> LENGTH: 7
<212> TYPE: PRT
<213> ORGANISM: Mus musculus

<400> SEQUENCE: 340

Gly Phe Asn Ile Lys Thr Thr
1               5

<210> SEQ ID NO 341
<211> LENGTH: 3
<212> TYPE: PRT
<213> ORGANISM: Mus musculus

<400> SEQUENCE: 341

Ala Asp Asp
1

<210> SEQ ID NO 342
<211> LENGTH: 8
```

<212> TYPE: PRT
<213> ORGANISM: Mus musculus

<400> SEQUENCE: 342

Phe Gly Tyr Val Ala Trp Phe Ala
1               5

<210> SEQ ID NO 343
<211> LENGTH: 7
<212> TYPE: PRT
<213> ORGANISM: Mus musculus

<400> SEQUENCE: 343

Ser Gln Ser Val Asp Asn Tyr
1               5

<210> SEQ ID NO 344
<211> LENGTH: 3
<212> TYPE: PRT
<213> ORGANISM: Mus musculus

<400> SEQUENCE: 344

Tyr Ala Ser
1

<210> SEQ ID NO 345
<211> LENGTH: 6
<212> TYPE: PRT
<213> ORGANISM: Mus musculus

<400> SEQUENCE: 345

His Tyr Ser Ser Pro Tyr
1               5

<210> SEQ ID NO 346
<211> LENGTH: 119
<212> TYPE: PRT
<213> ORGANISM: Mus musculus

<400> SEQUENCE: 346

Glu Val Gln Leu Gln Gln Ser Val Ala Glu Leu Val Arg Pro Gly Ala
1               5                   10                  15

Ser Val Lys Leu Ser Cys Thr Ala Ser Gly Phe Asn Ile Lys Thr Thr
            20                  25                  30

Tyr Met His Trp Val Lys Gln Arg Pro Glu Gln Gly Leu Glu Trp Ile
        35                  40                  45

Gly Arg Ile Asp Pro Ala Asp Asp Asn Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Ala Ala Ile Tyr Tyr Cys
                85                  90                  95

Val Arg Asp Phe Gly Tyr Val Ala Trp Phe Ala Tyr Trp Gly Gln Gly
                100                 105                 110

Thr Leu Val Thr Phe Ser Ala
        115

<210> SEQ ID NO 347
<211> LENGTH: 107
<212> TYPE: PRT
<213> ORGANISM: Mus musculus

<400> SEQUENCE: 347

```
Asn Ile Val Met Thr Pro Thr Pro Lys Phe Leu Pro Val Ser Ser Gly
1               5                   10                  15

Asp Arg Val Thr Met Thr Cys Arg Ala Ser Gln Ser Val Asp Asn Tyr
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Ile Gly Val Pro Asp Arg Phe Thr Gly
    50                  55                  60

Ser Gly Ser Gly Thr Asp Phe Thr Phe Thr Ile Ser Ser Val Gln Val
65                  70                  75                  80

Glu Asp Leu Ala Val Tyr Phe Cys Gln Gln His Tyr Ser Ser Pro Tyr
                85                  90                  95

Thr Phe Gly Ser Gly Thr Lys Leu Glu Ile Lys
            100                 105
```

<210> SEQ ID NO 348
<211> LENGTH: 7
<212> TYPE: PRT
<213> ORGANISM: Mus musculus

<400> SEQUENCE: 348

```
Gly Tyr Pro Phe Ser Glu Tyr
1               5
```

<210> SEQ ID NO 349
<211> LENGTH: 3
<212> TYPE: PRT
<213> ORGANISM: Mus musculus

<400> SEQUENCE: 349

```
Glu Thr Gly
1
```

<210> SEQ ID NO 350
<211> LENGTH: 4
<212> TYPE: PRT
<213> ORGANISM: Mus musculus

<400> SEQUENCE: 350

```
Gly Tyr Pro Ala
1
```

<210> SEQ ID NO 351
<211> LENGTH: 12
<212> TYPE: PRT
<213> ORGANISM: Mus musculus

<400> SEQUENCE: 351

```
Ser Arg Ser Ile Val His Ser Ser Gly Asn Thr Tyr
1               5                   10
```

<210> SEQ ID NO 352
<211> LENGTH: 3
<212> TYPE: PRT
<213> ORGANISM: Mus musculus

<400> SEQUENCE: 352

```
Lys Val Ser
1
```

-continued

<210> SEQ ID NO 353
<211> LENGTH: 5
<212> TYPE: PRT
<213> ORGANISM: Mus musculus

<400> SEQUENCE: 353

Asp Ser His Val Pro
1               5

<210> SEQ ID NO 354
<211> LENGTH: 115
<212> TYPE: PRT
<213> ORGANISM: Mus musculus

<400> SEQUENCE: 354

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Pro Phe Ser Glu Tyr
            20                  25                  30

Ser Ile His Trp Val Lys Gln Ala Pro Gly Lys Gly Leu Lys Trp Met
        35                  40                  45

Val Tyr Val Asn Thr Glu Thr Gly Gln Pro Ile Val Gly Asp Asp Phe
    50                  55                  60

Arg Gly Arg Phe Val Leu Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Gly Gly Gly Gly Tyr Pro Ala Tyr Trp Gly Gln Gly Thr Leu Val Thr
            100                 105                 110

Val Ser Ala
        115

<210> SEQ ID NO 355
<211> LENGTH: 112
<212> TYPE: PRT
<213> ORGANISM: Mus musculus

<400> SEQUENCE: 355

Asp Val Leu Met Thr Gln Thr Pro Leu Ser Leu Pro Val Ser Leu Gly
1               5                   10                  15

Asp Gln Ala Ser Ile Ser Cys Arg Ser Ser Arg Ser Ile Val His Ser
            20                  25                  30

Ser Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Asn Ile
65                  70                  75                  80

Ser Arg Val Glu Ala Glu Asp Leu Gly Val Tyr Tyr Cys Phe Gln Asp
                85                  90                  95

Ser His Val Pro Phe Thr Phe Gly Thr Gly Thr Lys Leu Glu Ile Lys
            100                 105                 110

<210> SEQ ID NO 356
<211> LENGTH: 7
<212> TYPE: PRT
<213> ORGANISM: Mus musculus

<400> SEQUENCE: 356

```
Gly Phe Thr Phe Ser Ser Ser
1               5
```

<210> SEQ ID NO 357
<211> LENGTH: 3
<212> TYPE: PRT
<213> ORGANISM: Mus musculus

<400> SEQUENCE: 357

```
Ala Thr Gly
1
```

<210> SEQ ID NO 358
<211> LENGTH: 8
<212> TYPE: PRT
<213> ORGANISM: Mus musculus

<400> SEQUENCE: 358

```
Tyr Pro His Tyr Tyr Ala Met Asp
1               5
```

<210> SEQ ID NO 359
<211> LENGTH: 7
<212> TYPE: PRT
<213> ORGANISM: Mus musculus

<400> SEQUENCE: 359

```
Ser Glu Asn Ile Phe Ser Asn
1               5
```

<210> SEQ ID NO 360
<211> LENGTH: 3
<212> TYPE: PRT
<213> ORGANISM: Mus musculus

<400> SEQUENCE: 360

```
Ser Ala Thr
1
```

<210> SEQ ID NO 361
<211> LENGTH: 6
<212> TYPE: PRT
<213> ORGANISM: Mus musculus

<400> SEQUENCE: 361

```
Phe Tyr Lys Ile Pro Phe
1               5
```

<210> SEQ ID NO 362
<211> LENGTH: 121
<212> TYPE: PRT
<213> ORGANISM: Mus musculus

<400> SEQUENCE: 362

```
Gln Gly Gln Met His Gln Ser Gly Ala Glu Leu Val Lys Pro Gly Ser
1               5                   10                  15

Ser Val Lys Leu Ser Cys Lys Thr Ser Gly Phe Thr Phe Ser Ser Ser
            20                  25                  30

Phe Ile Ser Trp Leu Lys Gln Lys Pro Gly Gln Ser Leu Glu Trp Ile
        35                  40                  45

Ala Trp Ile Tyr Ala Ala Thr Gly Ser Thr Ser Tyr Asn Gln Lys Phe
    50                  55                  60

Thr Asn Lys Ala Gln Leu Thr Val Asp Thr Ser Ser Ser Ala Ala Tyr
```

```
                65                  70                  75                  80
Met Gln Phe Ser Ser Leu Thr Thr Glu Asp Ser Ala Ile Tyr Tyr Cys
                        85                  90                  95
Ala Arg His Ala Gly Tyr Pro His Tyr Tyr Ala Met Asp Tyr Trp Gly
                       100                 105                 110
Gln Gly Thr Ser Val Thr Val Ser Ser
                       115                 120
```

<210> SEQ ID NO 363
<211> LENGTH: 107
<212> TYPE: PRT
<213> ORGANISM: Mus musculus

<400> SEQUENCE: 363

```
Asp Ile Gln Met Thr Gln Ser Pro Ala Ser Leu Ser Ala Ser Val Gly
1               5                   10                  15
Glu Thr Val Thr Ile Thr Cys Arg Ala Ser Glu Asn Ile Phe Ser Asn
                20                  25                  30
Leu Ala Trp Tyr Gln Gln Lys Gln Gly Lys Ser Pro Gln Leu Leu Val
            35                  40                  45
Tyr Ser Ala Thr Asn Leu Gly Asp Gly Val Pro Ser Arg Phe Ser Gly
        50                  55                  60
Ser Gly Ser Gly Thr Gln Phe Ser Leu Lys Ile Asn Ser Leu Gln Pro
65                  70                  75                  80
Glu Asp Phe Gly Asn Tyr Tyr Cys Gln His Phe Tyr Lys Ile Pro Phe
                85                  90                  95
Thr Phe Gly Thr Gly Thr Lys Leu Glu Ile Lys
                100                 105
```

<210> SEQ ID NO 364
<211> LENGTH: 7
<212> TYPE: PRT
<213> ORGANISM: Mus musculus

<400> SEQUENCE: 364

```
Gly Phe Asn Ile Lys Asp Tyr
1               5
```

<210> SEQ ID NO 365
<211> LENGTH: 3
<212> TYPE: PRT
<213> ORGANISM: Mus musculus

<400> SEQUENCE: 365

```
Glu Asp Gly
1
```

<210> SEQ ID NO 366
<211> LENGTH: 8
<212> TYPE: PRT
<213> ORGANISM: Mus musculus

<400> SEQUENCE: 366

```
His Gly Tyr Val Gly Trp Phe Ala
1               5
```

<210> SEQ ID NO 367
<211> LENGTH: 8
<212> TYPE: PRT
<213> ORGANISM: Mus musculus

<400> SEQUENCE: 367

Ala Ser Glu Asn Val Asp Thr Tyr
1               5

<210> SEQ ID NO 368
<211> LENGTH: 3
<212> TYPE: PRT
<213> ORGANISM: Mus musculus

<400> SEQUENCE: 368

Gly Ala Ser
1

<210> SEQ ID NO 369
<211> LENGTH: 6
<212> TYPE: PRT
<213> ORGANISM: Mus musculus

<400> SEQUENCE: 369

Ser Tyr Ser Tyr Pro Trp
1               5

<210> SEQ ID NO 370
<211> LENGTH: 119
<212> TYPE: PRT
<213> ORGANISM: Mus musculus

<400> SEQUENCE: 370

Glu Val Gln Leu Gln Gln Ser Gly Ala Glu Leu Lys Pro Gly Ala
1               5                   10                  15

Ser Val Lys Leu Thr Cys Thr Thr Ser Gly Phe Asn Ile Lys Asp Tyr
                20                  25                  30

Tyr Ile His Trp Val Lys Gln Arg Ser Asp Gln Gly Leu Glu Trp Ile
            35                  40                  45

Gly Arg Ile Asp Pro Glu Asp Gly Glu Leu Ile Tyr Ala Pro Lys Phe
        50                  55                  60

Gln Asp Lys Ala Thr Ile Thr Val Asp Thr Ser Ser Asn Ile Ala Tyr
65                  70                  75                  80

Leu Gln Leu Asn Ser Leu Thr Ser Glu Asp Thr Ala Val Tyr Tyr Cys
                85                  90                  95

Ser Arg Asp His Gly Tyr Val Gly Trp Phe Ala Tyr Trp Gly Gln Gly
            100                 105                 110

Thr Leu Val Thr Val Ser Ala
        115

<210> SEQ ID NO 371
<211> LENGTH: 107
<212> TYPE: PRT
<213> ORGANISM: Mus musculus

<400> SEQUENCE: 371

Asn Val Val Met Thr Gln Ser Pro Lys Ser Met Ile Met Ser Val Gly
1               5                   10                  15

Gln Arg Val Thr Leu Asn Cys Lys Ala Ser Glu Asn Val Asp Thr Tyr
                20                  25                  30

Val Ser Trp Tyr Gln Gln Lys Pro Glu Gln Ser Pro Lys Leu Leu Ile
            35                  40                  45

Tyr Gly Ala Ser Asn Arg Tyr Thr Gly Val Pro Asp Arg Phe Thr Gly
        50                  55                  60

```
Ser Arg Ser Ala Thr Asp Phe Thr Leu Thr Ile Ser Ser Val Gln Ala
 65                  70                  75                  80

Glu Asp Leu Ala Val Tyr Tyr Cys Gly Gln Ser Tyr Ser Tyr Pro Trp
                 85                  90                  95

Thr Phe Gly Gly Gly Thr Lys Leu Glu Phe Arg
            100                 105

<210> SEQ ID NO 372
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 372

Pro Thr Gly Ala Glu Phe Leu Gly Asp Gly Gly Asp Val Ser Phe Ser
 1               5                  10                  15

Thr Arg Gly Thr Gln Asn Trp Thr Val Glu Arg Leu Leu Gln Ala His
             20                  25                  30

Ala Gln Leu Glu Glu Arg Gly Tyr Val Phe Val Gly Tyr His Gly Thr
         35                  40                  45

Phe Leu Glu Ala Ala Gln Ser Ile Val Phe Gly Gly Val Ala Ala Arg
     50                  55                  60

Ser Gln Asp Leu Ala Ala Ile Trp Ala Gly Phe Tyr Ile Ala Gly Asp
 65                  70                  75                  80

Pro Ala Leu Ala Tyr Gly Tyr Ala Gln Asp Gln Glu Pro Asp Ala Ala
                 85                  90                  95

Gly Arg Ile Arg Asn Gly Ala Leu Leu Arg Val Tyr Val Pro Ala Ser
            100                 105                 110

Ser Leu Pro Gly Phe Tyr Arg Thr Ser Leu Thr Leu Ala Ala Pro Glu
        115                 120                 125

Ala Ala Gly Glu Val Glu Arg Leu Ile Gly His Pro Leu Pro Leu Ala
    130                 135                 140

Leu Asp Ala Ile Thr Gly Pro Glu Glu Gly Gly Arg Leu Glu Thr
145                 150                 155                 160

Ile Leu Gly Trp Pro Leu Ala Glu Arg Thr Val Val Ile Pro Ser Ala
                165                 170                 175

Ile Pro Thr Asp Pro Arg Asn Val Gly Gly Asp Leu Asp Pro Ser Ser
            180                 185                 190

Ile Pro Asp Lys Glu Gln Ala Ile Ser Ala Leu Pro Asp Tyr Ala Ser
        195                 200                 205

Gln Pro Gly Lys Pro Pro Arg Glu Asp Leu Lys
    210                 215

<210> SEQ ID NO 373
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 373

Pro Thr Gly Ala Glu Phe Leu Gly Asp Gly Gly Asp Val Ser Phe Ser
 1               5                  10                  15

Thr Arg Gly Thr Gln Asn Trp Thr Val Glu Arg Leu Leu Gln Ala His
```

```
                20                  25                  30
Ala Gln Leu Glu Glu Arg Gly Tyr Val Phe Val Gly Tyr His Gly Thr
         35                  40                  45

Ala Leu Glu Ala Ala Gln Ser Ile Val Phe Gly Gly Val Arg Ala Arg
 50                  55                  60

Ser Gln Asp Leu Arg Ala Ile Trp Arg Gly Phe Tyr Ile Ala Gly Asp
 65                  70                  75                  80

Pro Ala His Ala Tyr Gly Tyr Ala Gln Asp Gln Glu Pro Asp Ala Arg
                 85                  90                  95

Gly Arg Ile Ala Asn Gly Ala Leu Leu Arg Val Tyr Val Pro Ala Ser
            100                 105                 110

Ser Leu Pro Gly Phe Tyr Arg Thr Ser Leu Thr Leu Ala Ala Pro Glu
        115                 120                 125

Ala Ala Gly Glu Val Glu Arg Leu Ile Gly His Pro Leu Pro Leu Arg
    130                 135                 140

Leu Asp Ala Ile Thr Gly Pro Glu Glu Gly Gly Arg Glu Glu Thr
145                 150                 155                 160

Ile Leu Gly Trp Pro Leu Ala Glu Arg Thr Val Val Ile Pro Ser Ala
                165                 170                 175

Ile Pro Thr Asp Pro Arg Asn Val Gly Gly Asp Leu Asp Pro Ser Ser
            180                 185                 190

Ile Pro Asp Lys Glu Gln Ala Ile Ser Ala Leu Pro Asp Tyr Ala Ser
        195                 200                 205

Gln Pro Gly Lys Pro Pro Arg Glu Asp Leu Lys
    210                 215

<210> SEQ ID NO 374
<211> LENGTH: 107
<212> TYPE: PRT
<213> ORGANISM: Homo sapiens

<400> SEQUENCE: 374

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 375
<211> LENGTH: 105
<212> TYPE: PRT
<213> ORGANISM: Homo sapiens

<400> SEQUENCE: 375

Gln Pro Lys Ala Ala Pro Ser Val Thr Leu Phe Pro Pro Ser Ser Glu
 1               5                  10                  15

Glu Leu Gln Ala Asn Lys Ala Thr Leu Val Cys Leu Ile Ser Asp Phe
```

```
                    20                  25                  30
Tyr Pro Gly Ala Val Thr Val Ala Trp Lys Ala Asp Ser Ser Pro Val
                35                  40                  45

Lys Ala Gly Val Glu Thr Thr Thr Pro Ser Lys Gln Ser Asn Asn Lys
             50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Cys Ser
            100                 105

<210> SEQ ID NO 376
<211> LENGTH: 330
<212> TYPE: PRT
<213> ORGANISM: Homo sapiens

<400> SEQUENCE: 376

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
             50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 377
<211> LENGTH: 330
<212> TYPE: PRT
<213> ORGANISM: Homo sapiens

<400> SEQUENCE: 377

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 378
<211> LENGTH: 330
<212> TYPE: PRT
<213> ORGANISM: Homo sapiens

<400> SEQUENCE: 378

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 379
<211> LENGTH: 327
<212> TYPE: PRT
<213> ORGANISM: Homo sapiens

<400> SEQUENCE: 379

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 380
<211> LENGTH: 280
<212> TYPE: PRT
<213> ORGANISM: Homo sapiens

<400> SEQUENCE: 380

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
            20                  25                  30

Gly Lys Gly Ala Cys Pro Val Phe Glu Cys Gly Asn Val Val Leu Arg

```
                35                  40                  45
Thr Asp Glu Arg Asp Val Asn Tyr Trp Thr Ser Arg Tyr Trp Leu Asn
 50                  55                  60

Gly Asp Phe Arg Lys Gly Asp Val Ser Leu Thr Ile Glu Asn Val Thr
 65                  70                  75                  80

Leu Ala Asp Ser Gly Ile Tyr Cys Cys Arg Ile Gln Ile Pro Gly Ile
                 85                  90                  95

Met Asn Asp Glu Lys Phe Asn Leu Lys Leu Val Ile Lys Pro Ala Lys
                100                 105                 110

Val Thr Pro Ala Pro Thr Arg Gln Arg Asp Phe Thr Ala Ala Phe Pro
                115                 120                 125

Arg Met Leu Thr Thr Arg Gly His Gly Pro Ala Glu Thr Gln Thr Leu
        130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg Ile Gly Ile Tyr Ile Gly Ala Gly Ile Cys Ala Gly Leu
                180                 185                 190

Ala Leu Ala Leu Ile Phe Gly Ala Leu Ile Phe Lys Trp Tyr Ser His
        195                 200                 205

Ser Lys Glu Lys Ile Gln Asn Leu Ser Leu Ile Ser Leu Ala Asn Leu
210                 215                 220

Pro Pro Ser Gly Leu Ala Asn Ala Val Ala Glu Gly Ile Arg Ser Glu
225                 230                 235                 240

Glu Asn Ile Tyr Thr Ile Glu Glu Asn Val Tyr Val Glu Glu Pro
                245                 250                 255

Asn Glu Tyr Tyr Cys Tyr Val Ser Ser Arg Gln Gln Pro Ser Gln Pro
                260                 265                 270

Leu Gly Cys Arg Phe Ala Met Pro
        275                 280

<210> SEQ ID NO 381
<211> LENGTH: 181
<212> TYPE: PRT
<213> ORGANISM: Homo sapiens

<400> SEQUENCE: 381

Ser Glu Val Glu Tyr Arg Ala Glu Val Gly Gln Asn Ala Tyr Leu Pro
 1               5                  10                  15

Cys Phe Tyr Thr Pro Ala Ala Pro Gly Asn Leu Val Pro Val Cys Trp
                 20                  25                  30

Gly Lys Gly Ala Cys Pro Val Phe Glu Cys Gly Asn Val Val Leu Arg
         35                  40                  45

Thr Asp Glu Arg Asp Val Asn Tyr Trp Thr Ser Arg Tyr Trp Leu Asn
 50                  55                  60

Gly Asp Phe Arg Lys Gly Asp Val Ser Leu Thr Ile Glu Asn Val Thr
 65                  70                  75                  80

Leu Ala Asp Ser Gly Ile Tyr Cys Cys Arg Ile Gln Ile Pro Gly Ile
                 85                  90                  95

Met Asn Asp Glu Lys Phe Asn Leu Lys Leu Val Ile Lys Pro Ala Lys
                100                 105                 110

Val Thr Pro Ala Pro Thr Arg Gln Arg Asp Phe Thr Ala Ala Phe Pro
                115                 120                 125
```

```
Arg Met Leu Thr Thr Arg Gly His Gly Pro Ala Glu Thr Gln Thr Leu
            130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg Ile Gly
            180

<210> SEQ ID NO 382
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 382

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 383
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 383

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
```

```
                100             105

<210> SEQ ID NO 384
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (13)..(24)
<223> OTHER INFORMATION: /replace=" "
<220> FEATURE:
<221> NAME/KEY: MISC_FEATURE
<222> LOCATION: (1)..(24)
<223> OTHER INFORMATION: /note="This sequence may encompass 3-6 "Gly Gly
      Gly Ser" repeating units"
<220> FEATURE:
<221> NAME/KEY: MISC_FEATURE
<222> LOCATION: (1)..(24)
<223> OTHER INFORMATION: /note="Variant residues given in the sequence
      have no preference with respect to those in the annotations
      for variant positions"

<400> SEQUENCE: 384

Gly Gly Gly Ser Gly Gly Gly Ser Gly Gly Gly Ser Gly Gly Gly Ser
1               5                   10                  15

Gly Gly Gly Ser Gly Gly Gly Ser
            20

<210> SEQ ID NO 385
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (11)..(25)
<223> OTHER INFORMATION: /replace=" "
<220> FEATURE:
<221> NAME/KEY: MISC_FEATURE
<222> LOCATION: (1)..(25)
<223> OTHER INFORMATION: /note="This sequence may encompass 2-5 "Gly Gly
      Gly Gly Ser" repeating units"
<220> FEATURE:
<221> NAME/KEY: MISC_FEATURE
<222> LOCATION: (1)..(25)
<223> OTHER INFORMATION: /note="Variant residues given in the sequence
      have no preference with respect to those in the annotations
      for variant positions"

<400> SEQUENCE: 385

Gly Gly Gly Gly Ser Gly Gly Gly Gly Ser Gly Gly Gly Ser Gly
1               5                   10                  15

Gly Gly Gly Ser Gly Gly Gly Gly Ser
            20                  25

<210> SEQ ID NO 386
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 386
```

Gly Gly Gly Gly Ser Gly Gly Gly Gly Ser
1               5                   10

<210> SEQ ID NO 387
<211> LENGTH: 50
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (6)..(50)
<223> OTHER INFORMATION: /replace=" "
<220> FEATURE:
<221> NAME/KEY: MISC_FEATURE
<222> LOCATION: (1)..(50)
<223> OTHER INFORMATION: /note="This sequence may encompass 1-10 "Gly
      Gly Gly Gly Ser" repeating units"
<220> FEATURE:
<221> NAME/KEY: MISC_FEATURE
<222> LOCATION: (1)..(50)
<223> OTHER INFORMATION: /note="Variant residues given in the sequence
      have no preference with respect to those in the annotations
      for variant positions"

<400> SEQUENCE: 387

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 388
<211> LENGTH: 50
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (6)..(50)
<223> OTHER INFORMATION: /replace=" "
<220> FEATURE:
<221> NAME/KEY: MISC_FEATURE
<222> LOCATION: (1)..(50)
<223> OTHER INFORMATION: /note="This sequence may encompass 1-10 "Ser
      Gly Gly Gly Gly" repeating units"
<220> FEATURE:
<221> NAME/KEY: MISC_FEATURE
<222> LOCATION: (1)..(50)
<223> OTHER INFORMATION: /note="Variant residues given in the sequence
      have no preference with respect to those in the annotations
      for variant positions"

<400> SEQUENCE: 388

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser Gly Gly Gly Gly Ser Gly Gly
        35                  40                  45

```
Gly Gly
    50

<210> SEQ ID NO 389
<211> LENGTH: 54
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (10)..(54)
<223> OTHER INFORMATION: /replace=" "
<220> FEATURE:
<221> NAME/KEY: MISC_FEATURE
<222> LOCATION: (5)..(54)
<223> OTHER INFORMATION: /note="This region may encompass 1-10 "Ser Gly
      Gly Gly Gly" repeating units"
<220> FEATURE:
<221> NAME/KEY: MISC_FEATURE
<222> LOCATION: (1)..(54)
<223> OTHER INFORMATION: /note="Variant residues given in the sequence
      have no preference with respect to those in the annotations
      for variant positions"

<400> SEQUENCE: 389

Gly Gly Gly Gly Ser Gly Gly Gly Ser Gly Gly Gly Gly Ser Gly
1               5                   10                  15

Gly Gly Ser Gly Gly Gly Gly Ser Gly Gly Gly Gly Ser Gly Gly
                20                  25                  30

Gly Gly Ser Gly Gly Gly Gly Ser Gly Gly Gly Ser Gly Gly Gly
        35                  40                  45

Gly Ser Gly Gly Gly Gly
    50

<210> SEQ ID NO 390
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 390

Glu Pro Lys Ser Cys Gly Gly Gly Gly Ser Gly Gly Gly Gly Ser
1               5                   10                  15

<210> SEQ ID NO 391
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 391

Glu Pro Lys Ser Cys Asp Gly Gly Gly Ser Gly Gly Gly Gly Ser
1               5                   10                  15

<210> SEQ ID NO 392
<211> LENGTH: 5
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic 5xHis tag"

<400> SEQUENCE: 392

His His His His His
1               5

<210> SEQ ID NO 393
<211> LENGTH: 692
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 393

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr His Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Phe Phe Thr Gly Phe His Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Gly
    210                 215                 220

Gly Gly Gly Ser Gly Gly Gly Gly Ser Glu Val Gln Leu Leu Glu Ser
225                 230                 235                 240

Gly Gly Gly Leu Val Gln Pro Gly Gly Ser Leu Arg Leu Ser Cys Ala
                245                 250                 255

Ala Ser Gly Phe Thr Phe Ser Thr Tyr Ala Met Asn Trp Val Arg Gln
            260                 265                 270

Ala Pro Gly Lys Gly Leu Glu Trp Val Ser Arg Ile Arg Ser Lys Tyr
        275                 280                 285

Asn Asn Tyr Ala Thr Tyr Tyr Ala Asp Ser Val Lys Gly Arg Phe Thr
    290                 295                 300

Ile Ser Arg Asp Asp Ser Lys Asn Thr Leu Tyr Leu Gln Met Asn Ser
305                 310                 315                 320
```

Leu Arg Ala Glu Asp Thr Ala Val Tyr Tyr Cys Val Arg His Gly Asn
                325                 330                 335

Phe Gly Asn Ser Tyr Val Ser Trp Phe Ala Tyr Trp Gly Gln Gly Thr
            340                 345                 350

Leu Val Thr Val Ser Ser Ala Ser Val Ala Ala Pro Ser Val Phe Ile
        355                 360                 365

Phe Pro Pro Ser Asp Glu Gln Leu Lys Ser Gly Thr Ala Ser Val Val
370                 375                 380

Cys Leu Leu Asn Asn Phe Tyr Pro Arg Glu Ala Lys Val Gln Trp Lys
385                 390                 395                 400

Val Asp Asn Ala Leu Gln Ser Gly Asn Ser Gln Glu Ser Val Thr Glu
                405                 410                 415

Gln Asp Ser Lys Asp Ser Thr Tyr Ser Leu Ser Ser Thr Leu Thr Leu
            420                 425                 430

Ser Lys Ala Asp Tyr Glu Lys His Lys Val Tyr Ala Cys Glu Val Thr
        435                 440                 445

His Gln Gly Leu Ser Ser Pro Val Thr Lys Ser Phe Asn Arg Gly Glu
    450                 455                 460

Cys Asp Lys Thr His Thr Cys Pro Pro Cys Pro Ala Pro Glu Ala Ala
465                 470                 475                 480

Gly Gly Pro Ser Val Phe Leu Phe Pro Pro Lys Pro Lys Asp Thr Leu
                485                 490                 495

Met Ile Ser Arg Thr Pro Glu Val Thr Cys Val Val Val Asp Val Ser
            500                 505                 510

His Glu Asp Pro Glu Val Lys Phe Asn Trp Tyr Val Asp Gly Val Glu
        515                 520                 525

Val His Asn Ala Lys Thr Lys Pro Arg Glu Glu Gln Tyr Asn Ser Thr
    530                 535                 540

Tyr Arg Val Val Ser Val Leu Thr Val Leu His Gln Asp Trp Leu Asn
545                 550                 555                 560

Gly Lys Glu Tyr Lys Cys Lys Val Ser Asn Lys Ala Leu Gly Ala Pro
                565                 570                 575

Ile Glu Lys Thr Ile Ser Lys Ala Lys Gly Gln Pro Arg Glu Pro Gln
            580                 585                 590

Val Tyr Thr Leu Pro Pro Cys Arg Asp Glu Leu Thr Lys Asn Gln Val
        595                 600                 605

Ser Leu Trp Cys Leu Val Lys Gly Phe Tyr Pro Ser Asp Ile Ala Val
    610                 615                 620

Glu Trp Glu Ser Asn Gly Gln Pro Glu Asn Asn Tyr Lys Thr Thr Pro
625                 630                 635                 640

Pro Val Leu Asp Ser Asp Gly Ser Phe Phe Leu Tyr Ser Lys Leu Thr
                645                 650                 655

Val Asp Lys Ser Arg Trp Gln Gln Gly Asn Val Phe Ser Cys Ser Val
            660                 665                 670

Met His Glu Ala Leu His Asn His Tyr Thr Gln Lys Ser Leu Ser Leu
        675                 680                 685

Ser Pro Gly Lys
    690

<210> SEQ ID NO 394
<211> LENGTH: 449
<212> TYPE: PRT
<213> ORGANISM: Artificial Sequence
<220> FEATURE:

-continued

```
<221> NAME/KEY: source
<223> OTHER INFORMATION: /note="Description of Artificial Sequence:
      Synthetic polypeptide"

<400> SEQUENCE: 394

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr His Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Phe Phe Thr Gly Phe His Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
```

```
                385                 390                 395                 400
Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 395
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (201)..(201)
<223> OTHER INFORMATION: Any amino acid

<400> SEQUENCE: 395

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Thr Asn Glu His
                85                  90                  95

Tyr Tyr Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Xaa Gly Leu Ser Ser Pro Val Thr
        195                 200                 205

Lys Ser Phe Asn Arg Gly Glu Cys
    210                 215

<210> SEQ ID NO 396
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 396

Gly Thr Asn Ala Arg Ala Pro
1               5

<210> SEQ ID NO 397
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 397

Ala Leu Trp Tyr Ala Asn Leu Trp Val
1               5

<210> SEQ ID NO 398
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 398

Asn Ala Trp Met His
1               5

<210> SEQ ID NO 399
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 399

Ser Ile Lys Ser Lys Thr Asp Gly Gly Thr Thr Asp Tyr Ala Ala Pro
1               5                   10                  15

Val Lys Gly

<210> SEQ ID NO 400
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 400

Pro Tyr Glu Trp Ser Trp Tyr Asp Tyr
1               5

<210> SEQ ID NO 401
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 401

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Glu Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Tyr Glu Trp Ser Trp Tyr Asp Tyr Trp Gly Gln
            100                 105                 110

Gly Thr Leu Val Thr Val Ser Ser
        115                 120

<210> SEQ ID NO 402
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 402

Arg Ile Lys Ser Lys Thr Glu Gly Gly Thr Thr Asp Tyr Ala Ala Pro
1               5                   10                  15

Val Lys Gly

<210> SEQ ID NO 403
<211> LENGTH: 689
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 403

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Glu Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Tyr Glu Trp Ser Trp Tyr Asp Tyr Trp Gly Gln
            100                 105                 110

Gly Thr Leu Val Thr Val Ser Ser Ala Ser Thr Lys Gly Pro Ser Val
        115                 120                 125

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Gly Gly Gly Gly Ser Gly Gly Gly Ser Glu Val Gln Leu Leu Glu
225                 230                 235                 240

Ser Gly Gly Gly Leu Val Gln Pro Gly Gly Ser Leu Arg Leu Ser Cys
                245                 250                 255

Ala Ala Ser Gly Phe Thr Phe Ser Thr Tyr Ala Met Asn Trp Val Arg
            260                 265                 270

Gln Ala Pro Gly Lys Gly Leu Glu Trp Val Ser Arg Ile Arg Ser Lys
        275                 280                 285

Tyr Asn Asn Tyr Ala Thr Tyr Tyr Ala Asp Ser Val Lys Gly Arg Phe
    290                 295                 300

Thr Ile Ser Arg Asp Asp Ser Lys Asn Thr Leu Tyr Leu Gln Met Asn
305                 310                 315                 320

Ser Leu Arg Ala Glu Asp Thr Ala Val Tyr Tyr Cys Val Arg His Gly
                325                 330                 335

Asn Phe Gly Asn Ser Tyr Val Ser Trp Phe Ala Tyr Trp Gly Gln Gly
            340                 345                 350

Thr Leu Val Thr Val Ser Ser Ala Ser Thr Lys Gly Pro Ser Val Phe
        355                 360                 365

Pro Leu Ala Pro Ser Ser Lys Ser Thr Ser Gly Gly Thr Ala Ala Leu
    370                 375                 380

Gly Cys Leu Val Lys Asp Tyr Phe Pro Glu Pro Val Thr Val Ser Trp
385                 390                 395                 400

Asn Ser Gly Ala Leu Thr Ser Gly Val His Thr Phe Pro Ala Val Leu
                405                 410                 415

Gln Ser Ser Gly Leu Tyr Ser Leu Ser Ser Val Val Thr Val Pro Ser
            420                 425                 430

Ser Ser Leu Gly Thr Gln Thr Tyr Ile Cys Asn Val Asn His Lys Pro
        435                 440                 445

Ser Asn Thr Lys Val Asp Lys Lys Val Glu Pro Lys Ser Cys Asp Lys
    450                 455                 460

Thr His Thr Cys Pro Pro Cys Pro Ala Pro Glu Ala Ala Gly Gly Pro
465                 470                 475                 480

Ser Val Phe Leu Phe Pro Pro Lys Pro Lys Asp Thr Leu Met Ile Ser
                485                 490                 495

Arg Thr Pro Glu Val Thr Cys Val Val Val Asp Val Ser His Glu Asp
            500                 505                 510

Pro Glu Val Lys Phe Asn Trp Tyr Val Asp Gly Val Glu Val His Asn
        515                 520                 525

Ala Lys Thr Lys Pro Arg Glu Glu Gln Tyr Asn Ser Thr Tyr Arg Val
    530                 535                 540

Val Ser Val Leu Thr Val Leu His Gln Asp Trp Leu Asn Gly Lys Glu
```

```
545                 550                 555                 560
Tyr Lys Cys Lys Val Ser Asn Lys Ala Leu Gly Ala Pro Ile Glu Lys
                565                 570                 575
Thr Ile Ser Lys Ala Lys Gly Gln Pro Arg Glu Pro Gln Val Tyr Thr
                580                 585                 590
Leu Pro Pro Cys Arg Asp Glu Leu Thr Lys Asn Gln Val Ser Leu Trp
                595                 600                 605
Cys Leu Val Lys Gly Phe Tyr Pro Ser Asp Ile Ala Val Glu Trp Glu
                610                 615                 620
Ser Asn Gly Gln Pro Glu Asn Asn Tyr Lys Thr Thr Pro Pro Val Leu
625                 630                 635                 640
Asp Ser Asp Gly Ser Phe Phe Leu Tyr Ser Lys Leu Thr Val Asp Lys
                645                 650                 655
Ser Arg Trp Gln Gln Gly Asn Val Phe Ser Cys Ser Val Met His Glu
                660                 665                 670
Ala Leu His Asn His Tyr Thr Gln Lys Ser Leu Ser Leu Ser Pro Gly
                675                 680                 685
Lys

<210> SEQ ID NO 404
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 404

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asn Ala
                20                  25                  30
Trp Met Ser Trp Val Arg Gln Ala Pro Gly Lys Gly Leu Glu Trp Val
                35                  40                  45
Gly Arg Ile Lys Ser Lys Thr Glu Gly Gly Thr Thr Asp Tyr Ala Ala
                50                  55                  60
Pro Val Lys Gly Arg Phe Thr Ile Ser Arg Asp Asp Ser Lys Asn Thr
65                  70                  75                  80
Leu Tyr Leu Gln Met Asn Ser Leu Lys Thr Glu Asp Thr Ala Val Tyr
                85                  90                  95
Tyr Cys Thr Thr Pro Tyr Glu Trp Ser Trp Tyr Asp Tyr Trp Gly Gln
                100                 105                 110
Gly Thr Leu Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
                130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
```

Pro Ser Asn Thr Lys Val Asp Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn Arg Phe Thr Gln Lys Ser Leu Ser Leu Ser Pro
        435                 440                 445

Gly Lys
    450

<210> SEQ ID NO 405
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 405

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Arg Tyr Arg Tyr Phe Asp Tyr Trp Gly Gln Gly

Thr Leu Val Thr Val Ser Ser
            115

<210> SEQ ID NO 406
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 406

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Glu Ser Pro Pro Thr Gly
                85                  90                  95

Leu Val Val Phe Gly Gly Gly Thr Lys Leu Thr Val Leu
            100                 105

<210> SEQ ID NO 407
<211> LENGTH: 674
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 407

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Arg Tyr Arg Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Glu Lys Val Glu Pro Lys Ser Cys Asp Gly
    210                 215                 220

Gly Gly Gly Ser Gly Gly Gly Ser Gln Ala Val Val Thr Gln Glu
225                 230                 235                 240

Pro Ser Leu Thr Val Ser Pro Gly Gly Thr Val Thr Leu Thr Cys Gly
            245                 250                 255

Ser Ser Thr Gly Ala Val Thr Thr Ser Asn Tyr Ala Asn Trp Val Gln
            260                 265                 270

Glu Lys Pro Gly Gln Ala Phe Arg Gly Leu Ile Gly Gly Thr Asn Lys
            275                 280                 285

Arg Ala Pro Gly Thr Pro Ala Arg Phe Ser Gly Ser Leu Leu Gly Gly
    290                 295                 300

Lys Ala Ala Leu Thr Leu Ser Gly Ala Gln Pro Glu Asp Glu Ala Glu
305                 310                 315                 320

Tyr Tyr Cys Ala Leu Trp Tyr Ser Asn Leu Trp Val Phe Gly Gly Gly
            325                 330                 335

Thr Lys Leu Thr Val Leu Ser Ser Ala Ser Thr Lys Gly Pro Ser Val
            340                 345                 350

Phe Pro Leu Ala Pro Ser Ser Lys Ser Thr Ser Gly Gly Thr Ala Ala
            355                 360                 365

Leu Gly Cys Leu Val Lys Asp Tyr Phe Pro Glu Pro Val Thr Val Ser
    370                 375                 380

Trp Asn Ser Gly Ala Leu Thr Ser Gly Val His Thr Phe Pro Ala Val
385                 390                 395                 400

Leu Gln Ser Ser Gly Leu Tyr Ser Leu Ser Ser Val Val Thr Val Pro
            405                 410                 415

Ser Ser Ser Leu Gly Thr Gln Thr Tyr Ile Cys Asn Val Asn His Lys
            420                 425                 430

Pro Ser Asn Thr Lys Val Asp Lys Lys Val Glu Pro Lys Ser Cys Asp
    435                 440                 445

Lys Thr His Thr Cys Pro Pro Cys Pro Ala Pro Glu Ala Ala Gly Gly
    450                 455                 460

Pro Ser Val Phe Leu Phe Pro Pro Lys Pro Lys Asp Thr Leu Met Ile
465                 470                 475                 480

Ser Arg Thr Pro Glu Val Thr Cys Val Val Val Asp Val Ser His Glu
            485                 490                 495

Asp Pro Glu Val Lys Phe Asn Trp Tyr Val Asp Gly Val Glu Val His
            500                 505                 510

Asn Ala Lys Thr Lys Pro Arg Glu Glu Gln Tyr Asn Ser Thr Tyr Arg
    515                 520                 525

Val Val Ser Val Leu Thr Val Leu His Gln Asp Trp Leu Asn Gly Lys
    530                 535                 540

Glu Tyr Lys Cys Lys Val Ser Asn Lys Ala Leu Gly Ala Pro Ile Glu
545                 550                 555                 560

Lys Thr Ile Ser Lys Ala Lys Gly Gln Pro Arg Glu Pro Gln Val Tyr
            565                 570                 575
```

```
Thr Leu Pro Pro Cys Arg Asp Glu Leu Thr Lys Asn Gln Val Ser Leu
            580                 585                 590

Trp Cys Leu Val Lys Gly Phe Tyr Pro Ser Asp Ile Ala Val Glu Trp
        595                 600                 605

Glu Ser Asn Gly Gln Pro Glu Asn Asn Tyr Lys Thr Thr Pro Pro Val
    610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
                645                 650                 655

Glu Ala Leu His Asn His Tyr Thr Gln Lys Ser Leu Ser Leu Ser Pro
            660                 665                 670

Gly Lys

<210> SEQ ID NO 408
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 408

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Arg Tyr Arg Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
            355                 360                 365

Cys Ala Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 409
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 409

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Glu Ser Pro Pro Thr Gly
                85                  90                  95

Leu Val Val Phe Gly Gly Gly Thr Lys Leu Thr Val Leu Gly Gln Pro
            100                 105                 110

Lys Ala Ala Pro Ser Val Thr Leu Phe Pro Pro Ser Ser Lys Lys Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
```

```
                145                 150                 155                 160
Gly Val Glu Thr Thr Thr Pro Ser Lys Gln Ser Asn Asn Lys Tyr Ala
                    165                 170                 175

Ala Ser Ser Tyr Leu Ser Leu Thr Pro Glu Gln Trp Lys Ser His Arg
                    180                 185                 190

Ser Tyr Ser Cys Gln Val Thr His Glu Gly Ser Thr Val Glu Lys Thr
                        195                 200                 205

Val Ala Pro Thr Glu Cys Ser
                210                 215

<210> SEQ ID NO 410
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 410

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Trp Ser Tyr Tyr Met Asp Tyr Trp Gly Gln Gly Thr
                100                 105                 110

Leu Val Thr Val Ser Ser
            115

<210> SEQ ID NO 411
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 411

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95
```

Arg Gln Thr Pro Thr Phe Gly Gln Gly Thr Lys Val Glu Ile Lys
                100                 105                 110

<210> SEQ ID NO 412
<211> LENGTH: 673
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 412

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Trp Ser Tyr Tyr Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Glu Lys Val Glu Pro Lys Ser Cys Asp Gly Gly
    210                 215                 220

Gly Gly Ser Gly Gly Gly Gly Ser Gln Ala Val Val Thr Gln Glu Pro
225                 230                 235                 240

Ser Leu Thr Val Ser Pro Gly Gly Thr Val Thr Leu Thr Cys Gly Ser
                245                 250                 255

Ser Thr Gly Ala Val Thr Thr Ser Asn Tyr Ala Asn Trp Val Gln Glu
            260                 265                 270

Lys Pro Gly Gln Ala Phe Arg Gly Leu Ile Gly Gly Thr Asn Lys Arg
        275                 280                 285

Ala Pro Gly Thr Pro Ala Arg Phe Ser Gly Ser Leu Leu Gly Gly Lys
    290                 295                 300

Ala Ala Leu Thr Leu Ser Gly Ala Gln Pro Glu Asp Glu Ala Glu Tyr
305                 310                 315                 320

Tyr Cys Ala Leu Trp Tyr Ser Asn Leu Trp Val Phe Gly Gly Gly Thr
                325                 330                 335

```
Lys Leu Thr Val Leu Ser Ser Ala Ser Thr Lys Gly Pro Ser Val Phe
            340                 345                 350

Pro Leu Ala Pro Ser Ser Lys Ser Thr Ser Gly Gly Thr Ala Ala Leu
        355                 360                 365

Gly Cys Leu Val Lys Asp Tyr Phe Pro Glu Pro Val Thr Val Ser Trp
    370                 375                 380

Asn Ser Gly Ala Leu Thr Ser Gly Val His Thr Phe Pro Ala Val Leu
385                 390                 395                 400

Gln Ser Ser Gly Leu Tyr Ser Leu Ser Ser Val Val Thr Val Pro Ser
                405                 410                 415

Ser Ser Leu Gly Thr Gln Thr Tyr Ile Cys Asn Val Asn His Lys Pro
            420                 425                 430

Ser Asn Thr Lys Val Asp Lys Lys Val Glu Pro Lys Ser Cys Asp Lys
        435                 440                 445

Thr His Thr Cys Pro Pro Cys Pro Ala Pro Glu Ala Ala Gly Gly Pro
    450                 455                 460

Ser Val Phe Leu Phe Pro Pro Lys Pro Lys Asp Thr Leu Met Ile Ser
465                 470                 475                 480

Arg Thr Pro Glu Val Thr Cys Val Val Val Asp Val Ser His Glu Asp
                485                 490                 495

Pro Glu Val Lys Phe Asn Trp Tyr Val Asp Gly Val Glu Val His Asn
            500                 505                 510

Ala Lys Thr Lys Pro Arg Glu Glu Gln Tyr Asn Ser Thr Tyr Arg Val
        515                 520                 525

Val Ser Val Leu Thr Val Leu His Gln Asp Trp Leu Asn Gly Lys Glu
    530                 535                 540

Tyr Lys Cys Lys Val Ser Asn Lys Ala Leu Gly Ala Pro Ile Glu Lys
545                 550                 555                 560

Thr Ile Ser Lys Ala Lys Gly Gln Pro Arg Glu Pro Gln Val Tyr Thr
                565                 570                 575

Leu Pro Pro Cys Arg Asp Glu Leu Thr Lys Asn Gln Val Ser Leu Trp
            580                 585                 590

Cys Leu Val Lys Gly Phe Tyr Pro Ser Asp Ile Ala Val Glu Trp Glu
        595                 600                 605

Ser Asn Gly Gln Pro Glu Asn Asn Tyr Lys Thr Thr Pro Pro Val Leu
    610                 615                 620

Asp Ser Asp Gly Ser Phe Phe Leu Tyr Ser Lys Leu Thr Val Asp Lys
625                 630                 635                 640

Ser Arg Trp Gln Gln Gly Asn Val Phe Ser Cys Ser Val Met His Glu
                645                 650                 655

Ala Leu His Asn His Tyr Thr Gln Lys Ser Leu Ser Leu Ser Pro Gly
            660                 665                 670

Lys

<210> SEQ ID NO 413
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 413

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
            20                  25                  30
Tyr Met His Trp Val Arg Gln Ala Pro Gly Gln Gly Leu Glu Trp Met
            35                  40                  45
Gly Ile Ile Asn Pro Ser Gly Gly Ser Thr Ser Tyr Ala Gln Lys Phe
 50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
            85                  90                  95
Ala Arg Gly Asp Trp Ser Tyr Tyr Met Asp Tyr Trp Gly Gln Gly Thr
            100                 105                 110
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
 130                 135                 140
Cys Leu Val Glu Asp Tyr Phe Pro Glu Pro Val Thr Val Ser Trp Asn
 145                 150                 155                 160
Ser Gly Ala Leu Thr Ser Gly Val His Thr Phe Pro Ala Val Leu Gln
            165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
            195                 200                 205
Asn Thr Lys Val Asp Glu Lys Val Glu Pro Lys Ser Cys Asp Lys Thr
 210                 215                 220
His Thr Cys Pro Pro Cys Pro Ala Pro Glu Ala Ala Gly Gly Pro Ser
 225                 230                 235                 240
Val Phe Leu Phe Pro Pro Lys Pro Lys Asp Thr Leu Met Ile Ser Arg
            245                 250                 255
Thr Pro Glu Val Thr Cys Val Val Asp Val Ser His Glu Asp Pro
            260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
 290                 295                 300
Ser Val Leu Thr Val Leu His Gln Asp Trp Leu Asn Gly Lys Glu Tyr
 305                 310                 315                 320
Lys Cys Lys Val Ser Asn Lys Ala Leu Gly Ala Pro Ile Glu Lys Thr
            325                 330                 335
Ile Ser Lys Ala Lys Gly Gln Pro Arg Glu Pro Gln Val Cys Thr Leu
            340                 345                 350
Pro Pro Ser Arg Asp Glu Leu Thr Lys Asn Gln Val Ser Leu Ser Cys
            355                 360                 365
Ala Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
 385                 390                 395                 400
Ser Asp Gly Ser Phe Phe Leu Val Ser Lys Leu Thr Val Asp Lys Ser
            405                 410                 415
Arg Trp Gln Gln Gly Asn Val Phe Ser Cys Ser Val Met His Glu Ala
            420                 425                 430
```

Leu His Asn His Tyr Thr Gln Lys Ser Leu Ser Leu Ser Pro Gly Lys
            435                 440                 445

<210> SEQ ID NO 414
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 414

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gln Thr Pro Thr Phe Gly Gln Gly Thr Lys Val Glu Ile Lys Arg
            100                 105                 110

Thr Val Ala Ala Pro Ser Val Phe Ile Phe Pro Pro Ser Asp Arg Lys
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 415
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 415
gaggtgcaat tggtggaaag cggaggcggc ctcgtgaagc ctggcggatc tctgagactg      60
agctgtgccg ccagcggctt caccttcagc aacgcctgga tgagctgggt gcgccaggcc     120
cctggaaaag gactcgagtg ggtgggacgg atcaagagca agaccgaggg cggcaccacc     180
gactatgccg cccctgtgaa gggccggttc accatcagca gggacgacag caagaacacc     240
ctgtacctgc agatgaacag cctgaaaacc gaggacaccg ccgtgtacta ctgcaccacc     300

```
ccctacgagt ggtcttggta cgactactgg ggccagggca ccctcgtgac cgtgtcatct      360
```

<210> SEQ ID NO 416
<211> LENGTH: 2067
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 416

```
gaggtgcaat tggtggaaag cggaggcggc ctcgtgaagc ctggcggatc tctgagactg       60
agctgtgccg ccagcggctt caccttcagc aacgcctgga tgagctgggt gcgccaggcc      120
cctggaaaag gactcgagtg ggtgggacgg atcaagagca agaccgaggg cggcaccacc      180
gactatgccg cccctgtgaa gggccggttc accatcagca gggacgacag caagaacacc      240
ctgtacctgc agatgaacag cctgaaaacc gaggacaccg ccgtgtacta ctgcaccacc      300
ccctacgagt ggtcttggta cgactactgg ggccagggca ccctcgtgac cgtgtcatct      360
gctagcacaa agggcccctag cgtgttccct ctggccccca gcagcaagag cacaagcggc      420
ggaacagccg ccctgggctg cctcgtgaag gactacttcc ccgagcccgt gacagtgtct      480
tggaacagcg gagccctgac aagcggcgtg cacaccttcc ctgccgtgct gcagagcagc      540
ggcctgtact ccctgagcag cgtggtcacc gtgcctagca gcagcctggg cacccagacc      600
tacatctgca acgtgaacca caagcccagc aacaccaaag tggacaagaa ggtggagccc      660
aagagctgtg atggcggagg agggtccgga ggcggaggat ccgaggtgca gctgctggaa      720
tctggcggcg gactggtgca gcctggcgga tctctgagac tgagctgtgc cgccagcggc      780
ttcaccttca gcacctacgc catgaactgg gtgcgccagg cccctggcaa aggcctggaa      840
tgggtgtccc ggatcagaag caagtacaac aactacgcca cctactacgc cgacagcgtg      900
aagggccggt tcaccatcag ccgggacgac agcaagaaca ccctgtacct gcagatgaac      960
agcctgcggg ccgaggacac cgccgtgtac tattgtgtgc ggcacggcaa cttcggcaac     1020
agctatgtgt cttggtttgc ctactgggggc cagggcaccc tcgtgaccgt gtcaagcgct     1080
agtaccaagg gcccccagcgt gttccccctg gcacccagca gcaagagcac atctggcgga     1140
acagccgctc tgggctgtct ggtgaaagac tacttccccg agcccgtgac cgtgtcttgg     1200
aactctggcg ccctgaccag cggcgtgcac acctttccag ccgtgctgca gagcagcggc     1260
ctgtactccc tgtcctccgt ggtcaccgtg ccctctagct ccctgggaac acagacatat     1320
atctgtaatg tcaatcacaa gccttccaac accaaagtcg ataagaaagt cgagcccaag     1380
agctgcgaca aaactcacac atgcccaccg tgcccagcac ctgaagctgc aggggggaccg     1440
tcagtcttcc tcttcccccc aaaacccaag gacaccctca tgatctcccg gacccctgag     1500
gtcacatgcg tggtggtgga cgtgagccac gaagaccctg aggtcaagtt caactggtac     1560
gtggacggcg tggaggtgca taatgccaag acaaagccgc gggaggagca gtacaacagc     1620
acgtaccgtg tggtcagcgt cctcaccgtc ctgcaccagg actggctgaa tggcaaggag     1680
tacaagtgca aggtctccaa caaagccctc ggcgccccca tcgagaaaac catctccaaa     1740
gccaaagggc agccccgaga accacaggtg tacaccctgc cccatgccg ggatgagctg     1800
accaagaacc aggtcagcct gtggtgcctg gtcaaaggct tctatcccag cgacatcgcc     1860
gtggagtggg agagcaatgg gcagccggag aacaactaca agaccacgcc tcccgtgctg     1920
gactccgacg gctccttctt cctctacagc aagctcaccg tggacaagag caggtggcag     1980
```

| | |
|---|---|
| cagggaacg tcttctcatg ctccgtgatg catgaggctc tgcacaacca ctacacgcag | 2040 |
| aagagcctct ccctgtctcc gggtaaa | 2067 |

<210> SEQ ID NO 417
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 417

| | |
|---|---|
| gaggtgcaat tggtggaaag cggaggcggc ctcgtgaagc ctggcggatc tctgagactg | 60 |
| agctgtgccg ccagcggctt caccttcagc aacgcctgga tgagctgggt gcgccaggcc | 120 |
| cctggaaaag gactcgagtg ggtgggacgg atcaagagca agaccgaggg cggcaccacc | 180 |
| gactatgccg cccctgtgaa gggccggttc accatcagca gggacgacag caagaacacc | 240 |
| ctgtacctgc agatgaacag cctgaaaacc gaggacaccg ccgtgtacta ctgcaccacc | 300 |
| ccctacgagt ggtcttggta cgactactgg ggccagggca cctcgtgac cgtgtcatct | 360 |
| gctagcacca agggcccctc cgtgttcccc ctggccccca gcagcaagag caccagcggc | 420 |
| ggcacagccg ctctgggctg cctggtcaag gactacttcc ccgagcccgt gaccgtgtcc | 480 |
| tggaacagcg gagccctgac ctccggcgtg cacaccttcc ccgccgtgct gcagagttct | 540 |
| ggcctgtata gcctgagcag cgtggtcacc gtgccttcta gcagcctggg cacccagacc | 600 |
| tacatctgca acgtgaacca caagcccagc aacaccaagg tggacaagaa ggtggagccc | 660 |
| aagagctgcg acaaaactca cacatgccca ccgtgcccag cacctgaagc tgcaggggga | 720 |
| ccgtcagtct tcctcttccc cccaaaaccc aaggacaccc tcatgatctc ccggacccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacaac | 900 |
| agcacgtacc gtgtggtcag cgtcctcacc gtcctgcacc aggactggct gaatggcaag | 960 |
| gagtacaagt gcaaggtctc caacaaagcc ctcggcgccc catcgagaa aaccatctcc | 1020 |
| aaagccaaag gcagccccg agaaccacag gtgtgcaccc tgcccccatc ccgggatgag | 1080 |
| ctgaccaaga accaggtcag cctctcgtgc gcagtcaaag gcttctatcc cagcgacatc | 1140 |
| gccgtggagt gggagagcaa tgggcagccg gagaacaact acaagaccac gcctcccgtg | 1200 |
| ctggactccg acggctcctt cttcctcgtg agcaagctca ccgtggacaa gagcaggtgg | 1260 |
| cagcagggga acgtcttctc atgctccgtg atgcatgagg ctctgcacaa ccgcttcacg | 1320 |
| cagaagagcc tctccctgtc tccgggtaaa | 1350 |

<210> SEQ ID NO 418
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 418

| | |
|---|---|
| gaggtgcaat tgttggagtc tgggggaggc ttggtacagc ctgggggtc cctgagactc | 60 |
| tcctgtgcag cctccggatt caccttagc agttatgcca tgagctgggt ccgccaggct | 120 |

```
ccagggaagg ggctggagtg gtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gcgtggtgac     300
taccgttacc gttacttcga ctactggggc caaggaaccc tggtcaccgt ctcgagt       357
```

<210> SEQ ID NO 419
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 419

```
tcttctgaac tgactcaaga tccagctgtt agcgtggctc tgggtcagac tgtacgtatc      60
acctgccaag gcgattctct gcgctcctac tacgcaagct ggtaccagca gaaaccgggt     120
caggccccag ttctggtgat ttacggcaaa aacaaccgtc cgtctgggat cccggaccgt     180
ttctccggca gctcttccgg taacacggcg agcctcacca tcactggcgc tcaagcagaa     240
gacgaggccg actattactg taactctcgg gaaagcccac caaccggcct ggttgtcttc     300
ggtggcggta ccaagctgac cgtccta                                         327
```

<210> SEQ ID NO 420
<211> LENGTH: 2022
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 420

```
gaggtgcaat gttggagtc tgggggaggc ttggtacagc ctgggggtc cctgagactc       60 tcctgtgcag cctccggatt cacctttagc agttatgcca tgagctgggt ccgccaggct    120
ccagggaagg ggctggagtg gtctcagct attagtggta gtggtggtag cacatactac     180
gcagactccg tgaagggccg gttcaccatc tccagagaca attccaagaa cacgctgtat    240
ctgcagatga acagcctgag agccgaggac acggccgtat attactgtgc gcgtggtgac    300
taccgttacc gttacttcga ctactggggc caaggaaccc tggtcaccgt ctcgagtgct    360
agcaccaagg gcccctccgt gtttcctctg gccccttcca gcaagtccac ctctggcgga    420
actgccgctc tgggctgcct ggtggaagat tacttccccg agcccgtgac cgtgtcctgg    480
aattctggcg ctctgaccte cggcgtgcac acctttccag ctgtgctgca gtcctccggc    540
ctgtactccc tgtcctccgt cgtgacagtg ccctccagct ctctgggcac ccagacctac    600
atctgcaacg tgaaccacaa gcccteccaac accaaggtgg acgagaaggt ggaacccaag    660
tcctgcgacg gtggcggagg ttccggaggc ggaggatccc aggctgtcgt gacccaggaa    720
ccctccctga cagtgtctcc tggcggcacc gtgaccctga cctgtggatc ttctaccggc    780
gctgtgacca cctccaacta cgccaattgg gtgcaggaaa agcccggcca ggccttcaga    840
ggactgatcg gcggcaccaa caagagagcc cctggcaccc tgccagatt ctccggttct    900 ctgctgggcg gcaaggctgc cctgactctg tctggtgctc agcctgagga cgaggccgag    960
tactactgcg ccctgtggta ctccaacctg tgggtgttcg gcggaggcac caagctgacc   1020
gtgctgtcca gcgcttccac caagggaccc agtgtgttcc ccctggcccc cagctccaag   1080
```

```
tctacatccg gtggcacagc tgccctggga tgtctcgtga aggactactt tcctgagcct    1140
gtgacagtgt cttggaacag cggagccctg accagcggag tgcacacatt ccctgcagtg    1200
ctgcagagca gcggcctgta tagcctgagc agcgtcgtga ccgtgccttc ctctagcctg    1260
ggaacacaga catatatctg taatgtgaat cataagccca gtaataccaa agtggataag    1320
aaagtggaac ctaagagctg cgataagacc cacacctgtc cccctgccc tgctcctgaa    1380 gctgctggtg gccctagcgt gttcctgttc cccccaaagc caaggacac cctgatgatc    1440 tccccggaccc ccgaagtgac ctgcgtggtg gtggatgtgt cccacgagga ccctgaagtg    1500
aagttcaatt ggtacgtgga cggcgtgaa gtgcacaacg ccaagaccaa gcctagagag    1560
gaacagtaca actccaccta ccgggtggtg tccgtgctga cagtgctgca ccaggactgg    1620
ctgaacggca aagagtacaa gtgcaaggtg tccaacaagg ccctgggcgc tcccatcgaa    1680
aagaccatct ccaaggccaa gggccagccc cgggaacccc aggtgtacac cctgccccca    1740
tgccgggatg agctgaccaa gaaccaggtc agcctgtggt gcctggtcaa aggcttctat    1800
cccagcgaca tcgccgtgga gtgggagagc aatgggcagc cggagaacaa ctacaagacc    1860
acgcctcccg tgctggactc cgacggctcc ttcttcctct acagcaagct caccgtggac    1920
aagagcaggt ggcagcaggg gaacgtcttc tcatgctccg tgatgcatga ggctctgcac    1980
aaccactaca cgcagaagag cctctccctg tctccgggta aa    2022

<210> SEQ ID NO 421
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 421
gaggtgcaat tgttggagtc tgggggaggc ttggtacagc ctgggggtc cctgagactc      60 tcctgtgcag cctccggatt caccttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gcgtggtgac    300
taccgttacc gttacttcga ctactgggc caaggaaccc tggtcaccgt ctcgagtgct    360
agcaccaagg gcccctccgt gttccccctg gccccagca gcaagagcac cagcggcggc    420
acagccgctc tgggctgcct ggtcgaggac tacttccccg agcccgtgac cgtgtcctgg    480
aacagcggag ccctgacctc cggcgtgcac accttccccg ccgtgctgca gagttctggc    540
ctgtatagcc tgagcagcgt ggtcaccgtg ccttctagca gcctgggcac ccagacctac    600
atctgcaacg tgaaccacaa gcccagcaac accaaggtgg acgagaaggt ggagcccaag    660
agctgcgaca aaactcacac atgcccaccg tgcccagcac ctgaagctgc agggggaccg    720
tcagtcttcc tcttcccccc aaaacccaag gacacctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgaccagg actggctgaa tggcaaggag    960
tacaagtgca aggtctccaa caaagccctc ggcgccccca tcgagaaaac catctccaaa    1020
```

```
gccaaagggc agccccgaga accacaggtg tgcaccctgc ccccatcccg ggatgagctg    1080
accaagaacc aggtcagcct ctcgtgcgca gtcaaaggct tctatcccag cgacatcgcc    1140
gtggagtggg agagcaatgg gcagccggag aacaactaca agaccacgcc tcccgtgctg    1200
gactccgacg gctccttctt cctcgtgagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                        1347
```

<210> SEQ ID NO 422
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 422

```
tcttctgaac tgactcaaga tccagctgtt agcgtggctc tgggtcagac tgtacgtatc      60
acctgccaag gcgattctct gcgctcctac tacgcaagct ggtaccagca gaaaccgggt     120
caggccccag ttctggtgat ttacggcaaa aacaaccgtc cgtctgggat cccggaccgt     180
ttctccggca gctcttccgg taacacggcg agcctcacca tcactggcgc tcaagcagaa     240
gacgaggccg actattactg taactctcgg gaaagcccac caaccggcct ggttgtcttc     300
ggtggcggta ccaagctgac cgtcctaggt caacccaagg ctgcccccag cgtgaccctg     360 ttcccccca gcagcaagaa actgcaggcc aacaaggcca ccctggtctg cctgatcagc     420
gacttctacc caggcgccgt gaccgtggcc tggaaggccg acagcagccc cgtgaaggcc     480
ggcgtggaga ccaccacccc cagcaagcag agcaacaaca gtacgccgc cagcagctac     540 ctgagcctga ccccgagca gtggaagagc acaggtcct acagctgcca ggtgacccac     600
gagggcagca ccgtggagaa aaccgtggcc cccaccgagt gcagc                    645
```

<210> SEQ ID NO 423
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 423

```
caggtgcaat tggttcaatc tggtgctgaa gtaaaaaaac cgggcgcttc cgttaaagtg      60
agctgcaaag catccggata caccttcact tcctattaca tgcactgggt tcgtcaagcc     120
ccgggccagg gtctggaatg gatgggcatc attaacccaa gcggtggctc tacctcctac     180
gcgcagaaat tccagggtcg cgtcacgatg accgtgaca ctagcacctc taccgtttat     240
atggagctgt ccagcctgcg ttctgaagat actgcagtgt actactgtgc acgcggtgac     300
tggtcttact acatggacta ttggggtcaa ggcaccctcg taacggtttc ttct           354
```

<210> SEQ ID NO 424
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 424

```
gatattgtta tgactcaatc tccactgtct ctgccggtga ctccaggcga accggcgagc    60
atttcttgcc gttccagcca gtctctgctg cactccaacg gctacaacta tctcgattgg   120
tacctgcaaa aaccgggtca gagccctcag ctgctgatct acctgggctc taaccgcgct   180
tccggtgtac cggaccgttt cagcggctct ggatccggca ccgatttcac gttgaaaatc   240
agccgtgttg aagcagaaga cgtgggcgtt tattactgta tgcaggcacg gcagacccca   300
acttttggtc aaggcaccaa ggtcgaaatt aaa                                333
```

<210> SEQ ID NO 425
<211> LENGTH: 2019
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 425

```
caggtgcaat tggttcaatc tggtgctgaa gtaaaaaaac cgggcgcttc cgttaaagtg    60
agctgcaaag catccggata caccttcact tcctattaca tgcactgggt tcgtcaagcc   120
ccgggccagg gtctgaatg gatgggcatc attaacccaa gcgtggctc tacctcctac     180
gcgcagaaat tccagggtcg cgtcacgatg accgtgaca ctagcacctc taccgtttat    240
atggagctgt ccagcctgcg ttctgaagat actgcagtgt actactgtgc acgcggtgac   300
tggtcttact acatggacta ttggggtcaa ggcaccctcg taacggtttc ttctgctagc   360
accaagggcc cctccgtgtt cctctggcc cttccagca agtccacctc tggcggaact     420
gccgctctgg gctgcctggt ggaagattac ttccccgagc ccgtgaccgt gtcctggaat   480
tctggcgctc tgacctccgg cgtgcacacc tttccagctg tgctgcagtc ctccggcctg   540
tactcctgt cctccgtcgt gacagtgccc tccagctctc tgggcaccca gacctacatc    600
tgcaacgtga accacaagcc ctccaacacc aaggtggacg agaaggtgga acccaagtcc   660
tgcgacggtg gcggaggttc cggaggcgga ggatcccagg ctgtcgtgac ccaggaaccc   720
tccctgacag tgtctcctgg cggcaccgtg accctgacct gtggatcttc taccggcgct   780
gtgaccacct ccaactacgc caattgggtg caggaaaagc ccggccaggc cttcagagga   840
ctgatcggcg gcaccaacaa gagagcccct ggcaccctg ccagattctc cggttctctg    900
ctgggcggca aggctgccct gactctgtct ggtgctcagc ctgaggacga ggccgagtac   960
tactgcgccc tgtggtactc caacctgtgg gtgttcggcg gaggcaccaa gctgaccgtg  1020
ctgtccagcg cttccaccaa gggacccagt gtgttccccc tggcccccag ctccaagtct  1080
acatccggtg gcacagctgc cctgggatgt ctcgtgaagg actactttcc tgagcctgtg  1140
acagtgtctt ggaacagcgg agccctgacc agcggagtgc acacattccc tgcagtgctg  1200
cagagcagcg gcctgtatag cctgagcagc gtcgtgaccg tgccttcctc tagcctggga  1260
acacagacat atatctgtaa tgtgaatcat aagcccagta ataccaaagt ggataagaaa  1320
gtggaaccta gagctgcga taagacccac acctgtcccc cctgccctgc tcctgaagct  1380
gctggtggcc ctagcgtgtt cctgttcccc ccaaagccca aggacaccct gatgatctcc  1440
cggacccccg aagtgacctg cgtggtggtg gatgtgtccc acgaggaccc tgaagtgaag  1500
ttcaattggt acgtggacgg cgtggaagtg cacaacgcca agaccaagcc tagagaggaa  1560
```

```
cagtacaact ccacctaccg ggtggtgtcc gtgctgacag tgctgcacca ggactggctg    1620
aacggcaaag agtacaagtg caaggtgtcc aacaaggccc tgggcgctcc catcgaaaag    1680
accatctcca aggccaaggg ccagccccgg aaccccagg tgtacaccct gcccccatgc     1740
cgggatgagc tgaccaagaa ccaggtcagc ctgtggtgcc tggtcaaagg cttctatccc    1800
agcgacatcg ccgtggagtg ggagagcaat gggcagccgg agaacaacta caagaccacg    1860
cctcccgtgc tggactccga cggctccttc ttcctctaca gcaagctcac cgtggacaag    1920
agcaggtggc agcaggggaa cgtcttctca tgctccgtga tgcatgaggc tctgcacaac    1980
cactacacgc agaagagcct ctccctgtct ccgggtaaa                          2019
```

<210> SEQ ID NO 426
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 426

```
caggtgcaat tggttcaatc tggtgctgaa gtaaaaaaac cgggcgcttc cgttaaagtg     60
agctgcaaag catccggata caccttcact tcctattaca tgcactgggt tcgtcaagcc    120
ccgggccagg gtctggaatg gatgggcatc attaacccaa gcgtggctc tacctcctac     180 gcgcagaaat tccagggtcg cgtcacgatg acccgtgaca ctagcaccctc taccgtttat   240 atggagctgt ccagcctgcg ttctgaagat actgcagtgt actactgtgc acgcggtgac    300
tggtcttact acatggacta ttggggtcaa ggcaccctcg taacggtttc ttctgctagc    360
accaagggcc cctccgtgtt ccccctggcc ccagcagca agagcaccag cggcggcaca    420
gccgctctgg gctgcctggt cgaggactac ttccccgagc ccgtgaccgt gcctggaac    480 agcggagccc tgacctccgg cgtgcacacc ttccccgccg tgctgcagag ttctggcctg    540
tatagcctga gcagcgtggt caccgtgcct tctagcagcc tgggcaccca gacctacatc    600
tgcaacgtga accacaagcc cagcaacacc aaggtggacg agaaggtgga gcccaagagc    660
tgcgacaaaa ctcacacatg cccaccgtgc ccagcacctg aagctgcagg ggaccgtca    720 gtcttcctct ccccccaaa acccaaggac accctcatga tctcccggac ccctgaggtc    780
acatgcgtgg tggtggacgt gagccacgaa gaccctgagg tcaagttcaa ctggtacgtg    840
gacggcgtga aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctcggc gccccatcg agaaaaccat ctccaaagcc    1020
aaagggcagc cccgagaacc acaggtgtgc accctgcccc catcccggga tgagctgacc    1080
aagaaccagg tcagcctctc gtgcgcagtc aaaggcttct atcccagcga catcgccgtg    1140
gagtgggaga gcaatgggca gccggagaac aactacaaga ccacgcctcc cgtgctggac    1200
tccgacggct ccttcttcct cgtgagcaag ctcaccgtgg acaagagcag gtggcagcag    1260
gggaacgtct tctcatgctc cgtgatgcat gaggctctgc acaaccacta cacgcagaag    1320
agcctctccc tgtctccggg taaa                                         1344
```

<210> SEQ ID NO 427
<211> LENGTH: 654
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 427
gatattgtta tgactcaatc tccactgtct ctgccggtga ctccaggcga accggcgagc    60
atttcttgcc gttccagcca gtctctgctg cactccaacg gctacaacta tctcgattgg   120
tacctgcaaa aaccgggtca gagccctcag ctgctgatct acctgggctc taaccgcgct   180
tccggtgtac cggaccgttt cagcggctct ggatccggca ccgatttcac gttgaaaatc   240
agccgtgttg aagcagaaga cgtgggcgtt tattactgta tgcaggcacg gcagacccca   300
acttttggtc aaggcaccaa ggtcgaaatt aaacgtacgg tggctgcacc atctgtcttc   360
atcttcccgc catctgatcg aagttgaaa tctggaactg cctctgttgt gtgcctgctg    420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc    600 acccatcagg gcctgagctc gcccgtcaca aagagcttca caggggaga gtgt           654

<210> SEQ ID NO 428
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 428

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp
            100

<210> SEQ ID NO 429
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (13)..(24)
<223> OTHER INFORMATION: /replace=" "
<220> FEATURE:
<221> NAME/KEY: MISC_FEATURE
<222> LOCATION: (1)..(24)
<223> OTHER INFORMATION: /note="This region may encompass 3-6 "Gly Gly
```

```
        Gly Ser" repeating units"
<220> FEATURE:
<221> NAME/KEY: VARIANT
<222> LOCATION: (25)..(27)
<223> OTHER INFORMATION: /replace=" "
<220> FEATURE:
<221> NAME/KEY: MISC_FEATURE
<222> LOCATION: (1)..(27)
<223> OTHER INFORMATION: /note="Variant residues given in the sequence
        have no preference with respect to those in the annotations
        for variant positions"

<400> SEQUENCE: 429

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly
            20                  25

<210> SEQ ID NO 430
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"
<220> FEATURE:
<221> NAME/KEY: VARIANT
<222> LOCATION: (11)..(25)
<223> OTHER INFORMATION: /replace=" "
<220> FEATURE:
<221> NAME/KEY: MISC_FEATURE
<222> LOCATION: (1)..(25)
<223> OTHER INFORMATION: /note="This region may encompass 2-5 "Gly Gly
        Gly Gly Ser" repeating units"
<220> FEATURE:
<221> NAME/KEY: VARIANT
<222> LOCATION: (26)..(28)
<223> OTHER INFORMATION: /replace=" "
<220> FEATURE:
<221> NAME/KEY: MISC_FEATURE
<222> LOCATION: (1)..(28)
<223> OTHER INFORMATION: /note="Variant residues given in the sequence
        have no preference with respect to those in the annotations
        for variant positions"

<400> SEQUENCE: 430

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly
            20                  25
```

The invention claimed is:

1. A pharmaceutical composition comprising:
   (a) a T cell activating bispecific antigen-binding molecule, wherein the T cell activating bispecific antigen-binding molecule comprises a first antigen-binding moiety that binds to CD3 and a second antigen-binding moiety that binds to Folate Receptor 1 (FolR1), wherein the second antigen-binding moiety comprises:
      (i) a complementarity determining region (CDR) heavy chain 1 (CDR-H1) comprising the amino acid sequence of SEQ ID NO: 16,
      (ii) a CDR heavy chain 2 (CDR-H2) comprising the amino acid sequence of SEQ ID NO: 17,
      (iii) a CDR heavy chain 3 (CDR-H3) comprising the amino acid sequence of SEQ ID NO: 18,
      (iv) a CDR light chain 1 (CDR-L1) comprising the amino acid sequence of SEQ ID NO: 32,
      (v) a CDR light chain 2 (CDR-L2) comprising the amino acid sequence of SEQ ID NO: 33, and
      (vi) a CDR light chain 3 (CDR-L3) comprising the amino acid sequence of SEQ ID NO: 34; and
   (b) a pharmaceutically acceptable carrier.

2. The pharmaceutical composition of claim 1, wherein the T cell activating bispecific antigen-binding molecule further comprises a third antigen-binding moiety, wherein the third antigen-binding moiety binds to FolR1.

3. The pharmaceutical composition of claim 2, wherein the third antigen-binding moiety comprises:
   (a) a CDR-H1 comprising the amino acid sequence of SEQ ID NO: 16,
   (b) a CDR-H2 comprising the amino acid sequence of SEQ ID NO: 17,
   (c) a CDR-H3 comprising the amino acid sequence of SEQ ID NO: 18, (d) a CDR-L1 comprising the amino acid sequence of SEQ ID NO: 32,
(e) a CDR-L2 comprising the amino acid sequence of SEQ ID NO: 33, and
(f) a CDR-L3 comprising the amino acid sequence of SEQ ID NO: 34.

4. The pharmaceutical composition of claim 3, wherein the third antigen-binding moiety is identical to the second antigen-binding moiety.

5. The pharmaceutical composition of claim 2, wherein at least one of the first, second, and third antigen-binding moiety is a Fab molecule.

6. The pharmaceutical composition of claim 1, wherein the second antigen-binding moiety comprises a variable heavy chain comprising the amino acid sequence of SEQ ID NO: 15 and a variable light chain comprising the amino acid sequence of SEQ ID NO: 31.

7. The pharmaceutical composition of claim 1, further comprising a PD-1 axis binding antagonist antibody.

8. The pharmaceutical composition of claim 7, wherein the PD-1 axis binding antagonist antibody is selected from the group consisting of a PD-1 binding antagonist antibody, a PD-L1 binding antagonist antibody, and a PD-L2 binding antagonist antibody.

9. The pharmaceutical composition of claim 8, wherein the PD-1 axis binding antagonist antibody is a PD-1 binding antagonist antibody.

10. The pharmaceutical composition of claim 8, wherein the PD-1 axis binding antagonist antibody is a PD-L1 binding antagonist antibody.

11. The pharmaceutical composition of claim 8, wherein the PD-1 axis binding antagonist antibody is a PD-L2 binding antagonist antibody.

12. The pharmaceutical composition of claim 1, wherein the first antigen-binding moiety and the second antigen-binding moiety are Fab molecules.

13. The pharmaceutical composition of claim 1, further comprising a T cell immunoglobulin mucin 3 (TIM3) antagonist.

14. A kit comprising:
a T cell activating bispecific antigen-binding molecule, wherein the T cell activating bispecific antigen-binding molecule comprises a first antigen-binding moiety that binds to CD3 and a second antigen-binding moiety that binds to FoIR1, wherein the second antigen-binding moiety comprises:
(i) a CDR-H1 comprising the amino acid sequence of SEQ ID NO: 16,
(ii) a CDR-H2 comprising the amino acid sequence of SEQ D NO: 17,
(iii) a CDR-H3 comprising the amino acid sequence of SEQ ID NO: 18,
(iv) a CDR-L1 comprising the amino acid sequence of SEQ ID NO: 32,
(v) a CDR-L2 comprising the amino acid sequence of SEQ ID NO: 33, and
(vi) a CDR-L3 comprising the amino acid sequence of SEQ ID NO: 34.

15. The kit of claim 14, further comprising a package insert comprising instructions for using the T cell activating bispecific antigen-binding molecule with a PD-1 axis binding antagonist antibody to treat or delay progression of a cancer in an individual.

16. The kit of claim 15, further comprising the PD-1 axis binding antagonist antibody.

17. The kit of claim 14, wherein the T cell activating bispecific antigen-binding molecule further comprises a third antigen-binding moiety, wherein the third antigen-binding moiety binds to FoIR1.

18. The kit of claim 17, wherein the third antigen-binding moiety comprises:
(a) a CDR-H1 comprising the amino acid sequence of SEQ ID NO: 16,
(b) a CDR-H2 comprising the amino acid sequence of SEQ ID NO: 17,
(c) a CDR-H3 comprising the amino acid sequence of SEQ ID NO: 18,
(d) a CDR-L1 comprising the amino acid sequence of SEQ ID NO: 32,
(e) a CDR-L2 comprising the amino acid sequence of SEQ ID NO: 33, and
(f) a CDR-L3 comprising the amino acid sequence of SEQ ID NO: 34.

19. The kit of claim 18, wherein the third antigen-binding moiety is identical to the second antigen-binding moiety.

20. The kit of claim 17, wherein at least one of the first, second, and third antigen-binding moiety is a Fab molecule.

21. The kit of claim 14, wherein the second antigen-binding moiety comprises a variable heavy chain comprising the amino acid sequence of SEQ ID NO:15 and a variable light chain comprising the amino acid sequence of SEQ ID NO: 31.

22. The kit of claim 16, wherein the PD-1 axis binding antagonist antibody is selected from the group consisting of a PD-1 binding antagonist antibody, a PD-L1 binding antagonist antibody, and a PD-L2 binding antagonist antibody.

23. The kit of claim 22, wherein the PD-1 axis binding antagonist antibody is a PD-1 binding antagonist antibody.

24. The kit of claim 22, wherein the PD-1 axis binding antagonist antibody is a PD-L1 binding antagonist antibody.

25. The kit of claim 22, wherein the PD-1 axis binding antagonist antibody is a PD-L2 binding antagonist antibody.

26. The kit of claim 15, wherein the cancer is selected from the group consisting of ovarian cancer, lung cancer, breast cancer, renal cancer, colorectal cancer, and endometrial cancer.

27. The kit of claim 15, wherein the individual comprises less than about 15% PD-1 expressing tumor-infiltrating T cells.

28. The kit of claim 14, wherein the first antigen-binding moiety and the second antigen-binding moiety are Fab molecules.

29. The kit of claim 14, further comprising a TIM3 antagonist.

* * * * *